US011021480B2

(12) United States Patent
Harrison et al.

(10) Patent No.: US 11,021,480 B2
(45) Date of Patent: Jun. 1, 2021

(54) INHIBITING (α-V)(β-6) INTEGRIN

(71) Applicant: Morphic Therapeutic, Inc., Waltham, MA (US)

(72) Inventors: Bryce A. Harrison, Framingham, MA (US); James E. Dowling, Lexington, MA (US); Matthew G. Bursavich, Needham, MA (US); Dawn M. Troast, Bedford, MA (US); Blaise S. Lippa, Newton, MA (US); Bruce N. Rogers, Belmont, MA (US); Cheng Zhong, Belmont, MA (US); Qi Qiao, Natick, MA (US); Fu-Yang Lin, Sudbury, MA (US); Brian Sosa, Cambridge, MA (US); Aleksey I. Gerasyuto, Flemington, NJ (US); Andrea Bortolato, Metuchen, NJ (US)

(73) Assignee: Morphic Therapeutic, Inc., Waltham, MA (US)

( * ) Notice: Subject to any disclaimer, the term of this patent is extended or adjusted under 35 U.S.C. 154(b) by 0 days.

(21) Appl. No.: 17/001,086

(22) Filed: Aug. 24, 2020

(65) Prior Publication Data
US 2020/0385384 A1 Dec. 10, 2020

Related U.S. Application Data

(63) Continuation of application No. 16/555,589, filed on Aug. 29, 2019.

(60) Provisional application No. 62/859,457, filed on Jun. 10, 2019, provisional application No. 62/724,423, filed on Aug. 29, 2018.

(51) Int. Cl.
C07D 471/04 (2006.01)
A61K 9/00 (2006.01)
(52) U.S. Cl.
CPC .......... C07D 471/04 (2013.01); A61K 9/0053 (2013.01)
(58) Field of Classification Search
CPC .................................... C07D 471/04
USPC ......................................... 546/122
See application file for complete search history.

(56) References Cited

U.S. PATENT DOCUMENTS

| 5,952,341 | A | 9/1999 | Duggan et al. |
|---|---|---|---|
| 6,017,926 | A | 1/2000 | Askew et al. |
| 6,048,861 | A | 4/2000 | Askew et al. |
| 6,069,143 | A | 5/2000 | Ali et al. |
| 6,232,308 | B1 | 5/2001 | Askew |
| 6,358,970 | B1 | 3/2002 | Duggan et al. |
| 6,723,711 | B2 | 4/2004 | Biediger et al. |
| 8,716,226 | B2 | 5/2014 | Ruminski et al. |
| 9,572,801 | B2 | 2/2017 | Askew et al. |
| 2001/0034445 | A1 | 10/2001 | Ali et al. |
| 2002/0010176 | A1 | 1/2002 | Askew et al. |
| 2002/0035127 | A1 | 3/2002 | Head et al. |
| 2004/0043988 | A1 | 3/2004 | Khanna et al. |
| 2008/0045521 | A1 | 2/2008 | Arnould et al. |
| 2009/0104116 | A1 | 4/2009 | Zischinsky et al. |
| 2012/0289481 | A1 | 11/2012 | O'Neil et al. |
| 2014/0038910 | A1 | 2/2014 | Ruminski et al. |
| 2014/0051715 | A1 | 2/2014 | Ruminski et al. |
| 2014/0349968 | A1 | 11/2014 | O'Neil et al. |
| 2016/0280705 | A1 | 9/2016 | Anderson et al. |
| 2017/0290817 | A1 | 10/2017 | Anderson et al. |
| 2017/0369490 | A1 | 12/2017 | Askew et al. |
| 2018/0008583 | A1 | 1/2018 | Fukunaga et al. |
| 2018/0093984 | A1 | 4/2018 | Jiang et al. |
| 2018/0244648 | A1* | 8/2018 | Harrison et al. ..... C07D 401/12 546/122 |
| 2019/0248832 | A1 | 8/2019 | Almeida et al. |
| 2019/0276449 | A1 | 9/2019 | Cha et al. |
| 2020/0002334 | A1 | 1/2020 | Harrison et al. |
| 2020/0071322 | A1 | 3/2020 | Harrison et al. |
| 2020/0087299 | A1 | 3/2020 | Brewer et al. |
| 2020/0109141 | A1 | 4/2020 | Cha et al. |
| 2020/0157075 | A1 | 5/2020 | Harrison et al. |

FOREIGN PATENT DOCUMENTS

| EP | 0537696 A1 | 4/1993 |
|---|---|---|
| EP | 0623615 A1 | 11/1994 |
| EP | 2221308 A1 | 8/2010 |
| WO | WO-1993/10091 A2 | 5/1993 |
| WO | WO-93/14077 A1 | 7/1993 |
| WO | WO-97/24122 A1 | 7/1997 |
| WO | WO-97/24124 A1 | 7/1997 |
| WO | WO-97/25323 A1 | 7/1997 |
| WO | WO-97/36871 A1 | 10/1997 |
| WO | WO-98/08840 A1 | 3/1998 |
| WO | WO-98/46220 A1 | 10/1998 |
| WO | WO-1998/044797 A1 | 10/1998 |
| WO | WO-1999/026945 A1 | 6/1999 |
| WO | WO-1999/030713 A1 | 6/1999 |
| WO | WO-1999/031061 A1 | 6/1999 |
| WO | WO-1999/031099 A1 | 6/1999 |
| WO | WO-2000/006169 A1 | 2/2000 |

(Continued)

OTHER PUBLICATIONS

Extended European Search Report for EP Application No. 20190341.6 dated Sep. 28, 2020.
Anderson et al., "The discovery of an orally bioavailable pan-#v integrin inhibitor for idiopathic pulmonary fibrosis," J. Med. Chem., Just Accepted Manuscript, (2019).

(Continued)

*Primary Examiner* — Charanjit Aulakh
(74) *Attorney, Agent, or Firm* — Foley Hoag LLP; Dana M. Gordon; Lawrence P. Tardibono

(57) ABSTRACT

Disclosed are small molecule inhibitors of αvβ6 integrin, and methods of using them to treat a number of diseases and conditions.

2 Claims, 6 Drawing Sheets

(56) References Cited

FOREIGN PATENT DOCUMENTS

| WO | WO-2000/031067 A1 | 6/2000 |
| --- | --- | --- |
| WO | WO-2000/037487 A1 | 6/2000 |
| WO | WO-2000/072801 A2 | 12/2000 |
| WO | WO-2000/073260 A1 | 12/2000 |
| WO | WO-2000/78317 A1 | 12/2000 |
| WO | WO-2001/005810 A2 | 1/2001 |
| WO | WO-2001/023357 A2 | 4/2001 |
| WO | WO-2001/044194 A2 | 6/2001 |
| WO | WO-2001/053262 A1 | 7/2001 |
| WO | WO-2001/053297 A1 | 7/2001 |
| WO | WO-2001/096334 A2 | 12/2001 |
| WO | WO-2002/16328 A1 | 2/2002 |
| WO | WO-2002/022124 A1 | 3/2002 |
| WO | WO-2002/022615 A1 | 3/2002 |
| WO | WO-2002/022616 A2 | 3/2002 |
| WO | WO-2002/074730 A1 | 9/2002 |
| WO | WO-2002/090325 A2 | 11/2002 |
| WO | WO-2003/066594 A2 | 8/2003 |
| WO | WO-2004/020435 A1 | 3/2004 |
| WO | WO-2006/024699 A1 | 3/2006 |
| WO | WO-2008/157162 A1 | 12/2008 |
| WO | WO-2014/015054 A1 | 1/2014 |
| WO | WO-2014/154725 A1 | 10/2014 |
| WO | WO-2014/154809 A1 | 10/2014 |
| WO | WO-2015/103643 A2 | 7/2015 |
| WO | WO-2015/150557 A1 | 10/2015 |
| WO | WO-2015/179823 A2 | 11/2015 |
| WO | WO-2016/022851 A1 | 2/2016 |
| WO | WO-2016/046225 A1 | 3/2016 |
| WO | WO-2016/046226 A1 | 3/2016 |
| WO | WO-2016/046230 A1 | 3/2016 |
| WO | WO-2016/046241 A1 | 3/2016 |
| WO | WO-2016/176532 A1 | 11/2016 |
| WO | WO-2017/117538 A1 | 7/2017 |
| WO | WO-2017/158072 A1 | 9/2017 |
| WO | WO-2017/162570 A1 | 9/2017 |
| WO | WO-2017/162572 A1 | 9/2017 |
| WO | WO-2018/009501 A1 | 1/2018 |
| WO | WO-2018/049068 A1 | 3/2018 |
| WO | WO-2018/085552 A1 | 5/2018 |
| WO | WO-2018/085578 A1 | 5/2018 |
| WO | WO-2018/089353 A1 | 5/2018 |
| WO | WO-2018/089355 A1 | 5/2018 |
| WO | WO-2018/089357 A1 | 5/2018 |
| WO | WO-2018/089358 A1 | 5/2018 |
| WO | WO-2018/089360 A1 | 5/2018 |
| WO | WO-2018/119087 A1 | 6/2018 |
| WO | WO-2018/132268 A1 | 7/2018 |
| WO | WO-2018/160521 A2 | 9/2018 |
| WO | WO-2018/160522 A1 | 9/2018 |
| WO | WO-2019/173653 A1 | 9/2019 |
| WO | WO-2020/006315 A1 | 1/2020 |
| WO | WO-2020/009889 A1 | 1/2020 |
| WO | WO-2020/047207 A1 | 3/2020 |
| WO | WO-2020/047208 A1 | 3/2020 |
| WO | WO-2020/047239 A1 | 3/2020 |
| WO | WO-2020/076862 A1 | 4/2020 |
| WO | WO-2020/081154 A1 | 4/2020 |

OTHER PUBLICATIONS

Bennet et al., "Cecil Textbook of Medicine," 20th Edition, 1:1004-1010 (1996).
Brashear et al., "Non-Peptide $\alpha_v\beta_3$ Antagonists. Part 5: Identification of Potent RGD Mimetics Incorporating 2-Aryl β-Amino Acids as Aspartic Acid Replacements," Bioorganic & Medicinal Chemistry Letters 12: 3483-3486 (2002).
Breslin et al., "Nonpeptide $\alpha_v\beta_3$ antagonists. Part 10: In vitro and in vivo evaluation of a potent 7-methyl substituted tetrahydro-[1,8]naphthyridine derivative," Bioorganic & Medicinal Chemistry Letters, 14: 4515-4518 (2004).
Coleman et al., "Nonpeptide $\alpha_v\beta_3$ Antagonists. Part 11: Discovery and Preclinical Evaluation of Potent $\alpha_v\beta_3$ Antagonists for the Prevention and Treatment of Osteoporosis," J. Med. Chem. 47: 4829-4837 (2004).
Cui et al., "In Vitro and In Vivo Metabolism of a Potent and Selective Integrin $\alpha_v\beta_3$ Antagonists in Rats, Dogs, and Monkeys," Drug Metabolism and Disposition, 32(8): 848-861 (2004).
Database Accession No. 1380858-49-0., Database Registry [Online] Chemical Abstracts Service: XP002799454 (2012).
Database Accession No. 1380909-02-3., Database Registry [Online] Chemical Abstracts Service: XP002799455 (2012).
Database Accession No. 1380948-25-3., Database Registry [Online] Chemical Abstracts Service: XP002799456 (2012).
Database Accession No. 1380999-27-8., Database Registry [Online] Chemical Abstracts Service: XP002799457 (2012).
Database Accession No. 1571616-43-7., Database Registry [Online] Chemical Abstracts Service: XP002799458 (2014).
Database Accession No. 1623225-85-3., Database Registry [Online] Chemical Abstracts Service: XP002799459 (2014).
Database Accession No. 1837357-51-3., Database Registry [Online] Chemical Abstracts Service: XP002799460 (2015).
Database Accession No. 1838839-35-2., Database Registry [Online] Chemical Abstracts Service: XP002799461 (2015).
Database Accession No. 1940788-29-3., Database Registry [Online] Chemical Abstracts Service: XP002799462 (2016).
Database Accession No. 2038980-05-9., Database Registry [Online] Chemical Abstracts Service: XP002799463 (2016).
Dermeret et al., "Another Anniversary for the War on Cancer," Bio/Technology, 12:320 (1994).
Duggan et al., "Nonpeptide $\alpha_v\beta_3$ Antagonists. 1. Transformation of a Potent, Integrin-Selective $\alpha_{IIb}\beta_3$ Antagonist into a Potent $\alpha_v\beta_3$ Antagonist," J. Med. Chem. 43: 3736-3745 (2000).
Extended European Search Report for EP Application No. 18761396.3 dated Jul. 2, 2020.
Extended European Search Report for EP Application No. EP 18760393.1 dated Jul. 14, 2020.
Extended European Search Report for EP Application No. EP 19194490 dated Dec. 10, 2019.
Freshney et al., "Culture of Animal Cells, A Manual of Basic Technique," 4, (1983).
Goodman et al., "Nanomolar Small Molecule Inhibitors for $\alpha_v\beta_6$, $\alpha_v\beta_5$, and $\alpha_v\beta_3$ Integrins," J. Med. Chem. 45: 1045-1051 (2002).
Hall et al., "Characterisation of a novel, high affinity and selective $\alpha_v\beta_6$ integrin RGD-mimetic radioligand," Biochemical Pharmacology, 117(1): 88-96 (2016).
Hatley et al., "An αv-RGD integrin inhibitor toolbox: drug discovery insight, challenges and opportunities," Angew. Chem., 57(13): 3298-3321 (2017).
Hutchinson et al., "Nonpeptide $\alpha_v\beta_3$ Antagonists. 8. In Vitro and in Vivo Evaluation of a Potent $\alpha_v\beta_3$ Antagonist for the Prevention and Treatment of Osteoporosis," J. Med. Chem. 46: 4790-4798 (2003).
International Preliminary Report on Patentability for International Application No. PCT/EP00/06188 dated May 31, 2001.
International Preliminary Report on Patentability for International Application No. PCT/EP02/01836 dated Oct. 14, 2002.
International Preliminary Report on Patentability for International Application No. PCT/EP2003/000327 dated Dec. 3, 2003.
International Preliminary Report on Patentability for International Application No. PCT/EP2014/056167 dated Sep. 29, 2015.
International Preliminary Report on Patentability for International Application No. PCT/EP99/09842 dated Jan. 12, 2001.
International Preliminary Report on Patentability for International Application No. PCT/FI2005/050305 dated Feb. 28, 2007.
International Preliminary Report on Patentability for International Application No. PCT/GB00/02020 dated Sep. 19, 2001.
International Preliminary Report on Patentability for International Application No. PCT/GB00/04831 dated Oct. 1, 2002.
International Preliminary Report on Patentability for International Application No. PCT/US00/14901 dated Mar. 28, 2001.
International Preliminary Report on Patentability for International Application No. PCT/US00/16849 dated Jun. 29, 2001.

(56) References Cited

OTHER PUBLICATIONS

International Preliminary Report on Patentability for International Application No. PCT/US00/26537 dated Jan. 1, 2002.
International Preliminary Report on Patentability for International Application No. PCT/US01/01298 dated Oct. 8, 2001.
International Preliminary Report on Patentability for International Application No. PCT/US01/01953 dated Sep. 8, 2001.
International Preliminary Report on Patentability for International Application No. PCT/US01/28238 dated Jul. 31, 2002.
International Preliminary Report on Patentability for International Application No. PCT/US01/28404 dated Apr. 25, 2002.
International Preliminary Report on Patentability for International Application No. PCT/US01/42146 dated Sep. 5, 2002.
International Preliminary Report on Patentability for International Application No. PCT/US02/13457 dated Jul. 22, 2003.
International Search Report and Written Opinion for International Application No. PCT/US/18/19838 dated Aug. 8, 2018.
International Search Report and Written Opinion for International Application No. PCT/US18/19839 dated Aug. 9, 2018.
International Search Report and Written Opinion for International Application No. PCT/US2019/048734 dated Mar. 20, 2020.
International Search Report and Written Opinion for International Application No. PCT/US2019/048737 dated Dec. 27, 2019.
International Search Report and Written Opinion for International Application No. PCT/US2019/048738 dated Jan. 7, 2020.
International Search Report and Written Opinion for International Application No. PCT/US2019/048782 dated Dec. 27, 2019.
International Search Report for International Application No. PCT/US2019/055252 dated Jan. 23, 2020.
Invitation to Pay Additional Fees for International Application No. PCT/US2019/048737 dated Oct. 11, 2019.
Invitation to Pay Additional Fees for International Application No. PCT/US2019/048738 dated Oct. 11, 2019.
Invitation to Pay Additional Fees for International Application No. PCT/US2019/048782 dated Oct. 11, 2019.
Kinney el al., "Suzuki-Miyaura Approach to JNJ-26076713, an Orally Active Tetrahydroquinoline-Containing $\alpha_v\beta_3/\alpha_v\beta_5$ Integrin Antagonist. Enantioselective Synthesis and Stereochemical Studies," J. Org. Chem., 73: 2302-2310 (2008).
Macdonald et al., "Passing on the medicinal chemistry baton: training undergraduates to be industry-ready through research projects between the University of Nottingham and GlaxoSmithKline," Drug Discovery Today, 21(6): 880-887 (2016).
Meissner et al., "Nonpeptide avß3 antagonists. Part 2: constrained glycyl amides derived from the RGD tripeptide," Bioorganic & Medicinal Chemistry Letters, 12(1): 25-29 (2002).
Peng et al., "Integrin $\alpha_v\beta_6$ Critically Regulates Hepatic Progenitor Cell Function and Promotes Ductular Reaction, Fibrosis, and Tumorigenesis," Hepatology 63(1): 217-232 (2016).
Perkins et al., "Non-peptide $\alpha_v\beta_3$ Antagonists: Identification of Potent, Chain-Shortened RGD Mimetics that Incorporate a Central Pyrrolidinone Constraint," Bioorganic & Medicinal Chemistry Letters 13: 4285-4288 (2003).

Procopiou et al., "Discovery of (S)-3-(3-(3,5-Dimethyl-1H-pyrazol-1-yl)phenyl)-4-((R)-3-(2-(5,6,7,8-tetrahydro-1,8-naphthyridin-2-yl)ethyl)pyrrolidin-1-yl)butanoic Acid, a Nonpeptidic $\alpha_v\beta_6$ Integrin Inhibitor for the Inhaled Treatment of Idiopathic Pulmonary Fibrosis," Journal of Medicinal Chemistry, 6(18): 8417-8443 (2018).
Prueksaritanont et al., "Disposition of a novel and potent $\alpha_v\beta_3$ antagonist in animals, and extrapolation to man," Xenobiotica 34(1):103-115 (2004).
Prueksaritanont et al., "Renal elimination of a novel and potent $\alpha_v\beta_3$ integrin antagonist in animals," Xenobiotica 34(11/12):1059-1074 (2004).
Raab-Westphal et al., "Integrins as Therapeutic Targets: Successes and Cancers," Cancers, 9(110):1-28 (2017).
Rosenthal et al., "Evaluation of the safety, pharmacokinetics and treatment effects of an $\alpha_v\beta_3$ integrin inhibitor on bone turnover and disease activity in men with hormone-refractory prostate cancer and bone metastases," Asia-Pac J Clin Oncol 6:42-48 (2010).
Rosenthal et al., "Evaluation of the safety, pharmacokinetics and treatment effects of an $\alpha_v\beta_3$ integrin inhibitor on bone turnover and disease activity in men with hormone-refractory prostate cancer and bone metastases," Journal of Clinical Oncology 6: 42-48 (2010).
Rubtsov et al., "RGD-based Therapy: Principles of Selectivity," Current Pharmaceutical Design, 22: 925-932 (2016).
Santulli et al., "Studies with an Orally Bioavailable $\alpha_v$ Integrin Antagonist in Animal Models of Ocular Vasculopathy: Retinal Neovascularization in Mice and Retinal Vascular Permeability in Diabetic Rats," Journal of Pharmacology and Experimental Therapeutics, 324(3): 894-901 (2008).
Tipping et al., Relative Binding Affinities of Integrin Antagonists by Equilibrium Dialysis and Liquid Chromatography-Mass Spectrometry, Medicinal Chemistry Letters, 6(2): 221-224 (2015).
Wang et al., "Non-peptide $\alpha_v\beta_3$ antagonists. Part 7: 3-Substituted tetrahydro-[1,8]naphthyridine derivatives," Bioorganic & Medicinal Chemistry Letters, 14: 1049-1052 (2004).
Whilding et al., "The integrin $\alpha_v\beta_6$: a novel target for CAR T-cell immunotherapy?," Biochem. Soc. Trans., 44: 349-355 (2016).
Whitman et al., "Nonpeptide $\alpha_v\beta_3$ antagonists. Part 9: Improved pharmacokinetic profile through the use of an aliphatic, des-amide backbone," Bioorganic & Medicinal Chemistry Letters, 14: 4411-4415 (2004).
Written Opinion for International Application No. PCT/US2017/067622 dated Mar. 8, 2018.
Written Opinion for International Application No. PCT/US2019/021243 dated Jul. 5, 2019.
Written Opinion for International Application No. PCT/US2019/039624 dated Sep. 13, 2019.
Written Opinion for International Application No. PCT/US2019/055252 dated Jan. 23, 2020.
Zhou et al., "An integrin antagonist (MK-0429) decreases proteinuria and renal fibrosis in the ZSF1 rat diabetic nephropathy model," Pharmacology Research & Perspectives, 5(5): 1-14 (2017).

* cited by examiner

A: IC$_{50}$ <0.01 μM; B: 0.01 μM < IC$_{50}$ <0.1 μM; and C: 0.1 μM < IC$_{50}$ <1 μM.

| Compound | αvβ6 IC$_{50}$ | Compound | αvβ6 IC$_{50}$ | Compound | αvβ6 IC$_{50}$ |
|---|---|---|---|---|---|
| 1-E1 | A | 30-E1 | C | 63 | B |
| 1-E2 | C | 30-E2 | A | 64 | B |
| 2-E1 | A | 31-E1 | B | 65 | A |
| 2-E2 | C | 31-E2 | B | 66-E2 | B |
| 3-E2 | A | 32 | B | 67-E1 | B |
| 4-E1 | A | 33-E1 | A | 67-E2 | B |
| 4-E2 | C | 33-E2 | C | 68-E1 | C |
| 5-E1 | C | 34-E1 | B | 68-E2 | A |
| 5-E2 | A | 34-E2 | C | 69 | B |
| 6-E1 | C | 35 | B | 70 | B |
| 7-E2 | C | 36-E1 | B | 71 | B |
| 8 | A | 36-E2 | A | 72-E1 | B |
| 9-E1 | B | 37 | B | 72-E2 | B |
| 9-E2 | C | 38 | B | 73-E1 | A |
| 10 | B | 39-E1 | B | 73-E2 | B |
| 11-E2 | A | 40-E1 | B | 74 | A |
| 12 | B | 40-E2 | A | 75 | B |
| 13-E1 | A | 41-E2 | B | 76 | B |
| 13-E2 | B | 42 | B | 77 | B |
| 14-E2 | B | 43-E1 | C | 78 | B |
| 15-E1 | A | 43-E2 | B | 79-E1 | A |
| 15-E2 | C | 44-E1 | B | 79-E2 | C |
| 16-E1 | A | 44-E2 | C | 80-E1 | A |
| 16-E2 | B | 45 | B | 80-E2 | C |
| 17 | A | 46-E1 | A | 81 | B |
| 18-E1 | A | 46-E2 | C | 82-E1 | C |
| 18-E2 | B | 47 | C | 82-E2 | B |
| 19-E1 | A | 48 | C | 83 | A |
| 19-E2 | A | 49 | C | 84 | A |
| 19-E3 | C | 50-E1 | A | 85 | B |
| 19-E4 | C | 50-E2 | C | 86-E1 | C |
| 20-E1 | A | 51 | B | 87 | B |
| 20-E2 | A | 52 | A | 88 | B |

A: IC$_{50}$ <0.01 μM; B: 0.01 μM < IC$_{50}$ <0.1 μM; and C: 0.1 μM < IC$_{50}$ <1 μM.

| Compound | αvβ6 IC$_{50}$ | Compound | αvβ6 IC$_{50}$ | Compound | αvβ6 IC$_{50}$ |
|---|---|---|---|---|---|
| 21-B-E2 | A | 53-E1 | A | 89 | B |
| 21-A | B | 53-E2 | C | 90-E1 | A |
| 22-E1 | B | 54-E1 | A | 90-E2 | B |
| 22-E2 | C | 54-E2 | C | 91-A-E2 | A |
| 23-E1 | B | 55-E1 | A | 91-B-E1 | A |
| 24-E1 | C | 55-E2 | C | 91-B-E2 | C |
| 24-E2 | A | 56-E1 | B | 92-A-E1 | C |
| 25 | B | 57-E1 | C | 92-A-E2 | A |
| 26 | A | 57-E2 | C | 92-B-E1 | A |
| 27-E1 | B | 58 | B | 92-B-E2 | B |
| 27-E2 | C | 59 | A | 93-A-E1 | A |
| 28 | B | 60 | B | 93-A-E2 | C |
| 29-E1 | A | 61 | B | 93-B-E1 | B |
| 29-E2 | C | 62 | A | 93-B-E2 | B |

A: IC$_{50}$ <0.01 μM; B: 0.01 μM < IC$_{50}$ <0.1 μM; and C: 0.1 μM < IC$_{50}$ <1 μM.

| Compound | αvβ6 IC$_{50}$ | Compound | αvβ6 IC$_{50}$ | Compound | αvβ6 IC$_{50}$ |
|---|---|---|---|---|---|
| 94-E1 | A | 105-P1 | A | 117-E2 | C |
| 94-E2 | B | 105-P2 | B | 118-E1 | A |
| 95-E1 | A | 106-E1 | B | 118-E2 | C |
| 95-E2 | C | 106-E2 | C | 119-A-E1 | B |
| 96-E1 | C | 107-E2 | A | 119-B-E1 | A |
| 96-E2 | A | 108-E1 | A | 119-B-E2 | C |
| 97-A-E1 | A | 108-E2 | C | 120-E2 | B |
| 97-A-E2 | C | 109-E1 | B | 121-E1 | B |
| 97-B-E1 | A | 109-E2 | B | 121-E2 | B |
| 97-B-E2 | B | 110-E1 | C | 122-E1 | A |
| 98-A-E1 | A | 110-E2 | A | 123-E1 | A |
| 98-A-E2 | B | 111-E1 | A | 129-E1 | A |
| 98-B | B | 111-E2 | C | 129-E2 | C |
| 99-E1 | A | 112-A-E1 | A | 124-A-E1 | A |
| 99-E2 | B | 112-A-E2 | C | 124-A-E2 | C |
| 100-E1 | A | 113-E2 | B | 124-B-E1 | A |
| 100-E2 | C | 114-A-E1 | A | 125 | B |
| 101-A-E1 | A | 114-A-E2 | C | 126-E1 | A |
| 101-A-E2 | C | 114-B-E1 | A | 126-E2 | B |
| 101-B-E1 | A | 114-B-E2 | C | 127-E1 | A |
| 102-A-E1 | A | 115-A-E1 | A | 127-E2 | C |
| 102-A-E2 | B | 115-A-E2 | B | 127-E3 | A |
| 102-B | B | 115-B-E1 | C | 128-E1 | A |
| 103-E1 | A | 115-B-E2 | B | 128-E2 | A |
| 103-E2 | B | 116-E1 | C | 128-E3 | B |
| 104-P1 | C | 116-E2 | A | | |
| 104-P2 | A | 117-E1 | A | | |

Figure 3

MDCK-MDR1 with PGP inh (A->B) [10^6 cm/s]

A: >20; B: 15-20; C: 10-<15; D: 5-<10; E: <5; NT: not tested

| Compound | MDCK-MDR1 w/ PGP inh (A-B) | Compound | MDCK-MDR1 w/ PGP inh (A-B) | Compound | MDCK-MDR1 w/ PGP inh (A-B) |
|---|---|---|---|---|---|
| 1-E1 | E | 30-E1 | NT | 63 | E |
| 1-E2 | NT | 30-E2 | E | 64 | NT |
| 2-E1 | E | 31-E1 | NT | 65 | E |
| 2-E2 | NT | 31-E2 | NT | 66-E2 | D |
| 3-E2 | E | 32 | D | 67-E1 | NT |
| 4-E1 | C | 33-E1 | E | 67-E2 | NT |
| 4-E2 | NT | 33-E2 | NT | 68-E1 | NT |
| 5-E1 | NT | 34-E1 | NT | 68-E2 | E |
| 5-E2 | E | 34-E2 | NT | 69 | E |
| 6-E1 | NT | 35 | E | 70 | E |
| 7-E2 | NT | 36-E1 | NT | 71 | E |
| 8 | C | 36-E2 | B | 72-E1 | NT |
| 9-E1 | NT | 37 | C | 72-E2 | NT |
| 9-E2 | NT | 38 | NT | 73-E1 | D |
| 10 | E | 39-E1 | E | 73-E2 | NT |
| 11-E2 | D | 40-E1 | NT | 74 | E |
| 12 | E | 40-E2 | D | 75 | D |
| 13-E1 | E | 41-E2 | NT | 76 | B |
| 13-E2 | E | 42 | NT | 77 | NT |
| 14-E2 | D | 43-E1 | NT | 78 | NT |
| 15-E1 | D | 43-E2 | E | 79-E1 | E |
| 15-E2 | NT | 44-E1 | D | 79-E2 | NT |
| 16-E1 | E | 44-E2 | NT | 80-E1 | C |
| 16-E2 | NT | 45 | NT | 80-E2 | NT |
| 17 | E | 46-E1 | D | 81 | D |
| 18-E1 | D | 46-E2 | NT | 82-E1 | NT |
| 18-E2 | NT | 47 | NT | 82-E2 | NT |
| 19-E1 | C | 48 | NT | 83 | E |
| 19-E2 | C | 49 | NT | 84 | NT |
| 19-E3 | NT | 50-E1 | NT | 85 | NT |
| 19-E4 | NT | 50-E2 | NT | 86-E1 | NT |
| 20-E1 | NT | 51 | E | 87 | NT |
| 20-E2 | E | 52 | D | 88 | E |

Figure 3 (cont'd)

MDCK-MDR1 with PGP inh (A->B) [10^6 cm/s]

A: >20; B: 15-20; C: 10-<15; D: 5-<10; E: <5; NT: not tested

| Compound | MDCK-MDR1 w/ PGP inh (A-B) | Compound | MDCK-MDR1 w/ PGP inh (A-B) | Compound | MDCK-MDR1 w/ PGP inh (A-B) |
|---|---|---|---|---|---|
| 21-B-E2 | C | 53-E1 | NT | 89 | NT |
| 21-A | C | 53-E2 | NT | 90-E1 | D |
| 22-E1 | E | 54-E1 | A | 90-E2 | NT |
| 22-E2 | NT | 54-E2 | NT | 91-A-E2 | B |
| 23-E1 | NT | 55-E1 | A | 91-B-E1 | D |
| 24-E1 | NT | 55-E2 | NT | 91-B-E2 | NT |
| 24-E2 | E | 56-E1 | NT | 92-A-E1 | NT |
| 25 | NT | 57-E1 | NT | 92-A-E2 | B |
| 26 | E | 57-E2 | NT | 92-B-E1 | D |
| 27-E1 | NT | 58 | C | 92-B-E2 | NT |
| 27-E2 | NT | 59 | B | 93-A-E1 | NT |
| 28 | NT | 60 | D | 93-A-E2 | C |
| 29-E1 | E | 61 | E | 93-B-E1 | C |
| 29-E2 | NT | 62 | E | 93-B-E2 | NT |

Figure 4

MDCK-MDR1 with PGP inh (A->B) [10^6 cm/s]

A: >20; B: 15-20; C: 10-<15; D: 5-<10; E: <5; NT: not tested

| Compound | MDCK-MDR1 w/ PGP inh (A-B) | Compound | MDCK-MDR1 w/ PGP inh (A-B) | Compound | MDCK-MDR1 w/ PGP inh (A-B) |
|---|---|---|---|---|---|
| 94-E1 | E | 105-P1 | E | 117-E2 | NT |
| 94-E2 | NT | 105-P2 | NT | 118-E1 | D |
| 95-E1 | E | 106-E1 | NT | 118-E2 | NT |
| 95-E2 | NT | 106-E2 | NT | 119-A-E1 | NT |
| 96-E1 | C | 107-E2 | A | 119-B-E1 | D |
| 96-E2 | NT | 108-E1 | B | 119-B-E2 | NT |
| 97-A-E1 | D | 108-E2 | NT | 120-E2 | C |
| 97-A-E2 | NT | 109-E1 | NT | 121-E1 | E |
| 97-B-E1 | C | 109-E2 | NT | 121-E2 | NT |
| 97-B-E2 | NT | 110-E1 | NT | 122-E1 | D |
| 98-A-E1 | A | 110-E2 | A | 123-E1 | C |
| 98-A-E2 | NT | 111-E1 | D | 124-A-E1 | B |
| 98-B | NT | 111-E2 | NT | 124-A-E2 | NT |
| 99-E1 | B | 112-A-E1 | C | 124-B-E1 | C |
| 99-E2 | NT | 112-A-E2 | NT | 125 | NT |
| 100-E1 | D | 113-E2 | NT | 126-E1 | D |
| 100-E2 | NT | 114-A-E1 | NT | 126-E2 | NT |
| 101-A-E1 | NT | 114-A-E2 | NT | 127-E1 | A |
| 101-A-E2 | NT | 114-B-E1 | B | 127-E2 | NT |
| 101-B-E1 | C | 114-B-E2 | NT | 127-E3 | NT |
| 102-A-E1 | D | 115-A-E1 | C | 128-E1 | C |
| 102-A-E2 | NT | 115-A-E2 | NT | 128-E2 | NT |
| 102-B | NT | 115-B-E1 | NT | 128-E3 | NT |
| 103-E1 | E | 115-B-E2 | NT | 129-E1 | C |
| 103-E2 | NT | 116-E1 | NT | 129-E2 | NT |
| 104-P1 | NT | 116-E2 | E | | |
| 104-P2 | A | 117-E1 | C | | |

INHIBITING (α-V)(β-6) INTEGRIN

RELATED APPLICATIONS

This application is a continuation of U.S. patent application Ser. No. 16/555,589, filed Aug. 29, 2019; which claims the benefit of priority to U.S. Provisional Patent Application No. 62/724,423, filed Aug. 29, 2018; and U.S. Provisional Patent Application No. 62/859,457, filed Jun. 10, 2019.

TECHNICAL FIELD

This disclosure relates to novel chemical compounds and methods useful for inhibiting αvβ6 integrin.

BACKGROUND

The heterodimeric integrin family of receptors modulate cellular shape and cell adhesion to the extracellular matrix in response to extrinsic and intrinsic cues.

Integrin signaling controls cell survival, cell cycle progression, cell differentiation, and cell migration.

The integrin receptor exclusively can signal a cell bi-directionally, both "inside-out" and "outside-in." Thus, they mediate cell migration by transmitting forces from the extracellular matrix to the cytoskeleton and regulate cytoskeletal organization to achieve shape changes needed during cell migration. RGD-binding integrins can bind to and activate TGF-β, and have recently been implicated in fibrotic disease.

Integrins are expressed on the surface of most of human cells. Their pathology contributes to a diverse set of human diseases, including platelet disorders, atherosclerosis, cancer, osteoporosis, fibrosis, diabetic neuropathy of the kidney, macular degeneration and various autoimmune and chronic inflammation diseases.

The role of integrins as drug targets has long been recognized, and a total of six injectable integrin inhibitors have been approved by the Food and Drug Administration for the treatment of various therapeutic indications: inflammatory bowel disease (Entyvio®, Tysabri®), multiple sclerosis (Tysabri®), psoriasis (Raptiva®), and acute coronary syndrome (Reopro®, Aggrastat®, Integrilin®). Of the 24 known integrin heterodimers, as least half have relevance in inflammation, fibrosis, oncology and vascular disease.

There exists a need for new classes of integrin inhibitors. There has been a notable absence of therapeutic success with orally bioavailable integrin inhibitors. Accordingly, there remains a need for a small molecule integrin inhibitor of αvβ6 suitable for oral administration. The oral administration route is preferred for small-molecule delivery as it allows a wide range of doses to be administered, allows convenient patient self-administration, is adaptable to varying dosage regimens and needs no special equipment. Therefore, it is important to identify of αvβ6 integrin inhibitor compounds that are not only potent at the intended biological target, but are also demonstrating other characteristics relating to the ability of the compound to be absorbed in the body (e.g, after oral delivery) in a therapeutically effective manner. For example, αvβ6 integrin inhibitor compounds can be selected based on both potency and based on performance in an in vitro permeability assay (e.g., evaluating the ability of compounds to cross a layer of Madin-Darby Canine Kidney (MDCK) cells from the apical to basolateral side (A→B)).

SUMMARY

Applicants have discovered novel αvβ6 integrin inhibitor compounds and evaluated the possession, performance and utility of representative examples of such compounds, both for biochemical potency (e.g., using the assay of Example 35 to evaluate fluorescence polarization assays of compounds for αvβ6 binding) and in vitro permeability properties (e.g., using the assay of Example 36 to evaluate MDCK permeability).

In certain embodiments, the invention relates to a compound of Formula I:

$$A\text{-}B\text{---}C \qquad (I)$$

wherein:

A is 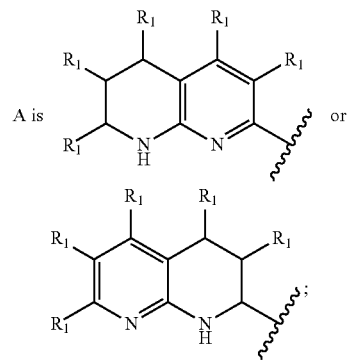

B is alkylene, -alkylene-(heterocyclyl)-alkylene-, -(heterocyclyl)-alkylene-, -cycloalkylene, -alkylene-O—, -cycloalkylene-O—, or -alkylene-O-alkylene-;

C is 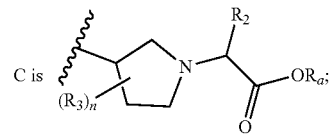

$R_1$ is independently H, alkyl, halide, alkoxy, $CF_3$, OH, alkylene-OH, $NO_2$, —N(H)R, or $NH_2$;

$R_2$ is 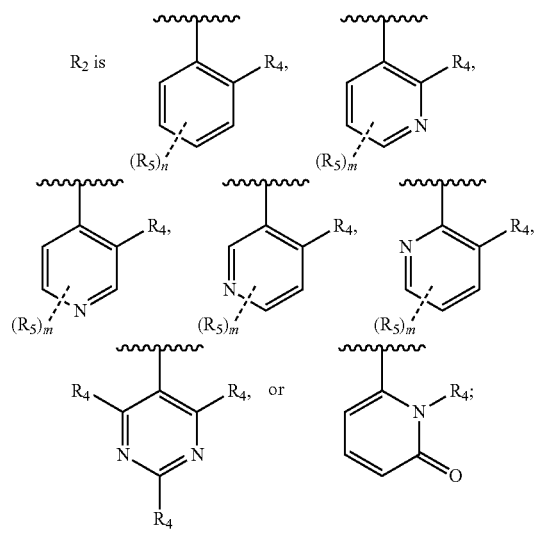

$R_3$ and $R_5$ are independently selected from H, CN, halide, $CF_3$, $C(H)F_2$, $C(F)H_2$, alkyl, cycloalkyl, -alkylene-alkoxy, aryl, hydroxyl, and alkoxy;

$R_4$ is independently selected from alkyl, —C($F_2$)$CH_3$, cycloalkyl, heterocycloalkyl, -alkylene-cycloalkyl, —O-alkylene-cycloalkyl; —O-cycloalkyl, —O-alkyl, -alkylene-O-alkyl, -alkylene-O-cycloalkyl, and -alkylene-O-alkylene-cycloalkyl;

$R_a$ is H, ($C_1$-$C_6$)alkyl, —($C_1$-$C_6$)alkylene-O—($C_1$-$C_6$)alkyl, or —($C_1$-$C_6$)alkylene-O—C(O)O($C_1$-$C_6$)alkyl;

n is independently 0, 1, 2, 3, or 4;

m is 0, 1, 2, or 3; and the absolute configuration at any stereocenter is R, S, or a mixture thereof, or a pharmaceutically acceptable salt thereof.

In certain embodiments, the invention relates to a compound of Formula I:

A-B—C  (I)

wherein:

A is

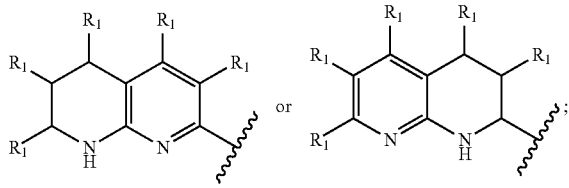

B is selected from the group consisting of:

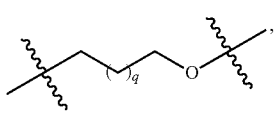

and

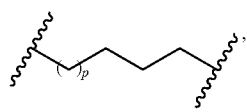

wherein
q is 0, 1, 2, or 3; and p is 0, 1, or 2;

C is

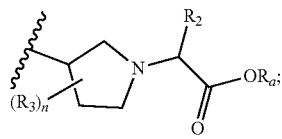

all instances of $R_1$ are H;

$R_2$ is

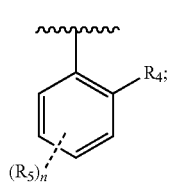

$R_3$ is H, halide, Me, OMe, or Ph.

$R_4$ is independently selected from alkyl, —C($F_2$)$CH_3$, cycloalkyl, heterocycloalkyl, -alkylene-cycloalkyl, —O-alkylene-cycloalkyl; —O-cycloalkyl, —O-alkyl, -alkylene-O-alkyl, -alkylene-O-cycloalkyl, and -alkylene-O-alkylene-cycloalkyl;

$R_5$ is F;

$R_a$ is H;

n is independently 0 or 1;

m is 0 or 1; and the absolute configuration at any stereocenter is R, S, or a mixture thereof, or a pharmaceutically acceptable salt thereof.

In certain embodiments, the invention relates to a compound of Formula I:

A-B—C  (I)

wherein:

A is

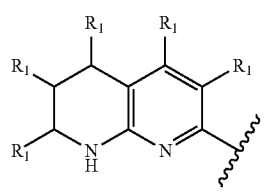

or

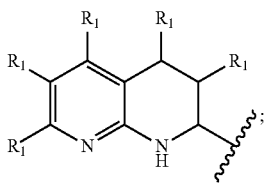

B is selected from the group consisting of:

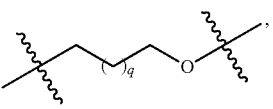

and

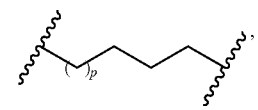

wherein
q is 0, 1, 2, or 3; and p is 0, 1, or 2;

C is

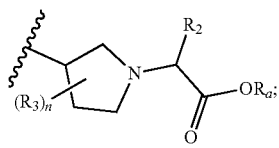

all instances of $R_1$ are H;
$R_2$ is

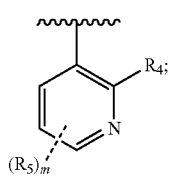

$R_3$ is H, halide, Me, OMe, or Ph;
$R_4$ is independently selected from alkyl, —C(F$_2$)CH$_3$, cycloalkyl, heterocycloalkyl, -alkylene-cycloalkyl, —O-alkylene-cycloalkyl; —O-cycloalkyl, —O-alkyl, -alkylene-O-alkyl, -alkylene-O-cycloalkyl, and -alkylene-O-alkylene-cycloalkyl;
$R_5$ is F;
$R_a$ is H;
n is 0 or 1;
m is 0 or 1; and
the absolute configuration at any stereocenter is R, S, or a mixture thereof,
or a pharmaceutically acceptable salt thereof.

In certain embodiments, the invention relates to a method of treating a disease or a condition selected from the group consisting of idiopathic pulmonary fibrosis, diabetic nephropathy, focal segmental glomerulosclerosis, chronic kidney disease, nonalcoholic steatohepatitis, primary biliary cholangitis, primary sclerosing cholangitis, solid tumors, hematological tumors, organ transplant, Alport syndrome, interstitial lung disease radiation-induced fibrosis, bleomycin-induced fibrosis, asbestos-induced fibrosis, flu-induced fibrosis, coagulation-induced fibrosis, vascular injury-induced fibrosis, aortic stenosis, and cardiac fibrosis comprising the step of: administering to a subject in need thereof a therapeutically effective amount of any one of the compounds described herein.

BRIEF DESCRIPTION OF THE FIGURES

FIG. 1 is a table summarizing inhibition of αvβ6 integrin by exemplary compounds, as measured in a fluorescence polarization assay.

FIG. 2 is a table summarizing inhibition of αvβ6 integrin by exemplary compounds, as measured in a fluorescence polarization assay.

FIG. 3 is a table summarizing permeability properties of exemplary compounds from FIG. 1 measured in a MDCK in vitro assay of Example 36.

FIG. 4 is a table summarizing permeability properties of exemplary compounds from FIG. 2 measured in a MDCK in vitro assay of Example 36.

DETAILED DESCRIPTION

In certain embodiments, the invention relates to compounds that inhibit αvβ6 integrin. In certain embodiments, the compounds are selective for αvβ6 integrin.

The compounds will be useful for the treatment of idiopathic pulmonary fibrosis, diabetic nephropathy, focal segmental glomerulosclerosis, chronic kidney disease, nonalcoholic steatohepatitis, primary biliary cholangitis, primary sclerosing cholangitis, solid tumors, hematological tumors, organ transplant, Alport syndrome, interstitial lung disease, radiation-induced fibrosis, bleomycin-induced fibrosis, asbestos-induced fibrosis, flu-induced fibrosis, coagulation-induced fibrosis, vascular injury-induced fibrosis, aortic stenosis, or cardiac fibrosis.

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Structures depicted herein are also meant to include compounds that differ only in the presence of one or more isotopically enriched atoms. For example, compounds produced by the replacement of a hydrogen with deuterium or tritium, or of a carbon with a $^{13}C$- or $^{14}C$-enriched carbon are within the scope of this invention.

The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salts" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al. (1977) "Pharmaceutical Salts", *J. Pharm. Sci.* 66:1-19.) In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

A "therapeutically effective amount" (or "effective amount") of a compound with respect to use in treatment, refers to an amount of the compound in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "patient" refers to a mammal in need of a particular treatment. In certain embodiments, a patient is a primate, canine, feline, or equine. In certain embodiments, a patient is a human.

An aliphatic chain comprises the classes of alkyl, alkenyl and alkynyl defined below. A straight aliphatic chain is limited to unbranched carbon chain moieties. As used herein, the term "aliphatic group" refers to a straight chain, branched-chain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Alkyl groups may be substituted or unsubstituted.

As used herein, the term "alkylene" refers to an alkyl group having the specified number of carbons, for example from 2 to 12 carbon atoms, that contains two points of attachment to the rest of the compound on its longest carbon chain. Non-limiting examples of alkylene groups include methylene —($CH_2$)—, ethylene —($CH_2CH_2$)—, n-propylene —($CH_2CH_2CH_2$)—, isopropylene —($CH_2CH(CH_3)$)—, and the like. Alkylene groups can be cyclic or acyclic, branched or unbranched carbon chain moiety, and may be optionally substituted with one or more substituents.

"Cycloalkyl" means mono- or bicyclic or bridged or spirocyclic, or polycyclic saturated carbocyclic rings, each having from 3 to 12 carbon atoms. Likewise, preferred cycloalkyls have from 3-10 carbon atoms in their ring structure, and more preferably have 3-6 carbons in the ring structure. Cycloalkyl groups may be substituted or unsubstituted.

Unless the number of carbons is otherwise specified, "lower alkyl," as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In certain embodiments, a substituent designated herein as alkyl is a lower alkyl.

"Alkenyl" refers to any cyclic or acyclic, branched or unbranched unsaturated carbon chain moiety having the number of carbon atoms specified, or up to 26 carbon atoms if no limitation on the number of carbon atoms is specified; and having one or more double bonds in the moiety. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl, and tetracosenyl, in their various isomeric forms, where the unsaturated bond(s) can be located anywhere in the moiety and can have either the (Z) or the (E) configuration about the double bond(s).

"Alkynyl" refers to hydrocarbyl moieties of the scope of alkenyl, but having one or more triple bonds in the moiety.

The term "alkylthio" refers to an alkyl group, as defined above, having a sulfur moiety attached thereto. In certain embodiments, the "alkylthio" moiety is represented by one of -(S)-alkyl, -(S)-alkenyl, -(S)-alkynyl, and -(S)-($CH_2$)$_m$—$R^1$, wherein m and $R^1$ are defined below. Representative alkylthio groups include methylthio, ethylthio, and the like. The terms "alkoxyl" or "alkoxy" as used herein refers to an alkyl group, as defined below, having an oxygen moiety attached thereto. Representative alkoxyl groups include methoxy, ethoxy, propoxy, tert-butoxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O— alkynyl, —O—($CH_2$)$_m$—$R_{10}$, where m and $R_{10}$ are described below.

The terms "amine" and "amino" are art-recognized and refer to both unsubstituted and substituted amines, e.g., a moiety that can be represented by the formulae:

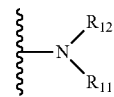

or

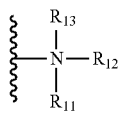

wherein $R_{11}$, $R_{12}$ and $R_{13}$ each independently represent a hydrogen, an alkyl, an alkenyl, —($CH_2$)$_m$—$R_{10}$, or $R_{11}$ and $R_{12}$ taken together with the N atom to which they are attached complete a heterocycle having from 4 to 8 atoms in the ring structure; $R_{10}$ represents an alkenyl, aryl, cycloalkyl, a cycloalkenyl, a heterocyclyl, or a polycyclyl; and m is zero or an integer in the range of 1 to 8. In certain embodiments, only one of $R_{11}$ or $R_{12}$ can be a carbonyl, e.g., $R_{11}$, $R_{12}$, and the nitrogen together do not form an imide. In even more certain embodiments, $R_{11}$ and $R_{12}$ (and optionally $R_{13}$) each independently represent a hydrogen, an alkyl, an alkenyl, or —$(CH_2)_m$—$R_{10}$. Thus, the term "alkylamine" as used herein means an amine group, as defined above, having a substituted or unsubstituted alkyl attached thereto, i.e., at least one of $R_{11}$ and $R_{12}$ is an alkyl group. In certain embodiments, an amino group or an alkylamine is basic, meaning it has a conjugate acid with a $pK_a>7.00$, i.e., the protonated forms of these functional groups have $pK_a$s relative to water above about 7.00.

The term "amide", as used herein, refers to a group

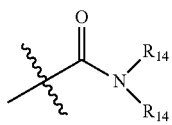

wherein each $R_{14}$ independently represent a hydrogen or hydrocarbyl group, or two $R_{14}$ are taken together with the N atom to which they are attached complete a heterocycle having from 4 to 8 atoms in the ring structure.

The term "aryl" as used herein includes 3- to 12-membered substituted or unsubstituted single-ring aromatic groups in which each atom of the ring is carbon (i.e., carbocyclic aryl) or where one or more atoms are heteroatoms (i.e., heteroaryl). Preferably, aryl groups include 5- to 12-membered rings, more preferably 6- to 10-membered rings The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carboycyclic aryl groups include benzene, naphthalene, phenanthrene, phenol, aniline, and the like. Heteroaryl groups include substituted or unsubstituted aromatic 3- to 12-membered ring structures, more preferably 5- to 12-membered rings, more preferably 5- to 10-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like. Aryl and heteroaryl can be monocyclic, bicyclic, or polycyclic. Each instance of an aryl group may be independently optionally substituted, i.e., unsubstituted (an "unsubstituted aryl") or substituted (a "substituted aryl") with one or more substituents; e.g., for instance from 1 to 5 substituents, 1 to 4 substituents, 1 to 3 substituents, 1 to 2 substituents or just 1 substituent. The aromatic ring may be substituted at one or more ring positions with one or more substituents, such as halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, fluoroalkyl (such as trifluromethyl), cyano, or the like. For example, in certain embodiments, the aryl group can be an unsubstituted $C_5$-$C_2$ aryl and in certain embodiments, the aryl group can be a substituted $C_5$-$C_{10}$ aryl.

The term "halo", "halide", or "halogen" as used herein means halogen and includes, for example, and without being limited thereto, fluoro, chloro, bromo, iodo and the like, in both radioactive and non-radioactive forms. In a preferred embodiment, halo is selected from the group consisting of fluoro, chloro and bromo.

The terms "heterocyclyl" or "heterocyclic group" refer to 3- to 12-membered ring structures, more preferably 5- to 12-membered rings, more preferably 5- to 10-membered rings, whose ring structures include one to four heteroatoms. Heterocycles can be monocyclic, bicyclic, spirocyclic, or polycyclic. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —$CF_3$, —CN, and the like.

The term "carbonyl" is art-recognized and includes such moieties as can be represented by the formula:

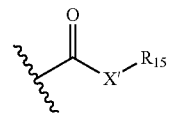

or

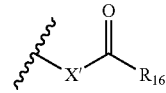

wherein X' is a bond or represents an oxygen or a sulfur, and $R_{15}$ represents a hydrogen, an alkyl, an alkenyl, —$(CH_2)_m$—$R_{10}$ or a pharmaceutically acceptable salt, $R_{16}$ represents a hydrogen, an alkyl, an alkenyl or —$(CH_2)_m$—$R_{10}$, where m and $R_{10}$ are as defined above. Where X' is an oxygen and $R_{15}$ or $R_{16}$ is not hydrogen, the formula represents an "ester." Where X' is an oxygen, and $R_{15}$ is as defined above, the moiety is referred to herein as a carboxyl group, and particularly when $R_{15}$ is a hydrogen, the formula represents a "carboxylic acid". Where X' is an oxygen, and $R_{16}$ is a hydrogen, the formula represents a "formate." In general, where the oxygen atom of the above formula is replaced by a sulfur, the formula represents a "thiocarbonyl" group. Where X' is a sulfur and $R_{15}$ or $R_{16}$ is not hydrogen, the formula represents a "thioester" group. Where X' is a sulfur and $R_{15}$ is a hydrogen, the formula represents a "thiocarboxylic acid" group. Where X' is a sulfur and $R_{16}$ is a hydrogen, the formula represents a "thioformate" group. On the other hand, where X' is a bond, and $R_{15}$ is not hydrogen, the above formula represents a "ketone" group. Where X' is a bond, and $R_{15}$ is a hydrogen, the above formula represents an "aldehyde" group.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "nitro" means $-NO_2$; the term "halogen" designates $-F$, $-Cl$, $-Br$, or $-I$; the term "sulfhydryl" means $-SH$; the term "hydroxyl" means $-OH$; the term "sulfonyl" means $-SO_2-$; the term "azido" means $-N_3$; the term "cyano" means $-CN$; the term "isocyanato" means $-NCO$; the term "thiocyanato" means $-SCN$; the term "isothiocyanato" means $-NCS$; and the term "cyanato" means $-OCN$.

The term "sulfamoyl" is art-recognized and includes a moiety that can be represented by the formula:

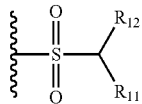

in which $R_{11}$ and $R_{12}$ are as defined above.

The term "sulfate" is art recognized and includes a moiety that can be represented by the formula:

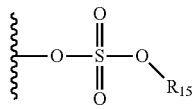

in which $R_{15}$ as defined above.

The term "sulfonamide" is art recognized and includes a moiety that can be represented by the formula:

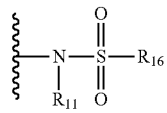

in which $R_{11}$ and $R_{16}$ are as defined above.

The term "sulfonate" is art-recognized and includes a moiety that can be represented by the formula:

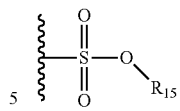

in which $R_{54}$ is an electron pair, hydrogen, alkyl, cycloalkyl, or aryl.

The terms "sulfoxido" or "sulfinyl", as used herein, refers to a moiety that can be represented by the formula:

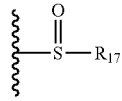

in which $R_{17}$ is selected from the group consisting of hydrogen, alkyl, alkenyl, alkynyl, cycloalkyl, heterocyclyl, aralkyl, or aryl.

The term "urea" is art-recognized and may be represented by the general formula

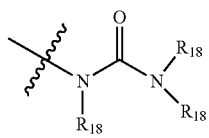

wherein each $R_{18}$ independently represents hydrogen or a hydrocarbyl, such as alkyl, or any occurrence of $R_{18}$ taken together with another and the intervening atom(s) complete a heterocycle having from 4 to 8 atoms in the ring structure.

As used herein, the definition of each expression, e.g., alkyl, m, n, etc., when it occurs more than once in any structure, is intended to be independent of its definition elsewhere in the same structure.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

For purposes of this invention, the chemical elements are identified in accordance with the Periodic Table of the Elements, CAS version, Handbook of Chemistry and Physics, 67th Ed., 1986-87, inside cover.

Exemplary Compounds of the Invention

In certain embodiments, the invention relates to a compound of Formula I:

A-B—C  (I)

wherein:

A is

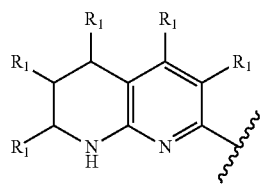

or

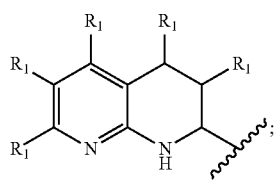

B is alkylene, -alkylene-(heterocyclyl)-alkylene-, -(heterocyclyl)-alkylene-, -cycloalkylene, -alkylene-O—, -cycloalkylene-O—, or -alkylene-O-alkylene-;

C is

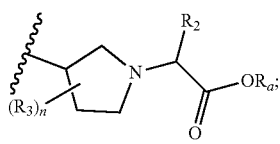

$R_1$ is independently H, alkyl, halide, alkoxy, $CF_3$, OH, alkylene-OH, $NO_2$, —N(H)R, or $NH_2$;

$R_2$ is

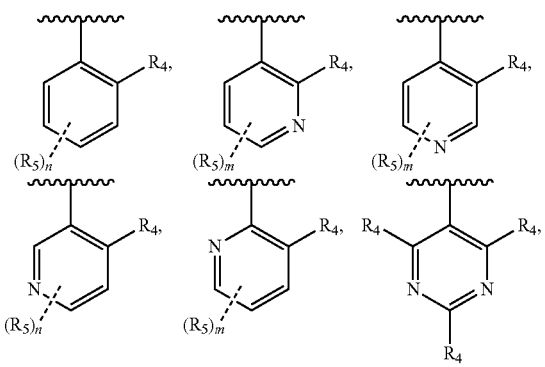

or

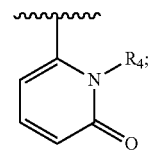

$R_3$ and $R_5$ are independently selected from H, halide, $CF_3$, $C(H)F_2$, $C(F)H2$, alkyl, cycloalkyl, -alkylene-alkoxy, aryl, hydroxyl, and alkoxy;

$R_4$ is independently selected from alkyl, —$C(F_2)CH_3$, cycloalkyl, heterocycloalkyl, -alkylene-cycloalkyl, —O-alkylene-cycloalkyl; —O-cycloalkyl, —O-alkyl, -alkylene-O-alkyl, -alkylene-O-cycloalkyl, and -alkylene-O-alkylene-cycloalkyl;

$R_a$ is H, ($C_1$-$C_6$)alkyl, —($C_1$-$C_6$)alkylene-O—($C_1$-$C_6$)alkyl, or —($C_1$-$C_6$)alkylene-O—C(O)O($C_1$-$C_6$)alkyl;

n is independently 0, 1, 2, 3, or 4;

m is 0, 1, 2, or 3; and the absolute configuration at any stereocenter is R, S, or a mixture thereof, or a pharmaceutically acceptable salt thereof.

In certain embodiments, the invention relates to a compound of Formula I:

A-B—C  (I)

wherein:

A is

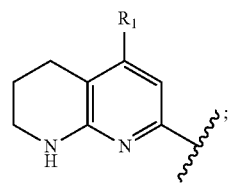

B is alkylene, -alkylene-(heterocyclyl)-alkylene-, -(heterocyclyl)-alkylene-, -cycloalkylene, -alkylene-O—, -cycloalkylene-O—, or -alkylene-O-alkylene-;

C is

R₁ is H, or alkoxy;
R₂ is or

R₃ and R₅ are independently selected from H, halide, CF₃, C(H)F₂, C(F)H2, alkyl, cycloalkyl, -alkylene-alkoxy, aryl, hydroxyl, and alkoxy;

R₄ is independently selected from alkyl, —C(F₂)CH₃, cycloalkyl, heterocycloalkyl, -alkylene-cycloalkyl, —O-alkylene-cycloalkyl; —O-cycloalkyl, —O-alkyl, -alkylene-O-alkyl, -alkylene-O-cycloalkyl, and -alkylene-O-alkylene-cycloalkyl;

$R_a$ is H, ($C_1$-$C_6$)alkyl, —($C_1$-$C_6$)alkylene-O—($C_1$-$C_6$)alkyl, or —($C_1$-$C_6$)alkylene-O—C(O)O($C_1$-$C_6$)alkyl;

n is independently 0, 1, 2, 3, or 4;

m is 0, 1, 2, or 3; and the absolute configuration at any stereocenter is R, S, or a mixture thereof, or a pharmaceutically acceptable salt thereof.

In certain embodiments, the invention relates to a compound of Formula I:

A-B—C     (I)

wherein:
A is

B is alkylene, -alkylene-O—, or -alkylene-O-alkylene-;

C is

R₁ is H;
R₂ is or

R₃ and R₅ are independently selected from H, halide, CF₃, C(H)F₂, C(F)H2, alkyl, cycloalkyl, -alkylene-alkoxy, aryl, hydroxyl, and alkoxy;

R₄ is independently selected from alkyl, —C(F₂)CH₃, cycloalkyl, heterocycloalkyl, -alkylene-cycloalkyl, —O-alkylene-cycloalkyl; —O-cycloalkyl, —O-alkyl, -alkylene-O-alkyl, -alkylene-O-cycloalkyl, and -alkylene-O-alkylene-cycloalkyl;

$R_a$ is H, ($C_1$-$C_6$)alkyl, —($C_1$-$C_6$)alkylene-O—($C_1$-$C_6$)alkyl, or —($C_1$-$C_6$)alkylene-O—C(O)O($C_1$-$C_6$)alkyl;

n is independently 0, 1, 2, 3, or 4;

m is 0, 1, 2, or 3; and the absolute configuration at any stereocenter is R, S, or a mixture thereof, or a pharmaceutically acceptable salt thereof.

In certain embodiments, the invention relates to a compound of Formula I:

A-B—C     (I)

wherein:
A is

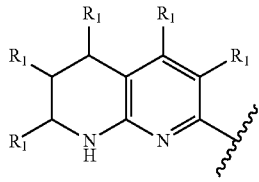

or

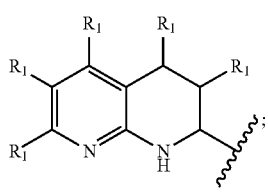

B is alkylene, or -alkylene-O—;
C is

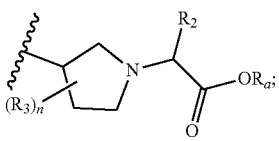

R₁ is H;
R₂ is

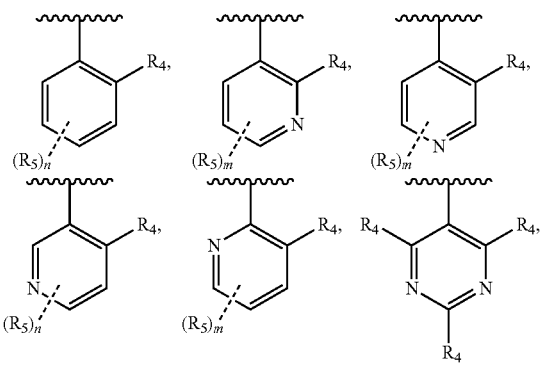

or

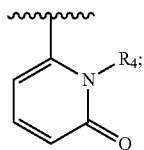

R₅ is independently selected from H, halide, CF₃, C(H)F₂, C(F)H₂, alkyl, cycloalkyl, -alkylene-alkoxy, aryl, hydroxyl, and alkoxy;
R₄ is independently selected from alkyl, —C(F₂)CH₃, cycloalkyl, heterocycloalkyl, -alkylene-cycloalkyl, —O-cycloalkyl, —O-alkyl, -alkylene-O-alkyl, -alkylene-O-cycloalkyl, and -alkylene-O-alkylene-cycloalkyl;

R$_a$ is H;
n is 0;
m is 0, 1, 2, or 3; and
the absolute configuration at any stereocenter is R, S, or a mixture thereof,
or a pharmaceutically acceptable salt thereof.

In certain embodiments, the invention relates to a compound of Formula I:

A-B—C    (I)

wherein:
A is

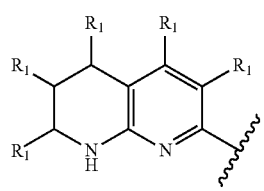

or

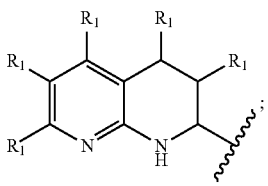

B is

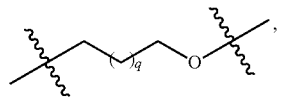

wherein q is 0, 1, 2, or 3;
C is

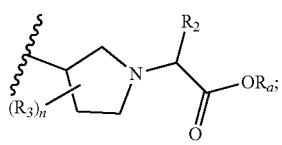

R₁ is independently H, alkyl, halide, alkoxy, CF₃, OH, alkylene-OH, NO₂, —N(H)R, or NH₂;
R₂ is

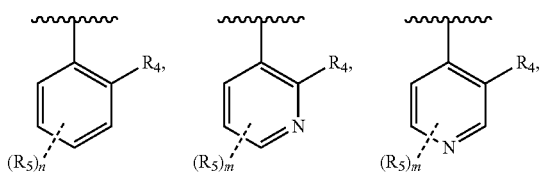

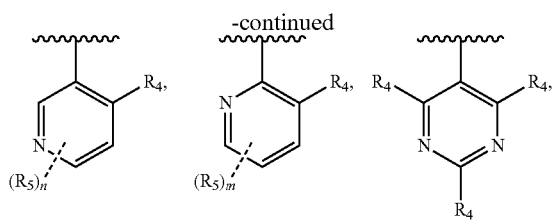

or

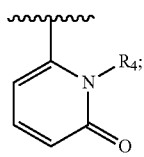

R$_5$ is independently selected from H, halide, CF$_3$, C(H)F$_2$, C(F)H$_2$, alkyl, cycloalkyl, -alkylene-alkoxy, aryl, hydroxyl, and alkoxy;

R$_4$ is independently selected from alkyl, —C(F$_2$)CH$_3$, cycloalkyl, heterocycloalkyl, -alkylene-cycloalkyl, —O-alkylene-cycloalkyl; —O-cycloalkyl, —O-alkyl, -alkylene-O-alkyl, -alkylene-O-cycloalkyl, and -alkylene-O-alkylene-cycloalkyl;

R$_a$ is H, (C$_1$-C$_6$)alkyl, —(C$_1$-C$_6$)alkylene-O—(C$_1$-C$_6$)alkyl, or —(C$_1$-C$_6$)alkylene-O—C(O)O(C$_1$-C$_6$)alkyl;

n is 0;

m is 0, 1, 2, or 3; and the absolute configuration at any stereocenter is R, S, or a mixture thereof, or a pharmaceutically acceptable salt thereof.

In certain embodiments, the invention relates to any one of the aforementioned compounds, wherein A is

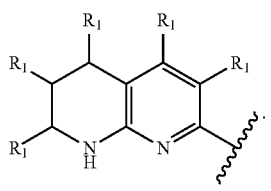

In certain embodiments, the invention relates to any one of the aforementioned compounds, wherein A is

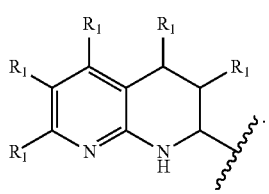

In certain embodiments, the invention relates to any one of the aforementioned compounds, wherein B is alkylene. In certain embodiments, the invention relates to any one of the aforementioned compounds, wherein B is -alkylene-(heterocyclyl)-alkylene-. In certain embodiments, the invention relates to any one of the aforementioned compounds, wherein B is -(heterocyclyl)-alkylene-. In certain embodiments, the invention relates to any one of the aforementioned compounds, wherein B is -cycloalkylene. In certain embodiments, the invention relates to any one of the aforementioned compounds, wherein B is -alkylene-O—. In certain embodiments, the invention relates to any one of the aforementioned compounds, wherein B is -cycloalkylene-O—. In certain embodiments, the invention relates to any one of the aforementioned compounds, wherein B is -alkylene-O-alkylene-. In some embodiments, -alkylene-O-alkylene-is -methylene-O-propylene, -ethylene-O-ethylene, or -propylene-O-methylene. In certain embodiments, the invention relates to any one of the aforementioned compounds, wherein B is selected from the group consisting of:

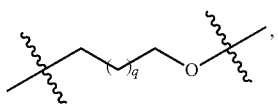

and

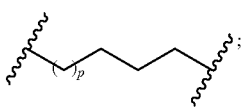

q is 0, 1, 2, or 3; and p is 0, 1, or 2.

In some embodiments, B is

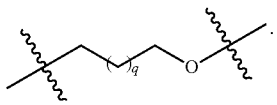

In some embodiments, B is

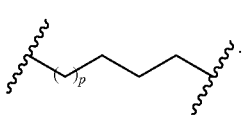

In some embodiments, q is 2. In some embodiments, q is 3. In some embodiments, p is 0. In some embodiments, p is 1. In some embodiments, p is 2.

In certain embodiments, the invention relates to any one of the aforementioned compounds, wherein R$_1$ is H. In certain embodiments, the invention relates to any one of the aforementioned compounds, wherein R$_1$ is alkyl. In certain embodiments, R$_1$ is methyl. In certain embodiments, the invention relates to any one of the aforementioned compounds, wherein R$_1$ is halide. In certain embodiments, the invention relates to any one of the aforementioned compounds, wherein R$_1$ is alkoxy. In some embodiments, alkoxy is methoxy, ethoxy, iso-propyloxy, iso-butyloxy, or tert-butyloxy. In certain embodiments, the invention relates to any one of the aforementioned compounds, wherein R$_1$ is CF$_3$. In certain embodiments, the invention relates to any one of the aforementioned compounds, wherein R$_1$ is OH. In certain embodiments, the invention relates to any one of the aforementioned compounds, wherein R$_1$ is alkylene-OH. In certain embodiments, the invention relates to any one of the aforementioned compounds, wherein R$_1$ is NO$_2$. In certain embodiments, the invention relates to any one of the aforementioned compounds, wherein $R_1$ is —N(H)$R_a$. In certain embodiments, the invention relates to any one of the aforementioned compounds, wherein $R_1$ is NH$_2$. In some embodiments, at least one instance of $R_1$ is alkyl, halide, OMe, OH, alkylene-OH, or NH$_2$. In some embodiments, at least one instance of $R_1$ is OMe. In some embodiments, all instances of $R_1$ are H.

In certain embodiments, the invention relates to any one of the aforementioned compounds, wherein $R_2$ is

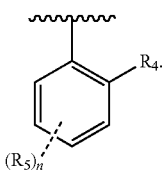

In certain embodiments, the invention relates to any one of the aforementioned compounds, wherein $R_2$ is

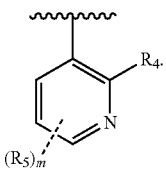

In certain embodiments, the invention relates to any one of the aforementioned compounds, wherein $R_2$ is

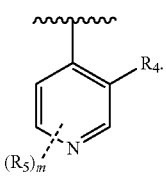

In certain embodiments, the invention relates to any one of the aforementioned compounds, wherein $R_2$ is

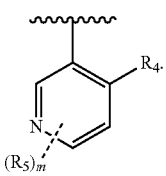

In certain embodiments, the invention relates to any one of the aforementioned compounds, wherein $R_2$ is

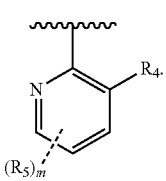

In certain embodiments, the invention relates to any one of the aforementioned compounds, wherein $R_2$ is

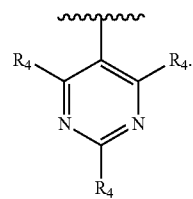

In certain embodiments, the invention relates to any one of the aforementioned compounds, wherein $R_2$ is

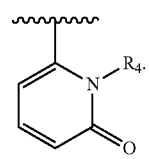

In certain embodiments, the invention relates to any one of the aforementioned compounds, wherein n is 0. In certain embodiments, the invention relates to any one of the aforementioned compounds, wherein n is 1. In certain embodiments, the invention relates to any one of the aforementioned compounds, wherein n is 2. In certain embodiments, the invention relates to any one of the aforementioned compounds, wherein n is 3. In certain embodiments, the invention relates to any one of the aforementioned compounds, wherein n is 4.

In certain embodiments, the invention relates to any one of the aforementioned compounds, wherein m is 0. In certain embodiments, the invention relates to any one of the aforementioned compounds, wherein m is 1. In certain embodiments, the invention relates to any one of the aforementioned compounds, wherein m is 2. In certain embodiments, the invention relates to any one of the aforementioned compounds, wherein m is 3.

In certain embodiments, the invention relates to any one of the aforementioned compounds, wherein $R_3$ is H. In certain embodiments, the invention relates to any one of the aforementioned compounds, wherein $R_3$ is halide. In certain embodiments, the invention relates to any one of the aforementioned compounds, wherein $R_3$ is CN. In certain embodiments, the invention relates to any one of the aforementioned compounds, wherein $R_3$ is CF$_3$. In certain embodiments, the invention relates to any one of the aforementioned compounds, wherein $R_3$ is C(H)F$_2$. In certain embodiments, the invention relates to any one of the aforementioned compounds, wherein $R_3$ is C(F)H$_2$. In certain embodiments, the invention relates to any one of the aforementioned compounds, wherein $R_3$ is alkyl. In some embodiments, alkyl is methyl, ethyl, iso-propyl, or tert-butyl. In certain embodiments, the invention relates to any one of the aforementioned compounds, wherein $R_3$ is cycloalkyl. In some embodiments, cycloalkyl is cyclopropyl, cyclobutyl, cylcopentyl, or cyclohexyl. In certain embodiments, the invention relates to any one of the aforementioned compounds, wherein $R_3$ is -alkylene-alkoxy. In certain embodiments, the invention relates to any one of the aforementioned compounds, wherein $R_3$ is aryl. In certain embodiments, the invention relates to any one of the aforementioned compounds, wherein $R_3$ is hydroxyl. In certain embodiments, the invention relates to any one of the aforementioned compounds, wherein $R_3$ is alkoxy. In certain embodiments, the invention relates to any one of the aforementioned compounds, wherein $R_3$ is H, halide, Me, OMe, or Ph.

In certain embodiments, the invention relates to any one of the aforementioned compounds, wherein $R_4$ is alkyl. In certain embodiments, the invention relates to any one of the aforementioned compounds, wherein $R_4$ is —C(F$_2$)CH$_3$. In certain embodiments, the invention relates to any one of the aforementioned compounds, wherein $R_4$ is cycloalkyl. In certain embodiments, the invention relates to any one of the aforementioned compounds, wherein $R_4$ is heterocycloalkyl. In certain embodiments, the invention relates to any one of the aforementioned compounds, wherein $R_4$ is -alkylene-cycloalkyl. In certain embodiments, the invention relates to any one of the aforementioned compounds, wherein $R_4$ is —O— alkylene-cycloalkyl. In certain embodiments, the invention relates to any one of the aforementioned compounds, wherein $R_4$ is —O-cycloalkyl. In certain embodiments, the invention relates to any one of the aforementioned compounds, wherein $R_4$ is —O-alkyl. In certain embodiments, the invention relates to any one of the aforementioned compounds, wherein $R_4$ is -alkylene-O-alkyl. In certain embodiments, the invention relates to any one of the aforementioned compounds, wherein $R_4$ is -alkylene-O-cycloalkyl. In certain embodiments, the invention relates to any one of the aforementioned compounds, wherein $R_4$ is -alkylene-O-alkylene-cycloalkyl. In certain embodiments, the invention relates to any one of the aforementioned compounds, wherein $R_4$ is selected from -alkylene-cycloalkyl, —O— alkylene-cycloalkyl; -alkylene-O-alkyl, -alkylene-O-cycloalkyl, and -alkylene-O-alkylene-cycloalkyl. In some embodiments, alkylene $R_4$ is methylene or ethylene.

In certain embodiments, the invention relates to any one of the aforementioned compounds, $R_4$ is selected from

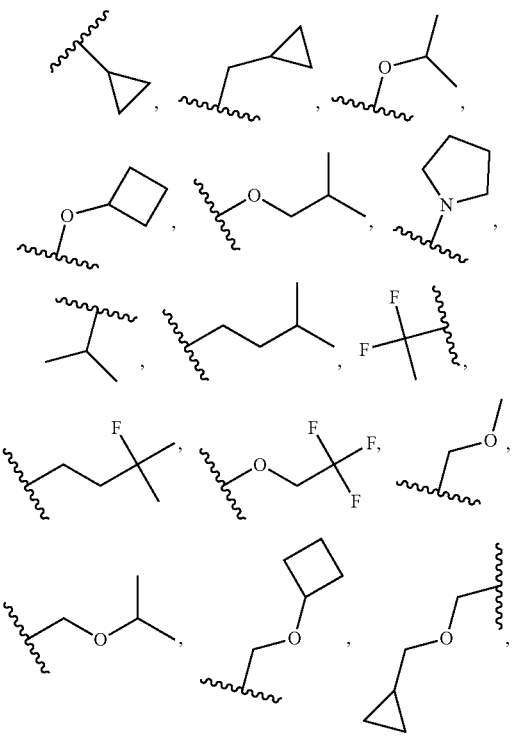

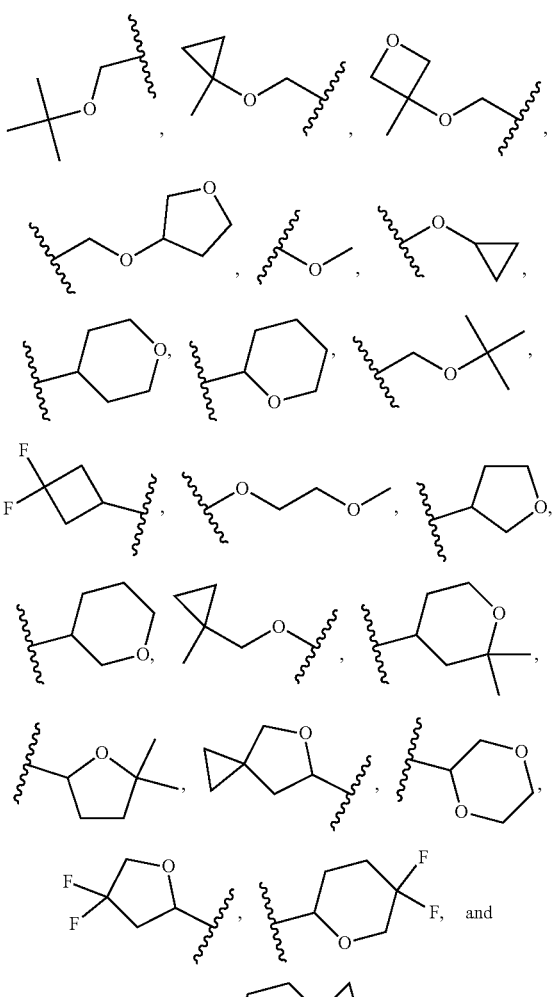

In certain embodiments, the invention relates to any one of the aforementioned compounds, $R_4$ is selected from optionally substituted

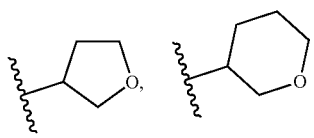

or

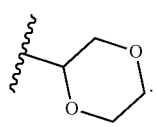 [SMILES: *C1COCCO1]

In certain embodiments, the invention relates to any one of the aforementioned compounds, $R_4$ is In certain embodiments, the invention relates to any one of the aforementioned compounds, R₄ is

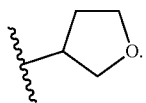

In certain embodiments, the invention relates to any one of the aforementioned compounds, R₄ is

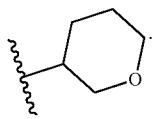

In certain embodiments, the invention relates to any one of the aforementioned compounds, R₄ is


In certain embodiments, the invention relates to any one of the aforementioned compounds, wherein R₄ is selected from

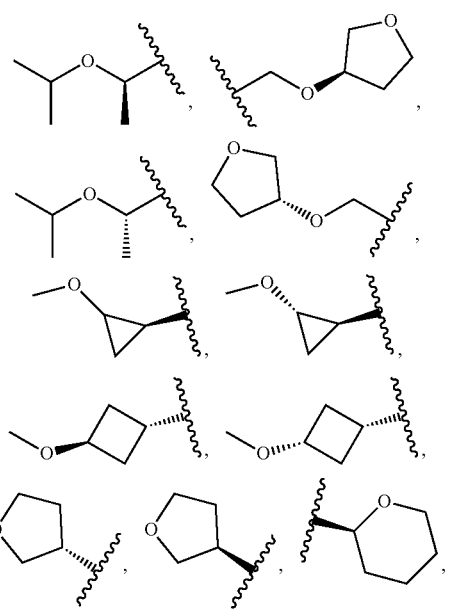
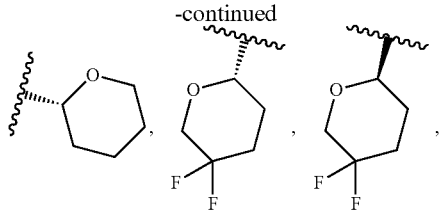
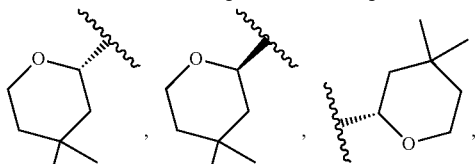
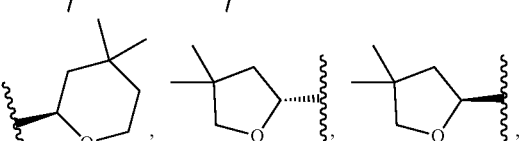
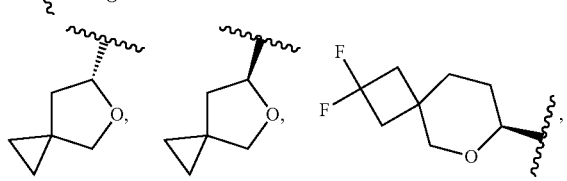
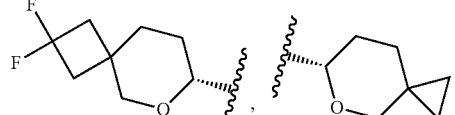
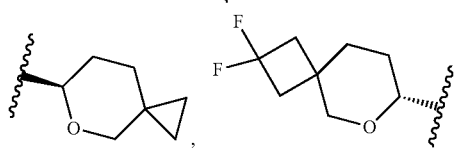
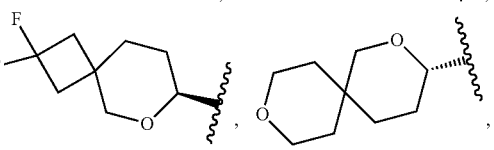
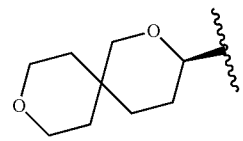
, and In certain embodiments, the invention relates to any one of the aforementioned compounds, wherein R₅ is H. In certain embodiments, the invention relates to any one of the aforementioned compounds, wherein R₅ is halide. In certain embodiments, the invention relates to any one of the aforementioned compounds, wherein R₅ is F. In certain embodiments, the invention relates to any one of the aforementioned compounds, wherein R₅ is CN. In certain embodiments, the invention relates to any one of the aforementioned compounds, wherein R₅ is CF₃. In certain embodiments, the invention relates to any one of the aforementioned compounds, wherein R₅ is C(H)F₂. In certain embodiments, the invention relates to any one of the aforementioned compounds, wherein R₅ is C(F)H₂. In certain embodiments, the invention relates to any one of the aforementioned compounds, wherein R₅ is alkyl. In some embodiments, alkyl is methyl, ethyl, iso-propyl, or tert-butyl. In certain embodiments, the invention relates to any one of the aforementioned compounds, wherein $R_5$ is cycloalkyl. In some embodiments, cycloalkyl is cyclopropyl, cyclobutyl, cylcopentyl, or cyclohexyl. In certain embodiments, the invention relates to any one of the aforementioned compounds, wherein $R_5$ is -alkylene-alkoxy. In certain embodiments, the invention relates to any one of the aforementioned compounds, wherein $R_5$ is aryl. In certain embodiments, the invention relates to any one of the aforementioned compounds, wherein $R_5$ is hydroxyl. In certain embodiments, the invention relates to any one of the aforementioned compounds, wherein $R_5$ is alkoxy. In certain embodiments, the invention relates to any one of the aforementioned compounds, wherein $R_5$ is H, halide, Me, OMe, or Ph.

In certain embodiments, the invention relates to any one of the aforementioned compounds, $R_a$ is H. In certain embodiments, the invention relates to any one of the aforementioned compounds, $R_a$ is $(C_1$-$C_6)$alkyl. In some embodiments, $(C_1$-$C_6)$alkyl is methyl, ethyl, n-propyl, i-propyl, n-butyl, i-butyl, or t-butyl. In certain embodiments, the invention relates to any one of the aforementioned compounds, $R_a$ is —$(C_1$-$C_6)$alkylene-O—$(C_1$-$C_6)$alkyl. In certain embodiments, the invention relates to any one of the aforementioned compounds, $R_a$ is —$(C_1$-$C_6)$alkylene-O—C(O)O$(C_1$-$C_6)$alkyl;

In certain embodiments, the invention relates to any one of the aforementioned compounds, wherein the absolute configuration at any stereocenter is R. In certain embodiments, the invention relates to any one of the aforementioned compounds, wherein the absolute configuration at any stereocenter is S. In certain embodiments, the invention relates to any one of the aforementioned compounds, wherein the absolute configuration at any stereocenter is a mixture of R and S.

In certain embodiments, the invention relates to any one of the aforementioned compounds, wherein the compound is a pharmaceutically acceptable salt.

In certain embodiments, the invention relates to a compound selected from the group consisting of:

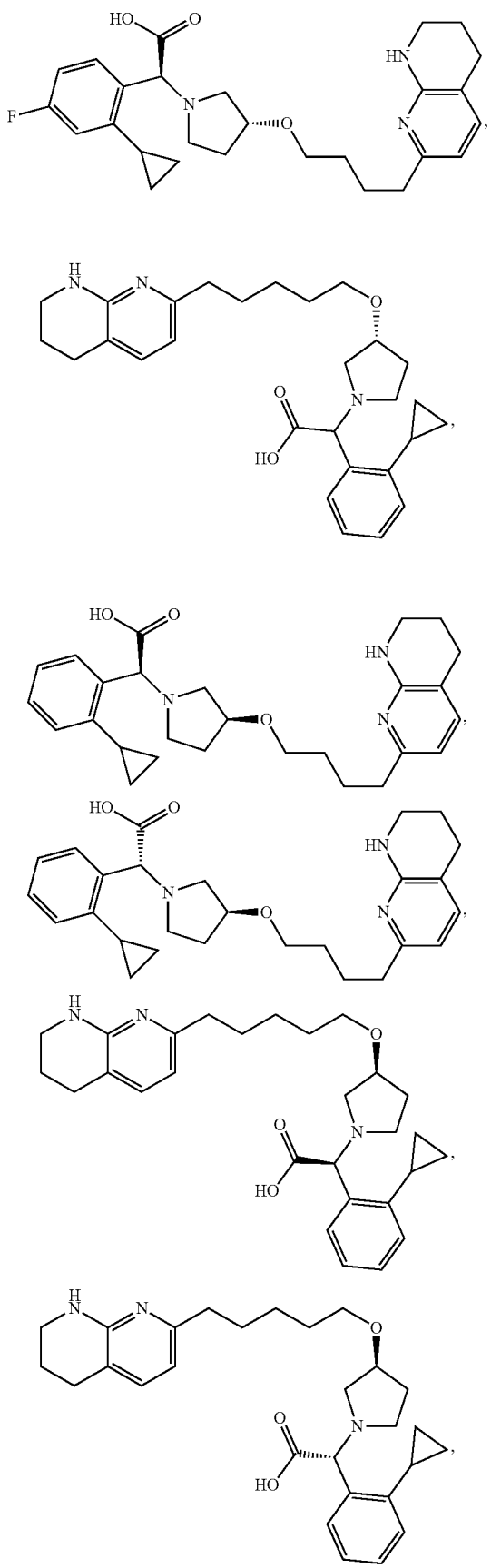

31
-continued
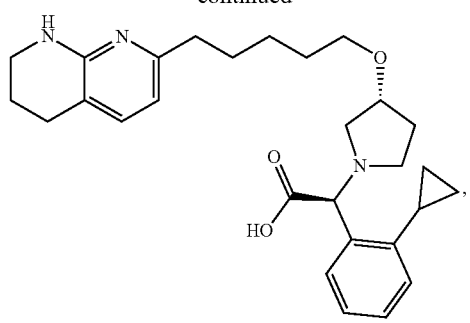
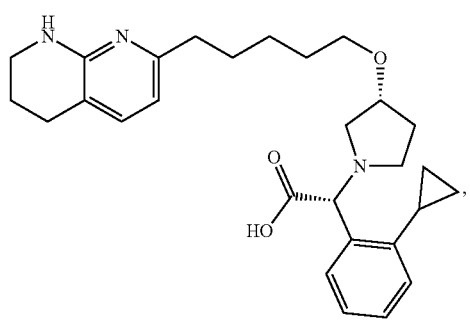
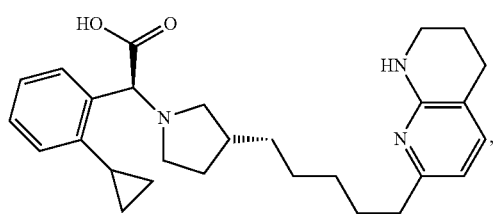
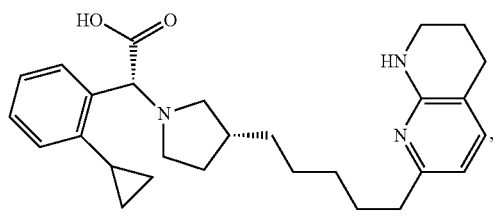
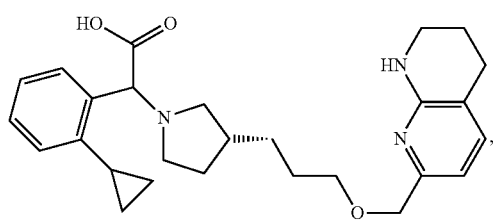
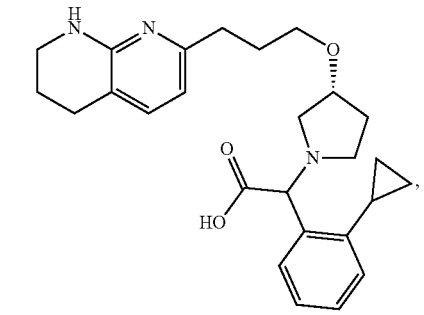
32
-continued
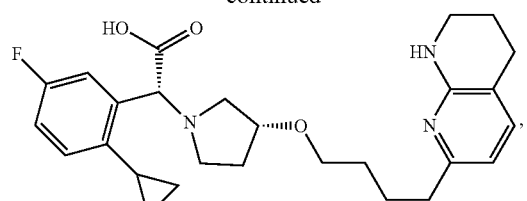
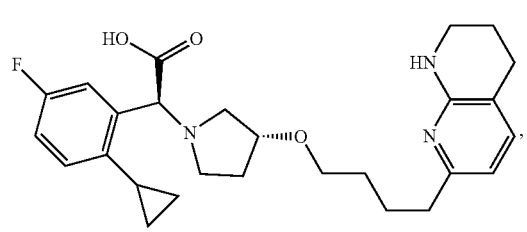
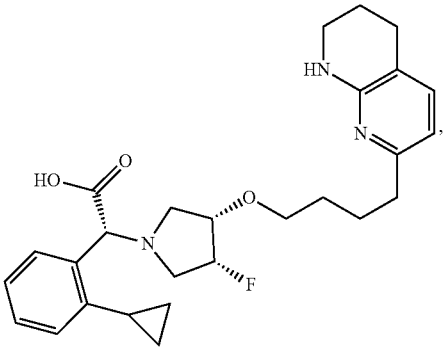
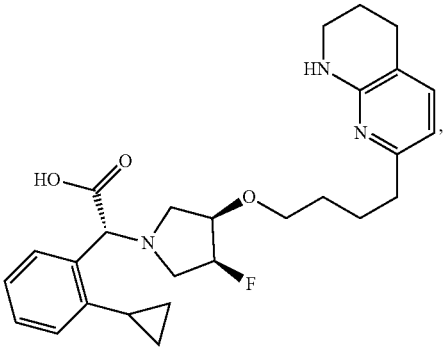
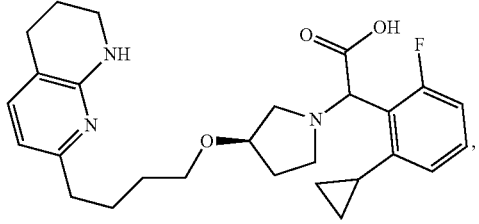
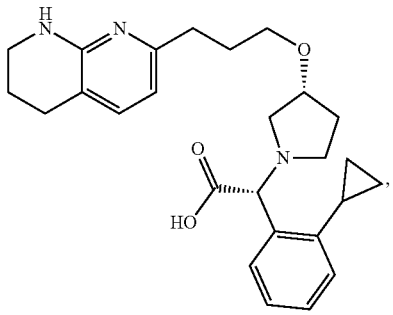

33
-continued
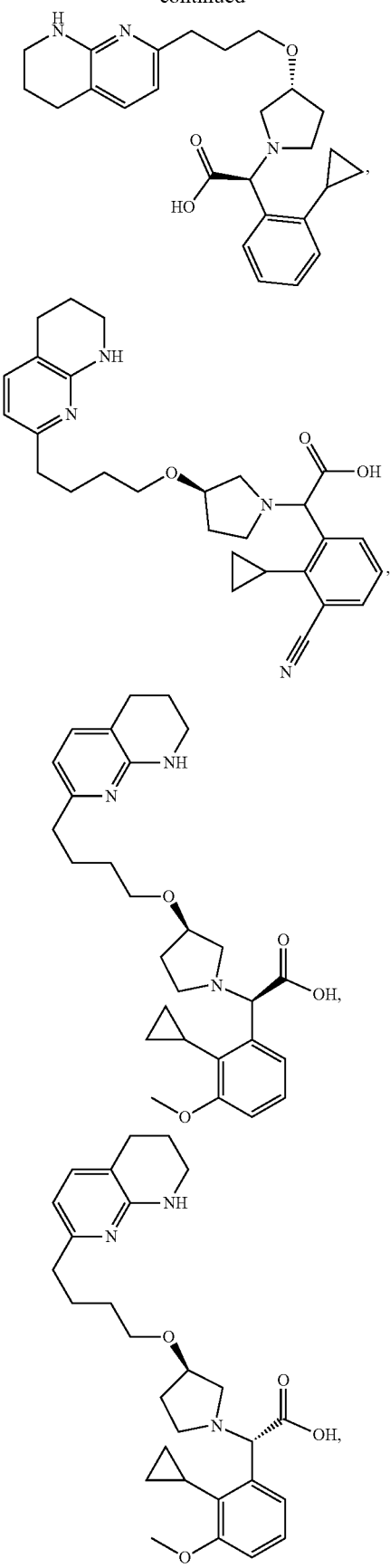
34
-continued
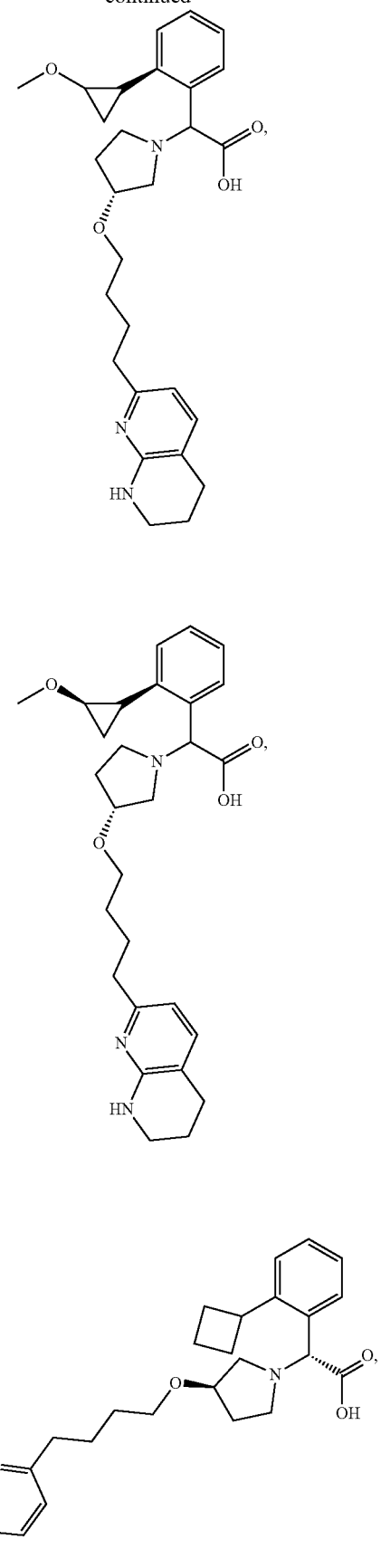

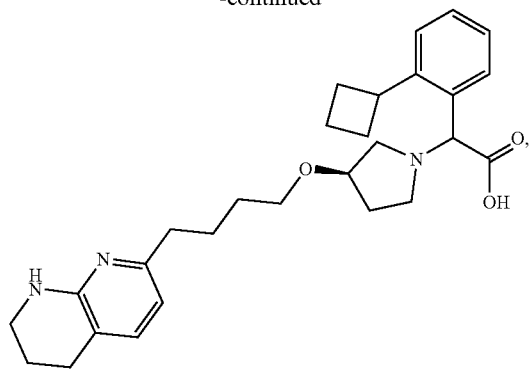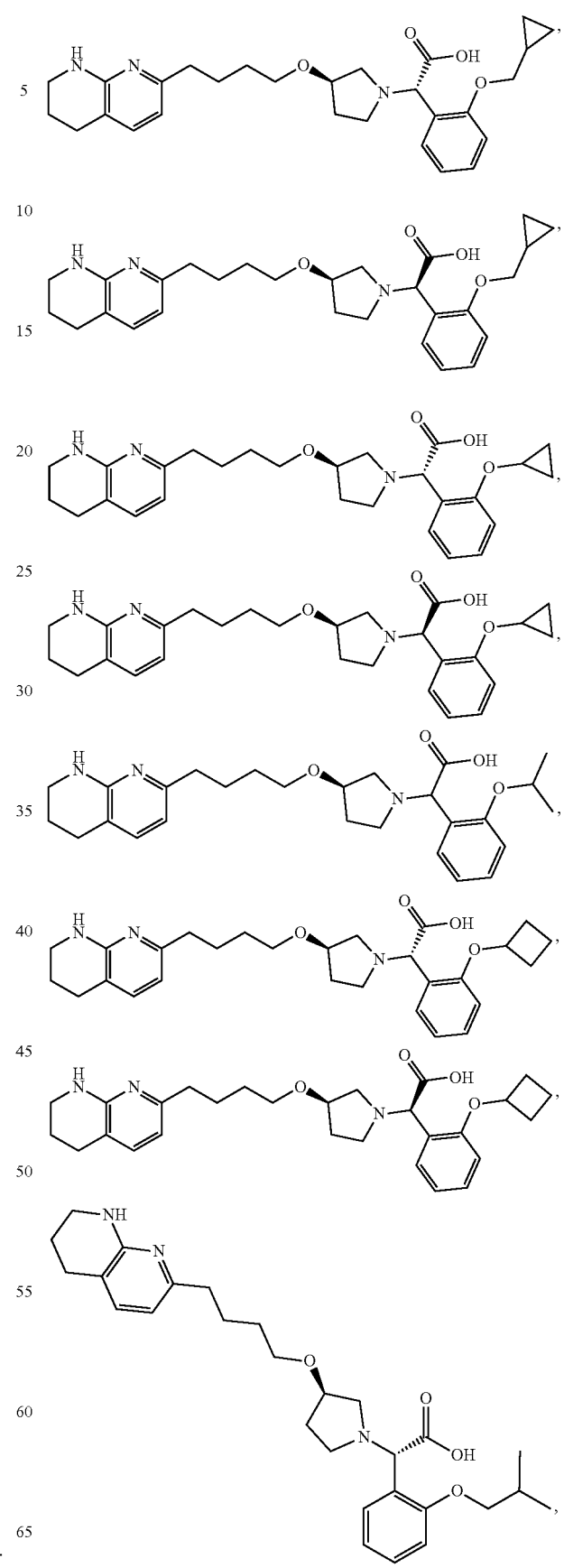
In certain embodiments, the invention relates to a compound selected from the group consisting of:

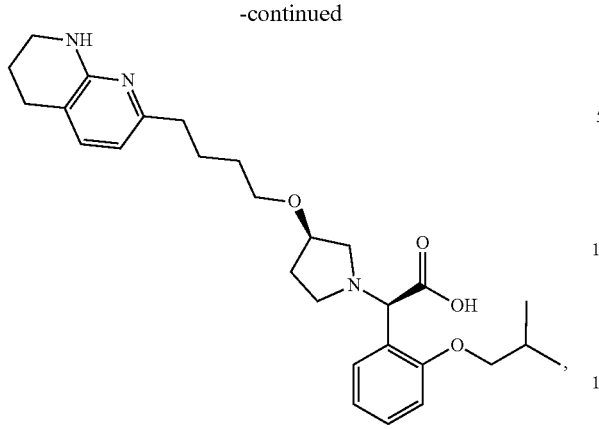
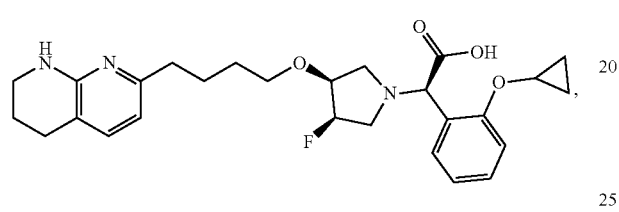
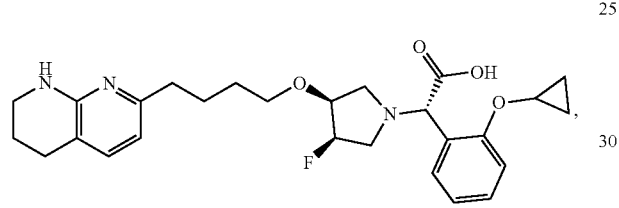
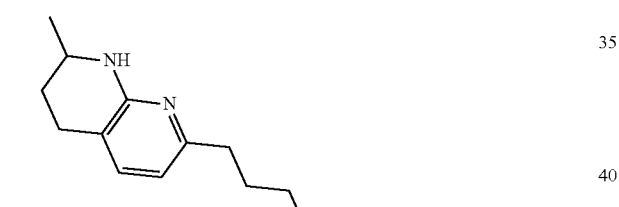
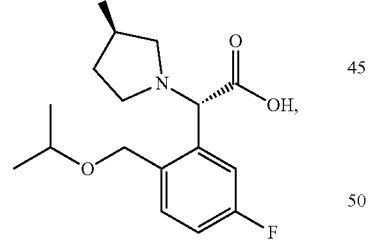
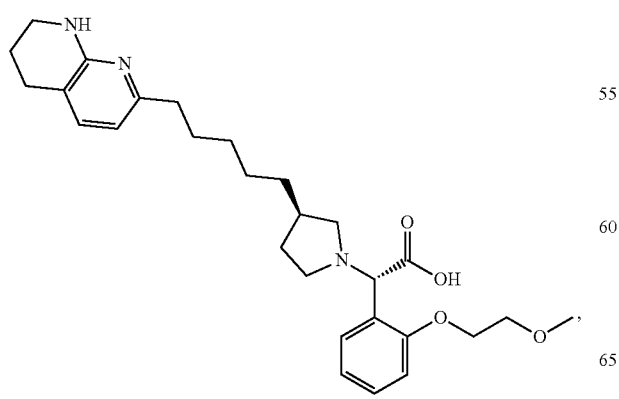
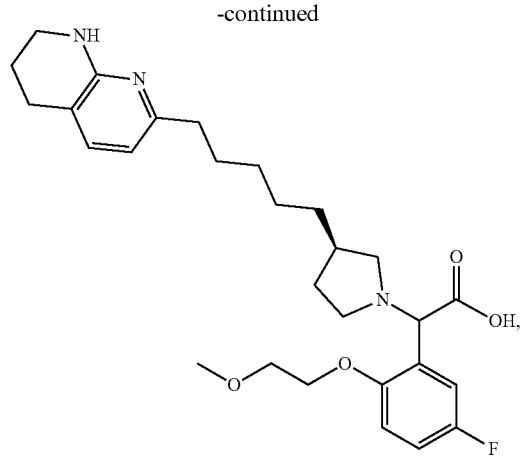
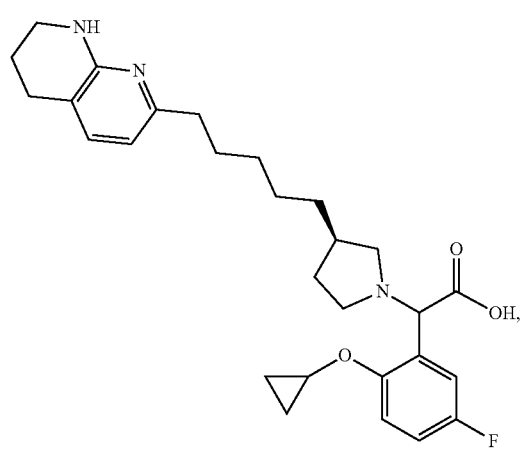
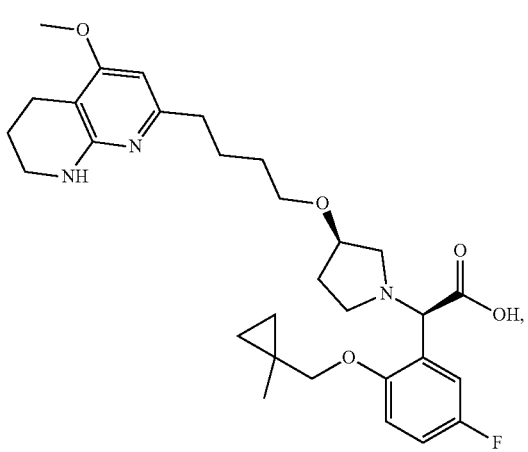

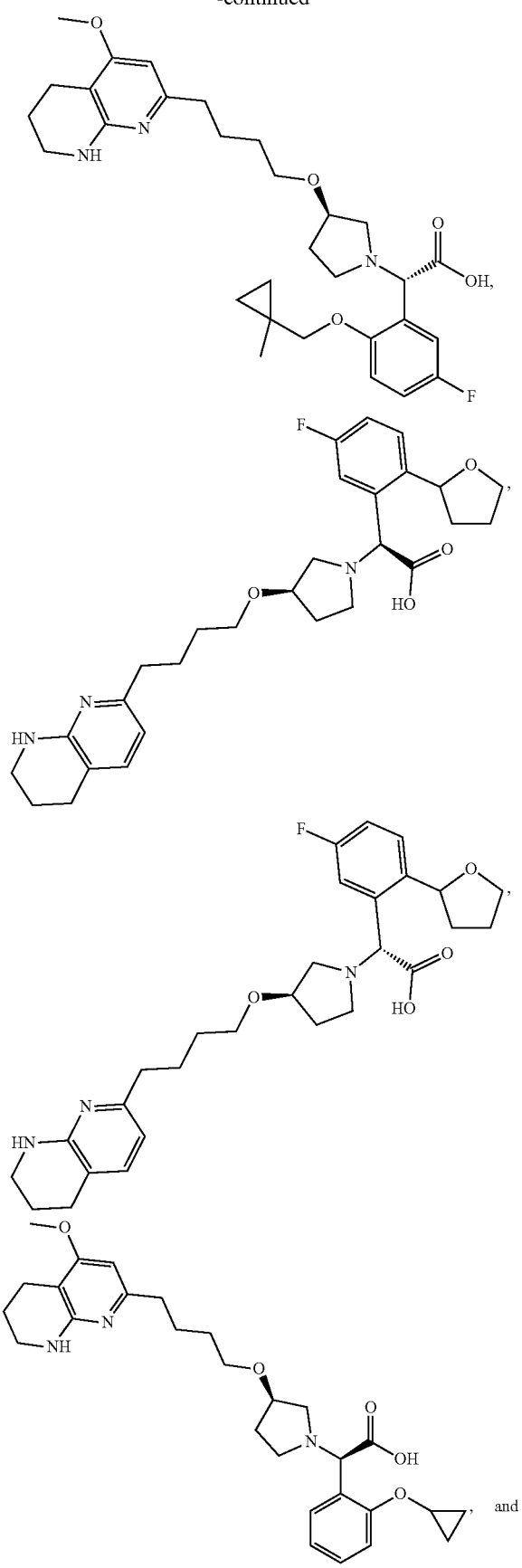
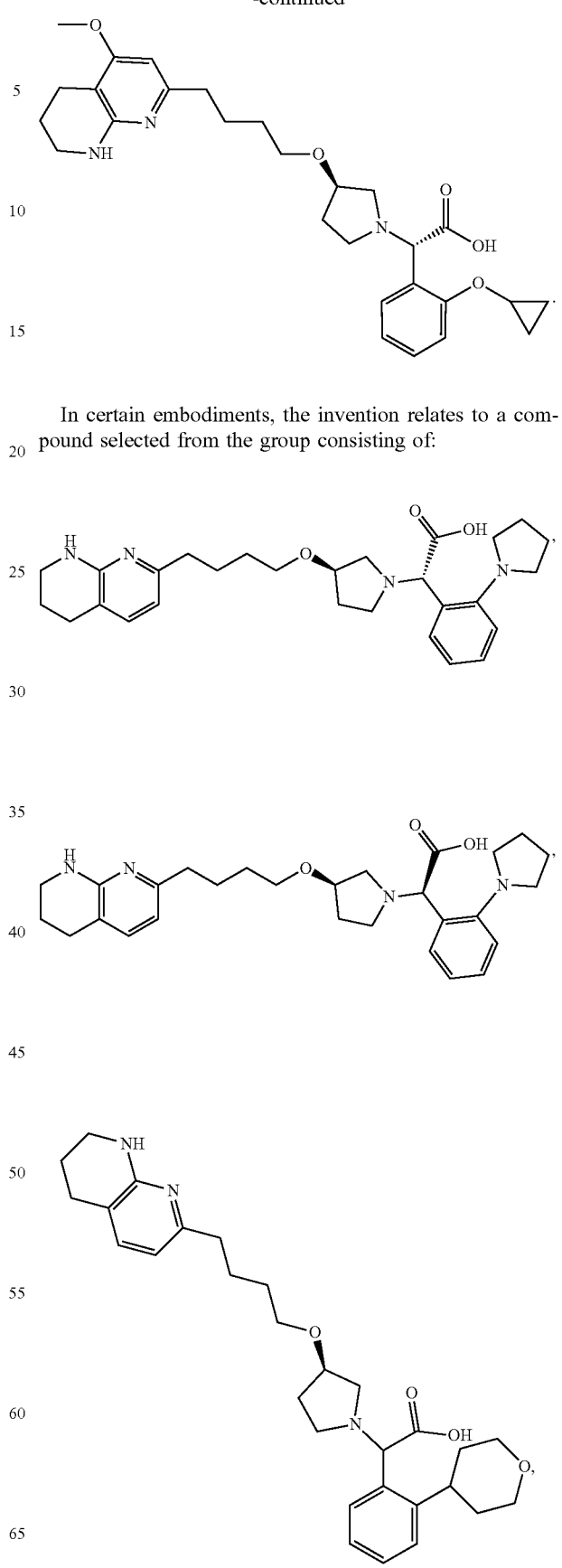
In certain embodiments, the invention relates to a compound selected from the group consisting of:

-continued
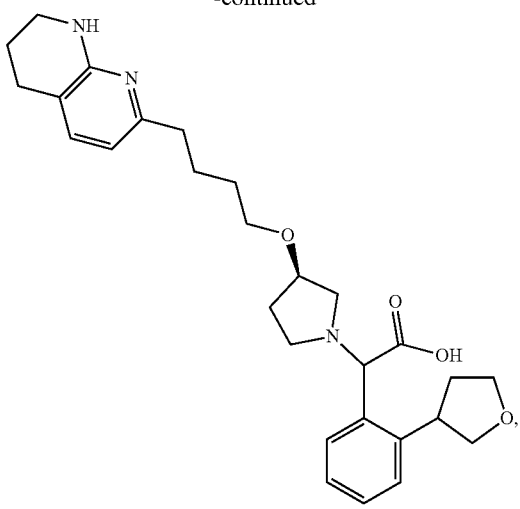
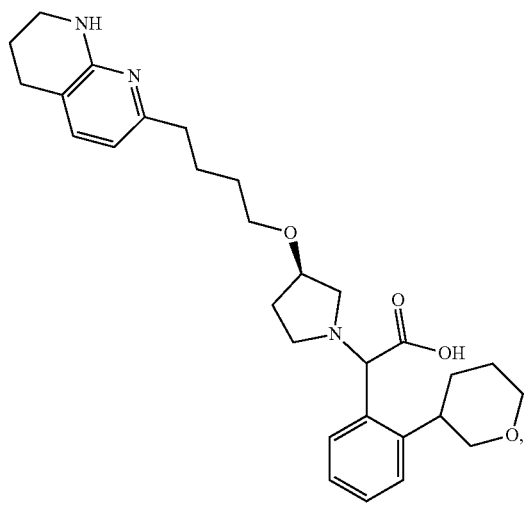
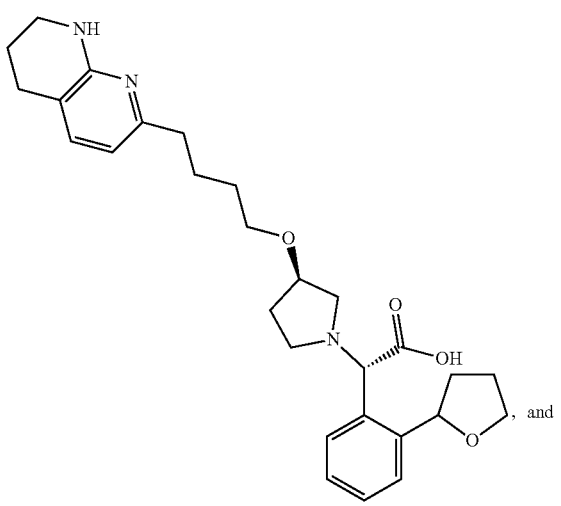, and
-continued
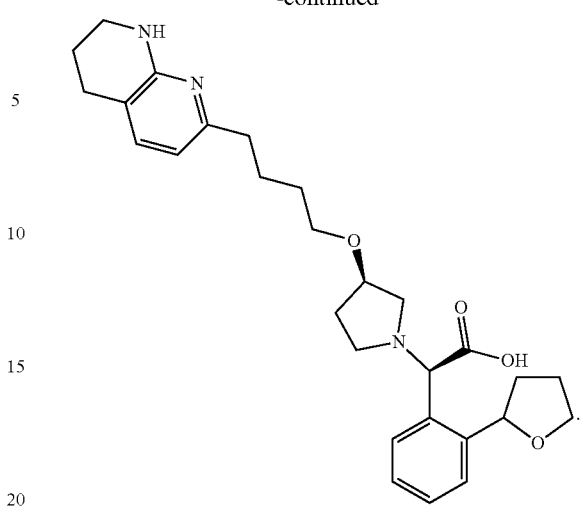
In certain embodiments, the invention relates to a compound selected from the group consisting of:
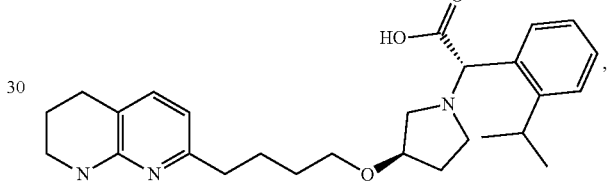
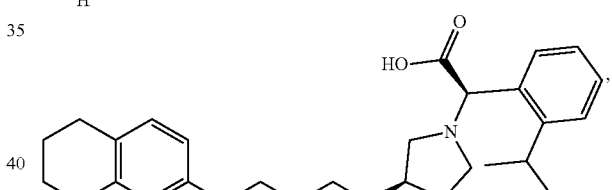
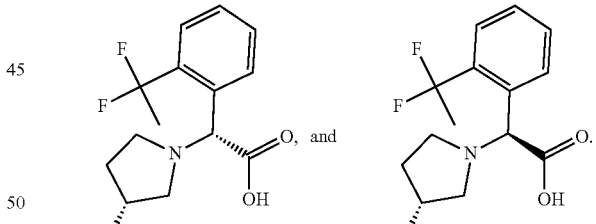

In certain embodiments, the invention relates to a compound selected from the group consisting of:
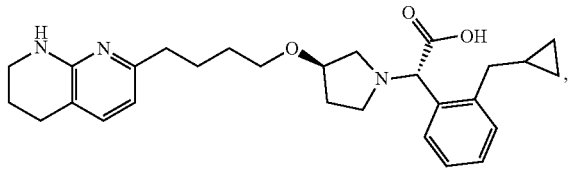 [SMILES: O=C(O)[C@H](c1ccccc1CC1CC1)N1CC[C@@H](OCCCCc2ccc3c(n2)NCCC3)C1]
and
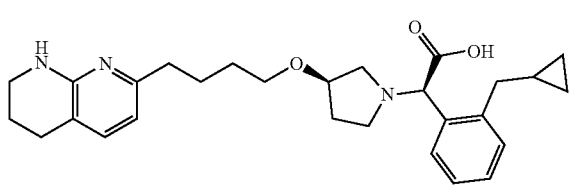 [SMILES: O=C(O)[C@@H](c1ccccc1CC1CC1)N1CC[C@@H](OCCCCc2ccc3c(n2)NCCC3)C1]
In certain embodiments, the invention relates to a compound selected from the group consisting of:
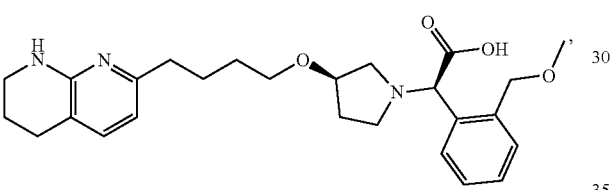

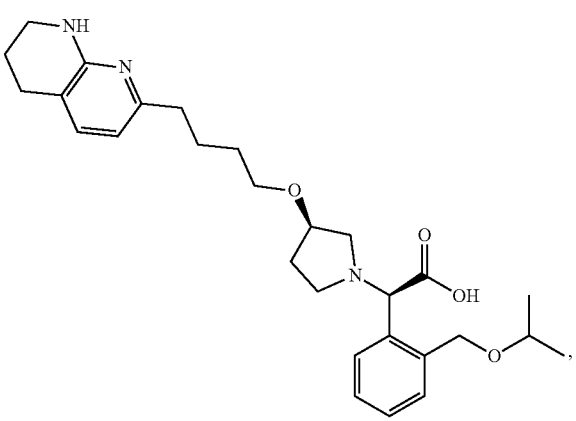
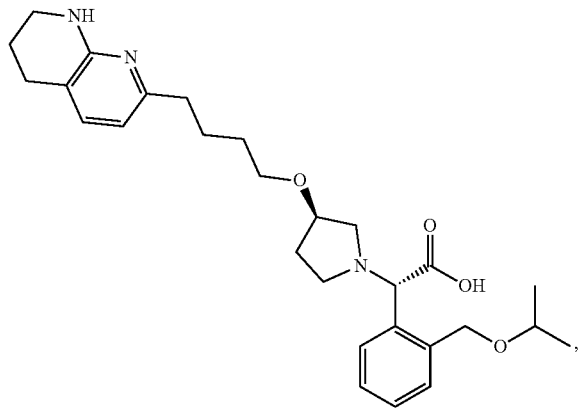 [SMILES: CC(C)(F)CCc1ncccc1C(C(=O)O)N1CC[C@@H](OCCCCc2ccc3c(n2)NCCC3)C1]
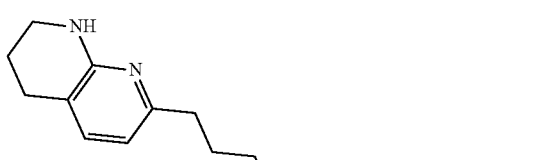
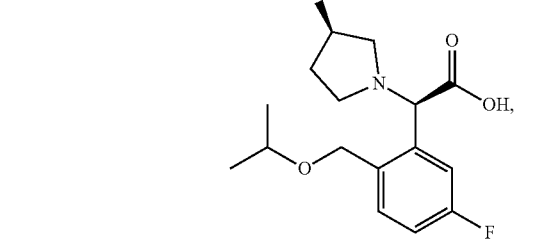
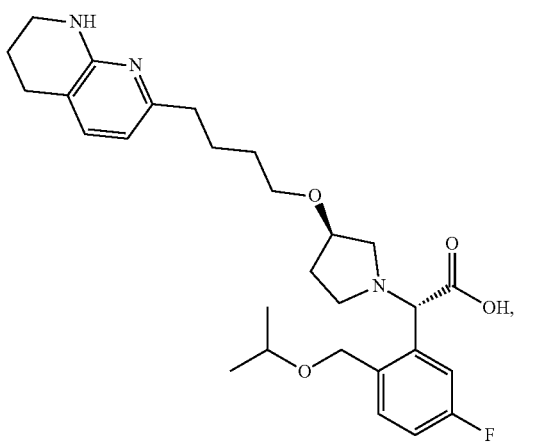
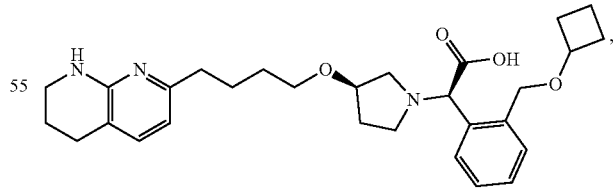
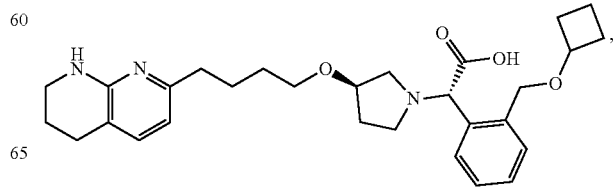

-continued
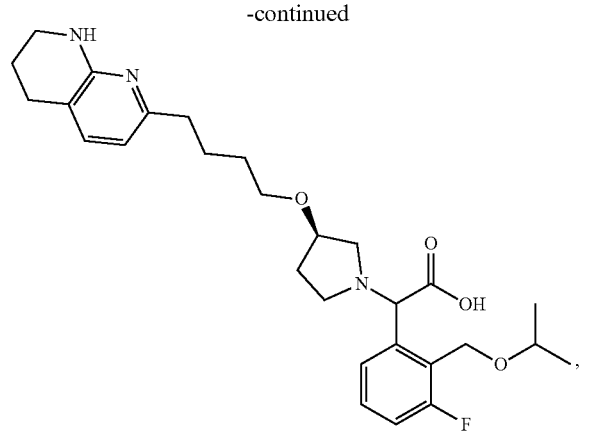
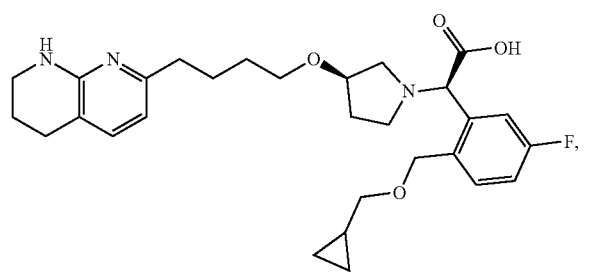
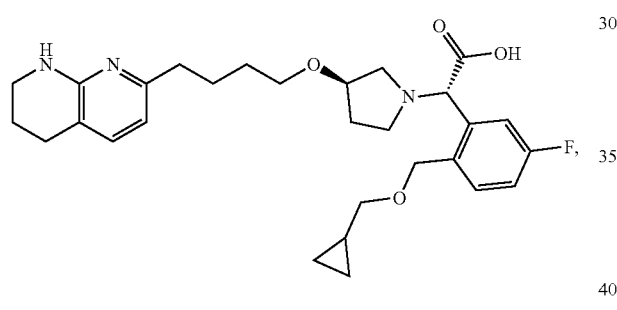
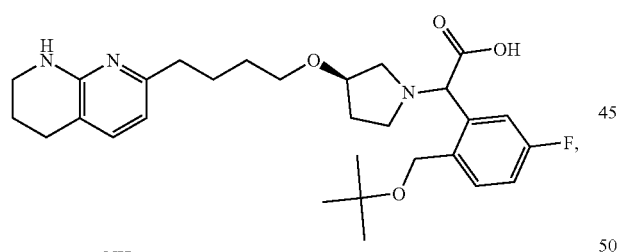
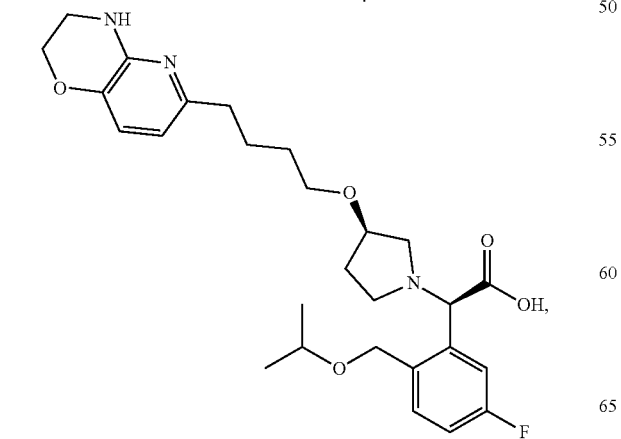
-continued
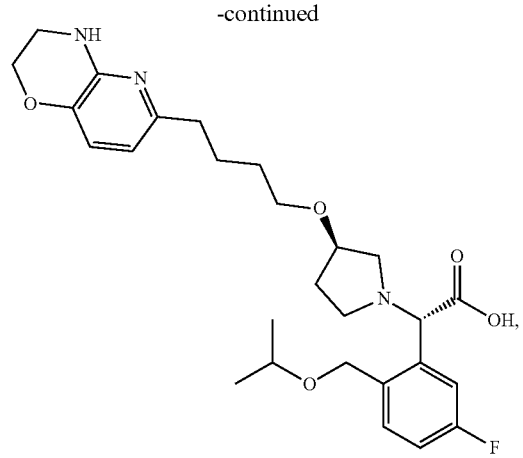
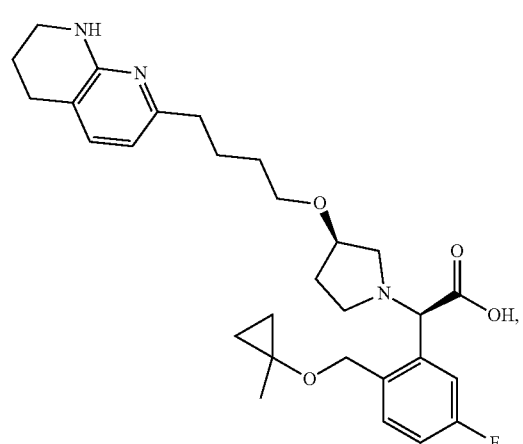
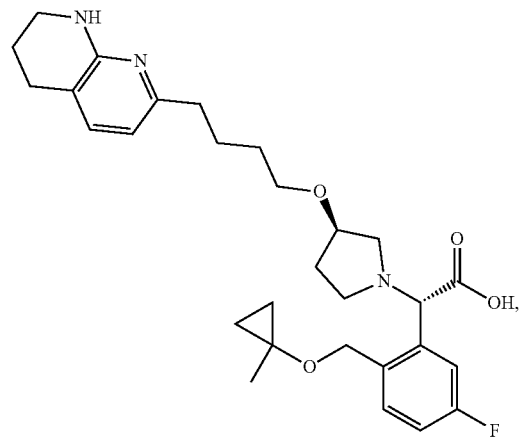

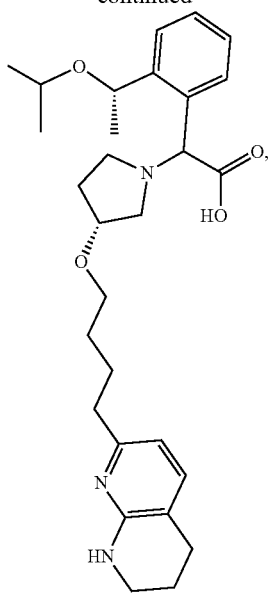
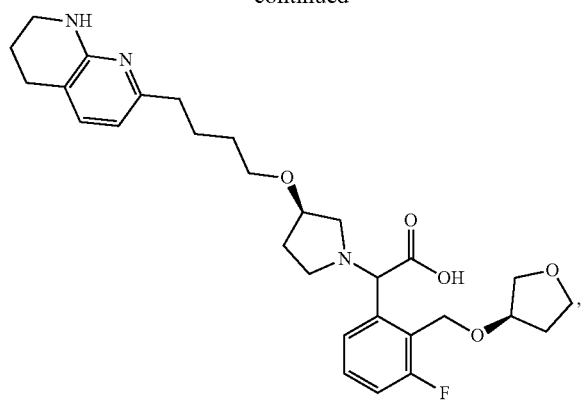
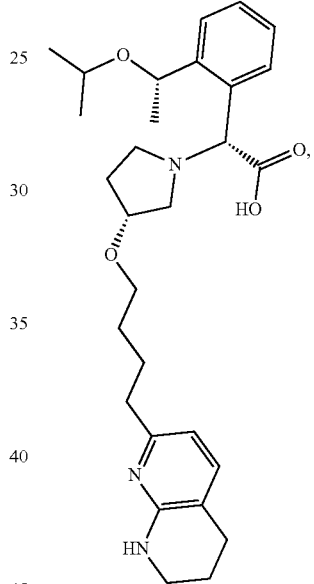
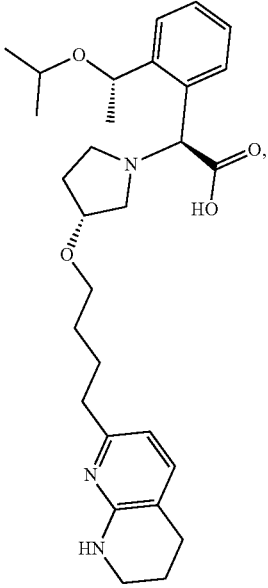
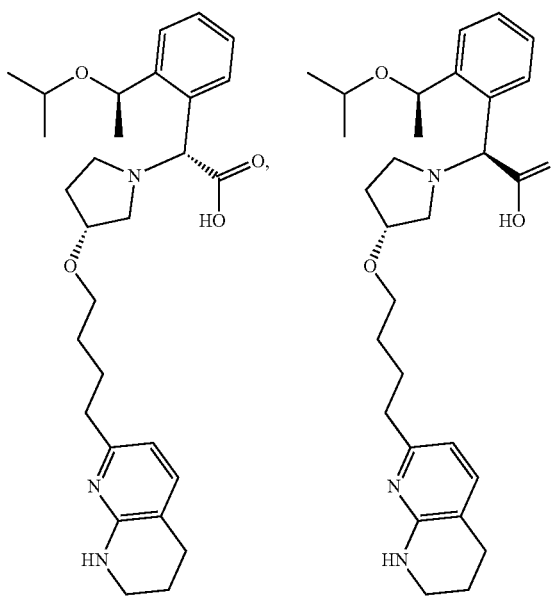
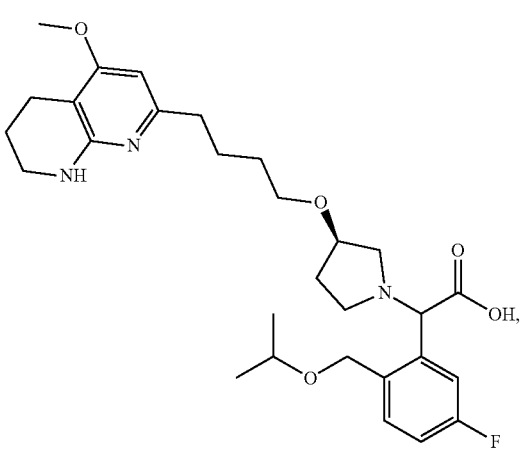

49
-continued
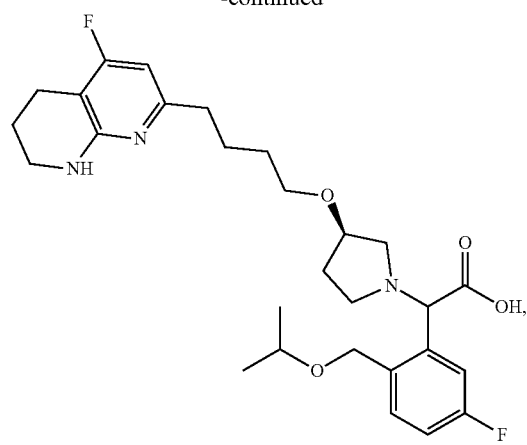
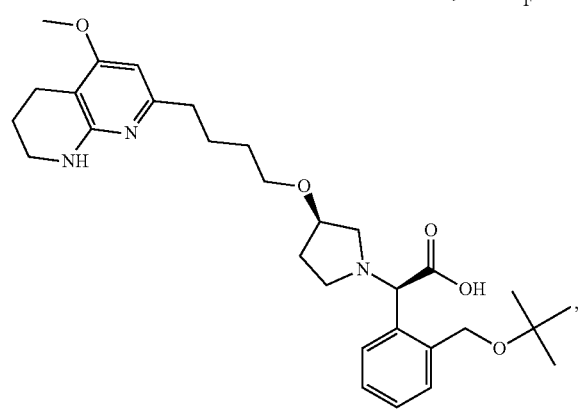
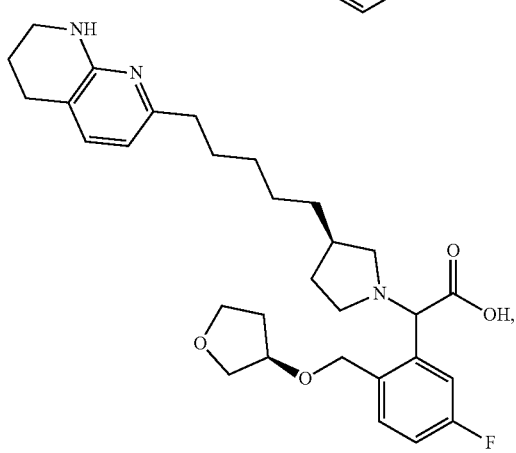
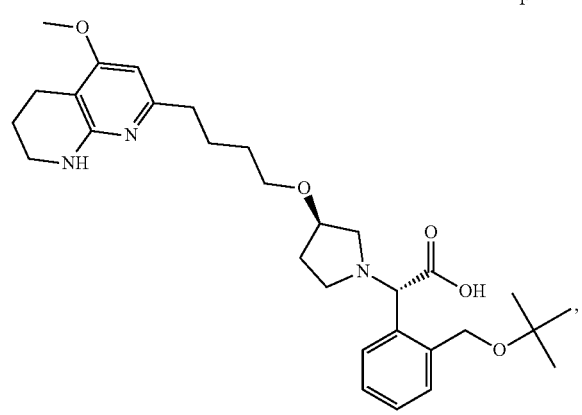
and
50
-continued
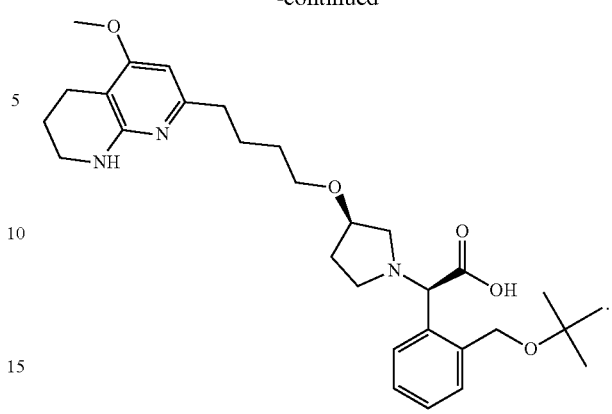
In certain embodiments, the invention relates to a compound of formula:
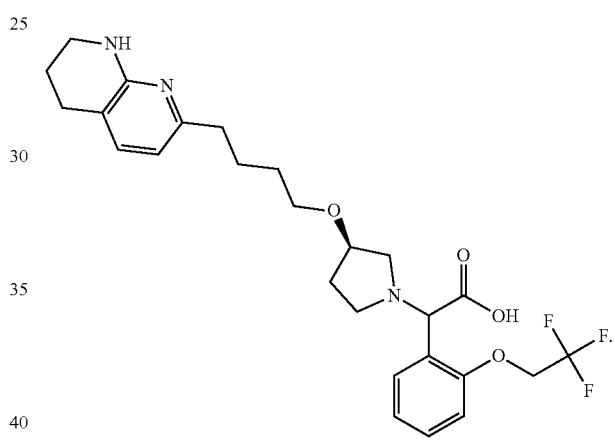
In certain embodiments, the invention relates to a compound selected from the group consisting of:
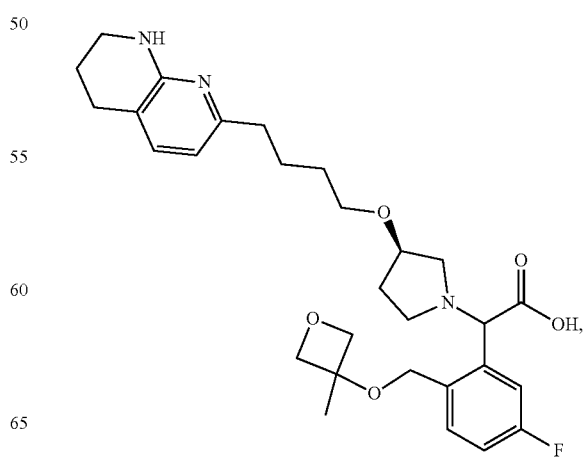

51
-continued
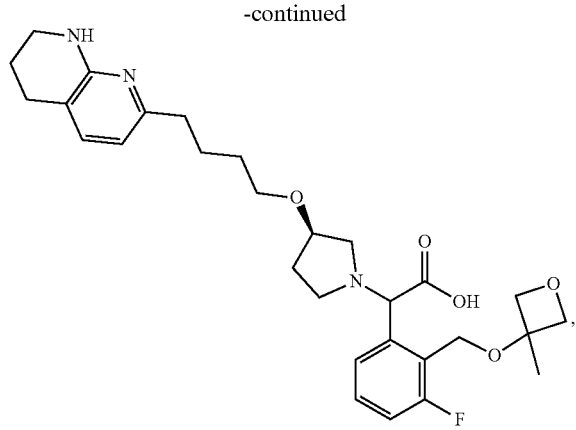
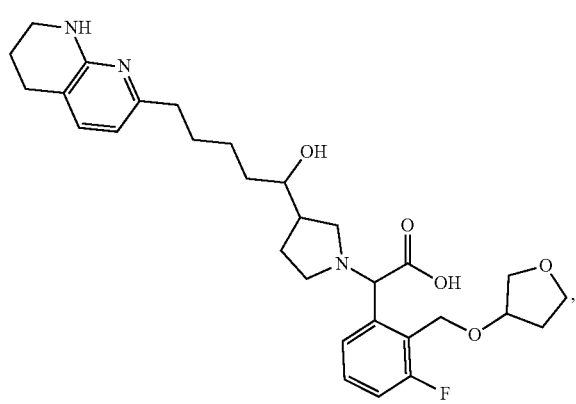
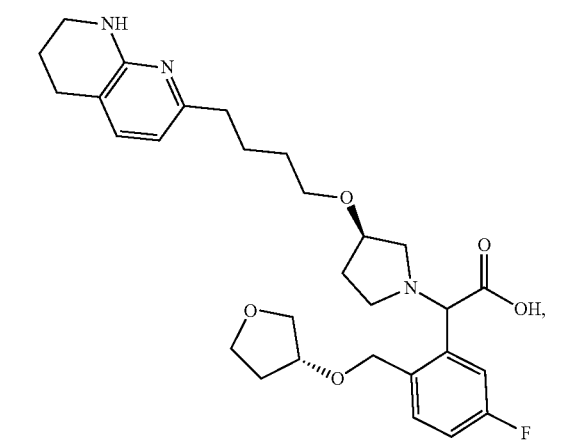
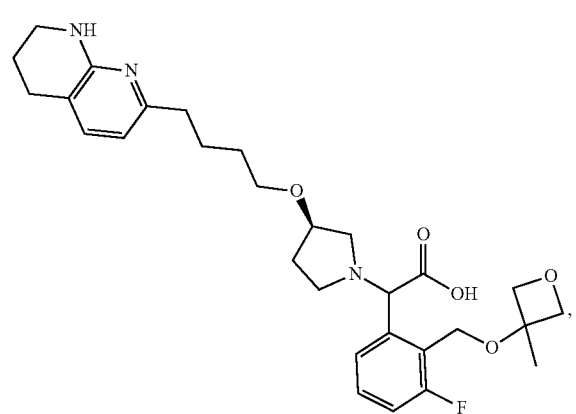
52
-continued
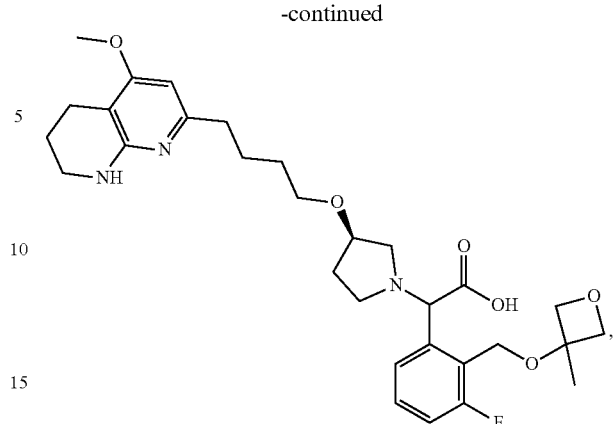
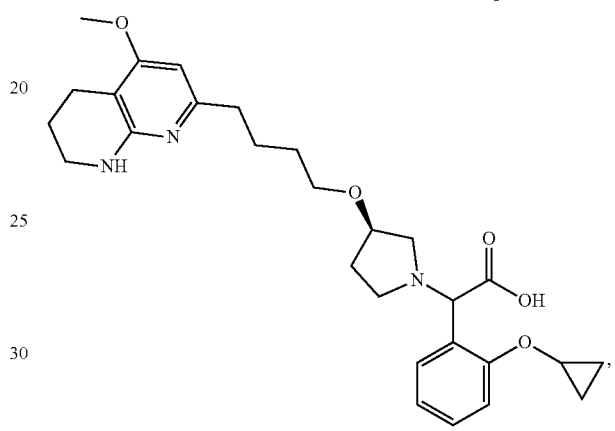
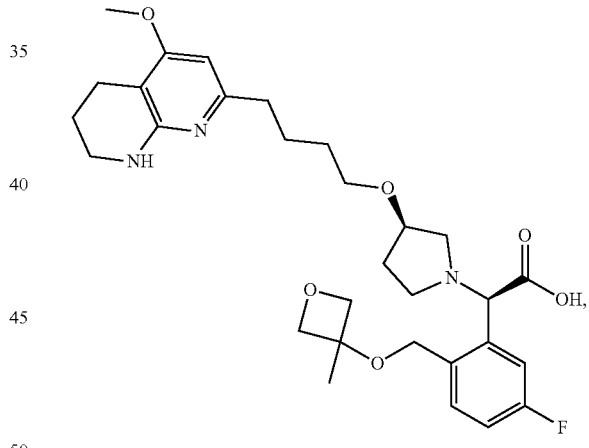
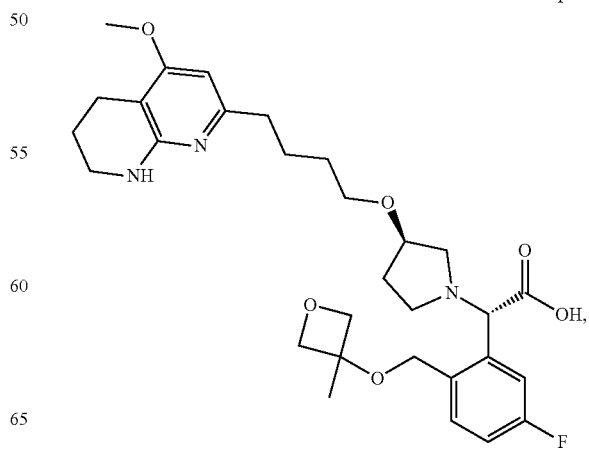

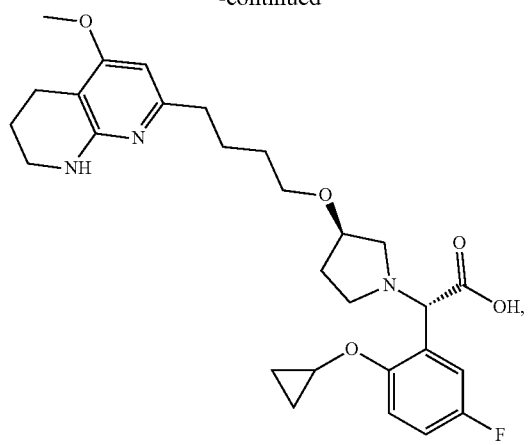
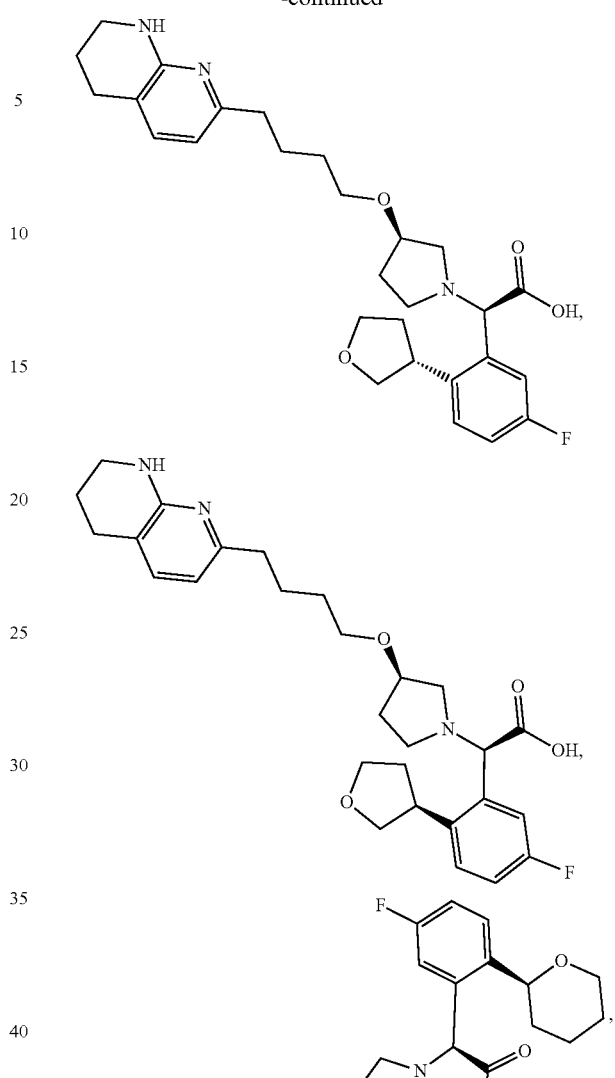
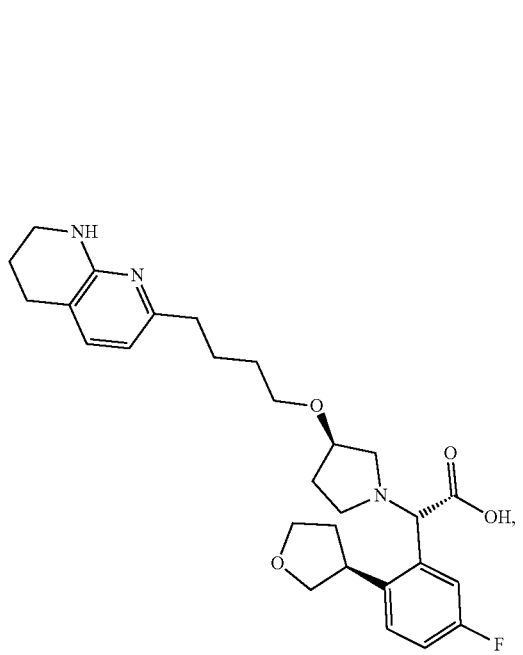
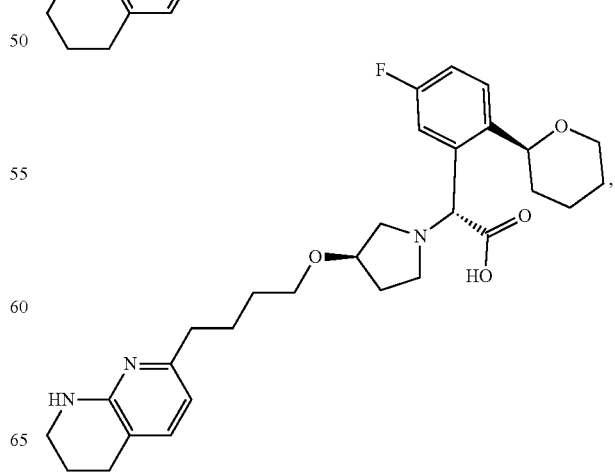

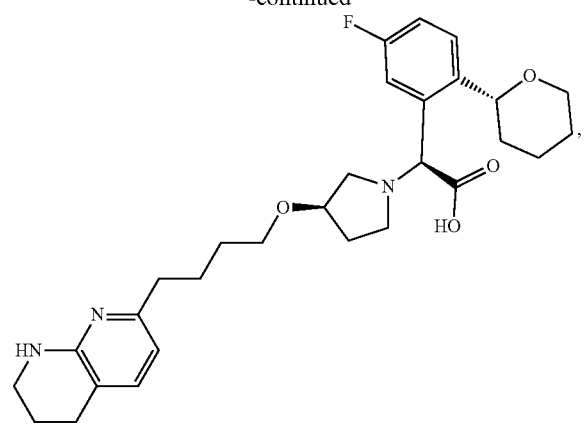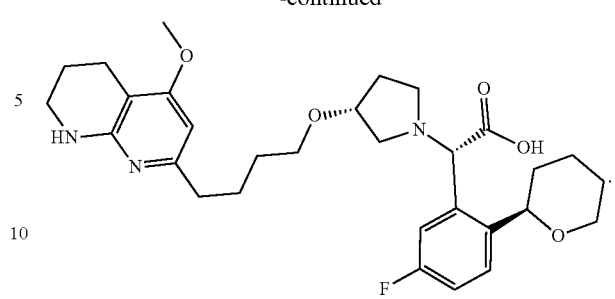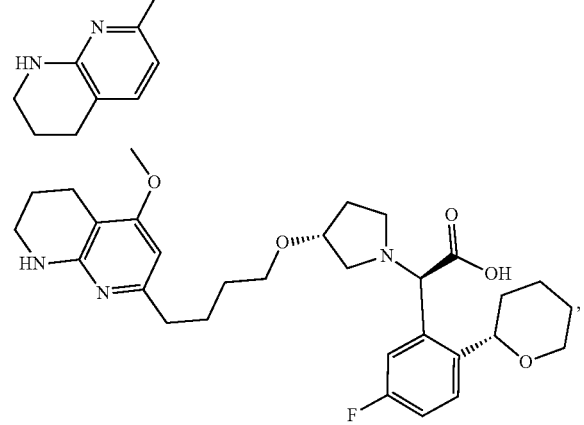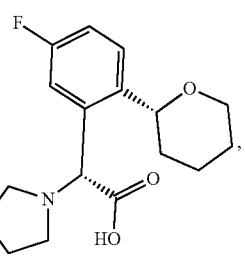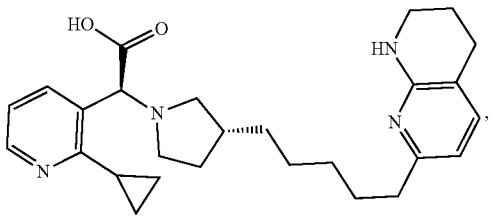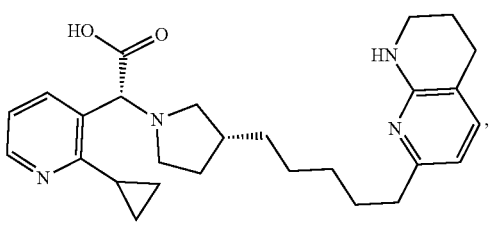
In certain embodiments, the invention relates to a compound selected from the group consisting of:
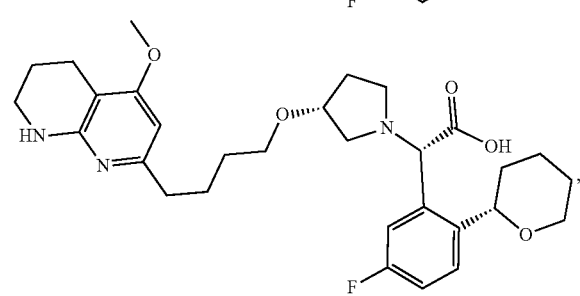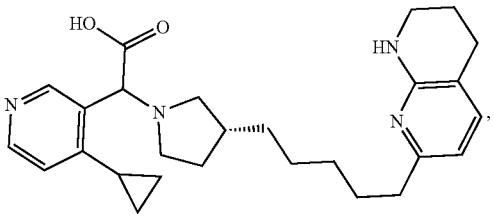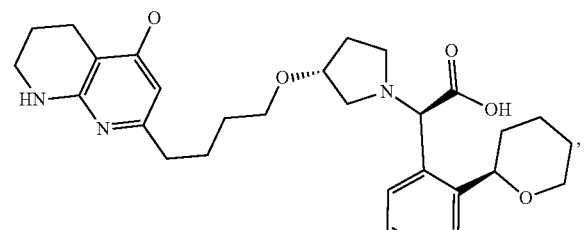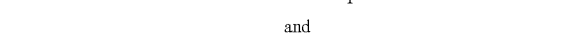and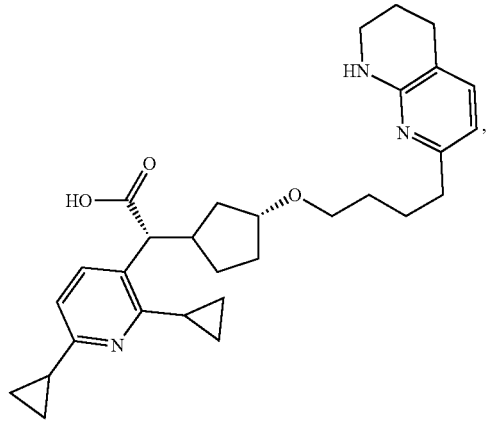

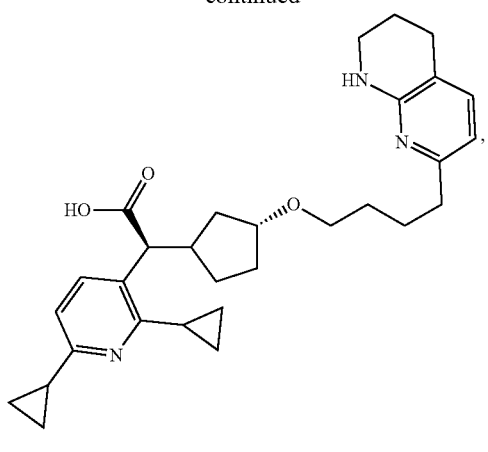
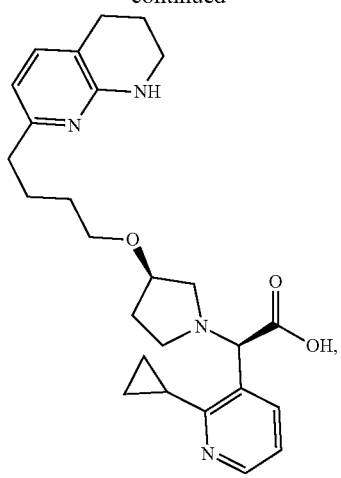

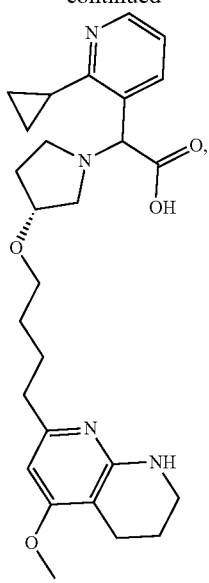
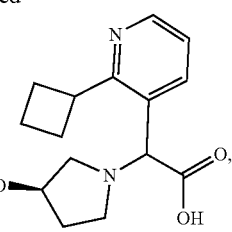
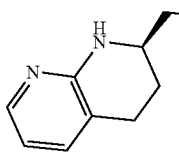
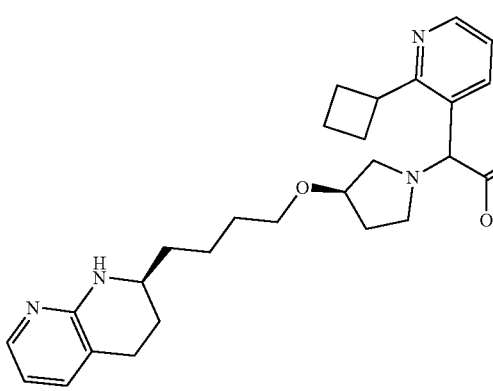
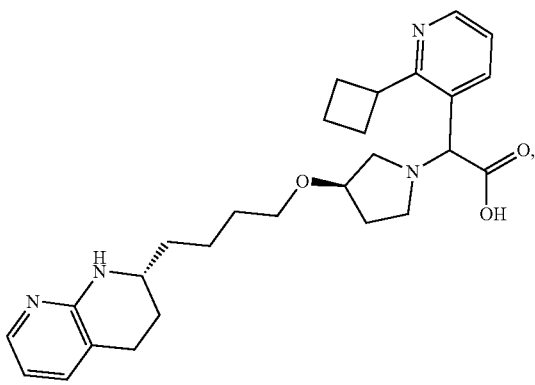
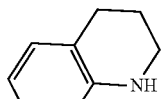
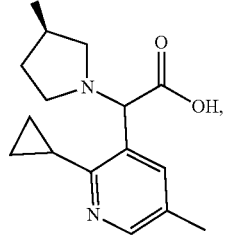

61
-continued
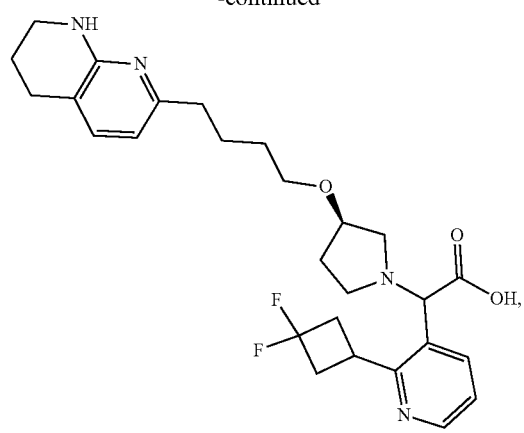
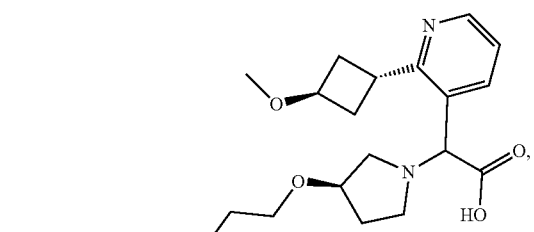
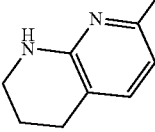
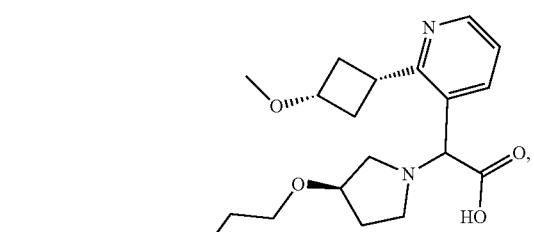
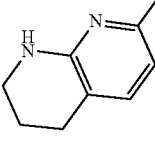
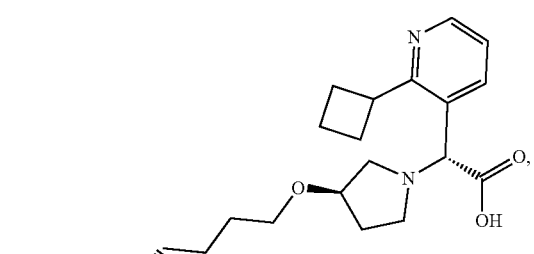
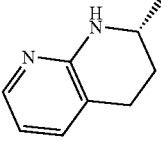
and
62
-continued
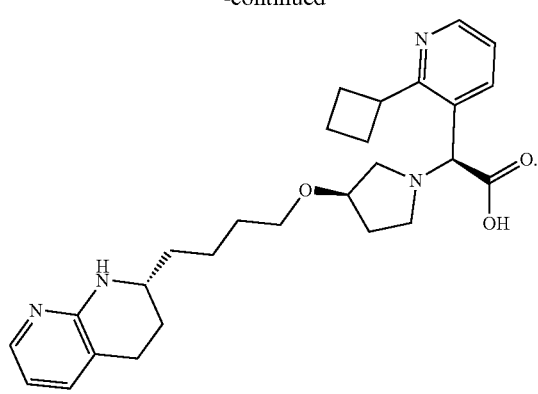
In certain embodiments, the invention relates to a compound selected from the group consisting of:
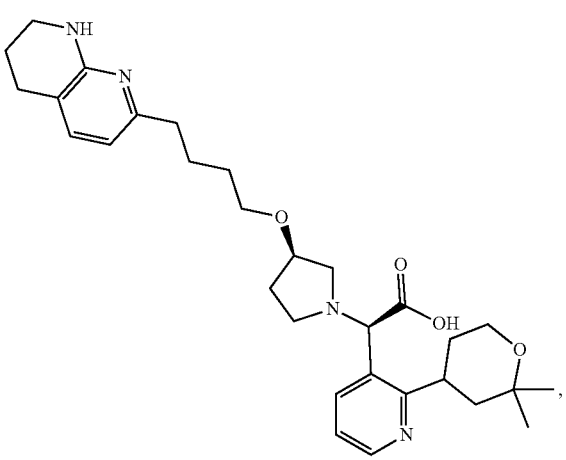
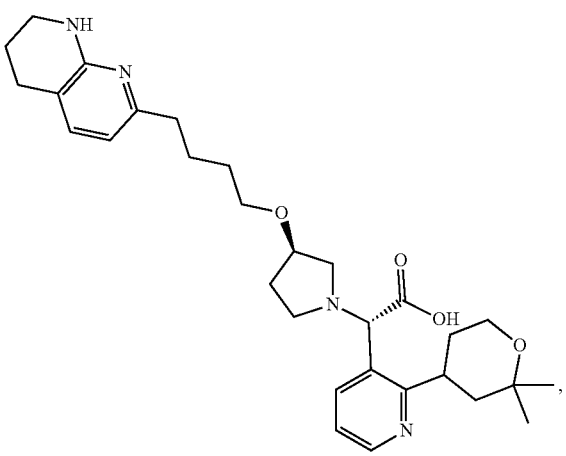

-continued
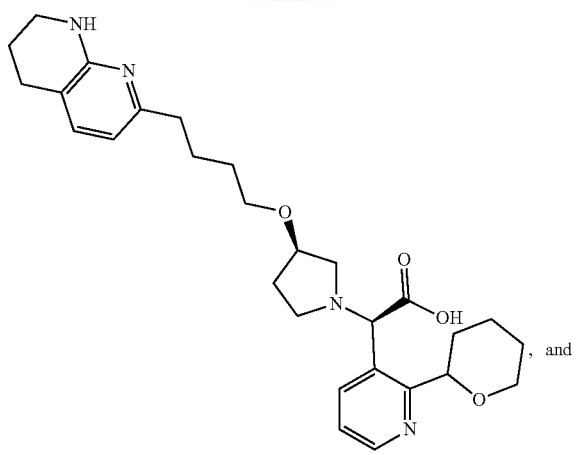
, and
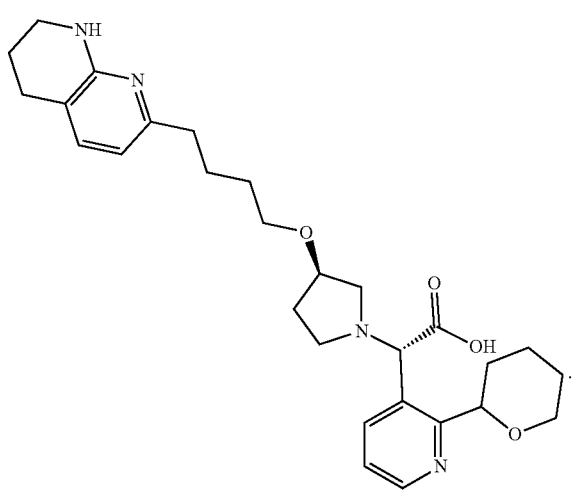
In certain embodiments, the invention relates to a compound selected from the group consisting of:
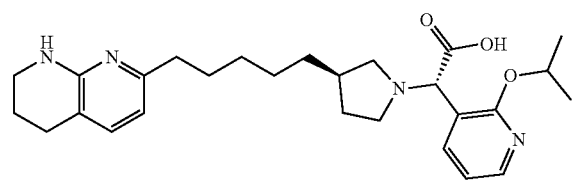
,
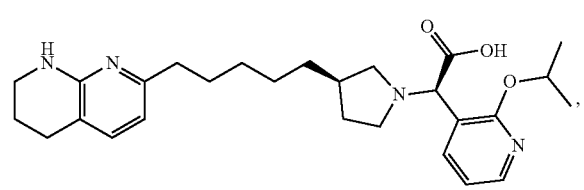
,
-continued
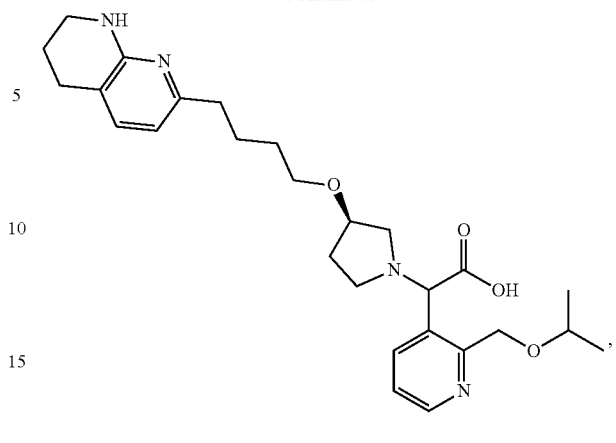
;
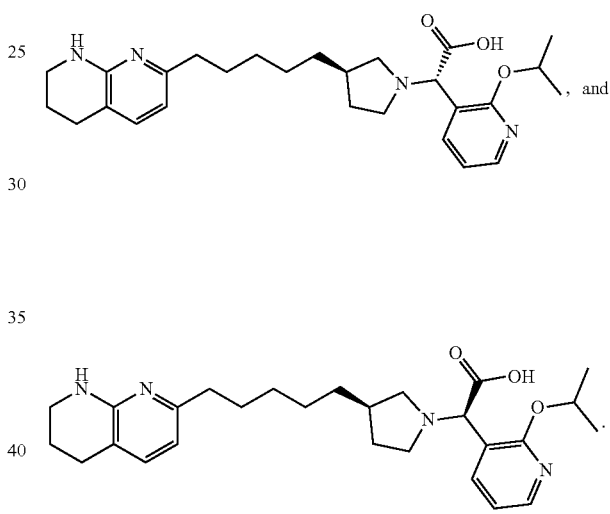
, and
In certain embodiments, the invention relates to a compound of formula:
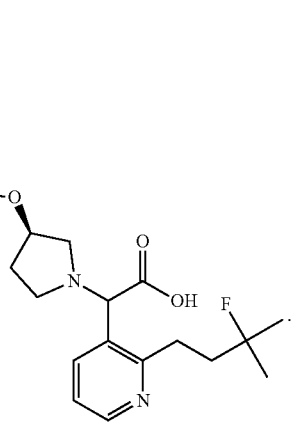
In certain embodiments, the invention relates to a compound of formula:

In certain embodiments, the invention relates to a compound selected from the group consisting of:
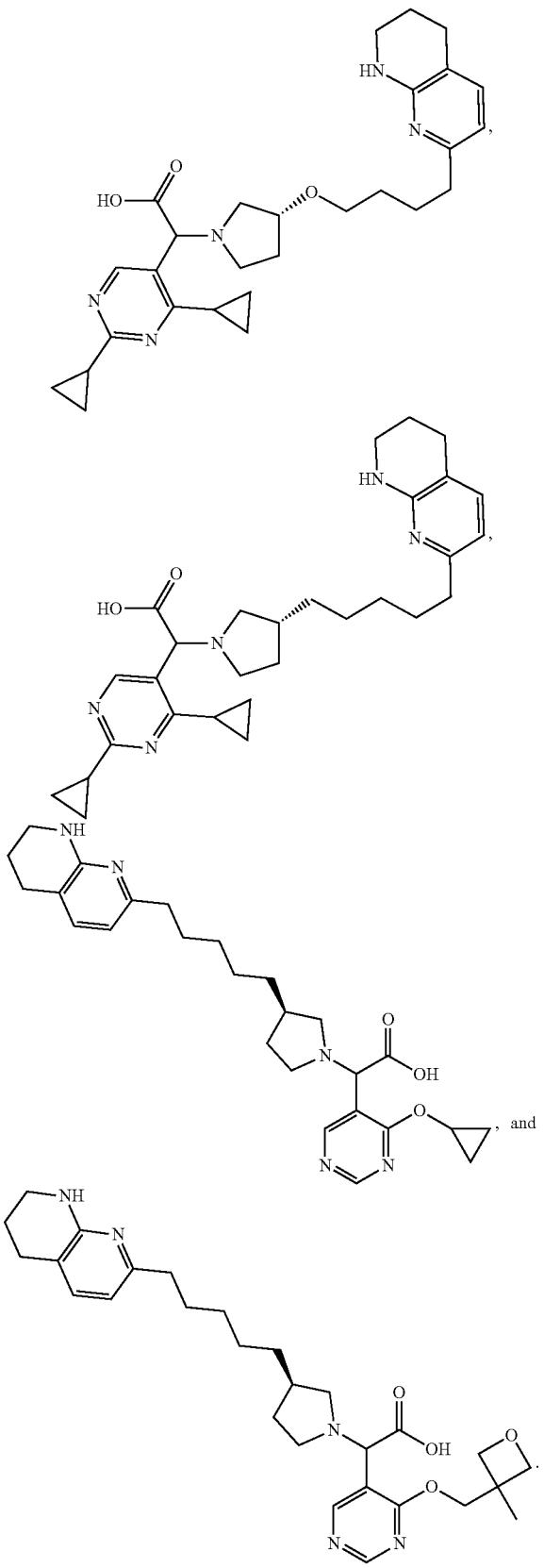
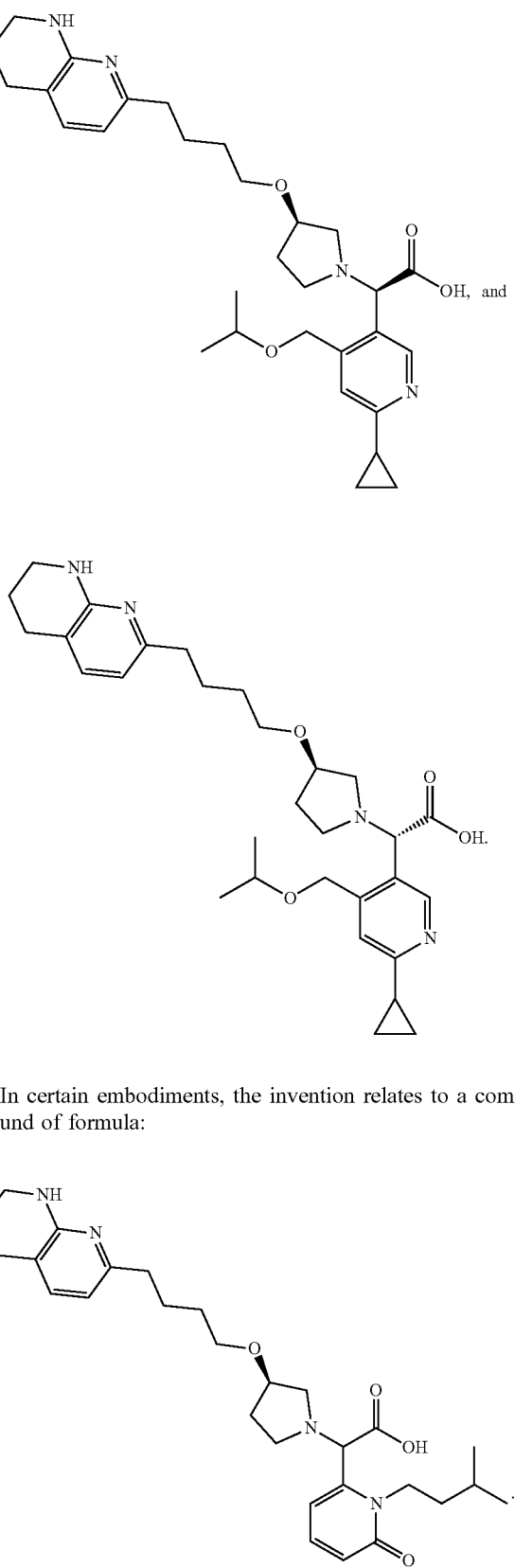
In certain embodiments, the invention relates to a compound of formula:
In certain embodiments, the invention relates to a compound selected from the group consisting of:

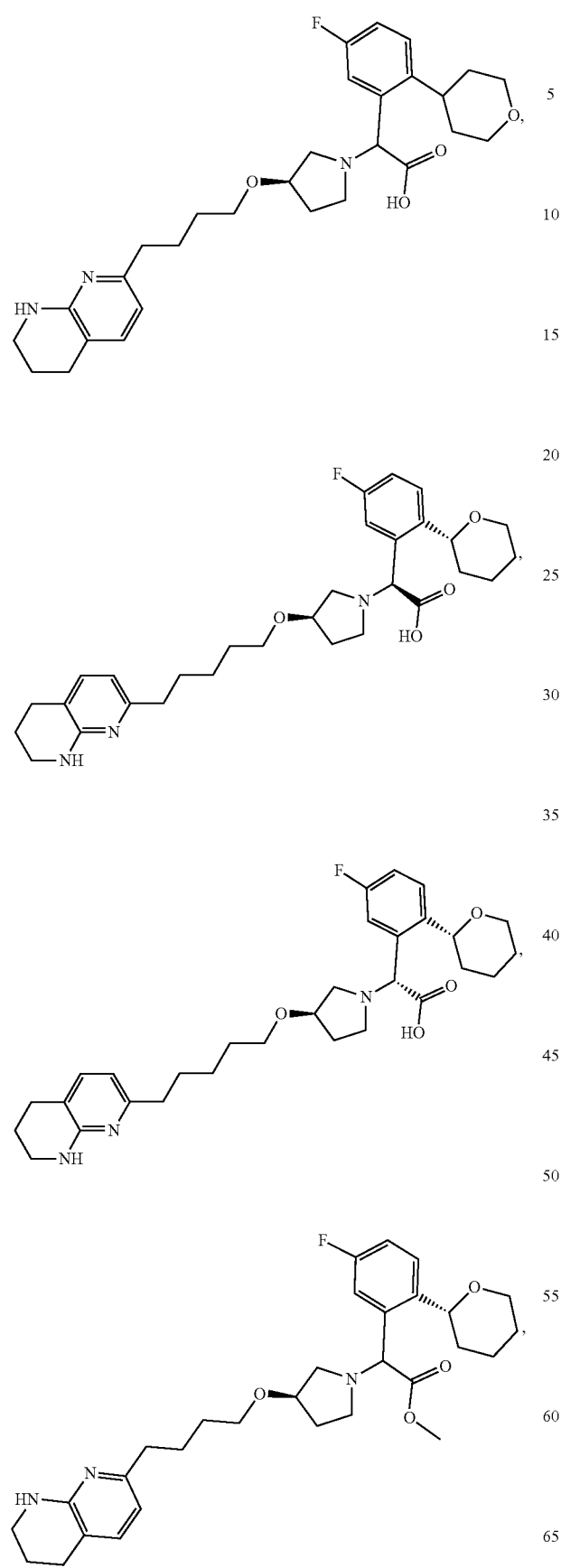
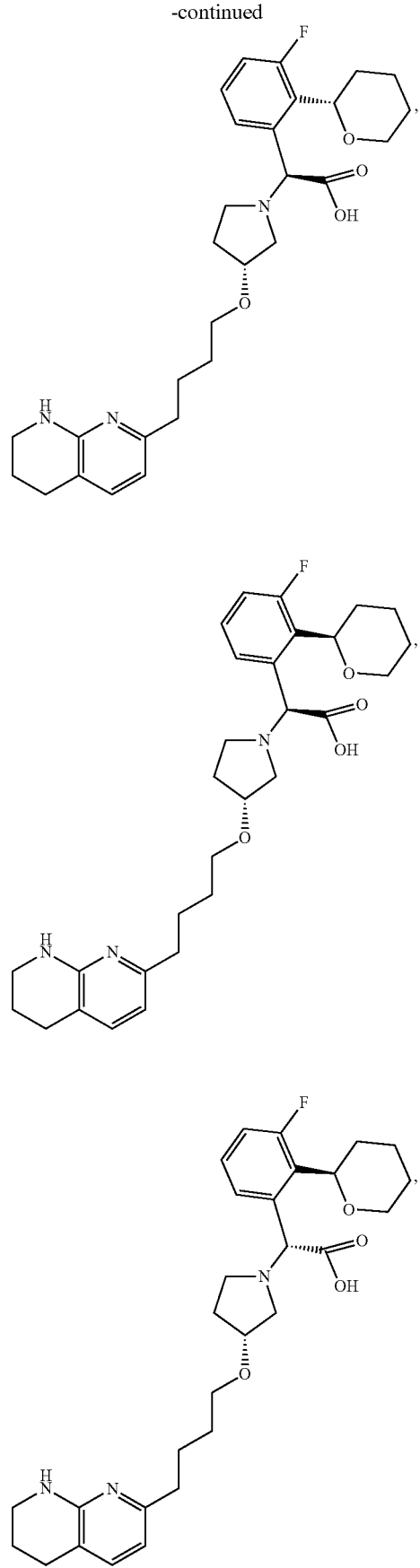

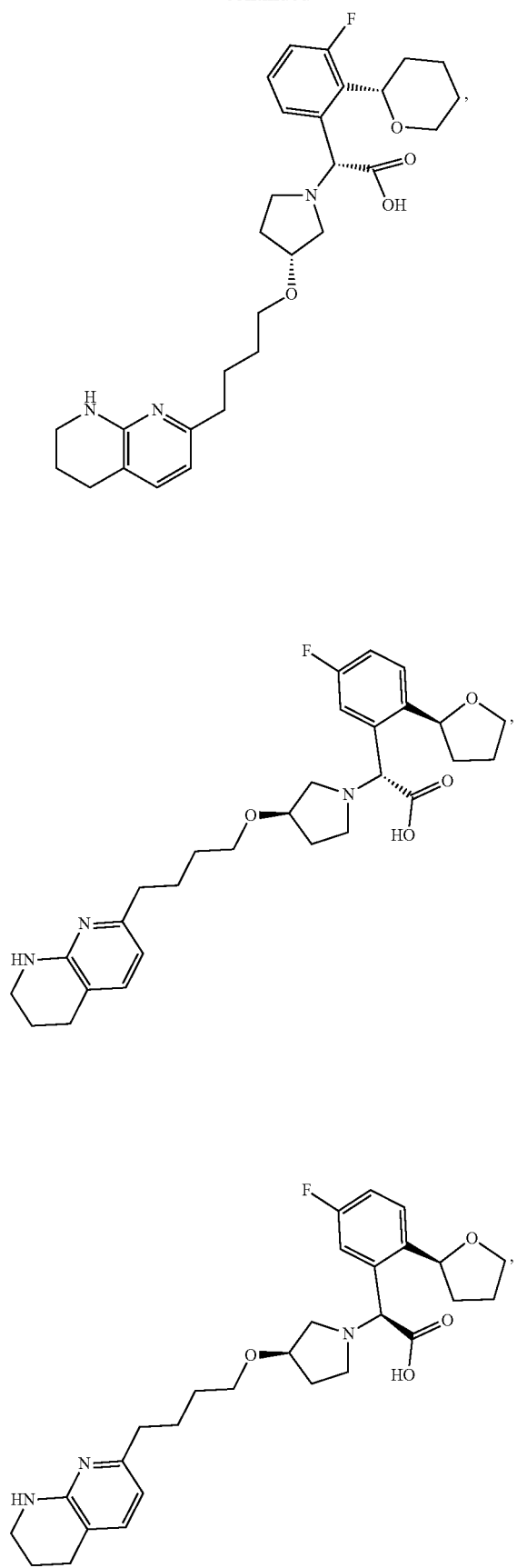
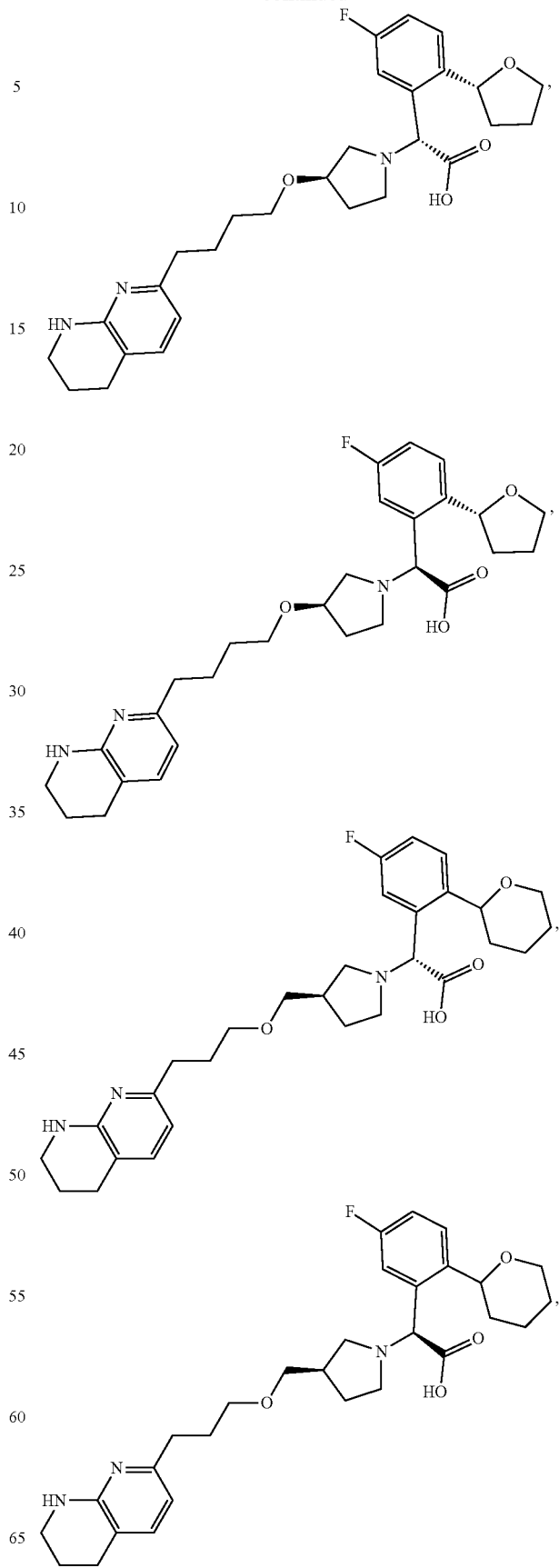

71
-continued
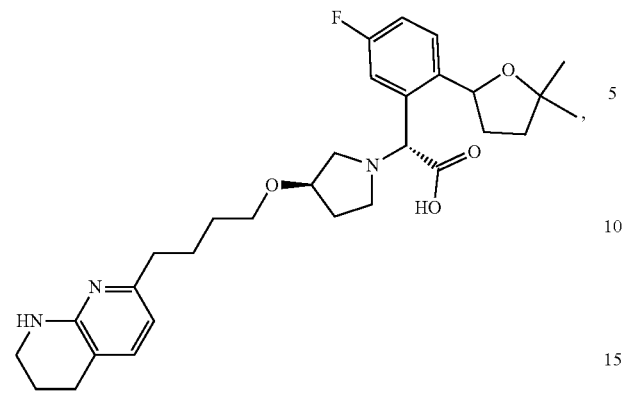
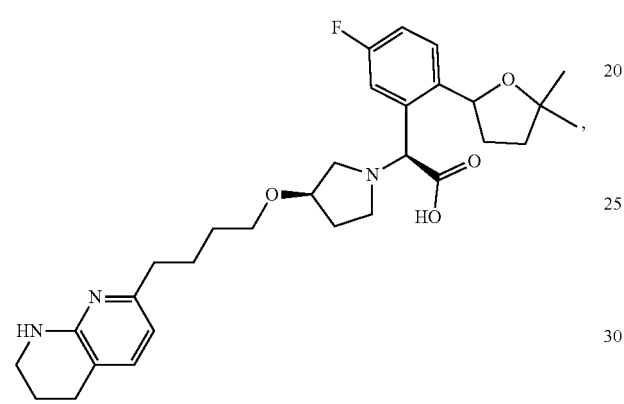
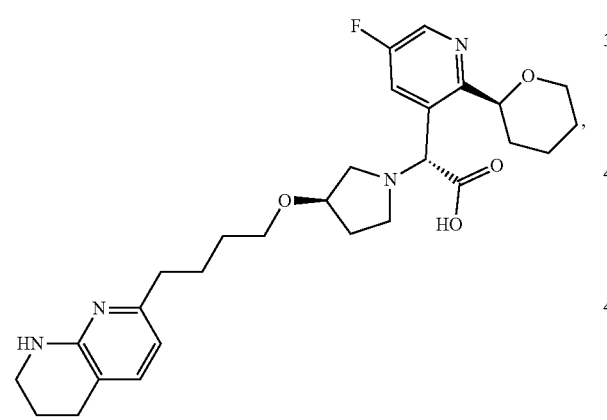
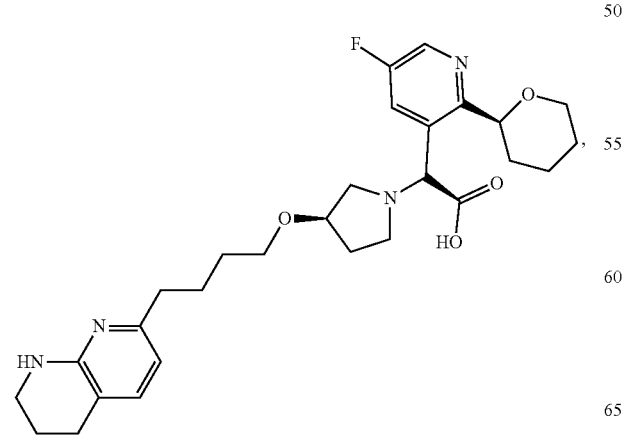
72
-continued
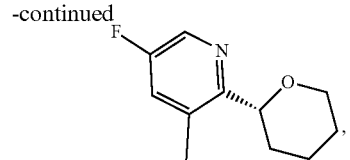
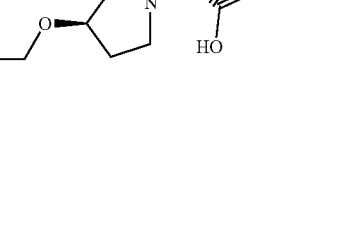
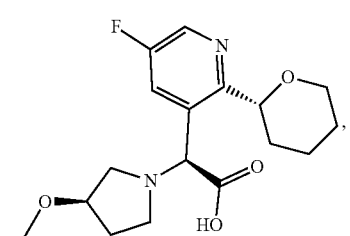
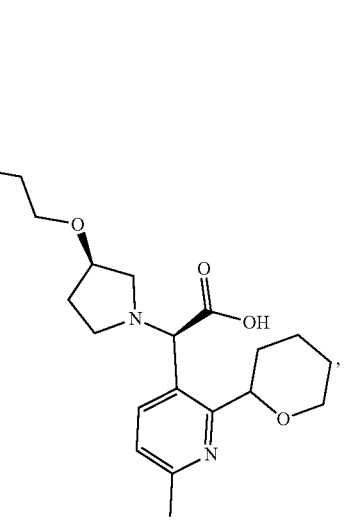

73
-continued
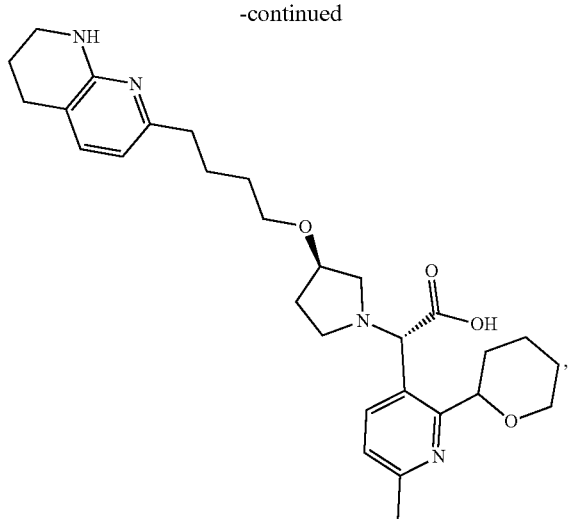
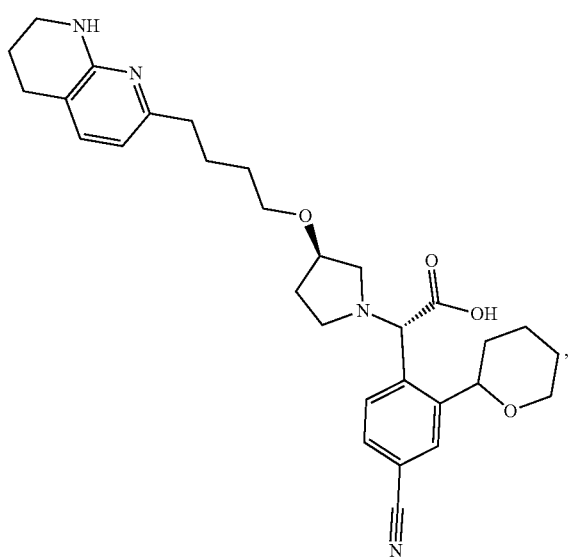
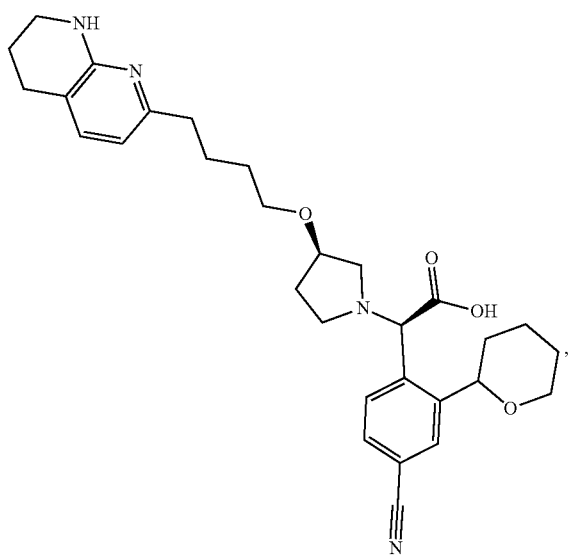
74
-continued
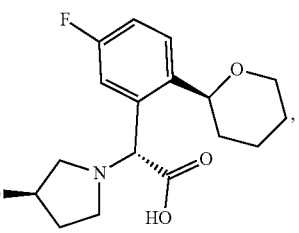
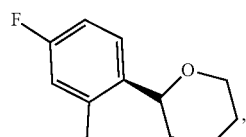
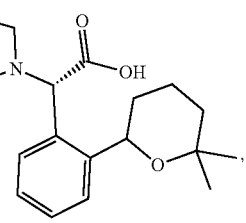

75
-continued
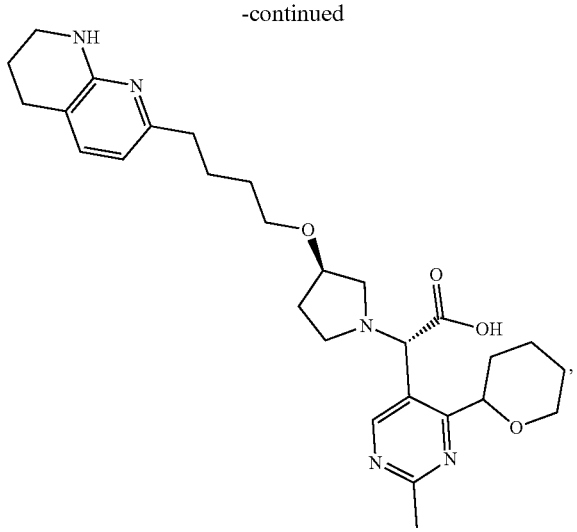
76
-continued
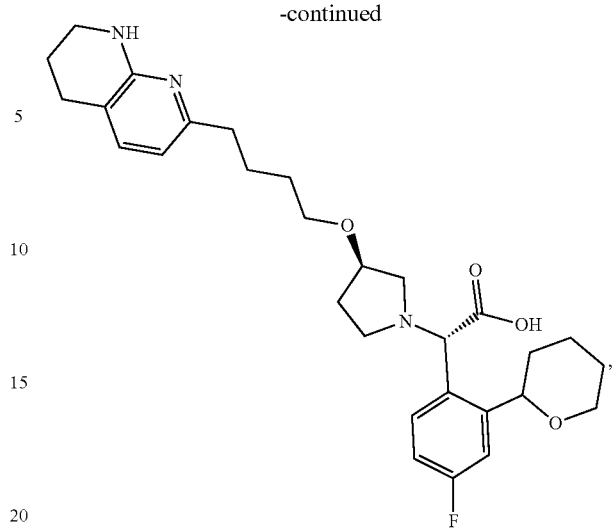
and
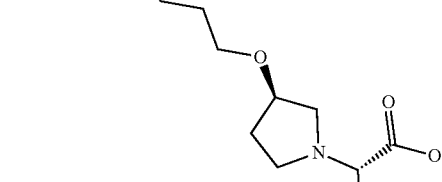
In certain embodiments, the invention relates to a compound selected from the group consisting of:

77
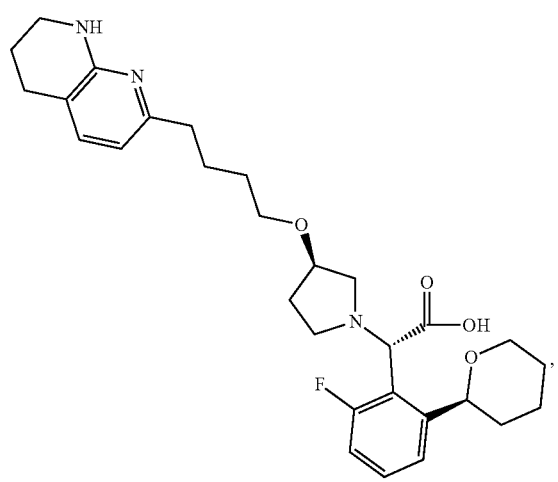
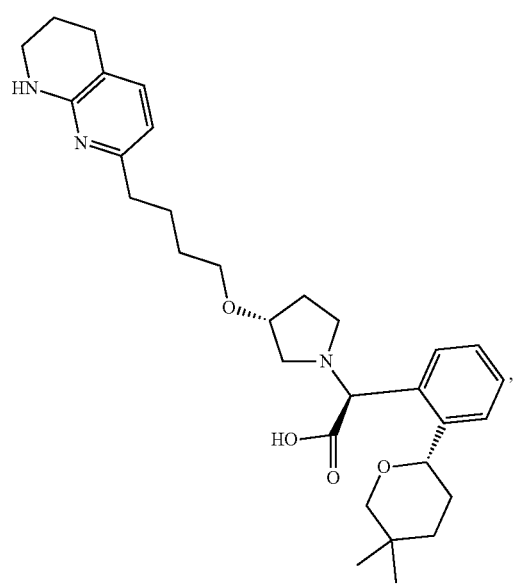
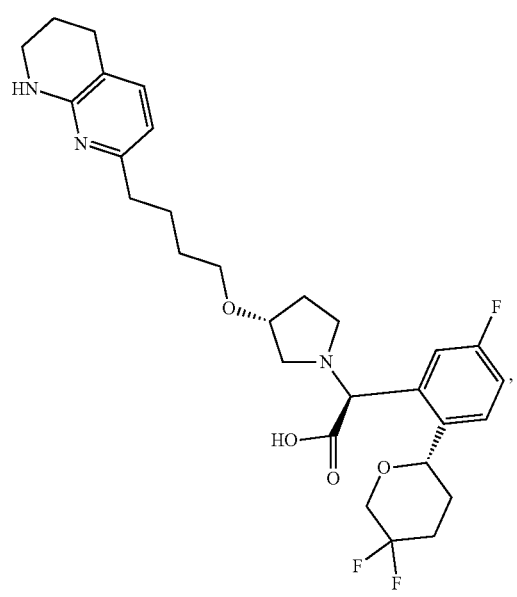
78
-continued
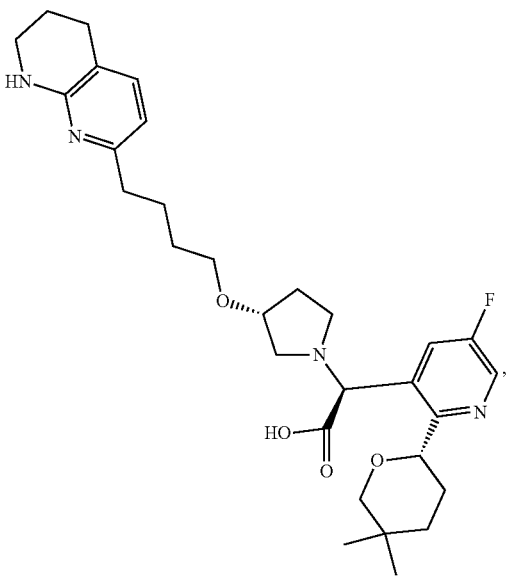
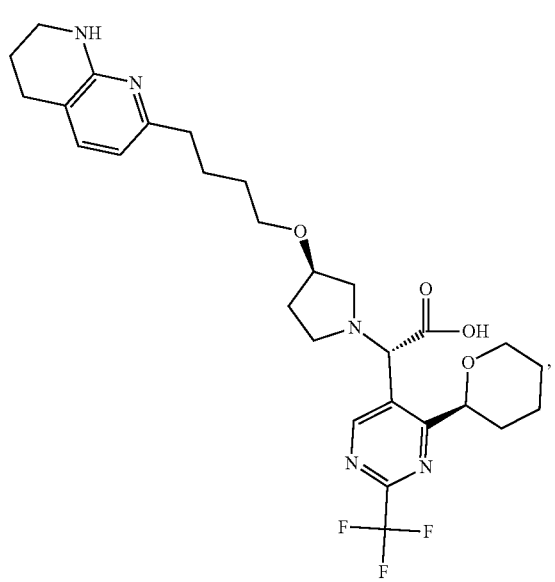
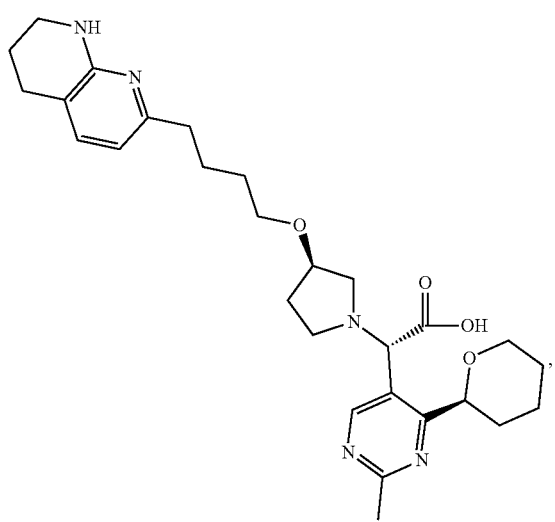

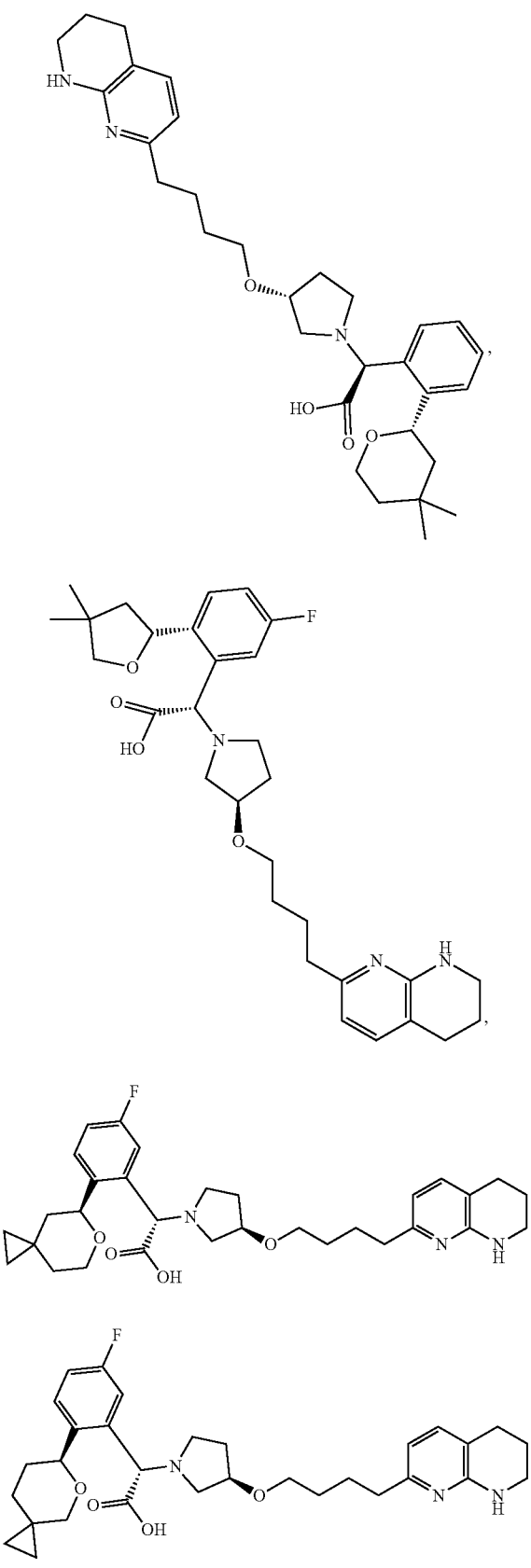
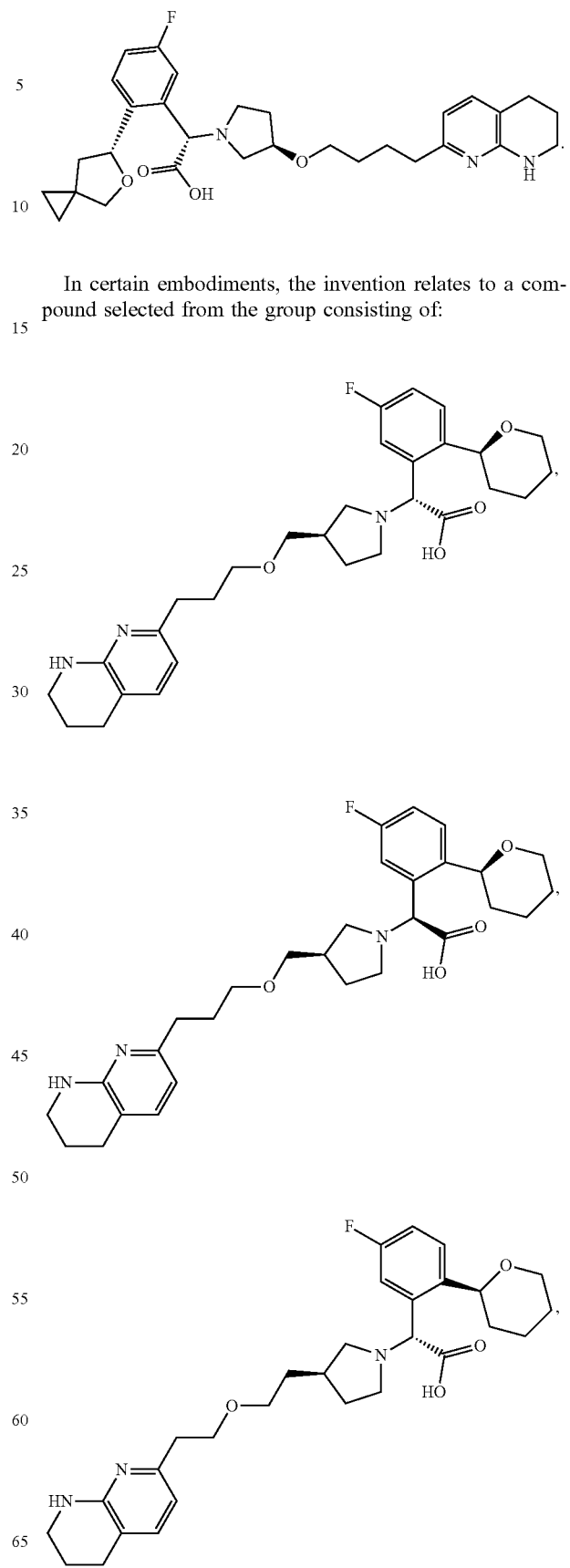
In certain embodiments, the invention relates to a compound selected from the group consisting of:

81
-continued
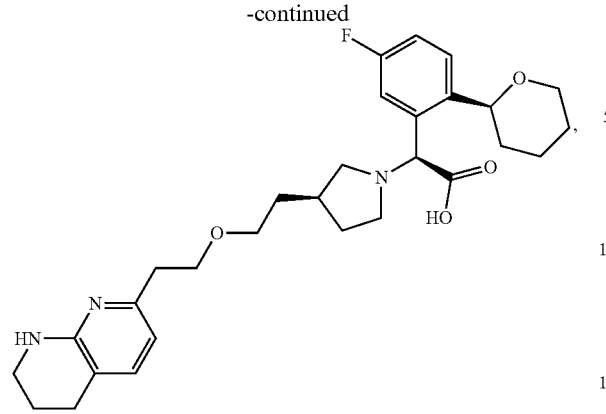
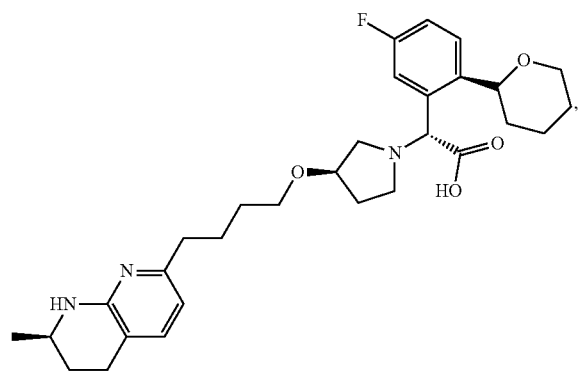
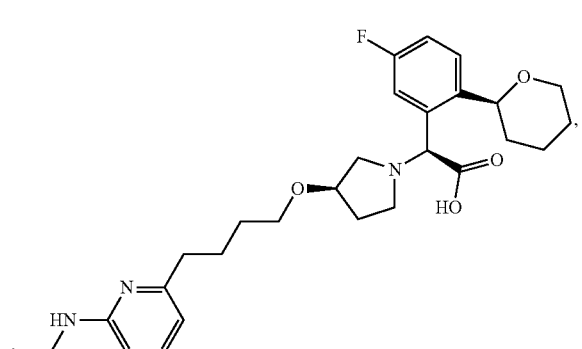
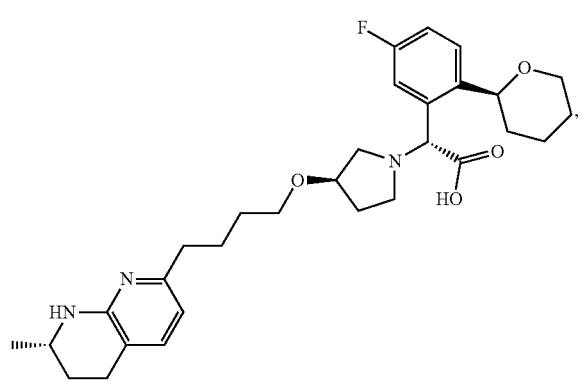
82
-continued
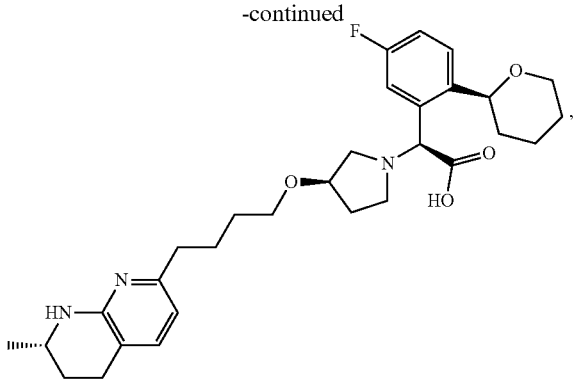
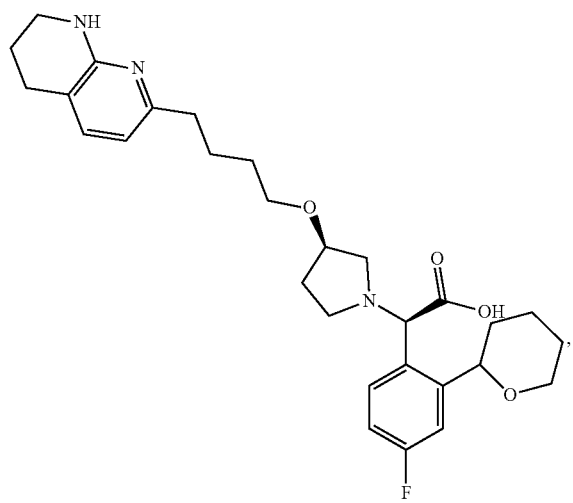
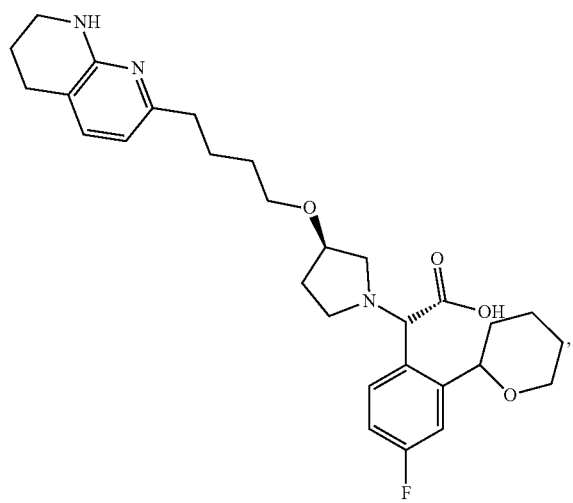

83
-continued
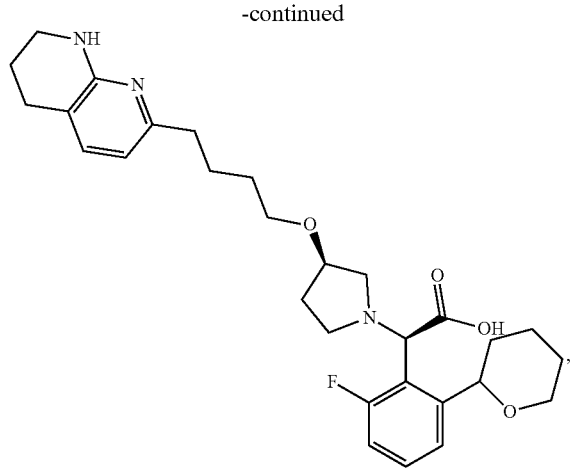
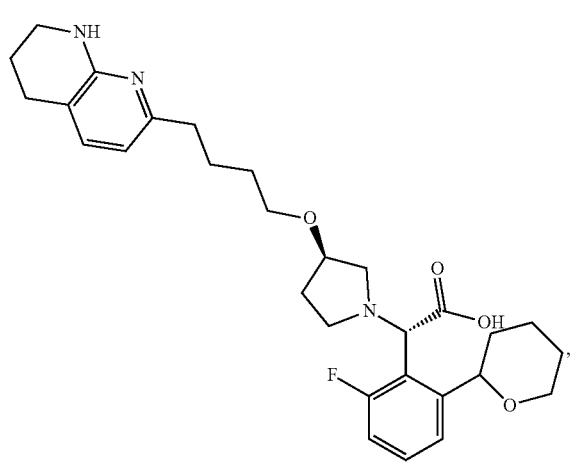
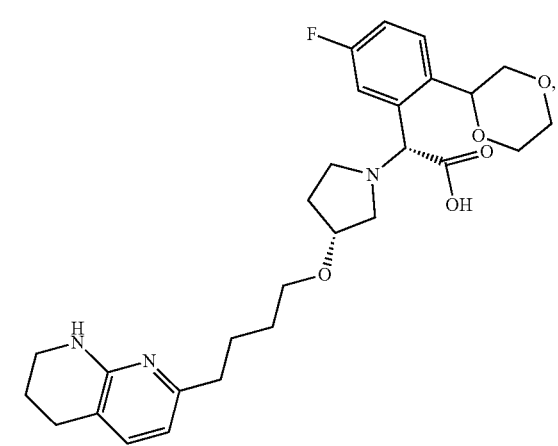
84
-continued
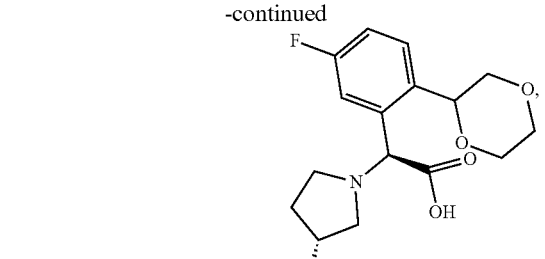
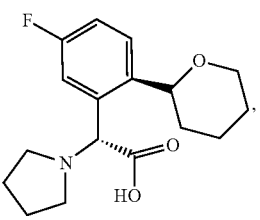
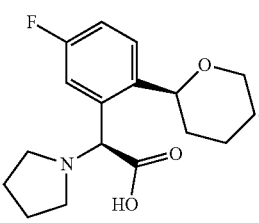
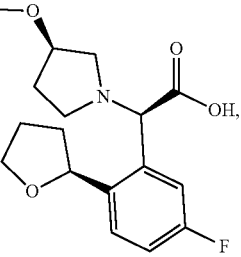

85
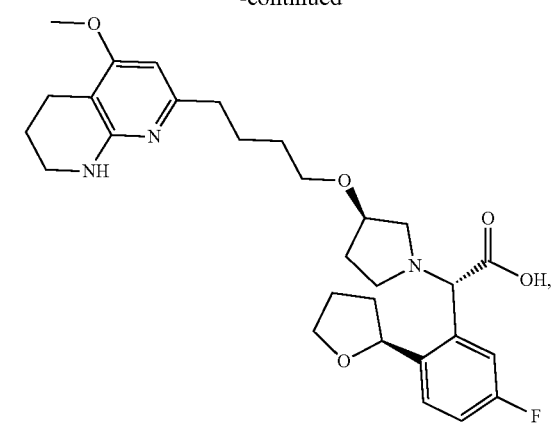
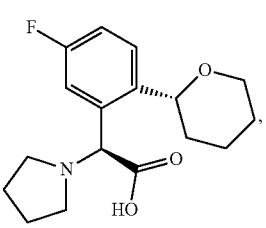
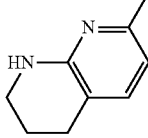
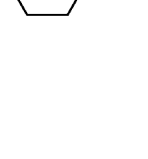
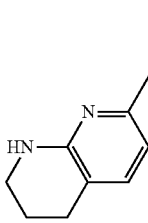
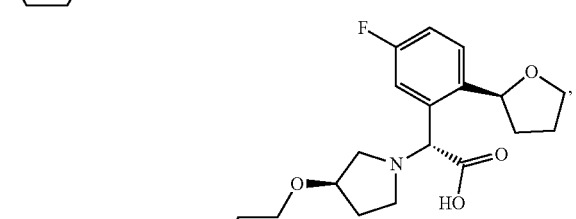
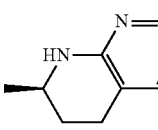
86
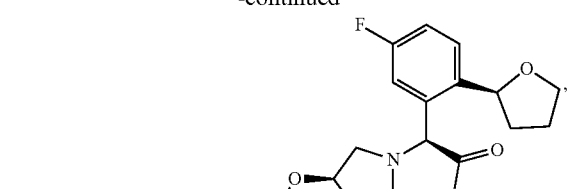
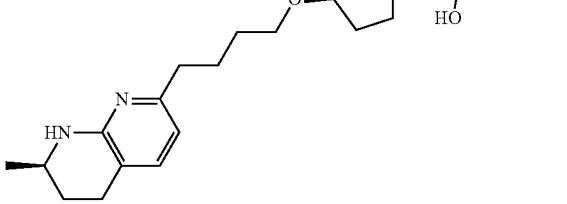
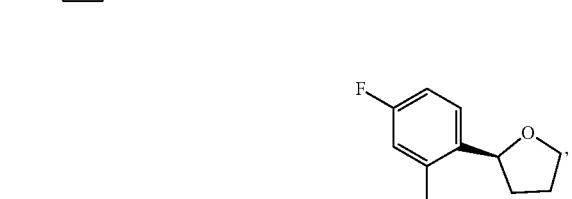
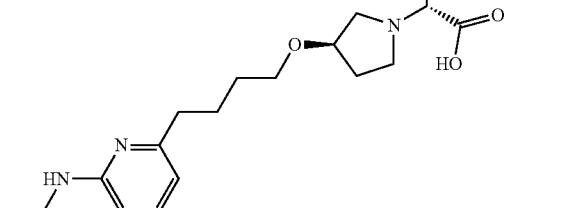
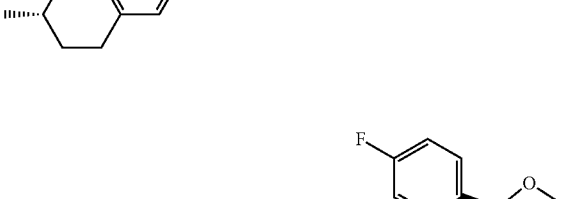
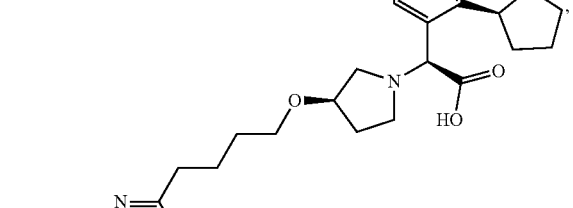
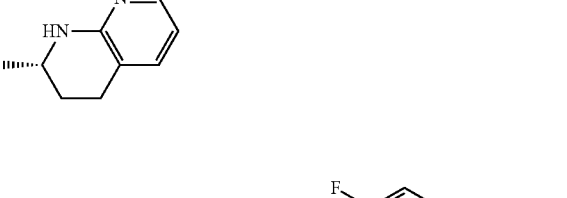
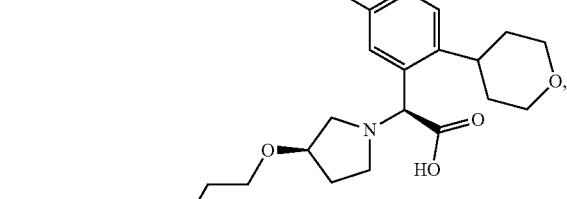
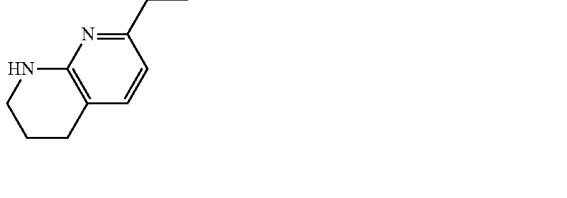

87
-continued
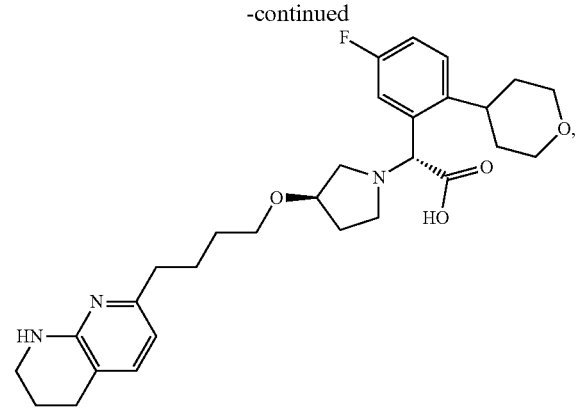
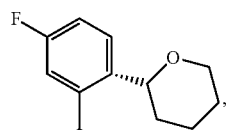
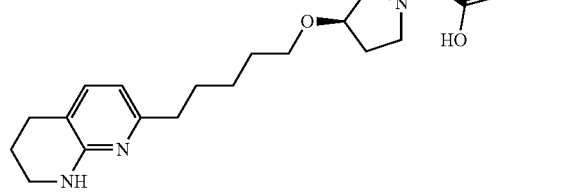
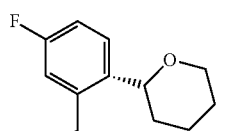
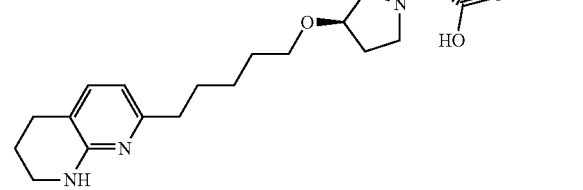
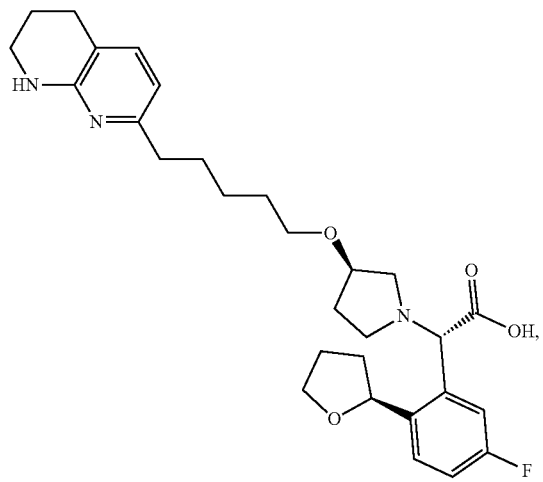
88
-continued
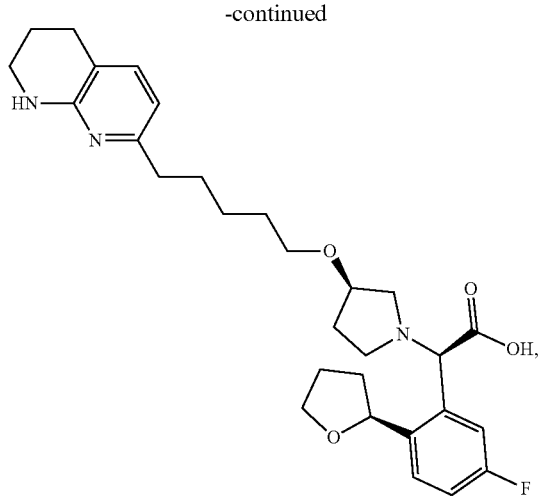
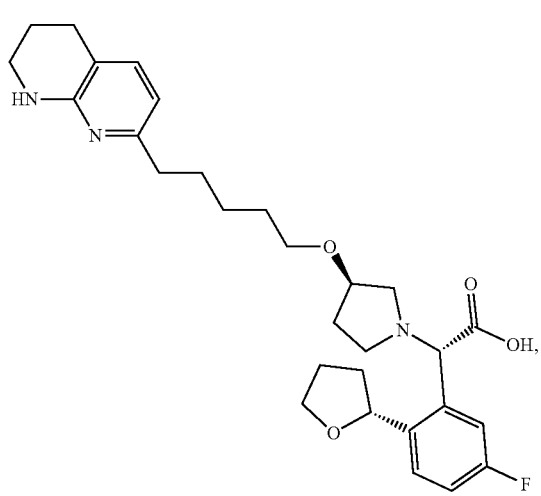
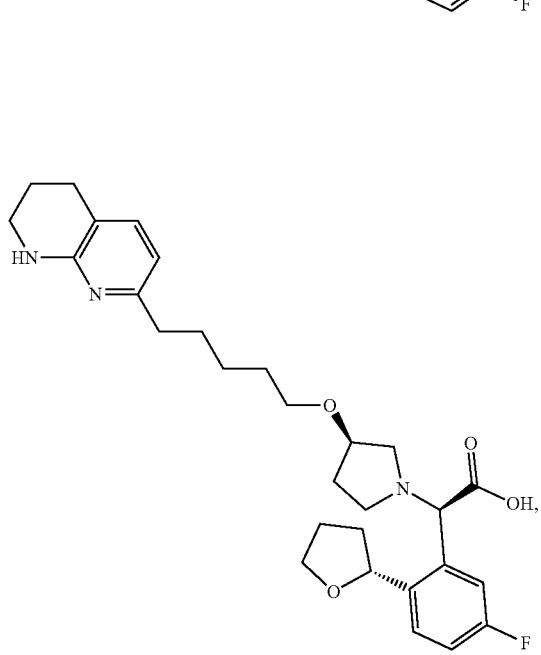

89
-continued
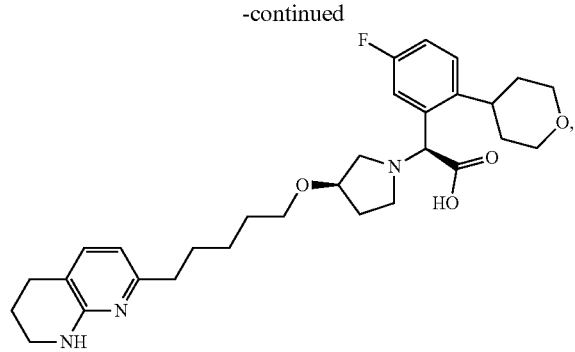
and
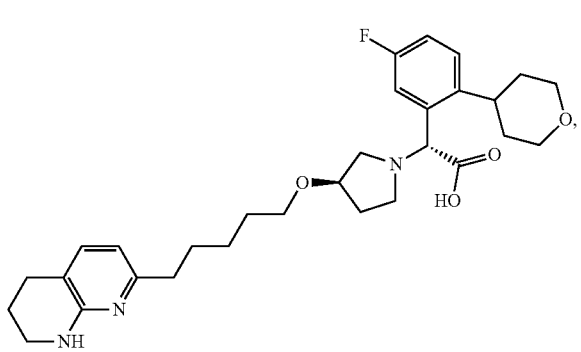
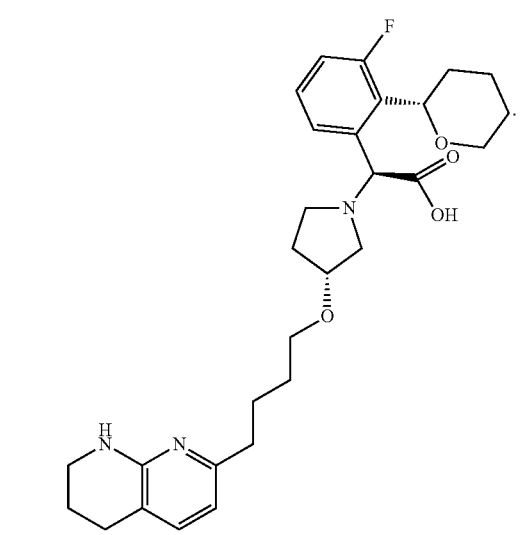 [SMILES: O=C(O)[C@H](c1cccc(F)c1[C@@H]1CCCCO1)N1CC[C@@H](OCCCCc2ccc3c(n2)NCCC3)C1]
In certain embodiments, the invention relates to a compound selected from the group consisting of:
90
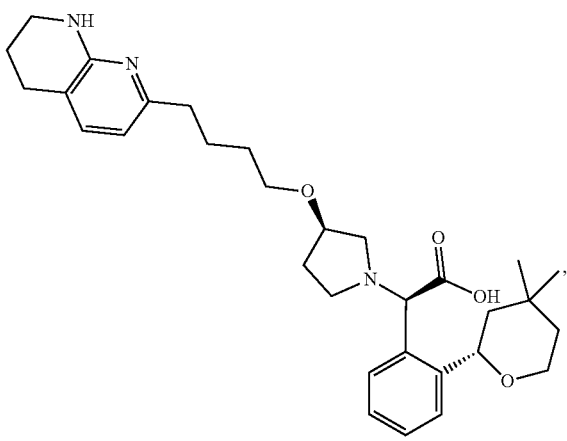
, and In certain embodiments, the invention relates to a compound selected from the group consisting of:
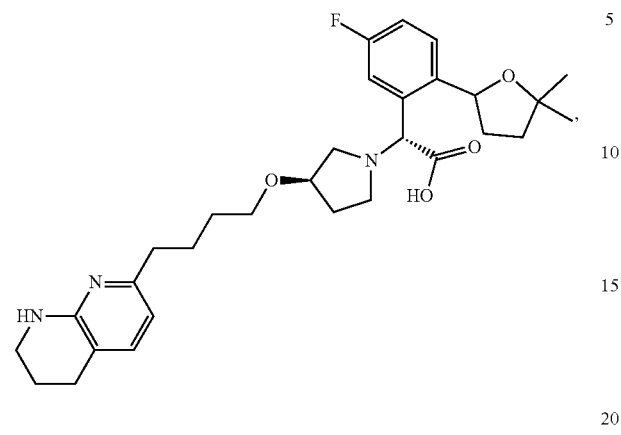
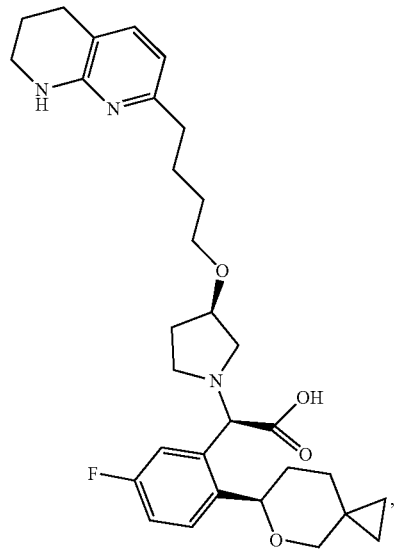
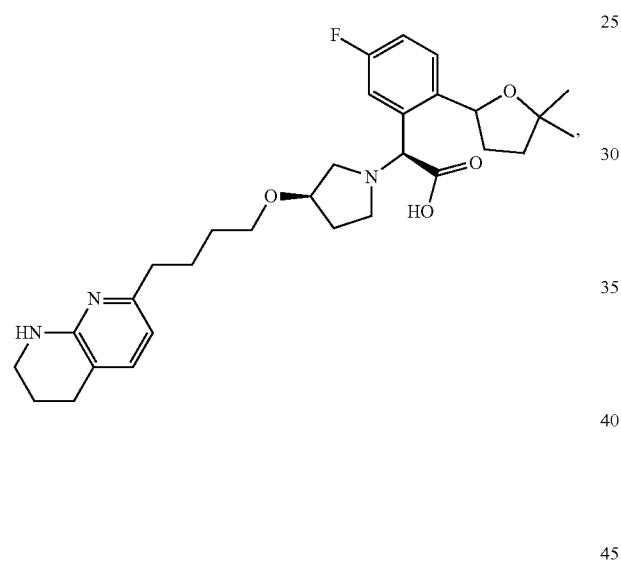
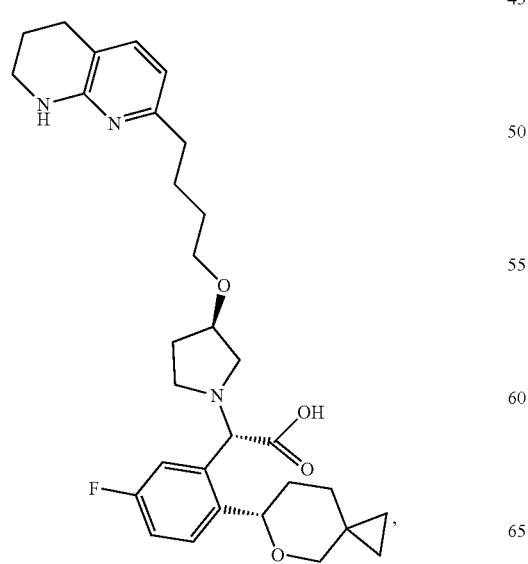
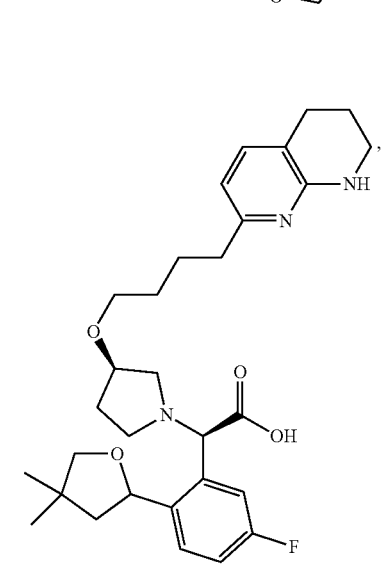

93
-continued
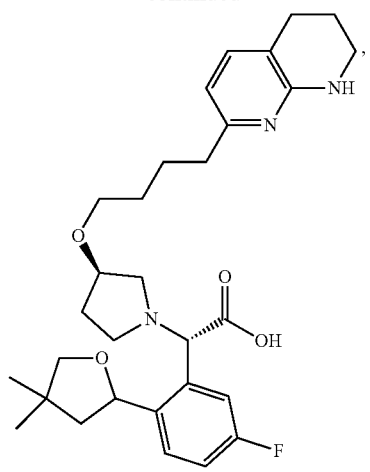
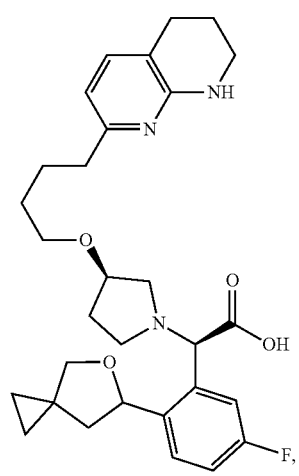
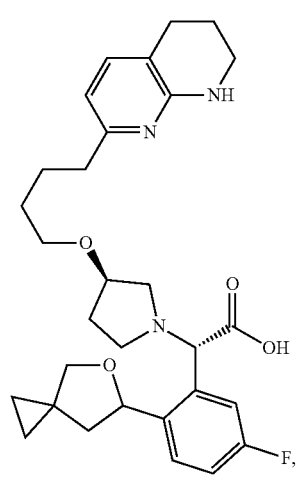
94
-continued
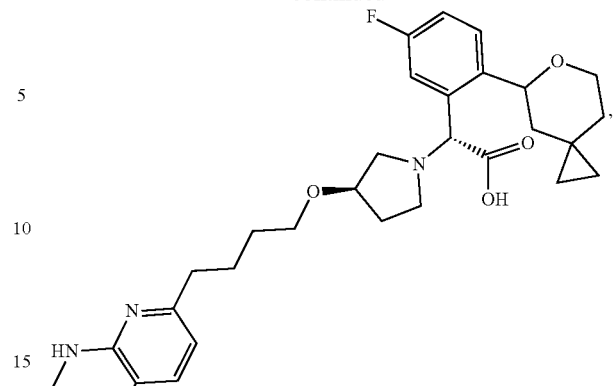
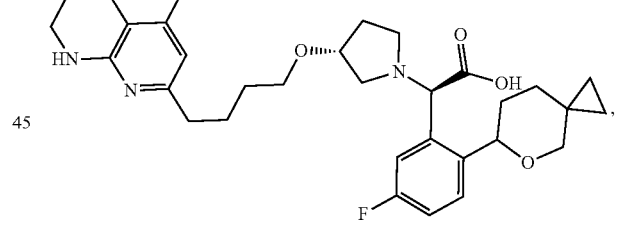
and
In certain embodiments, the invention relates to a compound selected from the group consisting of:

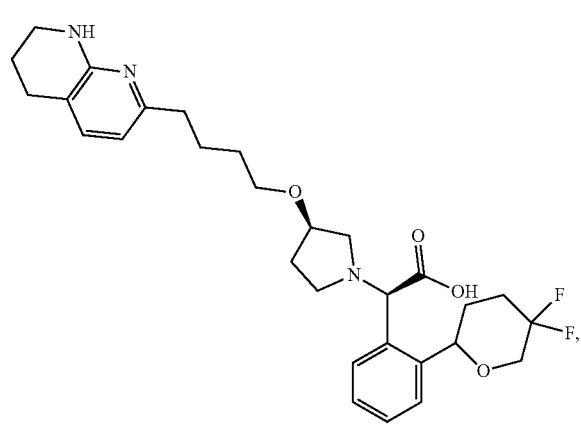 [SMILES: O=C(O)[C@@H](c1ccccc1C1CCC(F)(F)CO1)N1CC[C@@H](OCCCCc2ccc3c(n2)NCCC3)C1]
and
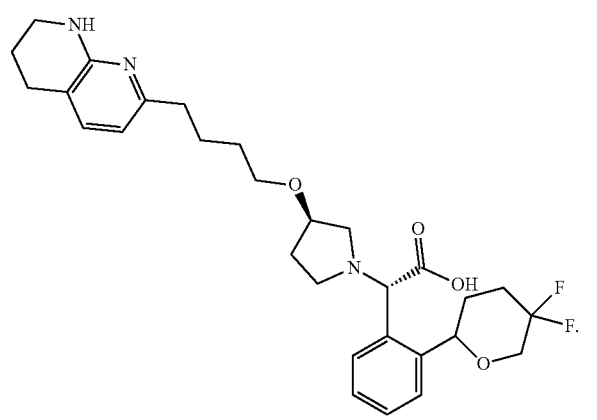 [SMILES: O=C(O)[C@H](c1ccccc1C1CCC(F)(F)CO1)N1CC[C@@H](OCCCCc2ccc3c(n2)NCCC3)C1]
In certain embodiments, the invention relates to a compound selected from the group consisting of:
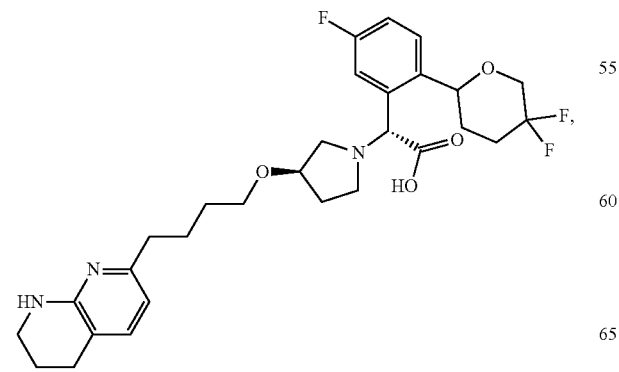
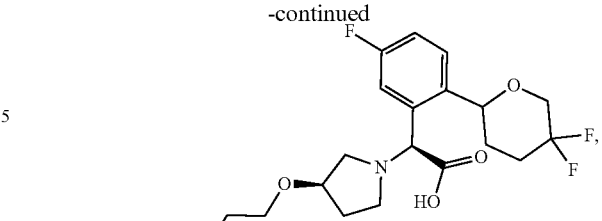
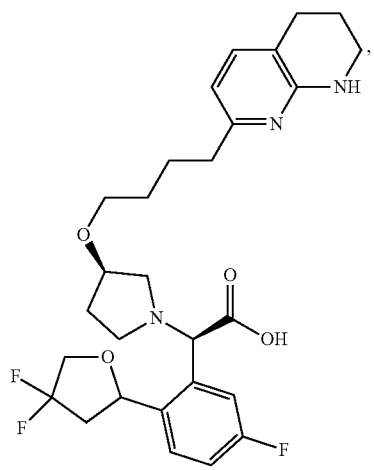
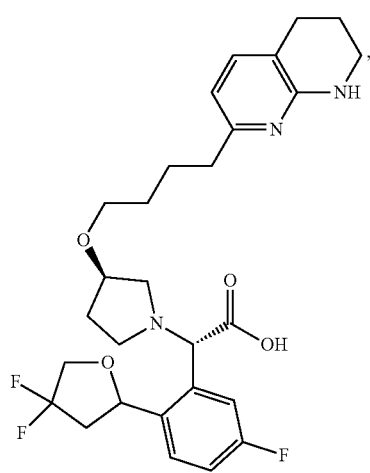

97
-continued
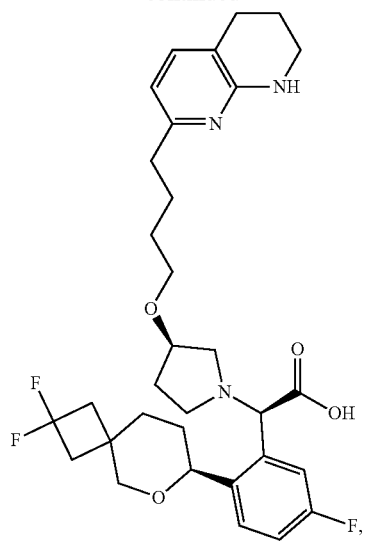
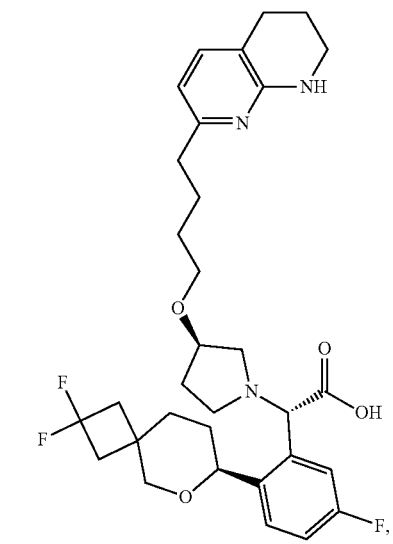
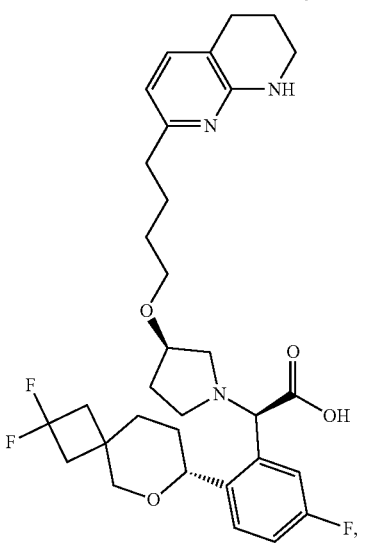
, and
98
-continued
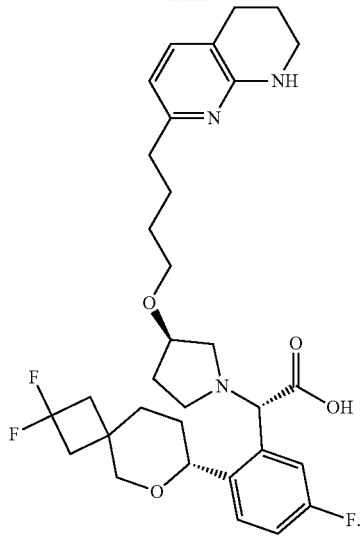 [SMILES: O=C(O)[C@H](c1cc(F)ccc1[C@H]1CCC2(CO1)CC(F)(F)C2)N1CC[C@@H](OCCCCc2ccc3c(n2)NCCC3)C1]
In certain embodiments, the invention relates to a compound selected from the group consisting of:
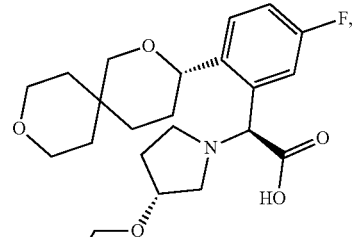
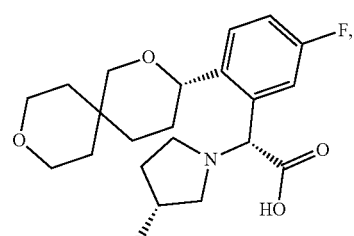
and

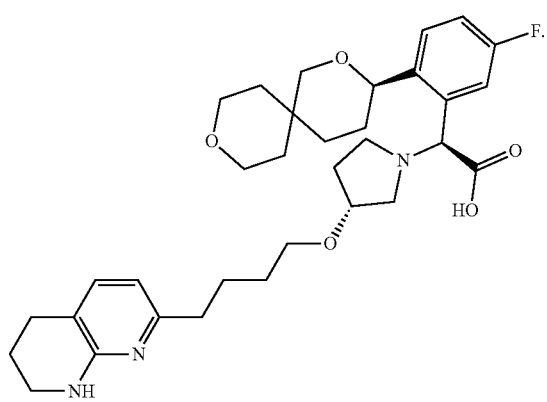 [SMILES: O=C(O)[C@H](c1cc(F)ccc1[C@H]1CCC2(CCOCC2)CO1)N1CC[C@@H](OCCCCc2ccc3c(n2)NCCC3)C1]
In certain embodiments, the invention relates to a compound selected from the group consisting of:
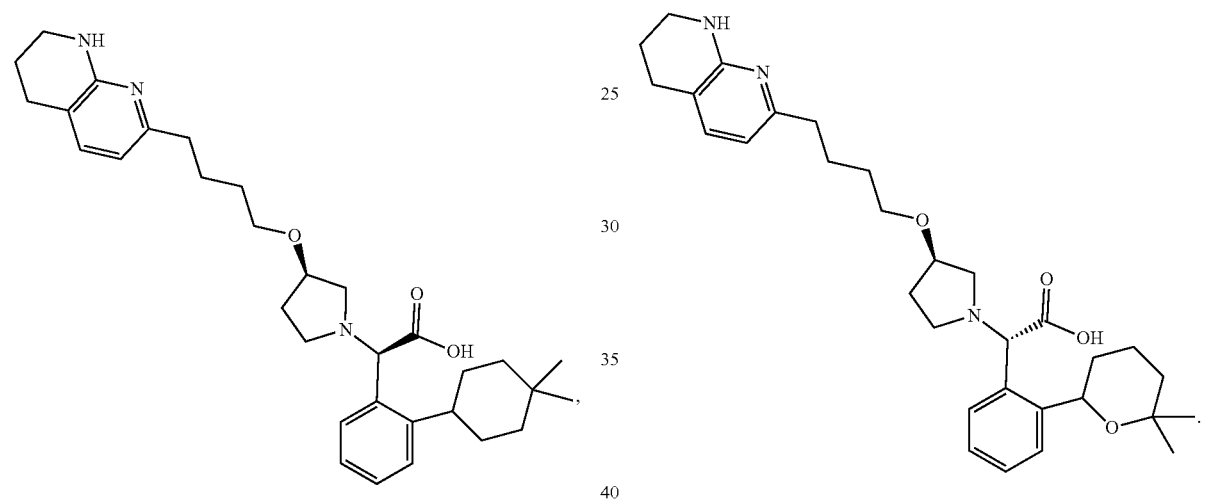
and
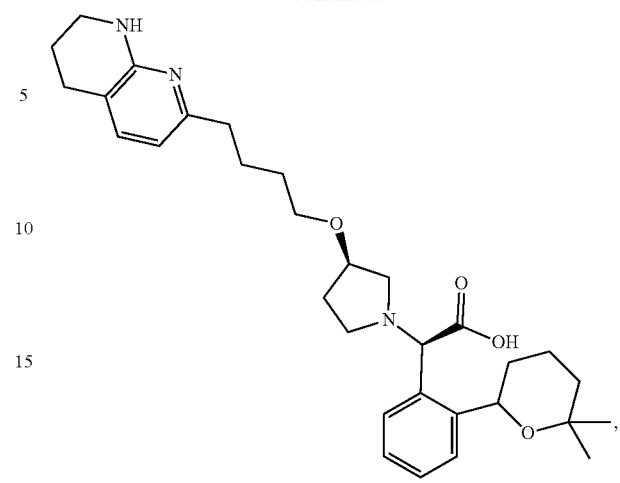
In certain embodiments, the invention relates to a compound selected from the group consisting of:
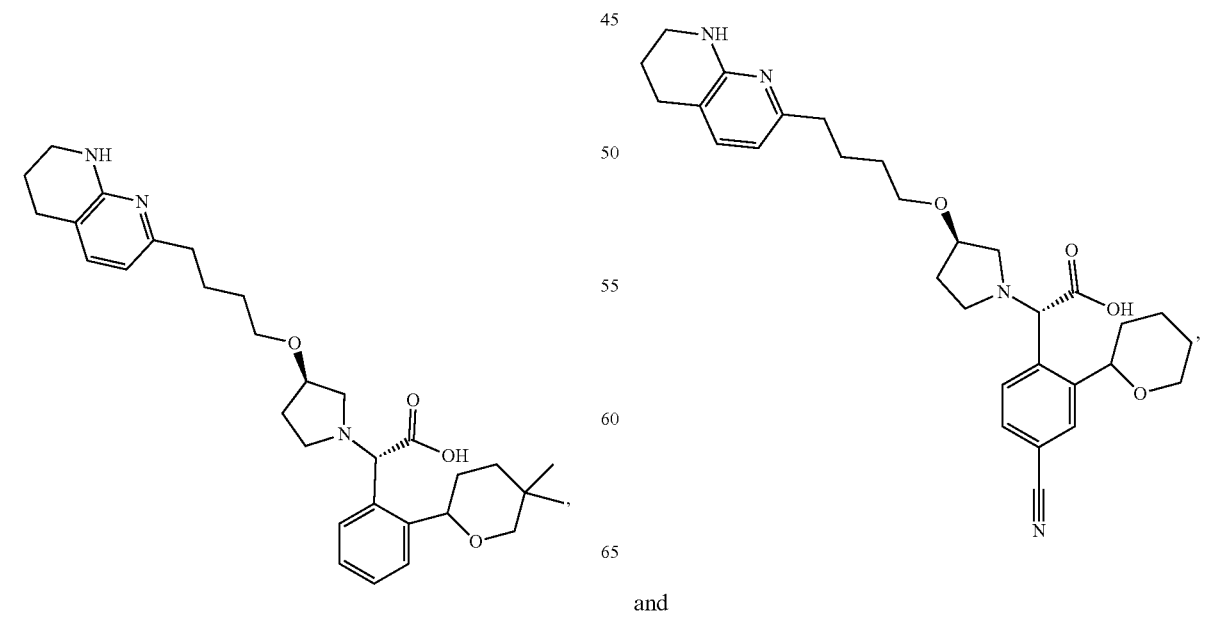
and

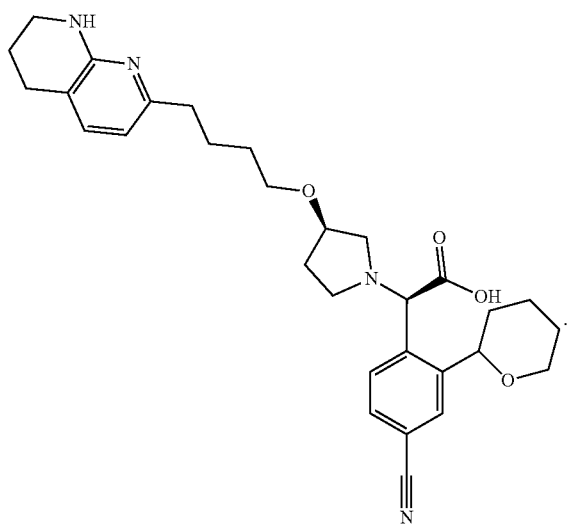 [SMILES: N#Cc1ccc([C@H](C(=O)O)N2CC[C@@H](OCCCCc3ccc4c(n3)NCCC4)C2)c(C2CCCCO2)c1]
In certain embodiments, the invention relates to a compound selected from the group consisting of:
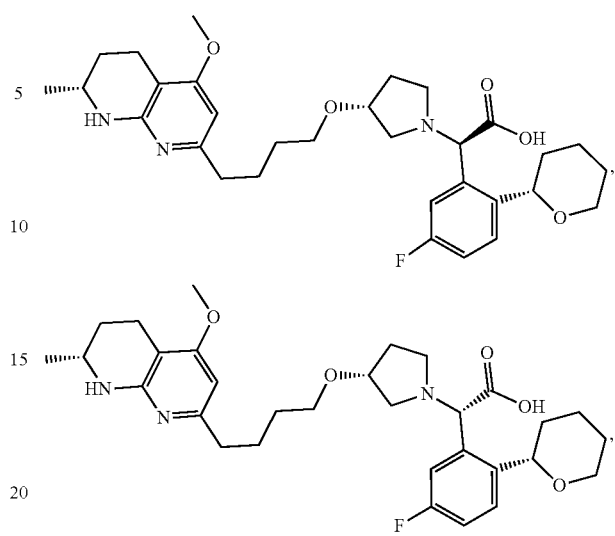
and
In certain embodiments, the invention relates to a compound selected from the group consisting of:
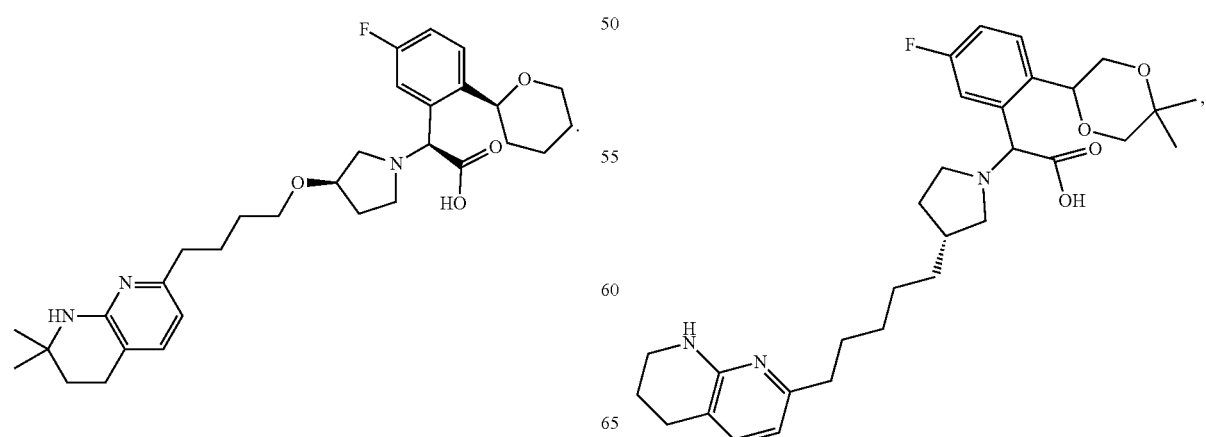
In certain embodiments, the invention relates to a compound selected from the group consisting of:

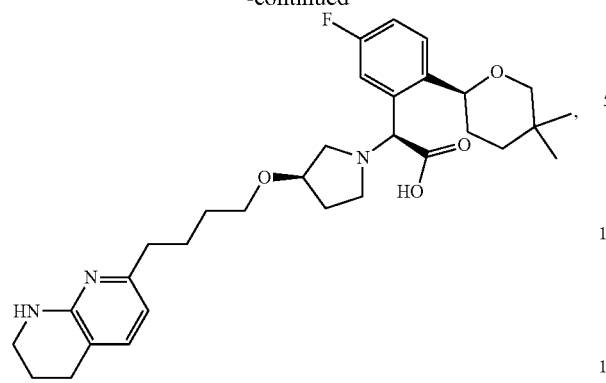
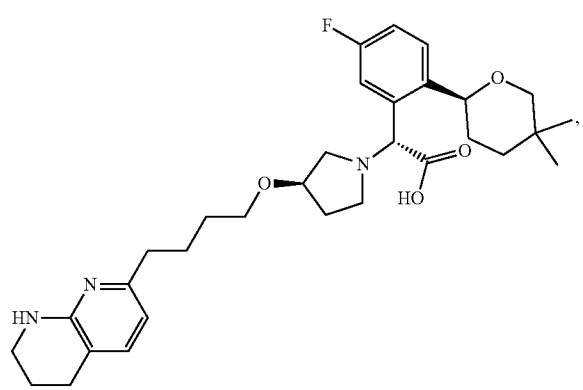
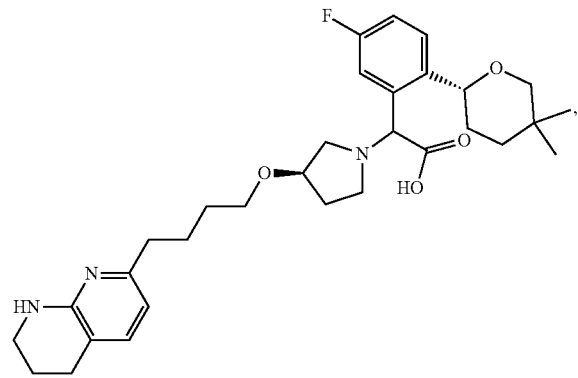
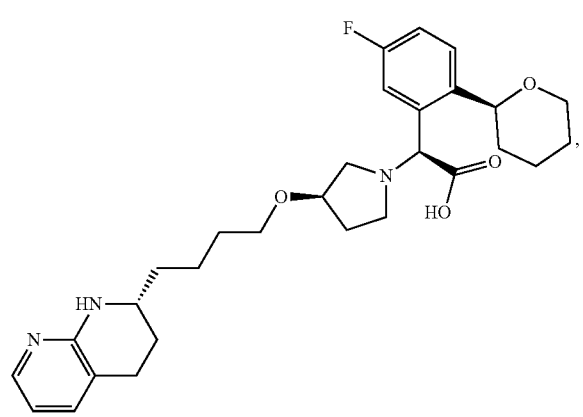
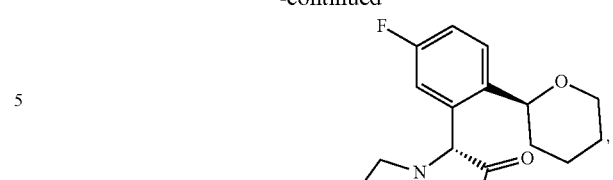
and
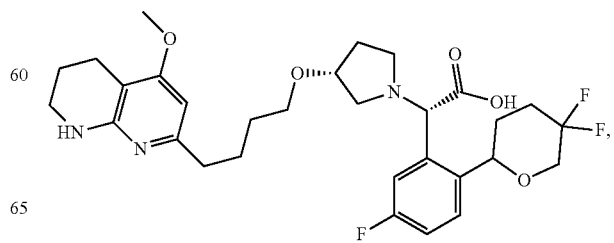
In certain embodiments, the invention relates to a compound selected from the group consisting of:

-continued


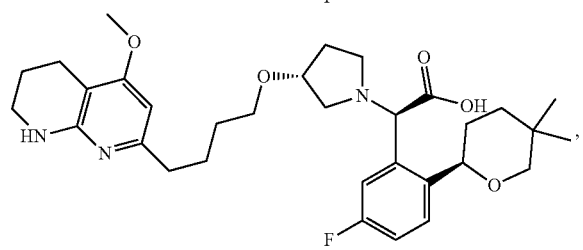

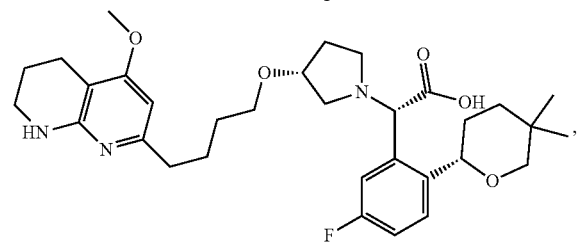

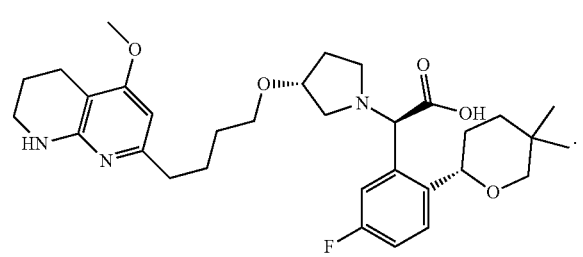

In certain embodiments, the invention relates to a compound selected from the group consisting of:

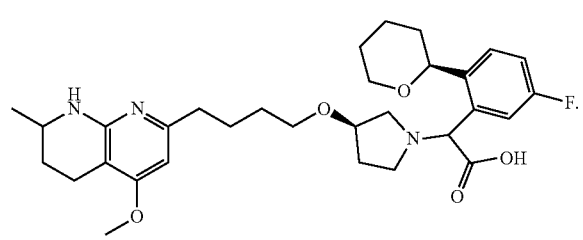 [SMILES: COc1cc(CCCCO[C@@H]2CCN(C(C(=O)O)c3cc(F)ccc3[C@@H]3CCCCO3)C2)nc2c1CCC(C)N2]

In some embodiments, the invention relates to a compound selected from the group consisting of:

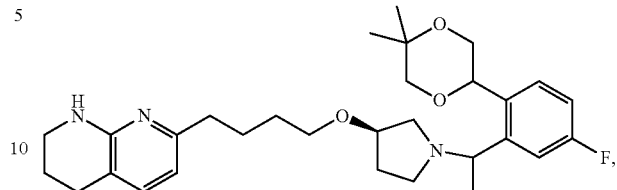

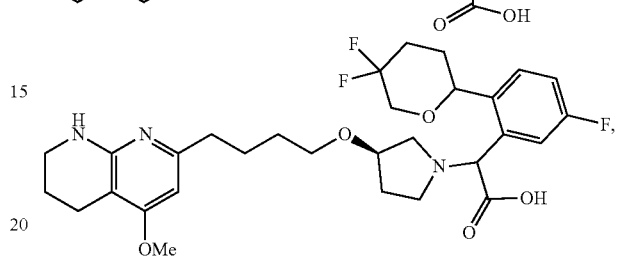

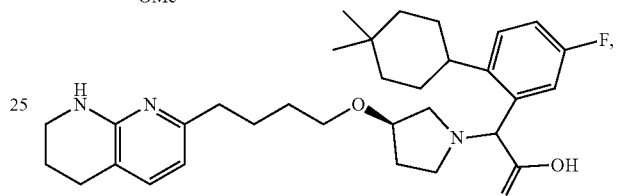

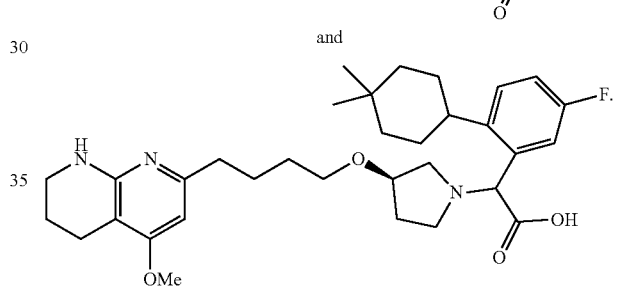

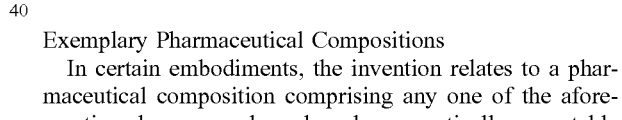

Exemplary Pharmaceutical Compositions

In certain embodiments, the invention relates to a pharmaceutical composition comprising any one of the aforementioned compounds and a pharmaceutically acceptable carrier.

Patients, including but not limited to humans, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

In certain embodiments, the mode of administration of the active compound is oral. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, unit dosage forms can contain various other materials that modify the physical form of the dosage unit, for example, coatings of sugar, shellac, or other enteric agents.

The compound can be administered as a component of an elixir, suspension, syrup, wafer, chewing gum or the like. A syrup can contain, in addition to the active compound(s), sucrose or sweetener as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories or other antivirals, including but not limited to nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents, such as ethylenediaminetetraacetic acid; buffers, such as acetates, citrates or phosphates, and agents for the adjustment of tonicity, such as sodium chloride or dextrose. The parental preparation can be enclosed in ampoules, disposable syringes or multiple dose vials made of glass or plastic.

If administered intravenously, carriers include physiological saline and phosphate buffered saline (PBS).

In certain embodiments, the active compounds are prepared with carriers that will protect the compound against rapid elimination from the body, such as a controlled release formulation, including but not limited to implants and microencapsulated delivery systems. Biodegradable, biocompatible polymers can be used, such as ethylene vinyl acetate, polyanhydrides, polyglycolic acid, collagen, polyorthoesters and polylactic acid. For example, enterically coated compounds can be used to protect cleavage by stomach acid. Methods for preparation of such formulations will be apparent to those skilled in the art. Suitable materials can also be obtained commercially.

Liposomal suspensions (including but not limited to liposomes targeted to infected cells with monoclonal antibodies to viral antigens) are also preferred as pharmaceutically acceptable carriers. These can be prepared according to methods known to those skilled in the art, for example, as described in U.S. Pat. No. 4,522,811 (incorporated by reference). For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

Exemplary Methods of the Invention

In certain embodiments, the invention relates to a method of treating a disease or a condition selected from the group consisting of idiopathic pulmonary fibrosis, diabetic nephropathy, focal segmental glomerulosclerosis, chronic kidney disease, nonalcoholic steatohepatitis, primary biliary cholangitis, primary sclerosing cholangitis, solid tumors, hematological tumors, organ transplant, Alport syndrome, interstitial lung disease, radiation-induced fibrosis, bleomycin-induced fibrosis, asbestos-induced fibrosis, flu-induced fibrosis, coagulation-induced fibrosis, vascular injury-induced fibrosis, aortic stenosis, and cardiac fibrosis comprising the step of: administering to a subject in need thereof a therapeutically effective amount of any one of the aforementioned compounds.

In certain embodiments, the invention relates to any one of the aforementioned methods, wherein the disease or condition is a solid tumor (sarcomas, carcinomas, and lymphonas). Exemplary tumors that may be treated in accordance with the invention include e.g., Ewing's sarcoma, rhabdomyosarcoma, osteosarcoma, myelosarcoma, chondrosarcoma, liposarcoma, leiomyosarcoma, soft tissue sarcoma, non-small cell lung cancer, small cell lung cancer, bronchus cancer, prostate cancer, breast cancer, pancreatic cancer, gastrointestinal cancer, colon cancer, rectum cancer, colon carcinoma, colorectal adenoma, thyroid cancer, liver cancer, intrahepatic bile duct cancer, hepatocellular cancer, adrenal gland cancer, stomach cancer, gastric cancer, glioma (e.g., adult, childhood brain stem, childhood cerebral astrocytoma, childhood visual pathway and hypothalamic), glioblastoma, endometrial cancer, melanoma, kidney cancer, renal pelvis cancer, urinary bladder cancer, uterine corpus, uterine cervical cancer, vaginal cancer, ovarian cancer, multiple myeloma, esophageal cancer, brain cancer (e.g., brain stem glioma, cerebellar astrocytoma, cerebral astrocytoma/malignant glioma, ependymoma, medulloblastoma, supratentorial primitive neuroectodermal tumors, visual pathway and hypothalamic glioma), lip and oral cavity and pharynx, larynx, small intestine, melanoma, villous colon adenoma, a neoplasia, a neoplasia of epithelial character, lymphomas (e.g., AIDS-related, Burkitt's, cutaneous T-cell, Hodgkin, non-Hodgkin, and primary central nervous system), a mammary carcinoma, basal cell carcinoma, squamous cell carcinoma, actinic keratosis, tumor diseases, including solid tumors, a tumor of the neck or head, polycythemia vera, essential thrombocythemia, myelofibrosis with myeloid metaplasia, Waldenstrom's macroglobulinemia, adrenocortical carcinoma, AIDS-related cancers, childhood cerebellar astrocytoma, childhood cerebellar astrocytoma, basal cell carcinoma, extrahepatic bile duct cancer, malignant fibrous histiocytoma bone cancer, bronchial adenomas/carcinoids, carcinoid tumor, gastrointestinal carcinoid tumor, primary central nervous system, cerebellar astrocytoma, childhood cancers, ependymoma, extracranial germ cell tumor, extragonadal germ cell tumor, extrahepatic bile duct cancer, intraocular melanoma eye cancer, retinoblastoma eye cancer, gallbladder cancer, gastrointestinal carcinoid tumor, germ cell tumors (e.g., extracranial, extragonadal, and ovarian), gestational trophoblastic tumor, hepatocellular cancer, hypopharyngeal cancer, hypothalamic and visual pathway glioma, islet cell carcinoma (endocrine pancreas), laryngeal cancer, malignant fibroushistiocytoma of bone/osteosarcoma, medulloblastoma, mesothelioma, metastatic squamous neck cancer with occult primary, multiple endocrine neoplasia syndrome, multiple myeloma/plasma cell neoplasm, mycosis fungoides, nasal cavity and paranasal sinus cancer, nasopharyngeal cancer, neuroblastoma, oral cancer, oropharyngeal cancer, ovarian epithelial cancer, ovarian germ cell tumor, ovarian low malignant potential tumor, islet cell pancreatic cancer, parathyroid cancer, pheochromocytoma, pineoblastoma, pituitary tumor, pleuropulmonary blastoma, ureter transitional cell cancer, retinoblastoma, rhabdomyosarcoma, salivary gland cancer, Sezary syndrome, non-melanoma skin cancer, Merkel cell carcinoma, squamous cell carcinoma, testicular cancer, thymoma, gestational trophoblastic tumor, and Wilms' tumor.

In certain embodiments, the invention relates to any one of the aforementioned methods, wherein the disease is disease or condition is a hematological tumor. Exemplary homatological tumors that may be treated in accordance with the invention include e.g., acute lymphocytic leukemia, acute myelogenous leukemia, chronic lymphocytic leukemia, chronic myelogenous leukemia, Hodgkin lymphoma, non-Hodgkin lymphoma, and multiple myeloma.

In certain embodiments, the invention relates to any one of the aforementioned methods, wherein the disease or condition is selected from the group consisting of idiopathic pulmonary fibrosis, systemic sclerosis associated interstitial lung disease, myositis associated interstitial lung disease, systemic lupus erythematosus associated interstitial lung disease, rheumatoid arthritis, and associated interstitial lung disease.

In certain embodiments, the invention relates to any one of the aforementioned methods, wherein the disease or condition is selected from the group consisting of diabetic nephropathy, focal segmental glomerulosclerosis, and chronic kidney disease.

In certain embodiments, the invention relates to any one of the aforementioned methods, wherein the disease or condition is selected from the group consisting of nonalcoholic steatohepatitis, primary biliary cholangitis, and primary sclerosing cholangitis.

In certain embodiments, the invention relates to any one of the aforementioned methods, wherein the subject is a mammal. In certain embodiments, the invention relates to any one of the aforementioned methods, wherein the subject is human.

Additional Numeric Embodiments

1. A compound of formula (I):

A-B—C  (I)

wherein:
A is

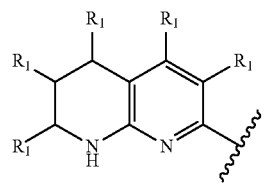

or

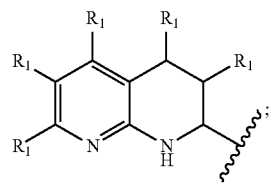

B is alkylene, -alkylene-(heterocyclyl)-alkylene-, -(heterocyclyl)-alkylene-, -cycloalkylene, -alkylene-O—, -cycloalkylene-O—, or -alkylene-O-alkylene-;

C is

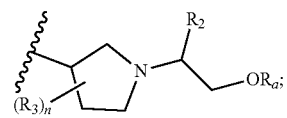

$R_1$ is independently H, alkyl, halide, alkoxy, $CF_3$, OH, alkylene-OH, $NO_2$, or —N(H)$R_a$;

$R_2$ is

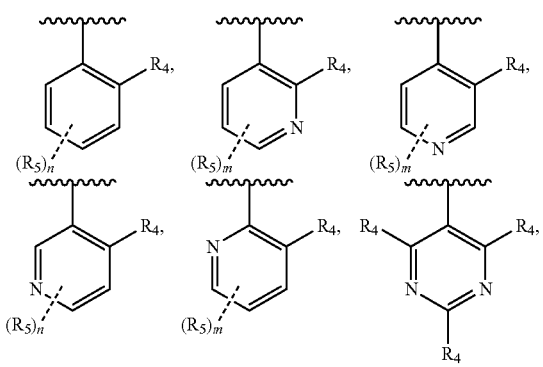

or

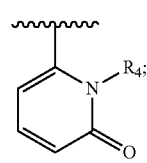

$R_3$ and $R_5$ are independently selected from H, —CN, halide, $CF_3$, C(H)$F_2$, C(F)$H_2$, alkyl, cycloalkyl, -alkylene-alkoxy, aryl, hydroxyl, and alkoxy;

R$_4$ is independently selected from alkyl, —C(F$_2$)CH$_3$, cycloalkyl, heterocycloalkyl, -alkylene-cycloalkyl, —O-alkylene-cycloalkyl, —O-cycloalkyl, —O-alkyl, -alkylene-O-alkyl, -alkylene-O-cycloalkyl, and -alkylene-O-alkylene-cycloalkyl;

R$_a$ is H, (C$_1$-C$_6$)alkyl, —(C$_1$-C$_6$)alkylene-O—(C$_1$-C$_6$)alkyl, or —(C$_1$-C$_6$)alkylene-O—C(O)O(C$_1$-C$_6$)alkyl;

n is independently 0, 1, 2, 3, or 4;

m is 0, 1, 2, or 3; and the absolute configuration at any stereocenter is R, S, or a mixture thereof, or a pharmaceutically acceptable salt thereof.

2. The compound of embodiment 1, wherein B is selected from the group consisting of:

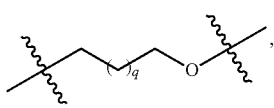

and

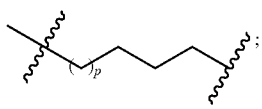

q is 0, 1, 2, or 3; and p is 0, 1, or 2.

3. The compound of embodiment 1, wherein B is -alkylene-O-alkylene-.

4. The compound of embodiment 3, wherein -alkylene-O-alkylene- is -methylene-O-propylene, -ethylene-O-ethylene, or -propylene-O-methylene.

5. The compound of anyone of embodiments 1-4, wherein at least one instance of R$_1$ is alkyl, halide, OMe, OH, alkylene-OH, or NH$_2$.

6. The compound of embodiment 5, wherein the at least one instance of R$_1$ is OMe.

7. The compound of anyone of embodiments 1-4, wherein all instances of R$_1$ are H.

8. The compound of any one of embodiments 1-7, wherein R$_2$ is

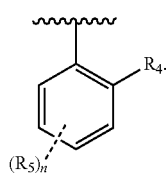

9. The compound of embodiment 8, wherein n in R$_2$ is 0.

10. The compound of embodiment 8, wherein n in R$_2$ is 1.

11. The compound of any one of embodiments 1-7, wherein R$_2$ is

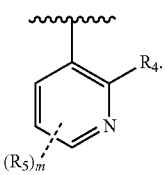

12. The compound of embodiment 11, wherein m in R$_2$ is 0.

13. The compound of embodiment 11, wherein m in R$_2$ is 1.

14. The compound of embodiment 1, 8, 10, 11, or 13, wherein R$_5$ is F.

15. The compound of embodiment 1, 8, 10, 11, or 13, wherein R$_5$ is CN.

16. The compound of any one of embodiments 1-7, wherein R$_2$ is

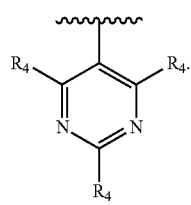

17. The compound of any one of embodiments 1-16, wherein cycloalkyl is cyclopropyl, cyclobutyl, cylcopentyl, or cyclohexyl.

18. The compound of any one of embodiments 1-16, wherein alkyl is methyl, ethyl, iso-propyl, or tert-butyl.

19. The compound of any one of embodiments 1-18, wherein R$_3$ is H, halide, Me, OMe, or Ph.

20. The compound of any one of embodiments 1-19, wherein R$_4$ is independently selected from -alkylene-cycloalkyl, —O-alkylene-cycloalkyl; -alkylene-O-alkyl, -alkylene-O-cycloalkyl, and -alkylene-O-alkylene-cycloalkyl.

21. The compound of embodiment 20, wherein alkylene in R$_4$ is methylene or ethylene.

22. The compound of any one of embodiments 1-19, wherein R$_4$ is selected from

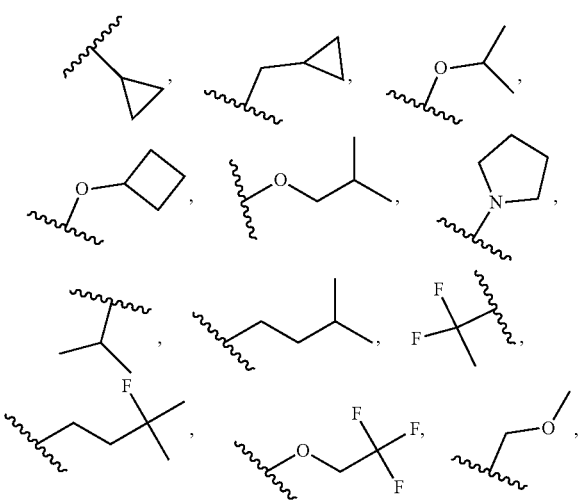

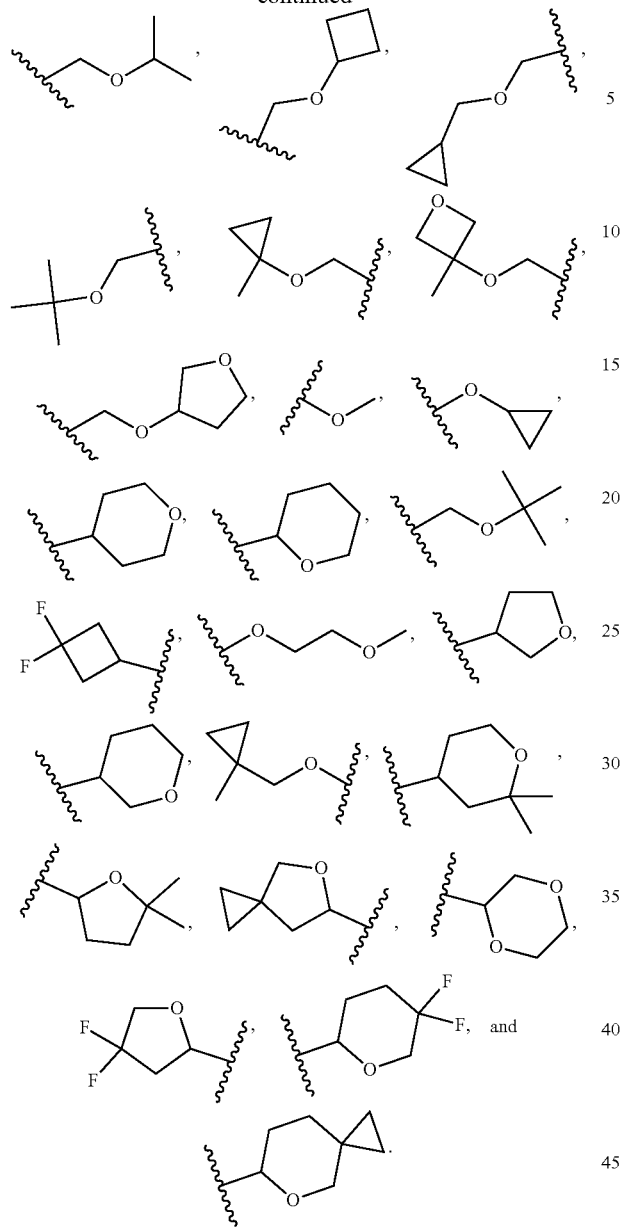

23. The compound of any one of embodiments 1-19, wherein $R_4$ is selected from

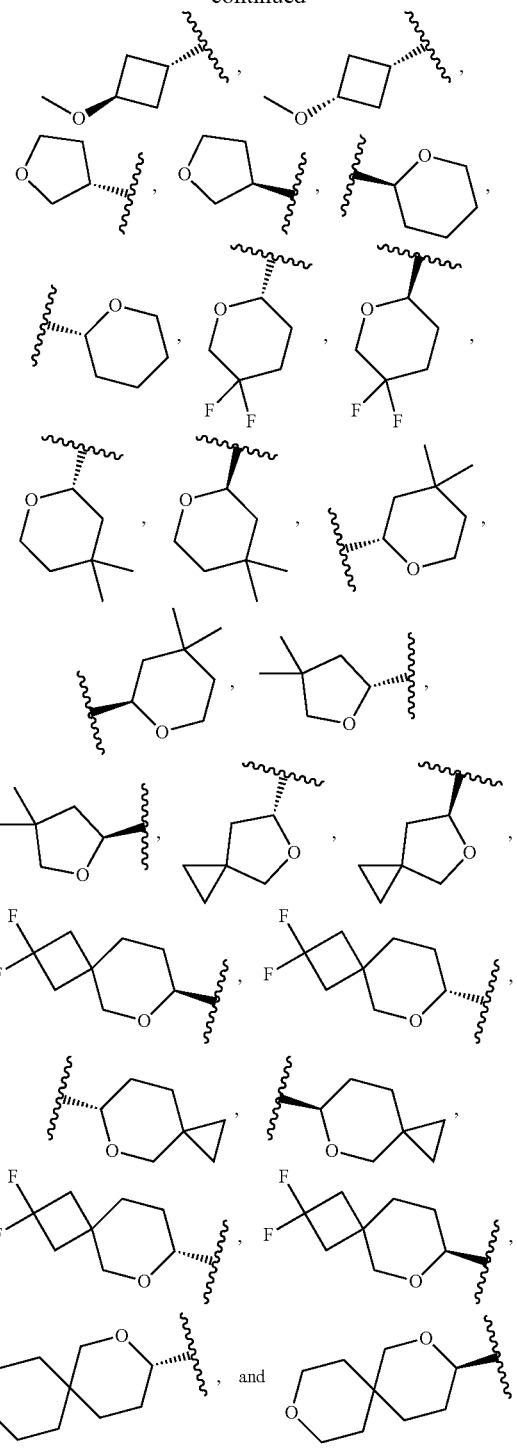

24. The compound of any one of embodiments 1-23, wherein $R_a$ is H.

EXEMPLIFICATION

The invention now being generally described, it will be more readily understood by reference to the following examples, which are included merely for purposes of illustration of certain aspects and embodiments of the present invention, and are not intended to limit the invention.

General Schemes and Procedures for the Preparation of Compounds of the Invention The moiety $R_1$ and $R_2$ represents appropriate substituents; L represents an appropriate linker, and X represents an appropriate halogen, such as Br, Cl or I, or another leaving group such as mesylate or tosylate.

represents an appropriate optionally substituted pyrrolidine.

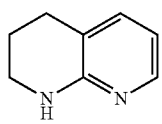

represents an appropriate optionally substituted tetrahydronaphthyridine.

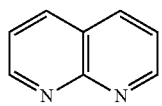

represents an appropriate optionally substituted naphthyridine.

General Schemes for the synthesis of αvβ6 inhibitors

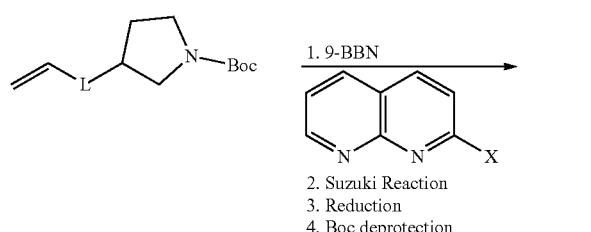

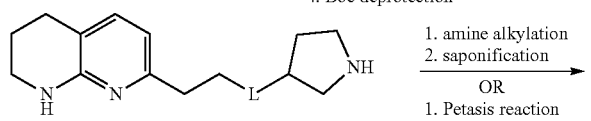

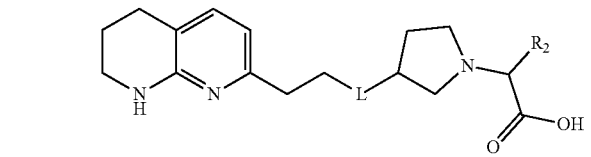

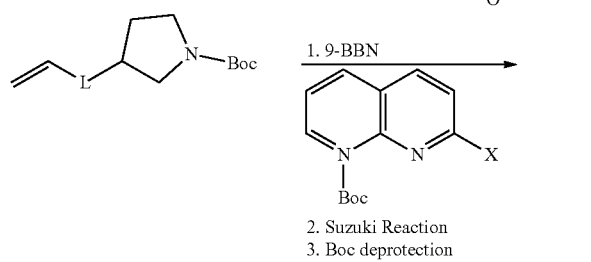

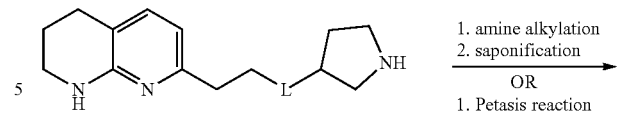

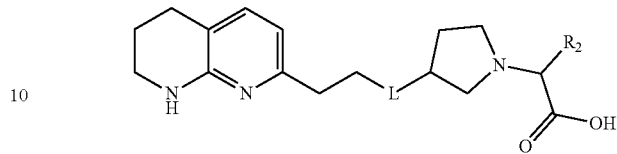

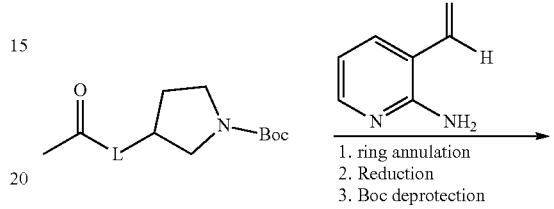

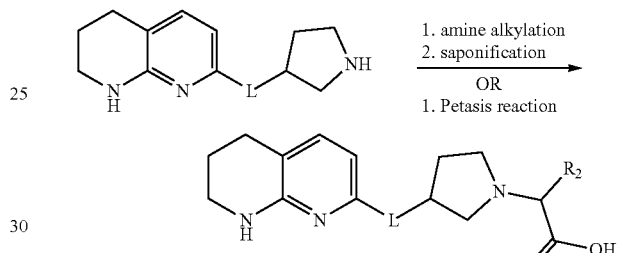

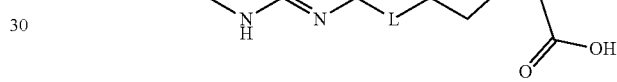

General Procedures

9-BBN and Suzuki Reactions

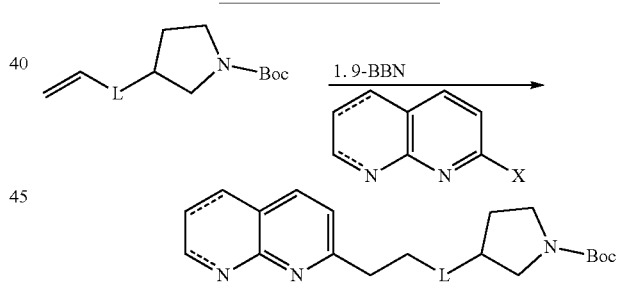

Alkene intermediates may be cross-coupled to 2-halo naphthyridines or tetrahydronaphthyridines by the following procedure. To a solution of alkene (1 equiv.) in dry THF (2-10 mL/mmol) under Ar was added 9-BBN (0.5M solution in THF, 1-2 equiv.). The reaction was stirred at 40-80° C. for 1-4 hours, then cooled to room temperature. This solution was added to a mixture of 2-halonaphthyridine or Boc-protected 2-halotetrahydronaphthyridine (1-1.5 equiv.), cesium carbonate (2-5 equiv.) and Pd(PPh3)4 or another appropriate Pd/ligand combination (0.05 to 0.1 equiv.) in 1,4-Dioxane (2-10 mL/mmol). The reaction was stirred at 80-100° C. for 12-24 hours. Solvent was removed in vacuo, and the residue was purified by silica gel column to give the alkyl linked naphthyridine product.

Ring Annulations

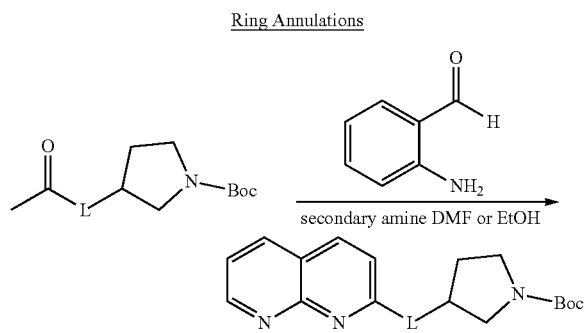

Naphthyridines may also be made from methyl ketones by the following procedure. A mixture of methyl ketone (1 equiv.), 2-aminonicotinaldehyde (1-2 equiv.) and secondary amine such as pyrrolidine or L-proline (1-2 equiv.) in DMF or EtOH (1-10 mL/mmol) was stirred at 70-100° C. for 2-10 hours. Solvent was removed in vacuo, and the residue was purified by silica gel column to give the desired naphthyridine product.

Naphthyridine Reduction

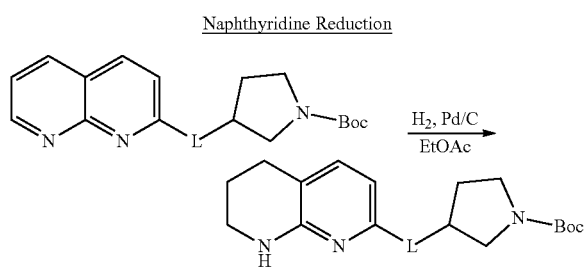

Naphthyridines may be reduced to tetrahydronaphthyridines by the following procedure. A mixture of an appropriate naphthyridine (1 equiv.) and Pd/C (5-20 weight percent Pd, 0.05 to 0.2 equiv.) in ethyl acetate or another appropriate solvent (2-10 mL/mmol) was stirred under $H_2$ balloon at room temperature to 50° C. for 2-20 hours. The reaction was filtered and concentrated in vacuo to give the desired tetrahydronaphthyridine product.

Boc Deprotection

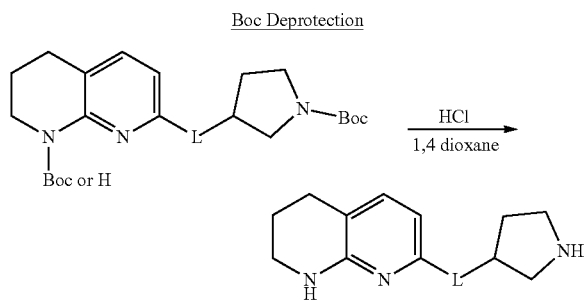

Boc-protected amine (1 equiv.) was treated with HCl (4-100 equiv.) in 1,4-dioxane (1-50 mL/mmol amine) at room temperature to 50° C. for 1-4 hours. The reaction was concentrated in vacuo, and the amine product was used crude or after purification by silica gel column. The amine could be used crude as a dihydrochloride salt or converted to the free base by dissolving in an appropriate solvent and washing with aqueous $NaHCO_3$.

Amine alkylation:

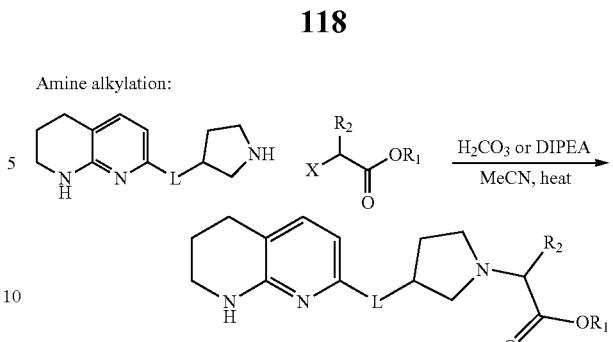

A mixture of amine (1 equiv.), alkylating agent (1-1.5 equiv.) and K2CO3 or N,N-diisopropylethylamine (2-10 equiv.) in MeCN or DMF (3-10 mL/mmole amine) was stirred at room temperature to 80° C. for 4-16 hours. The reaction was concentrated in vacuo, and the residue was purified by silica gel column to give the desired amino acetic acid ester. The amine used may be the free base or a salt such hydrochloride or dihydrochloride. If the reaction is done with a salt of the amine, additional equivalents of base may be needed.

Saponification:

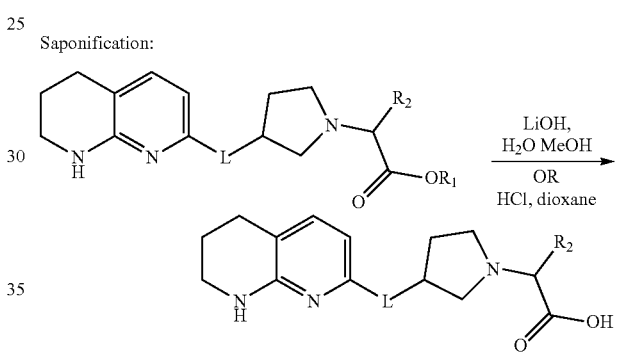

For certain esters such as $R_1$=Me or ethyl, the ester may be saponified under basic conditions. The ester (1 equiv.) was treated with $LiOH \cdot H_2O$ (3-5 equiv.) in MeOH (3-10 mL/mmol ester) and water (3-10 mL/mmol ester) at room temperature to 50° C. for 1-16 hours. The reaction was concentrated in vacuo, and the residue was purified by prep HPLC to give the desired carboxylic acid product.

For certain esters such as $R_1$=tert-butyl, the ester may be saponified under acidic conditions. The ester (1 equiv.) was treated with 4 N HCl (4-100 equiv.) in 1,4-dioxane (1-25 mL/mmol ester) at room temperature to 50° C. for 1-16 hours. The reaction was concentrated in vacuo, and the residue was purified by prep HPLC to give the desired carboxylic acid product.

Petasis reaction:

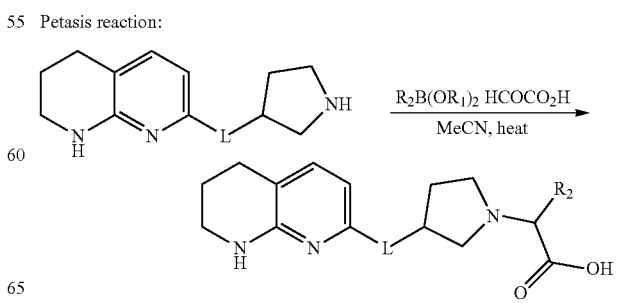

As an alternative to the amine alkylation/saponification sequence, a Petasis reaction can be used to prepare certain aryl analogs: A mixture of amine (1 equiv.) aryl boronic acid or aryl boronate ester (1-1.5 equiv.) and 2-oxoacetic acid (1.5-2 equiv.) in MeCN or DMF (2-10 mL/mmole amine) was stirred at 50-80° C. for 2-16 hours. The reaction was concentrated in vacuo, and the residue was purified by prep HPLC to give the desired amino acetic acid.

Analytical Methods

Prep-HPLC Methods

Crude samples were dissolved in MeOH and purified by prep HPLC using a Gilson 215 instrument, detection wavelength 214 nm:

Prep HPLC A: column: XBridge C18, 21.2*250 mm, 10 μm; mobile phase: A water (10 mM ammonium hydrogen carbonate), B $CH_3CN$; gradient elution as in text; flow rate: 20 mL/min.

Prep HPLC B: column: XBridge C18, 21.2*250 mm, 10 μm; mobile phase: A water (10 mM formic acid), B $CH_3CN$; gradient elution as in text; flow rate: 20 mL/min.

Prep HPLC C: column: XBridge OBD C18, 19*100 mm, 5 μm; mobile phase: A water, B $CH_3CN$; gradient elution as in text; flow rate: 20 mL/min.

Prep Chiral SFC Methods

Racemic products were separated to individual enantiomers by chiral Prep SFC using an SFC-80 (Thar, Waters) instrument, detection wavelength 214 nm:

Prep chiral SFC A: column: (R,R)-Whelk-O1, 20*250 mm, 5 μm (Decial), column temperature: 35° C., mobile phase: $CO_2$/methanol (0.2% methanol ammonia)=60/40, flow rate: 80 g/min, back pressure: 100 bar.

Prep chiral SFC B: column: AD 20*250 mm, 10 μm (Daicel), column temperature: 35° C.,
mobile phase: $CO_2$/methanol (0.2% methanol ammonia)=60/40, flow rate: 80 g/min, back pressure: 100 bar.

Prep chiral SFC C: column: AS 20*250 mm, 10 μm (Daicel), column temperature: 35° C.,
mobile phase: $CO_2$/methanol (0.2% methanol ammonia)=60/40, flow rate: 80 g/min, back pressure: 100 bar.

Prep chiral SFC D: column: OD 20*250 mm, 10 μm (Daicel), column temperature: 35° C.,
mobile phase: $CO_2$/methanol (0.2% methanol ammonia)=60/40, flow rate: 80 g/min, back pressure: 100 bar.

Prep chiral SFC E: column: Cellulose-SC 20*250 mm, 10 μm (Daicel), column temperature: 35° C., mobile phase: $CO_2$/methanol (0.2% methanol ammonia)=60/40, flow rate: 80 g/min, back pressure: 100 bar.

Prep chiral SFC F: column: OZ 20*250 mm, 10 μm (Daicel), column temperature: 35° C., mobile phase: $CO_2$/methanol (0.2% methanol ammonia)=60/40, flow rate: 80 g/min, back pressure: 100 bar.

Prep chiral SFC G: column: IC 20*250 mm, 10 μm (Daicel), column temperature: 35° C., mobile phase: $CO_2$/methanol (0.2% methanol ammonia)=60/40, flow rate: 80 g/min, back pressure: 100 bar.

Prep chiral SFC H: column: (S,S)-Whelk-O1, 20*250 mm, 5 μm (Decial), column temperature: 35° C., mobile phase: $CO_2$/methanol (0.2% methanol ammonia)=60/40, flow rate: 80 g/min, back pressure: 100 bar.

Analytical Chiral SFC Methods

Chiral products were analyzed by chiral SFC using an SFC-80 (Thar, Waters) instrument, detection wavelength 214 nm:

Chiral SFC A: column: (R,R)-Whelk-01, 4.6*100 mm, 5 μm (Decial), column temperature: 40° C., mobile phase: $CO_2$/methanol (0.2% methanol ammonia), isocratic elution as in text, flow rate: 4 g/min, back pressure: 120 bar.

Chiral SFC B: column: AD 4.6*100 mm, 5 μm (Daicel), column temperature: 40° C.,
mobile phase: $CO_2$/methanol (0.2% methanol ammonia), isocratic elution as in text, flow rate: 4 g/min, back pressure: 120 bar.

Chiral SFC C: column: AS 4.6*100 mm, 5 μm (Daicel), column temperature: 40° C.,
mobile phase: $CO_2$/methanol (0.2% methanol ammonia), isocratic elution as in text, flow rate: 4 g/min, back pressure: 120 bar.

Chiral SFC D: column: OD 4.6*100 mm, 5 μm (Daicel), column temperature: 40° C., mobile phase: $CO_2$/methanol (0.2% methanol ammonia), isocratic elution as in text, flow rate: 4 g/min, back pressure: 120 bar.

Chiral SFC E: column: Cellulose-SC 4.6*100 mm, 5 μm (Daicel), column temperature: 40° C., mobile phase: $CO_2$/methanol (0.2% methanol ammonia), isocratic elution as in text, flow rate: 4 g/min, back pressure: 120 bar.

Chiral SFC F: column: OZ 4.6*100 mm, 5 μm (Daicel), column temperature: 40° C.,
mobile phase: $CO_2$/methanol (0.2% methanol ammonia), isocratic elution as in text, flow rate: 4 g/min, back pressure: 120 bar.

Chiral SFC G: column: IC 4.6*100 mm, 5 μm (Daicel), column temperature: 40° C.,
mobile phase: $CO_2$/methanol (0.2% methanol ammonia), isocratic elution as in text, flow rate: 4 g/min, back pressure: 120 bar.

Chiral SFC H: column: (S,S)-Whelk-O1, 4.6*100 mm, 5 μm (Decial), column temperature: 40° C., mobile phase: $CO_2$/methanol (0.2% methanol ammonia), isocratic elution as in text, flow rate: 4 g/min, back pressure: 120 bar.

Chiral SFC I: column: IC 4.6*250 mm, 5 μm (SHIMADZU), column temperature: 40° C.,
mobile phase: n-Hexane(0.1% DEA):EtOH(0.1% DEA), isocratic elution as in text, flow rate: 1 mL/min.

Chiral SFC J: column: (S,S)-Whelk-O1 4.6*250 mm, 5 μm (SHIMADZU), column temperature: 40° C., mobile phase: n-Hexane(0.1% DEA):EtOH(0.1% DEA), isocratic elution as in text, flow rate: 1 mL/min.

Chiral SFC K: column: OZ-H 4.6*250 mm, 5 μm (SHIMADZU), column temperature: 40° C., mobile phase: n-Hexane(0.1% DEA):EtOH(0.1% DEA), isocratic elution as in text, flow rate: 1 mL/min.

Chiral SFC L: column: chiral PAK IG 4.6*250 mm, 5 μm (SHIMADZU), column temperature: 35° C., mobile phase: n-Hexane(0.1% DEA):EtOH(0.1% DEA), isocratic elution as in text, flow rate: 1 mL/min.

Chiral SFC M: column: EnantioPak OJ 4.6*250 mm, 5 μm (Decial), column temperature: 40° C., mobile phase: n-Hexane(0.1% DEA):EtOH(0.1% DEA), isocratic elution as in text, flow rate: 1 mL/min.

Synthesis of Intermediates

The following intermediates were prepared according to the procedures below for use in synthesizing examples:

Preparation of (R)-7-(4-(pyrrolidin-3-yloxy)butyl)-1,2,3,4-tetrahydro-1,8-naphthyridine Dihydrochloride Step 1: tert (R)-3-(4-(2-methyl-1,3-dioxolan-2-yl)butoxy)pyrrolidine-1-carboxylate

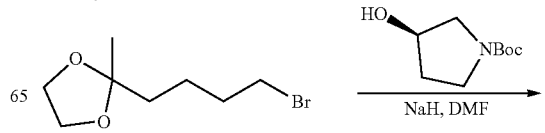

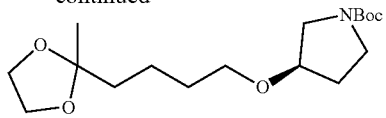

A mixture of (R)-tert-butyl 3-hydroxypyrrolidine-1-carboxylate (1.09 g, 5.41 mmol), 2-(4-bromobutyl)-2-methyl-1,3-dioxolane (1.2 g, 5.41 mmol) and sodium hydride (260 mg, 10.82 mmol) in DMF (5 mL) was stirred at 100° C. for 6 h. Solvent was removed in vacuo, and the residue was purified by silica gel column (pet ether:EtOAc 10:1) to give the desired product (R)-tert-butyl 3-(4-(2-methyl-1,3-dioxolan-2-yl)butoxy)pyrrolidine-1-carboxylate as a colorless oil (380 mg). Yield 21% (ESI 330.2 (M+H)+).

Step 2: (R)-tert-butyl3-(5-oxohexyloxy)pyrrolidine-1-carboxylate

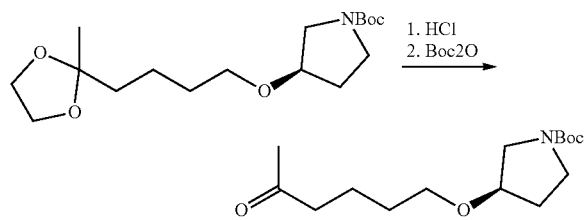

(R)-tert-butyl3-(4-(2-methyl-1,3-dioxolan-2-yl)butoxy)pyrrolidine-1-carboxylate (1.3 g, 3.95 mmol) was treated with a solution of HCl/dioxane (4.0 M, 10 mL) at room temperature for 2 hours. The solvent was removed in vacuo, and the residue was diluted with acetone (10 mL) and H₂O (1 mL). Potassium carbonate was added to adjust the pH to 8-9, followed by Boc₂O (1.24 g, 5.69 mmol). The reaction was stirred at room temperature for 3, then filtered and concentrated under vacuum. The residue was purified by silica gel column (pet ether: EtOAc 15:1) to give the desired product (R)-tert-butyl3-(5-oxohexyloxy)pyrrolidine-1-carboxylate as a colorless oil (820 mg). Yield 73% (ESI 186 (M−100)+, 230 (M−56)+).

Step 3: (R)-tert-butyl 3-(4-(1,8-naphthyridin-2-yl)butoxy)pyrrolidine-1-carboxylate

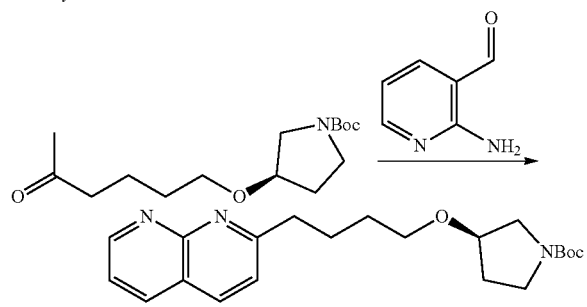

A mixture of (R)-tert-butyl3-(5-oxohexyloxy)pyrrolidine-1-carboxylate (820 mg, 2.88 mmol), 2-aminonicotinaldehyde (456 mg, 3.77 mmol) and pyrrolidine (265 mg, 3.77 mmol) in DMF (5 mL) was stirred at 85° C. for 4 h. Solvent was removed in vacuo, and the residue was purified by silica gel column (DCM:MeOH 15:1) to give the desired product (R)-tert-butyl 3-(4-(1,8-naphthyridin-2-yl)butoxy)pyrrolidine-1-carboxylate as a colorless oil (750 mg). Yield 70% (ESI 372.2 (M+H)+).

Step 4: (R)-7-(4-(pyrrolidin-3-yloxy)butyl)-1,2,3,4-tetrahydro-1,8-naphthyridine dihydrochloride

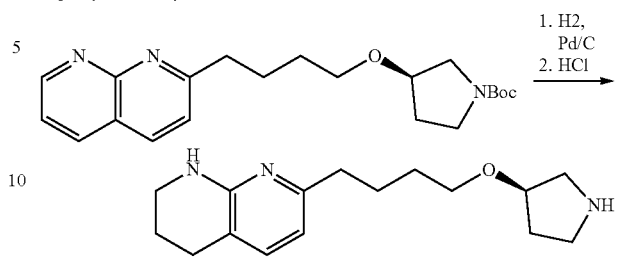

A mixture of (R)-tert-butyl 3-(4-(1,8-naphthyridin-2-yl)butoxy)pyrrolidine-1-carboxylate (750 mg, 2.02 mmol), Pd/C (10%, 500 mg) in EtOAc (10 mL) was stirred at 60° C. for 6 hours under hydrogen. The reaction was filtered and concentrated in vacuo. The residue was treated with a solution of HCl/dioxane (4.0 M, 4 mL) at room temperate for 2 hours, and the solvent was removed in vacuo to give the desired product (R)-7-(4-(pyrrolidin-3-yloxy)butyl)-1,2,3,4-tetrahydro-1,8-naphthyridine dihydrochloride as a white solid (600 mg). Yield 96% (ESI 276.2 (M+H)+).

Preparation of (R)-5-methoxy-7-(4-(pyrrolidin-3-yloxy)butyl)-1,2,3,4-tetrahydro-1,8-naphthyridine Dihydrochloride Step 1: (R)-tert-butyl 3-(4-bromobutoxy)pyrrolidine-1-carboxylate

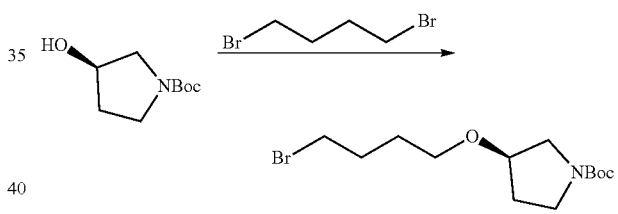

To a solution of tert-butyl (R)-3-hydroxypyrrolidine-1-carboxylate (500 mg, 2.67 mmol) in n-Heptane (10 mL) was added sodium hydroxide 50% solution in water (5 mL, 31.2 mmol), tetrabutylammonium bromide (43.0 mg, 0.13 mmol) and 1,4-dibromobutane (1.595 mL, 13.35 mmol). The mixture was stirred at 80° C. for 2 hours, then cooled to room temperature, diluted with water (10 mL) and extracted with diethyl ether (3×10 mL). The combined organic layers were dried over Na2SO4, filtered and concentrated in vacuo. The residue was purified by silica gel column (pet ether:EtOAc=4:1) to give the desired product (R)-tert-butyl 3-(4-bromobutoxy)pyrrolidine-1-carboxylate as a colorless oil (686 mg). Yield 80% (ESI 314 (M+H-Boc)+).

Step 2: (R)-tert-butyl 3-(but-3-enyloxy)pyrrolidine-1-carboxylate

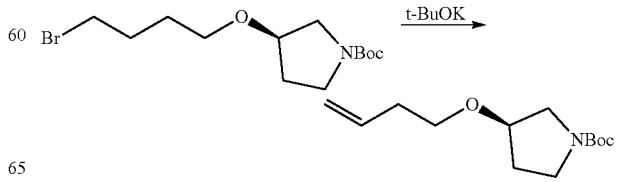

To a solution of tert-butyl (R)-3-(4-bromobutoxy)pyrrolidine-1-carboxylate (512 mg, 1.58 mmol) in THF (10 mL) at 0° C. was added t-BuOK (446 mg, 3.97 mmol). The reaction was stirred at room temperature for 1 hour, then diluted with water (20 mL) and extracted with diethyl ether (3×20 mL). The combined organic layers were dried over sodium sulfate, filtered and concentrated in vacuo to give the desired product (R)-tert-butyl 3-(but-3-enyloxy)pyrrolidine-1-carboxylate as a colorless oil (355 mg). Yield 90% (ESI 186 (M+H-Boc)+).

Step 3: (R)-tert-butyl 3-(4-(4-chloro-1,8-naphthyridin-2-yl)butoxy)pyrrolidine-1-carboxylate

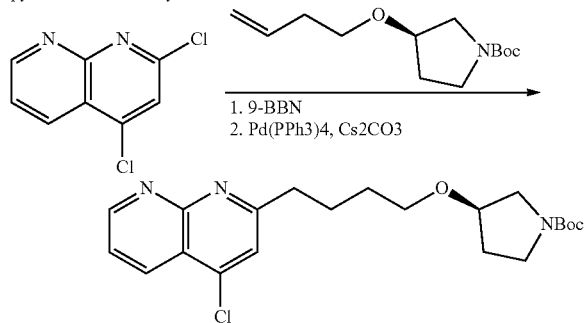

To a solution of tert-butyl (R)-tert-butyl 3-(but-3-enyloxy)pyrrolidine-1-carboxylate (486 mg, 1.8 mmol) in THF (dry, 2 mL) under Ar was added 9-BBN (0.5 M solution in THF, 7.2 mL, 3.6 mmol). The reaction was stirred at 50° C. for 2 hours, then cooled to room temperature. This solution was added to a mixture of 2,4-dichloro-1,8-naphthyridine (360 mg, 1.8 mmol), cesium carbonate (1730 mg, 5.4 mmol) and Pd(PPh3)4 (208 mg, 0.18 mmol) in 1,4-dioxane (7 mL). The reaction was stirred at 90° C. for 1.5 hours. Solvent was removed in vacuo, and the residue was purified by silica gel column (pet ether: EtOAc 1:1 to 1:10) to give the desired product (R)-tert-butyl 3-(4-(4-chloro-1,8-naphthyridin-2-yl)butoxy)pyrrolidine-1-carboxylate as a yellow oil (300 mg). Yield 41% (ESI 406 (M+H)+).

Step 4: (R)-tert-butyl 3-(4-(4-methoxy-1,8-naphthyridin-2-yl)butoxy)pyrrolidine-1-carboxylate

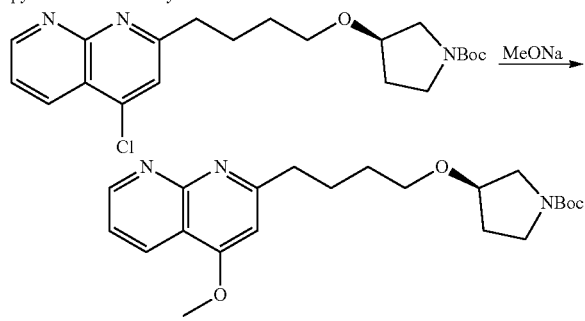

To a solution of (R)-tert-butyl 3-(4-(4-chloro-1,8-naphthyridin-2-yl)butoxy)pyrrolidine-1-carboxylate (76 mg, 0.13 mmol) in MeOH (5 mL) was added NaOMe (45 mg, 0.26 mmol). The reaction was stirred under reflux overnight, then concentrated in vacuo, diluted with ethyl acetate (30 mL), washed with water (2×20 mL), dried over MgSO4, filtered and concentrated in vacuo to give the desired product (R)-tert-butyl 3-(4-(4-methoxy-1,8-naphthyridin-2-yl)butoxy)pyrrolidine-1-carboxylate as a colorless oil (60 mg). Yield 80% (ESI 402 (M+H)+).

Step 5: (R)-5-methoxy-7-(4-(pyrrolidin-3-yloxy)butyl)-1,2,3,4-tetrahydro-1,8-naphthyridine dihydrochloride

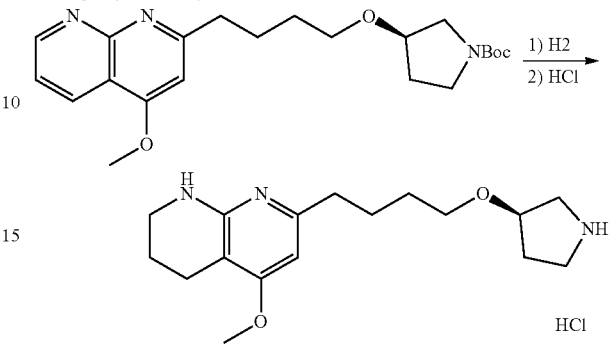

A mixture of (R)-tert-butyl 3-(4-(4-methoxy-1,8-naphthyridin-2-yl)butoxy)pyrrolidine-1-carboxylate (60 mg, 0.15 mmol) and Pd/C (10%, 30 mg) in EtOAc (10 mL) was stirred under balloon hydrogen at 30° C. for 17 hours. The mixture was filtered and concentrated in vacuo. The residue was treated with 4M HCl in dioxane (3 mL, 12 mmol) at room temperature for 2 hours. Solvent was removed in vacuo to give the desired product (R)-5-methoxy-7-(4-(pyrrolidin-3-yloxy)butyl)-1,2,3,4-tetrahydro-1,8-naphthyridine dihydrochloride as a colorless oil (45 mg). Yield 88% (ESI 306 (M+H)+).

Preparation of (R)-7-(5-(pyrrolidin-3-yl)pentyl)-1,2,3,4-tetrahydro-1,8-naphthyridine Dihydrochloride Step 1: (R)-tert-butyl 3-(iodomethyl)pyrrolidine-1-carboxylate

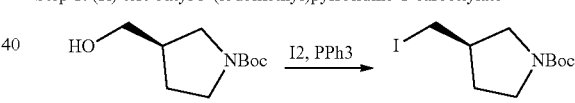

A solution of PPh3 (5.11 g, 19.5 mmol) and 1H-imidazole (1.33 g, 19.5 mmol) in DCM (50 mL) was cooled to 0° C., and then slowly treated with I2 (4.95 g, 19.5 mmol). After stirred at 0° C. for 30 mins, a solution of (R)-tert-butyl 3-(hydroxymethyl)pyrrolidine-1-carboxylate in DCM (10 mL) was added and the reaction was stirred at room temperature overnight. The reaction was diluted with water (50 mL), extracted with DCM (30 mL*3). The combined organic layer was dried over Na2SO4, filtered and removed in vacuo. The residue was purified by silica gel column (pet ether: EtOAc 10:1) to give the desired product (R)-tert-butyl 3-(iodomethyl)pyrrolidine-1-carboxylate as a colorless oil (3.7 g). Yield 80%. (ESI 256 (M+H−56)+).

Step 2: (R)-((1-(tert-butoxycarbonyl)pyrrolidin-3-yl)methyl)triphenylphosphonium

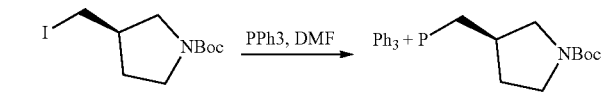

A solution of (R)-tert-butyl 3-(iodomethyl)pyrrolidine-1-carboxylate (3.7 g, 12 mmol) and PPh3 (4.1 g, 15.5 mmol)

in DMF (50 mL) was stirred at room temperature overnight. Solvent was removed in vacuo, and the residue was purified by silica gel column (DCM:MeOH 10:1) to give the crude product. Diethyl ether (30 mL) was added to the crude product and stirred at r.t for 30 mins, filtered. The filter cake was dried under vacuum to give the desired product (R)-((1-(tert-butoxycarbonyl)pyrrolidin-3-yl)methyl)triphenylphosphonium as a white solid (5.6 g). Yield 84%. (ESI N/A).

Step 3: ethyl 4-(2-methyl-1,3-dioxolan-2-yl)butanoate

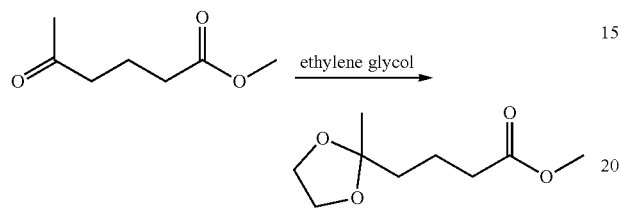

A solution of ethyl 5-oxohexanoate(2 g, 13.9 mmol), ethylene glycol (2.6 g, 42 mmol) and p-Toluene sulfonic acid (478 mg, 2.78 mmol) in toluene(50 mL) was stirred under reflux to remove water by Dean-stark trap for 6 hours. Solvent was removed in vacuo, and the residue was purified by silica gel column (pet ether: EtOAc 10:1) to give the desired product ethyl 4-(2-methyl-1,3-dioxolan-2-yl)butanoate as a colourless oil (1.4 g, 50% yield). (ESI 203 (M+H)

Step 4: 4-(2-methyl-1,3-dioxolan-2-yl)butanal

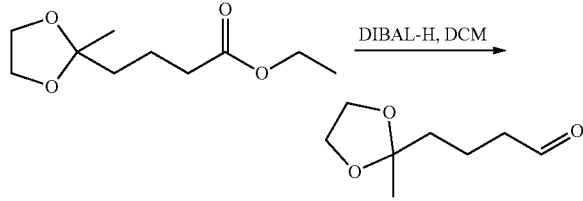

To a solution of ethyl 4-(2-methyl-1,3-dioxolan-2-yl)butanoate(500 mg, 2.48 mmol) in DCM(10 mL) at −78° C. under Ar, was added DIBAL-H(1 M, 3.7 mL, 3.7 mmol) slowly. The reaction was stirred at −78° C. for 30 mins, then 20 mL of water was added, warmed to r.t, extracted with DCM (20 mL*3). The combined organic layer was dried over Na2SO4, filtered and concentrated under vacuum. The residue was purified by silica gel column (pet ether: EtOAc 2:1) to give the desired product 4-(2-methyl-1,3-dioxolan-2-yl)butanal as a colorless oil (220 mg). Yield 56%. (ESI 159 (M+H)+).

Step 5: (S)-tert-butyl 3-(5-(2-methyl-1,3-dioxolan-2-yl)pent-1-enyl)pyrrolidine-1-carboxylate

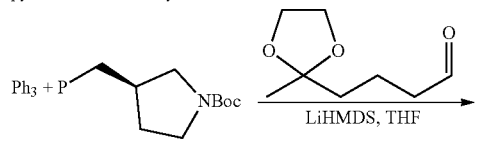

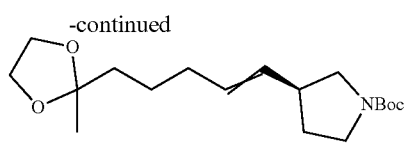

To a solution of (R)-((1-(tert-butoxycarbonyl)pyrrolidin-3-yl)methyl)triphenylphosphonium (2.0 g, 3.6 mmol) in DCM (30 mL) at 0° C. under N2, was added LiHMDS (1 M, 5.4 mL, 5.4 mmol). The mixture was stirred at 0° C. for 30 mins, then 4-(2-methyl-1,3-dioxolan-2-yl)butanal(565 mg, 3.6 mmol) was added. The reaction was stirred at r.t for 4 hours, then MeOH (20 mL) was added. Solvent was removed in vacuo, and the residue was purified by silica gel column (pet ether: EtOAc 3:1) to give the desired product (S)-tert-butyl 3-(5-(2-methyl-1,3-dioxolan-2-yl)pent-1-enyl)pyrrolidine-1-carboxylate as a yellow oil (500 mg). Yield 43%. (ESI 226 (M+H−100)+).

Step 6: (R)-tert-butyl 3-(6-oxoheptyl)pyrrolidine-1-carboxylate

To a solution of (S)-tert-butyl 3-(5-(2-methyl-1,3-dioxolan-2-yl)pent-1-enyl)pyrrolidine-1-carboxylate (500 mg, 1.54 mmol) in EtOAc (20 mL), was added Pd/C (10%, 50 mg) and the mixture was stirred at 40° C. overnight under H2. The reaction was filtered and the filtrate was concentrated in vacuo. The residue was treated with TsOH (264 mg, 1.54 mmol) in acetone (5 mL). The mixture was stirred at r.t for 6 hours, then EtOAc (20 mL) was added, washed with sat. NaHCO3 solution (20 mL) and brine. The organic layer was dried over Na2SO4, filtered and concentrated in vacuo to give the desired product (R)-tert-butyl 3-(6-oxoheptyl)pyrrolidine-1-carboxylate as a yellow oil (200 mg). Yield 46% (ESI 184 (M+H−100)+).

Step 7: (R)-tert-butyl 3-(5-(1,8-naphthyridin-2-yl)pentyl)pyrrolidine-1-carboxylate

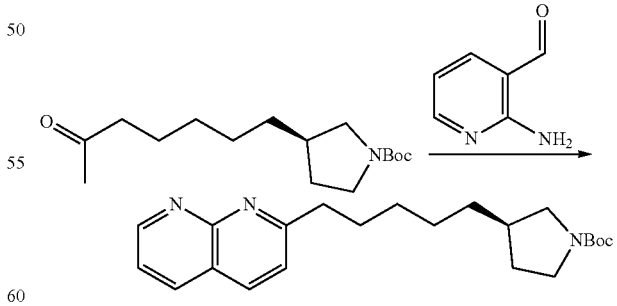

To a solution of (R)-tert-butyl 3-(6-oxoheptyl)pyrrolidine-1-carboxylate (300 mg, 1.06 mmol) in EtOH (10 mL), was added 2-aminonicotinaldehyde(155 mg, 1.27 mmol) and pyrrolidine (90 mg, 1.27 mmol). The reaction was heated to reflux overnight. Solvent was removed in vacuo, and the residue was purified by silica gel column (DCM:

MeOH=20:1) to give the desired product (R)-tert-butyl 3-(5-(1,8-naphthyridin-2-yl)pentyl)pyrrolidine-1-carboxylate as a yellow oil (220 mg). Yield 56%. (ESI 370 (M+H)+).

Step 8: (R)-7-(5-(pyrrolidin-3-yl)pentyl)-1,2,3,4-tetrahydro-1,8-naphthyridine dihydrochloride

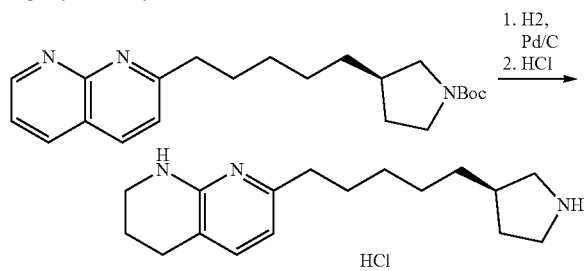

To a solution of (R)-tert-butyl 3-(5-(1,8-naphthyridin-2-yl)pentyl)pyrrolidine-1-carboxylate (220 mg, 0.60 mmol) in EtOAc(10 mL) was added Pd/C (10%, 30 mg). The mixture was stirred at 40° C. under H$_2$ overnight. The reaction was filtered and the filtrate was concentrated in vacuo. The residue was treated with a solution of HCl/dioxane (4.0 M, 5 mL) at room temperate for 2 hours, then the solvent was removed in vacuo to give the desired product (R)-7-(5-(pyrrolidin-3-yl)pentyl)-1,2,3,4-tetrahydro-1,8-naphthyridine dihydrochloride as a yellow oil (160 mg). Yield 86%. (ESI 274 (M+H)+).

Preparation of (R)-7-(3-(pyrrolidin-3-yloxy)propyl)-1,2,3,4-tetrahydro-1,8-naphthyridine Dihydrochloride Step 1: 2-(3-bromopropyl)-2-methyl-1,3-dioxolane

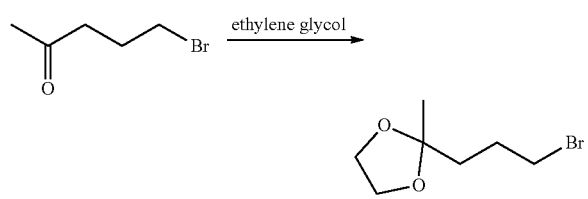

In a flame dried round-bottomed flask equipped with a magnetic stir bar and a Dean-Stark trap under N$_2$, a solution of 5-bromopentan-2-one (2.0 g, 12.12 mmol) in toluene (40 mL) was treated with ethylene glycol (6.93 g, 111.7 mmol) and TsOH (384 mg, 0.22 mmol). The reaction mixture was heated to reflux for 1 h, allowed to cool to room temperature, diluted with saturated aqueous NaHCO$_3$(60 mL) and extracted with ethyl acetate (100 mL). The organic layer was washed with water (2×100 mL), dried over MgSO4, filtered and concentrated in vacuo. The residue was purified by silica gel column (pet ether:EtOAc 4:1) to give the desired product as a colorless oil (1.5 g). Yield 59%.

Step 2: (R)-tert-butyl 3-(3-(2-methyl-1,3-dioxolan-2-yl)propoxy)pyrrolidine-1-carboxylate

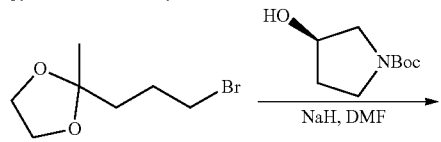

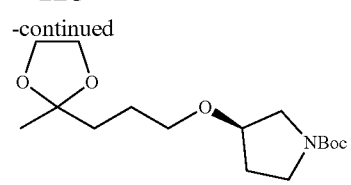

A mixture of (R)-tert-butyl 3-hydroxypyrrolidine-1-carboxylate (894 mg, 4.78 mmol) and NaH (287 mg, 7.18 mmol) in DMF (10 mL) was stirred at 0° C. for 1 hour. A solution of 2-(3-bromopropyl)-2-methyl-1,3-dioxolane (1 g, 4.78 mmol) in DMF (5 mL) was added dropwise at 0° C., and the reaction mixture was stirred at 100° C. overnight. Solvent was removed in vacuo, and the residue was purified by silica gel column (pet ether:EtOAc 1:1) to give the desired product as a colorless oil (500 mg). Yield 33% (ESI 216 (M+H−100)+).

Step 3: (R)-tert-butyl 3-(4-oxopentyloxy)pyrrolidine-1-carboxylate

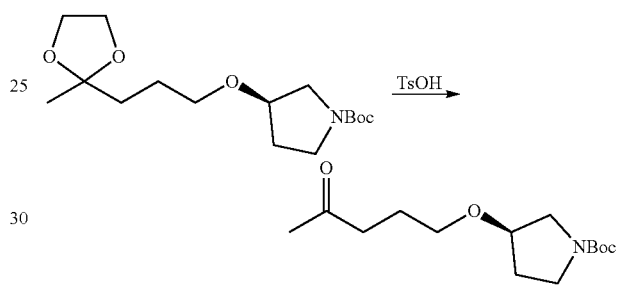

A mixture of (R)-tert-butyl3-(3-(2-methyl-1,3-dioxolan-2-yl)propoxy)pyrrolidine-1-carboxylate (500 mg, 1.59 mmol) and p-toluenesulfonic acid monohydrate (151 mg 0.79 mmol) in acetone (10 mL) and H$_2$O (5 mL) was stirred at room temperature for 4 hours. The reaction was diluted with H$_2$O (10 mL) and extracted with EtOAc (3×10 mL). The combined organic layers were dried over Na2SO4, filtered and concentrated in vacuo to give the desired product as a colorless oil (380 mg). Yield 88% (ESI 172 (M+H−100)+).

Step 4: (R)-tert-butyl 3-(3-(1,8-naphthyridin-2-yl)propoxy)pyrrolidine-1-carboxylate

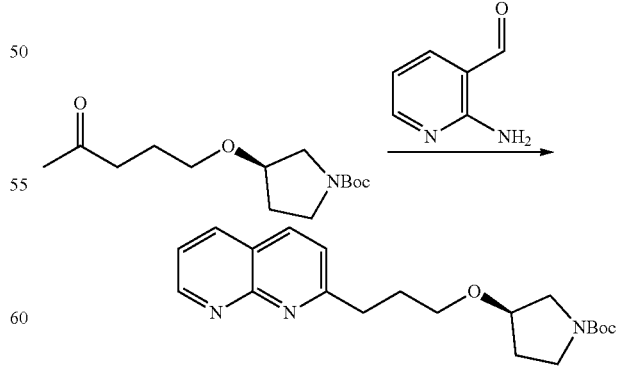

A mixture of (R)-tert-butyl 3-(4-oxopentyloxy)pyrrolidine-1-carboxylate (380 mg, 1.40 mmol), 2-aminonicotinaldehyde (171 mg, 1.40 mmol) and pyrrolidine (99 mg, 1.40 mmol) in ethanol (8 mL) was refluxed overnight. Solvent was removed in vacuo, and the residue was purified by silica gel column (DCM:MeOH 40:1) to give the desired product as a colorless oil (310 mg). Yield 62% (ESI 358 (M+H)+).

Step 5: (R)-7-(3-(pyrrolidin-3-yloxy)propyl)-1,2,3,4-tetrahydro-1,8-naphthyridine dihydrochloride

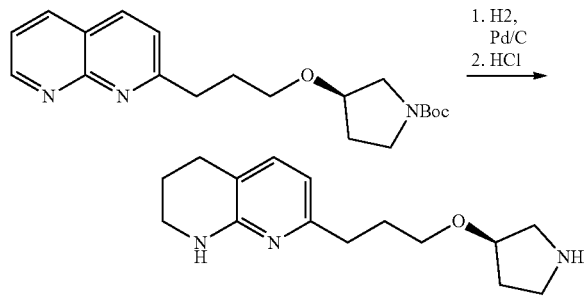

A mixture of (R)-tert-butyl 3-(3-(1,8-naphthyridin-2-yl)propoxy)pyrrolidine-1-carboxylate (310 mg, 0.87 mmol) and Pd/C (10%, 30 mg) in EtOAc (30 mL) was stirred under balloon hydrogen at room temperature for 16 hours. The mixture was filtered and concentrated in vacuo. The residue was treated with HCl in 1,4-dioxane (4M, 5 mL) at 25° C. for 2 hours. Solvent was removed in vacuo to give (R)-7-(3-(pyrrolidin-3-yloxy)propyl)-1,2,3,4-tetrahydro-1,8-naphthyridine dihydrochloride as a colorless oil (240 mg). Yield 83% (ESI 262 (M+H)+).

Preparation of (R)-7-(5-(pyrrolidin-3-yloxy)pentyl)-1,2,3,4-tetrahydro-1,8-naphthyridine Dihydrochloride Step 1: 2-(5-bromopentyl)-2-methyl-1,3-dioxolane

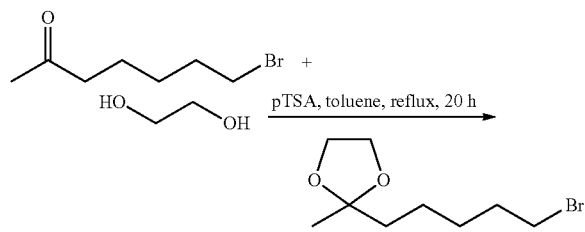

To a solution of 7-bromoheptan-2-one (14 g, 73 mmol) in toluene (150 mL) in a three-necked flask equipped with Dean-Stark trap was added ethane-1,2-diol (15 g, 255 mmol) and p-toluenesulfonic acid (251 mg, 1.46 mmol). The reaction mixture was stirred at reflux for 20 h. The reaction mixture was cooled to room temperature and washed with sat NaHCO₃ solution, water and brine. The organic phase was concentrated, and the residue was separated by silica gel column (7% EtOAc in petroleum ether) to give 2-(5-bromopentyl)-2-methyl-1,3-dioxolane (16 g, 92%).

Step 2: (R)-tert-butyl 3-(5-(2-methyl-1,3-dioxolan-2-yl)pyrrolidine-1-carboxylate

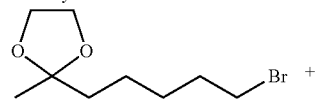

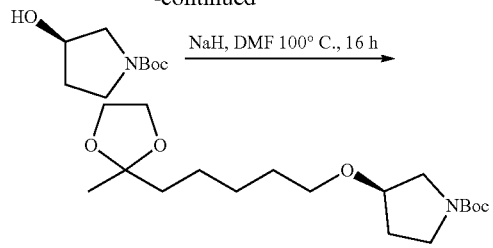

To a solution of (R)-tert-butyl 3-hydroxypyrrolidine-1-carboxylate (3.5 g, 18.7 mmol) in DMF (25 mL) was added NaH (830 mg, 20.6 mmol) in portions at 0° C. The reaction mixture was stirred at 0° C. for 1 h. 2-(5-bromopentyl)-2-methyl-1,3-dioxolane (4.9 g, 20.6 mmol) was added and the reaction mixture was stirred at 100° C. for 16 h. The reaction mixture was poured into ice water and extracted with EtOAc (150 mL×3). The combined organic phase was washed with brine, dried over Na2SO4. The organic phase was concentrated, and the residue was chromatographed on silica gel (20% EtOAc in pet. Ether) to give the product (R)-tert-butyl 3-(5-(2-methyl-1,3-dioxolan-2-yl)pentyloxy)pyrrolidine-1-carboxylate as yellow oil (3.7 g, 57%); (ESI 344.3 (M+H)⁺).

Step 3: (R)-tert-butyl 3-(6-oxoheptyloxy)pyrrolidine-1-carboxylate

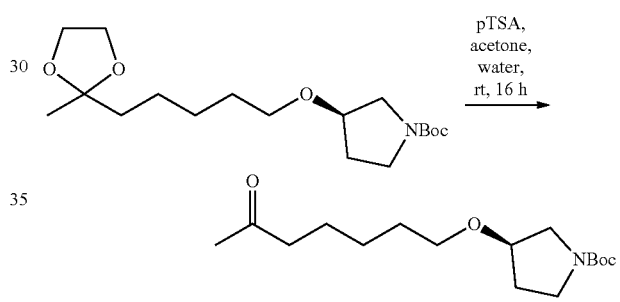

To a solution of (R)-tert-butyl 3-(5-(2-methyl-1,3-dioxolan-2-yl)pentyloxy)pyrrolidine-1-carboxylate (3.7 g, 10.8 mmol) in acetone (70 mL) and water (7 mL) was added p-toluenesulfonic acid (927 mg, 5.4 mmol). The reaction mixture was stirred at room temperature for 16 h. The reaction mixture was neutralized with saturated aqueous NaHCO₃ solution and concentrated under reduced pressure. The residue was extracted with EtOAc (100 mL×3). The combined organic phase was washed with brine, dried over Na2SO4 and concentrated to give the product (R)-tert-butyl 3-(6-oxoheptyloxy)pyrrolidine-1-carboxylate as yellow oil (2.99 g, 92%); (ESI 300.1 (M+H)⁺).

Step 4: (R)-tert-butyl 3-(5-(1,8-naphthyridin-2-yl)pentyloxy)pyrrolidine-1-carboxylate

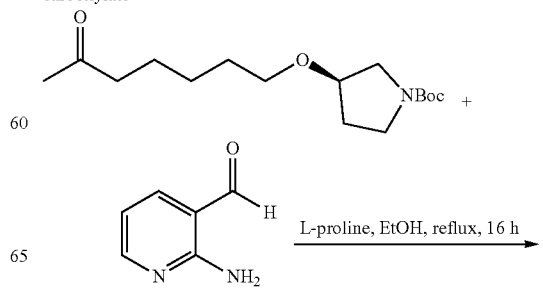

131

-continued

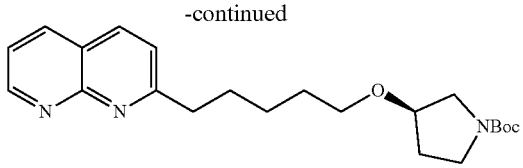

To a solution of (R)-tert-butyl 3-(6-oxoheptyloxy)pyrrolidine-1-carboxylate (2.9 g, 9.7 mmol) in EtOH (40 mL) was added 2-aminonicotinaldehyde (1.2 g, 9.7 mmol) and L-proline (558 mg, 4.8 mmol). The reaction mixture was stirred at reflux for 16 h. Then the reaction mixture was concentrated, and the residue was separated by silica gel column (5% MeOH in EtOAc) to give (R)-tert-butyl 3-(5-(1,8-naphthyridin-2-yl)pentyloxy)pyrrolidine-1-carboxylate as a yellow solid (2.4 g, 64%); (95% purity, UV=214 nm, ESI 386.0 (M+H)).

Step 5: (R)-tert-butyl 3-(5-(5,6,7,8-tetrahydro-1,8-naphthyridin-2-yl)pentyloxy)pyrrolidine-1-carboxylate

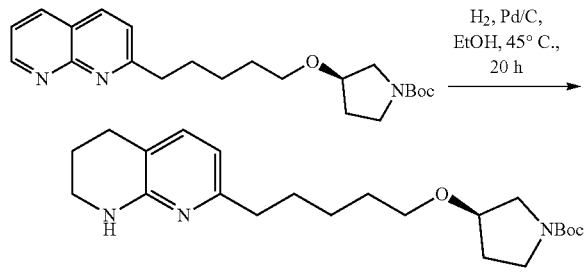

To a solution of (R)-tert-butyl 3-(5-(1,8-naphthyridin-2-yl)pentyloxy)pyrrolidine-1-carboxylate (2.4 g, 6.2 mmol) in EtOH (30 mL) was added Pd/C (10%, 300 mg). The reaction mixture was degassed and purged with $H_2$ for 3 times and stirred at 45° C. under $H_2$ for 20 h. The reaction mixture was filtered and the filtrate was concentrated to give (R)-tert-butyl 3-(5-(5,6,7,8-tetrahydro-1,8-naphthyridin-2-yl)pentyloxy)pyrrolidine-1-carboxylate as a yellow oil (2.5 g, 100%); (ESI 390.5 (M+H)$^+$).

Step 6: (R)-7-(5-(pyrrolidin-3-yloxy)pentyl)-1,2,3,4-tetrahydro-1,8-naphthyridine dihydrochloride

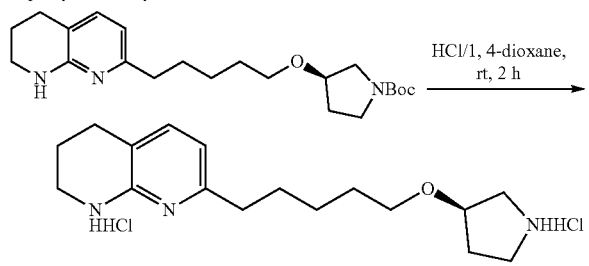

To a solution of (R)-tert-butyl 3-(5-(5,6,7,8-tetrahydro-1,8-naphthyridin-2-yl)pentyloxy)pyrrolidine-1-carboxylate (2.4 g, 6.2 mmol) in DCM (10 mL) was added HCl/1,4-dioxane (4 mol/L, 30 mL). The reaction mixture was stirred at room temperature for 2 h. The reaction mixture was concentrated to give (R)-7-(5-(pyrrolidin-3-yloxy)pentyl)-1,2,3,4-tetrahydro-1,8-naphthyridine dihydrochloride as a yellow oil (2.9 g, 100%); (ESI 290.4 (M−55)$^+$).

132

Preparation of 7-(5-(3-fluoropyrrolidin-3-yl)pentyl)-1,2,3,4-tetrahydro-1,8-naphthyridine Dihydrochloride Step 1: tert-butyl 3-(4-(benzyloxy)butyl)-3-hydroxypyrrolidine-1-carboxylate

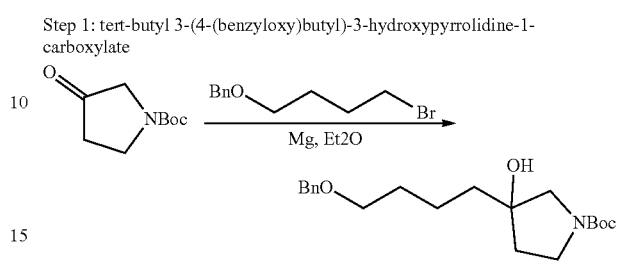

To a mixture of ((4-bromobutoxy)methyl)benzene (9.45 g, 38.87 mmol) and Mg (1.89 g, 77.74 mmol) in Et$_2$O (20 mL) was added I2 (202 mg, 1.09 mmol). The reaction mixture was stirred at 40° C. for 1 h. After cooled to room temperature, the mixture was added to a solution of tert-butyl 3-oxopyrrolidine-1-carboxylate (2.4 g, 12.96 mmol) in 30 mL of Et$_2$O at 5° C. The reaction was stirred at room temperature overnight, then quenched with aq. NH$_4$Cl (10 mL) and extracted with EtOAc (30 mL×3). The combined organic layer was dried over sodium sulfate, filtered and concentrated in vacuo. The residue was purified by silica gel column (pet ether:EtOAc 5:1-2:1) to give the desired product tert-butyl 3-(4-(benzyloxy)butyl)-3-hydroxypyrrolidine-1-carboxylate as a yellow oil (1.7 g). Yield 38% (ESI 294 (M+H−56)$^+$).

Step 2: tert-butyl 3-(4-(benzyloxy)butyl)-3-fluoropyrrolidine-1-carboxylate

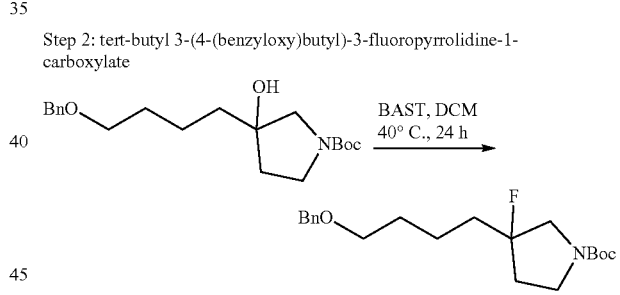

A mixture of tert-butyl 3-(4-(benzyloxy)butyl)-3-hydroxypyrrolidine-1-carboxylateas (1.7 g, 4.86 mmol) and BAST (10.76 g, 48.6 mmol) in DCM (30 mL) was stirred at 40° C. for 24 h.

The reaction was diluted with MeOH (2 mL), washed with water (20 mL), dried over sodium sulfate, filtered and concentrated in vacuo. The residue was purified by silica gel column (pet ether:EtOAc 20:1-10:1) to give the desired product tert-butyl 3-(4-(benzyloxy)butyl)-3-fluoropyrrolidine-1-carboxylate as a light yellow oil (1.1 g). Yield 64% (ESI 296 (M+H−56)$^+$).

Step 3: (tert-butyl 3-fluoro-3-(4-hydroxybutyl)pyrrolidine-1-carboxylate

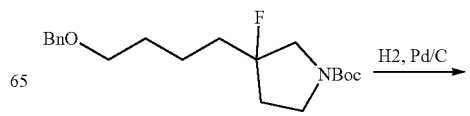

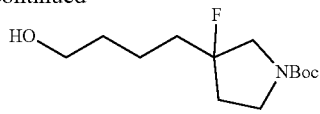

A mixture of tert-butyl 3-(4-(benzyloxy)butyl)-3-fluoropyrrolidine-1-carboxylate (1.1 g, 3.13 mmol) and Pd/C (5%, 1.1 g) in EtOAc (100 mL) was stirred under hydrogen at 45° C. overnight. The mixture was filtered and concentrated in vacuo to give the desired product tert-butyl 3-fluoro-3-(4-hydroxybutyl)pyrrolidine-1-carboxylate as a light yellow oil (780 mg). Yield 95% (ESI 206 (M+H−56)⁺).

Step 4: tert-butyl 3-fluoro-3-(4-iodobutyl)pyrrolidine-1-carboxylate

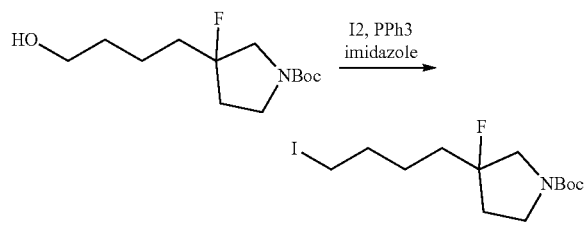

To a solution of triphenylphosphine (1.58 g, 6.04 mmol) and imidazole (411 mg, 6.04 mmol) in DCM (40 mL) at 5° C. was added I2 (835 mg, 3.29 mmol). The reaction mixture was stirred at 5° C. for 15 min, and then a solution of (tert-butyl 3-fluoro-3-(4-hydroxybutyl)pyrrolidine-1-carboxylate (780 mg, 2.99 mmol) in DCM (15 mL) was added. The reaction mixture was stirred at 5° C. for 1 h, then concentrated in vacuo at 15° C., and the residue was purified by silica gel column (pet ether:EtOAc 20:110:1) to give the desired product tert-butyl 3-fluoro-3-(4-iodobutyl)pyrrolidine-1-carboxylate as a light yellow oil (700 mg). Yield 63% (ESI 316 (M+H−56)⁺).

Step 5: tert-butyl 3-(5-(1,8-naphthyridin-2-yl)pentyl)-3-fluoropyrrolidine-1-carboxylate

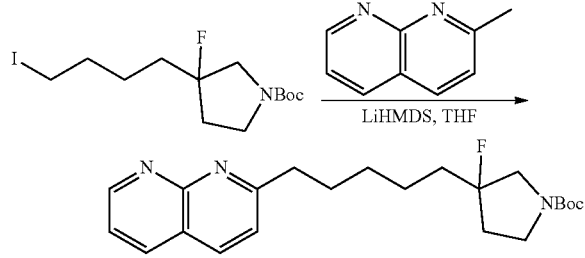

To a solution of (R)-tert-butyl 3-(1,1-difluoro-4-iodobutyl)pyrrolidine-1-carboxylate (700 mg, 1.88 mmol) and 2-methyl-1,8-naphthyridine (407 mg, 2.82 mmol) in THF (12 mL) at 0° C. was added LiHMDS (2.82 mL, 1M, 2.82 mmol). The reaction mixture was stirred at 0° C. for 3 h, then quenched with saturated ammonium chloride solution (6 mL), diluted with water (15 mL) and extracted with EtOAc (30 mL×2). The combined organic layers were dried over sodium sulfate, filtered and concentrated in vacuo. The residue was purified by prep-TLC to give the desired product tert-butyl 3-(5-(1, 8-naphthyridin-2-yl)pentyl)-3-fluoropyrrolidine-1-carboxylate as a light yellow solid (350 mg). Yield 48% (ESI 388 (M+H)⁺).

Step 6: 7-(5-(3-(fluoropyrrolidin-3-yl)pentyl)-1,2,3,4-tetrahydro-1,8-naphthyridine dihydrochloride

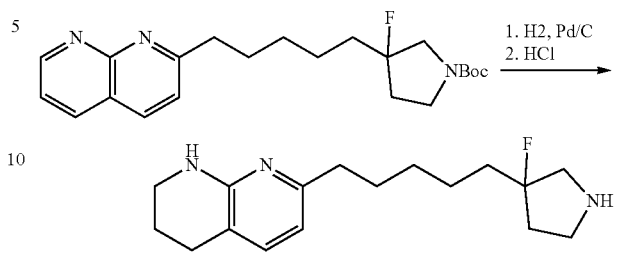

A mixture of 3-(5-(1, 8-naphthyridin-2-yl)pentyl)-3-fluoropyrrolidine-1-carboxylate (200 mg, 0.516 mmol) and Pd/C (5%, 200 mg) in EtOAc (20 mL) under hydrogen was stirred at 45° C. overnight. The reaction mixture was filtered and concentrated in vacuo. To the residue was added 1, 4-dioxane (2 mL) and HCl/dioxane (2 mL, 4M) at room temperature. The reaction mixture was stirred at room temperature for 3 h, then concentrated in vacuo to give the desired product 7-(5-(3-fluoropyrrolidin-3-yl)pentyl)-1,2,3, 4-tetrahydro-1,8-naphthyridine dihydrochloride as a light yellow solid (140 mg). Yield 93% (ESI 292 (M+H)⁺).

Preparation of 2-(4-(((R)-pyrrolidin-3-yl)oxy)butyl)-1,2,3,4-tetrahydro-1,8-naphthyridine Dihydrochloride Step 1: Tert-butyl (R)-3-(hex-5-en-1-loxy)pyrrolidine-1-carboxylate

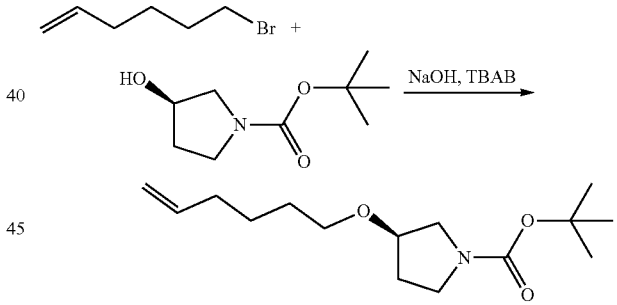

To a suspension of tert-butyl (R)-3-hydroxypyrrolidine-1-carboxylate (12.8 g, 68.4 mmol), tetrabutylammonium bromide (1.102 g, 3.42 mmol) and 6-bromo-1-hexene (13.71 mL, 103 mmol) in heptane (256 mL) was added sodium hydroxide (128 mL, 68.4 mmol, 50 wt % solution in water). The mixture was vigorously stirred at 80° C. for 2 hours, then cooled to room temperature, diluted with water and extracted with heptane and twice with diethyl ether/heptane. The combined organic layers were washed with brine, dried over sodium sulfate and concentrated in vacuo. Purification by column chromatography (600 g silica, 5→14% ethyl acetate in heptane) afforded the desired product tert-butyl (R)-3-(hex-5-en-1-yloxy)pyrrolidine-1-carboxylate (14.93 g). Yield 81%. ¹H NMR (400 MHz, Chloroform-d) δ 5.87-5.74 (m, 1H), 5.05-4.91 (m, 2H), 4.04-3.95 (m, 1H), 3.48-3.27 (m, 6H), 2.07 (q, J=7.2 Hz, 2H), 2.02-1.84 (m, 2H), 1.60-1.51 (m, 2H), 1.51-1.38 (m, 11H).

Step 2: tert-butyl (R)-3-((5-oxopentyl)oxy)pyrrolidine-1-carboxylate

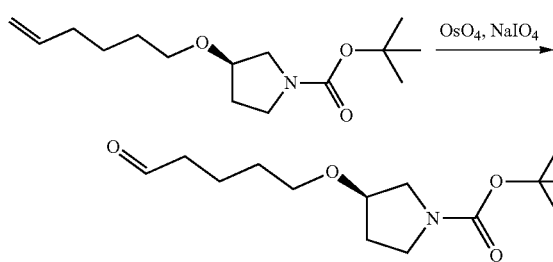

To a solution of tert-butyl (R)-3-(hex-5-en-1-yloxy)pyrrolidine-1-carboxylate (14.93 g, 55.4 mmol) in THF (420 mL) and water (140 mL) was added sodium periodate (26.1 g, 122 mmol) and osmium tetroxide (1.5 mL, 0.232 mmol, 4% solution in water). After 1 hour, additional sodium periodate (5 g, 23.38 mmol) was added. After 30 minutes, the mixture was diluted with water and extracted three times with ethyl acetate. The combined organic layers were washed with brine, dried over sodium sulfate and concentrated in vacuo. The residue was purified by flash column chromatography (~600 g silica, 20→50% ethyl acetate in heptane). This afforded the desired product tert-butyl (R)-3-((5-oxopentyl)oxy)pyrrolidine-1-carboxylate (10.97 g). Yield 72%. $^1$H NMR (400 MHz, Chloroform-d) δ 9.77 (s, 1H), 4.03-3.94 (m, 1H), 3.50-3.27 (m, 6H), 2.47 (t, J=7.2 Hz, 2H), 2.02-1.84 (m, 2H), 1.77-1.65 (m, 2H), 1.65-1.54 (m, 2H), 1.46 (s, 9H).

Step 3: tert-butyl (3R)-3-(5-hydroxyhept-6-en-1-yl)pyrrolidine-1-carboxylate

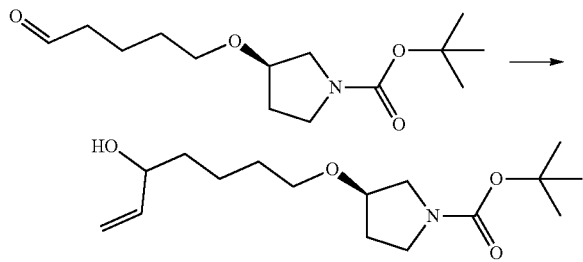

To a solution of tert-butyl (R)-3-((5-oxopentyl)oxy)pyrrolidine-1-carboxylate (10.97 g, 40.4 mmol) in THF (70 mL) at 0° C. was added dropwise vinylmagnesium bromide (66.4 mL, 46.5 mmol, 0.7 M solution in THF). After 16 hours, the mixture was quenched with aqueous saturated ammonium chloride and extracted with ethyl acetate. The organic layer was washed with brine, dried over sodium sulfate and concentrated, and the residue was purified by flash column chromatography (20→50% EtOAc in heptane) to give the desired product tert-butyl (3R)-3-((5-hydroxyhept-6-en-1-yl)oxy)pyrrolidine-1-carboxylate (7.68 g). Yield 63%. $^1$H NMR (400 MHz, Chloroform-d) δ 5.93-5.80 (m, 1H), 5.28-5.17 (m, 1H), 5.15-5.06 (m, 1H), 4.17-4.05 (m, 1H), 3.99 (s, 1H), 3.52-3.23 (m, 6H), 2.03-1.83 (m, 2H), 1.65-1.50 (m, 5H), 1.50-1.33 (m, 11H).

Step 4: tert-butyl (R)-3-((7-(2-chloropyridin-3-yl)-5-oxoheptyl)oxy)pyrrolidine-1-carboxylate

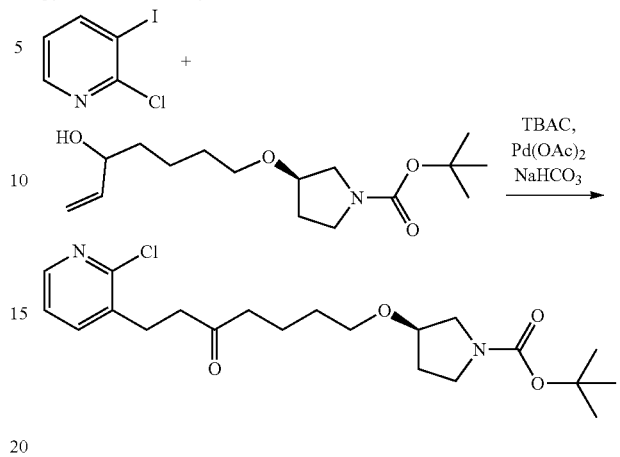

Tert-butyl (3R)-3-((5-hydroxyhept-6-en-1-yl)oxy)pyrrolidine-1-carboxylate (10.48 g, 35.0 mmol), 2-chloro-3-iodopyridine (4.19 g, 17.50 mmol), tetrabutylammonium chloride (0.486 g, 1.750 mmol) and sodium hydrogencarbonate (3.68 g, 43.8 mmol) were dissolved/suspended under argon in DMF (35 mL), and argon was bubbled through this mixture for 15 minutes. Palladium(II) acetate (0.393 g, 1.750 mmol) was added, and the mixture was heated to 50° C. for 24 hours, then cooled to room temperature, diluted with water and extracted three times with ethyl acetate. The combined organic layers were washed three times with brine, dried over sodium sulfate and concentrated, and the residue was purified by column chromatography (silica, 20→55% EtOAc in heptane) to afford the desired product tert-butyl (R)-3-((7-(2-chloropyridin-3-yl)-5-oxoheptyl)oxy)pyrrolidine-1-carboxylate (3.05 g). Yield 42%. $^1$H NMR (400 MHz, Chloroform-d) δ 8.25 (dd, J=4.7, 1.9 Hz, 1H), 7.62 (dd, J=7.5, 1.9 Hz, 1H), 7.17 (dd, J=7.5, 4.7 Hz, 1H), 4.04-3.93 (m, 1H), 3.51-3.25 (m, 6H), 2.99 (t, J=7.3 Hz, 2H), 2.79 (t, J=7.3 Hz, 2H), 2.43 (t, J=7.2 Hz, 2H), 2.01-1.83 (m, 2H), 1.72-1.48 (m, 4H), 1.30 (s, 9H).

Step 5: tert-butyl (R)-3-((5-(((R)-tert-butylsulfinyl)imino)-7-(2-chloropyridin-3-yl)heptyl)oxy)pyrrolidine-1-carboxylate

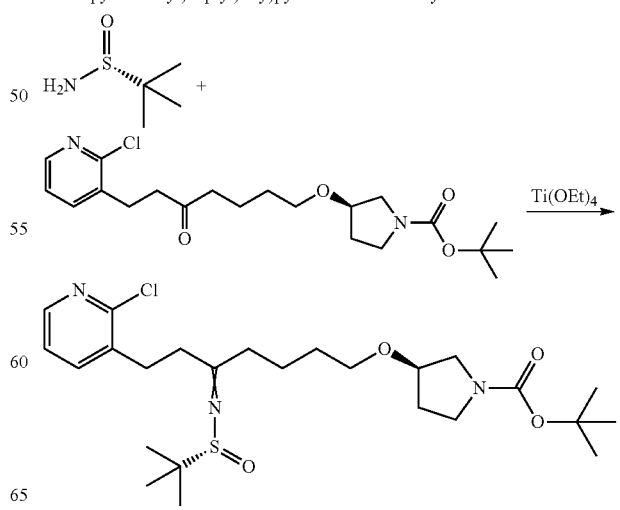

To a solution of (R)-(+)-2-methyl-2-propanesulfinamide (1.799 g, 14.84 mmol) and tert-butyl (R)-3-((7-(2-chloropyridin-3-yl)-5-oxoheptyl)oxy)pyrrolidine-1-carboxylate (3.05 g, 7.42 mmol) in THF (30 mL) was added titanium(IV) ethoxide (7.24 mL, 22.27 mmol). The resulting mixture was heated to 50° C. for 20 hours, then poured out on half-saturated aqueous sodium hydrogencarbonate, stirred for 10 minutes, transferred to 2 centrifuge vials and centrifuged for min at 7800 rpm. The liquids were decanted into a separation funnel. The vials were then filled with ethyl acetate, shaken vigorously and centrifuged again for 5 minutes at 7800 rpm. The liquids were combined in the separation funnel. The layers were separated, and the aqueous phase was extracted once more with ethyl acetate. The combined organic layers were washed with brine, dried over sodium sulfate and concentrated, and the residue was purified by flash column chromatography (300 g silica, 35-65% EtOAc in heptane) to afford the desired product tert-butyl (R)-3-((5-(((R)-tert-butylsulfinyl)imino)-7-(2-chloropyridin-3-yl)heptyl)oxy)pyrrolidine-1-carboxylate (3.15 g). Yield 78% (ESI 514/516 (M+H)+). ¹H NMR (400 MHz, Chloroform-d) δ 8.27 (dd, J=4.7, 1.9 Hz, 1H), 7.64 (dd, J=62.5, 7.4 Hz, 1H), 7.19 (dd, J=7.5, 4.8 Hz, 1H), 3.99 (s, 1H), 3.54-3.24 (m, 6H), 3.16-2.87 (m, 2H), 2.87-2.60 (m, 2H), 2.60-2.35 (m, 1H), 1.94 (s, 2H), 1.77-1.53 (m, 5H), 1.45 (s, 9H), 1.35-1.11 (m, 9H).

Step 6: tert-butyl (3R)-3-((5-(((R)-tert-butylsulfinyl)amino)-7-(2-chloropyridin-3-yl)heptyl)oxy)pyrrolidine-1-carboxylate

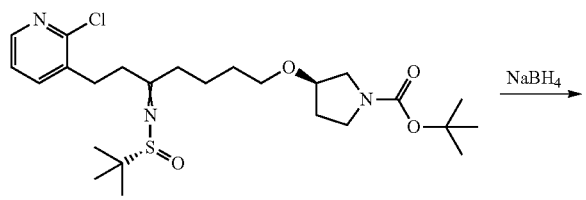

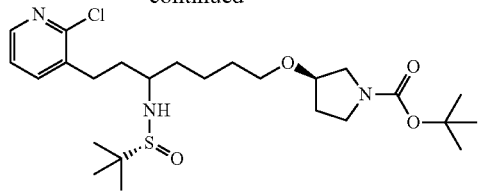

To a solution of tert-butyl (R)-3-((5-(((R)-tert-butylsulfinyl)imino)-7-(2-chloropyridin-3-yl)heptyl)oxy)pyrrolidine-1-carboxylate (3.15 g, 6.13 mmol) in methanol (20 mL) was added sodium borohydride (0.278 g, 7.35 mmol). After 2 hours, the mixture was quenched with saturated aqueous ammonium chloride and extracted three times with ethyl acetate. The combined organic layers were washed with brine, dried over sodium sulfate and concentrated, and the residue was purified by flash column chromatography (50→100% EtOAc in heptane) to afford the desired product tert-butyl (3R)-3-((5-(((R)-tert-butylsulfinyl)amino)-7-(2-chloropyridin-3-yl)heptyl)oxy)pyrrolidine-1-carboxylate (3.05 g). Yield 85%. ¹H NMR (400 MHz, Chloroform-d) δ 8.28-8.22 (m, 1H), 7.72-7.51 (m, 1H), 7.22-7.15 (m, 1H), 4.03-3.95 (m, 1H), 3.49-3.22 (m, 7H), 3.16-3.06 (m, 1H), 2.96-2.64 (m, 2H), 2.00-1.83 (m, 4H), 1.80-1.70 (m, 1H), 1.65-1.51 (m, 3H), 1.51-1.37 (m, 11H), 1.25 (s, 9H).

Step 7: tert-butyl (3R)-3-(4-(1-((R)-tert-butylsulfinyl)-1,2,3,4-tetrahydro-1,8-naphthyridin-2-yl)butoxy)pyrrolidine-1-carboxylate

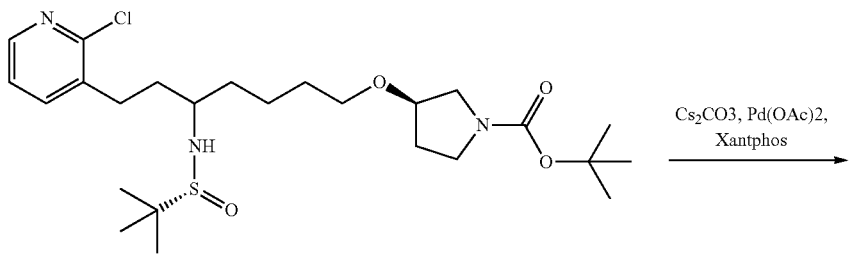

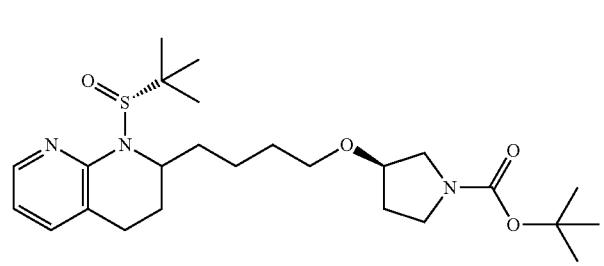

To a solution of tert-butyl (3R)-3-((5-(((R)-tert-butylsulfinyl)amino)-7-(2-chloropyridin-3-yl)heptyl)oxy)pyrrolidine-1-carboxylate (3.05 g, 5.20 mmol) in 1,4-dioxane (25 mL) was added Xantphos (0.602 g, 1.040 mmol) and cesium carbonate (3.39 g, 10.40 mmol). The mixture was bubbled through with argon for 15 minutes. Palladium(II) acetate (0.117 g, 0.520 mmol) was added, and the reaction was bubbled through with argon for 1 minute and stirred at 100° C. for 16 hours, then cooled to room temperature, quenched with water and extracted three times with ethyl acetate. The combined organic layers were washed with brine, dried over sodium sulfate and concentrated, and the residue was purified by flash column chromatography (40→100% EtOAc in heptane) to afford the desired product tert-butyl (3R)-3-(4-(1-((R)-tert-butylsulfinyl)-1,2,3,4-tetrahydro-1,8-naphthyridin-2-yl)butoxy)pyrrolidine-1-carboxylate (928 mg). Yield 36% (ESI 480 (M+H)+). The compound was separated by chiral SFC to give stereoisomer A and stereoisomer B. Apparatus: Waters Prep 100 SFC UV directed system; Waters 2998 Photodiode Array (PDA) Detector; Waters 2767 Sample Manager; Masslynx™ Software; FractionLynx™ Application Manager, Acq. Method: Cell-2_f70_10_50_8mn_SW_120bar, Loading: 50 mg, Column: Phenomenex Lux Cellulose-2 (250×21.2 mm, 5 m), Flow: 70 mL/min, Column temp: 35° C.; ABPR: 120 bar; Eluent A: CO2, Eluent B: 20 mM ammonia in methanol, Linear gradient: t=0 min 10% B, t=5 min 50% B, t=7.5 min 50% B, t=8 min 10% B. Injection: Sandwich 100 µl methanol, Detection PDA: 210-320 nm, Collection: Based on PDA TIC.

tert-butyl (3R)-3-(4-(1-((R)-tert-butylsulfinyl)-1,2,3,4-tetrahydro-1,8-naphthyridin-2-yl)butoxy)pyrrolidine-1-carboxylate stereoisomer A: 0.58 grams, LC/MS ESI 480 (M+H)+. $^1$H NMR (400 MHz, Chloroform-d) δ 8.06-7.98 (m, 1H), 7.37-7.29 (m, 1H), 6.73-6.63 (m, 1H), 4.20-4.09 (m, 1H), 4.03-3.93 (m, 1H), 3.50-3.25 (m, 6H), 2.94-2.79 (m, 1H), 2.77-2.65 (m, 1H), 2.20-2.08 (m, 1H), 2.00-1.49 (m, 7H), 1.46 (s, 9H), 1.43-1.27 (m, 2H), 1.21 (s, 9H).

tert-butyl (3R)-3-(4-(1-((R)-tert-butylsulfinyl)-1,2,3,4-tetrahydro-1,8-naphthyridin-2-yl)butoxy)pyrrolidine-1-carboxylate stereoisomer B: 0.45 grams, LC/MS ESI 480 (M+H)+. $^1$H NMR (400 MHz, Chloroform-d) δ 8.20-8.09 (m, 1H), 7.39-7.31 (m, 1H), 6.90-6.80 (m, 1H), 4.25-4.12 (m, 1H), 4.04-3.92 (m, 1H), 3.51-3.24 (m, 6H), 2.87-2.62 (m, 2H), 2.11-1.83 (m, 3H), 1.76-1.49 (m, 6H), 1.46 (s, 9H), 1.40-1.27 (m, 10H).

Step 8: 2-(4-(((R)-pyrrolidin-3-yl)oxy)butyl)-1,2,3,4-tetrahydro-1,8-naphthyridine stereoisomer A dihydrochloride

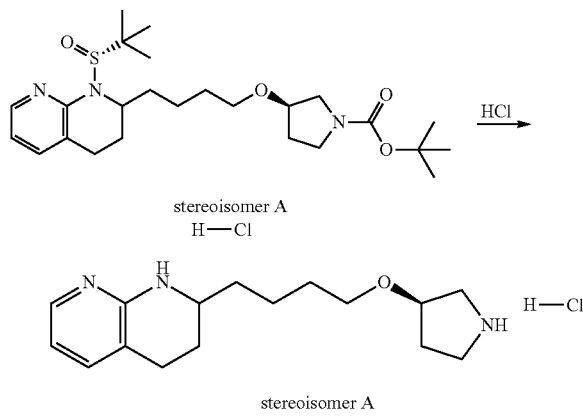

stereoisomer A
H—Cl stereoisomer A

To a solution of tert-butyl (3R)-3-(4-(1-((R)-tert-butylsulfinyl)-1,2,3,4-tetrahydro-1,8-naphthyridin-2-yl)butoxy)pyrrolidine-1-carboxylate stereoisomer A (0.58 g, 1.209 mmol) in methanol (5 mL) was added hydrochloric acid (5 mL, 20.00 mmol, 4N solution in dioxane). The mixture was stirred at room temperature for 3 hours, then concentrated in vacuo and coevaporated with methanol. Diethyl ether was added which started a slow crystallisation of the product. After standing overnight the crystallised material was scratched loose, and the material was triturated with diethyl ether. After a few hours the solids were collected by filtration, rinsed with fresh diethyl ether and dried under vacuum to afford the desired product 2-(4-(((R)-pyrrolidin-3-yl)oxy)butyl)-1,2,3,4-tetrahydro-1,8-naphthyridine stereoisomer A dihydrochloride (438 mg) as a beige solid. Yield 100%. LC/MS ESI 276 (M−2HC+H)+. $^1$H NMR (400 MHz, Methanol-d4) δ 7.75-7.66 (m, 2H), 6.80 (t, J=6.8 Hz, 1H), 4.30-4.23 (m, 1H), 3.67-3.56 (m, 1H), 3.56-3.44 (m, 2H), 3.44-3.33 (m, 3H), 3.25 (dd, J=12.5, 4.2 Hz, 1H), 2.96-2.78 (m, 2H), 2.26-2.16 (m, 1H), 2.13-1.99 (m, 2H), 1.77-1.46 (m, 7H), 1.23-1.12 (m, 1H). Specific Optical Rotation: 33.9° c.=0.5, MeOH, 22.7° C., 589 nm.

Step 9: 2-(4-(((R)-pyrrolidin-3-yl)oxy)butyl)-1,2,3,4-tetrahydro-1,8-naphthyridine stereoisomer B dihydrochloride

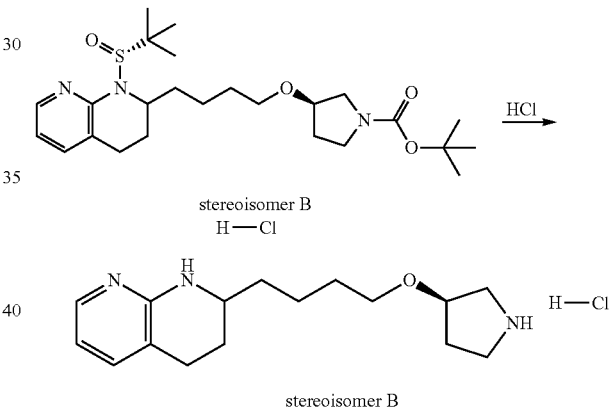

stereoisomer B
H—Cl stereoisomer B

To a solution of tert-butyl (3R)-3-(4-(1-((R)-tert-butylsulfinyl)-1,2,3,4-tetrahydro-1,8-naphthyridin-2-yl)butoxy)pyrrolidine-1-carboxylate stereoisomer B (0.45 g, 0.938 mmol) in methanol (5 mL) was added hydrochloric acid (5 mL, 20.00 mmol, 4N solution in dioxane). The mixture was stirred at room temperature for 3 hours, then concentrated in vacuo and coevaporated with methanol. Diethyl ether was added which started a slow crystallisation of the product. After standing overnight the crystallised material was scratched loose, and the material was triturated with diethyl ether. After a few hours, the solids were collected by filtration, rinsed with fresh diethyl ether and dried under vacuum to afford the desired product 2-(4-(((R)-pyrrolidin-3-yl)oxy)butyl)-1,2,3,4-tetrahydro-1,8-naphthyridine stereoisomer B dihydrochloride (289 mg) as a beige solid. Yield 85%. LC/MS ESI 276 (M−2HCl+H)+. $^1$H NMR (400 MHz, Methanol-d4) δ 7.74-7.66 (m, 2H), 6.80 (t, J=6.8 Hz, 1H), 4.30-4.23 (m, 1H), 3.66-3.57 (m, 1H), 3.57-3.45 (m, 2H), 3.45-3.33 (m, 3H), 3.29-3.21 (m, 1H), 2.96-2.78 (m, 2H), 2.26-2.16 (m, 1H), 2.13-1.97 (m, 2H), 1.76-1.44 (m, 7H). Specific Optical Rotation: −48.3° c.=0.5, MeOH, 22.7° C., 589 nm.

The following methods were used to prepare compounds 1-21:

Example 1: Preparation of 2-(2-cyclopropylphenyl)-2-((R)-3-(4-(5,6,7,8-tetrahydro-1,8-naphthyridin-2-yl)butoxy)pyrrolidin-1-yl)acetic Acid (Compounds 1-E1 and 1-E2)

Step 1: ethyl 2-(2-cyclopropylphenyl)acetate

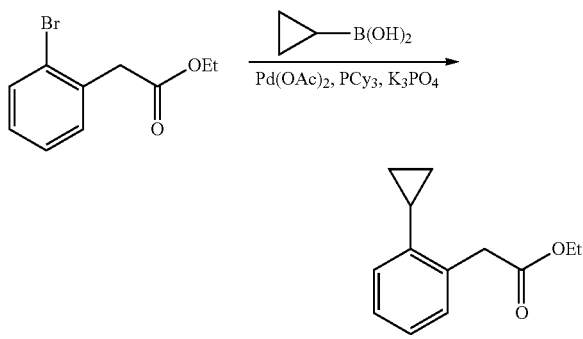

A mixture of ethyl 2-(2-bromophenyl)acetate (5.0 g, 20.57 mmol), cyclopropylboronic acid (3.54 g, 41.14 mmol), Pd(OAc)$_2$ (922 mg, 4.12 mmol), tricyclohexylphosphine (1.73 g, 6.17 mmol) and tripotassium phosphate (15.3 g, 72.01 mmol) in toluene (60 mL) and water (7.5 mL) was stirred at 120° C. overnight. Solvent was removed in vacuo, and the residue was purified by silica gel column (pet ether: EtOAc 20:1) to give the desired product ethyl 2-(2-cyclopropylphenyl) acetate as a colorless oil (4.0 g). Yield 95%. $^1$H NMR (400 MHz, CDCl3) δ 7.21-7.18 (m, 4H), 4.18-4.16 (q, 2H), 3.83 (s, 2H), 1.52-1.48 (m, 1H), 1.29-1.18 (t, 3H), 0.94-0.64 (m, 4H).

Step 2: ethyl 2-bromo-2-(2-cyclopropylphenyl)acetate

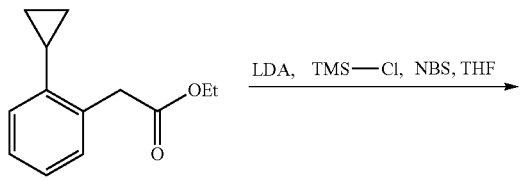

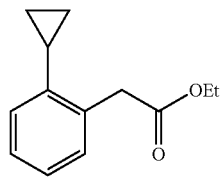

To a solution of ethyl 2-(2-cyclopropylphenyl) acetate (1 g, 4.9 mmol) in THF (16 mL) at −78° C. was added lithium diisopropylamide solution 2.0 M in THF/hexanes (6.2 mL, 12.4 mmol) dropwise. The reaction was stirred at −78° C. for 30 min. Then a solution of chlorotrimethylsilane (1.3 g, 12.25 mmol) in THF (5 mL) was added, and the reaction was stirred at −78° C. for another 30 min. Then a solution of NBS (1.5 g, 12.25 mmol) in THF (10 mL) was added and the reaction was stirred at −78° C. for 1 hour. The reaction was quenched with MeOH (2 mL) and concentrated in vacuo, and the residue was purified by silica gel column (pet ether: EtOAc 10:1) to give the desired product ethyl 2-bromo-2-(2-cyclopropylphenyl)acetate as a yellow oil (350 mg). Yield 25%.

Step 3: ethyl 2-(2-cyclopropylphenyl)-2-((R)-3-(4-(5,6,7,8-tetrahydro-1,8-naphthyridin-2-yl)butoxy)pyrrolidin-1-yl)acetate

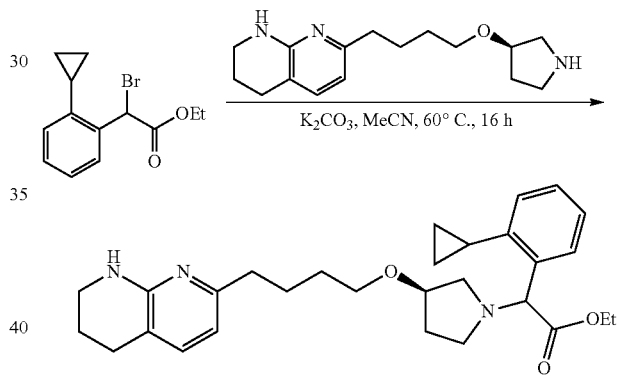

A mixture of ethyl 2-bromo-2-(2-cyclopropylphenyl)acetate (350 mg, 1.24 mmol), (R)-7-(4-(pyrrolidin-3-yloxy)butyl)-1,2,3,4-tetrahydro-1,8-naphthyridine (341 mg, 1.24 mmol) and K2CO3 (513 mg, 3.72 mmol) in acetonitrile (8 mL) was stirred 60° C. for 16 h. Solvent was removed in vacuo, and the residue was purified by silica gel column (DCM:MeOH 20:1) to give the desired product ethyl 2-(2-cyclopropylphenyl)-2-((R)-3-(4-(5,6,7,8-tetrahydro-1,8-naphthyridin-2-yl)butoxy)pyrrolidin-1-yl)acetate as a yellow oil (150 mg). Yield 25% (ESI 478 (M+H)+).

Step 4: 2-(2-cyclopropylphenyl)-2-((R)-3-(4-(5,6,7,8-tetrahydro-1,8-naphthyridin-2-yl)butoxy)pyrrolidin-1-yl)acetic acid (compounds 1-E1 and 1-E2)

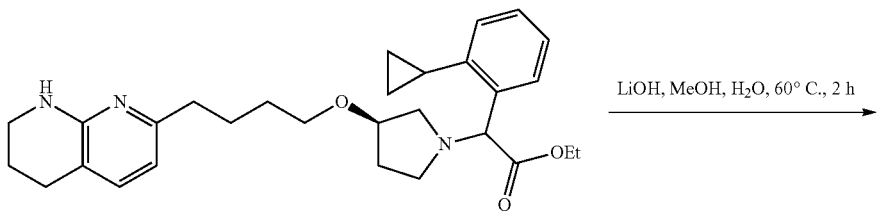

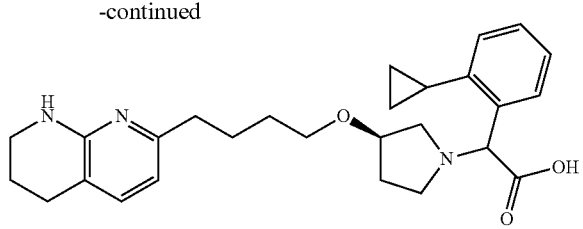

Ethyl 2-(2-cyclopropylphenyl)-2-((R)-3-(4-(5,6,7,8-tetrahydro-1,8-naphthyridin-2-yl)butoxy)pyrrolidin-1-yl)acetate (150 mg, 0.31 mmol) was treated with LiOH—H₂O (52 mg, 1.24 mmol) in MeOH (4 mL) and H₂O (1 mL) at 60° C. for 2 hours. Solvent was removed in vacuo, and the residue was purified by Prep-HPLC A (30-65% MeCN) to give compound 1 as a white solid (110 mg, 77% yield). The racemic product was separated by Prep chiral SFC A to give diastereomeric products compound 1-E1 (25 mg) and compound 1-E2 (26 mg) as white solids.

Compound 1-E1 LC/MS ESI 450.6 (M+H)+. 1H NMR (400 MHz, MeOD) δ 7.60 (d, J=7.6 Hz, 1H), 7.28 (m, 2H), 7.15 (d, J=7.3 Hz, 2H), 6.37 (d, J=7.3 Hz, 1H), 5.31 (s, 1H), 4.21 (s, 1H), 3.72-3.32 (m, 6H), 3.24-3.02 (m, 2H), 2.71 (t, J=6.3 Hz, 2H), 2.54 (t, J=7.5 Hz, 2H), 2.31-1.95 (m, 3H), 1.94-1.79 (m, 2H), 1.77-1.66 (m, 2H), 1.58 (m, 2H), 1.05-0.87 (m, 3H), 0.67-0.38 (m, 1H). Chiral SFC A (45% MeOH): ee 98%, Rt=1.97 min Compound 1-E2 LC/MS ESI 450.6 (M+H)+. 1H NMR (400 MHz, MeOD) δ 7.60 (d, J=7.6 Hz, 1H), 7.28 (m, 2H), 7.15 (d, J=7.3 Hz, 2H), 6.37 (d, J=7.3 Hz, 1H), 5.31 (s, 1H), 4.21 (s, 1H), 3.72-3.32 (m, 6H), 3.24-3.02 (m, 2H), 2.71 (t, J=6.3 Hz, 2H), 2.54 (t, J=7.5 Hz, 2H), 2.31-1.95 (m, 3H), 1.94-1.79 (m, 2H), 1.77-1.66 (m, 2H), 1.58 (m, 2H), 1.05-0.87 (m, 3H), 0.67-0.38 (m, 1H). Chiral SFC A (45% MeOH): ee 98%, Rt=2.59 min Example 2: Preparation of 2-(2-cyclopropoxyphenyl)-2-((R)-3-(4-(5,6,7,8-tetrahydro-1,8-naphthyridin-2-yl)butoxy)pyrrolidin-1-yl)acetic Acid (Compounds 2-E1 and 2-E2)

Step 1: 1-bromo-2-cyclopropoxybenzene

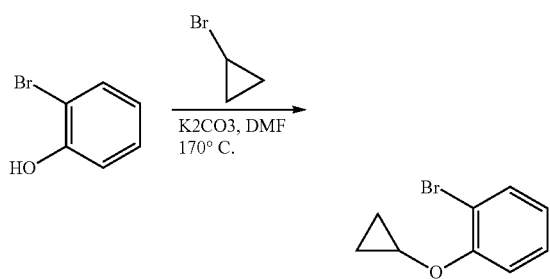

A mixture of 2-bromophenol (2.0 g, 11.6 mmol), bromocyclopropane (4.6 g, 38.1 mmol) and K2CO3 (5.2 g, 38.1 mmol) in dry DMF (10 mL) was sealed in a tube and heated by microwave at 140° C. for 2 hours. The reaction mixture was cooled to room temperature, diluted with water and extracted with diethyl ether (3×100 mL). The combined organic layer was washed with brine and concentrated in vacuo. The residue was purified by silica gel column (eluting with 0-10 percent EtOAc/hexanes) to afford the desired product as colorless oil (400 mg). Yield 17% 1H NMR (400 MHz, CDCL3) δ 7.52 (d, J=7.2 Hz, 1H), 7.30-7.27 (m, 2H), 6.88-6.84 (m, 1H), 3.83-3.80 (m, 1H), 0.90-0.82 (m, 4H).

Step 2: 2-cyclopropoxyphenylboronic acid

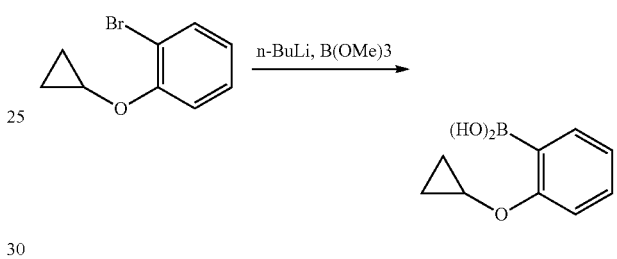

To a solution of 1-bromo-2-cyclopropoxybenzene(800 mg, 3.75 mmol) in THE (20 mL) was added n-BuLi (2.5M, 4.5 mmol) dropwise. The reaction was stirred for 1 h at −78° C. under Ar. A solution of trimethyl borate (779 mg, 7.5 mmol) in THE (5 mL) was added dropwise, and the reaction stirred for another 1 hour at −78° C., then slowly warmed to room temperature and stirred overnight. Aqueous HCl (1N, 20 mL) was added, and the reaction was stirred at room temperature for 30 min, then extracted with DCM (3×20 mL). The combined organic layers were dried over Na2SO4, filtered, and concentrated in vacuo. The residue was purified by silica gel column (pet ether:EtOAc=1:1) to give the desired product as a white solid (400 mg). Yield: 60% (ESI: 178 [M−H]−).

Step 3: 2-(2-cyclopropoxyphenyl)-2-((R)-3-(4-(5,6,7,8-tetrahydro-1,8-naphthyridin-2-yl)butoxy)pyrrolidin-1-yl)acetic acid (compounds 2-E1 and 2-E2)

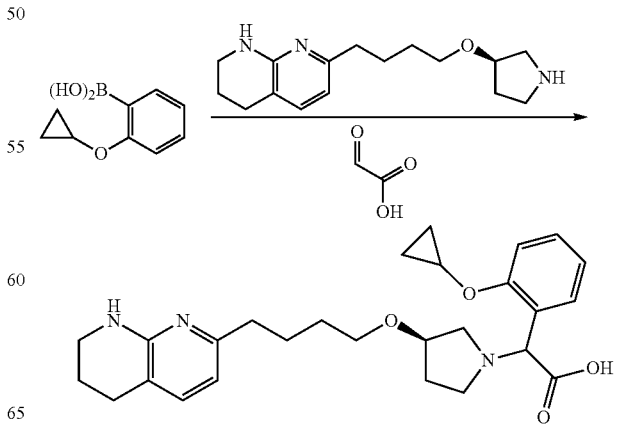

A mixture of 2-cyclopropoxyphenylboronic acid (400 mg, 2.25 mmol), (R)-7-(4-(pyrrolidin-3-yloxy)butyl)-1,2,3,4-tetrahydro-1,8-naphthyridine (476 mg, 1.73 mmol) and 2-oxoacetic acid (304 mg 3.45 mmol) in DCM (5 mL) was stirred at room temperature for 8 hours. Solvent was removed in vacuo, and the residue was purified by Prep-HPLC A (30-65% MeCN) to give compound 2 as a white solid (205 mg, 26% yield). The racemic product was separated by Prep chiral SFC A to give diastereomeric products compound 2-E1 (110 mg) and compound 2-E2 (79 mg) as white solids.

Compound 2-E1 LC/MS ESI 466 (M+H)+1H NMR (400 MHz, MeOD) δ 7.48 (d, J=7.6 Hz, 1H), 7.41-7.40 (m, 2H), 7.13 (d, J=7.6 Hz, 1H), 7.04-7.00 (m, 1H), 6.38 (d, J=7.6 Hz, 1H), 4.92 (s, 1H), 4.18-4.16 (m, 1H), 3.90-3.85 (m, 1H), 3.56-3.36 (m, 5H), 3.27-3.01 (m, 3H), 2.70 (t, J=6.0 Hz, 2H), 2.56 (t, J=7.2 Hz, 2H), 2.09-1.55 (m, 8H), 0.85-0.70 (m, 4H). Chiral SFC A (40% MeOH): ee 85.4%, Rt=2.39 min Compound 2-E2 LC/MS ESI 466 (M+H)+1H NMR (400 MHz, MeOD) δ 7.52 (d, J=7.6 Hz, 1H), 7.41-7.40 (m, 2H), 7.13 (d, J=7.2 Hz, 1H), 7.03-6.99 (m, 1H), 6.37 (d, J=7.2 Hz, 1H), 4.86 (s, 1H), 4.15-4.12 (m, 1H), 3.92-3.75 (m, 1H), 3.56-3.36 (m, 5H), 3.27-3.14 (m, 3H), 2.70 (t, J=6.0 Hz, 2H), 2.53 (t, J=7.6 Hz, 2H), 2.20-1.55 (m, 8H), 0.85-0.70 (m, 4H). Chiral SFC A (40% MeOH): ee 95.4%, Rt=3.27 min Example 3: Preparation of 2-(2-cyclopropylpyridin-3-yl)-2-((R)-3-(5-(5,6,7,8-tetrahydro-1,8-naphthyridin-2-yl)pentyl)pyrrolidin-1-yl)acetic Acid (Compounds 3-E1 and 3-E2)

Step 1: 3-bromo-2-cyclopropylpyridine

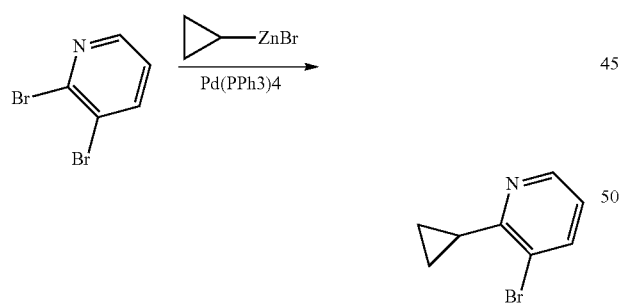

To a solution of 2,3-dibromopyridine (3 g, 12.8 mmol) and cyclopropylzinc(II) bromide (76 mL, 0.5 M in THF) in THF (30 mL) was added Pd(PPh3)4 (740 mg, 0.64 mmol). The mixture was stirred at 70° C. under N2 for 4 hours, then diluted with water (50 mL) and extracted with EtOAc (3×50 mL). The combined organic layers were dried over Na2SO4, filtered, and concentrated in vacuo. The residue was purified by silica gel column (pet ether: EtOAc 10:1) to give the desired product 3-bromo-2-cyclopropylpyridine as a yellow oil (1.2 g). Yield 48% (ESI 198(M+H)+).

Step 2: ethyl 2-(2-cyclopropylpyridin-3-yl)-2-hydroxyacetate

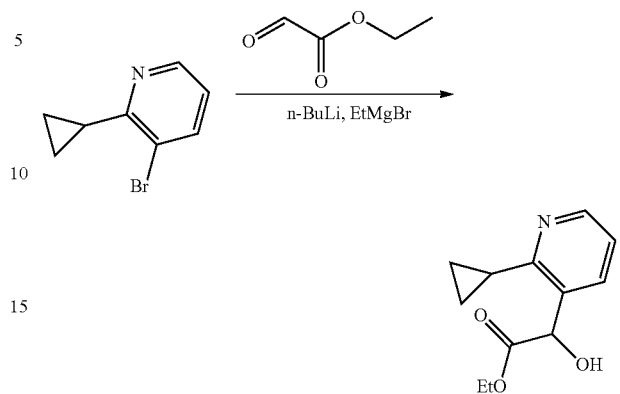

To a solution of EtMgBr (1 M, 3.65 mL, 3.65 mmol) in THF (20 mL) at 0° C. under N2, was added n-BuLi (2.9 mL, 7.3 mmol). The solution was stirred at 0° C. for 30 min, then a solution of 3-bromo-2-cyclopropylpyridine (1.2 g, 6.1 mmol) in THF (5 mL) was added at −10° C. The mixture was stirred at that temperature for 30 min, and ethyl 2-oxoacetate (50% in toluene, 5 g, 24.4 mmol) was added. The reaction was stirred at 0° C. for 2 hours, then quenched with saturated K2CO3 solution (20 mL) and extracted with EtOAc (3×50 mL). The combined organic layers were dried over Na2SO4, filtered and concentrated in vacuo. The residue was purified by flash chromatography on silica gel (pet ether: EtOAc 2:1) to give the desired product ethyl 2-(2-cyclopropylpyridin-3-yl)-2-hydroxyacetate as a yellow oil (700 mg). Yield 52% (ESI 222 (M+H)+).

Step 3: ethyl 2-(2-cyclopropylpyridin-3-yl)-2-(methylsulfonyloxy)acetate

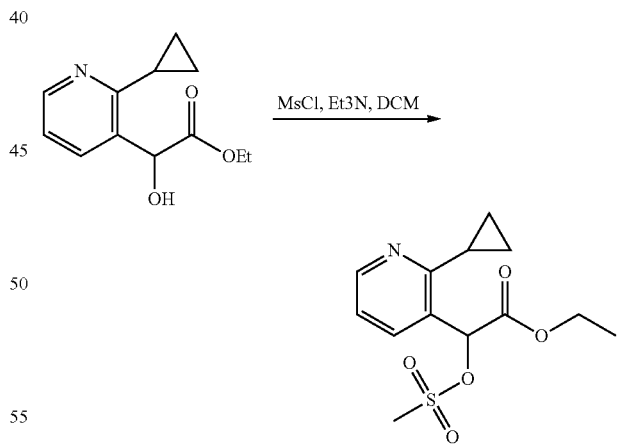

To a solution of ethyl 2-(2-cyclopropylpyridin-3-yl)-2-hydroxyacetate(300 mg, 1.36 mmol) and triethylamine (411 mg, 4.1 mmol) in DCM (5 mL) at 0° C. was added MsCl(232 mg, 2 mmol). The reaction was stirred at room temperature for 2 hours, then concentrated in vacuo and purified by silica gel column (pet ether: EtOAc 4:1) to get the desired product ethyl 2-(2-cyclopropylpyridin-3-yl)-2-(methylsulfonyloxy)acetate as a yellow oil (190 mg). Yield 47% (ESI 300 (M+H)+).

Step 4: ethyl 2-(2-cyclopropylpyridin-3-yl)-2-((R)-3-(5-(5,6,7,8-tetrahydro-1,8-naphthyridin-2-yl)pentyl)pyrrolidin-1-yl)acetate

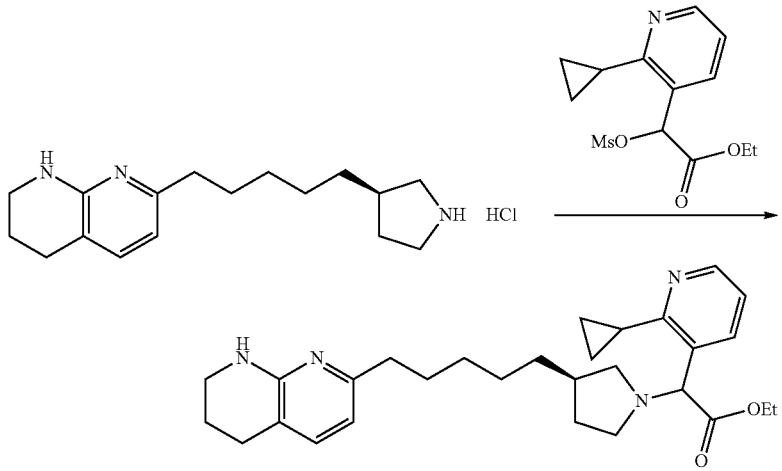

A mixture of (R)-7-(5-(pyrrolidin-3-yl)pentyl)-1,2,3,4-tetrahydro-1,8-naphthyridine hydrochloride (300 mg, 0.87 mmol), ethyl 2-(2-cyclopropylpyridin-3-yl)-2-(methylsulfonyloxy)acetate (286 mg, 0.96 mmol) and diisopropylethylamine (337 mg, 2.6 mmol) in acetonitrile (10 mL) was stirred at 50° C. overnight. Solvent was removed in vacuo, and the residue was purified by silica gel column (DCM:MeOH=0%~20%) to give the desired product as a yellow oil (245 mg). Yield 54% (ESI 477 (M+H)+).

Step 2: 2-(2-cyclopropylpyridin-3-yl)-2-((R)-3-(5-(5,6,7,8-tetrahydro-1,8-naphthyridin-2-yl)pentyl)pyrrolidin-1-yl)acetic acid
(compounds 3-E1 and 3-E2)

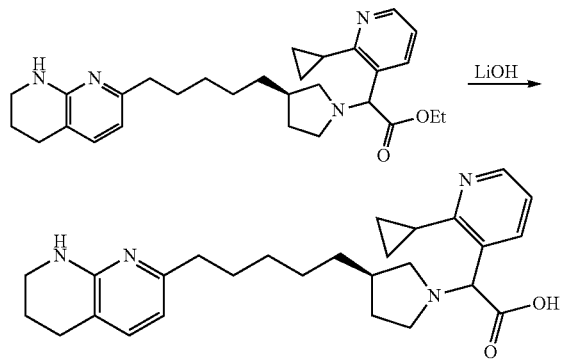

Ethyl 2-(2-cyclopropylpyridin-3-yl)-2-((R)-3-(5-(5,6,7,8-tetrahydro-1,8-naphthyridin-2-yl)pentyl)pyrrolidin-1-yl)acetate (245 mg, 0.51 mmol) was treated with LiOH—H$_2$O (210 mg, 5.0 mmol) in MeOH (4 mL) and H$_2$O (1 mL) at room temperature for 2 hours. Solvent was removed in vacuo, and the residue was purified by Prep-HPLC A (30-60% MeCN) to give compound 3 as a white solid (110 mg, 48% yield). The racemic product was separated by Prep chiral SFC H to give diastereomeric products compound 3-E1 (42 mg) and compound 3-E2 (45 mg) as white solids.

Compound 3-E1 LC/MS ESI 449 (M+H)+ $^1$H NMR (400 MHz, MeOD) δ 8.39 (t, J=6.1 Hz, 1H), 7.98 (d, J=7.9 Hz, 1H), 7.19-7.10 (m, 2H), 6.35 (d, J=7.3 Hz, 1H), 5.06 (s, 1H), 3.40-3.31 (m, 3H), 3.15-3.08 (m, 2H), 2.84-2.81 (m, 1H), 2.70-2.67 (m, 2H), 2.59-2.56 (m, 1H), 2.55-2.47 (m, 2H), 2.36-2.26 (m, 1H), 2.21-2.13 (m, 1H), 1.90-1.84 (m, 2H), 1.66-1.57 (m, 3H), 1.44-1.26 (m, 7H), 1.08-1.05 (m, 2H), 0.93-0.90 (m, 1H). Chiral SFC H (45% MeOH): ee 92%, Rt=2.11 min Compound 3-E2 LC/MS ESI 449 (M+H)+ $^1$H NMR (400 MHz, MeOD) δ 8.36 (t, J=6.1 Hz, 1H), 8.01 (d, J=7.9 Hz, 1H), 7.20-7.11 (m, 2H), 6.35 (d, J=8 Hz, 1H), 4.91 (s, 1H), 3.51-3.36 (m, 3H), 3.20-2.91 (m, 2H), 2.71-2.29 (m, 7H), 2.14-2.09 (m, 1H), 1.90-1.84 (m, 2H), 1.64-1.57 (m, 3H), 1.433-1.23 (m, 7H), 1.06-1.01 (m, 2H), 0.92-0.88 (m, 1H). Chiral SFC H (45% MeOH): ee 100%, Rt=3.77 min Example 4: Preparation of 2-(2-cyclopropyl-5-fluorophenyl)-2-((R)-3-(4-(5,6,7,8-tetrahydro-1,8-naphthyridin-2-yl)butoxy)pyrrolidin-1-yl)acetic Acid (Compounds 4-E1 and 4-E2)

Step 1: 2-cyclopropyl-5-fluoroaniline

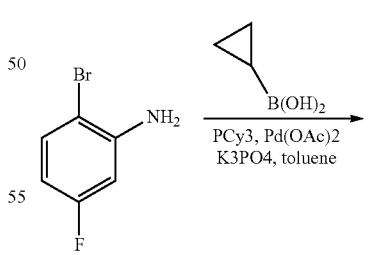

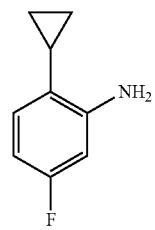

A mixture of 2-bromo-5-fluoroaniline (3.0 g, 15.8 mmol), cyclopropylboronic acid (2.7 g, 31.4 mmol), PCy3 (440 mg, 1.57 mmol), Pd(OAc)2 (352 mg, 1.57 mmol) and K3PO4 (20 g, 94.3 mmol) in toluene (50 mL) and H2O (10 mL) was stirred at 100° C. for 4 hours. The reaction mixture was cooled to room temperature, diluted with H2O (10 mL) and extracted with EtOAc (3×100 mL). The combined organic layer was washed with brine and concentrated in vacuo. The residue was purified by silica gel column (pet ether: EtOAc 2:1) to afford the desired product as a colorless oil (1.8 g). Yield 75% (ESI: 152[M+H]+).

Step 2: 1-cyclopropyl-4-fluoro-2-iodobenzene

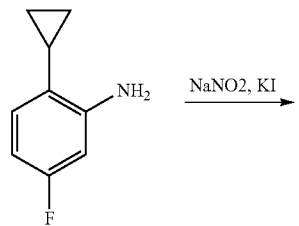

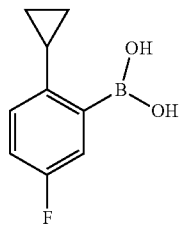

2-cyclopropyl-5-fluoroaniline (1.8 g, 11.9 mmol) was added to a solution of para-toluene sulfonic acid monohydrate (6.8 g, 35.8 mmol) in acetonitrile (60 mL). The reaction was stirred for 10 minutes at room temperature and then cooled to 10° C. A solution of sodium nitrite (2.0 g, 29.0 mmol) and potassium iodide (4.0 g, 24.1 mmol) in water (20 mL) was added dropwise over 30 minutes. The reaction mixture was stirred at room temperature for 4 hours, then basified to pH 9-10 with aqueous sodium bicarbonate, then diluted with EtOAc (100 mL) and 10% aqueous sodium metabisulphite (20 mL). The phases were separated, and the aqueous layer was extracted with EtOAc (2×100 mL). Organics were combined, washed with brine, dried over Na2SO4, filtered and concentrated in vacuo. The residue was purified by silica gel column (pet ether: EtOAc 10:1) to afford the desired product as a colorless oil (1.3 g). Yield 42% (ESI: N/A).

Step 3: 2-cyclopropyl-5-fluorophenylboronic acid

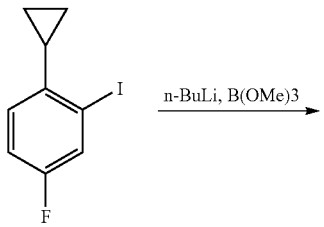

To a solution of 1-cyclopropyl-4-fluoro-2-iodobenzene (1.3 g, 4.96 mmol) in THF (50 mL) was added n-BuLi (2.5M, 2.2 mL, 5.5 mmol) dropwise. The reaction was stirred for 1 h at −78° C. under Ar. A solution of trimethyl borate (1.0 g, 9.62 mmol) in THF (10 mL) was added dropwise, and the reaction was stirred for another 1 hour at −78° C., then slowly warmed to room temperature and stirred overnight. Aqueous HCl (1N, 20 mL) was added, and the mixture was stirred at room temperature for 30 min, then extracted with DCM (3×20 mL). The combined organic layers were dried over Na2SO4, filtered, and concentrated in vacuo. The residue was purified by silica gel column (pet ether:EtOAc=1:1) to give the desired product as a white solid (500 mg). Yield: 56% (ESI: 179[M−H]−).

Step 4: 2-(2-cyclopropyl-5-fluorophenyl)-2-((R)-3-(4-(5,6,7,8-tetrahydro-1,8-naphthyridin-2-yl)butoxy)pyrrolidin-1-yl)acetic acid (compounds 4-E1 and 4-E2)

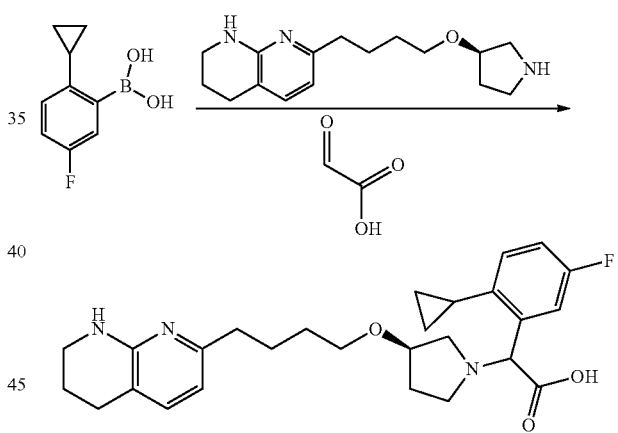

A mixture of 2-cyclopropyl-5-fluorophenylboronic acid (200 mg, 1.11 mmol), (R)-7-(4-(pyrrolidin-3-yloxy)butyl)-1,2,3,4-tetrahydro-1,8-naphthyridine (306 mg, 1.11 mmol) and 2-oxoacetic acid (123 mg 1.66 mmol) in MeCN (5 mL) was stirred at 60° C. for 15 hours. Solvent was removed in vacuo, and the residue was purified by Prep-HPLC A (30-65% MeCN) to give compound 4 as a white solid (120 mg, 23% yield). The racemic product was separated by Prep chiral SFC A to give diastereomeric products compound 4-E1 (34 mg) and compound 4-E2 (41 mg) as white solids.

Compound 4-E1 LC/MS ESI 468 (M+H)+1H NMR (400 MHz, MeOD) δ 7.41 (d, J=10.0 Hz, 1H), 7.20-7.01 (m, 3H), 6.38 (d, J=7.2 Hz, 1H), 5.28 (s, 1H), 4.21 (s, 1H), 3.55-3.05 (m, 8H), 2.71 (t, J=6.4 Hz, 2H), 2.55 (t, J=7.6 Hz, 2H), 2.19-2.05 (m, 3H), 1.92-1.55 (m, 6H), 0.95-0.80 (m, 3H), 0.55-0.50 (m, 1H). Chiral SFC A (35% MeOH): ee 100%, Rt=2.69 min Compound 4-E2 LC/MS ESI 468 (M+H)+1H NMR (400 MHz, MeOD) δ 7.41 (d, J=10.0 Hz, 1H), 7.20-7.01 (m, 3H), 6.38 (d, J=7.2 Hz, 1H), 5.19 (s, 1H), 4.18 (s, 1H), 3.54-3.19 (m, 8H), 2.71 (t, J=6.0 Hz, 2H), 2.59-2.53 (m, 2H), 2.22-2.14 (m, 3H), 1.92-1.55 (m, 6H), 0.98-0.85 (m, 3H), 0.55-0.50 (m, 1H). Chiral SFC A (35% MeOH): ee 97%, Rt=3.26 min Example 5: Preparation of 2-(2-cyclopropylphenyl)-2-((R)-3-(3-(5,6,7,8-tetrahydro-1,8-naphthyridin-2-yl)propoxy)pyrrolidin-1-yl)acetic Acid (Compounds 5-E1 and 5-E2)

Step 1: 2-(2-cyclopropylphenyl)-2-(((R)-3-(3-(5,6,7,8-tetrahydro-1,8-naphthyridin-2-yl)propoxy)pyrrolidin-1-yl)acetic acid (compounds 5-E1 and 5-E2)

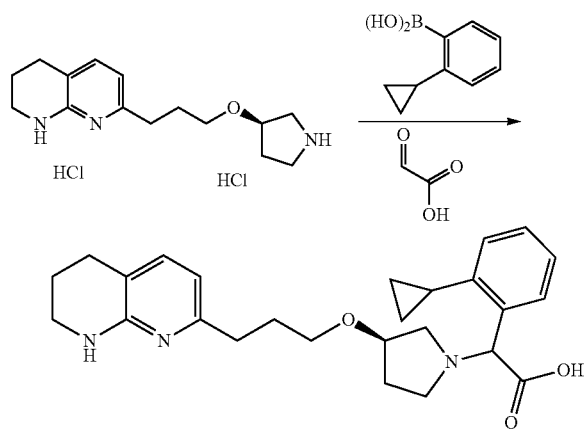

A mixture of 2-cyclopropylphenylboronic acid (102 mg, 0.63 mmol), (R)-7-(4-(pyrrolidin-3-yloxy)butyl)-1,2,3,4-tetrahydro-1,8-naphthyridine (140 mg, 0.42 mmol) and 2-oxoacetic acid (47 mg 0.63 mmol) in DCM (5 mL) was stirred at room temperature for 8 hours. Solvent was removed in vacuo, and the residue was purified by Prep-HPLC A (30-65% MeCN) to give compound 5 as a white solid (95 mg, 52% yield). The racemic product was separated by Prep chiral SFC H to give diastereomeric products compound 5-E1 (15 mg) and compound 5-E2 (9 mg) as white solids.

Compound 5-E1 LC/MS ESI 436.4 (M+H)+ $^1$H NMR (400 MHz, MeOD) δ 7.64 (d, J=7.6 Hz, 1H), 7.33-7.12 (m, 4H), 6.36 (d, J=7.2 Hz, 1H), 5.26 (s, 1H), 4.18 (s, 1H), 3.55-3.22 (m, 8H), 2.69 (t, J=6.4 Hz, 2H), 2.60 (t, J=7.2 Hz, 2H), 2.30-2.13 (m, 3H), 1.92-1.84 (m, 4H), 1.08-0.90 (m, 3H), 0.65-0.55 (m, 1H). Chiral SFC H (35% MeOH): ee 98%, Rt=2.74 min Compound 5-E2 LC/MS ESI 436.4 (M+H)+ $^1$H NMR (400 MHz, MeOD) δ 7.61 (d, J=7.6 Hz, 1H), 7.32-7.12 (m, 4H), 6.36 (d, J=7.2 Hz, 1H), 5.33 (s, 1H), 4.21 (s, 1H), 3.55-3.09 (m, 8H), 2.70 (t, J=6.4 Hz, 2H), 2.60 (t, J=7.2 Hz, 2H), 2.25-2.00 (m, 3H), 1.93-1.84 (m, 4H), 1.08-0.90 (m, 3H), 0.65-0.55 (m, 1H). Chiral SFC H (35% MeOH): ee 99%, Rt=3.55 min Example 6: Preparation of 2-(2,6-dicyclopropylpyridin-3-yl)-2-((R)-3-(4-(5,6,7,8-tetrahydro-1,8-naphthyridin-2-yl)butoxy)pyrrolidin-1-yl)acetic Acid (Compounds 6-E1 and 6-E2)

Step 1: 2,6-dicyclopropylpyridin-3-amine

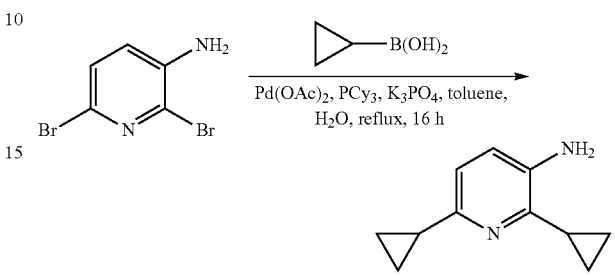

A mixture of ethyl 2,6-dibromopyridin-3-amine (6.0 g, 23.8 mmol), cyclopropylboronic acid (6.14 g, 71.4 mmol), Pd(OAc)2 (267 mg, 2.38 mmol), tricyclohexylphosphine (668 mg, 6.17 mmol) and tripotassium phosphate (17.7 g, 83.3 mmol) in toluene (80 mL) and water (10 mL) was stirred at 120° C. overnight. Solvent was removed in vacuo, and the residue was purified by silica gel column (pet ether: EtOAc 4:1) to give the desired product 2,6-dicyclopropylpyridin-3-amine as a colorless oil (3.0 g). Yield 95% (ESI 175.0 (M+H)+).

Step 2: 2,6-dicyclopropylpyridin-3-amine

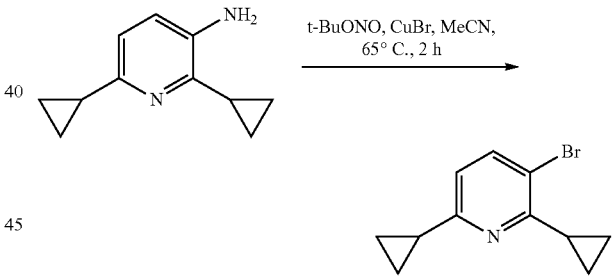

A mixture of ethyl 2,6-dicyclopropylpyridin-3-amine (3.0 g, 17.2 mmol), tert-butyl nitrite (2.66 g, 25.8 mmol) and cuprousbromide (17.7 g, 25.8 mmol) in acetonitrile (20 mL) was stirred at 65° C. for 2 hours. Solvent was removed in vacuo, and the residue was purified by silica gel column (pet ether: EtOAc 6:1) to give the desired product 3-bromo-2,6-dicyclopropylpyridine as a yellow oil (820 mg). Yield 20% (ESI 239.0 (M+H)+).

Step 3: tert-butyl 2-(2,6-dicyclopropylpyridin-3-yl)acetate

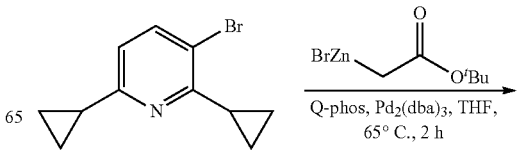

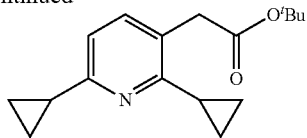

A mixture of 3-bromo-2,6-dicyclopropylpyridine (800 mg, 3.36 mmol), (2-tert-butoxy-2-oxoethyl)zinc(II) bromide solution 0.5 M in THF (26.9 mL, 13.44 mmol), Pd2(dba)3 (156 mg, 0.17 mmol) and Qphos (121 mg, 0.17 mmol) in THF (12 mL) was stirred at 65° C. for 2 hours. Solvent was removed in vacuo, and the residue was purified by silica gel column (pet ether: EtOAc 4:1) to give the desired product tert-butyl 2-(2,6-dicyclopropylpyridin-3-yl)acetate as a yellow oil (550 mg). Yield 60% (ESI 274.0 (M+H)+).

Step 4: tert-butyl 2-bromo-2-(2,6-dicyclopropylpyridin-3-yl)acetate

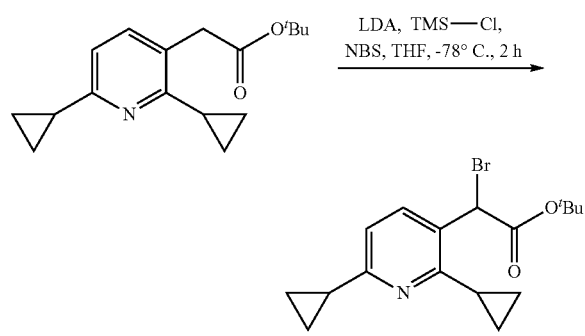

To a solution of tert-butyl 2-(2,6-dicyclopropylpyridin-3-yl)acetate (300 mg, 1.1 mmol) in THF (10 mL) at −78° C. was added lithium diisopropylamide solution 2.0 M in THF/hexanes (1.4 mL, 2.8 mmol) dropwise. The reaction was stirred at −78° C. for 30 min, and then a solution of chlorotrimethylsilane (297 mg, 2.75 mmol) in THF (5 mL) was added. The reaction was stirred at −78° C. for another 30 min. Then a solution of NBS (325 mg, 2.75 mmol) in THF (5 mL) was added, and the reaction was stirred at −78° C. for 1 hour. The reaction was quenched with MeOH (2 mL), concentrated in vacuo and purified by silica gel column (pet ether: EtOAc 4:1) to give the desired product tert-butyl 2-bromo-2-(2,6-dicyclopropylpyridin-3-yl)acetate as a yellow oil (80 mg). Yield 21% (ESI 353 (M+H)+).

Step 5: tert-butyl 2-(2,6-dicyclopropylpyridin-3-yl)-2-((R)-3-(4-(5,6,7,8-tetrahydro-1,8-naphthyridin-2-yl)butoxy)pyrrolidin-1-yl)acetate

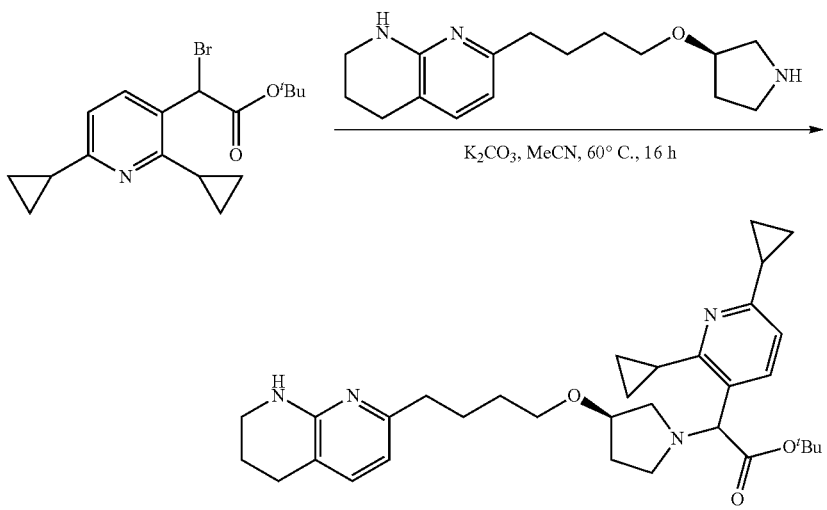

A mixture of tert-butyl 2-bromo-2-(2,6-dicyclopropylpyridin-3-yl)acetate (80 mg, 0.23 mmol), ((R)-7-(4-(pyrrolidin-3-yloxy)butyl)-1,2,3,4-tetrahydro-1,8-naphthyridine (64 mg, 0.23 mmol) and K2CO3 (96 mg, 0.69 mmol) in acetonitrile (8 mL) was stirred 60° C. for 16 hours. Solvent was removed in vacuo, and the residue was purified by silica gel column (DCM:MeOH 20:1) to give the desired product tert-butyl 2-(2,6-dicyclopropylpyridin-3-yl)-2-((R)-3-(4-(5,6,7,8-tetrahydro-1,8-naphthyridin-2-yl)butoxy)pyrrolidin-1-yl)acetate as a yellow oil (90 mg). Yield 72% (ESI 547 (M+H)+).

Step 6: 2-(2,6-dicyclopropylpyridin-3-yl)-2-((R)-3-(4-(5,6,7,8-tetrahydro-1,8-naphthyridin-2-yl)butoxy)pyrrolidin-1-yl) actetic acid (compounds 6-E1 and 6-E2)

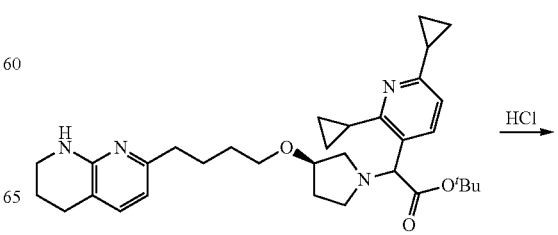

-continued

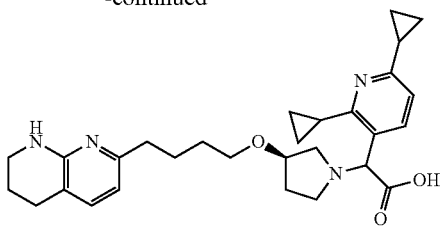

Tert-butyl 2-(2,6-dicyclopropylpyridin-3-yl)-2-((R)-3-(4-(5,6,7,8-tetrahydro-1,8-naphthyridin-2-yl)butoxy)pyrrolidin-1-yl)acetate (90 mg, 0.16 mmol) was treated with HCl in 1,4-dioxane (4M, 4 mL) at 25° C. for 2 hours. Solvent was removed in vacuo, and the residue was purified by Prep-HPLC A (30-65% MeCN) to give diastereomeric products compound 6-E1(11 mg) and compound 6-E2 (38 mg) as white solids.

Compound 6-E1 LC/MS ESI 491.6 (M+H)+. 1H NMR (400 MHz, MeOD) δ 8.52 (s, 1H), 7.77 (d, J=7.9 Hz, 1H), 7.67-7.44 (m, 1H), 7.03 (d, J=7.9 Hz, 1H), 6.53 (d, J=7.3 Hz, 1H), 5.18 (s, 1H), 4.22 (s, 1H), 3.76-3.40 (m, 6H), 3.31-3.28 (m, 2H), 2.79-2.66 (m, 4H), 2.39 (d, J=5.6 Hz, 1H), 2.19 (s, 2H), 1.98-1.93 (m, 3H), 1.76-1.74 (m, 2H), 1.64-1.62 (m, 2H), 1.25-1.14 (m, 1H), 1.06-0.72 (m, 8H).

Compound 6-E2 LC/MS ESI 491.6 (M+H)+. 1H NMR (400 MHz, MeOD) δ 8.52 (s, 1H), 7.77 (d, J=7.9 Hz, 1H), 7.67-7.44 (m, 1H), 7.03 (d, J=7.9 Hz, 1H), 6.53 (d, J=7.3 Hz, 1H), 5.27 (s, 1H), 4.23 (s, 1H), 3.76-3.40 (m, 6H), 3.31-3.28 (m, 2H), 2.79-2.66 (m, 4H), 2.39 (d, J=5.6 Hz, 1H), 2.19 (s, 2H), 1.98-1.93 (m, 3H), 1.76-1.74 (m, 2H), 1.64-1.62 (m, 2H), 1.25-1.14 (m, 1H), 1.06-0.72 (m, 8H).

Example 7: Preparation of 2-(2-(isopropoxymethyl)phenyl)-2-((R)-3-(4-(5,6,7,8-tetrahydro-1,8-naphthyridin-2-yl)butoxy)pyrrolidin-1-yl)acetic Acid (Compounds 7-E1 and 7-E2)

Step 1: 1-bromo-2-(isopropoxymethyl)benzene

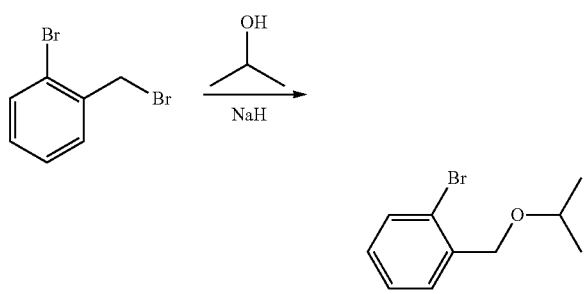

To a solution of isopropanol (0.72 g, 12 mmol) in DMF (15 mL) at 0° C. was added NaH (480 mg, 12 mmol). The reaction was stirred at 0° C. for 0.5 hour, then 1-bromo-2-(bromomethyl)benzene (3.0 g, 12 mmol) in DMF (5 mL) was added dropwise. The reaction was stirred at room temperature for 16 hours, then quenched with H₂O (10 mL) and extracted with EtOAc (2×20 mL). The combined organic layer was concentrated in vacuo, and the residue was purified by silica gel column (pet ether:EtOAc=10:1) to give the desired product 1-bromo-2-(isopropoxymethyl)benzene (1.6 g). Yield 58% (ESI 229 (M+H)+).

Step 2: 2-(isopropoxymethyl)phenylboronic acid

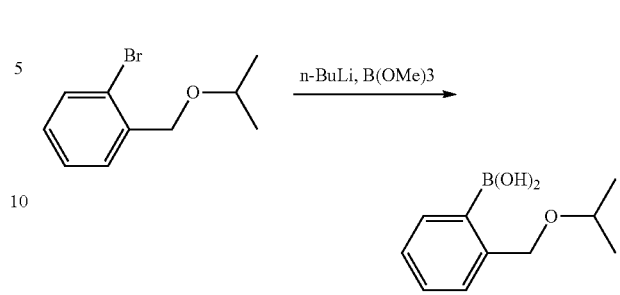

To a solution of 1-bromo-2-(isopropoxymethyl)benzene (300 mg, 1.32 mmol) in THF (5 mL) at −78° C., was added nBuLi (2.5M, 0.6 mL, 1.45 mmol) dropwise. The reaction was stirred at −78° C. for 1 hour, and trimethyl borate (500 mg, 2.64 mmol) in THF (2 mL) was added dropwise. The reaction was stirred at room temperature for 1 hour, then quenched with aqueous HCl (1N, 10 mL) and extracted with EtOAc (3×10 mL). The combined organic layer was concentrated in vacuo, and the residue was purified by silica gel column (pet ether:EtOAc=2:1) to give the desired product 2-(isopropoxymethyl)phenylboronic acid as a white solid (120 mg). Yield: 47% (ESI 193(M−H)−.

Step 3: 2-(2-(isopropoxymethyl)phenyl)-2-((R)-3-(4-(5,6,7,8-tetrahydro-1,8-naphthyridin-2-yl)butoxy)pyrrolidin-1-yl)acetic acid (compounds 7-E1 and 7-E2)

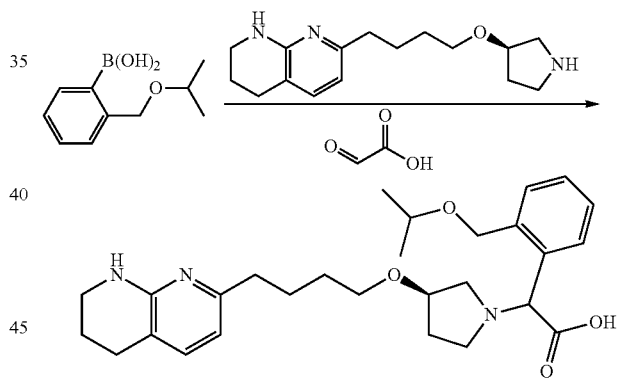

A mixture of (3R)-tert-butyl 3-(4-(5-methyl-1,2,3,4-tetrahydro-1,8-naphthyridin-2-yl)butoxy)pyrrolidine-1-carboxylate (131 mg, 0.48 mmol), 2-(isopropoxymethyl)phenylboronic acid (120 mg, 0.62 mmol) and 50% 2-oxoacetic acid (92 mg, 0.62 mmol) in MeCN (5 mL) was stirred at 70° C. for 16 hours. Solvent was removed in vacuo, and the residue was purified by Prep-HPLC B (30-65% MeCN) to give diastereomeric products compound 7-E1(40 mg) and compound 7-E2 (34 mg) as HCOOH salts.

Compound 7-E1 LC/MS ESI 482 (M+H)+. 1H NMR (400 MHz, MeOD) δ 8.33 (s, 2H), 7.68-7.66 (m, 1H), 7.52-7.50 (m, 1H), 7.46-7.42 (m, 3H), 6.56 (d, J=7.2 Hz, 1H), 5.09 (s, 1H), 4.90-4.88 (m, 1H), 4.52-4.50 (m, 1H), 4.23-4.21 (m, 1H), 3.82-3.80 (m, 1H), 3.66-3.44 (m, 7H), 3.21-3.19 (m, 1H), 2.81-1.60 (m, 12H), 1.25-1.23 (m, 6H).

Compound 7-E2 LC/MS ESI 482 (M+H)+. 1H NMR (400 MHz, MeOD) δ 8.33 (s, 2H), 7.65-7.63 (m, 1H), 7.52-7.50 (m, 1H), 7.44-7.42 (m, 3H), 6.56 (d, J=7.2 Hz, 1H), 4.97 (s, 1H), 4.86-4.50 (m, 2H), 4.26-4.24 (m, 1H), 3.85-3.82 (m, 1H), 3.61-3.40 (m, 5H), 3.26-3.22 (m, 3H), 2.81-1.60 (m, 12H), 1.28-1.23 (m, 6H).

Example 8: Preparation of 2-(2-(tert-butoxymethyl)-5-fluorophenyl)-2-((R)-3-(4-(5,6,7,8-tetrahydro-1,8-naphthyridin-2-yl)butoxy)pyrrolidin-1-yl)acetic Acid (Compound 8)

Step 1: 1-bromo-2-(tert-butoxymethyl)-4-fluorobenzene

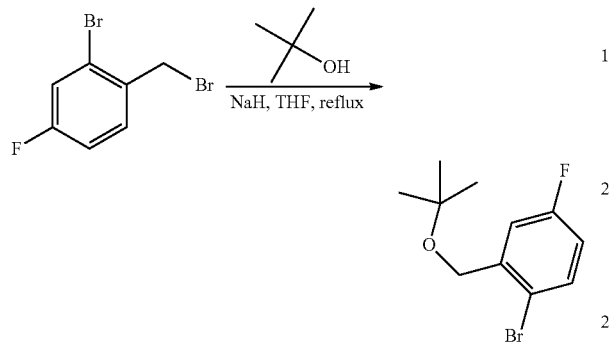

NaH (60%, 600 mg, 15 mmol) was added to a solution of 2-methylpropan-2-ol (7.4 g, 100 mmol) in THF (30 mL) at 0° C. The mixture was stirred at 0° C. for 0.5 hour, and 2-bromo-1-(bromomethyl)-4-fluorobenzene (2.68 g, 10 mmol) was added. The mixture was stirred at 80° C. overnight, then cooled to room temperature, quenched with water (50 mL) and extracted with EtOAc (50 mL). The organic layer was dried over Na2SO4, filtered and concentrated in vacuo. The residue was purified by silica gel column (pet ether:EtOAc 15:1) to give the desired product as a yellow oil (300 mg). Yield 11% (ESI 261 (M+H)+).

Step 2: 2-(tert-butoxymethyl)-4-fluorophenylboronic acid

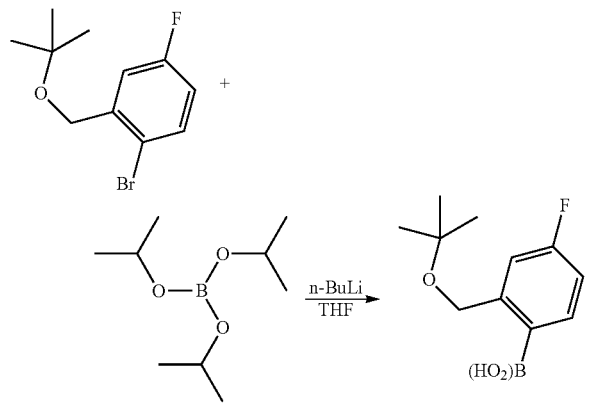

n-BuLi (0.4 mL, 2.5 M in hexane, 1 mmol) was added dropwise to a solution of 1-bromo-2-(tert-butoxymethyl)-4-fluorobenzene (150 mg, 0.57 mmol) and triisopropyl borate (188 mg, 1 mmol) in THF (5 mL) at −78° C. The mixture was stirred at −78° C. for 1 hour, then stirred at 25° C. for another 1 hour. The mixture was quenched with aqueous HCl (2N) to pH=5, then extracted with EtOAc (10 mL). The organic layer was dried over Na2SO4, filtered and concentrated in vacuo. The residue was purified by silica gel column (pet ether:EtOAc 2:1) to give the desired product as a colorless oil (70 mg). Yield 54% (ESI 225 (M−H)−).

Step 3: 2-(2-(tert-butoxymethyl)-5-fluorophenyl)-2-((R)-3-(4-(5,6,7,8-tetrahydro-1,8-naphthyridin-2-yl)butoxy)pyrrolidin-1-yl)acetic acid (compound 8)

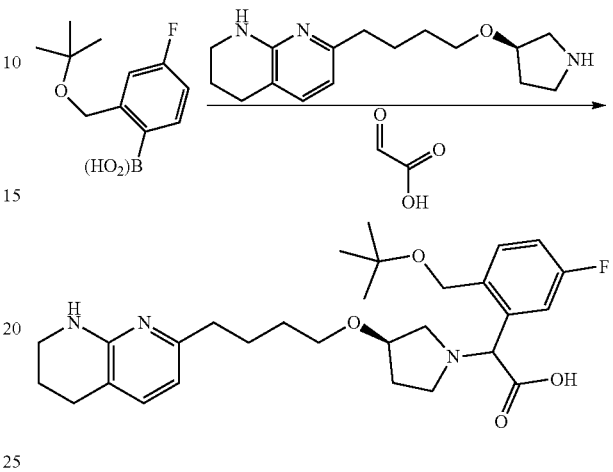

A mixture of 2-(tert-butoxymethyl)-4-fluorophenylboronic acid (75 mg, 0.33 mmol), 2-oxoacetic acid (88 mg, 50% in water, 0.6 mmol) and (R)-7-(4-(pyrrolidin-3-yloxy)butyl)-1,2,3,4-tetrahydro-1,8-naphthyridine (91 mg, 0.33 mmol) in CH3CN (5 mL) was stirred at 60° C. overnight. Solvent was removed in vacuo, and the residue was purified by Prep-HPLC A (33-65% MeCN) to give compound 8 as a white solid (22 mg, 13% yield).

Compound 8 LC/MS ESI 514 (M+H)+ 1H NMR (400 MHz, MeOD) δ 7.50-7.42 (m, 2H), 7.17-7.08 (m, 2H), 6.37 (d, J=7.2 Hz, 1H), 4.81-4.74 (m, 2H), 4.55-4.43 (m, 1H), 4.17 (s, 1H), 3.55-3.32 (m, 6H), 3.20-2.95 (m, 2H), 2.72-2.52 (m, 4H), 2.25-1.55 (m, 8H), 1.34-1.28 (m, 9H).

Example 9: Preparation of 2-(2-cyclopropylpyridin-3-yl)-2-(3-fluoro-3-(5-(5,6,7,8-tetrahydro-1,8-naphthyridin-2-yl)pentyl)pyrrolidin-1-yl)acetic Acid (Compounds 9-E1 and 9-E2)

Step 1: ethyl 2-chloro-2-(2-cyclopropylpyridin-3-yl)acetate

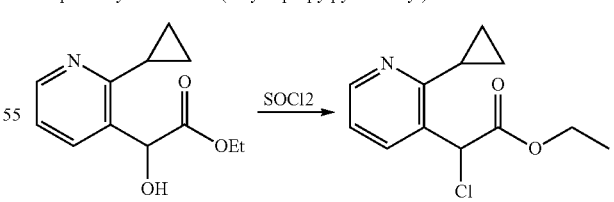

A solution of ethyl 2-(2-cyclopropylpyridin-3-yl)-2-hydroxyacetate(500 mg, 2.26 mmol) in SOCl2 (5 mL) was stirred at rt for 17 hours. Solvent was removed in vacuo, and the residue was purified by silica gel column (pet ether:EtOAc 4:1) to get the desired product ethyl 2-chloro-2-(2-cyclopropylpyridin-3-yl)acetate as a yellow oil (210 mg). Yield 39% (ESI 240 (M+H)+).

Step 2: ethyl 2-(2-cyclopropylpyridin-3-yl)-2-(3-fluoro-3-(5,6,7,8-tetrahydro-1,8-naphthyridin-2-yl)pentyl)pyrrolidin-1-yl)acetate

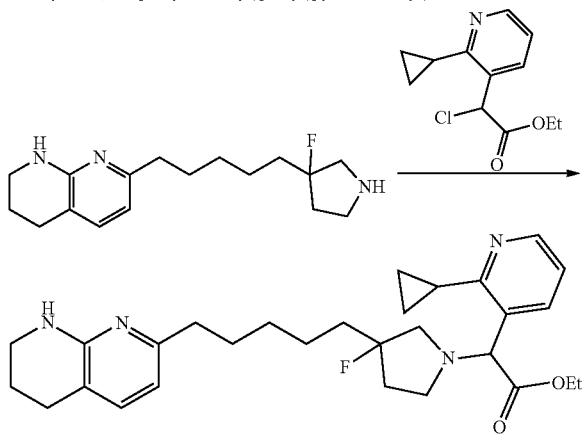

A mixture of 7-(5-(3-fluoropyrrolidin-3-yl)pentyl)-1,2,3,4-tetrahydro-1,8-naphthyridine(230 mg, 0.632 mmol), ethyl 2-chloro-2-(2-cyclopropylpyridin-3-yl)acetate (378 mg, 1.580 mmol) and K2CO3 (262 mg, 1.896 mmol) in acetonitrile (8 mL) was stirred at 60° C. for 16 hours. Solvent was removed in vacuo, and the residue was purified by silica gel column (DCM: MeOH 20:1) to give the desired product ethyl 2-(2-cyclopropylpyridin-3-yl)-2-(3-fluoro-3-(5-(5,6,7,8-tetrahydro-1,8-naphthyridin-2-yl)pentyl)pyrrolidin-1-yl) acetate as a yellow oil (120 mg). Yield 38% (ESI 495 (M+H)+).

Step 3: 2-(2-cyclopropylpyridin-3-yl)-2-(3-fluoro-3-(5,6,7,8-tetrahydro-1,8-naphthyridin-2-yl)pentyl)pyrrolidin-1-yl)acetic acid (compounds 9-E1 and 9-E2)

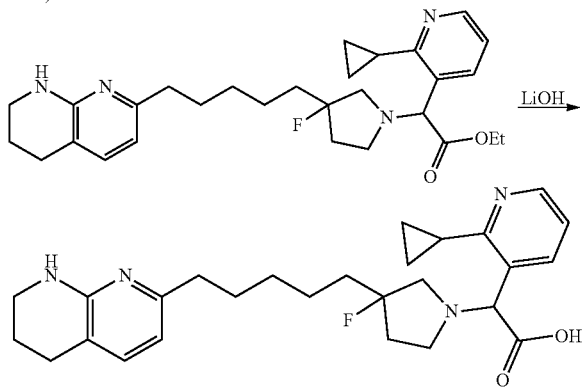

ethyl ethyl 2-(2-cyclopropylpyridin-3-yl)-2-(3-fluoro-3-(5-(5,6,7,8-tetrahydro-1,8-naphthyridin-2-yl)pentyl)pyrrolidin-1-yl)acetate (120 mg, 0.24 mmol) was treated with LiOH—H2O (40 mg, 0.97 mmol) in MeOH (4 mL) and H2O (1 mL) at 60° C. for 2 hours. Solvent was removed in vacuo, and the residue was purified by Prep-HPLC A (30-65% MeCN) to give compound 9 as a white solid (60 mg, 53% yield). The racemic product was separated by Prep chiral SFC F to give diastereomeric products compound 9-E1 (10 mg) and compound 9-E2 (10 mg) as white solids, each as a mixture of 2 stereoisomers.

Compound 9-E1 (mixture of 2 stereoisomers) LC/MS ESI 467.4 (M+H)+. 1H NMR (400 MHz, MeOD) δ 8.32 (s, 1H), 8.03 (d, J=7.3 Hz, 1H) 7.28 (m, 2H), 6.41 (d, J=7.3 Hz, 1H), 4.81 (s, 1H), 3.40-2.95 (m, 6H), 2.80-2.50 (m, 5H), 2.25-1.20 (m, 12H), 1.10-0.85 (m, 4H). Chiral SFC F (45% MeOH): ee 76%, Rt=2.72 min Compound 9-E1 (mixture of 2 stereoisomers) LC/MS ESI 467.4 (M+H)+. 1H NMR (400 MHz, MeOD) δ 8.39 (s, 1H), 8.01 (d, J=7.3 Hz, 1H) 7.33 (m, 2H), 6.47 (d, J=7.3 Hz, 1H), 4.96 (s, 1H), 3.45-2.95 (m, 6H), 2.80-2.50 (m, 5H), 2.25-1.20 (m, 12H), 1.10-0.85 (m, 4H). Chiral SFC F (45% MeOH): ee 53%, Rt=3.36 min Example 10: Preparation of 2-(2-cyclopropylpyridin-3-yl)-2-((R)-3-(4-(4-methoxy-5,6,7,8-tetrahydro-1,8-naphthyridin-2-yl)butoxy)pyrrolidin-1-yl)acetic Acid (Compound 10)

Step 1: ethyl 2-(2-cyclopropylpyridin-3-yl)-2-((R)-3-(4-(4-methoxy-5,6,7,8-tetrahydro-1,8-naphthyridin-2-yl)butoxy)pyrrolidin-1-yl)acetate

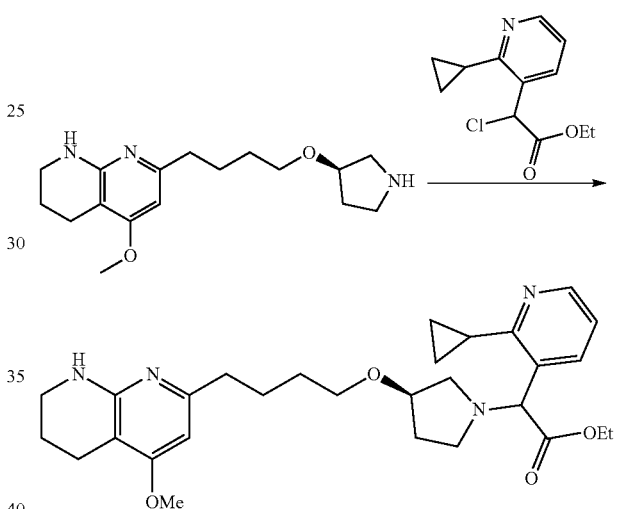

A mixture of (R)-5-methoxy-7-(4-(pyrrolidin-3-yloxy) butyl)-1,2,3,4-tetrahydro-1,8-naphthyridine hydrochloride (215 mg, 0.63 mmol), ethyl 2-chloro-2-(2-cyclopropylpyridin-3-yl)acetate (150 mg, 0.63 mmol) and diisopropylethylamine (245 mg, 1.89 mmol) in acetonitrile (8 mL) was stirred under reflux for 24 hours. Solvent was removed in vacuo, and the residue was purified by silica gel column (DCM:MeOH 20:1) to give the desired product ethyl 2-(2-cyclopropylpyridin-3-yl)-2-((R)-3-(4-(4-methoxy-5,6,7,8-tetrahydro-1,8-naphthyridin-2-yl)butoxy)pyrrolidin-1-yl) acetate as a yellow oil (80 mg). Yield 25% (ESI 509 (M+H)+).

Step 2: 2-(2-cyclopropylpyridin-3-yl)-2-((R)-3-(4-(4-methoxy-5,6,7,8-tetrahydro-1,8-naphthyridin-2-yl)butoxy)pyrrolidin-1-yl)acetic acid (compound 10)

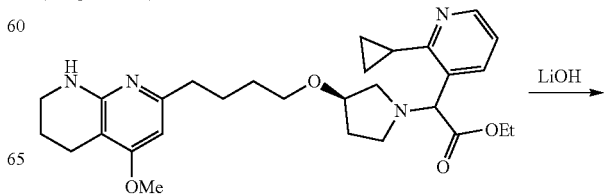

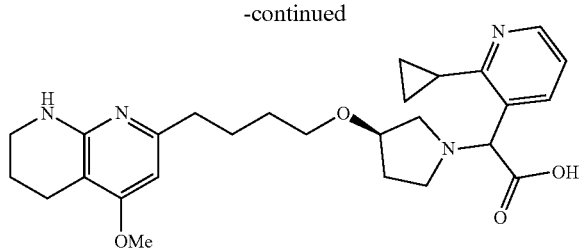

Ethyl 2-(2-cyclopropylpyridin-3-yl)-2-((R)-3-(4-(4-methoxy-5,6,7,8-tetrahydro-1,8-naphthyridin-2-yl)butoxy)pyrrolidin-1-yl)acetate (105 mg, 0.21 mmol) was treated with LiOH—H₂O (87 mg, 2.1 mmol) in MeOH (4 mL) and H₂O (1 mL) at room temperature for 17 hours. Solvent was removed in vacuo, and the residue was purified by Prep-HPLC A (30-65% MeCN) to give compound 10 as a white solid (25 mg, 25% yield).

Compound 10 LC/MS ESI 481 (M+H)+. 1H NMR (400 MHz, MeOD) δ 8.26-8.25 (m, 1H), 8.08-8.06 (m, 1H), 7.15-7.11 (m, 1H), 6.26-6.24 (m, 1H), 4.57-4.52 (m, 1H), 4.08-4.07 (m, 1H), 3.85 (s, 1H), 3.46-3.41 (m, 2H), 3.25-2.50 (m, 7H), 2.10-1.50 (m, 8H), 1.10-0.80 (m, 4H).

Example 11: Preparation of 2-(2-cyclobutylpyridin-3-yl)-2-((R)-3-(4-(5,6,7,8-tetrahydro-1,8-naphthyridin-2-yl)butoxy)pyrrolidin-1-yl)acetic Acid (Compounds 11-E1 and 11-E2)

Step 1: 3-bromo-2-cyclobutylpyridine

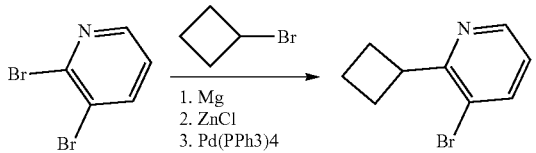

A mixture of magnesium turnings (612 mg, 25.5 mmol) and cyclobutyl bromide (3.4 g, 25.5 mmol) in anhydrous THF(50 mL) was heated for 3 hours at 60° C. until complete dissolution of the magnesium. The solution was cooled to −78° C. and treated with ZnCl2 (3.48 g, 25.5 mmol) in THF (50 mL). The resulting white suspension was warmed gradually to room temperature and stirred for 1 hour. Then a solution of 2,3-dibromopyridine (4 g, 17 mmol) and Pd(PPh3)4 (983 mg, 0.85 mmol) in THF (30 mL) was added to the reaction. The mixture was stirred at 60° C. for 1 hour under N2, then diluted with water (100 mL) and extracted with EtOAc (3×50 mL). The combined organic layers were dried over Na2SO4, filtered and concentrated in vacuo, and the residue was purified by silica gel column (pet ether: EtOAc=10:1) to give the desired product 3-bromo-2-cyclopropylpyridine as a yellow oil (2.3 g). Yield 94% (ESI 212(M+H)+).

Step 2: ethyl 2-(2-cyclobutylpyridin-3-yl)-2-hydroxyacetate

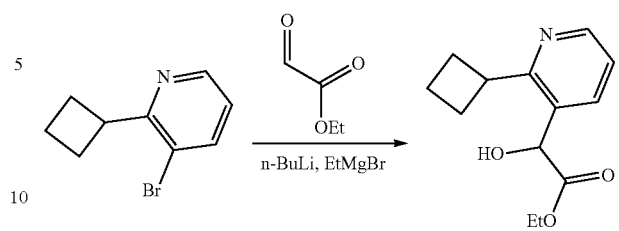

To a solution of EtMgBr (1 M, 6.54 mL, 6.54 mmol) in THF (20 mL) at 0° C. under N2 was added n-BuLi (2.5M, 5.2 mL, 13.08 mmol). The solution was stirred at 0° C. for 30 min, then a solution of 3-bromo-2-cyclobutylpyridine (2.3 g, 10.9 mmol) in THF (5 mL) was added at −10° C. The mixture was stirred at that temperature for 30 min. Then ethyl 2-oxoacetate (50% in toluene, 8.9 g, 43.6 mmol) was added, and the reaction was stirred at 0° C. for 2 hours, then poured into 20 mL of a saturated K2CO3 solution and extracted with EtOAc (3×50 mL). The combined organic layers were dried over Na2SO4, filtered and concentrated in vacuo. The residue was purified by silica gel column (pet ether:EtOAc=2:1) to give the desired product ethyl 2-(2-cyclopropylpyridin-3-yl)-2-hydroxyacetate as a yellow oil (1.1 g). Yield 43% (ESI 236(M+H)+).

Step 3: ethyl 2-chloro-2-(2-cyclobutylpyridin-3-yl)acetate

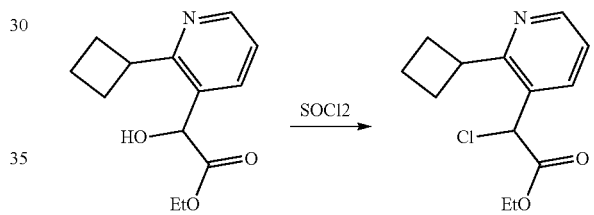

A solution of ethyl 2-(2-cyclobutylpyridin-3-yl)-2-hydroxyacetate (480 mg, 2 mmol) in SOCl2 (5 mL) was stirred at room temperature overnight. The mixture was concentrated in vacuo, adjusted to pH=8 with aq NaHCO₃ and extracted with EtOAc (3×20 mL). The combined organic layers were dried over Na2SO4, filtered and concentrated in vacuo. The residue was purified by silica gel column (pet ether:EtOAc=10:1) to give the desired product ethyl 2-chloro-2-(2-cyclobutylpyridin-3-yl)acetate as a yellow oil (310 mg). Yield 47% (ESI 254(M+H)+).

Step 4: ethyl 2-(2-cyclobutylpyridin-3-yl)-2-((R)-3-(4-(5,6,7,8-tetrahydro-1,8-naphthyridin-2-yl)butoxy)pyrrolidin-1-yl)acetate

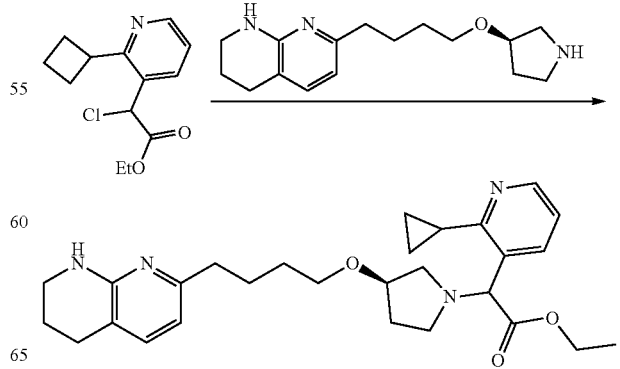

A mixture of ethyl 2-chloro-2-(2-cyclobutylpyridin-3-yl)acetate (310 mg, 1.2 mmol), (R)-7-(4-(pyrrolidin-3-yloxy)butyl)-1,2,3,4-tetrahydro-1,8-naphthyridine(370 mg, 1.35 mmol) and diisopropylethylamine (464 mg, 3.6 mmol) in acetonitrile (10 mL) was stirred at 50° C. overnight. Solvent was removed in vacuo, and the residue was purified by silica gel column (DCM: MeOH=0%10%) to give the desired product ethyl 2-(2-cyclobutylpyridin-3-yl)-2-((R)-3-(4-(5,6,7,8-tetrahydro-1,8-naphthyridin-2-yl)butoxy)pyrrolidin-1-yl)acetate as a colorless oil (165 mg, 0.36 mmol). Yield 28% (ESI 493(M+H)+).

Step 5: 2-(2-cyclobutylpyridin-3-yl)-2-((R)-3-(4-(5,6,7,8-tetrahydro-1,8-naphthyridin-2-yl)butoxy)pyrrolidin-1-yl)acetic acid (compounds 11-E1 and E2)

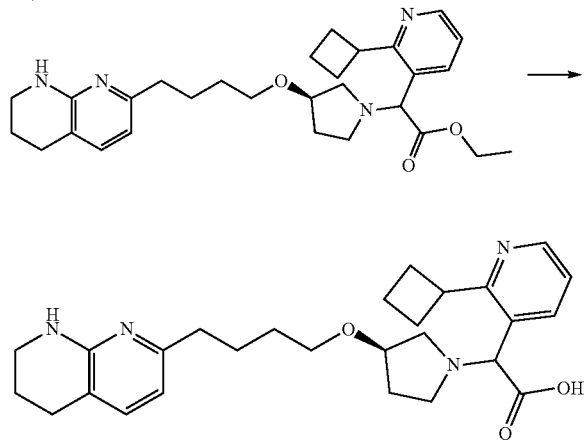

Ethyl 2-(2-cyclobutylpyridin-3-yl)-2-((R)-3-(4-(5,6,7,8-tetrahydro-1,8-naphthyridin-2-yl)butoxy)pyrrolidin-1-yl) acetate (165 mg, 0.36 mmol) was treated with LiOH—$H_2O$ (70 mg, 1.8 mmol) in MeOH (4 mL) and $H_2O$ (1 mL) at room temperature for 2 hours. Solvent was removed in vacuo, and the residue was purified by Prep-HPLC A (30-60% MeCN) to give compound 11 as a white solid (110 mg, 70% yield). The racemic product was separated by Prep chiral SFC A to give diastereomeric products compound 11-E1 (35 mg) and compound 11-E2 (35 mg) as white solids.

Compound 11-E1 LC/MS ESI 465 (M+H)+. $^1$H NMR (500 MHz, MeOD) δ 8.54 (d, J=4.5 Hz, 1H), 8.02 (d, J=7.5 Hz, 1H), 7.29-7.23 (m, 2H), 6.43 (d, J=7.0 Hz, 1H), 4.71 (s, 1H), 4.26-4.15 (m, 2H), 3.54-3.38 (m, 4H), 3.22-3.07 (m, 4H), 2.75-2.55 (m, 5H), 2.44-2.33 (m, 3H), 2.13-2.05 (m, 3H), 1.92-1.87 (m, 3H), 1.79-1.74 (m, 2H), 1.67-1.63 (m, 2H). Chiral SFC E (45% MeOH): ee 100%, Rt=2.99 min.

Compound 11-E2 LC/MS ESI 465 (M+H)+. $^1$H NMR (500 MHz, MeOD) δ 8.55 (d, J=4.5 Hz, 1H), 7.99 (d, J=7.5 Hz, 1H), 7.30-7.22 (m, 2H), 6.44 (d, J=6.0 Hz, 1H), 4.80 (s, 1H), 4.20-4.16 (m, 2H), 3.51-3.39 (m, 5H), 3.24-3.22 (m, 1H), 3.01-2.91 (m, 2H), 2.75-2.59 (m, 5H), 2.42-2.30 (m, 3H), 2.08-2.02 (m, 3H), 1.92-1.64 (m, 7H). Chiral SFC E (45% MeOH): ee 100%, Rt=5.21 min.

Example 12: Preparation of 2-((R)-3-(4-(5,6,7,8-tetrahydro-1,8-naphthyridin-2-yl)butoxy)pyrrolidin-1-yl)-2-(2-(tetrahydro-2H-pyran-4-yl)phenyl)acetic Acid (Compound 12)

Step 1: methyl 2-(2-iodophenyl)acetate

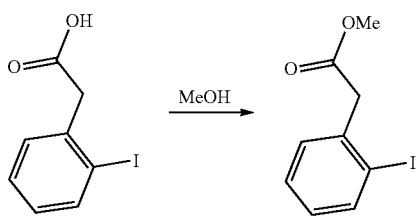

To a solution of 2-(2-iodophenyl)acetic acid (3.67 g, 14 mmol) in MeOH (35 mL) was added 2 mL of concentrated H2SO4. The reaction was stirred at 85° C. for 2 hours, then concentrated in vacuo, adjusted to pH=7-8 with sat.NaHCO3 solution and extracted with EtOAc (2×30 mL). The combined organic phase was washed with brine, dried over Na2SO4 and concentrated to give the desired product methyl 2-(2-iodophenyl)acetate (3.7 g) as an orange oil. Yield 96% (ESI 277 (M+H)+).

Step 2: methyl 2-(2-(3,6-dihydro-2H-pyran-4-yl)phenyl)acetate

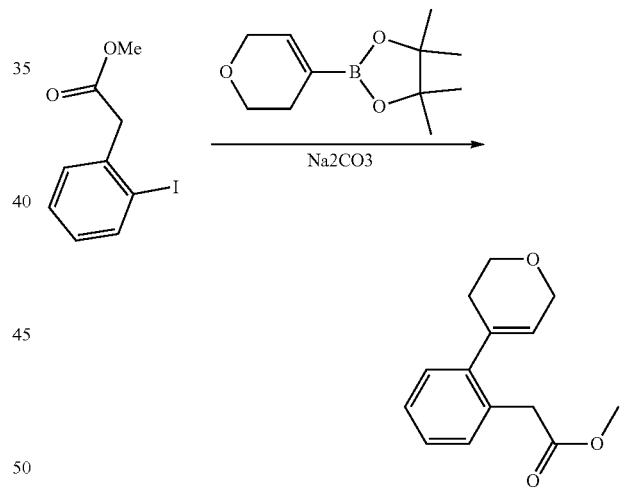

A mixture of methyl 2-(2-iodophenyl)acetate (828 mg, 3.0 mmol), 2-(3,6-dihydro-2H-pyran-4-yl)-4,4,5,5-tetramethyl-1,3,2-dioxaborolane (945 mg, 4.5 mmol), $PdCl_2(PPh_3)_2$(89 mg, 0.12 mmol) and Na2CO3(636 mg, 6. mmol) in 1,4-dioxane(30 mL) and water (6 mL) was stirred under N2 at 90° C. overnight. The mixture was diluted with H2O (10 mL) and extracted with EtOAc (20 mL). The organic phase was concentrated in vacuo, and the residue was purified by silica gel column (pet ether:EtOAc 10:1) to give the desired product tert-butyl 2-(3-(2-methoxypropan-2-yl)isochroman-5-yl)acetate as a pale orange oil (488 mg). Yield 70% (ESI 255.1 (M+Na)+).

Step 3: methyl 2-(2-(tetrahydro-2H-pyran-4-yl)phenyl)acetate

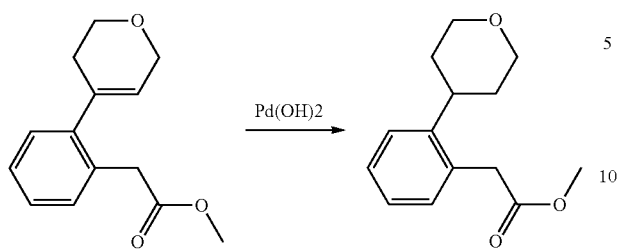

A mixture of tert-butyl 2-(3-(2-methoxypropan-2-yl)isochroman-5-yl)acetate (488 mg, 2.1 mmol) and Pd(OH)2/C (20%, 120 mg) in MeOH (20 mL) was stirred under balloon hydrogen at 35° C. for 6 hours. The reaction was filtered and concentrated in vacuo to provide the desired product methyl 2-(2-(tetrahydro-2H-pyran-4-yl)phenyl)acetate (460 mg) as a colorless oil. Yield 95% (ESI 235.2 (M+H)+).

Step 4: tert-butyl 2-bromo-2-(3-(2-methoxypropan-2-yl)isochroman-5-yl)acetate

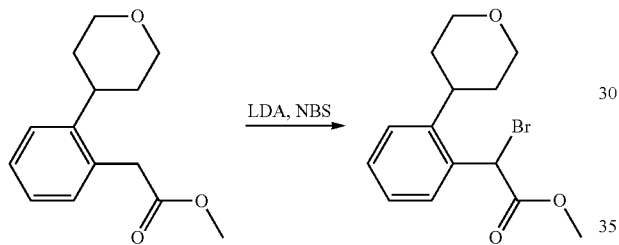

To a solution of 2-(2-(tetrahydro-2H-pyran-4-yl)phenyl)acetate (234 mg, 1.0 mmol) in THF (10 mL) at −78° C. was added lithium diisopropylamide solution 2.0 M in THF/hexanes (1.0 mL, 2.0 mmol) dropwise. The reaction was stirred at −78° C. for 20 min. Then a solution of chlorotrimethylsilane (218 mg, 2.0 mmol) in THF (0.5 mL) was added, and the reaction was stirred at −78° C. for another 10 min. Then a solution of NBS (356 mg, 2.0 mmol) in THF (4 mL) was added, and the reaction was stirred at −78° C. for 10 min, then poured into water (10 mL) and extracted with EtOAc (20 mL). The organic phase was washed with sat.NaHCO3 solution and water and concentrated in vacuo to give the crude product as a yellow oil (320 mg). Yield 48% (ESI 315.1 (M+H)+).

Step 5: methyl 2-((R)-3-(4-(5,6,7,8-tetrahydro-1,8-naphthyridin-2-yl)butoxy)pyrrolidin-1-yl)-2-(2-(tetrahydro-2H-pyran-4-yl)phenyl)acetate

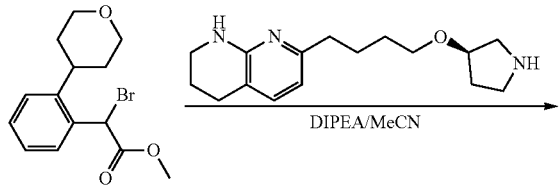

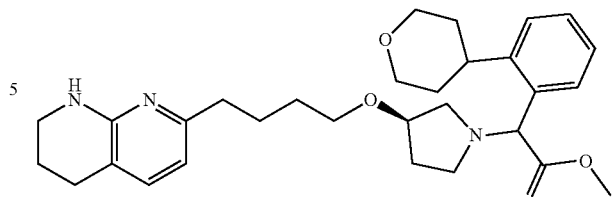

A mixture of tert-butyl 2-bromo-2-(3-(2-methoxypropan-2-yl)isochroman-5-yl)acetate (320 mg, 47% purity, 0.48 mmol), (R)-7-(4-(pyrrolidin-3-yloxy)butyl)-1,2,3,4-tetrahydro-1,8-naphthyridine (132 mg, 0.48 mmol) and diisopropylethylamine (186 mg, 1.44 mmol) in acetonitrile (12 mL) was stirred at room temperature for 1 hour. The mixture was diluted with water (8 mL) and extracted with EtOAc (25 mL). The organic phase was washed with brine, dried over Na2SO4 and concentrated in vacuo. The residue was purified by Prep-HPLC (NH4HCO3, H2O/MeCN) to give methyl 2-((R)-3-(4-(5,6,7,8-tetrahydro-1,8-naphthyridin-2-yl)butoxy)pyrrolidin-1-yl)-2-(2-(tetrahydro-2H-pyran-4-yl)phenyl)acetate as a white solid (135 mg). Yield 55% (ESI 508.1 (M+H)+).

Step 6: Preparation of 2-((R)-3-(4-(5,6,7,8-tetrahydro-1,8-naphthyridin-2-yl)butoxy)pyrrolidin-1-yl)-2-(2-(tetrahydro-2H-pyran-4-yl)phenyl)acetic acid (compound 12)

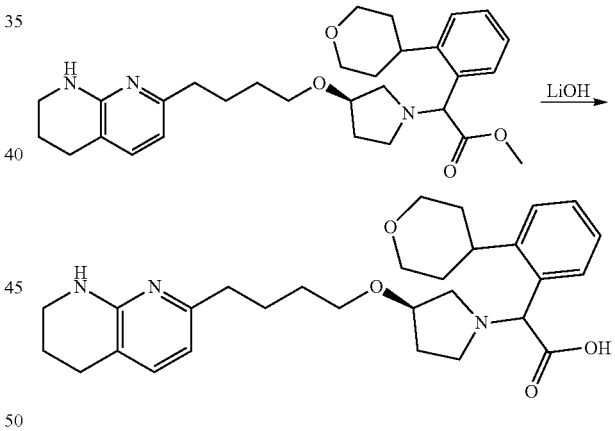

A solution of methyl 2-((R)-3-(4-(5,6,7,8-tetrahydro-1,8-naphthyridin-2-yl)butoxy)pyrrolidin-1-yl)-2-(2-(tetrahydro-2H-pyran-4-yl)phenyl)acetate (115 mg) in THF (5 mL) was treated with LiOH (1 M in H2O, 2.7 mL) at room temperature overnight. Solvent was removed in vacuo, and the residue was purified by prep HPLC A (30-64% MeCN/H2O) to give compound 12 as white solid (82 mg).

Compound 12 LC/MS ESI 494.2 (M+H)+. 1H NMR (500 MHz, MeOD) δ7.64 (m, 1H), 7.41 (m, 2H), 7.28 (m, 1H), 7.16 (m, 1H), 6.39 (m, 1H), 4.94 (m, 1H), 4.22 (m, 1H), 4.01 (m, 2H), 3.55-3.64 (m, 4H), 3.40 (m, 3H), 3.33-3.37 (m, 3H), 2.72 (t, J=6.5 Hz, 2H), 2.57 (t, J=6.5 Hz, 2H), 2.01-2.24 (m, 2H), 1.88-1.98 (m, 4H), 1.61-1.77 (m, 6H).

Example 13: Preparation of 2-((R)-3-(4-(5,6,7,8-tetrahydro-1,8-naphthyridin-2-yl)butoxy)pyrrolidin-1-yl)-2-(2-(tetrahydro-2H-pyran-4-yl)phenyl)acetic Acid (Compounds 13-E1 and 13-E2)

Step 1: methyl 2-(2-chloropyridin-3-yl)acetate

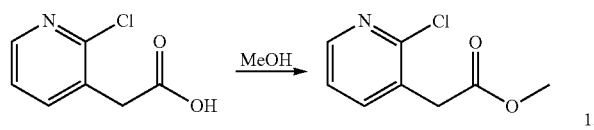

To a solution of 2-(2-chloropyridin-3-yl)acetic acid (1.71 g, 10 mmol) in MeOH (35 mL) was added concentrated H2SO4 (2 mL). The reaction was stirred at 85° C. for 2 hours, then concentrated in vacuo, adjusted to pH=7-8 with sat. NaHCO₃ solution and extracted with EtOAc (2×30 mL). The combined organic phase was washed with brine, dried over Na2SO4 and concentrated to give the desired product methyl 2-(2-chloropyridin-3-yl)acetate as an orange oil (1.51 g, Yield 81%). (ESI 186 (M+H)+).

Step 2: methyl 2-(2-(3,4-dihydro-2H-pyran-6-yl)pyridin-3-yl)acetate

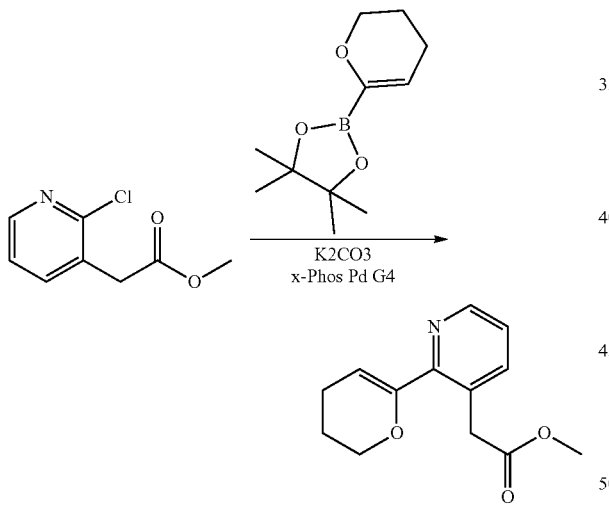

A mixture of methyl 2-(2-chloropyridin-3-yl)acetate (372 mg, 2.0 mmol), 2-(3,4-dihydro-2H-pyran-6-yl)-4,4,5,5-tetramethyl-1,3,2-dioxaborolane (420 mg, 2.0 mmol), X-Phos Pd G4 (68 mg, 0.08 mmol) and K2CO3 (552 mg, 4 mmol) in 1,4-dioxane(10 mL) and water (2.5 mL) was heated at 115° C. by microwave for 2 hours. The mixture was diluted with H₂O (10 mL) and extracted with EtOAc (20 mL). The organic phase was concentrated in vacuo, and the residue was purified by silica gel column (pet ether:EtOAc 10:1) to give the desired product methyl 2-(2-(3,4-dihydro-2H-pyran-6-yl)pyridin-3-yl)acetate as a pale orange oil (308 mg). Yield 66% (ESI 234.1 (M+H)+).

Step 3: methyl 2-(2-(tetrahydro-2H-pyran-4-yl)phenyl)acetate

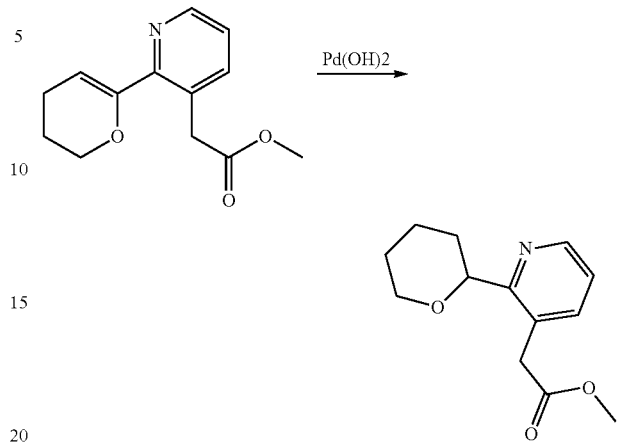

A mixture of methyl 2-(2-(3,4-dihydro-2H-pyran-6-yl)pyridin-3-yl)acetate (302 mg, 1.3 mmol) and Pd(OH)₂/C (20%, 100 mg) in MeOH (16 mL) was stirred under balloon H2 at 35° C. for 4 hours. The reaction was filtered and concentrated in vacuo to give the desired product methyl 2-(2-(tetrahydro-2H-pyran-2-yl)pyridin-3-yl)acetate as an orange oil (301 mg). Yield 94% (ESI 236.2 (M+H)+).

Step 4: methyl 2-bromo-2-(2-(tetrahydro-2H-pyran-2-yl)pyridin-3-yl)acetate

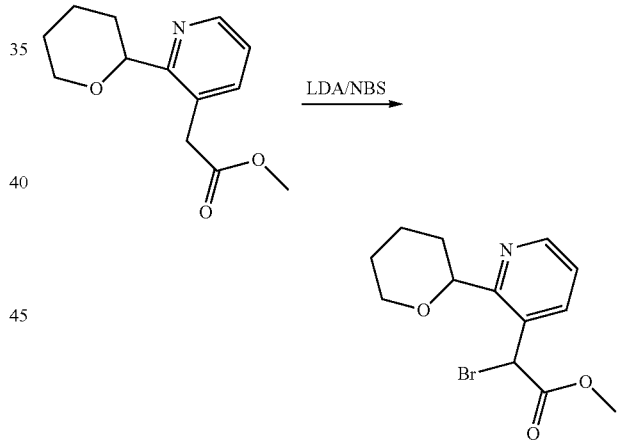

To a solution of 2-(2-(tetrahydro-2H-pyran-4-yl)phenyl)acetate methyl 2-(2-(tetrahydro-2H-pyran-2-yl)pyridin-3-yl)acetate (301 mg, 1.28 mmol) in THF (8 mL) at −78° C., was added lithium diisopropylamide solution 2.0 M in THF/hexanes (1.28 mL, 2.56 mmol) dropwise. The reaction was stirred at −78° C. for 20 min. Then a solution of chlorotrimethylsilane (278 mg, 2.56 mmol) in THF (0.5 mL) was added, and the reaction was stirred at −78° C. for another 10 min. Then a solution of NBS (456 mg, 2.56 mmol) in THF (4 mL) was added, and the reaction was stirred at −78° C. for 10 min, then poured into water (0 mL) and extracted with EtOAc (20 mL). The organic phase was washed with sat.NaHCO3 solution and water and concentrated in vacuo to give the crude product as a yellow oil (390 mg, purity 40%). Yield 39%. (ESI 315.1 (M+H)+).

Step 5: methyl 2-((R)-3-(4-(5,6,7,8-tetrahydro-1,8-naphthyridin-2-yl)butoxy)pyrrolidin-1-yl)-2-(2-(tetrahydro-2H-pyran-2-yl)pyridin-3-yl)acetate

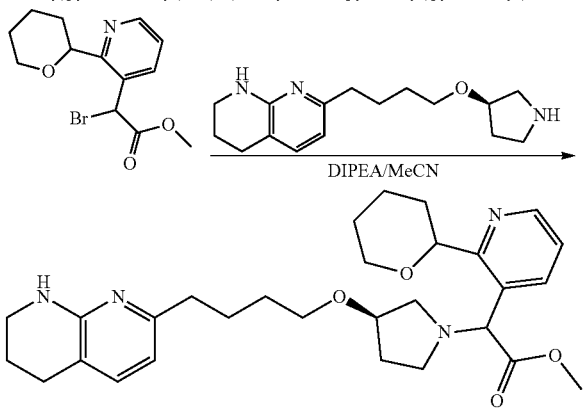

A mixture of methyl 2-bromo-2-(2-(tetrahydro-2H-pyran-2-yl)pyridin-3-yl)acetate (390 mg, 40% purity), (R)-7-(4-(pyrrolidin-3-yloxy)butyl)-1,2,3,4-tetrahydro-1,8-naphthyridine (137 mg, 0.50 mmol) and diisopropylethylamine (194 mg, 1.50 mmol) in acetonitrile (10 mL) was stirred at room temperature for 2 hours. The mixture was diluted with water (8 mL) and extracted with EtOAc(25 mL). The organic phase was washed with brine, dried over Na2SO4, filtered and concentrated in vacuo. The residue was purified by Prep-HPLC A (40-75% MeCN) to give the desired product methyl 2-((R)-3-(4-(5,6,7,8-tetrahydro-1,8-naphthyridin-2-yl)butoxy)pyrrolidin-1-yl)-2-(2-(tetrahydro-2H-pyran-2-yl)pyridin-3-yl)acetate (105 mg) as a white sold. Yield 41% (ESI 509.2 (M+H)+).

Step 6: Preparation of 2-((R)-3-(4-(5,6,7,8-tetrahydro-1,8-naphthyridin-2-yl)butoxy)pyrrolidin-1-yl)-2-(2-(tetrahydro-2H-pyran-4-yl)phenyl)acetic acid (compounds 13-E1 and 13-E2)

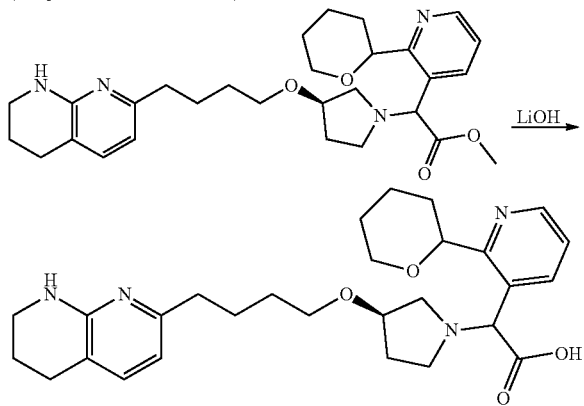

A solution of ethyl 2-((R)-3-(4-(5,6,7,8-tetrahydro-1,8-naphthyridin-2-yl)butoxy)pyrrolidin-1-yl)-2-(2-(tetrahydro-2H-pyran-4-yl)phenyl)acetate (71 mg, 0.14 mmol) in THF (5 mL) was treated with LiOH (1 M in H$_2$O, 2.1 mL) at room temperature overnight. The mixture was adjusted to pH=5-6 with aqueous HCl (1N) and concentrated in vacuo, and the residue was purified by preparatory HPLC A (30-64% MeCN) to give diastereomeric products compound 13-E1 (23 mg) and compound 13-E2 (12 mg) as white solids, each as a mixture of 2 stereoisomers.

Compound 13-E1 (mixture of 2 stereoisomers) LC/MS ESI 495.3 (M+H)+. 1H NMR (500 MHz, MeOD) δ8.46 (m, 1H), 8.21 (m, 1H), 7.33 (m, 1H), 7.16 (m, 1H), 6.38 (m, 1H), 5.12 (m, 1H), 4.41 (m, 1H), 4.05 (m, 2H), 3.75 (m, 1H), 3.75-3.37 (m, 4H), 3.30-2.80 (m, 2H), 2.73-2.69 (m, 4H), 2.64-2.54 (m, 2H), 1.96 (m, 1H), 1.91-1.87 (m, 6H), 1.78-1.58 (m, 7H).

Compound 13-E2 (mixture of 2 stereoisomers) LC/MS ESI 495.3 (M+H)+. 1H NMR (500 MHz, MeOD) δ8.46 (m, 1H), 8.14 (m, 1H), 7.34 (m, 1H), 7.16 (m, 1H), 6.38 (m, 1H), 5.04 (m, 1H), 4.11 (m, 2H), 3.68 (m, 1H), 3.69-3.37 (m, 5H), 3.11-2.98 (m, 2H), 2.87-2.70 (m, 4H), 2.56-2.54 (m, 2H), 2.06-1.80 (m, 7H), 1.78-1.59 (m, 7H).

Example 14: Preparation of 2-(2-cyclopropylpyridin-3-yl)-2-((R)-3-(4-(5,6,7,8-tetrahydro-1,8-naphthyridin-2-yl)butoxy)pyrrolidin-1-yl)acetic Acid (Compounds 14-E1 and 14-E2)

Step 1: sodium (2-cyclopropylpyridin-3-yl)(hydroxy)methanesulfonate

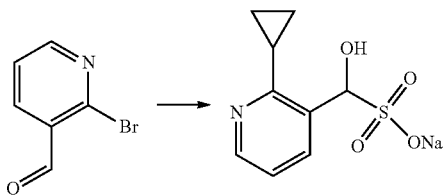

2-Bromo-3-pyridinecarboxaldehyde (1 g, 5.38 mmol), cyclopropylboronic acid (1.385 g, 16.13 mmol) and sodium carbonate (2.279 g, 21.50 mmol) were dissolved in 1,2-dimethoxyethane (20 mL) and water (5 mL). The mixture was flushed with argon and bis(triphenylphosphine)palladium(II) dichloride (0.377 g, 0.538 mmol) was added. The reaction was sealed and heated at 100° C. for 16 hours, then diluted with water and extracted with diethyl ether. The organic layer was washed twice with water, and a solution of sodium bisulfite (1.119 g, 10.75 mmol) in water and some methanol were added. The diethyl ether was evaporated in vacuo, and the resulting water/methanol mixture was used as such in the next step.

Step 2: 2-(2-cyclopropylpyridin-3-yl)-2-((R)-3-(4-(5,6,7,8-tetrahydro-1,8-naphthyridin-2-yl)butoxy)pyrrolidin-1-yl)acetonitrile

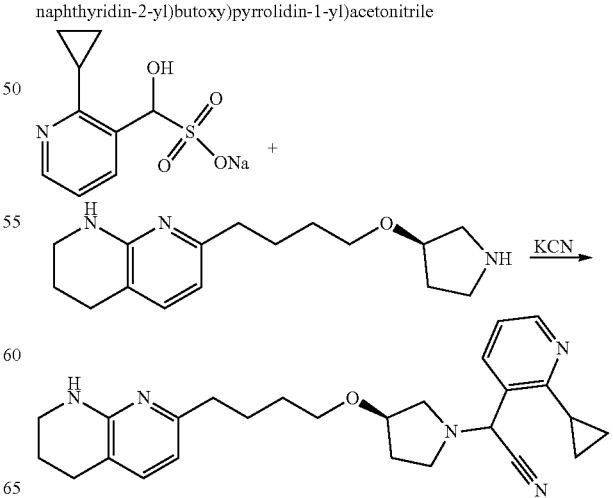

A water/methanol mixture containing sodium (2-cyclopropylpyridin-3-yl)(hydroxy)methanesulfonate (1.352 g, 5.38 mmol) was added to (R)-7-(4-(pyrrolidin-3-yloxy)butyl)-1,2,3,4-tetrahydro-1,8-naphthyridine (0.963 g, 3.50 mmol), followed by potassium cyanide (1.752 g, 26.9 mmol). After 16 hours some methanol was added. After 64 hours, the reaction mixture was diluted with water and extracted three times with ethyl acetate. The combined organic layers were dried over sodium sulfate and concentrated in vacuo to afford the desired product 2-(2-cyclopropylpyridin-3-yl)-2-((R)-3-(4-(5,6,7,8-tetrahydro-1,8-naphthyridin-2-yl)butoxy)pyrrolidin-1-yl)acetonitrile (1.511 g). Yield 65% (ESI 430 (M–H)–).

Step 3: 2-(2-cyclopropylpyridin-3-yl)-2-((R)-3-(4-(5,6,7,8-tetrahydro-1,8-naphthyridin-2-yl)butoxy)pyrrolidin-1-yl)acetamide

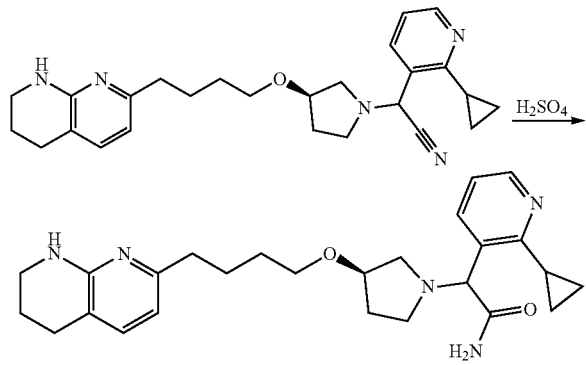

To a solution of 2-(2-cyclopropylpyridin-3-yl)-2-((R)-3-(4-(5,6,7,8-tetrahydro-1,8-naphthyridin-2-yl)butoxy)pyrrolidin-1-yl)acetonitrile (1.511 g, 3.5 mmol) in dichloromethane (10 mL) was added sulfuric acid (25 mL, 469 mmol). The reaction was stirred at room temperature for 24 hours, then quenched on ice, neutralised using aqueous ammonia and extracted three times with ethyl acetate. The combined organic layers were washed with brine, dried over sodium sulfate and concentrated, and the residue was purified by reversed phase chromatography (10 mM solution of ammonium hydrogen carbonate in water, 20-60% acetonitrile) to afford the desired product 2-(2-cyclopropylpyridin-3-yl)-2-((R)-3-(4-(5,6,7,8-tetrahydro-1,8-naphthyridin-2-yl)butoxy)pyrrolidin-1-yl)acetamide (399 mg). Yield 25% (ESI 450 (M+H)+).

Step 4: 2-(2-cyclopropylpyridin-3-yl)-2-((R)-3-(4-(5,6,7,8-tetrahydro-1,8-naphthyridin-2-yl)butoxy)pyrrolidin-1-yl)acetic acid (Compounds 14-E1 and 14-E2)

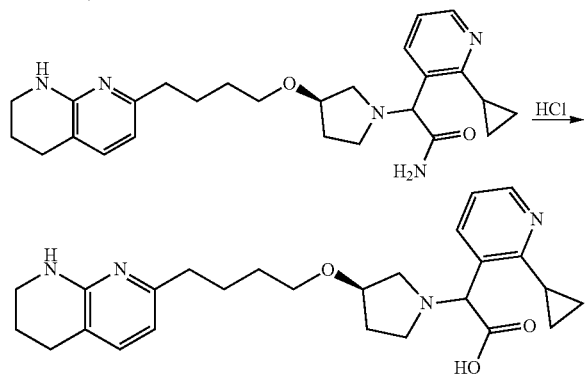

A solution of 2-(2-cyclopropylpyridin-3-yl)-2-((R)-3-(4-(5,6,7,8-tetrahydro-1,8-naphthyridin-2-yl)butoxy)pyrrolidin-1-yl)acetamide (399 mg, 0.887 mmol) in hydrochloric acid (10 mL, 40 mmol, 4N solution in water) was stirred at 70° C. for 88 hours. The mixture was concentrated, and the residue was dissolved in water and then freeze-dried. The residue was dissolved in water (10 mL) and this was purified using reversed phase chromatography to afford 2-(2-cyclopropylpyridin-3-yl)-2-((R)-3-(4-(5,6,7,8-tetrahydro-1,8-naphthyridin-2-yl)butoxy)pyrrolidin-1-yl)acetic acid compound 14 (311 mg) as a diastereoisomeric mixture. Yield 78% (ESI 451 (M+H)+). The mixture was separated by chiral SFC to give diastereomeric products compound 14-E1 (107 mg) and compound 14-E2 (100 mg). Method: Water Acquity UPC2 (Binary Solvent Manager, Isocratic Solvent Manager, Sample Manager, Column Manager 30S, Convergence Manager, PDA Detector, Acquity QDa Detector); Column: Chiralpak IC for SFC use (100×4.6 mm, 5 μm). Temperature: 35° C. Back Pressure: 170 bar. Flow: 2.5 mL/min. Eluent A: $CO_2$. Eluent B: Methanol+20 mM Ammonia. Gradient: t0=5% B, t2.5 min=50% B, t30 min=50% B, Post time: 0.5 min. Detection PDA: 210-320 nm. Detection MS: ESI, Mass Range: 700-1250 (positive) 1 Hz, Cone: 15 V.

Compound 14-E1: 107 mg, LC/MS ESI 451 (M+H)+. $^1$H NMR (400 MHz, Methanol-d4) δ 8.37 (dd, J=4.7, 1.7 Hz, 1H), 7.97 (dd, J=8.0, 1.8 Hz, 1H), 7.24-7.08 (m, 2H), 6.40 (d, J=7.3 Hz, 1H), 5.04 (s, 1H), 4.22-4.13 (m, 1H), 3.55-3.33 (m, 5H), 3.23-3.10 (m, 2H), 2.79-2.66 (m, 2H), 2.66-2.46 (m, 3H), 2.22-2.05 (m, 2H), 1.94-1.82 (m, 2H), 1.80-1.45 (m, 5H), 1.27-1.15 (m, 1H), 1.07-0.88 (m, 3H).

Compound 14-E2: 100 mg, LC/MS ESI 451 (M+H)+. $^1$H NMR (400 MHz, Methanol-d4) δ 8.38 (dd, J=4.8, 1.7 Hz, 1H), 7.94 (dd, J=7.8, 1.7 Hz, 1H), 7.24-7.13 (m, 2H), 6.40 (d, J=7.3 Hz, 1H), 5.13 (s, 1H), 4.25-4.14 (m, 1H), 3.58-3.32 (m, 6H), 3.27-3.14 (m, 1H), 3.07-2.95 (m, 1H), 2.78-2.66 (m, 2H), 2.64-2.49 (m, 2H), 2.49-2.38 (m, 1H), 2.18-2.02 (m, 2H), 1.95-1.82 (m, 2H), 1.81-1.45 (m, 5H), 1.30-1.15 (m, 1H), 1.06-0.86 (m, 3H).

Example 15: Preparation of 2-(2-cyclopropylphenyl)-2-((R)-3-(5-(5,6,7,8-tetrahydro-1,8-naphthyridin-2-yl)pentyloxy)pyrrolidin-1-yl)acetic Acid (Compounds 15-E1 and 15-E2)

Step 1: 2-(2-cyclopropylphenyl)-2-((R)-3-(4-(5,6,7,8-tetrahydro-1,8-naphthyridin-2-yl)pentyloxy)pyrrolidin-1-yl)acetic acid (Compounds 15-E1 and 15-E2)

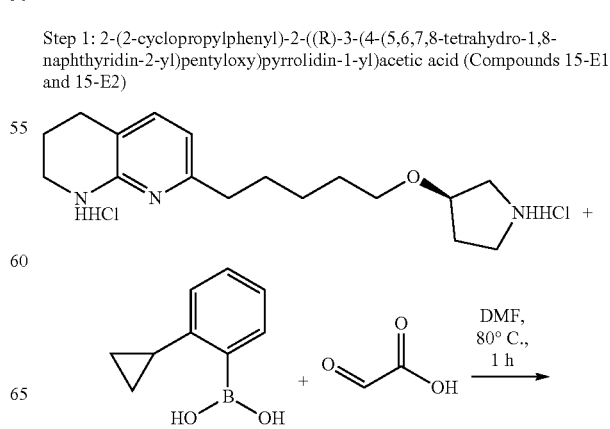

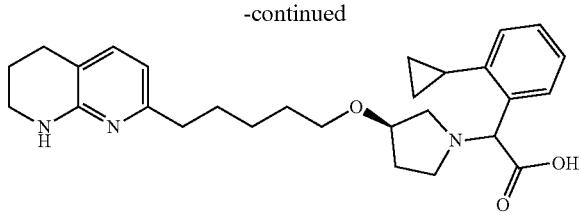

To a solution of (R)-7-(5-(pyrrolidin-3-yloxy)pentyl)-1,2,3,4-tetrahydro-1,8-naphthyridine dihydrochloride (200 mg, 0.55 mmol) in DMF (2 mL) was added 2-cyclopropylphenylboronic acid (116 mg, 0.72 mmol) and 2-oxoacetic acid (56 mg, 0.6 mmol). The reaction was stirred at 80° C. for 1 h. The reaction mixture was purified by prep-HPLC (40-65% MeCN) to give 90 mg racemic compound 15. The racemic product was separated by prep chrial SFC A to give diastereomeric products compound 15-E1 (23 mg) and compound 15-E2 (22 mg) as white solids.

Compound 15-E1 LC/MS ESI 464.2 (M+H)$^+$. $^1$H NMR (500 MHz, MeOD) δ 7.61 (d, J=7.1 Hz, 1H), 7.31 (m, 2H), 7.16 (dd, J=21.5, 7.4 Hz, 2H), 6.37 (d, J=7.3 Hz, 1H), 5.35 (s, 1H), 4.23 (s, 1H), 3.65 (m, 1H), 3.49 (t, J=6.4 Hz, 2H), 3.42-3.36 (m, 2H), 3.30-2.99 (m, 3H), 2.70 (t, J=6.3 Hz, 2H), 2.53 (t, J=7.5 Hz, 2H), 2.21 (m, 3H), 1.88 (m, 2H), 1.12-0.94 (m, 3H), 0.70-0.51 (m, 1H). Chiral SFC A (40% MeOH): ee 98%, Rt=2.46 min.

Compound 15-E2 LC/MS ESI 464.2 (M+H)+. $^1$H NMR (500 MHz, MeOD) δ 7.54 (d, J=7.5 Hz, 1H), 7.17 (m, 2H), 7.07-6.97 (m, 2H), 6.26 (d, J=7.3 Hz, 1H), 5.08 (s, 1H), 4.06 (s, 1H), 3.43-3.24 (m, 5H), 3.14-2.98 (m, 2H), 2.59 (t, J=6.2 Hz, 2H), 2.48-2.36 (m, 2H), 2.15 (m, 3H), 1.81-1.70 (m, 2H), 1.63-1.45 (m, 4H), 1.39-1.26 (m, 2H), 0.96-0.77 (m, 3H), 0.55-0.42 (m, 1H). Chiral SFC A (40% MeOH): ee 98%, Rt=3.5 min.

Example 16: Preparation of 2-((R)-3-(4-(5,6,7,8-tetrahydro-1,8-naphthyridin-2-yl)butoxy)pyrrolidin-1-yl)-2-(2-(tetrahydrofuran-2-yl)phenyl)acetic Acid (Compounds 16-E1 and 16-E2)

Step 1: methyl 2-(2-(furan-2-yl)phenyl) acetate

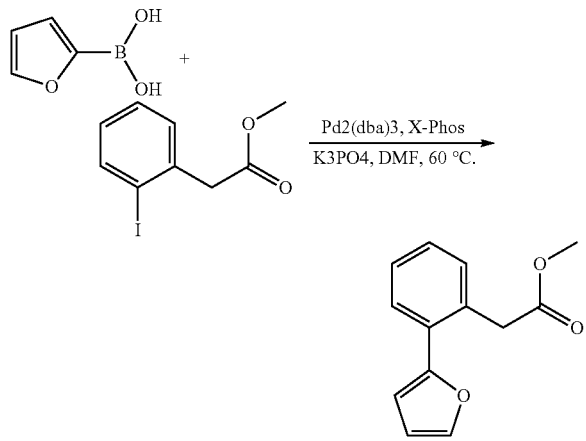

To a solution of methyl 2-(2-iodophenyl)acetate (552 mg, 2 mmol) in 5 mL dry DMF was added furan-2-ylboronic acid (224 mg, 2 mmol), tris(dibenzylideneacetone) dipalladium (0) (91.5 mg, 0.1 mmol), X-Phos (47.6 mg, 0.1 mmol), and potassium phosphate (424 mg, 2 mmol). The mixture was stirred at 60° C. for 1 hour under N2. The reaction was allowed to cool and diluted with ethyl acetate (20 mL) and water (20 mL). The organic layer was separated and the aqueous layer was extracted with ethyl acetate three times (20 mL×2). The combined organic layer was washed with brine and dried over anhydrous Na2SO4. After filtration and concentration, the residue was chromatographed (Combiflash), using 520% EtOAc/petroleum ether as eluent, to give methyl 2-(2-(furan-2-yl)phenyl) acetate 340 mg (78.3%); (ESI 217 (M+H)$^+$).

Step 2: methyl 2-(2-(tetrahydrofuran-2-yl)phenyl) acetate

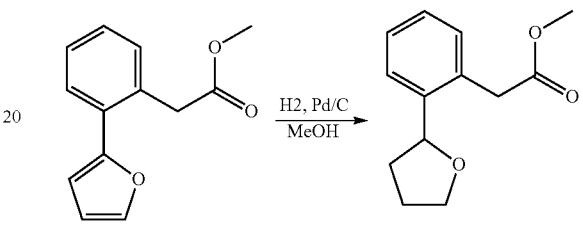

To a solution of methyl 2-(2-(furan-2-yl) phenyl) acetate (340 mg, 1.57 mmol) in 10 ml anhydrous MeOH was added Pd/C (30 mg). The mixture was stirred for 3 hours at 40° C. under H$_2$ atmosphere (balloon). After the reaction was over, the catalyst was removed by filtration and the filtrate was concentrated under reduced pressure. The residue was chromatographed (Combiflash), using 5-20% EtOAc/petroleum ether as eluent, to give methyl 2-(2-(tetrahydrofuran-2-yl)phenyl)acetate (290 mg, 84%) as an oil. (ESI 221 (M+H)$^+$)

Step 3: methyl 2-bromo-2-(2-(tetrahydrofuran-2-yl)phenyl) acetate

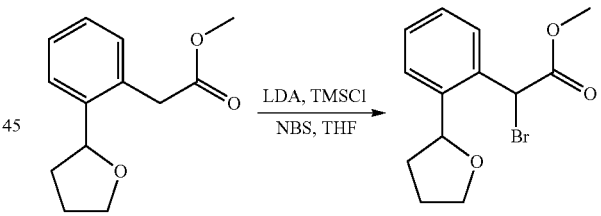

A solution of methyl 2-(2-(tetrahydrofuran-2-yl)phenyl) acetate (220 mg, 1 mmol) in 10 mL THE under N2 was cooled to −78° C. and treated with LDA (1.25 mL, 2.5 mmol, 2M in THF). The reaction was stirred for 0.5 h, treated with TMSCl (324 mg, 3 mmol) and, after 0.25 h, NBS (534 mg, 3 mmol) as a solution in 10 mL dry THF. The mixture was stirred for 0.5 h at −78° C. and water (10 mL) was added to quench the reaction. The mixture was extracted with ethyl acetate (20 mL×2). The combined organic layer was washed with brine and dried over anhydrous Na2SO4. After filtration and concentration, the residue was chromatographed (Combiflash), using 0-20% EtOAc/petroleum ether as eluent, to give methyl 2-bromo-2-(2-(tetrahydrofuran-2-yl)phenyl) acetate (210 mg, 70.5%); (ESI 299 (M+H)$^+$)

Step 4: methyl 2-((R)-3-(4-(5,6,7,8-tetrahydro-1,8-naphthyridin-2-yl)butoxy)pyrrolidin-1-yl)-2-(2-(tetrahydrofuran-2-yl)phenyl)acetate

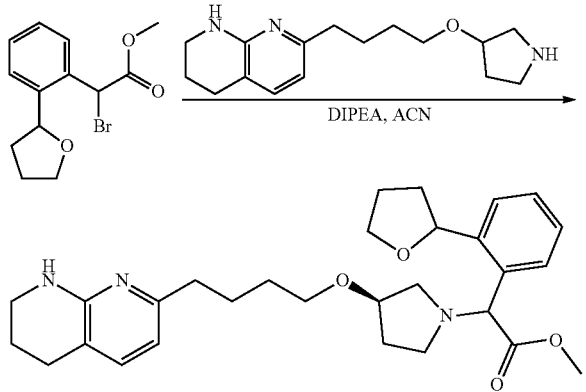

To a solution of methyl 2-bromo-2-(2-(tetrahydrofuran-2-yl)phenyl)acetate (100 mg, 0.33 mmol) in 5 mL acetonitrile was added (R)-7-(4-(pyrrolidin-3-yloxy)butyl)-1,2,3,4-tetrahydro-1,8-naphthyridine (92 mg, 0.33 mmol) and diisopropylethylamine (129 mg, 1 mmol). The reaction was stirred for 2 hours, diluted with water (10 mL) and extracted with ethyl acetate (20 mL×3). The combined organic layers were washed with brine and dried over anhydrous Na2SO4. After filtration and concentration, the residue was chromatographed (Combiflash), using 20-80% EtOAc/petroleum ether as eluent, to give methyl 2-((R)-3-(4-(5,6,7,8-tetrahydro-1,8-naphthyridin-2-yl)butoxy)pyrrolidin-1-yl)-2-(2-(tetrahydrofuran-2-yl)phenyl)acetate (90 mg, 54.4%). (ESI 494 (M+H)$^+$)

Step 5: 2-((R)-3-(4-(5,6,7,8-tetrahydro-1,8-naphthyridin-2-yl)butoxy)pyrrolidin-1-yl)-2-(2-(tetrahydrofuran-2-yl)phenyl)acetic acid (compounds 16-E1 and 16-E2)

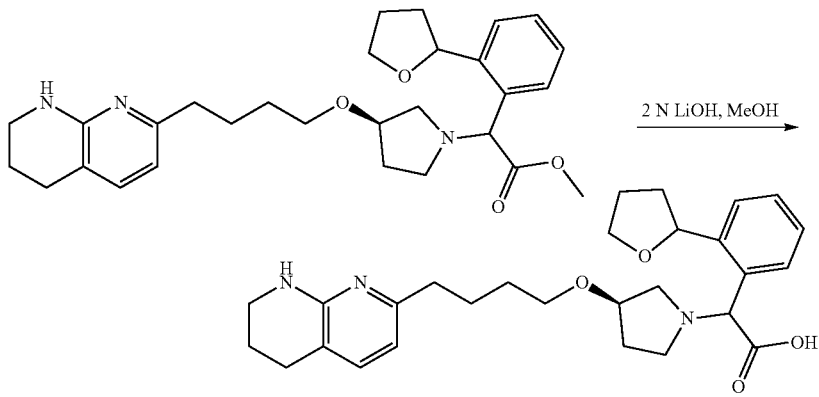

To a solution of methyl 2-((R)-3-(4-(5,6,7,8-tetrahydro-1,8-naphthyridin-2-yl)butoxy)pyrrolidin-1-yl)-2-(2-(tetrahydrofuran-2-yl)phenyl)acetate (90 mg, 0.18 mmol) in 5 mL methanol was added LiOH (9 mg, 0.4 mmol) and water (2 mL). The reaction was stirred for 5 h, filtered and concentrated under reduced pressure. The residue was purified using reversed-phase semi-preparative HPLC to give diastereomeric products compound 16-E1 (40 mg, Yield 45.7%) and compound 16-E2 (19 mg, Yield 22.7%), each as a mixture of two stereoisomers.

Compound 16-E1 (mixture of 2 stereoisomers): LC/MS ESI 480.2 (M+H)+. $^1$H NMR (500 MHz, MeOD) δ 7.69 (dd, J=11.4, 7.8 Hz, 1H), 7.55 (d, J=7.8 Hz, 1H), 7.41 (t, J=7.5 Hz, 1H), 7.38-7.29 (m, 1H), 7.15 (d, J=7.3 Hz, 1H), 6.39 (dd, J=7.3, 2.7 Hz, 1H), 5.30 (dt, J=33.4, 7.0 Hz, 1H), 4.97 (s, 1H), 4.17 (d, J=21.0 Hz, 1H), 4.08 (dd, J=14.1, 6.9 Hz, 1H), 3.90 (ddt, J=14.0, 9.6, 6.9 Hz, 1H), 3.57 (s, 1H), 3.51-3.35 (m, 4H), 3.29-2.98 (m, 3H), 2.71 (t, J=6.3 Hz, 2H), 2.56 (t, J=7.6 Hz, 2H), 2.52-2.42 (m, 1H), 2.18-1.94 (m, 5H), 1.88 (dd, J=11.5, 6.1 Hz, 2H), 1.77-1.69 (m, 2H), 1.62 (dd, J=13.6, 6.7 Hz, 2H).

Compound 16-E2 (mixture of 2 stereoisomers) LC/MS ESI 480.2 (M+H)+. $^1$H NMR (500 MHz, MeOD) δ 7.65 (d, J=5.5 Hz, 1H), 7.46 (d, J=7.6 Hz, 1H), 7.41-7.30 (m, 2H), 7.16 (d, J=7.3 Hz, 1H), 6.39 (dd, J=7.3, 1.6 Hz, 1H), 5.23-5.10 (m, 1H), 4.96 (s, 1H), 4.19-4.06 (m, 2H), 3.93-3.84 (m, 1H), 3.57 (s, 1H), 3.50-3.36 (m, 5H), 3.16-2.96 (m, 2H), 2.75-2.65 (m, 2H), 2.56 (t, J=7.4 Hz, 2H), 2.45-2.35 (m, 1H), 2.16-1.99 (m, 5H), 1.88 (dd, J=11.4, 5.8 Hz, 2H), 1.76-1.68 (m, 2H), 1.65-1.59 (m, 2H).

Example 17: Preparation of 2-((R)-3-(4-(5,6,7,8-tetrahydro-1,8-naphthyridin-2-yl)butoxy) pyrrolidin-1-yl)-2-(2-(tetrahydro-2H-pyran-2-yl)phenyl)acetic Acid (Compound 17)

Step 1: methyl 2-(2-(3,4-dihydro-2H-pyran-6-yl)phenyl)acetate

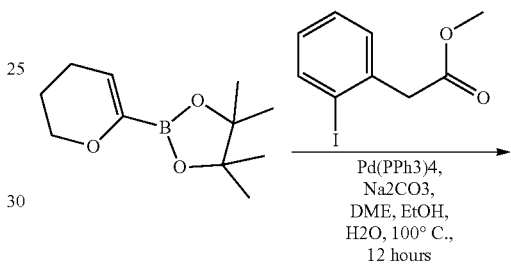

-continued

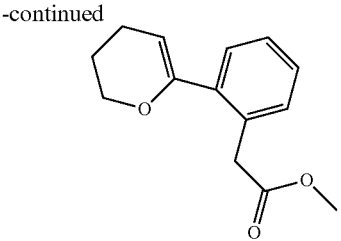

To a solution of methyl 2-(2-iodophenyl)acetate (1.3 g, 4.8 mmol) in 20 mL dry DME and EtOH (5 mL) were added 3,4-dihydro-2H-pyran-6-boronic acid pinacol ester (1.0 g, 4.8 mmol), tetrakis(triphenylphosphine)palladium (0) (277 mg, 0.24 mmol), and sodium carbonate (1.0 g, 9.6 mmol) and the mixture was heated at 100° C. for 12 h under N₂. The mixture was allowed to cool to room temperature and diluted with ethyl acetate (50 mL) and water (10 mL). The organic layer was separated and the aqueous layer was extracted with ethyl acetate (50 mL×3). The organic phases were combined, washed with brine and dried over anhydrous Na2SO4. After filtration and concentration, the residue was chromatographed (Combiflash), using 0-20% EtOAc/petroleum ether as eluent, to give methyl 2-(2-(3,4-dihydro-2H-pyran-6-yl)phenyl)acetate (0.4 g, 36%) as an oil. (ESI 233.1 (m+1)⁺).

Step 2: methyl 2-(2-(tetrahydro-2H-pyran-2-yl)phenyl)acetate

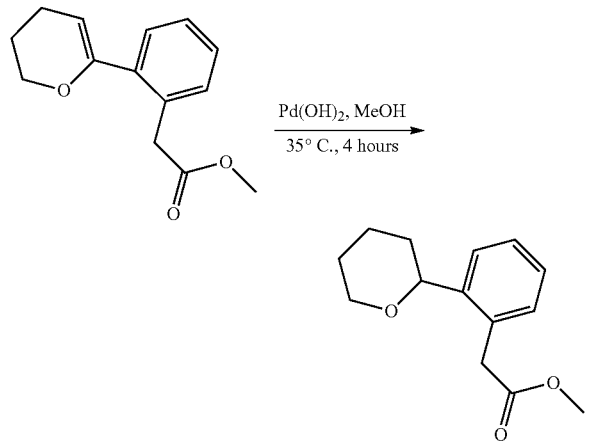

A mixture of methyl 2-(2-(3,4-dihydro-2H-pyran-6-yl)phenyl)acetate (300 mg, 1.3 mmol) and Pd(OH)₂/C (100 mg) in MeOH (25 mL) was hydrogenated (balloon) for 3 h at 35° C. The catalyst was removed by filtration and the filtrate was concentrated under reduced pressure. The resulting residue was chromatographed (Combiflash), using 0-20% EtOAc/petroleum ether as eluent, to give methyl 2-(2-(tetrahydro-2H-pyran-2-yl)phenyl)acetate (180 mg, 60%) as an oil. (ESI 235.1 (m+1)⁺).

Step 3: methyl 2-bromo-2-(2-(tetrahydro-2H-pyran-2-yl)phenyl)acetate

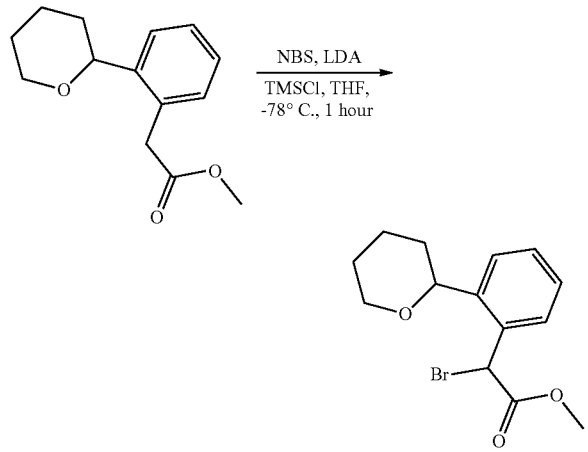

To a stirred solution of methyl 2-(2-(tetrahydro-2H-pyran-2-yl)phenyl)acetate (150 mg, 0.64 mmol) in THF (10 mL) at −78° C. under N₂ was added LDA (1.25 mL, 2.5 mmol, 2M in THF) and the reaction was stirred for 0.5 h, TMSCl (324 mg, 3.0 mmol) was added, the reaction was stirred for 0.25 h, then NBS (445 mg, 2.5 mmol) was added as a solution in THF (10 mL). The reaction was stirred for 0.5 h at −78° C. and quenched by the addition of water (10 mL). The mixture was extracted with ethyl acetate (30 mL×3) and the combined organic phases were washed with brine and dried over anhydrous Na2SO4. After filtration and concentration, was chromatographed (Combiflash), using 0-20% EtOAc/petroleum ether as eluent, to give methyl 2-bromo-2-(2-(tetrahydro-2H-pyran-2-yl)phenyl)acetate (65 mg, 33%). (ESI 313.2 (m+1)).

Step 4: methyl 2-((R)-3-(4-(5,6,7,8-tetrahydro-1,8-naphthyridin-2-yl)butoxy)pyrrolidin-1-yl)-2-(2-(tetrahydro-2H-pyran-2-yl)phenyl)acetate

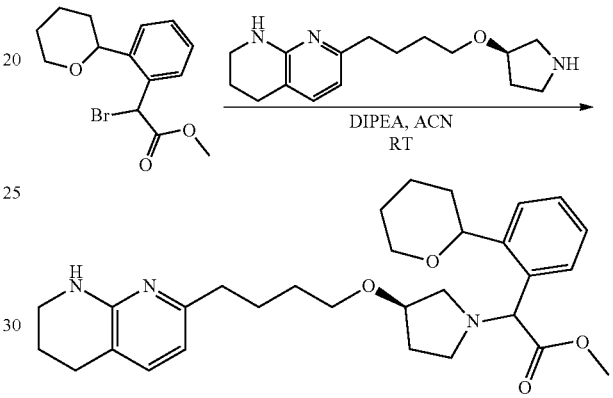

A mixture of methyl 2-bromo-2-(2-(tetrahydro-2H-pyran-2-yl)phenyl)acetate (65 mg, 0.21 mmol), (57 mg, 0.21 mmol) and diisopropylethylamine (65 mg, 0.5 mmol) in acetonitrile (8 mL) was stirred at 25° C. for 16 h. The solvent was removed under reduced pressure and the residue was chromatographed on silica gel (DCM:MeOH 20:1) to give ethyl methyl 2-((R)-3-(4-(5,6,7,8-tetrahydro-1,8-naphthyridin-2-yl)butoxy)pyrrolidin-1-yl)-2-(2-(tetrahydro-2H-pyran-2-yl)phenyl)acetate (30 mg, 28%) as an oil. (ESI 508.1 (m+1)⁺)

Step 5: 2-((R)-3-(4-(5,6,7,8-tetrahydro-1,8-naphthyridin-2-yl)butoxy)pyrrolidin-1-yl)-2-(2-(tetrahydro-2H-pyran-2-yl)phenyl)acetic acid (compound 17)

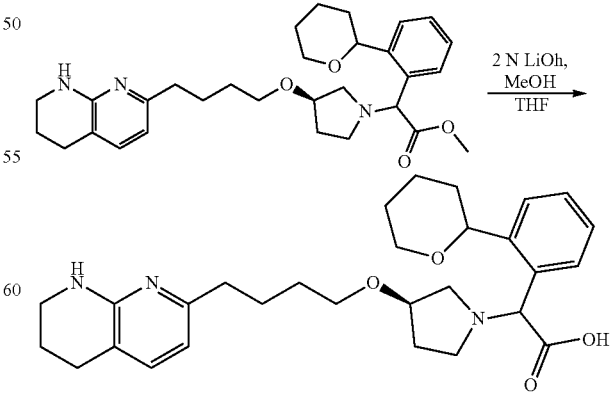

Methyl 2-(2-cyclopropylphenyl)-2-((R)-3-(4-(5,6,7,8-tetrahydro-1,8-naphthyridin-2-yl) butoxy) pyrrolidin-1-yl)acetate (30 mg, 0.28 mmol) was treated with LiOH (52 mg, 1.24 mmol) in MeOH (4 mL) and H₂O (1 mL) at 25° C. for 3 hours. The solvent was removed under reduced pressure and the residue was separated using semi-preparative reversed-phase HPLC (Prep HPLC A, 30-65% MeCN) to give compound 17 as a solid (10 mg, 34%).

Compound 17: LC/MS ESI 494.2 (M+H)+. 1H NMR (400 MHz, MeOD) δ ¹H NMR (500 MHz, MeOD) δ 7.68 (t, J=8.3 Hz, 1H), 7.57 (d, J=7.8 Hz, 1H), 7.40 (dt, J=13.8, 7.5 Hz, 2H), 7.15 (d, J=7.3 Hz, 1H), 6.38 (dd, J=7.3, 3.3 Hz, 1H), 4.89-4.76 (m, 2H), 4.18 (d, J=17.9 Hz, 1H), 4.09-3.94 (m, 1H), 3.72 (dd, J=22.4, 10.7 Hz, 1H), 3.54-3.43 (m, 2H), 3.38 (dd, J=10.1, 4.5 Hz, 3H), 2.77-2.65 (m, 2H), 2.55 (t, J=6.7 Hz, 2H), 2.17-1.97 (m, 4H), 1.93-1.85 (m, 2H), 1.81-1.58 (m, 8H), 1.51-1.45 (m, 1H), 1.33 (d, J=22.7 Hz, 3H).

Example 18: Preparation of 2-(5-fluoro-2-(tetrahydro-2H-pyran-2-yl)phenyl)-2-((R)-3-(4-(5,6,7,8-tetrahydro-1,8-naphthyridin-2-yl)butoxy)pyrrolidin-1-yl)acetic Acid (Compounds 18-E1 and 18-E2)

Step 1: methyl 2-(2-bromo-5-fluorophenyl)acetate

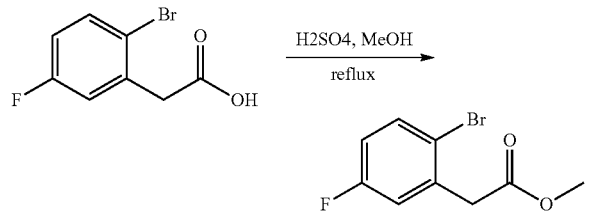

To a solution of 2-(2-bromo-5-fluorophenyl) acetic acid (10 g, 43 mmol) in 60 mL MeOH was added 0.5 mL H₂SO4. The mixture was refluxed for 4 hours, allowed to cool to room temperature and concentrated under reduced pressure. The resulting pale yellow oil (10 g, 94.3%) was used without any further purification. (ESI 246.1 (M+H)⁺)

Step 2: methyl 2-(2-(3,4-dihydro-2H-pyran-6-yl)-5-fluorophenyl)acetate

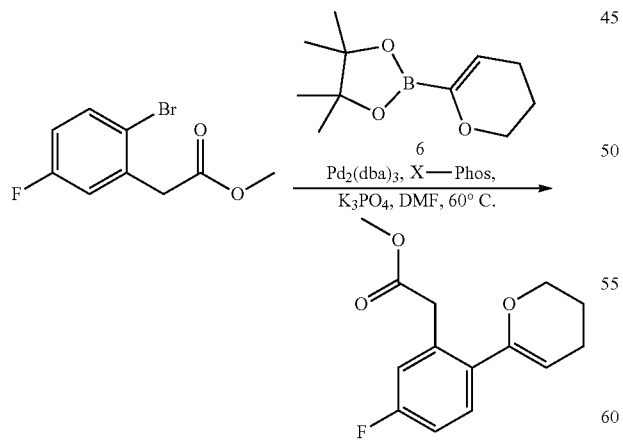

To solution of methyl 2-(2-bromo-5-fluorophenyl)acetate (6.3 g, 25.6 mmol) in DMF (60 mL) was added 3,4-dihydro-2H-pyran-6-boronic acid pinacol ester (5 g, 23.8 mmol), tris(dibenzylideneacetone) dipalladium (0) (468 mg, 0.52 mmol), X-Phos (238 mg, 0.52 mmol), and potassium phosphate (2.1 g, 25.6 mmol). The mixture was stirred at 60° C. for 12 hours under N2. The mixture was allowed to cool to room temperature an partitioned between ethyl acetate (120 mL) and water (120 mL). The organic layer was separated and the aqueous layer was extracted with ethyl acetate (60 mL×3). The combined organic phases were washed with brine and dried over anhydrous Na₂SO₄. After filtration and concentration, the residue was chromatographed (Combiflash), using 0-20% EtOAc/petroleum ether as eluent, to give methyl 2-(2-(3,4-dihydro-2H-pyran-6-yl)-5-fluorophenyl)acetate (5.2 g, 87.4%). (ESI 251.1 (M+H)⁺)

Step 3: methyl 2-(5-fluoro-2-(tetrahydro-2H-pyran-2-yl)phenyl)acetate

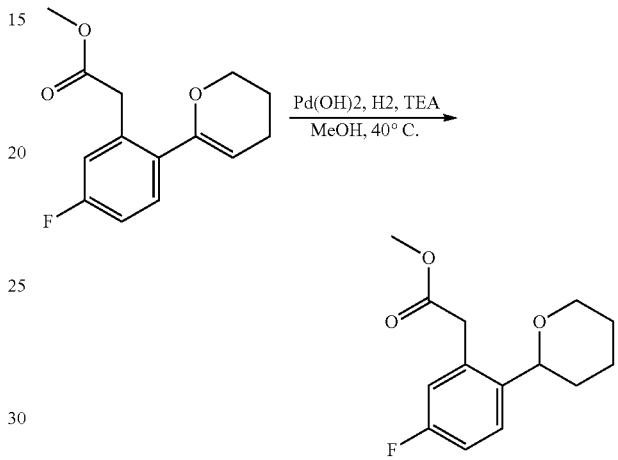

To a solution of methyl 2-(2-(3,4-dihydro-2H-pyran-6-yl)-5-fluorophenyl)acetate (500 mg, 2 mmol) in 25 ml anhydrous MeOH was added diisopropylethylamine (0.5 ml) and Pd/C (100 mg). The mixture was stirred for 3 hours at 40° C. under H₂ (balloon). The catalyst was removed by filtration and the filtrate was concentrated under reduced pressure. The residue was chromatographed (Combiflash), using 0-20% EtOAc/petroleum ether as eluent, to give methyl 2-(2-(3,4-dihydro-2H-pyran-6-yl)-5-fluorophenyl)acetate (260 mg, 52%) as an oil. (ESI 253.1 (M+H)⁺)

Step 4: methyl 2-bromo-2-(5-fluoro-2-(tetrahydro-2H-pyran-2-yl)phenyl)acetate

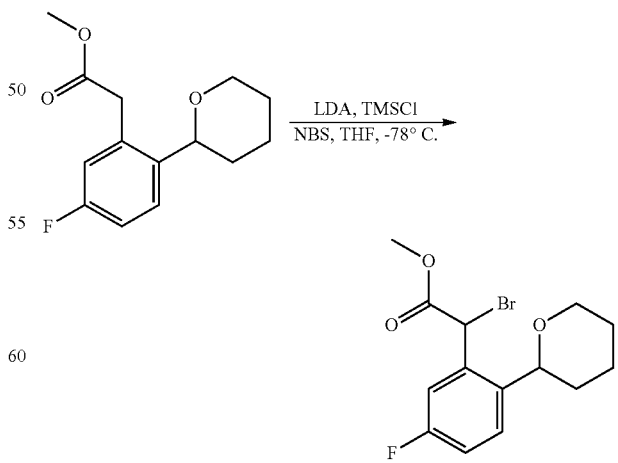

LDA (1.25 ml, 2.5 mmol, 2M in THF) was added to a solution of methyl 2-(5-fluoro-2-(tetrahydro-2H-pyran-2-yl)

phenyl)acetate (260 mg, 1.03 mmol) in 10 mL THF at −78° C. under $N_2$. The reaction was stirred for 0.5 h and TMSCl (324 mg, 3 mmol) was added. After an additional 0.25 h a solution of NBS (534 mg, 3 mmol) in 10 mL THF was added and reaction was stirred for 0.5 h at −78° C. The mixture was allowed to warm to room temperature and diluted with water (10 mL). The mixture was extracted with ethyl acetate (30 mL×3) and the combined organic phases were washed with brine and dried over anhydrous Na2SO4. After filtration and concentration, the residue was chromatographed (Combiflash), using 0-20% EtOAc/petroleum ether as eluent, to give methyl 2-bromo-2-(5-fluoro-2-(tetrahydro-2H-pyran-2-yl)phenyl)acetate (280 mg, 84.8%). (ESI 333.1 (M+H)$^+$).

Step 5: methyl 2-(5-fluoro-2-(tetrahydro-2H-pyran-2-yl)phenyl)-2-((R)-3-(4-(5,6,7,8-tetrahydro-1,8-naphthyridin-2-yl)butoxy)pyrrolidin-1-yl)acetate

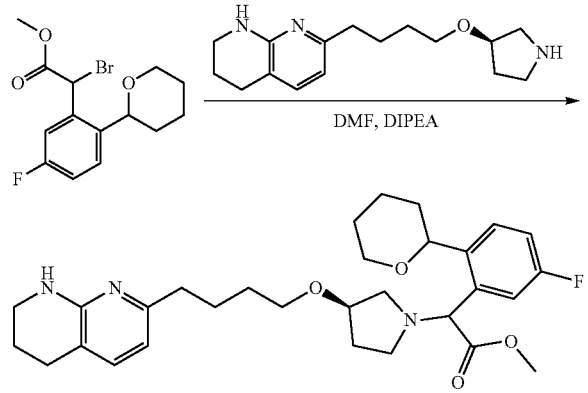

To a solution of methyl 2-bromo-2-(5-fluoro-2-(tetrahydro-2H-pyran-2-yl)phenyl)acetate (70 mg, 0.21 mmol) in DMF (5 mL) was added (R)-7-(4-(pyrrolidin-3-yloxy)butyl)-1,2,3,4-tetrahydro-1,8-naphthyridine (57 mg, 0.21 mmol) and diisopropylethylamine (81 mg, 0.63 mmol) and the reaction was stirred for 2 h. The mixture was diluted with water (10 mL) and extracted with EtOAc (20 mL, ×2). The combined organic phases were washed with brine and dried over anhydrous Na2SO4. After filtration and concentration, the residue was chromatographed (Combiflash), using 20-80% EtOAc/petroleum ether as eluent, to give methyl 2-(5-fluoro-2-(tetrahydro-2H-pyran-2-yl)phenyl)-2-((R)-3-(4-(5,6,7,8-tetrahydro-1,8-naphthyridin-2-yl)butoxy)pyrrolidin-1-yl)acetate (70 mg, 62.8%). (ESI 526.2 (M+H)$^+$)

Step 6: 2-(5-fluoro-2-(tetrahydro-2H-pyran-2-yl)phenyl)-2-((R)-3-(4-(5,6,7,8-tetrahydro-1,8-naphthyridin-2-yl)butoxy)pyrrolidin-1-yl)acetic acid (compounds 18-E1 and 18-E2)

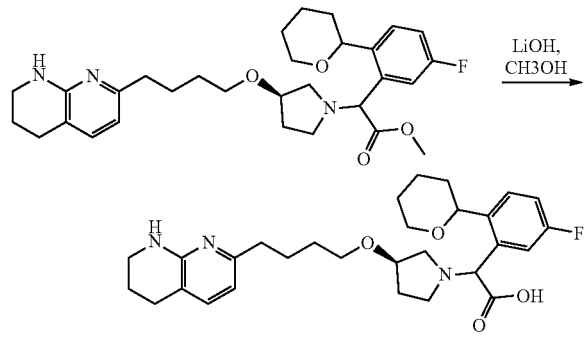

To a solution of methyl 2-(5-fluoro-2-(tetrahydro-2H-pyran-2-yl)phenyl)-2-((R)-3-(4-(5,6,7,8-tetrahydro-1,8-naphthyridin-2-yl)butoxy)pyrrolidin-1-yl)acetate (70 mg, 0.13 mmol) in 5 mL MeOH was added LiOH (10 mg, 0.4 mmol) and water (2 mL). The reaction was stirred for 2 hours, filtered and concentrated under reduced pressure. The residue was chromatographed by semi-preparative reversed-phase HPLC to give diastereomeric products compound 18-E1 (25 mg, 36.7%) and compound 18-E2 (13 mg, yield 18.3%), each as a mixture of 2 stereoisomers.

Compound 18-E1 (mixture of 2 stereoisomers) LC/MS ESI 512.2 (M+H)+. $^1$H NMR (500 MHz, MeOD) δ 7.58 (dd, J=8.8, 5.9 Hz, 1H), 7.52-7.42 (m, 1H), 7.21-7.11 (m, 2H), 6.40 (d, J=7.3 Hz, 1H), 4.80 (dd, J=21.1, 11.7 Hz, 2H), 4.22-4.12 (m, 1H), 4.04 (dd, J=10.4, 5.6 Hz, 1H), 3.76-3.66 (m, 1H), 3.61 (d, J=8.1 Hz, 1H), 3.49 (dtd, J=12.6, 6.3, 3.3 Hz, 2H), 3.42-3.34 (m, 3H), 3.22-2.99 (m, 2H), 2.72 (t, J=6.2 Hz, 2H), 2.60-2.51 (m, 2H), 2.16-1.96 (m, 4H), 1.92-1.82 (m, 2H), 1.70 (dddd, J=28.3, 22.6, 9.4, 4.8 Hz, 9H).

Compound 18-E2 (mixture of 2 stereoisomers) LC/MS ESI 512.2 (M+H)+. $^1$H NMR (500 MHz, MeOD) δ 7.44 (dt, J=8.5, 6.0 Hz, 2H), 7.18 (t, J=7.7 Hz, 1H), 7.10 (qd, J=8.4, 2.6 Hz, 1H), 6.39 (dd, J=7.3, 4.0 Hz, 1H), 5.21 (s, 1H), 4.74 (dd, J=29.6, 11.1 Hz, 1H), 4.10 (dd, J=26.7, 15.4 Hz, 2H), 3.66 (dd, J=20.8, 9.7 Hz, 1H), 3.54-3.37 (m, 6H), 3.15-2.96 (m, 2H), 2.72 (t, J=6.2 Hz, 2H), 2.58 (dt, J=14.9, 6.9 Hz, 2H), 2.10 (dd, J=34.9, 11.9 Hz, 2H), 1.99-1.80 (m, 5H), 1.77-1.66 (m, 4H), 1.63-1.55 (m, 3H).

Example 19: Preparation of 2-(5-fluoro-2-(tetrahydrofuran-3-yl)phenyl)-2-((R)-3-(4-(5,6,7,8-tetrahydro-1,8-naphthyridin-2-yl)butoxy)pyrrolidin-1-yl) acetic Acid (Compounds 19-E1, 19-E2, 19-E3 and 19-E4)

Step 1: Methyl 2-(2-bromo-5-fluorophenyl)acetate

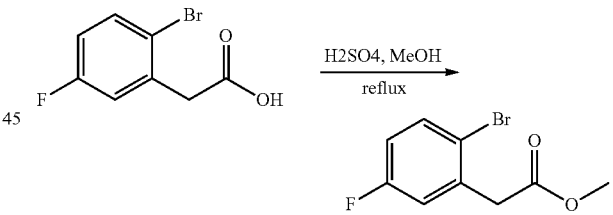

To a solution of 2-(2-bromo-5-fluorophenyl) acetic acid (10 g, 43 mmol) in MeOH (60 mL) was added 0.5 mL $H_2SO_4$. The mixture was refluxed for 4 hours, allowed to cool to room temperature and the solvent was removed under reduced pressure. The resulting oil (10 g, 94.3%) was used without further purification. (ESI 246.1 (M+H)$^+$)

Step 2: Methyl 2-(2-(2,5-dihydrofuran-3-yl)-5-flourophenyl)acetate

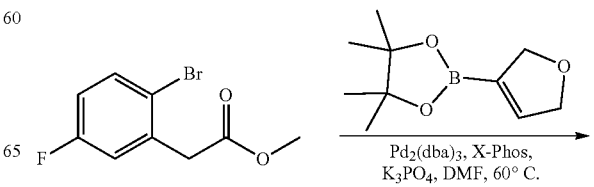

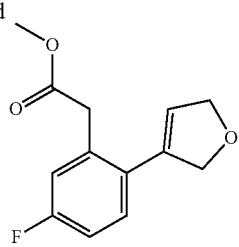

To a solution of methyl 2-(2-bromo-5-fluorophenyl)acetate (492 mg, 2 mmol) in DMF (5 mL) was added 2-(2,5-dihydrofuran-3-yl)-4,4,5,5-tetramethyl-1,3,2-dioxaborolane (392 mg, 2 mmol), tris(dibenzylideneacetone) dipalladium (0) (91 mg, 0.1 mmol), X-Phos (47.6 mg, 0.1 mmol), and potassium phosphate (424 mg, 2 mmol). The resulting mixture was stirred at 60° C. for 2 hours under $N_2$, allowed to cool to room temperature and partitioned between ethyl acetate (20 mL) and water (20 mL). The organic layer was separated and the aqueous layer was extracted with ethyl acetate (20 mL×3). The combined organic phases were washed with brine and dried over anhydrous Na2SO4. After filtration and concentration, the residue was chromatographed (Combiflash), using 20-80% EtOAc/petroleum ether as eluent, to give methyl 2-(2-(2,5-dihydrofuran-3-yl)-5-fluorophenyl)acetate (350 mg, 73%). (ESI 237.2 (M+H)$^+$)

Step 3: Methyl 2-(5-fluoro-2-(tetrahydrofuran-3-yl)phenyl)acetate

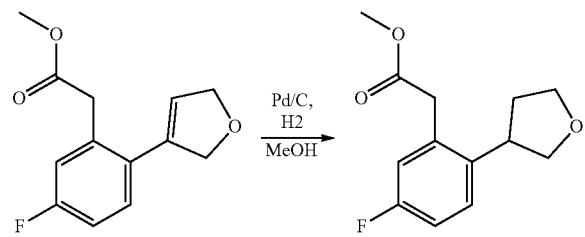

To a solution of methyl 2-(2-(2,5-dihydrofuran-3-yl)-5-fluorophenyl) acetate (350 mg, 1.48 mmol) in methanol (10 mL) was added Pd/C (50 mg). The mixture was stirred for 3 hours at 40° C. under $H_2$ (balloon). The catalyst was removed by filtration and the filtrate was concentrated under reduced pressure. The residue was chromatographed (Combiflash), using 5-20% EtOAc/petroleum ether as eluent, to give methyl 2-(5-fluoro-2-(tetrahydrofuran-3-yl)phenyl)acetate (260 mg, 73%) as an oil. LCMS: 239(M+H)$^+$ Step 4: methyl 2-bromo-2-(5-fluoro-2-(tetrahydrofuran-3-yl)phenyl)acetate

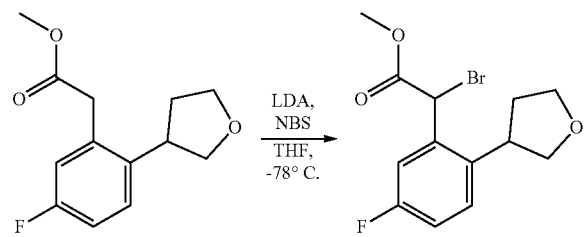

A solution of methyl 2-(5-fluoro-2-(tetrahydrofuran-3-yl)phenyl)acetate (260 mg, 1.09 mmol) in THF (10 mL) under $N_2$ was cooled to −78° C. and treated with LDA (1.25 mL, 2.5 mmol, 2 M in THF) and the mixture was stirred for 0.5 h. TMSCl (324 mg, 3 mmol) was added, the reaction was stirred for 0.25 h and NBS (534 mg, 3 mmol) in THF (10 mL) was added. The reaction was stirred for 0.5 h, diluted with water and extracted with ethyl acetate (30 mL×3). The combined organic phases were washed with brine and dried over anhydrous Na2SO4. After filtration and concentration, The residue was chromatographed (Combiflash), using 5-20% EtOAc/petroleum ether as eluent, to give methyl 2-bromo-2-(5-fluoro-2-(tetrahydrofuran-3-yl)phenyl)acetate (250 mg, 71.8%) as an oil. (ESI 317.2) (M+H)$^+$ Step 5: methyl 2-(5-fluoro-2-(tetrahydrofuran-3-yl)phenyl)-2-((R)-3-(4-(5,6,7,8-tetrahydro-1,8-naphthyridin-2-yl)butoxy)pyrrolidin-1-yl)actetate

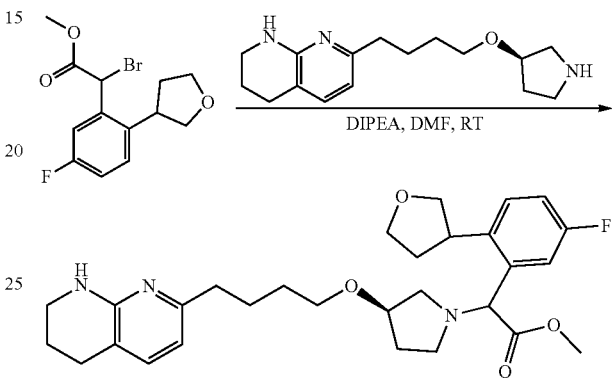

To a solution of methyl 2-bromo-2-(5-fluoro-2-(tetrahydrofuran-3-yl)phenyl)acetate (100 mg, 0.31 mmol) in 5 mL dry DMF was added (R)-7-(4-(pyrrolidin-3-yloxy)butyl)-1,2,3,4-tetrahydro-1,8-naphthyridine (87 mg, 0.31 mmol) and diisopropylethylamine (120 mg, 0.93 mmol). The reaction was stirred for 2 h, diluted with water (10 mL) and extracted with ethyl acetate (20 mL×3). The combined organic phases were washed with brine and dried over anhydrous Na2SO4. After filtration and concentration, the residue was chromatographed (Combiflash), using 20-80% EtOAc/petroleum ether as eluent, to give methyl 2-(5-fluoro-2-(tetrahydrofuran-3-yl)phenyl)-2-((R)-3-(4-(5,6,7,8-tetrahydro-1,8-naphthyridin-2-yl)butoxy)pyrrolidin-1-yl)acetate (110 mg, 68%) as a solid. (ESI 512 (M+H)$^+$).

Step 6: 2-(5-fluoro-2-(tetrahydrofuran-3-yl)phenyl)-2-((R)-3-(4-(5,6,7,8-tetrahydro-1,8-naphthyridin-2-yl)butoxy)pyrrolidin-1-yl)acetic acid (Compounds 19-E1, 19-E2, 19-E3 and 19-E4)

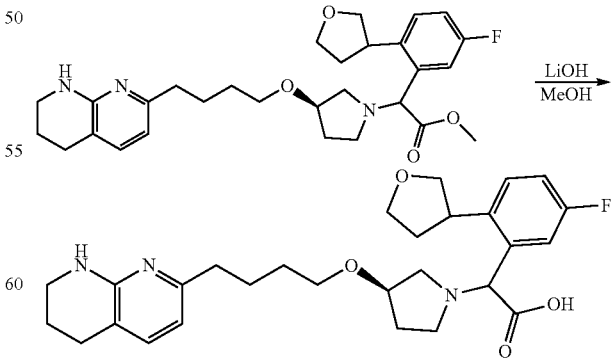

To a solution of methyl 2-(5-fluoro-2-(tetrahydrofuran-3-yl)phenyl)-2-((R)-3-(4-(5,6,7,8-tetrahydro-1,8-naphthyridin-2-yl)butoxy)pyrrolidin-1-yl)acetate (110 mg, 0.21 mmol) in methanol (5 mL) was added LiOH (20 mg, 0.8 mmol) and water (4 mL). The reaction was stirred for 2 h, filtered and concentrated under reduced pressure. The resulting the residue was chromatographed using semi-preparative reversed-phase HPLC to give diastereomeric compounds compound 19-E1 (10 mg, yield 9.3%), compound 19-E2(10 mg, yield 9.3%), compound 19-E3 (10 mg, yield 9.3%) and compound 19-E4 (10 mg, yield 9.3%).

Compound 19-E1: LC/MS ESI 498.2 (M+H)+. 1H NMR (500 MHz, MeOD) δ 7.48 (dd, J=8.8, 5.7 Hz, 1H), 7.42 (dd, J=10.1, 2.7 Hz, 1H), 7.23 (d, J=7.3 Hz, 1H), 7.14 (td, J=8.4, 2.8 Hz, 1H), 6.41 (dd, J=20.8, 7.3 Hz, 1H), 4.95 (s, 1H), 4.58-4.46 (m, 1H), 4.18 (d, J=18.9 Hz, 1H), 4.05-3.98 (m, 2H), 3.86 (dd, J=15.5, 7.5 Hz, 2H), 3.79 (dd, J=8.3, 6.3 Hz, 1H), 3.50 (t, J=6.2 Hz, 2H), 3.42 (dd, J=14.2, 8.7 Hz, 3H), 3.28 (s, 1H), 3.12-2.98 (m, 2H), 2.73 (t, J=6.2 Hz, 2H), 2.60 (ddd, J=15.0, 9.5, 5.5 Hz, 2H), 2.51-2.38 (m, 1H), 2.08 (ddd, J=14.9, 8.4, 4.6 Hz, 3H), 1.90 (dd, J=11.8, 5.7 Hz, 2H), 1.80-1.60 (m, 4H).

Compound 19-E2: LC/MS ESI 498.2 (M+H)+. 1H NMR (500 MHz, MeOD) δ 7.51-7.46 (m, 1H), 7.42 (dd, J=10.1, 2.7 Hz, 1H), 7.23 (d, J=7.3 Hz, 1H), 7.13 (td, J=8.4, 2.8 Hz, 1H), 6.43 (d, J=7.3 Hz, 1H), 4.94 (s, 1H), 4.17 (dd, J=19.1, 11.5 Hz, 2H), 4.11-4.03 (m, 1H), 3.95-3.80 (m, 3H), 3.76-3.68 (m, 1H), 3.52-3.46 (m, 3H), 3.43-3.37 (m, 2H), 3.26 (d, J=12.5 Hz, 1H), 3.13-2.99 (m, 2H), 2.73 (t, J=6.2 Hz, 2H), 2.60 (t, J=7.2 Hz, 2H), 2.42-2.29 (m, 1H), 2.07 (dtd, J=42.5, 12.5, 7.8 Hz, 4H), 1.94-1.86 (m, 2H), 1.78-1.69 (m, 2H), 1.68-1.58 (m, 3H).

Compound 19-E3: LC/MS ESI 498.2 (M+H)+. 1H NMR (500 MHz, MeOD) δ 7.52-7.39 (m, 2H), 7.23 (d, J=7.3 Hz, 1H), 7.13 (td, J=8.4, 2.8 Hz, 1H), 6.42 (t, J=10.9 Hz, 1H), 4.87-4.81 (m, 1H), 4.17 (s, 1H), 4.04 (ddt, J=33.6, 28.5, 7.3 Hz, 3H), 3.88 (dd, J=15.7, 7.6 Hz, 1H), 3.79 (dd, J=8.2, 6.2 Hz, 1H), 3.56-3.51 (m, 1H), 3.46-3.34 (m, 4H), 3.16 (ddd, J=16.9, 15.7, 6.6 Hz, 3H), 2.73 (t, J=6.2 Hz, 2H), 2.62 (dd, J=16.3, 7.8 Hz, 2H), 2.48 (d, J=7.6 Hz, 1H), 2.18-2.12 (m, 2H), 2.09-2.01 (m, 1H), 1.92-1.86 (m, 2H), 1.75 (dd, J=12.1, 7.4 Hz, 2H), 1.68-1.60 (m, 2H).

Compound 19-E4: LC/MS ESI 498.2 (M+H)+. 1H NMR (500 MHz, MeOD) δ 7.46 (ddd, J=13.0, 9.5, 4.3 Hz, 2H), 7.24 (d, J=7.3 Hz, 1H), 7.13 (td, J=8.4, 2.8 Hz, 1H), 6.43 (d, J=7.3 Hz, 1H), 4.86 (s, 1H), 4.23-4.14 (m, 2H), 4.09 (td, J=8.3, 4.6 Hz, 1H), 3.98 (dd, J=14.8, 7.4 Hz, 1H), 3.86 (dd, J=15.9, 7.7 Hz, 1H), 3.71 (dd, J=8.6, 6.5 Hz, 1H), 3.54 (dt, J=9.1, 6.1 Hz, 1H), 3.46-3.35 (m, 4H), 3.25-3.08 (m, 3H), 2.73 (t, J=6.2 Hz, 2H), 2.69-2.54 (m, 2H), 2.39 (d, J=7.8 Hz, 1H), 2.16 (d, J=3.6 Hz, 2H), 2.02 (dq, J=12.4, 7.8 Hz, 1H), 1.95-1.83 (m, 2H), 1.75 (dd, J=12.3, 7.4 Hz, 2H), 1.62 (dd, J=13.6, 7.0 Hz, 2H).

Example 20: Preparation of 2-(2-cyclopropoxy-5-fluorophenyl)-2-((R)-3-(5-(5,6,7,8-tetrahydro-1,8-naphthyridin-2-yl)pentyl)pyrrolidin-1-yl)acetic Acid (Compounds 20-E1 and 20-E2)

Step 1: 2-bromo-1-cyclopropoxy-4-fluorobenzene

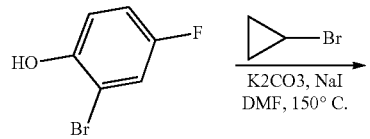

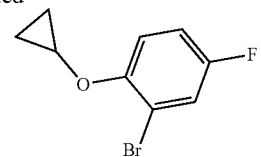

A mixture of 2-bromo-4-fluorophenol (250 mg, 1.31 mmol), bromocyclopropane (792 mg, 6.54 mmol), NaI (2 mg, 0.013 mmol) and K2CO3 (543 mg, 3.93 mmol) in DMF (4 mL) was stirred and heated to 150° C. under microwave irradiation (Biotage) for 2 hours. The reaction mixture was diluted with water (10 mL) and ethyl acetate (10 mL), the organic layer was separated and the aqueous layer was extracted with ethyl acetate (10 mL×3). The combined organic layers were washed with brine and dried over anhydrous Na2SO4. After filtration and concentration, the residue was chromatographed (Combiflash), using EtOAc/petroleum ether (1:10) as eluent, to give 2-bromo-1-cyclopropoxy-4-fluorobenzene (50 mg, 16.5%) 1H NMR (500 MHz, CDCl3) δ 7.28-7.22 (m, 1H), 7.18 (dd, J=9.1, 4.9 Hz, 1H), 7.03-6.94 (m, 1H), 3.76 (tt, J=5.9, 3.1 Hz, 1H), 0.87-0.69 (m, 4H).

Step 2: 2-cyclopropoxy-5-fluorophenylboronic acid

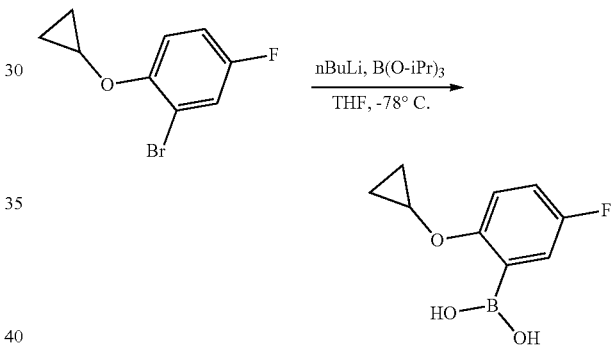

To a solution of 2-bromo-1-cyclopropoxy-4-fluorobenzene (250 mg, 1.08 mmol) in THF (15 mL) at −78° C. under Ar was added nBuLi (0.87 mL, 2.16 mmol, 2.5 M in THF). The mixture was stirred for 0.5 h, then triisopropyl borate (224 mg, 1.19 mmol) was slowly added via syringe. The mixture was stirred continuously for 2 h at −78° C., then quenched by the addition of saturated aqueous NH4Cl solution (5 mL). The mixture was allowed to warm to room temperature and partitioned between water (10 mL) and ethyl acetate (10 mL). The organic layer was separated and the aqueous layer was extracted with ethyl acetate (15 mL×3), washed with brine and dried over anhydrous Na2SO4. The organic phase was concentrated to dryness to give 2-bromo-1-cyclopropoxy-4-fluorobenzene (70 mg, yield 33.0%)

Step 3 2-(2-cyclopropoxy-5-fluorophenyl)-2-((R)-3-(5-(5,6,7,8-tetrahydro-1,8-naphthyridin-2-yl)pentyl)pyrrolidin-1-yl)acetic acid (Compounds 20-E1 and 20-E2)

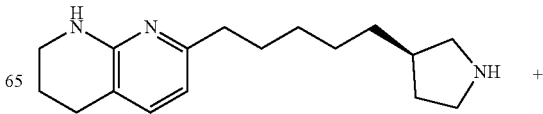

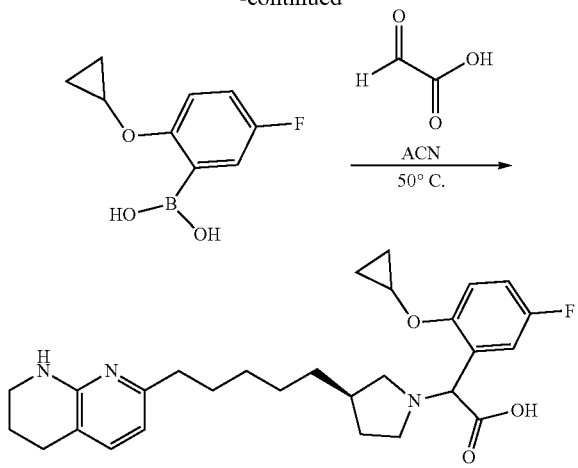

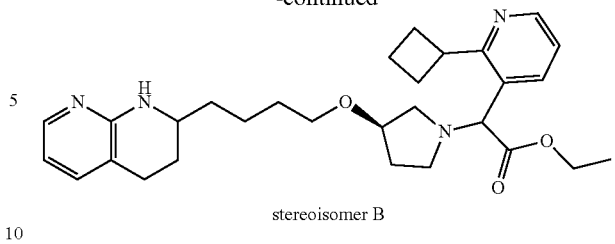

A mixture of 2-(4-(((R)-pyrrolidin-3-yl)oxy)butyl)-1,2,3,4-tetrahydro-1,8-naphthyridine stereoisomer B (120 mg, 0.44 mmol), ethyl 2-chloro-2-(2-cyclobutylpyridin-3-yl)acetate (110 mg, 0.44 mmol) and diisopropylethylamine (513 mg, 3.72 mmol) in acetonitrile (8 mL) was stirred at 50° C. for 16 hours. Solvent was removed in vacuo, and the residue was purified by silica gel column (DCM:MeOH 20:1) to give the desired product ethyl 2-(2-cyclobutylpyridin-3-yl)-2-((R)-3-(4-((R)-1,2,3,4-tetrahydro-1,8-naphthyridin-2-yl)butoxy)pyrrolidin-1-yl)acetate stereoisomer B as a yellow oil (95 mg). Yield 44% (ESI 493 (M+H)+).

A mixture of (R)-7-(5-(pyrrolidin-3-yl)pentyl)-1,2,3,4-tetrahydro-1,8-naphthyridine (60 mg, 0.22 mmol), 2-cyclopropoxy-5-fluorophenylboronic acid (47 mg, 0.24 mmol) and 2-oxoacetic acid (18 mg, 0.24 mmol) in MeCN (4 mL) was stirred for 2 hours. The residue was chromatographed using semi-preparative reversed-phase HPLC (30-65% MeCN) to give compound 20 (45 mg, 42.6%). The racemic product was separated by chiral SFC to diastereomeric products compound 20-E1 (9.3 mg) and compound 20-E2 (11.1 mg).

Compound 20-E1 LC/MS ESI 482.2 (M+H)+. $^1$H NMR (500 MHz, MeOD) δ 7.42 (dd, J=9.1, 4.5 Hz, 1H), 7.31 (dd, J=8.9, 2.8 Hz, 1H), 7.16 (ddd, J=20.7, 12.9, 5.2 Hz, 2H), 6.35 (d, J=7.3 Hz, 1H), 4.86 (s, 1H), 4.11-3.80 (m, 1H), 3.48-3.35 (m, 3H), 3.17 (dd, J=23.9, 15.4 Hz, 2H), 2.87 (s, 1H), 2.71 (t, J=6.3 Hz, 2H), 2.50 (t, J=7.6 Hz, 2H), 2.38-2.25 (m, 1H), 2.24-2.08 (m, 1H), 1.89 (dt, J=12.2, 6.1 Hz, 2H), 1.62 (dd, J=13.5, 7.4 Hz, 3H), 1.41 (s, 2H), 1.32 (dd, J=22.3, 9.5 Hz, 5H), 0.98-0.71 (m, 4H).

Compound 20-E2 LC/MS ESI 482.2 (M+H)+. $^1$H NMR (500 MHz, MeOD) δ 7.43 (dd, J=9.1, 4.5 Hz, 1H), 7.33 (dd, J=8.9, 2.9 Hz, 1H), 7.22-7.15 (m, 1H), 7.14 (d, J=7.3 Hz, 1H), 6.36 (t, J=5.8 Hz, 1H), 4.88-4.82 (m, 1H), 4.00-3.87 (m, 1H), 3.60 (s, 1H), 3.44-3.34 (m, 3H), 3.16-3.04 (m, 1H), 2.72 (dd, J=15.9, 9.5 Hz, 3H), 2.56-2.46 (m, 2H), 2.42-2.31 (m, 1H), 2.22-2.07 (m, 1H), 1.94-1.83 (m, 2H), 1.67-1.60 (m, 3H), 1.43 (s, 2H), 1.35 (d, J=4.6 Hz, 5H), 0.95-0.70 (m, 4H).

Example 21: Preparation of 2-(2-cyclobutylpyridin-3-yl)-2-((3R)-3-(4-(1,2,3,4-tetrahydro-1,8-naphthyridin-2-yl)butoxy)pyrrolidin-1-yl)acetic Acid (Compounds 21-B-E1, 21-B-E2 and 21-A)

Step 1: ethyl 2-(2-cyclobutylpyridin-3-yl)-2-((R)-3-(4-((R)-1,2,3,4-tetrahydro-1,8-naphthyridin-2-yl)butoxy)pyrrolidin-1-yl)acetate stereoisomer B

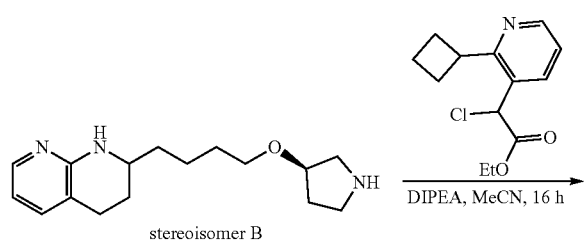

Step 2: 2-(2-cyclobutylpyridin-3-yl)-2-((3R)-3-(4-(1,2,3,4-tetrahydro-1,8-naphthyridin-2-yl)butoxy)pyrrolidin-1-yl)acetic acid stereoisomer B (compounds 21-B-E1 and 21-B-E2)

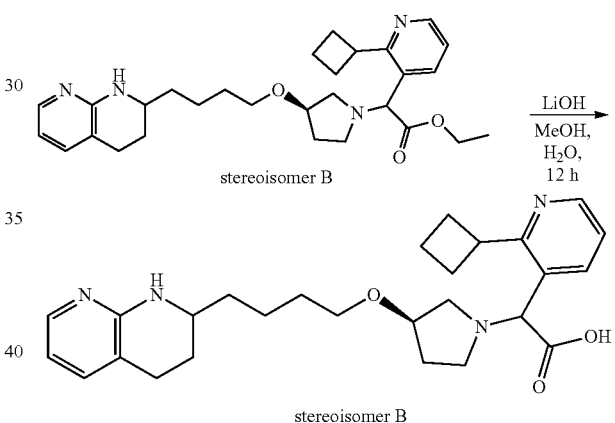

Ethyl 2-(2-cyclobutylpyridin-3-yl)-2-((R)-3-(4-((R)-1,2,3,4-tetrahydro-1,8-naphthyridin-2-yl)butoxy)pyrrolidin-1-yl)acetate stereoisomer B (95 mg, 0.19 mmol) was treated with LiOH—H$_2$O (52 mg, 1.24 mmol) in MeOH (4 mL) and H$_2$O (1 mL) at 40° C. for 4 hours. Solvent was removed in vacuo, and the residue was purified by Prep-HPLC A (30-65% MeCN) to give compound 21-B as a white solid (68 mg, 77% yield). The racemic product was separated by Prep chiral SFC F to give diastereomeric products compound 21-B-E1 (4 mg) and compound 21-B-E2 (6 mg) as white solids.

Compound 21-B-E1 LC/MS ESI 465(M+H)+. 1H NMR (500 MHz, MeOD) δ 8.68 (m, 1H), 8.08 (d, J=9.5 Hz, 1H), 7.71 (m, 1H), 7.31 (m, 2H), 6.52 (m, 1H), 4.82 (s, 1H), 4.23 (m, 2H), 3.55-3.35 (m, 4H), 3.20 (m, 3H), 2.76 (m, 2H), 2.63-1.86 (m, 9H), 1.75-1.50 (m, 7H), Chiral SFC F: ee 100%, Rt=7.78 min.

Compound 21-B-E2 LC/MS ESI 465(M+H)+. 1H NMR (500 MHz, MeOD) δ 8.58 (m, 1H), 8.08 (d, J=9.5 Hz, 1H), 7.75 (m, 1H), 7.31 (m, 2H), 6.52 (m, 1H), 4.82 (s, 1H), 4.23 (m, 2H), 3.55-3.35 (m, 4H), 3.20 (m, 3H), 2.76 (m, 2H), 2.63-1.86 (m, 9H), 1.75-1.50 (m, 7H), Chiral SFC F: ee 100%, Rt=12.02 min.

Step 3: 2-(2-cyclobutylpyridin-3-yl)-2-((R)-3-(4-((S)-1,2,3,4-tetrahydro-1,8-naphthyridin-2-yl)butoxy)pyrrolidin-1-yl)acetic acid stereoisomer A (compound 21-A)

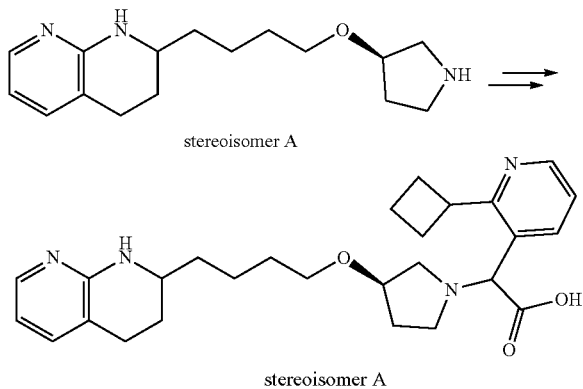

2-(2-cyclobutylpyridin-3-yl)-2-((R)-3-(4-((S)-1,2,3,4-tetrahydro-1,8-naphthyridin-2-yl)butoxy)pyrrolidin-1-yl)acetic acid stereoisomer A (compound 21-A) was synthesized from 2-(4-(((R)-pyrrolidin-3-yl)oxy)butyl)-1,2,3,4-tetrahydro-1,8-naphthyridine stereoisomer A by the same procedures as for stereoisomer B.

Compound 21-A LC/MS ESI 465.3 (M+H)+1H NMR (500 MHz, MeOD) δ 8.56-8.54 (m, 1H), 8.08-8.01 (m, 1H), 7.72-7.70 (m, 1H), 7.32-7.29 (m, 2H), 6.56-6.52 (m, 1H), 4.82-4.73 (m, 1H), 4.30-4.18 (m, 2H), 3.78-3.35 (m, 4H), 3.28-2.95 (m, 3H), 2.81-2.28 (m, 6H), 2.24-1.88 (m, 5H), 1.74-1.48 (m, 7H).

Example 22: Preparation of 2-(5-fluoro-2-(tetrahydro-2H-pyran-2-yl)phenyl)-2-((R)-3-(4-(5,6,7,8-tetrahydro-1,8-naphthyridin-2-yl)butoxy)pyrrolidin-1-yl)acetic Acid (Diastereomeric Compounds 92-A-E1, 92-A-E2, 92-B-E1 and 92-B-E2)

Step 1: Methyl 2-(5-fluoro-2-(tetrahydro-2H-pyran-2-yl)phenyl)acetate

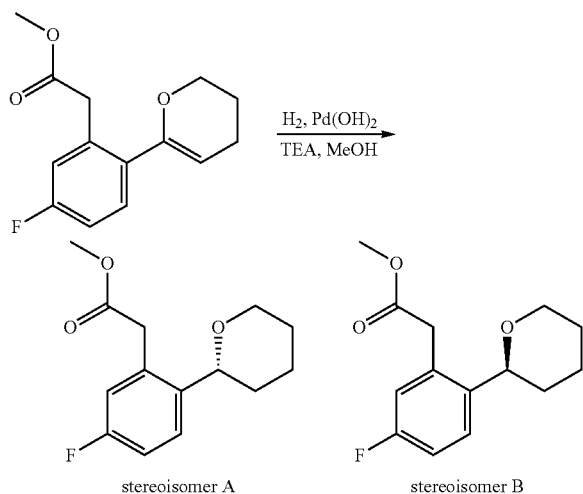

To a solution of methyl 2-(5-fluoro-2-(tetrahydro-2H-pyran-2-yl)phenyl)acetate (2.4 g, 9.6 mmol) in 100 mL anhydrous MeOH was added Pd(OH)$_2$ (100 mg) and TEA (2 mL). The mixture was stirred for 8 hours at 40° C. under an atmosphere of H$_2$ (balloon). The catalyst was removed by filtration and the filtrate was concentrated under reduced pressure. The residue was chromatographed on silica (Combiflash) using 5-20% EtOAc/petroleum ether as eluent, to give racemic methyl 2-(5-fluoro-2-(tetrahydro-2H-pyran-2-yl)phenyl)acetate (2.2 g, 92%). Chiral separation using SFC (AY-H (250*4.6 mm Sum) Moblie Phase=Hexane (0.1% DEA): EtOH (0.1% DEA)=95:5) gave stereoisomer A (identified as methyl (R)-2-(5-fluoro-2-(tetrahydro-2H-pyran-2-yl)phenyl)acetate, 960 mg, 43.5%) and stereoisomer B (identified as methyl (S)-2-(5-fluoro-2-(tetrahydro-2H-pyran-2-yl)phenyl)acetate, 904 mg, 40.7%); (ESI 253.2 (M+H)+).

Step 2: Methyl 2-bromo-2-(5-fluoro-2-((S)-tetrahydro-2H-pyran-2-yl)phenyl)acetate(stereoisomer B)

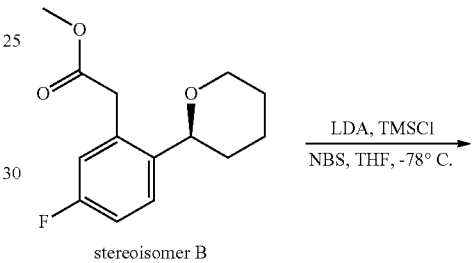

LDA (25 mL, 50 mmol, 2M in THF) was added to a solution of (S)-methyl 2-(5-fluoro-2-(tetrahydro-2H-pyran-2-yl)phenyl)acetate (stereoisomer B, 4.2 g, 16.7 mmol) in THF (100 mL) under an atmosphere of N$_2$ at −78° C. The reaction was stirred for 0.5 h and TMSCl (5.4 g, 50 mmol) was added. After an additional 15 min, a solution of NBS (8.9 g, 50 mmol) in THF (50 mL) was added and the reaction was stirred for 0.5 h at −78° C. The reaction was diluted with water (10 mL) and extracted with ethyl acetate (50 mL×2). The combined organic phases were washed with brine and dried over anhydrous Na2SO4. After filtration and concentration, the residue was chromatographed on silica (Combiflash) using 0-20% EtOAc/petroleum ether as eluent, to give methyl 2-bromo-2-(5-fluoro-2-((S)-tetrahydro-2H-pyran-2-yl)phenyl)acetate (stereoisomer B, 4.1 g, 74.5%); (ESI 331.3 (M+H)+.

Step 3: Methyl 2-(5-fluoro-2-((S)-tetrahydro-2H-pyran-2-yl)phenyl)-2-((R)-3-(4-(5,6,7,8-tetrahydro-1,8-naphthyridin-2-yl)butoxy)pyrrolidin-1-yl)acetate (stereoisomer B)

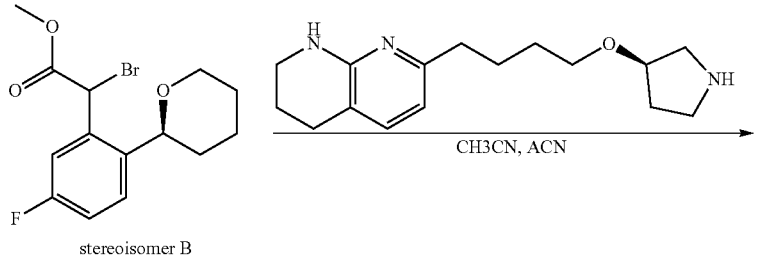

stereoisomer B

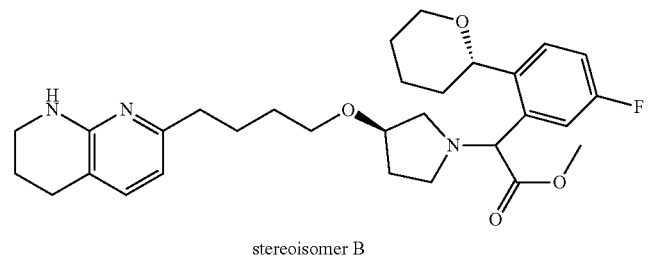

stereoisomer B

To a solution of methyl 2-bromo-2-(5-fluoro-2-((S)-tetrahydro-2H-pyran-2-yl)phenyl)acetate (stereoisomer B, 4.1 g, 12.4 mmol) in acetonitrile (30 mL) was added (R)-7-(4-(pyrrolidin-3-yloxy)butyl)-1,2,3,4-tetrahydro-1,8-naphthyridine (3.4 g, 12.4 mmol) and DIPEA (4.8 g, 37.2 mmol). The reaction was stirred for 1 c, diluted with water (50 mL) and extracted with ethyl acetate (50 mL×3). The combined organic phase was washed with brine and dried over anhydrous Na2SO4. After filtration and concentration, the residue was chromatographed on silica (Combiflash) using 20-80% EtOAc/petroleum ether as eluent, to give methyl 2-(5-fluoro-2-((S)-tetrahydro-2H-pyran-2-yl)phenyl)-2-((R)-3-(4-(5,6,7,8-tetrahydro-1,8-naphthyridin-2-yl)butoxy)pyrrolidin-1-yl)acetate as a mixture of diastereomers (stereoisomer B, 4.9 g, 75%); (ESI 526.2 (M+H)$^+$); $^1$H NMR (500 MHz, MeOD) δ 7.51 (ddd, J=20.9, 8.7, 5.9 Hz, 1H), 7.34 (dt, J=10.3, 3.4 Hz, 1H), 7.11 (d, J=7.3 Hz, 1H), 7.09-7.03 (m, 1H), 6.36 (d, J=7.3 Hz, 1H), 4.86 (m, 2H), 4.47 (m, 1H), 4.08-3.97 (m, 2H), 3.69-3.61 (m, 4H), 3.39 (m, 3H), 2.87 (m, 1H), 2.75-2.63 (m, 3H), 2.56-2.35 (m, 4H), 2.00 (m, 1H), 1.97-1.75 (m, 5H), 1.72-1.63 (m, 4H), 1.57 (m, 4H).

Step 4: 2-(5-fluoro-2-((S)-tetrahydro-2H-pyran-2-yl)phenyl)-2-((R)-3-(4-(5,6,7,8-tetrahydro-1,8-naphthyridin-2-yl)butoxy)pyrrolidin-1-yl)acetic acid (compounds 92-B-E1 and 92-B-E2)

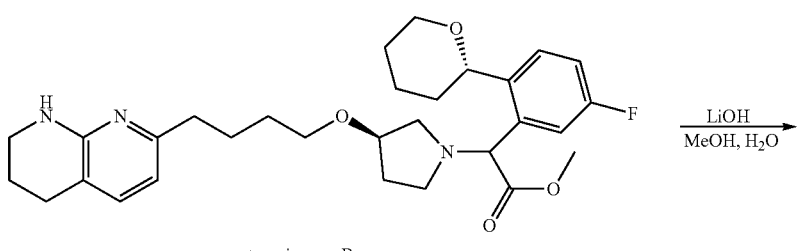

stereoisomer B

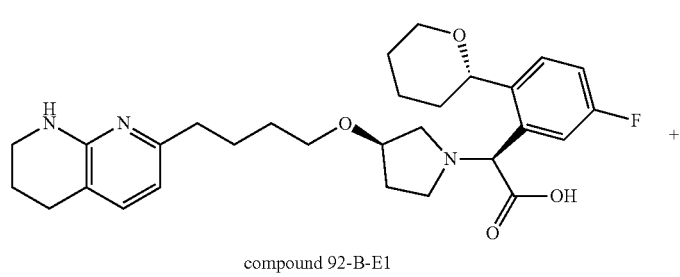

compound 92-B-E1

-continued

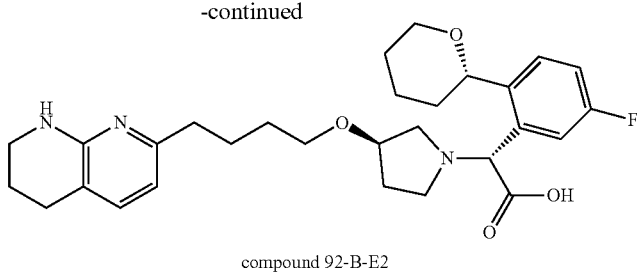

compound 92-B-E2

To a solution of methyl 2-(5-fluoro-2-((S)-tetrahydro-2H-pyran-2-yl)phenyl)-2-((R)-3-(4-(5,6,7,8-tetrahydro-1,8-naphthyridin-2-yl)butoxy)pyrrolidin-1-yl)acetate (stereoisomer B, 4.9 g, 9.3 mmol) in methanol (50 mL) was added LiOH (480 mg, 20 mmol) and water (20 mL). The reaction was stirred for 16 h at 25° C., filtered and concentrated under reduced pressure then purified with semi-preparative reversed-phase HPLC to give individual diastereomers (S)-2-(5-fluoro-2-((S)-tetrahydro-2H-pyran-2-yl)phenyl)-2-((R)-3-(4-(5,6,7,8-tetrahydro-1,8-naphthyridin-2-yl)butoxy)pyrrolidin-1-yl)acetic acid compound 92-B-E1 (1.88 g), (Yield 39.4%) and (R)-2-(5-fluoro-2-((S)-tetrahydro-2H-pyran-2-yl)phenyl)-2-((R)-3-(4-(5,6,7,8-tetrahydro-1,8-naphthyridin-2-yl)butoxy)pyrrolidin-1-yl)acetic acid compound 92-B-E2 (1.33 g) (Yield 27.9%).

Compound 92-B-E1 LC/MS ESI 512.3 (M+H)+. 1H NMR (400 MHz, MeOD) δ 7.58 (dd, J=8.8, 5.9 Hz, 1H), 7.46 (dd, J=10.0, 2.7 Hz, 1H), 7.22-7.11 (m, 2H), 6.40 (d, J=7.3 Hz, 1H), 4.90 (s, 1H), 4.77 (d, J=10.3 Hz, 1H), 4.20 (m, 1H), 4.04 (dd, J=7.5, 5.6 Hz, 1H), 3.68 (t, J=11.6 Hz, 1H), 3.62 (d, J=9.2 Hz, 1H), 3.49 (t, J=5.6 Hz, 2H), 3.42-3.35 (m, 3H), 3.23 (d, J=12.6 Hz, 1H), 3.04 (m, 1H), 2.72 (t, J=6.2 Hz, 2H), 2.57 (t, J=7.6 Hz, 2H), 2.2-1.95 (m, 4H), 1.9-1.8 (m, 2H), 1.8-1.55 (m, 8H).

Compound 92-B-E2: LC/MS ESI 512.3 (M+H)+. 1H NMR (500 MHz, MeOD) δ 7.47-7.39 (m, 2H), 7.19 (d, J=7.3 Hz, 1H), 7.11 (td, J=8.4, 2.6 Hz, 1H), 6.40 (d, J=7.3 Hz, 1H), 4.75 (d, J=11.1 Hz, 2H), 4.15 (d, J=9.4 Hz, 1H), 4.08 (s, 1H), 3.67 (t, J=10.7 Hz, 1H), 3.53-3.42 (m, 3H), 3.38 (d, J=5.3 Hz, 2H), 3.10 (m, 2H), 2.72 (t, J=6.2 Hz, 2H), 2.58 (m, 2H), 2.15 (s, 1H), 2.09 (s, 1H), 1.95 (d, J=7.8 Hz, 2H), 1.92-1.82 (m, 3H), 1.73 (m, 4H), 1.61 (m, 4H).

Step 5: 2-(5-fluoro-2-((R)-tetrahydro-2H-pyran-2-yl)phenyl)-2-((R)-3-(4-(5,6,7,8-tetrahydro-1,8-naphthyridin-2-yl)butoxy)pyrrolidin-1-yl)acetic acid (compounds 92-A-E1 and 92-A-E2)

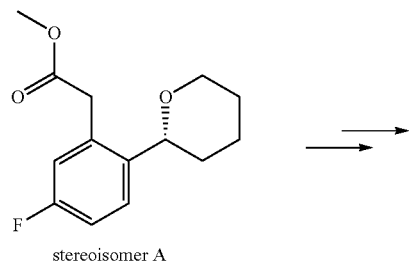

stereoisomer A

-continued

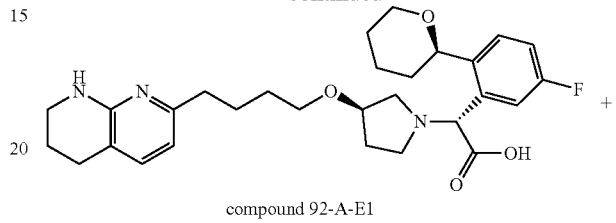

compound 92-A-E1

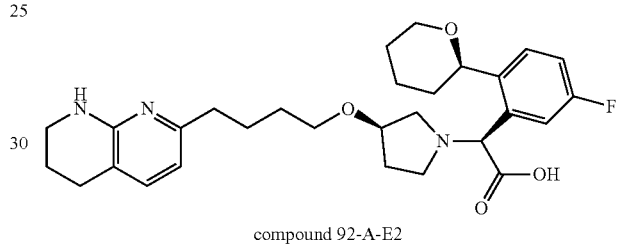

compound 92-A-E2

(R)-2-(5-fluoro-2-((R)-tetrahydro-2H-pyran-2-yl)phenyl)-2-((R)-3-(4-(5,6,7,8-tetrahydro-1,8-naphthyridin-2-yl)butoxy)pyrrolidin-1-yl)acetic acid compound 92-A-E1 and (S)-2-(5-fluoro-2-((R)-tetrahydro-2H-pyran-2-yl)phenyl)-2-((R)-3-(4-(5,6,7,8-tetrahydro-1,8-naphthyridin-2-yl)butoxy)pyrrolidin-1-yl)acetic acid compound 92-A-E2 were synthesized from methyl (R)-2-(5-fluoro-2-(tetrahydro-2H-pyran-2-yl)phenyl)acetate (stereoisomer A) by the same procedures as for stereoisomer B.

Compound 92-A-E1 LC/MS ESI 512.1 (M+H)+, 1H NMR (500 MHz, MeOD) δ 7.58-7.50 (m, 2H), 7.16 (d, J=7.4 Hz, 1H), 7.11-7.04 (m, 1H), 6.38 (d, J=7.3 Hz, 1H), 4.87 (d, J=10.9 Hz, 1H), 4.62 (s, 1H), 4.11 (d, J=2.5 Hz, 1H), 4.04 (m, 1H), 3.72 (m, 1H), 3.47-3.35 (m, 5H), 3.16-3.03 (m, 2H), 2.70 (d, J=6.1 Hz, 2H), 2.58-2.50 (m, 2H), 2.16-1.95 (m, 4H), 1.90-1.85 (m, 2H), 1.73-1.65 (m, 4H), 1.64-1.56 (m, 4H).

Compound 92-A-E2: LC/MS ESI 512.1 (M+H)+, 1H NMR (500 MHz, MeOD) δ 7.50-7.39 (m, 2H), 7.16 (d, J=7.3 Hz, 1H), 7.09 (td, J=8.4, 2.7 Hz, 1H), 6.38 (d, J=7.3 Hz, 1H), 5.08 (s, 1H), 4.76 (d, J=11.0 Hz, 1H), 4.14 (d, J=3.5 Hz, 1H), 4.07 (d, J=12.2 Hz, 1H), 3.44 (m, 3H), 3.38 (d, J=5.5 Hz, 3H), 2.99-2.92 (m, 1H), 2.71 (t, J=6.2 Hz, 2H), 2.55 (t, J=7.5 Hz, 2H), 2.10-2.03 (m, 2H), 1.95-1.81 (m, 5H), 1.73-1.67 (m, 4H), 1.60 (m, 4H).

Example 23: Preparation of 2-(5-fluoro-2-(tetrahydrofuran-2-yl)phenyl)-2-((R)-3-(4-(5,6,7,8-tetrahydro-1,8-naphthyridin-2-yl)butoxy)pyrrolidin-1-yl) acetic Acid (Compounds 93-A-E1, 93-A-E2, 93-B-E1 and 93-B-E2)

Step 1: methyl 2-(2-bromo-5-fluorophenyl)acetate

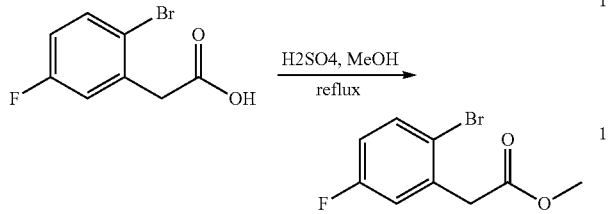

To a solution of 2-(2-bromo-5-fluorophenyl) acetic acid (10 g, 43 mmol) in 60 mL of MeOH was added 0.5 mL H$_2$SO$_4$ and the mixture was heated under reflux for 4 hours. The solvent was removed under reduced pressure to give methyl 2-(2-bromo-5-fluorophenyl)acetate as an oil (10 g, yield: 94.3%) that was used without any further purification. (ESI 246.1 (M+H)$^+$)

Step 2: methyl 2-(5-fluoro-2-(furan-2-yl)phenyl)acetate

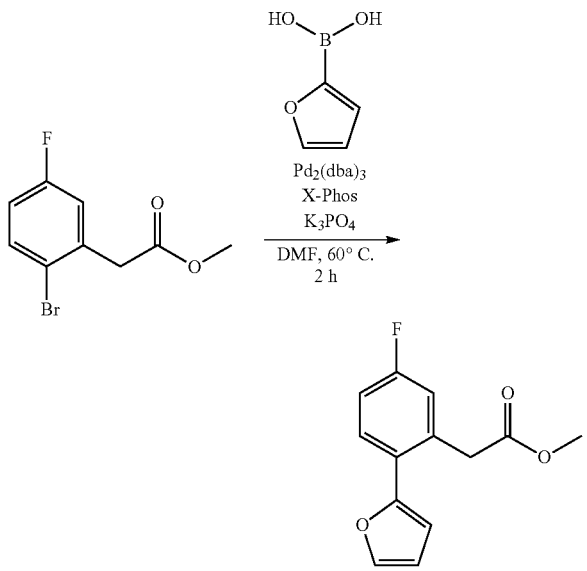

To a solution of methyl 2-(2-bromo-5-fluorophenyl)acetate (5 g, 20.2 mmol) in 100 mL of DMF was added furan-2-ylboronic acid (2.72 g, 24 mmol), tris(dibenzylideneacetone) dipalladium (0) (915 mg, 1 mmol), X-Phos (476 mg, 1 mmol), and potassium phosphate (8.5 g, 40 mmol). The mixture was stirred at 60° C. for 8 hours under N$_2$. The reaction was diluted with 200 mL ethyl acetate and 200 mL water, and the organic layer was separated. The aqueous layer was extracted with ethyl acetate three times (200 mL×3), and the combined organic layer was washed with brine and dried over anhydrous Na2SO4. After filtration and concentration, the residue was chromatographed on silica (Combiflash) using 0-20% ethyl acetate/petroleum ether as eluent, to give methyl 2-(5-fluoro-2-(furan-2-yl)phenyl)acetate (3.9 g, Yield 82.7%); ESI 237.2 (M+H)$^+$ Step 3: methyl 2-(5-fluoro-2-(tetrahydrofuran-2-yl)phenyl)acetate

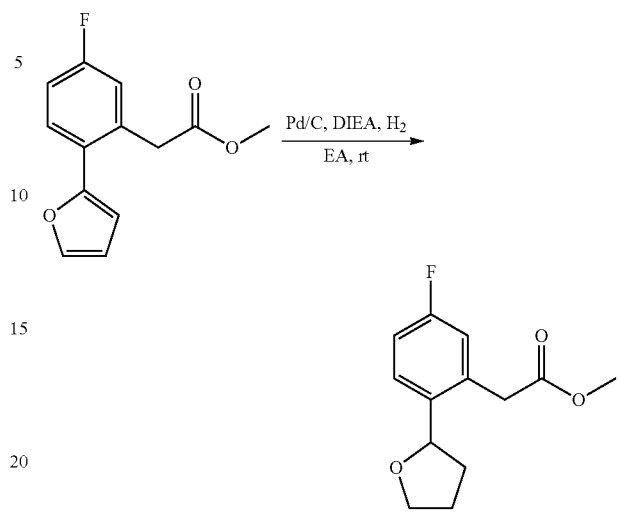

To a solution of methyl 2-(5-fluoro-2-(furan-2-yl)phenyl) acetate (2.34 g, 10 mmol) in 30 mL EtOAC was added Pd/C (1 g) and DIEA (2.58 g, 20 mmol). The mixture was stirred for 5 hours at 35° C. under H$_2$ atmosphere (balloon). After the reaction was over, the catalyst was removed by filtration, and the filtrate was concentrated under reduced pressure. The residue was chromatographed on silica (Combiflash) using 5-20% ethyl acetate/petroleum ether as eluent to give methyl 2-(5-fluoro-2-(tetrahydrofuran-2-yl)phenyl)acetate (1.56 g, 66.7%) as an oil.

The racemic compound was separated by SFC (SFC (AY-H (250*4.6 mm Sum) Mobile Phase:Hexane (0.1% DEA): EtOH (0.1% DEA)=95:5) to give stereoisomer A (950 mg) and stereoisomer B (920 mg) as oils; ESI 239.1 (M+H)$^+$ Step 4: Methyl 2-bromo-2-(5-fluoro-2-(tetrahydrofuran-2-yl)phenyl) acetate stereoisomer A

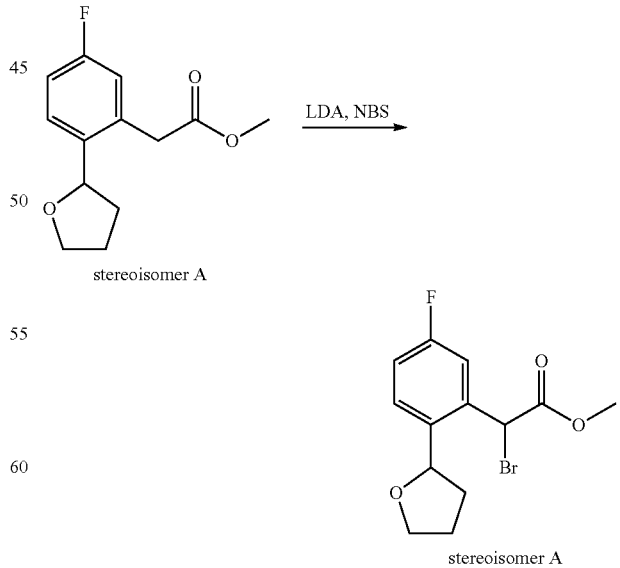

To a solution of methyl 2-(5-fluoro-2-(tetrahydrofuran-2-yl)phenyl)acetate stereoisomer A (250 mg, 1.05 mmol) in 10 mL dry THF under $N_2$ at −78° C. was added LDA (1.25 mL, 2.5 mmol, 2 M in THF). The reaction was stirred for 0.5 h and TMSCl (324 mg, 3 mmol) was added. After stirring for 15 minutes, NBS (534 mg, 3 mmol) in 10 mL THF was added and the mixture was stirred for 0.5 h at −78° C. The mixture was diluted with water and extracted with ethyl acetate (30 mL×3). The combined organic layer was washed with brine and dried over anhydrous Na2SO4. After filtration and concentration, the residue was chromatographed on silica (Combiflash) using 5-20% ethyl acetate/petroleum ether as eluent to give methyl 2-bromo-2-(5-fluoro-2-(tetrahydrofuran-2-yl)phenyl)acetate stereoisomer A (240 mg, 71%) as an oil; ESI 317.2 $(M+H)^+$ Step 5: Methyl 2-(5-fluoro-2-(tetrahydrofuran-2-yl)phenyl)-2-((R)-3-(4-(5,6,7,8-tetrahydro-1,8-naphthyridin-2-yl)butoxy)pyrrolidin-1-yl)acetate stereoisomer A

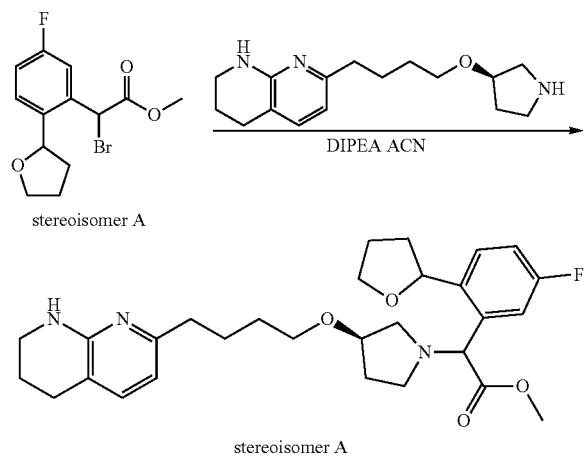

To a solution of methyl 2-bromo-2-(5-fluoro-2-(tetrahydrofuran-2-yl)phenyl)acetate stereoisomer A (240 mg, 0.76 mmol) in 10 mL ACN was added (R)-7-(4-(pyrrolidin-3-yloxy)butyl)-1,2,3,4-tetrahydro-1,8-naphthyridine (213 mg, 0.76 mmol) and DIPEA (295 mg, 2.28 mmol). The reaction was stirred for 4 hours, diluted with water (30 mL) water and extracted with ethyl acetate (50 mL×3). The combined organic layer was washed with brine, dried over anhydrous $Na_2SO_4$, filtered and concentrated under reduced pressure. The residue was chromatographed on silica (Combiflash) using 20-80% ethyl acetate/petroleum ether as eluent to give methyl 2-(5-fluoro-2-((S)-tetrahydrofuran-2-yl)phenyl)-2-((R)-3-(4-(5,6,7,8-tetrahydro-1,8-naphthyridin-2-yl)butoxy)pyrrolidin-1-yl)acetate stereoisomer A (300 mg, 77%) as a solid; ESI 512 $(M+H)^+$ Step 6: 2-(5-fluoro-2-((S)-tetrahydrofuran-2-yl)phenyl)-2-((R)-3-(4-(5,6,7,8-tetrahydro-1,8-naphthyridin-2-yl)butoxy)pyrrolidin-1-yl)acetic acid stereoisomer B (Compounds 93-A-E1 and 93-A-E2)

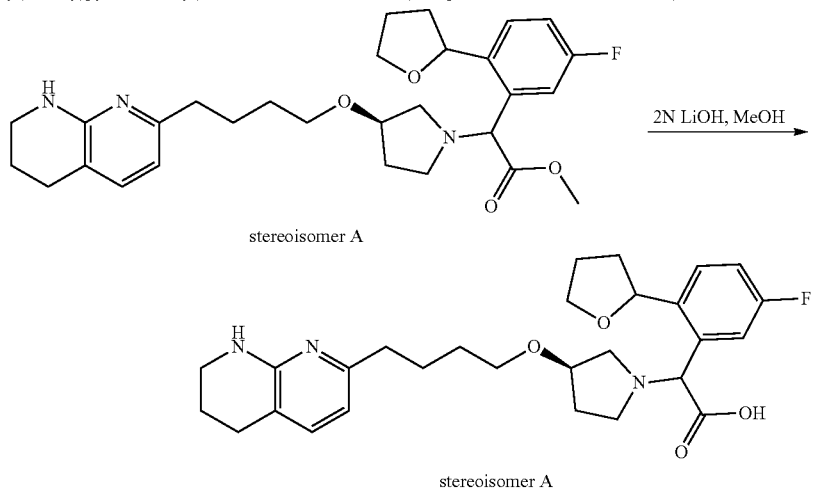

To a solution of methyl 2-(5-fluoro-2-(tetrahydrofuran-2-yl)phenyl)-2-((R)-3-(4-(5,6,7,8-tetrahydro-1,8-naphthyridin-2-yl)butoxy)pyrrolidin-1-yl)acetate stereoisomer A (330 mg, 0.59 mmol) in 10 mL methanol was added LiOH (40 mg, 1.6 mmol) and water (10 mL). The reaction was stirred for 16 hours at 25° C. To the mixture was added 1 N HCl to adjust the pH to 5-6. The mixture was concentrated under reduced pressure and the residue was purified with semi-preparative HPLC to give compound 93-A-E1 (56 mg, 18%) as a solid, and compound 93-A-E2 (45 mg, 15%) as a solid.

Compound 93-A-E1 ESI 498.2 $(M+H)^+$, $^1H$ NMR (500 MHz, MeOD) δ 7.58 (dd, J=8.8, 5.9 Hz, 1H), 7.45 (dd, J=10.0, 2.7 Hz, 1H), 7.18 (d, J=7.4 Hz, 1H), 7.15 (dd, J=8.4, 5.8 Hz, 1H), 6.41 (d, J=7.3 Hz, 1H), 5.22 (t, J=7.0 Hz, 1H), 4.96 (s, 1H), 4.19 (s, 1H), 4.07 (dd, J=14.4, 7.3 Hz, 1H), 3.88 (dt, J=14.1, 7.0 Hz, 1H), 3.60-3.43 (m, 3H), 3.43-3.37 (m, 2H), 3.26 (dd, J=33.4, 10.4 Hz, 2H), 3.04 (t, J=7.6 Hz, 1H), 2.72 (t, J=6.2 Hz, 2H), 2.58 (t, J=7.6 Hz, 2H), 2.44 (dt, J=12.0, 5.9 Hz, 1H), 2.16-1.93 (m, 5H), 1.92-1.86 (m, 2H), 1.75 (m, 2H), 1.68-1.56 (m, 2H)

Compound 93-A-E2 ESI 498.2 $(M+H)^+$, $^1H$ NMR (500 MHz, MeOD) δ 7.49 (dd, J=8.7, 5.9 Hz, 1H), 7.46 (d, J=10.3 Hz, 1H), 7.21 (d, J=7.2 Hz, 1H), 7.11 (t, J=6.9 Hz, 1H), 6.42 (d, J=7.3 Hz, 1H), 5.18 (s, 1H), 4.87-4.81 (m, 1H), 4.16 (s, 1H), 4.16-4.09 (m, 1H), 3.88 (t, J=7.1 Hz, 1H), 3.50 (t, J=6.1 Hz, 3H), 3.42-3.36 (m, 2H), 3.10 (d, J=7.6 Hz, 2H), 2.73 (t, J=6.2 Hz, 2H), 2.67-2.54 (m, 2H), 2.41 (d, J=10.7 Hz, 1H), 2.16-1.96 (m, 5H), 1.93-1.85 (m, 2H), 1.75 (m, 2H), 1.64 (m, 2H).

Step 7: Methyl 2-bromo-2-(5-fluoro-2-(tetrahydrofuran-2-yl)phenyl)acetate stereoisomer B

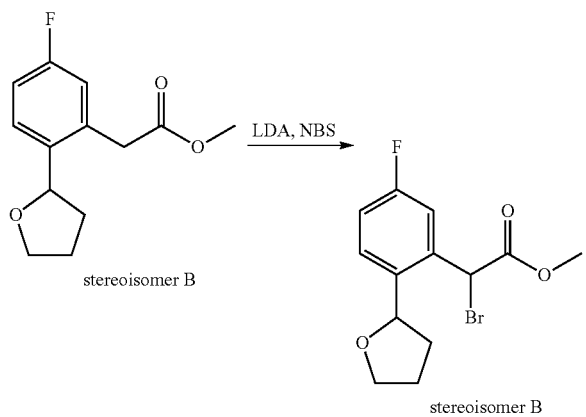

To a solution of methyl 2-(5-fluoro-2-(tetrahydrofuran-2-yl)phenyl)acetate stereoisomer B (250 mg, 1.05 mmol) in 10 mL dry THE under $N_2$ at −78° C. was added LDA (1.25 mL, 2.5 mmol, 2 M in THF). The reaction was stirred for 0.5 h and TMSCl (324 mg, 3 mmol) was added. After stirring for 15 minutes, NBS (534 mg, 3 mmol) in 10 mL, THE was added and the mixture was stirred for 0.5 h at −78° C. The mixture was diluted with water and extracted with ethyl acetate (30 mL×3). The combined organic layer was washed with brine and dried over anhydrous $Na_2SO_4$. After filtration and concentration, the residue was chromatographed on silica (Combiflash) using 5-20% ethyl acetate/petroleum ether as eluent to give methyl 2-bromo-2-(5-fluoro-2-(tetrahydrofuran-2-yl)phenyl)acetate stereoisomer B (235 mg, 70.8%) as an oil; ESI 317.2) (M+H)+

Step 8: methyl 2-(5-fluoro-2-(tetrahydrofuran-2-yl)phenyl)-2-((R)-3-(4-(5,6,7,8-tetrahydro-1,8-naphthyridin-2-yl)butoxy)pyrrolidin-1-yl)acetate stereoisomer B

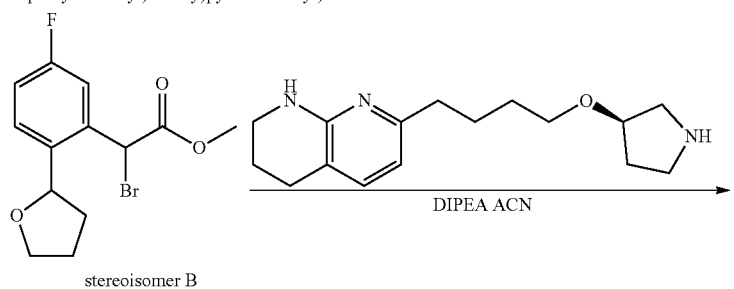

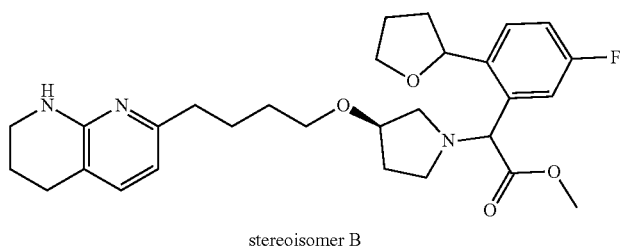

stereoisomer B

To a solution of methyl 2-bromo-2-(5-fluoro-2-(tetrahydrofuran-2-yl)phenyl)acetate stereoisomer B (100 mg, 0.31 mmol) in 5 mL ACN was added (R)-7-(4-(pyrrolidin-3-yloxy)butyl)-1,2,3,4-tetrahydro-1,8-naphthyridine (87 mg, 0.31 mmol) and DIPEA (120 mg, 0.93 mmol). The reaction was stirred for 4 hours, diluted with water (10 mL) water and extracted with ethyl acetate (20 mL×3). The combined organic layer was washed with brine, dried over anhydrous $Na_2SO_4$, filtered and concentrated under reduced pressure. The residue was chromatographed on silica (Combiflash) using 20-80% ethyl acetate/petroleum ether as eluent to give methyl 2-(5-fluoro-2-((S)-tetrahydrofuran-2-yl)phenyl)-2-((R)-3-(4-(5,6,7,8-tetrahydro-1,8-naphthyridin-2-yl)butoxy)pyrrolidin-1-yl)acetate stereoisomer B (120 mg, 78%) as a solid; ESI 512.2 (M+H)+

Step 9: 2-(5-fluoro-2-(tetrahydrofuran-2-yl)phenyl)-2-((R)-3-(4-(5,6,7,8-tetrahydro-1,8-naphthyridin-2-yl)butoxy)pyrrolidin-1-yl)acetic acid stereoisomer B (Compounds 93-B-E1 and 93-B-E2)

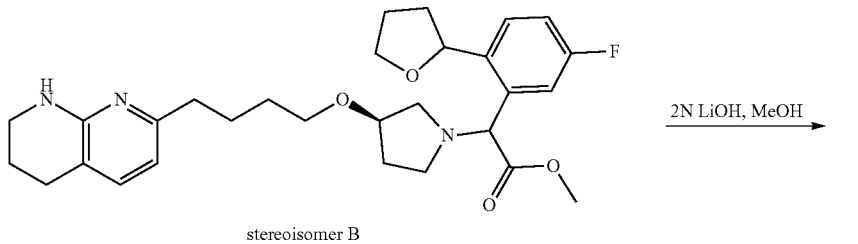

stereoisomer B

2N LiOH, MeOH →

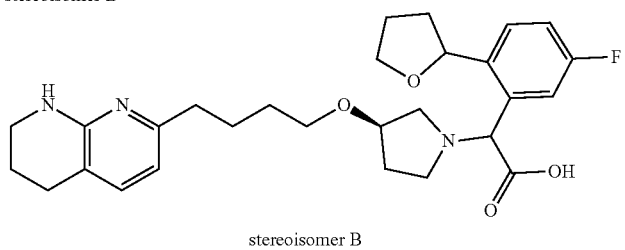

stereoisomer B

To a solution of methyl 2-(5-fluoro-2-(tetrahydrofuran-2-yl)phenyl)-2-((R)-3-(4-(5,6,7,8-tetrahydro-1,8-naphthyridin-2-yl)butoxy)pyrrolidin-1-yl)acetate stereoisomer B (300 mg, 0.59 mmol) in 10 mL methanol was added LiOH (40 mg, 1.6 mmol) and water (10 mL). The reaction was stirred for 16 hours at 25° C. To the mixture was added 1 N HCl to adjust the pH to 5-6. The mixture was concentrated under reduced pressure, and the residue was purified with semi-preparative HPLC to give compound 93-B-E1 (27 mg, 9%) as a solid, and compound 93-B-E2 (30 mg, 10%) as a solid.

Compound 93-B-E1 ESI 498.2 (M+H)$^+$, $^1$H NMR (500 MHz, MeOD) δ 7.58 (dd, J=8.8, 6.0 Hz, 1H), 7.48 (d, J=10.1 Hz, 1H), 7.17 (dd, J=20.5, 7.7 Hz, 2H), 6.41 (d, J=7.3 Hz, 1H), 5.29 (t, J=7.1 Hz, 1H), 4.9 (s, 1H), 4.17 (s, 1H), 4.08 (dd, J=14.6, 7.2 Hz, 1H), 3.89 (dd, J=13.8, 7.8 Hz, 1H), 3.60-3.38 (m, 5H), 3.16 (d, J=7.5 Hz, 1H), 2.72 (t, J=6.2 Hz, 2H), 2.59 (dd, J=14.4, 7.2 Hz, 2H), 2.48 (dd, J=11.9, 5.2 Hz, 1H), 2.18 (s, 2H), 2.12-1.99 (m, 2H), 2.01-1.85 (m, 4H), 1.74 (m, 2H), 1.64 (m, 2H).

Compound 93-B-E2 ESI 498.2 (M+H)$^+$, $^1$H NMR (500 MHz, MeOD) δ 7.49 (dd, J=8.7, 5.8 Hz, 1H), 7.44 (d, J=10.1 Hz, 1H), 7.19 (d, J=7.3 Hz, 1H), 7.12 (t, J=7.0 Hz, 1H), 6.41 (d, J=7.3 Hz, 1H), 5.12 (s, 1H), 4.97 (s, 1H), 4.18 (s, 1H), 4.14-4.08 (m, 1H), 3.86 (t, J=6.9 Hz, 1H), 3.48 (t, J=6.2 Hz, 3H), 3.42-3.38 (m, 3H), 3.19 (s, 1H), 3.04 (s, 1H), 2.73 (t, J=6.3 Hz, 2H), 2.58 (t, J=6.2 Hz, 2H), 2.37 (s, 1H), 2.17-1.99 (m, 5H), 1.94-1.84 (m, 2H), 1.74 (m, 2H), 1.64 (m, 2H).

Example 24: Preparation of 2-(5-fluoro-2-((S)-tetrahydro-2H-pyran-2-yl)phenyl)-2-((R)-3-((3-(5,6,7,8-tetrahydro-1,8-naphthyridin-2-yl)propoxy)methyl)pyrrolidin-1-yl)acetic Acid (Compounds 94-E1 and 94-E2)

Step 1: (R)-tert-butyl 3-(allyoxymethyl)pyrrolidine-1-carboxylate

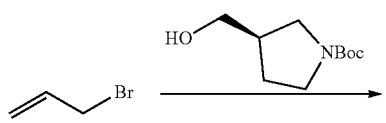

-continued

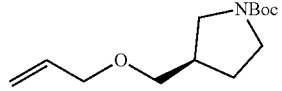

A mixture of (R)-tert-butyl 3-(hydroxymethyl)pyrrolidine-1-carboxylate (5 g, 24.8 mmol) and NaH (1.09 g, 27.3 mmol) in DMF (20 mL) was stirred at 0° C. for 1 hour. A solution of 3-bromoprop-1-ene (4.5 g, 37.2 mmol) in DMF (10 mL) was added dropwise to the above mixture at 0° C., and the reaction mixture was stirred at 50° C. overnight. Solvent was removed in vacuo, and the residue was purified by silica gel column (pet ether:EtOAc 1:1) to give the desired product as a colorless oil (5.1 g). Yield 85% (ESI 186 (M+H−56)$^+$).

Step 2: (R)-tert-butyl 3-((3-(1,8-naphthyridin-2-yl)propoxy)methyl)pyrrolidine-1-carboxylate

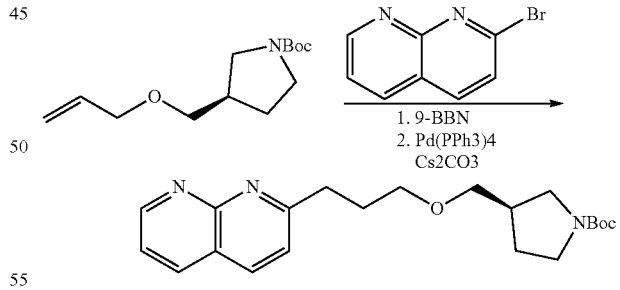

To a solution of (R)-tert-butyl 3-(allyloxymethyl)pyrrolidine-1-carboxylate (600 mg, 2.49 mmol) in THF (dry, 5 mL) under Ar, was added 9-BBN (0.5M solution in THF, 9.95 mL, 4.97 mmol). The reaction was stirred at 50° C. for 2 hours, then cooled to rt. This solution was added to a mixture of 2-bromo-1,8-naphthyridine (520 mg, 2.49 mmol), cesium carbonate (2.44 g, 7.47 mmol) and Pd(PPh3)4 (144 mg, 0.125 mmol) in 1,4-Dioxane (10 mL). The reaction was stirred at 90° C. for 1.5 hours. Solvent was removed in vacuo, and the residue was purified by silica gel column (DCM:MeOH 30:1) to give the desired product (R)-tertbutyl 3-((3-(1,8-naphthyridin-2-yl)propoxy)methyl)pyrrolidine-1-carboxylate as a yellow oil (200 mg). Yield 22% (ESI 372 (M+H)+).

Step 3: (R)-tert-butyl 3-((3-(5,6,7,8-tetrahydro-1,8-naphthyridin-2-yl)propoxy)methyl)pyrrolidine-1-carboxylate

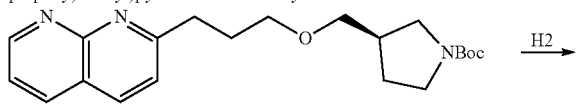

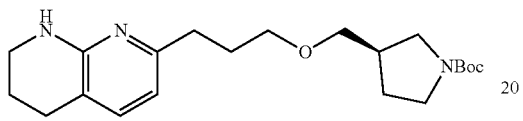

A mixture of (R)-tert-butyl 3-((3-(1,8-naphthyridin-2-yl)propoxy)methyl)pyrrolidine-1-carboxylate (200 mg, 0.54 mmol) and Pd/C (40 mg, 20 Wt %) in ethyl acetate (10 mL) was stirred under H₂ balloon at 40° C. for 16 hours. The solid was removed by filtration, the filtrate was concentrated in vacuo to give the desired product (R)-tert-butyl 3-((3-(5,6,7,8-tetrahydro-1,8-naphthyridin-2-yl)propoxy)methyl)pyrrolidine-1-carboxylate as a yellow oil (200 mg). Yield 99% (ESI 376 (M+H)+).

Step 4: (R)-7-(3-(pyrrolidin-3-ylmethoxy)propyl)-1,2,3,4-tetrahydro-1,8-naphthyridine

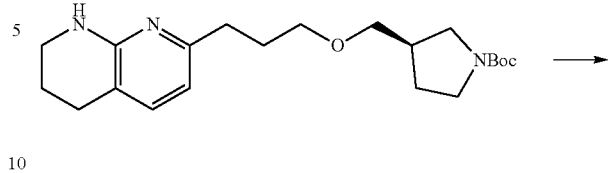

(R)-tert-butyl 3-((3-(5,6,7,8-tetrahydro-1,8-naphthyridin-2-yl)propoxy)methyl)pyrrolidine-1-carboxylate (200 mg, 0.53 mmol) was treated with HCl in 1,4-dioxane(4M, 10 mL) at rt for 2 hours. Solvent was removed in vacuo to give the desired product (R)-7-(3-(pyrrolidin-3-ylmethoxy)propyl)-1,2,3,4-tetrahydro-1,8-naphthyridine as a HCl salt (150 mg). Yield 81% (ESI 276 (M+H)+).

Step 5: methyl 2-(5-fluoro-2-((S)-tetrahydro-2H-pyran-2-yl)phenyl)-2-((R)-3-((3-(5,6,7,8-tetrahydro-1,8-naphthyridin-2-yl)propoxy)methyl)pyrrolidin-1-yl)acetate

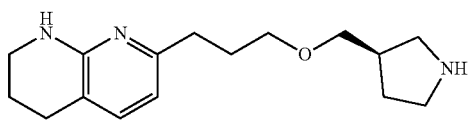 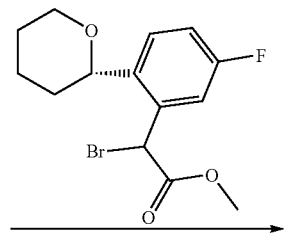

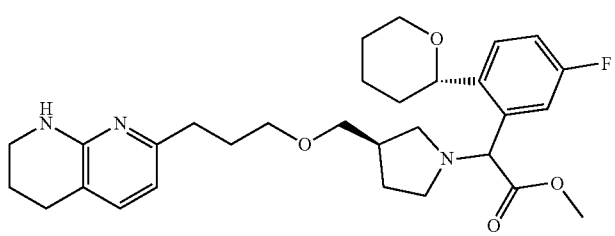

A mixture of (R)-7-(3-(pyrrolidin-3-ylmethoxy)propyl)-1,2,3,4-tetrahydro-1,8-naphthyridine (150 mg, 0.43 mmol), methyl 2-bromo-2-(5-fluoro-2-((S)-tetrahydro-2H-pyran-2-yl)phenyl)acetate (142 mg, 0.43 mmol) and DIPEA (166 mg, 1.29 mmol) in acetonitrile (10 mL) was stirred at rt for 3 hours. Solvent was removed in vacuo, and the residue was purified by silica gel column (DCM: MeOH 10:1) to give the desired product methyl 2-(5-fluoro-2-((S)-tetrahydro-2H-pyran-2-yl)phenyl)-2-((R)-3-((3-(5,6,7,8-tetrahydro-1,8-naphthyridin-2-yl)propoxy)methyl)pyrrolidin-1-yl)acetate as a yellow oil (140 mg). Yield 62%. (ESI 526 (M+H)+).

Step 6: 2-(5-fluoro-2-((S)-tetrahydro-2H-pyran-2-yl)phenyl)-2-((R)-3-((3-(5,6,7,8-tetrahydro-1,8-naphthyridin-2-yl)propoxy)methyl)pyrrolidin-1-yl) acetic acid (compounds 94-E1 and 94-E2)

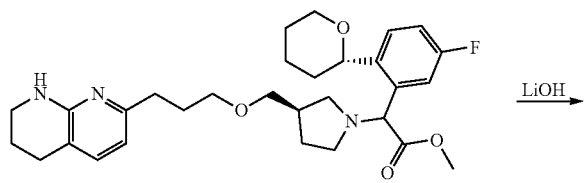

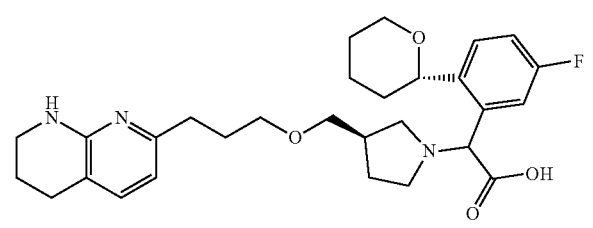

Methyl 2-(5-fluoro-2-((S)-tetrahydro-2H-pyran-2-yl)phenyl)-2-((R)-3-((3-(5,6,7,8-tetrahydro-1,8-naphthyridin-2-yl)propoxy)methyl)pyrrolidin-1-yl)acetate (140 mg, 0.27 mmol) was treated with LiOH—H$_2$O (126 mg, 3.0 mmol) in MeOH (4 mL) and H$_2$O (1 mL) at room temperature for 2 hours. Solvent was removed in vacuo, and the residue was purified by Prep-HPLC A (30-60% MeCN) to give diastereomeric products compound 94-E1 (17 mg) and compound 94-E2 (49 mg) as white solids.

Compound 94-E1 LC/MS ESI 512 (M+H)+ $^1$H NMR (500 MHz, MeOD) δ 7.65-7.54 (m, 2H), 7.36-7.21 (m, 2H), 6.62 (d, J=7.5 Hz, 1H), 5.06 (s, 1H), 4.77-4.75 (m, 1H), 4.11-4.08 (m, 1H), 3.81-3.33 (m, 8H), 3.25-3.14 (m, 2H), 2.95-2.66 (m, 5H), 2.37-1.58 (m, 13H).

Compound 94-E2 LC/MS ESI 512 (M+H)+ $^1$H NMR (500 MHz, MeOD) δ 7.48-7.39 (m, 2H), 7.15-7.08 (m, 2H), 6.35 (d, J=7.0 Hz, 1H), 5.25 (s, 1H), 4.73-4.71 (m, 1H), 4.14-4.12 (m, 1H), 3.81-3.33 (m, 8H), 3.25-3.14 (m, 2H), 2.73-2.56 (m, 5H), 2.18-1.52 (m, 13H).

Example 25: Preparation of 2-(5-fluoro-2-((S)-tetrahydro-2H-pyran-2-yl)phenyl)-2-((S)-3-(2-(2-(5,6,7,8-tetrahydro-1,8-naphthyridin-2-yl)ethoxy)ethyl)pyrrolidin-1-yl)acetic Acid (Compounds 95-E1 and 95-E2)

Step 1: (S)-tert-butyl 3-(2-(3-methoxy-3-oxoprop-1-enyloxy)ethyl)pyrrolidine-1-carboxylate

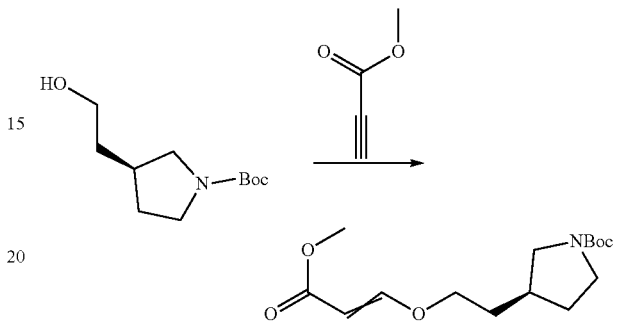

To a solution of (S)-tert-butyl 3-(2-hydroxyethyl)pyrrolidine-1-carboxylate (3.3 g, 15.5 mmol) and 4-methylmorpholine (1.85 g, 18.5 mmol) in DCM (40 mL) at room temperature, was added methyl propiolate (1.55 g, 18.5 mmol). The mixture was stirred at room temperature for 15 hours, then concentrated in vacuo. The residue was purified by silica gel column (pet ether: EtOAc 4:1) to give (S)-tert-butyl 3-(2-(3-methoxy-3-oxoprop-1-enyloxy)ethyl)pyrrolidine-1-carboxylate as a colorless oil (4.0 g). Yield 87% (ESI 200 (M+H-Boc)+).

Step 2: (S)-tert-butyl 3-(2-(3-methoxy-3-oxopropoxy)ethyl)pyrrolidine-1-carboxylate

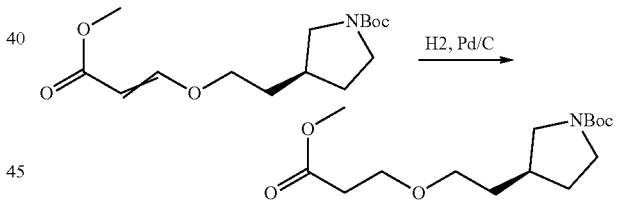

A mixture of (S)-tert-butyl 3-(2-(3-methoxy-3-oxoprop-1-enyloxy)ethyl)pyrrolidine-1-carboxylate (4.0 g, 16.0 mmol) and Pd/C (10%, 200 mg) in EtOAc (25 mL) was stirred under H$_2$ at rt overnight. The solid was removed by filtration, the filtrate was concentrated in vacuo to give the desired product (S)-tert-butyl 3-(2-(3-methoxy-3-oxopropoxy)ethyl)pyrrolidine-1-carboxylate as a yellow oil (4.0 g). Yield 96% (ESI 202 (M+H-Boc)+).

Step 3: (S)-tert butyl 3-(2-(4-(dimethyloxyphosphoryl)-3-oxobutoxy)ethyl)pyrrolidine-1-carboxylate

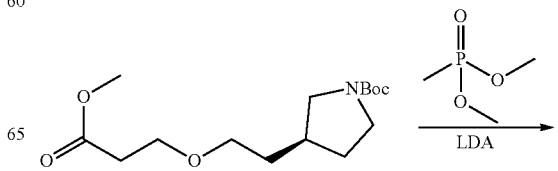

-continued

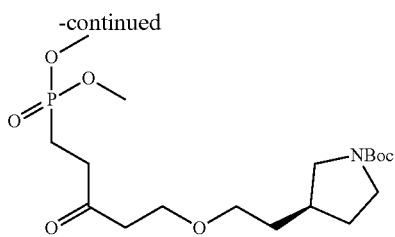

To a solution of (S)-tert-butyl 3-(2-(3-methoxy-3-oxo-propoxy)ethyl)pyrrolidine-1-carboxylate (1.5 g, 5.0 mmol) and dimethyl methylphosphonate (0.682 g, 5.5 mmol) in dry THF (10 mL) at 0° C. under Ar, LDA (2M in THF, 5.25 mL, 10.5 mmol) was added dropwise. After stirring at 0° C. for 10 mins, the reaction was quenched with MeOH (5 mL). The mixture was concentrated under vacuum, and the residual was purified by silica gel column (pet ether: EtOAc 2:1) to give the desired product (S)-tert-butyl 3-(2-(4-(dimethoxy-phosphoryl)-3-oxobutoxy)ethyl)pyrrolidine-1-carboxylate as a yellow oil (1.1 g). Yield 57% (ESI 394 (M+H)

Step 4: (S)-tert butyl 3-(2-(2-(1,8-naphthyridin-2-yl)ethoxy)ethyl)pyrrolidine-1-carboxylate

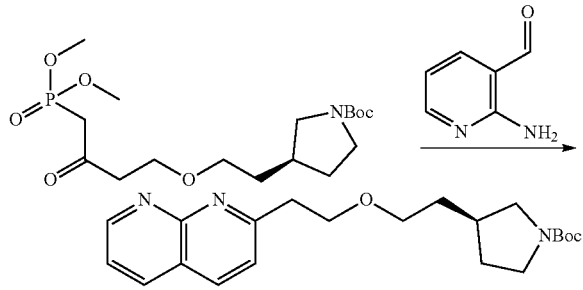

A mixture of 2-aminonicotinaldehyde (128 mg, 1.1 mmol), (S)-tert-butyl 3-(2-(4-(dimethoxyphosphoryl)-3-oxobutoxy)ethyl)pyrrolidine-1-carboxylate (400 mg, 1.1 mmol) and NaOH (81 mg, 2.2 mmol) in MeOH (6 mL) and $H_2O$ (2 mL) was stirred at rt overnight. Solvent was removed in vacuo, and the residue was purified by prep-HPLC A (40-70% MeCN) to give the desired product (S)-tert-butyl 3-(2-(2-(1,8-naphthyridin-2-yl)ethoxy)ethyl)pyrrolidine-1-carboxylate as a colorless oil (60 mg). Yield 16% (ESI 372 (M+H)+).

Step 5: (S)-7-(2-(2-(pyrrolidin-3-yl)ethoxy)ethyl)-1,2,3,4-tetrahydro-1,8-naphthyridine hydrochloride

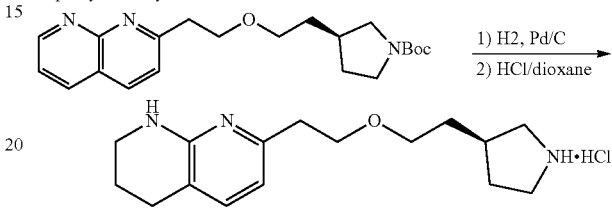

A mixture of (S)-tert-butyl 3-(2-(2-(1,8-naphthyridin-2-yl)ethoxy)ethyl)pyrrolidine-1-carboxylate (400 mg, 1.08 mmol) and Pd/C (80 mg, 10%) in EtOAc (20 mL) was stirred under H2 at room temperate overnight. The mixture was filtered and the filtrate was concentrated in vacuo. The residue was treated with a solution of HCl/dioxane (4.0 M, 4 mL) at room temperate for 2 hours, then the solvent was removed in vacuo to give the desired product (S)-7-(2-(2-(pyrrolidin-3-yl)ethoxy)ethyl)-1,2,3,4-tetrahydro-1,8-naphthyridine hydrochloride as a white solid (325 mg). Yield 96% (ESI 276.2 (M+H)+).

Step 6: Methyl 2-(5-fluoro-2-((S)-tetrahydro-2H-pyran-2-yl)phenyl)-2-((S)-3-(2-(2-(5,6,7,8-tetrahydro-1,8-naphthyridin-2-yl)ethoxy)ethyl)pyrrolidin-1-yl)acetate

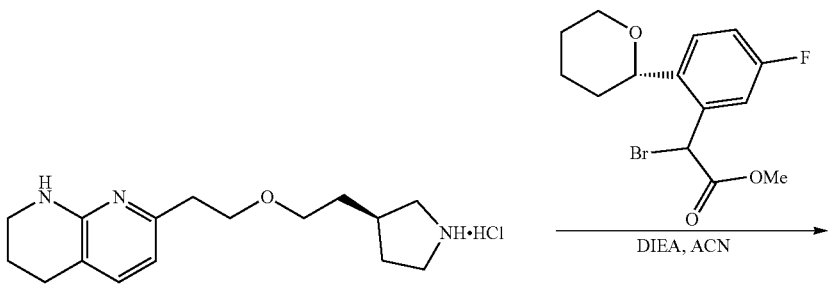

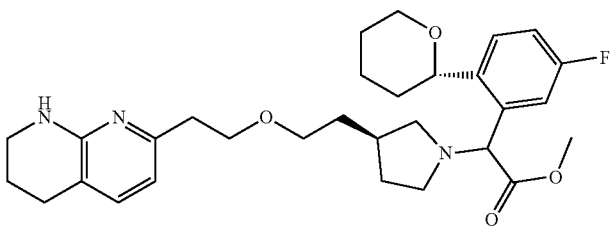

A mixture of (S)-7-(2-(2-(pyrrolidin-3-yl)ethoxy)ethyl)-1,2,3,4-tetrahydro-1,8-naphthyridine hydrochloride (226 mg, 0.65 mmol), methyl 2-bromo-2-(5-fluoro-2-((S)-tetrahydro-2H-pyran-2-yl)phenyl)acetate (240 mg, 0.65 mmol) and DIEA (252 mg, 1.95 mmol) in acetonitrile (10 mL) was stirred at RT overnight. Solvent was removed in vacuo, and the residue was purified by silica gel column (DCM:MeOH 20:1) to give the desired product methyl 2-(5-fluoro-2-((S)-tetrahydro-2H-pyran-2-yl)phenyl)-2-((S)-3-(2-(2-(5,6,7,8-tetrahydro-1,8-naphthyridin-2-yl)ethoxy)ethyl)pyrrolidin-1-yl)acetate as a yellow oil (310 mg). Yield 84% (ESI 526 (M+H)+).

Step 7: 2-(5-fluoro-2-((S)-tetrahydro-2H-pyran-2-yl)phenyl)-2-((S)-3-(2-(2-(5,6,7,8-tetrahydro-1,8-naphthyridin-2-yl)ethoxy)ethyl)pyrrolidin-1-yl)acetic acid (compounds 95-E1 and 95-E2)

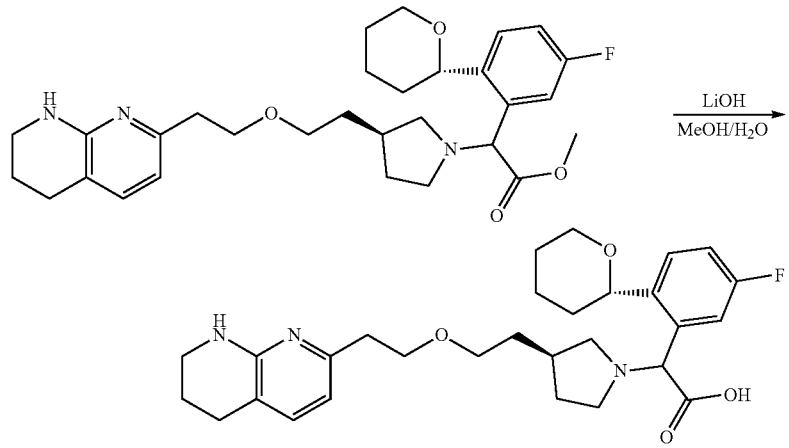

Methyl 2-(5-fluoro-2-((S)-tetrahydro-2H-pyran-2-yl)phenyl)-2-((S)-3-(2-(2-(5,6,7,8-tetrahydro-1,8-naphthyridin-2-yl)ethoxy)ethyl)pyrrolidin-1-yl)acetate (310 mg, 0.55 mmol) was treated with LiOH—H$_2$O (250 mg, 5.95 mmol) in MeOH (5 mL) and H$_2$O (1 mL) at 40° C. overnight. Solvent was removed in vacuo, and the residue was purified by Prep-HPLC A (30-60% MeCN) to give diastereomeric products compound 95-E1 (67 mg) and compound 95-E2 (37 mg) as white solids.

Compound 95-E1 LC/MS ESI 512.3 (M+H)+. 1H NMR (400 MHz, MeOD) δ 7.62-7.55 (m, 1H), 7.54-7.50 (m, 1H), 7.20-7.10 (m, 2H), 6.35 (d, J=7.3 Hz, 1H), 4.88-4.78 (m, 2H), 4.08-4.04 (m, 1H), 3.82-3.75 (m, 1H), 3.70-3.61 (m, 3H), 3.49-3.40 (m, 3H), 3.38-3.31 (m, 2H), 3.06-2.99 (m, 1H), 2.68-2.77 (m, 5H), 2.50-2.39 (m, 1H), 2.20-1.90 (m, 3H), 1.95-1.60 (m, 9H).

Compound 95-E2 LC/MS ESI 512.3 (M+H)+. 1H NMR (400 MHz, MeOD) δ 7.43-7.36 (m, 2H), 7.18-7.09 (m, 2H), 6.38-6.33 (d, J=7.3 Hz, 1H), 5.42 (s, 1H), 4.80-4.50 (m, 1H), 4.18-4.04 (m, 1H), 3.65-3.62 (m, 3H), 3.50-3.41 (m, 2H), 3.38-3.31 (m, 3H), 3.20-3.00 (m, 3H), 2.75-2.65 (m, 4H), 2.40-2.30 (m, 1H), 2.20-2.05 (m, 2H), 1.98-1.93 (m, 1H), 1.90-1.58 (m, 9H).

Example 26: Preparation of 2-(2-(5,5-dimethyltetrahydrofuran-2-yl)-5-fluorophenyl)-2-((R)-3-(4-(5,6,7,8-tetrahydro-1,8-naphthyridin-2-yl)butoxy)pyrrolidin-1-yl)acetic Acid (Compounds 96-E1 and 96-E2)

Step 1: 1-(2-bromo-4-fluorophenyl)-4-methylpent-4-en-1-ol

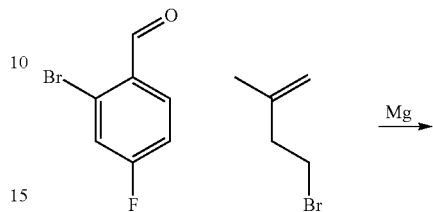

-continued

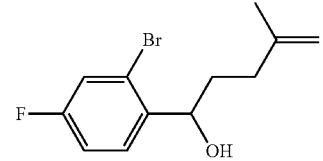

An oven dried 3-neck round bottom flask equipped with a magnetic stirring bar, cooler, nitrogen inlet and a septum was charged with magnesium (0.489 g, 20.1 mmol). The magnesium was dried using a heat gun under a nitrogen flow while stirring and then stirred under a nitrogen flow overnight. Next, dry tetrahydrofuran (12 mL) was added, and the mixture was brought to reflux using a heat gun. A small amount of 1,2-dibromoethane (0.116 mL, 1.34 mmol) was added, and the mixture was brought to reflux again. A solution of 4-bromo-2-methylbut-1-ene (1.6 mL, 13.4 mmol) in dry tetrahydrofuran (10 mL) was added dropwise at such a rate to keep an exothermic reaction going. Upon complete addition, the greyish brown reaction mixture was stirred for another 20 minutes and slowly cooled to room temperature. The Grignard reagent was drawn into a syringe and added dropwise to a solution of 2-bromo-4-fluorobenzaldehyde (2.72 g, 13.4 mmol) in dry tetrahydrofuran (15 mL) under argon atmosphere at 0° C. Upon complete addition, the mixture was allowed to come to room temperature, stirred for 30 minutes, quenched with saturated ammonium chloride and extracted twice with ethyl acetate. The combined organic layers were washed with brine, dried over sodium sulfate and concentrated in vacuo. Purification by column chromatography (silica, 1% to 15% diisopropyl ether in heptane) afforded the desired product 1-(2-bromo-4-fluorophenyl)-4-methylpent-4-en-1-ol (1.43 g). Yield 39%. $^1$H NMR (400 MHz, Chloroform-d) δ 7.58-7.51 (m, 1H), 7.30-7.23 (m, 1H), 7.11-7.02 (m, 1H), 5.09-5.01 (m, 1H), 4.76 (s, 2H), 2.29-2.10 (m, 2H), 2.03 (d, J=3.6 Hz, 1H), 1.96-1.83 (m, 1H), 1.83-1.68 (m, 4H).

Step 2: 5-(2-bromo-4-fluorophenyl)-2,2-dimethyltetrahydrofuran

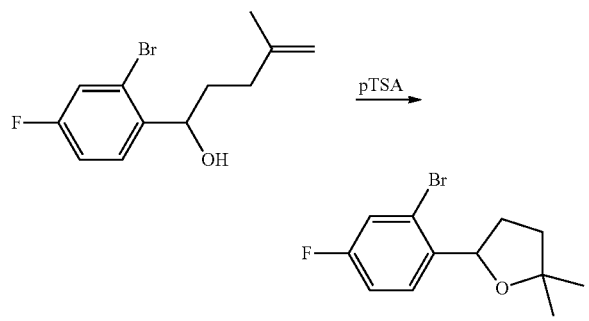

To a solution of 1-(2-bromo-4-fluorophenyl)-4-methylpent-4-en-1-ol (1.43 g, 5.24 mmol) in toluene (30 mL) was added p-toluenesulfonic acid monohydrate (0.996 g, 5.24 mmol). The mixture was stirred at 80° C. for an hour, cooled to room temperature, quenched with saturated aqueous sodium bicarbonate and extracted three times with dichloromethane. The combined organic layers were dried over sodium sulfate and concentrated in vacuo. Purification by column chromatography (silica, 0% to 8% diisopropylether in heptane) afforded the desired product 5-(2-bromo-4-fluorophenyl)-2,2-dimethyltetrahydrofuran (1.28 g). Yield 89%. $^1$H NMR (400 MHz, Chloroform-d) δ 7.60-7.52 (m, 1H), 7.29-7.21 (m, 1H), 7.07-6.98 (m, 1H), 5.19 (t, J=7.2 Hz, 1H), 2.64-2.53 (m, 1H), 1.93-1.77 (m, 2H), 1.74-1.61 (m, 1H), 1.42 (s, 3H), 1.36 (s, 3H).

Step 3: tert-butyl 2-(2-(5,5-dimethyltetrahydrofuran-2-yl)-5-fluorophenyl)acetate

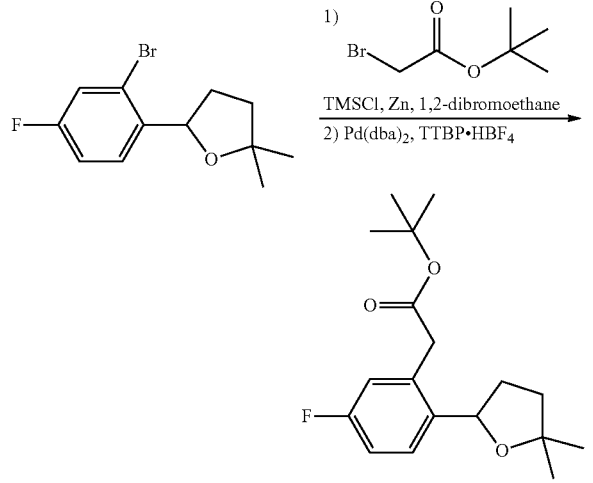

An oven dried flask was charged with zinc dust (1.202 g, 18.4 mmol) and heated with a heat gun under an argon flow. After cooling to room temperature, dry tetrahydrofuran (26 mL) was added, followed by 1,2-dibromoethane (0.04 mL, 0.46 mmol). The mixture was heated to reflux and cooled to room temperature 3 times. Then, trimethylsilyl chloride (0.059 mL, 0.46 mmol) was added which caused the mixture to reflux spontaneously and the zinc to change morphology. After stirring for 20 minutes, tert-butyl bromoacetate (1.34 mL, 9.19 mmol) was added dropwise, resulting in an exotherm. The mixture was kept at an elevated temperature (45° C.) for 30 minutes and then allowed to cool to room temperature. A separate flask was charged with 5-(2-bromo-4-fluorophenyl)-2,2-dimethyltetrahydrofuran (1.26 g, 4.59 mmol), tri-tert-butylphosphine tetrafluoroborate (0.147 g, 0.505 mmol) and bis-(dibenzylideneacetone)palladium (0.264 g, 0.459 mmol). The reaction vessel was flushed with argon, dry tetrahydrofuran (26 mL) was added and argon was bubbled through for five minutes. The zincate solution was added by syringe, and the reaction mixture was heated to reflux for 1 hour. The mixture was cooled to room temperature overnight, quenched with saturated aqueous ammonium chloride and extracted three times with heptane/ethyl acetate (1/1, v/v). The combined organic layers were dried over sodium sulfate and concentrated in vacuo. Purification by column chromatography (silica, 1% to 6% acetone in heptane) afforded the desired product tert-butyl 2-(2-(5,5-dimethyltetrahydrofuran-2-yl)-5-fluorophenyl)acetate (1.31 g). Yield 92%. $^1$H NMR (400 MHz, Chloroform-d) δ 7.51 (dd, J=8.6, 6.0 Hz, 1H), 7.00-6.88 (m, 2H), 5.10 (dd, J=8.5, 6.2 Hz, 1H), 3.57 (q, J=15.5 Hz, 2H), 2.38-2.28 (m, 1H), 1.92-1.71 (m, 3H), 1.43 (s, 9H), 1.40 (s, 3H), 1.34 (s, 3H).

Step 4: tert-butyl 2-bromo-2-(2-(5,5-dimethyltetrahydrofuran-2-yl)-5-fluorophenyl)acetate

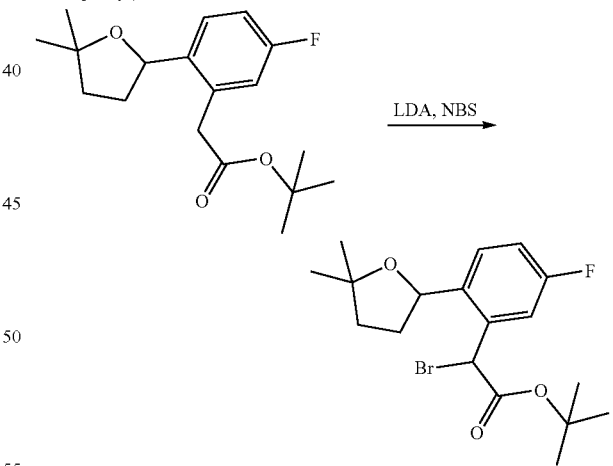

To a solution of tert-butyl 2-(2-(5,5-dimethyltetrahydrofuran-2-yl)-5-fluorophenyl)acetate (200 mg, 0.65 mmol) in THF (4 mL) at −78° C., was added lithium diisopropylamide solution 1.0 M in THF/hexanes (1.3 mL, 1.3 mmol) dropwise. The reaction was stirred at −78° C. for 30 min, then chlorotrimethylsilane (141 mg, 1.3 mmol) was added and the reaction was stirred at −78° C. for another 30 min. Then a solution of NBS (231 mg, 1.3 mmol) in THF (2 mL) was added and the reaction was stirred at −78° C. for 1 hour. The reaction was quenched with MeOH (2 mL), solvent was removed in vacuo, and the residue was purified by silica gel column (pet ether: EtOAc 10:1) to give the desired product tert-butyl 2-bromo-2-(2-(5,5-dimethyltetrahydrofuran-2-yl)-5-fluorophenyl)acetate as a colorless oil (180 mg). Yield: 72%. (ESI 387 (M+H)+).

25° C. for 2 hours. Solvent was removed in vacuo, and the residue was purified by Prep-HPLC A (33-65% MeCN) to give 96 as a white solid (220 mg, 44% yield). The racemic product was separated by Prep chiral SFC E to give diaste- Step 5: tert-butyl 2-(2-(5,5-dimethyltetrahydrofuran-2-yl)-5-fluorophenyl)-2-((R)-3-(4-(5,6,7,8-tetrahydro-1,8-naphthyridin-2-yl)butoxy)pyrrolidin-1-yl)acetate

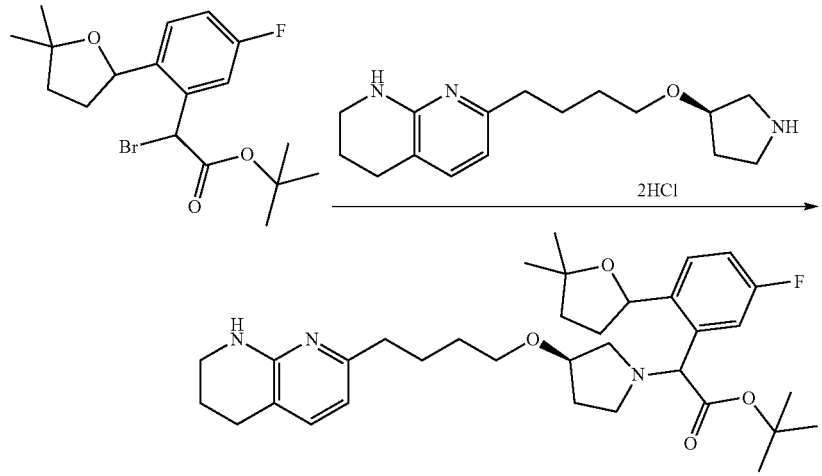

A mixture of tert-butyl 2-bromo-2-(2-(5,5-dimethyltetrahydrofuran-2-yl)-5-fluorophenyl)acetate (650 mg, 1.68 mmol), (R)-7-(4-(pyrrolidin-3-yloxy)butyl)-1,2,3,4-tetrahydro-1,8-naphthyridine (584 mg, 1.68 mmol) and DIPEA (650 mg, 5.04 mmol) in acetonitrile (20 mL) was stirred at rt for 3 hours. Solvent was removed in vacuo, and the residue was purified by silica gel column (DCM: MeOH 10:1) to give the desired product tert-butyl 2-(2-(5,5-dimethyltetrahydrofuran-2-yl)-5-fluorophenyl)-2-((R)-3-(4-(5,6,7,8-tetrahydro-1,8-naphthyridin-2-yl)butoxy)pyrrolidin-1-yl)acetate as a yellow oil (550 mg). Yield 56%. (ESI 582 (M+H)+).

Step 6: 2-(2-(5,5-dimethyltetrahydrofuran-2-yl)-5-fluorophenyl)-2-((R)-3-(4-(,5,6,7,8-tetrahydro-1,8-naphthyridin-2-yl)butoxy)pyrrolidin-1-yl)acetic acid (compounds 96-E1 and 96-E2)

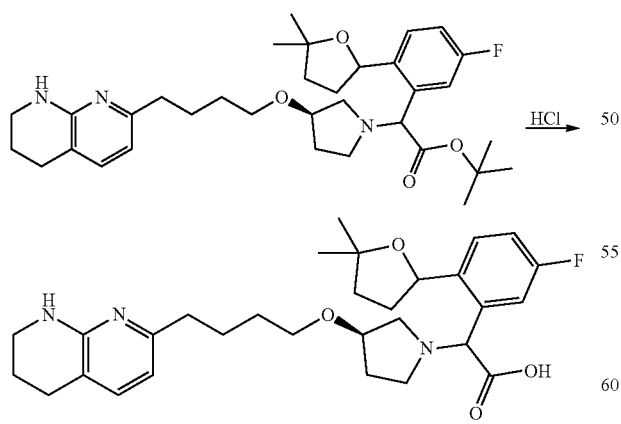

Tert-butyl 2-(2-(5,5-dimethyltetrahydrofuran-2-yl)-5-fluorophenyl)-2-((R)-3-(4-(5,6,7,8-tetrahydro-1,8-naphthyridin-2-yl)butoxy)pyrrolidin-1-yl)acetate (550 mg, 0.95 mmol) was treated with HCl in 1,4-dioxane(4M, 10 mL) at reomeric products 96-E1 (44 mg) and 96-E2 (49 mg) as white solids, each as a mixture of 2 stereoisomers.

Compound 96-E1 (mixture of 2 stereoisomers) LC/MS ESI 526 (M+H)+. 1H NMR (500 MHz, MeOD) δ 7.65-7.61 (m, 1H), 7.48 (dd, J=10 Hz, 2.5 Hz, 1H), 7.18-7.15 (m, 2H), 6.39 (d, J=7.5 Hz, 1H), 5.42 (m, 1H), 4.85 (s, 1H), 4.20 (s, 1H), 3.49-3.36 (m, 5H), 3.22-3.18 (m, 2H), 2.73-2.52 (m, 5H), 2.21-1.87 (m, 7H), 1.75-1.61 (m, 4H), 1.45-1.36 (m, 7H). Chiral SFC E (45% MeOH): ee 100%, Rt=3.49 min Compound 96-E2 (mixture of 2 stereoisomers) LC/MS ESI 526 (M+H)+. 1H NMR (500 MHz, MeOD) δ 7.65-7.61 (m, 1H), 7.45 (dd, J=10 Hz, 2.5 Hz, 1H), 7.18-7.16 (m, 2H), 6.39 (d, J=7.5 Hz, 1H), 5.35 (m, 1H), 4.97 (s, 1H), 4.20 (s, 1H), 3.54-3.36 (m, 5H), 3.22-3.05 (m, 2H), 2.73-2.50 (m, 5H), 2.22-1.88 (m, 7H), 1.76-1.62 (m, 4H), 1.41-1.36 (m, 7H). Chiral SFC E (45% MeOH): ee 98%, Rt=4.52 min.

Example 27: Preparation of 2-(2-(4,4-dimethyltetrahydro-2H-pyran-2-yl)phenyl)-2-((R)-3-(4-(5,6,7,8-tetrahydro-1,8-naphthyridin-2-yl)butoxy)pyrrolidin-1-yl)acetic Acid (Compounds 97-A-E1, 97-A-E2, 97-B-E1 and 97-B-E2)

Step 1: 4,4-dimethyltetrahydro-2H-pyran-2-one

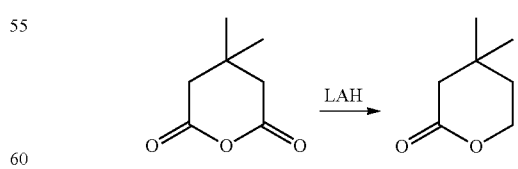

To a suspension of Lithium aluminum hydride (220 mg, 5.79 mmol) in THF (dry, 15 mL) at −55° C., was added a solution of 4,4-dimethyldihydro-2H-pyran-2,6(3H)-dione (1.42 g, 10.0 mmol) in THF (10 mL) dropwise. The reaction was gradually warmed to 0° C. and stirred for 20 min, then cooled to −15° C., added aqueous HCl (6 N, 4 mL) dropwise to quench the reaction. The mixture was extracted with ether (3×15 mL), and the combined organic layers were dried over Na2SO4. The solvent was removed in vacuo to afford the desired product 4,4-dimethyltetrahydro-2H-pyran-2-one as a oil (0.91 g, 71% yield). $^1$H NMR (400 MHz, CDCl3) δ4.40 (t, J=6.0 Hz, 2H), 2.35 (s, 2H), 1.75 (t, J=6.0 Hz, 2H), 1.10 (s, 6H).

Step 2: 2-(2-bromophenyl)-4,4-dimethyltetrahydro-2H-pyran-2-ol

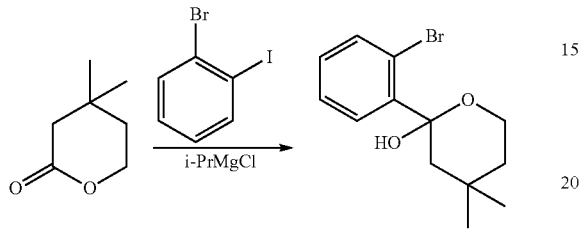

To a solution of 1-bromo-2-iodobenzene (727 mg, 2.58 mmol) in THF (15 mL) at −25° C. was added isopropylmagnesium chloride solution (2M in THF, 1.3 mL, 2.6 mmol) dropwise. The reaction mixture was stirred at −25° C. for 1 hour, then added a solution of 4,4-dimethyltetrahydro-2H-pyran-2-one (300 mg, 2.34 mmol) in THF (3 mL) dropwise at −25° C. The reaction mixture was warmed to RT in 1 hour, quenched with MeOH (5 mL) and concentrated in vacuum. The residue was purified by silica gel column (pet ether: EtOAc 4:1) to give the desired product 2-(2-bromophenyl)-4,4-dimethyltetrahydro-2H-pyran-2-ol as a yellow oil (130 mg). Yield 18% (ESI 285/287 [M+H]+).

Step 3: 2-(2-bromophenyl)-4,4-dimethyltetrahydro-2H-pyran

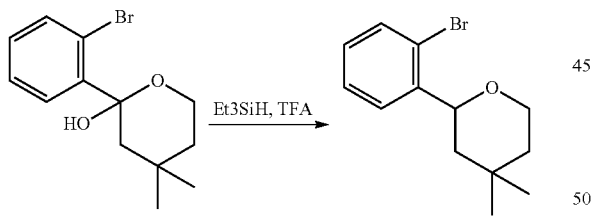

To a solution of 2-(2-bromophenyl)-4,4-dimethyltetrahydro-2H-pyran-2-ol (130 mg, 0.46 mmol) and TFA (0.23 mL) in DCM (6 mL) at 0° C., was added Et3SiH (267 mg, 2.3 mmol) dropwise. The reaction mixture was stirred at rt for 1 hour, then quenched with sat. NaHCO₃ solution (20 mL), extracted with DCM (3×10 mL). The combined organic layers were dried over Na2SO4, filtered and concentrated under vacuum. The residue was purified by silica gel column (pet ether: EtOAc 10:1) to give the desired product 2-(2-bromophenyl)-4,4-dimethyltetrahydro-2H-pyran as a yellow oil (90 mg). Yield 78% (ESI 269/271 [M+H]+).

Step 4: tert-butyl 2-(2(4,4-dimethyltetrahydro-2H-pyran-2-yl)phenyl)acetate

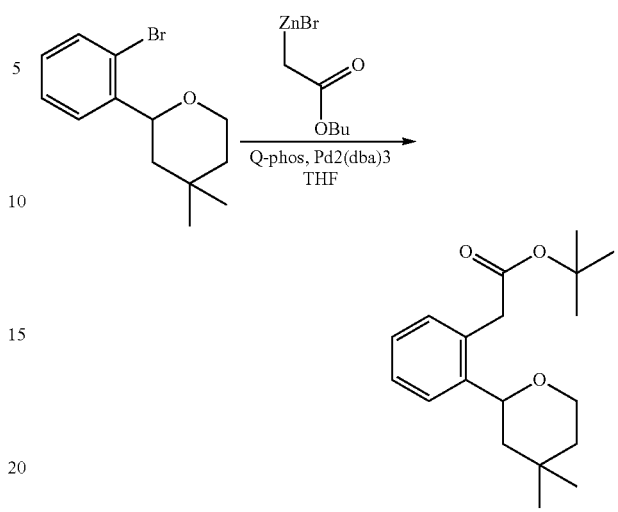

A mixture of 2-(2-bromophenyl)-4,4-dimethyltetrahydro-2H-pyran (180 mg, 0.68 mmol), (2-tert-butoxy-2-oxoethyl)zinc(II) bromide solution (0.5M in THF, 6.8 mL, 3.4 mmol), Pd2(dba)3 (35 mg, 0.034 mmol) and Q-phos (25 mg, 0.034 mmol) in THF (2 mL) was stirred at 80° C. for 2 hours. Then the reaction mixture was poured into sat. NaHCO₃ solution (50 mL), extracted with EtOAc (3×20 mL). The combined organic layers were dried over Na2SO4, filtered and concentrated under vacuum. The residue was purified by silica gel column (pet ether: EtOAc 10:1) to give the desired product tert-butyl 2-(2-(4,4-dimethyltetrahydro-2H-pyran-2-yl)phenyl)acetate as a red oil (150 mg). Yield 73% (ESI 327 [M+Na]+).

Step 5: tert-butyl 2-bromo-2-(2(4,4-dimethyltetrahydro-2H-pyran-2-yl)phenyl)acetate

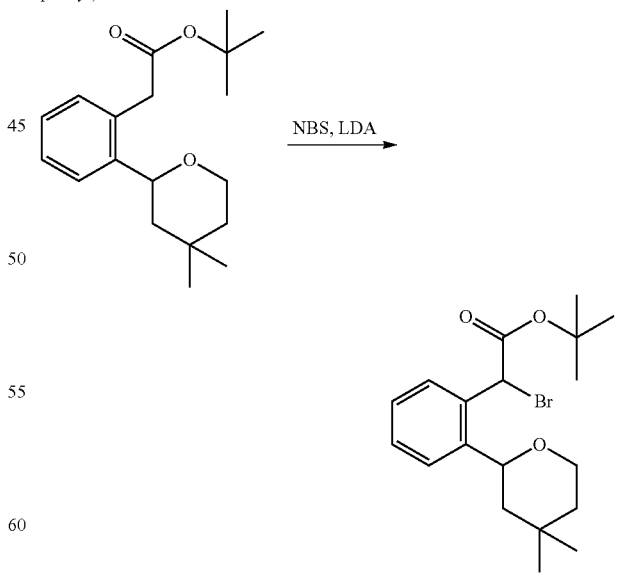

To a solution of tert-butyl 2-(3-isopropyl-3,4-dihydro-1H-pyrano[3,4-c]pyridin-5-yl)acetate (600 mg, 2.0 mmol) in THF (10 mL) at −78° C., was added lithium diisopropylamide solution (2.0 M, 2.5 mL, 5.0 mmol) dropwise. The reaction was stirred at −78° C. for 30 min, then a solution of chlorotrimethylsilane (540 mg, 5.0 mmol) in THF (1 mL) was added and the reaction was stirred at −78° C. for another 30 min. Then a solution of NBS (890 mg, 5.0 mmol) in THF (10 mL) was added and the reaction was stirred at −78° C. for 1 hour. The reaction was quenched with MeOH (2 mL), solvent was removed in vacuo, and the residue was purified by silica gel column (pet ether: EtOAc 10:1) to give the desired product tert-butyl 2-bromo-2-(2-(4,4-dimethyltetrahydro-2H-pyran-2-yl)phenyl)acetate as colorless oil (650 mg). Yield 86% (ESI 327 [M-Bu+H]+).

Step 6: tert-butyl 2-(2-(4,4-dimethyltetrahydro-2H-pyran-2-yl)phenyl)-2-((R)-3-(4-(5,6,7,8-tetrahydro-1,8-naphthyridin-2-yl)butoxy)pyrrolidin-1-yl)acetate

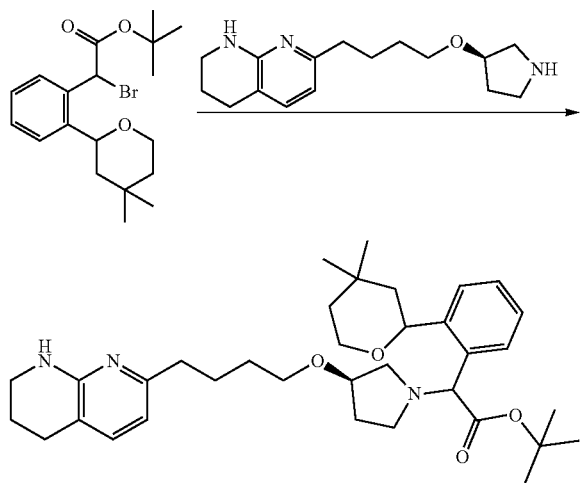

A mixture of tert-butyl 2-bromo-2-(2-(4,4-dimethyltetrahydro-2H-pyran-2-yl)phenyl)acetate (375 mg, 1.0 mmol), (R)-7-(4-(pyrrolidin-3-yloxy)butyl)-1,2,3,4-tetrahydro-1,8-naphthyridine (306 mg, 1.0 mmol), DIPEA (774 mg, 6.0 mmol) and NaI (50 mg) in acetonitrile (10 mL) was stirred at 40° C. for 12 hours. The mixture was diluted with water (8 mL) and EtOAc (25 mL). The organic phase was washed with brine, dried over Na2SO4, filtered and concentrated in vacuo. The residue was purified by silica gel column (DCM: MeOH 20:1) to give the desired product tert-butyl 2-(2-(4,4-dimethyltetrahydro-2H-pyran-2-yl)phenyl)-2-((R)-3-(4-(5,6,7,8-tetrahydro-1,8-naphthyridin-2-yl)butoxy)pyrrolidin-1-yl)acetate as a colorless oil (410 mg). Yield 72% (ESI 578 [M+H]+).

Step 7: 2-(2-(4,4-dimethyltetrahydro-2H-pyran-2-yl)phenyl)-2-((R)-3-(4-(5,6,7,8-tetrahydro-1,8-naphthyridin-2-yl)butoxy)pyrrolidin-1-yl)acetic acid (compounds 97-A-E1, 97-A-E2, 97-B-E1 and 97-B-E2)

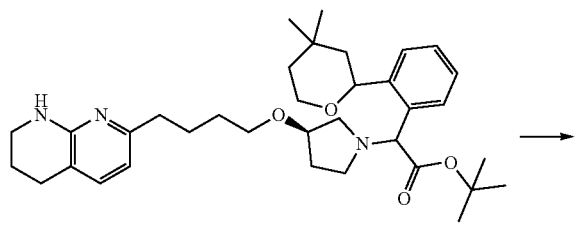

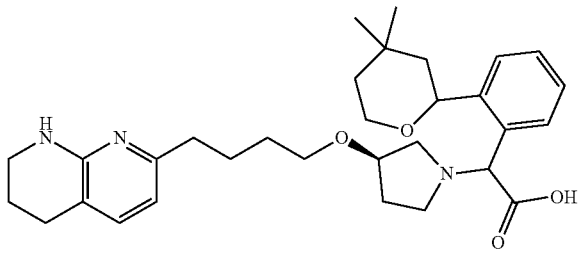

Tert-butyl 2-(2-(4,4-dimethyltetrahydro-2H-pyran-2-yl)phenyl)-2-((R)-3-(4-(5,6,7,8-tetrahydro-1,8-naphthyridin-2-yl)butoxy)pyrrolidin-1-yl)acetate (570 mg, 1.0 mmol) was treated with HCl in 1,4-dioxane(4M, 10 mL) at 25° C. for 6 hours. Solvent was removed in vacuo, and the residue was purified by prep-HPLC A (40-70% MeCN) to give 97-A (102 mg) and 97-B (130 mg). 97-A was separated by Prep chiral SFC H to give products 97-A-E1 (36 mg) and 97-A-E2 (31 mg) as white solids. 97-B was separated by Prep chiral SFC H to give products 97-B-E1 (30 mg) and 97-B-E2 (44 mg) as white solids.

Compound 97-A-E1 LC/MS ESI 522 (M+H)+. 1H NMR (400 MHz, MeOD) δ 7.68-7.66 (m, 1H), 7.54-7.52 (m, 1H), 7.41-7.34 (m, 2H), 7.15-7.13 (m, 1H), 6.36 (d, J=7.6 Hz, 1H), 5.02-4.95 (m, 2H), 4.21-4.19 (m, 1H), 3.88-3.86 (m, 2H), 3.62-3.60 (m, 1H), 3.50-3.41 (m, 5H), 3.20-3.18 (m, 1H), 3.05-3.02 (m, 1H), 2.70-2.68 (m, 2H), 2.55-2.52 (m, 2H), 2.10-2.07 (m, 2H), 1.90-1.50 (m, 9H), 1.31-1.29 (m, 1H), 1.20 (s, 3H), 1.05 (s, 3H). Chiral SFC H (40% MeOH): ee 100%, Rt=2.81 min.

Compound 97-A-E2 LC/MS ESI 522 (M+H)+. 1H NMR (400 MHz, MeOD) δ 7.69-7.67 (m, 1H), 7.54-7.52 (m, 1H), 7.41-7.31 (m, 2H), 7.15-7.13 (m, 1H), 6.36 (d, J=7.6 Hz, 1H), 5.02-5.00 (m, 1H), 4.84 (s, 1H), 4.16-4.14 (m, 1H), 3.90-3.88 (m, 2H), 3.62-3.60 (m, 1H), 3.50-3.41 (m, 5H), 3.20-3.18 (m, 2H), 2.70-2.68 (m, 2H), 2.54-2.52 (m, 2H), 2.10-2.07 (m, 2H), 1.90-1.50 (m, 9H), 1.31-1.29 (m, 1H), 1.20 (s, 3H), 1.05 (s, 3H). Chiral SFC H (40% MeOH): ee 100%, Rt=3.78 min.

Compound 97-B-E1 LC/MS ESI 522 (M+H)+. 1H NMR (400 MHz, MeOD) δ 7.68-7.66 (m, 1H), 7.54-7.52 (m, 1H), 7.41-7.34 (m, 2H), 7.15-7.13 (m, 1H), 6.36 (d, J=7.6 Hz, 1H), 5.02-4.90 (m, 2H), 4.16-4.14 (m, 1H), 3.90-3.88 (m, 2H), 3.62-3.60 (m, 1H), 3.50-3.41 (m, 5H), 3.20-3.18 (m, 1H), 3.05-3.02 (m, 1H), 2.70-2.68 (m, 2H), 2.54-2.52 (m, 2H), 2.10-2.07 (m, 2H), 1.90-1.50 (m, 9H), 1.31-1.29 (m, 1H), 1.20 (s, 3H), 1.05 (s, 3H). Chiral SFC H (40% MeOH): ee 100%, Rt=2.76 min.

Compound 97-B-E2 LC/MS ESI 522 (M+H)+. 1H NMR (400 MHz, MeOD) δ 7.68-7.66 (m, 1H), 7.54-7.52 (m, 1H), 7.44-7.34 (m, 3H), 6.49 (d, J=7.2 Hz, 1H), 5.02-4.90 (m, 2H), 4.16-4.14 (m, 1H), 3.92-3.90 (m, 2H), 3.70-3.20 (m, 8H), 2.70-2.68 (m, 2H), 2.54-2.52 (m, 2H), 2.10-2.07 (m, 2H), 1.90-1.50 (m, 9H), 1.31-1.29 (m, 1H), 1.20 (s, 3H), 1.05 (s, 3H). Chiral SFC H (40% MeOH): ee 100%, Rt=3.85 min.

Example 28: Preparation of 2-(5-fluoro-2-(5-oxaspiro[2.5]octan-6-yl)phenyl)-2-((R)-3-(4-(5,6,7,8-tetrahydro-1,8-naphthyridin-2-yl)butoxy)pyrrolidin-1-yl)acetic Acid (Compounds 98-A-E1, 98-A-E2 and 98-B)

Step 1: cyanomethyl 2-bromo-4-fluorobenzoate

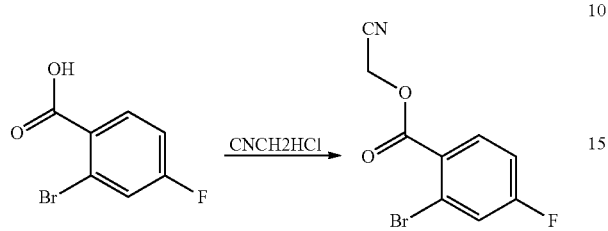

To a solution of 2-bromo-4-fluorobenzoic acid (5.0 g, 0.23 mol) in dry DCM (20 mL) at 0° C. was added triethylamine (9.2 g, 0.69 mol) and chloroacetonitrile (3.5 g, 0.46 mol). The reaction was then heated to reflux and stirred overnight. After cooling to room temperature, the reaction mixture was washed successively with aqueous HCl (2M, 20 mL) and sat. NaHCO$_3$ solution (20 mL). The organic phase was dried over anhydrous MgSO4 and concentrated in vacuo to afford the desired product cyanomethyl 2-bromo-4-fluorobenzoate as a pale yellow oil (4.0 g). Yield 68% (ESI 258/260 [M+H]+).

Step 2: 1-(2-bromo-4-fluorophenyl)-5-hydroxypentane-1,4-dione

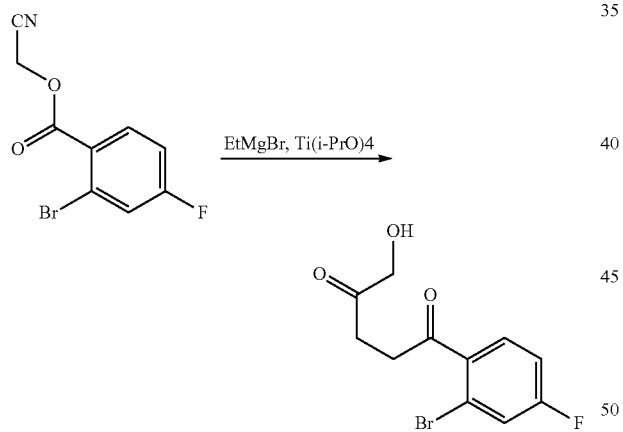

To a solution of cyanomethyl 2-bromo-4-fluorobenzoate (3.4 g, 13.2 mmol) and Ti(OiPr)4 (4.15 g, 14.6 mmol) in Et$_2$O (70 mL) at 0° C. under argon, was added EtMgBr (28 ml, 28 mmol, 1M in THF) dropwise. After the addition of the Grignard reagent, the mixture was warmed to RT and stirred for 1 hour. The turbid yellow mixture was quenched with water (10 mL), then 1M HCl (30 mL) were added, extracted with EtOAc (3*50 mL). The combined organic phases were washed with saturated aqueous NaHCO$_3$ and dried (MgSO4). After evaporation of the solvents, the residue was purified by silica gel column (pet ether: EtOAc 3:1) to afford the desired product 1-(2-bromo-4-fluorophenyl)-5-hydroxypentane-1,4-dione (901 mg) as a colorless oil. Yield 25% (ESI 289/271 [M+H]+).

Step 3: 6-(2-bromo-4-fluorophenyl)tetrahydro-2H-pyran-3-ol

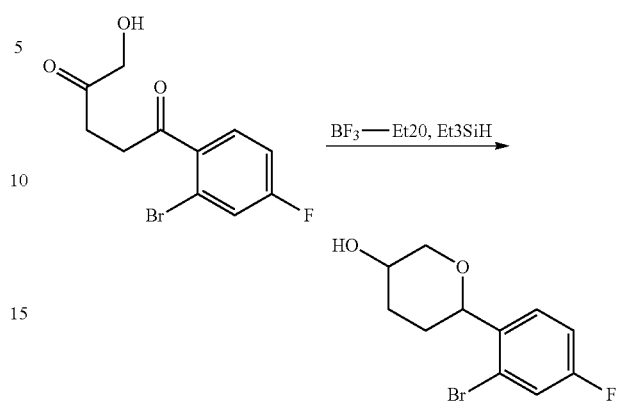

To a solution of 1-(2-bromo-4-fluorophenyl)-5-hydroxypentane-1,4-dione (900 mg, 3.13 mmol) in DCM (40 mL) at 0° C. was added Boron trifluoride (diethyl ether complex, 1110 mg, 7.8 mmol) dropwise. After the addition, triethylsilane (910 mg, 7.8 mmol) was added and the reaction was stirred at 0° C. for 1 hour. The reaction mixture was quenched with sat. NaHCO3 (20 mL), extracted with DCM (2*50 mL). The combined organic layers were dried over sodium sulfate, filtered and concentrated in vacuo. The residue was purified by silica gel column (pet ether: EtOAc 3:1) to give the desired product 6-(2-bromo-4-fluorophenyl)tetrahydro-2H-pyran-3-ol as a colorless oil (650 mg). Yield 80% (ESI 275/277 [M+H]+).

Step 4: 6-(2-bromo-4-fluorophenyl)dihydro-2H-pyran-3(4H)-one

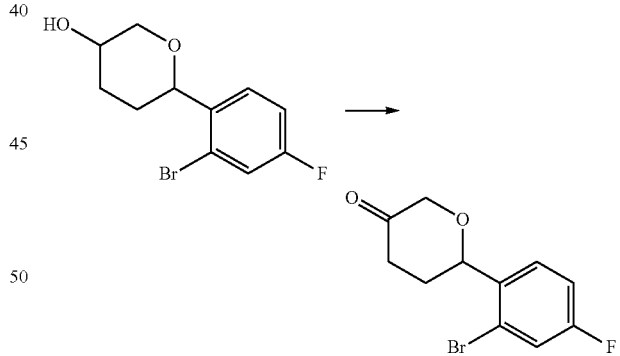

To a solution of 6-(2-bromo-4-fluorophenyl)tetrahydro-2H-pyran-3-ol (100 mg, 0.37 mmol) in DCM (5 mL) was added Dess-Martin Periodonane (150 mg, 0.50 mmol) in several portions. After the addition, the reaction mixture was stirred RT for 2 hours, then quenched with a solution of saturated NaHCO$_3$(5 mL). The organic layer was washed with brine, dried over sodium sulfate, filtered and concentrated in vacuo. The residue was purified by silica gel column (pet ether: EtOAc 10:1) to afford the desired product 6-(2-bromo-4-fluorophenyl)dihydro-2H-pyran-3(4H)-one as a colorless oil (20 mg). Yield 20% (ESI 273/275 [M+H]+).

Step 5: 2-(2-bromo-4-fluorophenyl)-5-methylenetetrahydro-2H-pyran

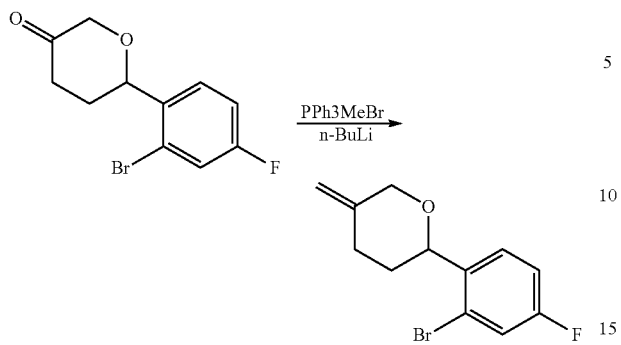

To a solution of methyltriphenylphosphonium bromide (134 mg, 0.52 mmol) in THF (3 mL) at 0° C., n-BuLi (2.5M in hexane, 0.21 mL, 0.52 mmol) was added and the reaction was stirred at 0° C. for 30 minutes, then added a solution of 6-(2-bromo-4-fluorophenyl)dihydro-2H-pyran-3(4H)-one (70 mg, 0.26 mmol) in THF (2 mL). The reaction was stirred at room temperature for 12 hours, quenched with sat. aq. NH4Cl and extracted with DCM (2*10 mL). The combined organic phase was dried over sodium sulfate, filtered and concentrated in vacuo. The residue was purified by silica gel column (pet ether: EtOAc 10:1) to afford the desired product 2-(2-bromo-4-fluorophenyl)-5-methylenetetrahydro-2H-pyran as a colorless oil (51 mg, 70% yield). 1H NMR (400 MHz, CDCl₃) δ 7.52-7.50 (m, 1H), 7.27-7.25 (m, 1H), 7.05-7.01 (m, 1H), 4.89-4.88 (m, 2H), 4.75-4.73 (m, 1H), 4.37-4.34 (m, 1H), 4.20-4.17 (m, 1H), 2.50-2.46 (m, 2H), 2.15-2.10 (m, 1H), 1.52-1.50 (m, 1H).

Step 6: 6-(2-bromo-4-fluorophenyl)-5-oxaspiro[2.5]octane

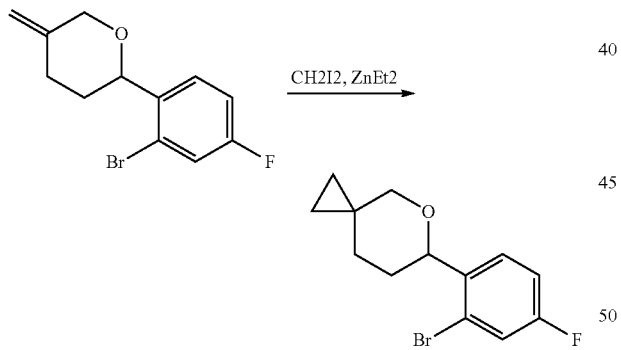

To a solution of ZnEt2 (1 M in THF, 6 mL, 6.0 mmol) in DCM (20 mL) at 0° C. was added TFA (690 mg, 6.0 mmol). The reaction was stirred at 0° C. for 0.5 hour, then CH2I2 (1.7 g, 6.0 mmol) was added dropwise. The reaction was stirred at 0° C. for 0.5 hour, then 2-(2-bromo-4-fluorophenyl)-5-methylenetetrahydro-2H-pyran(280 mg, 1.0 mmol) in DCM (1 mL) was added. The reaction mixture was stirred at rt for 2 hours, quenched with sat. NaHCO₃ solution (20 mL), and the DCM layer was dried over Na2SO4. The solvent was removed in vacuo and the residue was purified by silica gel column (pet ether: EtOAc 50:1) to give the desired product 6-(2-bromo-4-fluorophenyl)-5-oxaspiro [2.5]octane as a yellow oil (250 mg). Yield 80% (ESI 267/269 [M+H−H2O]+).

Step 7: tert-butyl 2-(5-fluoro-2-(5-oxaspiro[2.5]octane-6-yl)phenyl)acetate

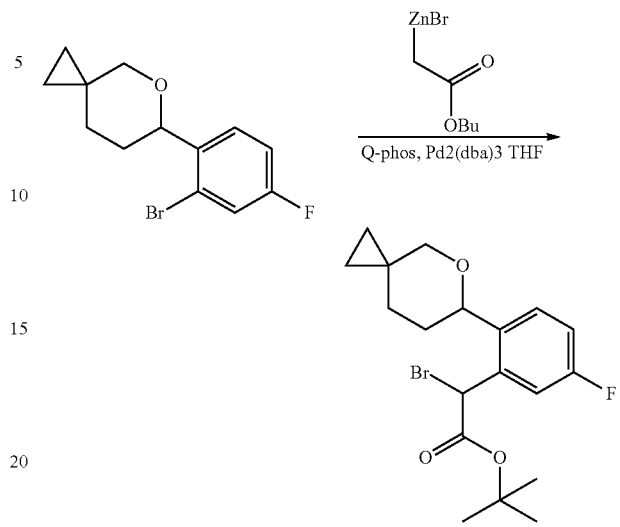

A mixture of 6-(2-bromo-4-fluorophenyl)-5-oxaspiro [2.5]octane (250 mg, 0.88 mmol), (2-tert-butoxy-2-oxo-ethyl)zinc(II) bromide solution 0.5 M in THF (10 mL, 5 mmol), Pd2(dba)3 (40 mg, 0.05 mmol) and Q-phos (31 mg, 0.05 mmol) in THF (2 mL) was stirred at 80° C. for 2 hours. Then the mixture was poured into sat. NaHCO₃ solution (50 mL) and EtOAc (60 mL). The mixture was filtered, the organic layer was washed with brine, dried over Na2SO4, concentrated in vacuo, and the residue was purified by silica gel column (pet ether: EtOAc 10:1) to give the desired product tert-butyl 2-(5-fluoro-2-(5-oxaspiro[2.5]octan-6-yl) phenyl)acetate as a red oil (160 mg). Yield 53% (ESI 343 [M+Na]+).

Step 8: tert-butyl 2-bromo-2-(5-fluoro-2-(5-oxaspiro[2.5]octan-6-yl)phenyl)acetate

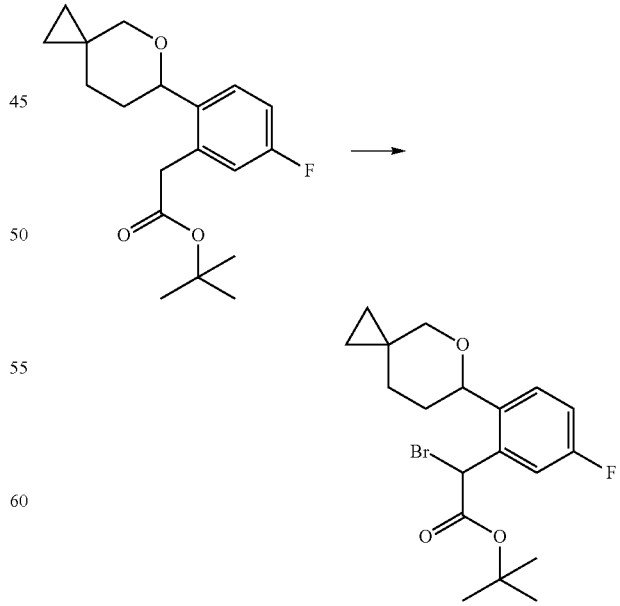

To a solution of tert-butyl 2-(5-fluoro-2-(5-oxaspiro[2.5] octan-6-yl)phenyl)acetate (160 mg, 0.5 mmol) in THF (5 mL) at −78° C., was added lithium diisopropylamide solution 2.0 M in THF/hexanes (0.62 mL, 1.25 mmol) dropwise. The reaction was stirred at −78° C. for 30 min, then a solution of chlorotrimethylsilane (135 mg, 1.25 mmol) in THF (1 mL) was added and the reaction was stirred at −78° C. for another 30 min. Then a solution of NBS (221 mg, 1.25 mmol) in THF (10 mL) was added and the reaction was stirred at −78° C. for 1 hour. The reaction was quenched with MeOH (2 mL), solvent was removed in vacuo, and the residue was purified by silica gel column (pet ether: EtOAc 10:1) to give the desired product tert-butyl 2-bromo-2-(5-fluoro-2-(5-oxaspiro[2.5]octan-6-yl)phenyl)acetate as a colorless oil (130 mg). Yield 60% (ESI 419/421 [M+Na]+).

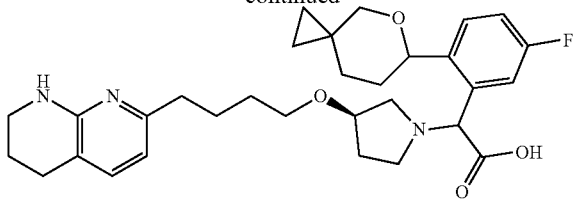

A solution of tert-butyl 2-(5-fluoro-2-(5-oxaspiro[2.5]octan-6-yl)phenyl)-2-((R)-3-(4-(5,6,7,8-tetrahydro-1,8-naphthyridin-2-yl)butoxy)pyrrolidin-1-yl)acetate (210 mg, 0.35

Step 9: tert-butyl 2-(5-fluoro-2-(5-oxaspiro[2.5]octan-6-yl)phenyl)-2-((R)-3-(4-(5,6,7,8-tetrahydro-1,8-naphthyridin-2-yl)butoxy)pyrrolidin-1-yl)acetate

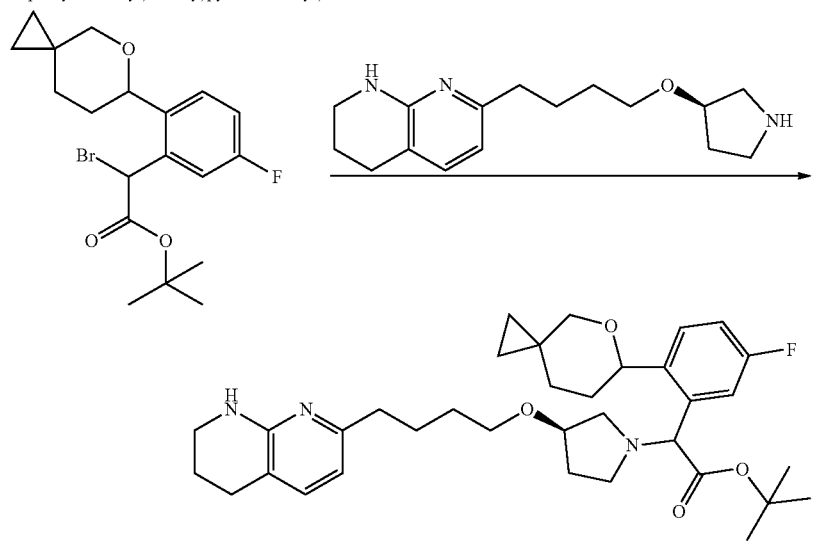

A mixture of tert-butyl 2-bromo-2-(5-fluoro-2-(5-oxaspiro[2.5]octan-6-yl)phenyl)acetate (130 mg, 0.33 mmol), (R)-7-(4-(pyrrolidin-3-yloxy)butyl)-1,2,3,4-tetrahydro-1,8-naphthyridine (101 mg, 0.33 mmol), DIPEA (126 mg, 0.99 mmol) and NaI (50 mg) in acetonitrile (10 mL) was stirred at 40° C. for 12 hours. The mixture was diluted with water (8 mL) and EtOAc (25 mL). The organic phase was washed with brine, dried over Na2SO4, filtered and concentrated in vacuo. The residue was purified by silica gel column (DCM: MeOH 20:1) to give the desired product tert-butyl 2-(5-fluoro-2-(5-oxaspiro[2.5]octan-6-yl)phenyl)-2-((R)-3-(4-(5,6,7,8-tetrahydro-1,8-naphthyridin-2-yl)butoxy)pyrrolidin-1-yl)acetate as a colorless oil (101 mg). Yield=52% (ESI 595 [M+H]+).

Step 10: 2-(5-fluoro-2-(5-oxaspiro[2.5]octan-6-yl)phenyl)-2-((R)-3-(4-(5,6,7,8-tetrahydro-1,8-naphthyridin-2-yl)butoxy)pyrrolidin-1-yl)acetic acid (compounds 98-A-E1, 98-A-E2 and 98-B)

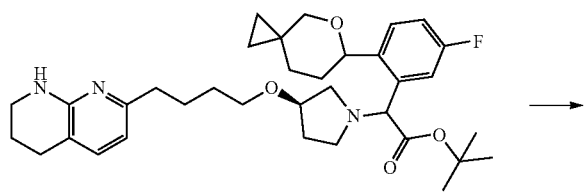

mmol) in TFA (2 mL) and DCM (2 mL) was stirred at room temperature for 15 hours. Then it was concentrated and purified by prep-HPLC A (40-70% MeCN) to give 98-A (106 mg) and 98-B (16 mg). 98-A was separated by Prep chiral SFC C to give products 98-A-E1 (35 mg) and 98-A-E2 (31 mg) as white solids.

Compound 98-A-E1 LC/MS ESI 538 (M+H)+. 1H NMR (500 MHz, MeOD) δ 7.64-7.61 (m, 1H), 7.49-7.46 (m, 1H), 7.18-7.16 (m, 2H), 6.39 (d, J=7.5 Hz, 1H), 4.93 (s, 1H), 4.82-4.85 (m, 1H), 4.19 (br s, 1H), 4.12-4.10 (m, 1H), 3.61 (m, 1H), 3.49 (t, J=6.5 Hz, 2H), 3.341-3.38 (m, 3H), 3.23 (d, J=12.5H, 1H), 3.11-3.09 (m, 2H), 2.72 (t, J=6.0 Hz, 2H), 2.56 (t, J=7.5 Hz, 2H), 2.3-2.2-(m, 1H), 2.11-2.00 (m, 4H), 1.90-1.88 (m, 2H), 1.74-1.72 (m, 2H), 1.65-1.63 (m, 2H), 1.2 (m, 1H), 0.6-0.3 (m, 4H). Chiral SFC C (20% EtOH): ee 100%, Rt=1.29 min.

Compound 98-A-E2 LC/MS ESI 538 (M+H)+. 1H NMR (400 MHz, MeOD) δ 7.63-7.61 (m, 1H), 7.50-7.48 (m, 1H), 7.22-7.16 (m, 2H), 6.39 (d, J=7.6 Hz, 1H), 4.82-4.80 (m, 1H), 4.20-4.12 (m, 2H), 3.60-3.32 (m, 6H), 3.30-3.05 (m, 4H), 2.75-2.55 (m, 4H), 2.25-1.58 (m, 12H), 0.58-0.30 (m, 4H). Chiral SFC C (20% EtOH): ee 100%, Rt=2.17 min.

Compound 98-B (mixture of 2 stereoisomers) LC/MS ESI 538 (M+H)+. 1H NMR (400 MHz, MeOD) δ 7.41-7.32 (m, 2H), 7.08-6.98 (m, 2H), 6.28-6.22 (m, 1H), 4.80-4.75 (m, 1H), 4.05-3.85 (m, 2H), 3.60-3.32 (m, 6H), 3.10-2.85 (m, 4H), 2.62-2.58 (m, 2H), 2.47-2.41 (m, 2H), 2.21-1.40 (m, 12H), 0.55-0.20 (m, 4H).

Example 29: Preparation of 2-(2-(5,5-difluorotetrahydro-2H-pyran-2-yl)-5-fluorophenyl)-2-((R)-3-(4-(5,6,7,8-tetrahydro-1,8-naphthyridin-2-yl)butoxy)pyrrolidin-1-yl)acetic Acid (Compounds 99-E1 and 99-E2)

Step 1: 1-(2-bromo-4-fluorophenyl)cyclopropanol

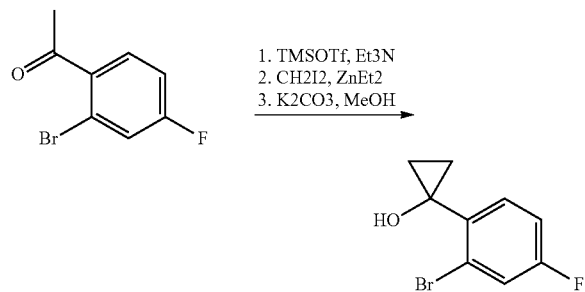

To a solution of 1-(2-bromo-4-fluorophenyl)ethanone (5.0 g, 23.1 mmol) and Et₃N (3.51 g, 34.7 mmol) in DCM (50 mL) at 0° C. under nitrogen, was added TMSOTf (6.17 g, 27.8 mmol) dropwise via syringe over a period of 10 min. The reaction mixture was stirred at RT overnight, then quenched with saturated NaHCO₃ aqueous (20 mL), extracted the aqueous with DCM (2×30 mL). The combined organic phase was washed with brine, dried over Na2SO4, filtered and concentrate in vacuo to obtain crude ether. The crude ether was dissolved in anhydrous DCM (50 mL), added diiodomethane (25.0 g, 92.4 mmol), cooled to 0° C., then added diethyl zinc (1 M in THF, 93 mL, 93 mmol) dropwise. The reaction was stirred at RT for 16 hours, then quenched with a saturated solution of NH4Cl (30 mL), extracted with DCM (2*50 mL). The combined organic phase was washed with brine, dried over Na2SO4, filtered and concentrate in vacuo to obtain crude material. The crude material was dissolved in MeOH (20 mL), followed by addition of K2CO3 (3.2 g, 23.1 mmol), then stirred at RT for 30 min. Solvent was removed under vacuum, added H2O (20 mL), extracted with EtOAc (2*40 mL). The combined organic phase was dried over sodium sulfate, filtered and concentrated in vacuo. The residue was purified by silica gel column (pet ether: EtOAc 5:1) to afford the desired product 1-(2-bromo-4-fluorophenyl)cyclopropanol as a colorless oil (3.1 g). Yield 86% (ESI 213/215 [M+H]+).

Step 2: ethyl 5-(2-bromo-4-fluorophenyl)-2,2-difluoro-5-oxopentanoate

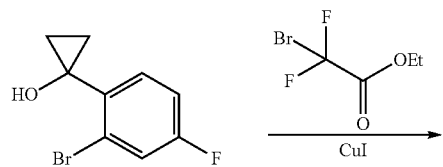

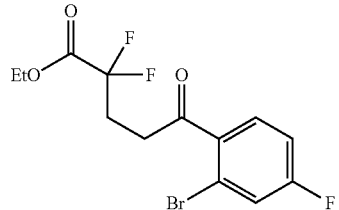

A mixture of 1-(2-bromo-4-fluorophenyl)cyclopropanol (100 mg, 0.44 mmol), ethyl 2-bromo-2,2-difluoroacetate (351 mg, 1.74 mmol), CuI (8.2 mg, 0.044 mmol), Phenanthroline (17.2 mg, 0.088 mmol) and K2CO3 (120 mg, 0.88 mmol) in MeCN (5 mL) was stirred at 90° C. for 17 hours. The reaction was quenched with water (10 mL), extracted with EtOAc (3*10 mL). The combined organic layers were washed with brine, dried over Na2SO4, concentrated in vacuo, and the residue was purified by silica gel column (pet ether: EtOAc 5:1) to afford the desired product ethyl 5-(2-bromo-4-fluorophenyl)-2,2-difluoro-5-oxopentanoate as a colorless oil (81 mg). Yield 53% (ESI 353/355 [M+H]+).

Step 3: 2-(2-bromo-4-fluorophenyl)-5,5-difluorotetrahydro-2H-pyran

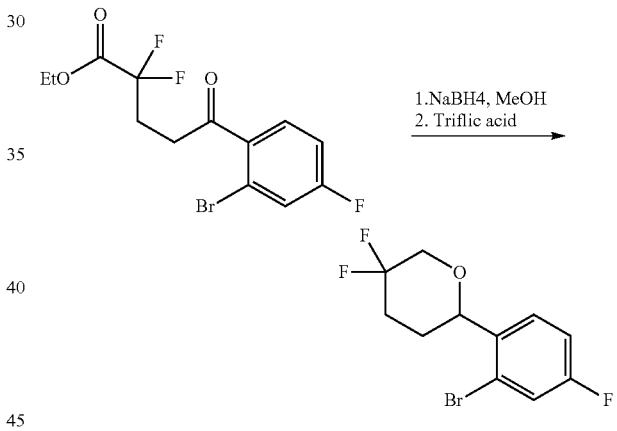

To a solution of ethyl 5-(2-bromo-4-fluorophenyl)-2,2-difluoro-5-oxopentanoate (100 mg, 0.28 mmol) in MeOH (5 mL) at 0° C. was added NaBH4 (44 mg, 1.12 mmol). The reaction solution was stirred at RT for 15 hours. Solvent was removed under vacuum, added H2O (10 mL), extracted with DCM (3*10 mL). The combined organic phase was dried over sodium sulfate, filtered and concentrated in vacuo. The residue was dissolved in DCM (3 mL) and triflic acid (100 mg, 0.32 mmol) was added. The reaction was stirred at RT for 15 hours, then quenched by sat. aq. NaHCO₃(5 mL), extracted with DCM (2×10 mL). The combined organic layers were washed with brine, dried over Na2SO4, concentrated in vacuo, and the residue was purified by silica gel column (pet ether: EtOAc 10:1) to give the desired product 2-(2-bromo-4-fluorophenyl)-5,5-difluorotetrahydro-2H-pyran a colorless oil (40 mg). Yield 47% (ESI 297/299 [M+H]+).

Step 4: tert-butyl 2-(2-(5,5-difluorotetrahydro-2H-pyran-2-yl)-5-fluorophenyl)acetate

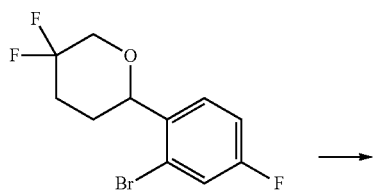

Step 5: tert-butyl 2-bromo-2-(2-(5,5-difluorotetrahydro-2H-pyran-2-yl)-5-fluorophenyl)acetate

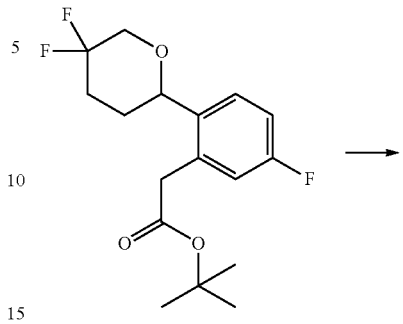

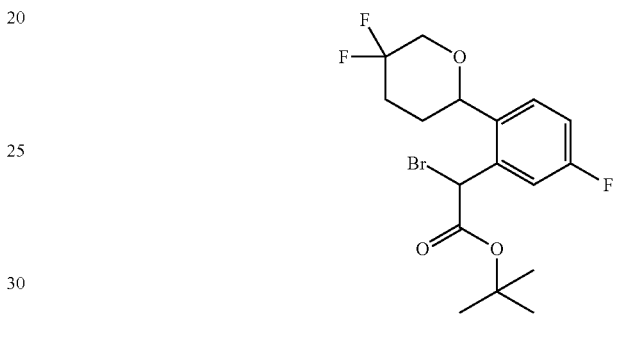

A mixture of 2-(2-bromo-4-fluorophenyl)-5,5-difluorotetrahydro-2H-pyran (800 mg, 2.93 mmol), (2-tert-butoxy-2-oxoethyl)zinc(II) bromide solution (0.5 M in THF, 30 mL, 15 mmol), Pd2(dba)3 (152 mg, 0.15 mmol) and Q-phos (105 mg, 0.15 mmol) in THF (2 mL) was stirred at 80° C. for 2 hours. The reaction mixture was poured into sat. NaHCO3 solution (20 mL) and EtOAc (30 mL). The mixture was filtered, the organic layer was washed with brine, dried over Na2SO4, concentrated in vacuo, and the residue was purified by silica gel column (pet ether: EtOAc 10:1) to give the desired product tert-butyl 2-(2-(5,5-difluorotetrahydro-2H-pyran-2-yl)-5-fluorophenyl)acetate as a red oil (703 mg). Yield 78% (ESI 275 [M+H-tBu]+).

To a solution of tert-butyl 2-(2-(5,5-difluorotetrahydro-2H-pyran-2-yl)-5-fluorophenyl)acetate (703 mg, 2.12 mmol) in THF (5 mL) at −78° C., was added lithium diisopropylamide solution (2M, 2.65 mL, 5.3 mmol) dropwise. The reaction was stirred at −78° C. for 30 min, then a solution of chlorotrimethylsilane (573 mg, 5.3 mmol) in THF (1 mL) was added and the reaction was stirred at −78° C. for another 30 min. Then a solution of NBS (944 mg, 5.3 mmol) in THF (10 mL) was added and the reaction was stirred at −78° C. for 1 hour. The reaction was quenched with MeOH (2 mL), solvent was removed in vacuo, and the residue was purified by silica gel column (pet ether: EtOAc 10:1) to give the desired product tert-butyl 2-bromo-2-(2-(5,5-difluorotetrahydro-2H-pyran-2-yl)-5-fluorophenyl)acetate as a red oil (816 mg). Yield 66% (ESI 352/354 [M+H-tBu]+).

Step 6: tert-butyl 2-(2-(5,5-difluorotetrahydro-2H-pyran-2-yl)-5-fluorophenyl)-2-((R)-3-(4-(5,6,7,8-tetrahydro-1,8-naphthyridin-2-yl)butoxy)pyrrolidin-1-yl)acetate

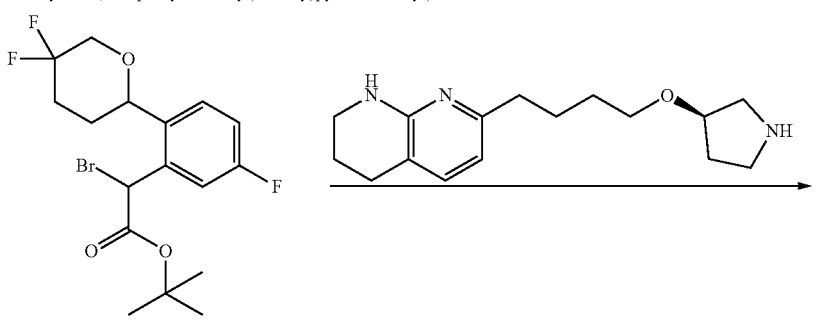

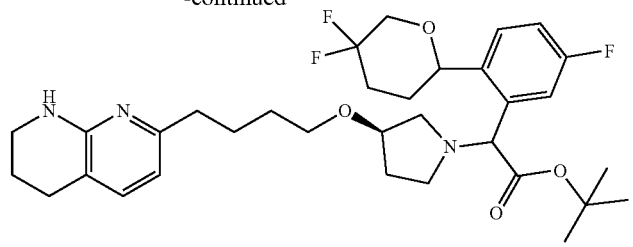

A mixture of tert-butyl 2-bromo-2-(2-(5,5-difluorotetrahydro-2H-pyran-2-yl)-5-fluorophenyl)acetate (816 mg, 2.0 mmol), (R)-7-(4-(pyrrolidin-3-yloxy)butyl)-1,2,3,4-tetrahydro-1,8-naphthyridine (660 mg, 2.0 mmol), DIPEA (821 mg, 6.0 mmol) and NaI (50 mg) in acetonitrile (20 mL) was stirred at 40° C. for 6 hours. The mixture was diluted with water (8 mL) and EtOAc (25 mL). The organic phase was washed with brine, dried over Na2SO4, filtered and concentrated in vacuo. The residue was purified by silica gel column (DCM:MeOH 20:1) to give the desired product tert-butyl 2-(2-(5,5-difluorotetrahydro-2H-pyran-2-yl)-5-fluorophenyl)-2-((R)-3-(4-(5,6,7,8-tetrahydro-1,8-naphthyridin-2-yl)butoxy)pyrrolidin-1-yl)acetate as a colorless oil (710 mg). Yield 58% (ESI 604 [M+H]+).

1.82-1.80 (m, 2H), 1.75-1.60 (m, 4H). Chiral SFC A (40% MeOH): ee 100%, Rt=1.92 min.

Compound 99-E2 LC/MS ESI 548 (M+H)+. 1H NMR (400 MHz, MeOD) δ 7.62-7.60 (m, 1H), 7.53-7.51 (m, 1H), 7.28 (d, J=7.6 Hz, 1H), 7.17-7.14 (m, 1H), 6.44 (d, J=7.2 Hz, 1H), 4.99-4.90 (m, 1H), 4.79 (s, 1H), 4.19-4.17 (m, 1H), 4.01-3.80 (m, 2H), 3.60-3.35 (m, 6H), 3.20-3.18 (m, 2H), 2.81-2.79 (m, 2H), 2.62-2.59 (m, 2H), 2.30-2.01 (m, 6H), 1.82-1.80 (m, 2H), 1.75-1.60 (m, 4H). Chiral SFC A (40% MeOH): ee 98%, Rt=2.47 min.

Step 7: 2-(2-(5,5-difluorotetrahydro-2H-pyran-2-yl)-5-fluorophenyl)-2-((R)-3-(4-(5,6,7,8-tetrahydro-1,8-naphthyridin-2-yl)butoxy)pyrrolidin-1-yl)acetic acid (compounds 99-E1 and 99-E2)

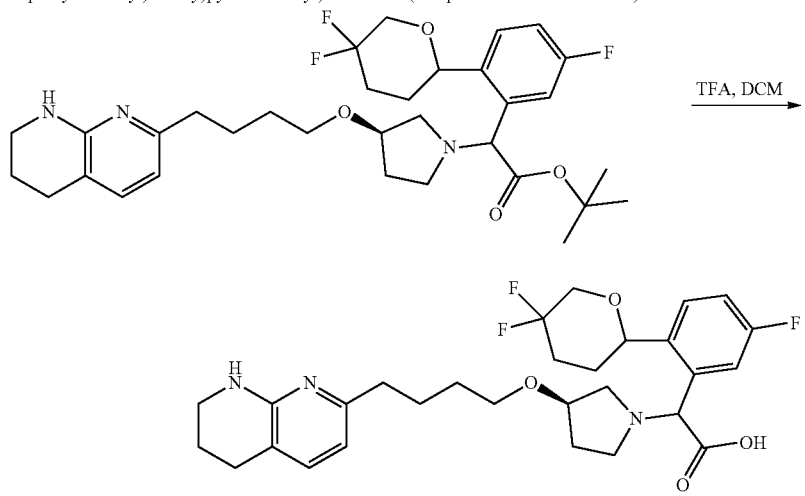

To a solution of tert-butyl 2-(2-(5,5-difluorotetrahydro-2H-pyran-2-yl)-5-fluorophenyl)-2-((R)-3-(4-(5,6,7,8-tetrahydro-1,8-naphthyridin-2-yl)butoxy)pyrrolidin-1-yl)acetate (710 mg, 1.2 mmol) in DCM (10 mL) was added TFA (10 mL). The reaction was stirred at RT for 15 hours. Then it was concentrated and purified by prep-HPLC A (40-70% MeCN) to give 99 as a white solid (400 mg, 63% yield). The racemic product was separated by Prep chiral SFC A to give diastereomeric products 99-E1 (74 mg) and 99-E2 (88 mg) as white solids.

Compound 99-E1 LC/MS ESI 548 (M+H)+. 1H NMR (400 MHz, MeOD) δ 7.61-7.59 (m, 1H), 7.51-7.48 (m, 1H), 7.22-7.13 (m, 2H), 6.41 (d, J=7.2 Hz, 1H), 4.99-4.90 (m, 1H), 4.80 (s, 1H), 4.19-4.17 (m, 1H), 4.01-3.80 (m, 2H), 3.50-3.35 (m, 6H), 3.20-3.18 (m, 1H), 3.02-2.98 (m, 1H), 2.81-2.79 (m, 2H), 2.62-2.59 (m, 2H), 2.30-2.01 (m, 6H), Example 30: Preparation of 2-(2-(5,5-dimethyltetrahydro-2H-pyran-2-yl)phenyl)-2-((R)-3-(4-(5,6,7,8-tetrahydro-1,8-naphthyridin-2-yl)butoxy)pyrrolidin-1-yl)acetic Acid (Compounds 100-E1 and 100-E2)

Step 1: Ethyl 3-(2-bromophenyl)acrylate

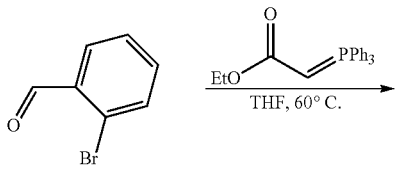

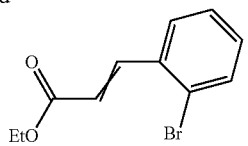

To a solution of 2-bromobenzaldehyde (5.00 g, 27.0 mmol) in THF (30 mL) was added ethyl 2-(triphenyl-15-phosphaneylidene)acetate (9.89 g, 28.4 mmol), then the mixture was stirred at 60° C. overnight. The solvent was removed in vacuo and the residue was purified by silica gel column (pet ether: EtOAc 10:1) to give the desired product as a yellow oil (6.51 g). Yield 93%. $^1$H NMR (400 MHz, $CDCl_3$) δ 8.06 (d, 1H), 7.61 (m, 2H), 7.24-7.19 (m, 2H), 6.40 (d, 1H), 4.31-4.08 (m, 2H), 1.36-1.15 (m, 3H).

Step 2: 3-(2-bromophenyl)prop-2-en-1-ol

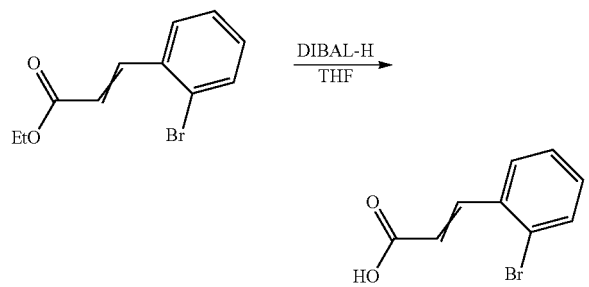

To a solution of 3-(2-bromophenyl)acrylate (6.5 g, 30.7 mmol) in THF (dry, 50 mL) at 0° C., was added DIBAL-H (1 M, 61.3 mL, 61.3 mmol) dropwise. The mixture was stirred at 0° C. for 30 min, then warmed to RT for an hour. The reaction solvents was poured into aqueous HCl (1N, 200 mL) and stirred at rt overnight. The mixture was extracted with ethyl acetate (50 mL×3). The combined organic layer was dried over sodium sulfate, filtered and concentrated in vacuo. The residue was purified by silica gel column (pet ether: EtOAc 10:3) to afford the desired product as a light yellow oil (5.10 g). Yield 89%. $^1$H NMR (400 MHz, CDCl3) δ 7.59-7.30 (m, 3H), 7.18-7.08 (m, 2H), 6.34-6.30 (m, 1H), 4.37-4.27 (m, 2H).

Step 3: 1-bromo-2-(3-bromoprop-1-enyl)benezene

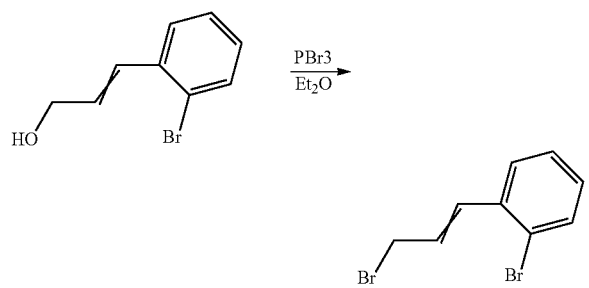

To a solution of 3-(2-bromophenyl)prop-2-en-1-ol (4.80 g, 22.64 mmol) in diethyl ether (dry, 50 mL) at 0° C. was added phosphorus tribromide (1.27 mL, 9.06 mmol). The reaction was stirred at 0° C. for 1 hour, then quenched with sat. $NaHCO_3$, extracted with diethyl ether (50 mL×2). The combined organic layers were washed with brine, dried over sodium sulfate, filtered and concentrated in vacuo to afford the desired product 1-bromo-2-(3-bromoprop-1-enyl)benzene as a yellow oil (5.20 g). Yield 79%. $^1$H NMR (400 MHz, CDCl3) δ 7.56-7.46 (m, 2H), 7.34-7.26 (m, 2H), 6.36-6.34 (m, 1H), 4.18-4.03 (m, 2H).

Step 4: methyl 5-(2-bromophenyl)-2,2-dimethylpent-4-enoate

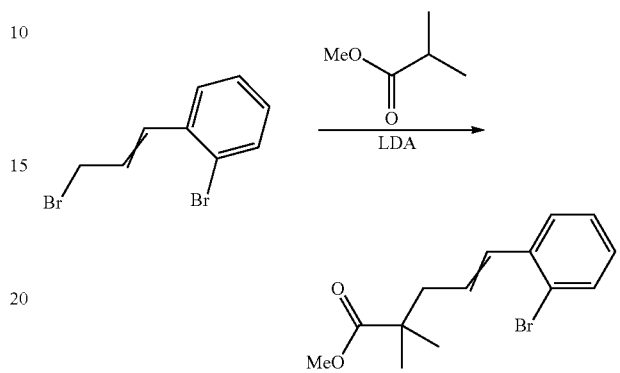

To a solution of methyl isobutyrate (2.13 g, 20.88 mmol) in THF (dry, 40 mL) at −78° C. was added LDA (1 M, 20.88 mL, 20.88 mmol) dropwise. The mixture was stirred at −78° C. for 30 min, then added a solution of 1-bromo-2-(3-bromoprop-1-en-1-yl)benzene (5.20 g, 18.98 mmol) in THF (10 mL) dropwise. The reaction was stirred at −78° C. for 30 min, then warmed to RT for another 1 hour. The reaction was quenched with sat. NH4Cl and extracted with EtOAc (50 mL×3). The combined organic layers were washed with brine, dried over sodium sulfate, filtered and concentrated in vacuo. The residue was purified by silica gel column (pet ether: EtOAc 5:1) to afford the desired product as a yellow oil (4.36 g, 78% yield).1H NMR (400 MHz, CDCl3) δ 7.58-7.46 (m, 2H), 7.23-7.09 (m, 2H), 6.74-6.51 (m, 1H), 6.10-6.02 (m, 1H), 3.69-3.64 (m, 3H), 2.48-2.40 (m, 2H), 1.24-1.15 (m, 6H).

Step 5: 5-(2-bromophenyl)-2,2-dimethylpent-4-en-1-ol

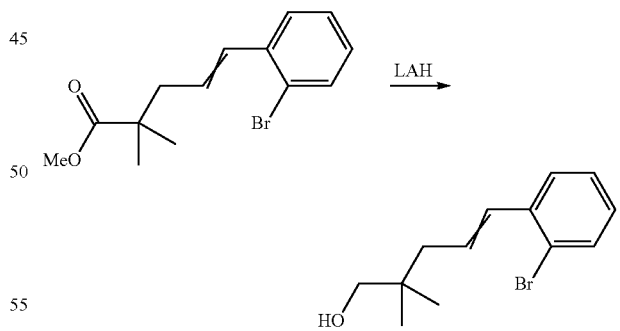

To a solution of methyl 5-(2-bromophenyl)-2,2-dimethylpent-4-enoate (4.36 g, 14.53 mmol) in THF (dry, 20 mL) at −78° C., was added dropwise a solution of lithium aluminium hydride in tetrahydrofuran (2.4 M, 6.66 mL, 11.80 mmol). The mixture was stirred at −78° C. for 3 hours, then quenched with 1M HCl (~100 mL, started dropwise). The reaction was extracted with EtOAc (50 mL×3). The combined organic layers were washed with brine, dried over sodium sulfate, filtered and concentrated in vacuo. The residue was purified by silica gel column (pet ether: EtOAc 10:3) to afford the desired product as a yellow oil (3.74 g, 93% yield). ESI: 267 (M+H)+

Steps 6: Ethyl 3-(2-bromophenyl)acrylate

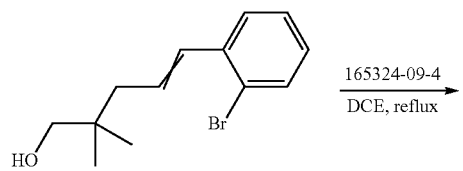

To a solution of 5-(2-bromophenyl)-2,2-dimethylpent-4-en-1-ol (3.74 g, 13.95 mmol) in dichloro ethane (20 mL) was added Tetrabutylammonium Hexafluorophosphate (0.27 g, 0.70 mmol) and Calcium(II) Bis(trifluoromethanesulfonyl)imide (0.22 g, 0.70 mmol). The mixture was stirred at 90° C. for 20 hours, concentrated in vacuo and the residue was purified by silica gel column (pet ether: EtOAc 10:1) to afford the desired product ethyl 3-(2-bromophenyl)acrylate as a yellow oil (1.50 g, 40% yield). 1H NMR (400 MHz, CDCl$_3$) δ 7.54 (d, J=6.8 Hz, 2H), 7.33 (t, J=8.0 Hz, 1H), 7.10 (t, J=7.2 Hz, 1H), 4.56 (d, J=9.6 Hz, 1H), 3.3 (d, J=11.2 Hz, 1H), 3.38 (d, J=11.2 Hz, 1H), 1.88-1.84 (m, 1H), 1.59-1.53 (m, 4H), 1.13 (s, 3H), 0.88 (s, 3H).

Step 7: butyl 2-(2-(5,5-dimethyltetrahydro-2H-pyran-2-yl)phenyl)acetate

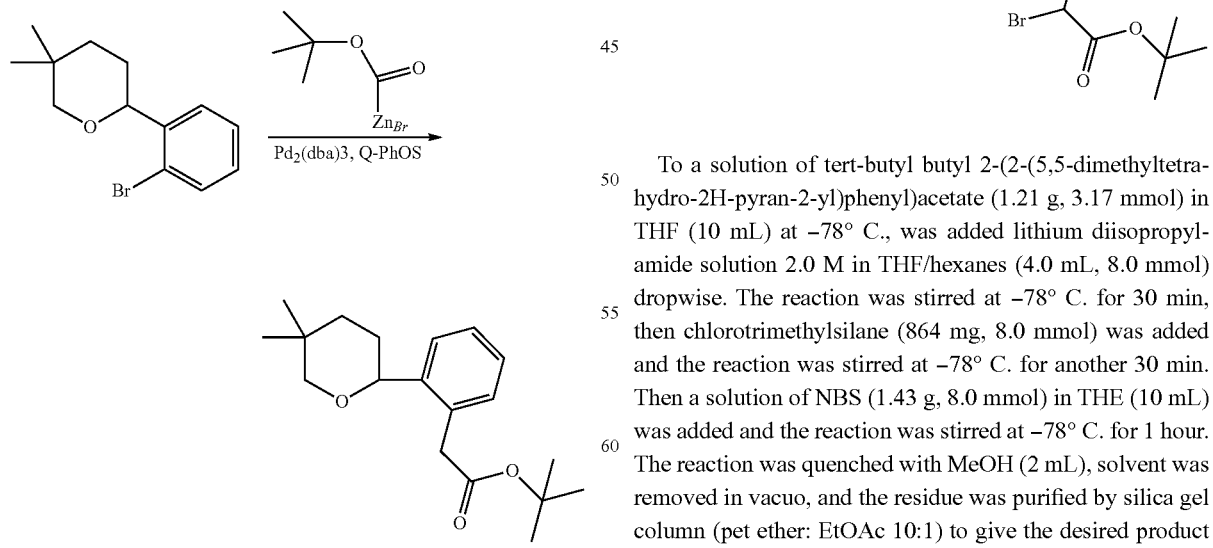

To a mixture of ethyl 3-(2-bromophenyl)acrylate (1.50 g, 5.60 mmol), tris(dibenzylideneacetone)dipalladium (0.29 g, 0.28 mmol) and 1, 2, 3, 4, 5-Pentaphenyl-1′-(di-tert-butylphosphino)ferrocene (0.20 g, 0.28 mmol) in THF (10 mL) was added (2-tert-butoxy-2-oxoethyl)zinc(II) bromide (1 M in THF, 28 mL, 28 mmol). The reaction was stirred at 60° C. for 2 hours. The reaction mixture was poured into sat. NaHCO$_3$(100 mL), extracted with EtOAc (50 mL×3). The combined organic layers were washed with brine, dried over sodium sulfate, filtered and concentrated in vacuo. The residue was purified by silica gel column (pet ether: EtOAc 10:1) to afford the desired product as a red oil (1.21 g, 71% yield). ESI: 249 (M-C$_4$H$_9$+H)+

Step 8: tert-butyl 2-bromo-2-(2-(5,5-dimethyltetrahydro-2H-pyran-2-yl)phenyl)acetate

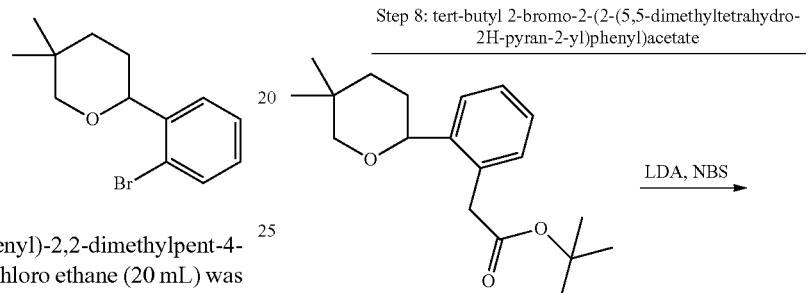

To a solution of tert-butyl butyl 2-(2-(5,5-dimethyltetrahydro-2H-pyran-2-yl)phenyl)acetate (1.21 g, 3.17 mmol) in THF (10 mL) at −78° C., was added lithium diisopropylamide solution 2.0 M in THF/hexanes (4.0 mL, 8.0 mmol) dropwise. The reaction was stirred at −78° C. for 30 min, then chlorotrimethylsilane (864 mg, 8.0 mmol) was added and the reaction was stirred at −78° C. for another 30 min. Then a solution of NBS (1.43 g, 8.0 mmol) in THF (10 mL) was added and the reaction was stirred at −78° C. for 1 hour. The reaction was quenched with MeOH (2 mL), solvent was removed in vacuo, and the residue was purified by silica gel column (pet ether: EtOAc 10:1) to give the desired product tert-butyl 2-bromo-2-(2-(5,5-dimethyltetrahydro-2H-pyran-2-yl)phenyl)acetate as a yellow oil (1.31 g, 85% yield). ESI: 327 (M-C$_4$H$_9$+H)$^+$ Step 9: tert-butyl 2-(2-(5,5-dimethyltetrahydro-2H-pyran-2-yl)phenyl)-2-((R)-3-(4-(5,6,7,8-tetrahydro-1,8-naphthyridin-2-yl)butoxy)pyrrolidin-1-yl)acetate

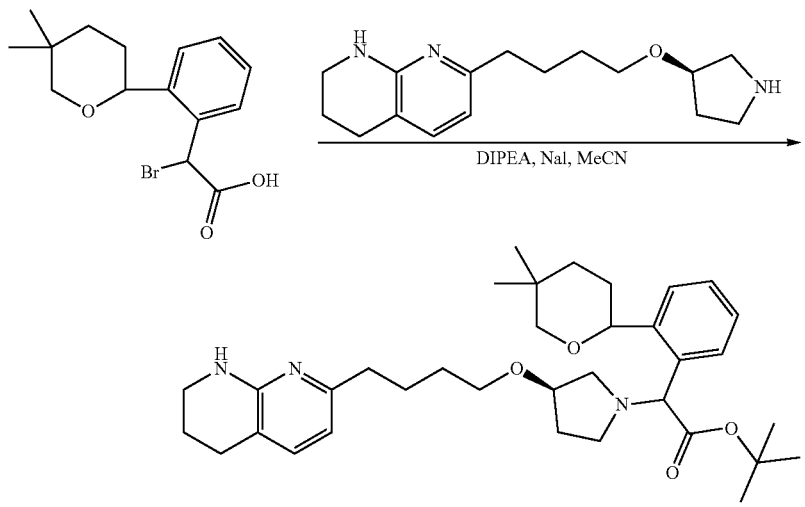

A mixture of (S)-7-(4,4-difluoro-5-(pyrrolidin-3-yl)pentyl)-1,2,3,4-tetrahydro-1,8-naphthyridine (200 mg, 0.65 mmol, 2-bromo-2-(2-(5,5-dimethyltetrahydro-2H-pyran-2-yl)phenyl)acetate (220 mg, 0.65 mmol), DIEA(252 mg, 1.95 mmol) and NaI (19.5 mg, 0.13 mmol) in acetonitrile (10 mL) was stirred at 50° C. for 6 hours. Solvent was removed in vacuo, and the residue was purified by silica gel column (DCM:MeOH 20:1) to give the desired product tert-butyl 2-(2-(5,5-dimethyltetrahydro-2H-pyran-2-yl)phenyl)-2-((R)-3-(4-(5,6,7,8-tetrahydro-1,8-naphthyridin-2-yl)butoxy)pyrrolidin-1-yl)acetate as a yellow oil (150 mg, 45% yield). ESI: 578 (M+H)+

Step 10: tert-butyl 2-(2-(5,5-dimethyltetrahydro-2H-pyran-2-yl) phenyl)-2-((R)-3-(4-(5,6,7,8-tetrahydro-1,8-naphthyridin-2-yl) butoxy)pyrrolidin-1-yl) acetic acid (compounds 100-E1 and 100-E2)

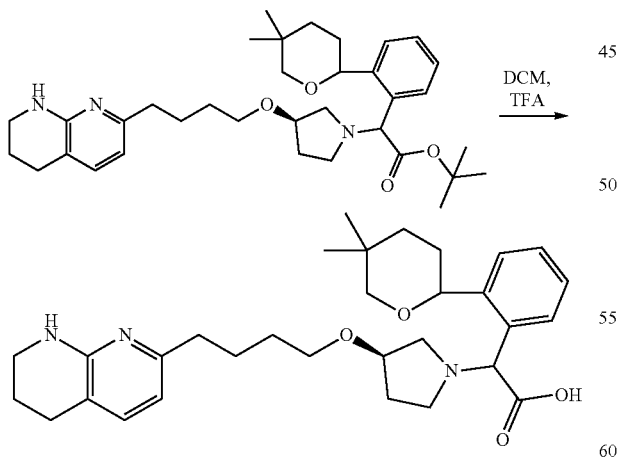

Tert-butyl 2-(2-(5,5-dimethyltetrahydro-2H-pyran-2-yl) phenyl)-2-((R)-3-(4-(5,6,7,8-tetrahydro-1,8-naphthyridin-2-yl)butoxy)pyrrolidin-1-yl)acetate (150 mg, 0.26 mmol) was treated with a mixture of DCM (3 mL) and TFA (3 mL) at 25° C. overnight. Solvent was removed in vacuo, and the residue was purified by Prep-HPLC A (30-65% MeCN) to give the desired product tert-butyl 2-(2-(5,5-dimethyltetrahydro-2H-pyran-2-yl)phenyl)-2-((R)-3-(4-(5,6,7,8-tetrahydro-1,8-naphthyridin-2-yl)butoxy)pyrrolidin-1-yl) acetic acid (Compound 100) as a white solid (96 mg, 70%). The racemic product was separated by Prep chiral SFC H to give diastereomeric products 100-E1 (29 mg) and 100-E2 (26 mg) as white solids.

Compound 100-E1 LC/MS ESI 522.7 (M+H)+. $^1$H NMR (400 MHz, MeOD) δ 7.68 (d, J=8.0 Hz, 1H), 7.59 (d, J=8.0 Hz, 1H), 7.45-7.38 (m, 2H), 7.15 (d, J=8.0 Hz, 1H), 6.37 (d, J=7.2 Hz, 1H), 4.93 (s, 1H), 4.73 (d, J=8.0 Hz, 1H), 4.19 (s, 1H), 3.56-3.36 (m, 7H), 3.22-3.05 (m, 3H), 2.70 (t, J=6.0 Hz, 2H), 2.57 (t, J=6.0 Hz, 2H), 2.14-1.92 (m, 6H), 1.76-1.61 (m, 6H), 1.15 (s, 3H), 0.95 (s, 3H). Chiral SFC H (45% MeOH): ee 98%, Rt=1.54 min.

Compound 100-E2 LC/MS ESI 522.7 (M+H)+. $^1$H NMR (400 MHz, MeOD) δ 7.68 (d, J=8.0 Hz, 1H), 7.59 (d, J=8.0 Hz, 1H), 7.45-7.38 (m, 2H), 7.15 (d, J=8.0 Hz, 1H), 6.37 (d, J=7.2 Hz, 1H), 4.81-4.78 (m, 2H), 4.17 (s, 1H), 3.58-3.32 (m, 8H), 3.22-3.15 (m, 2H), 2.70 (t, J=6.0 Hz, 2H), 2.55 (t, J=6.0 Hz, 2H), 2.18-1.92 (m, 6H), 1.76-1.61 (m, 6H), 1.12 (s, 3H), 0.89 (s, 3H). Chiral SFC H (45% MeOH): ee 100%, Rt=2.35 min.

Example 31: Preparation of 2-(5-fluoro-2-((S)-tetrahydro-2H-pyran-2-yl)phenyl)-2-((R)-3-(4-(7-methyl-5,6,7,8-tetrahydro-1,8-naphthyridin-2-yl)butoxy) pyrrolidin-1-yl)acetic Acid (Diastereomeric Compounds 101-A-E1, 101-A-E2, 101-B-E1 and 101-B-E2)

Step 1: 4-(2,6-dichloropyridin-3-yl)but-3-en-2-one

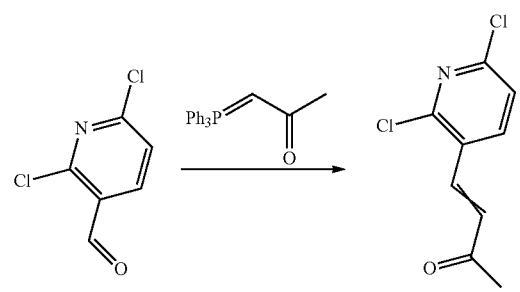

A mixture of 2, 6-dichloronicotinaldehyde (25 g, 143.5 mmol) and 1-(triphenylphosphoranylidene)-2-propanone (57.2 g, 179.6 mmol) in toluene (180 mL) was stirred at 110° C. for 16 hours. The mixture was cooled to room temperature, added H2O (40 mL), extracted with ethyl acetate (3×50 mL). The combined organic layer was dried over Na2SO4, filtered, solvent was removed in vacuo. The residue was purified by silica gel column (pet ether: EtOAc 1:1) to give the desired product as a yellow solid (13.3 g). Yield 43% (ESI 216.0 (M+H)+).

Step 2: 4-(2,6-dichloropyridin-3-yl)butan-2-amine

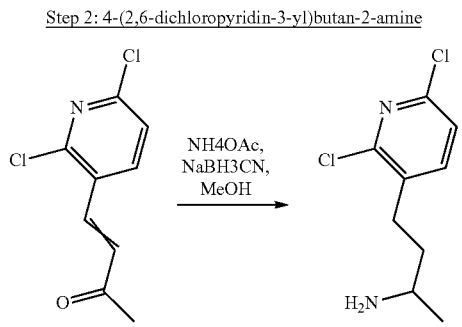

A mixture of 4-(2,6-dichloropyridin-3-yl)but-3-en-2-one (12 g, 55.8 mmol), NH4OAc (21.5 g, 279.1 mmol) and NaBH3CN (10.6 g, 167.4 mmol) in MeOH (100 mL) was stirred at 30° C. for 16 hours. The mixture was concentrated in vacuo, and the residue was purified by silica gel column (DCM: MeOH 40:1) to give the desired product as a yellow oil (7.94 g). Yield 58% (ESI 219.0 (M+H)+).

Step 3: (R)-7-chloro-2-methyl-1,2,3,4-tetrahydro-1,8-naphthyridine and (S)-7-chloro-2-methyl-1,2,3,4-tetrahydro-1,8-naphthyridine

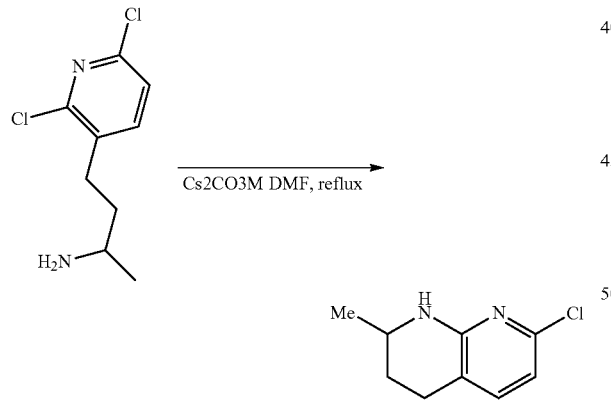

A mixture of 4-(2,6-dichloropyridin-3-yl)butan-2-amine (7 g, 32.1 mmol) and Cs2CO3 (52 g, 160.6 mmol) in DMF (120 mL) was stirred at 140° C. for 16 hours. The mixture was cooled to room temperature, added EtOAc (100 mL) and washed with H2O (3×100 mL). The organic layer was removed in vacuo and the residue was purified by silica gel column (pet ether: EtOAc 1:1) to give the desired product as a yellow oil (1.9 g). Yield 32% (ESI 183.0 (M+H)+). The racemic product was separated by Prep chiral SFC B to give stereoisomer A (870 mg) and stereoisomer B (890 mg) as yellow oils.

Step 4: (R)-tert-butyl 7-chloro-2-methyl-3,4-dihydro-1,8-naphthyridine-1(2H)-carboxylate stereoisomer A

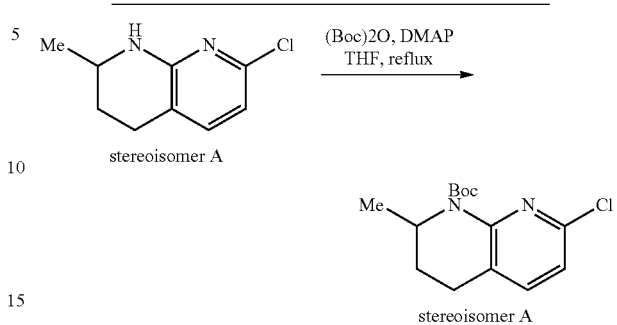

A mixture of 7-chloro-2-methyl-1,2,3,4-tetrahydro-1,8-naphthyridine stereoisomer A (870 mg, 4.75 mmol), (Boc)2O (3.13 g, 14.35 mmol) and DMAP (1.75 g, 14.35 mmol) in THF (40 mL) was stirred at 60° C. for 2 hours. Solvent was removed in vacuo and the residue was purified by silica gel column (pet ether: EtOAc 10:1) to give the desired product as a yellow solid (1.2 g). Yield 89% (ESI 283.0 (M+H)+).

Step 5: tert-butyl 7-(4-((R)-1-(tert-butoxycarbonyl)pyrrolidin-3-yloxy)butyl)-2-methyl-3,4-dihydro-1,8-naphthyridine-1(2H)-carboxylate stereoisomer A

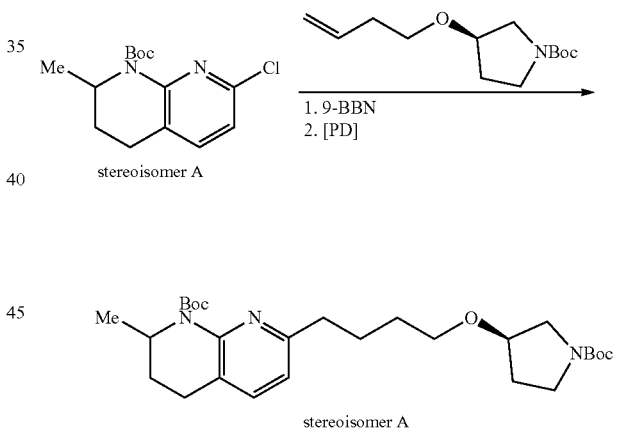

To a solution of (R)-tert-butyl 3-(but-3-enyloxy)pyrrolidine-1-carboxylate (512 mg, 2.13 mmol) in THF (dry, 5 mL) under Ar, was added 9-BBN (0.5M solution in THF, 8.5 mL, 4.25 mmol). The reaction was stirred at 50° C. for 2 hours, then cooled to rt, added tert-butyl 7-chloro-2-methyl-3,4-dihydro-1,8-naphthyridine-1(2H)-carboxylate stereoisomer A (600 mg, 2.13 mmol), tricyclohexylphosphine (60 mg, 0.21 mmol), Pd(OAc)2 (47 mg, 0.21 mmol) and NaOH (127 mg, 3.19 mmol). The mixture was stirred at 70° C. for 2 hours. Solvent was removed in vacuo and the residue was purified by silica gel column (pet ether: EtOAc 8:1) to give the desired product as a yellow solid (988 mg). Yield 95% (ESI 490.0 (M+H)+).

Step 6: 2-methyl-7-(4-((R)-pyrrolidin-3-yloxy)butyl)-1,2,3,4-tetrahydro-1,8-naphthyridine stereoisomer A

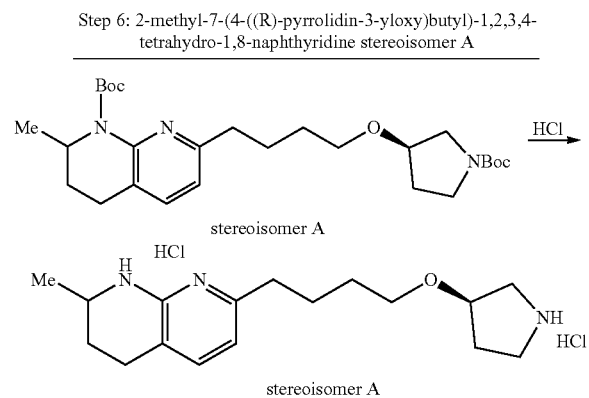

stereoisomer A stereoisomer A

Tert-butyl 7-(4-((R)-1-(tert-butoxycarbonyl)pyrrolidin-3-yloxy)butyl)-2-methyl-3,4-dihydro-1,8-naphthyridine-1(2H)-carboxylate stereoisomer A (1.2 g, 2.45 mmol) was treated with HCl in 1,4-dioxane(4M, 8 mL) at 25° C. for 16 hours. Solvent was removed in vacuo to give the desired product (781.7 mg) as a white solid. Yield 88% (ESI 290.0 (M+H)+).

Step 8: 2-(5-fluoro-2-((S)-tetrahydro-2H-pyran-2-yl)phenyl)-2-((R)-3-(4-(7-methyl-5,6,7,8-tetrahydro-1,8-naphthyridin-2-yl)butoxy)pyrrolidin-1-yl)acetic acid stereoisomer A
(compounds 101-A-E1 and 101-A-E2)

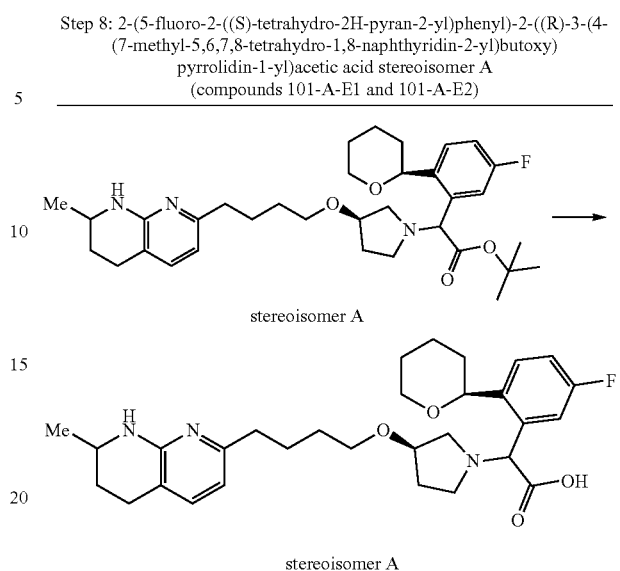

stereoisomer A stereoisomer A

Step 7: tert-butyl 2-(5-fluoro-2-((S)-tetrahydro-2H-pyran-2-yl)phenyl)-2-((R)-3-(4-(7-methyl-5,6,7,8-tertrahydro-1,8-naphthyridin-2-yl)butoxy)pyrrolidin-1-yl)acetate stereoisomer A

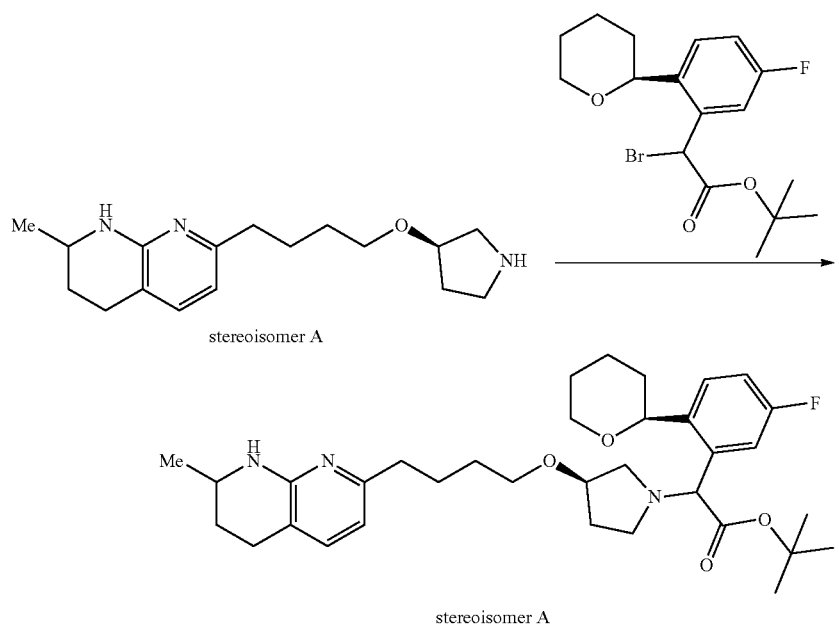

stereoisomer A stereoisomer A

A mixture of 2-methyl-7-(4-((R)-pyrrolidin-3-yloxy)butyl)-1,2,3,4-tetrahydro-1,8-naphthyridine stereoisomer A (200 mg, 0.55 mmol), tert-butyl 2-bromo-2-(5-fluoro-2-((S)-tetrahydro-2H-pyran-2-yl)phenyl)acetate (206 mg, 0.55 mmol) and DIPEA(178 mg, 1.38 mmol) in acetonitrile (8 mL) was stirred at 50° C. for 4 hours. Solvent was removed in vacuo, and the residue was purified by silica gel column (DCM: MeOH 10:1) to give the desired product tert-butyl 2-(5-fluoro-2-((S)-tetrahydro-2H-pyran-2-yl)phenyl)-2-((R)-3-(4-(7-methyl-5,6,7,8-tetrahydro-1,8-naphthyridin-2-yl)butoxy)pyrrolidin-1-yl)acetate stereoisomer A as a yellow oil (120 mg). Yield 37% (ESI 582.3 (M+H)+).

To a solution of tert-butyl 2-(5-fluoro-2-((S)-tetrahydro-2H-pyran-2-yl)phenyl)-2-((R)-3-(4-(7-methyl-5,6,7,8-tetrahydro-1,8-naphthyridin-2-yl)butoxy)pyrrolidin-1-yl)acetate stereoisomer A (120 mg, 0.21 mmol) in DCM(2.5 mL) was added TFA (2.5 mL), then the mixture was stirred at rt for 16 hours. Solvent was removed in vacuo, and the residue was purified by Prep-HPLC A (30-65% MeCN) to give diastereomeric products compound 101-A-E1 (40 mg) and compound 101-A-E2 (1.5 mg) as white solids.

Compound 101-A-E1 LC/MS ESI 526.3 (M+H)+. 1H NMR (400 MHz, MeOD) δ 7.62-7.58 (m, 1H), 7.46-7.43 (m, 1H) 7.28-7.18 (m, 2H), 6.45 (d, J=7.2 Hz, 1H), 5.02 (s, 1H), 4.74 (d, J=10.8 Hz, 1H), 4.21 (s, 1H), 4.01 (d, J=7.2 Hz, 1H), 3.71-3.69 (m, 1H), 3.59-3.40 (m, 5H), 3.15-3.10 (m, 1H), 2.77-2.74 (m, 2H), 2.62-2.58 (m, 2H), 2.05-1.89 (m, 5H), 1.88-1.42 (m, 10H), 1.22 (d, J=10.8 Hz, 3H).

Compound 101-A-E2 LC/MS ESI 526.3 (M+H)+. 1H NMR (400 MHz, MeOD) δ 7.46-7.41 (m, 2H), 7.31-7.29 (m, 1H) 7.16-7.13 (m, 1H), 6.47 (d, J=7.2 Hz, 1H), 5.32 (s, 1H), 4.70 (d, J=6.8 Hz, 1H), 4.19 (s, 1H), 4.10 (d, J=10.0 Hz, 1H), 3.71-3.40 (m, 4H), 3.19-3.16 (m, 3H), 2.78-2.76 (m, 2H), 2.65-2.61 (m, 2H), 2.25-2.02 (m, 2H), 2.00-1.96 (m, 3H), 1.88-1.42 (m, 10H), 1.22 (d, J=10.8 Hz, 3H).

Step 9: 2-(5-fluoro-2-((S)-tetrahydro-2H-pyran-2-yl)phenyl) -2-((R)-3-(4-(7-methyl-5,6,7,8-tetrahydro-1,8-naphthyridin-2-yl)butoxy)pyrrolidin-1-yl)acetic acid stereoisomer B (compounds 101-B-E1 and 101-B-E2)

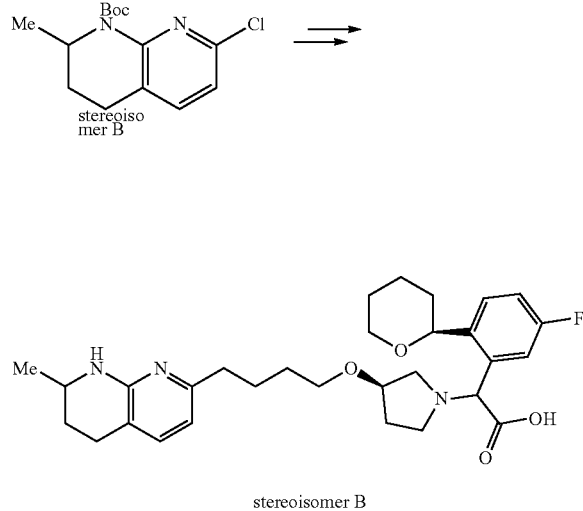

stereoisomer B 2-(5-fluoro-2-((S)-tetrahydro-2H-pyran-2-yl)phenyl)-2-((R)-3-(4-(7-methyl-5,6,7,8-tetrahydro-1,8-naphthyridin-2-yl)butoxy)pyrrolidin-1-yl)acetic acid stereoisomer B (compounds 101-B-E1 and 101-B-E2) was synthesized from tert-butyl 7-chloro-2-methyl-3,4-dihydro-1,8-naphthyridine-1(2H)-carboxylate stereoisomer B by the same methods as stereoisomer A.

Compound 101-B-E1 LC/MS ESI 526.3 (M+H)+. 1H NMR (400 MHz, MeOD) δ 7.62-7.58 (m, 1H), 7.46-7.43 (m, 1H) 7.26-7.18 (m, 2H), 6.44 (d, J=7.2 Hz, 1H), 4.99 (s, 1H), 4.74 (d, J=10.4 Hz, 1H), 4.21 (s, 1H), 4.03 (d, J=10.8 Hz, 1H), 3.71-3.69 (m, 1H), 3.59-3.40 (m, 5H), 3.10 (s, 1H), 2.76-2.73 (m, 2H), 2.61-2.57 (m, 2H), 2.20-1.89 (m, 5H), 1.81-1.42 (m, 10H), 1.22 (d, J=10.8 Hz, 3H).

Compound 101-B-E2 LC/MS ESI 526.3 (M+H)+. 1H NMR (400 MHz, MeOD) δ 7.47-7.37 (m, 3H), 7.17-7.12 (m, 1H), 6.49 (d, J=7.2 Hz, 1H), 5.32 (s, 1H), 4.69 (d, J=9.2 Hz, 1H), 4.19 (s, 1H), 4.10 (d, J=10.0 Hz, 1H), 3.71-3.40 (m, 5H), 3.19-3.16 (m, 2H), 2.79-2.76 (m, 2H), 2.68-2.63 (m, 2H), 2.35-2.22 (m, 1H), 2.10-1.96 (m, 4H), 1.86-1.44 (m, 10H), 1.22 (d, J=10.8 Hz, 1H).

Example 32: Preparation of 2-(5-fluoro-2-(2,9-dioxaspiro[5.5]undecan-3-yl)phenyl)-2-((R)-3-(4-(5,6,7,8-tetrahydro-1,8-naphthyridin-2-yl)butoxy)pyrrolidin-1-yl)acetate (Compounds 102-A-E1, 102-A-E2 and 102-B)

Step 1: ethyl 4-(but-3-en-1-yl)tetrahydro-2H-pyran-4-carboxylate

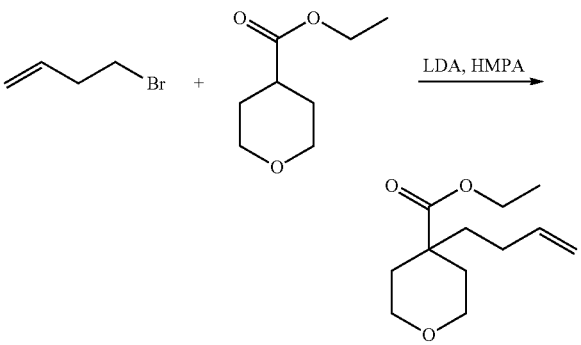

To a solution of diisopropylamine (3.19 mL, 22.8 mmol) in dry tetrahydrofuran (20 mL) under nitrogen atmosphere at −78° C. was added n-butyllithium in hexanes (2.5 M, 7.28 mL, 18.2 mmol). This mixture was stirred for 45 minutes at −78° C., then ethyl tetrahydropyran-4-carboxylate (2.87 mL, 19.0 mmol) was added dropwise, and the mixture was stirred for 30 minutes at −78° C. A mixture of 4-bromo-1-butene (2.5 mL, 24.6 mmol) and HMPA (1.85 mL, 10.6 mmol) in dry tetrahydrofuran (5 mL) was added dropwise. The mixture was stirred for five minutes at −78° C., taken out of the acetone/dry ice bath and stirred in an ice/water bath at 0° C. for 20 minutes, then stirred for 25 minutes at room temperature. The reaction mixture was quenched with saturated aqueous ammonium chloride and extracted three times with diethyl ether. The combined organic layers were washed with brine, dried over sodium sulfate and concentrated in vacuo. Purification by column chromatography (silica, 3% to 15% diethyl ether in pentane) afforded the desired ethyl 4-(but-3-en-1-yl)tetrahydro-2H-pyran-4-carboxylate (3.19 g). Yield 79%. $^1$H NMR (400 MHz, Chloroform-d) δ 5.82-5.69 (m, 1H), 5.04-4.91 (m, 2H), 4.19 (q, J=7.1 Hz, 2H), 3.87-3.78 (m, 2H), 3.53-3.39 (m, 2H), 2.14-2.05 (m, 2H), 2.02-1.92 (m, 2H), 1.66-1.59 (m, 2H), 1.55-1.45 (m, 2H), 1.28 (t, J=7.1 Hz, 3H).

Step 2: (4-(but-3-en-1-yl)tetrahydro-2H-pyran-4-yl)methanol

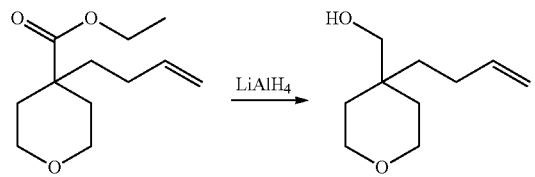

To a solution of ethyl 4-(but-3-en-1-yl)tetrahydro-2H-pyran-4-carboxylate (3.17 g, 14.9 mmol) in dry tetrahydrofuran (30 mL) under argon atmosphere at 0° C. was added lithium aluminium hydride in tetrahydrofuran (2.4 M, 6.22 mL, 14.9 mmol). The mixture was stirred at room temperature for 1 hour and quenched by slow addition of ethyl acetate (20 mL). The mixture was washed with 1M hydrochloric acid, the layers were separated and the water layer was extracted with ethyl acetate. The combined organic layers were washed with 1M hydrochloric acid and brine, dried over sodium sulfate and concentrated in vacuo. Purification by column chromatography (silica, 15% to 50% ethyl acetate in heptane afforded the desired product (4-(but-3-en-1-yl)tetrahydro-2H-pyran-4-yl)methanol (2.21 g). Yield 87%. ¹H NMR (400 MHz, Chloroform-d) δ 5.91-5.78 (m, 1H), 5.10-4.92 (m, 2H), 3.76-3.60 (m, 4H), 3.53 (s, 2H), 2.09-1.98 (m, 2H), 1.59-1.48 (m, 4H), 1.48-1.40 (m, 2H), 1.36 (br. s, 1H).

Step 3: (4-(but-3-en-1-yl)tetrahydro-1H-pyran-4-yl)methyl 4-methylbenzenesulfonate

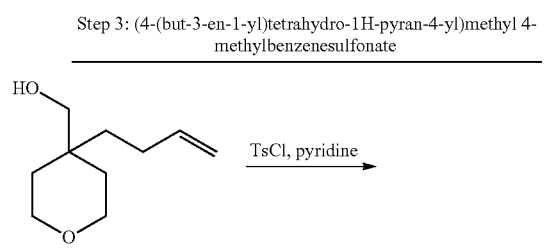

To a solution of (4-(but-3-en-1-yl)tetrahydro-2H-pyran-4-yl)methanol (1.75 g, 10.3 mmol) in dichloromethane (39 mL) at 0° C. was added pyridine (2.5 mL, 30.9 mmol) and p-toluenesulfonyl chloride (3.14 g, 16.5 mmol). The reaction mixture was stirred at room temperature for 4 days, concentrated in vacuo, diluted saturated aqueous sodium hydrogen carbonate and extracted three times with ethyl acetate. The combined organic layers were washed with brine, dried over sodium sulfate and concentrated in vacuo. Purification by column chromatography (silica, 10 to 30% ethyl acetate in heptane) afforded the desired product (4-(but-3-en-1-yl) tetrahydro-2H-pyran-4-yl)methyl 4-methylbenzenesulfonate (3.15 g). Yield 94%. ¹H NMR (400 MHz, Chloroform-d) δ 7.84-7.75 (m, 2H), 7.36 (d, J=8.0 Hz, 2H), 5.78-5.64 (m, 1H), 5.00-4.89 (m, 2H), 3.88 (s, 2H), 3.67-3.47 (m, 4H), 2.46 (s, 3H), 1.90-1.79 (m, 2H), 1.56-1.47 (m, 2H), 1.44 (t, J=5.6 Hz, 4H).

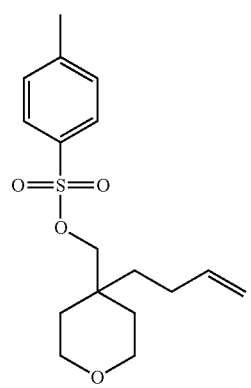

Step 4: (4-(3-oxopropyl)tetrahydro-2H-pyran-4-yl)methyl 4-methylbenzenesulfonate

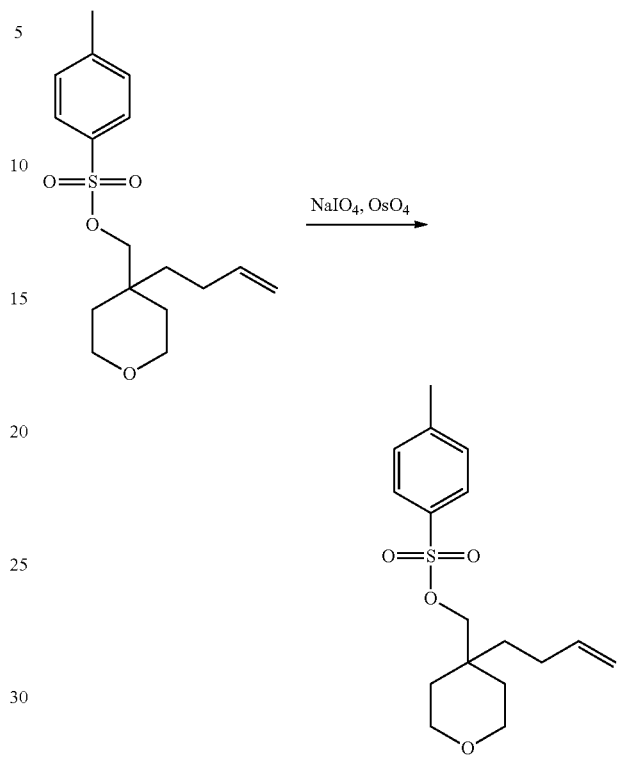

To a solution of (4-(but-3-en-1-yl)tetrahydro-2H-pyran-4-yl)methyl 4-methylbenzenesulfonate (3.15 g, 9.70 mmol) in tetrahydrofuran (74 mL) and water (24 mL) was added sodium periodate (5.19 g, 24.3 mmol) and osmium tetroxide solution (4 wt % in water, 9.9 mg, 0.04 mmol). The mixture was stirred at room temperature for 1.5 hours, diluted with water and extracted three times with ethyl acetate. The combined organic layers were washed with brine, dried over sodium sulfate and concentrated in vacuo. This afforded the desired product (4-(3-oxopropyl)tetrahydro-2H-pyran-4-yl) methyl 4-methylbenzenesulfonate (3.17 g). Yield 100%. ¹H NMR (400 MHz, Chloroform-d) δ 9.73 (d, J=1.7 Hz, 1H), 7.83-7.75 (m, 2H), 7.37 (d, J=8.1 Hz, 2H), 3.87 (s, 2H), 3.70-3.57 (m, 2H), 3.57-3.46 (m, 2H), 2.47 (s, 3H), 2.36-2.25 (m, 2H), 1.84-1.72 (m, 2H), 1.50-1.36 (m, 4H).

Step 5: (4-(3-(2-bromo-4-fluorophenyl)-3-hydroxypropyl)tetrahydro-2H-pyran-4-yl)methyl 4-methylbenzenesulfonate

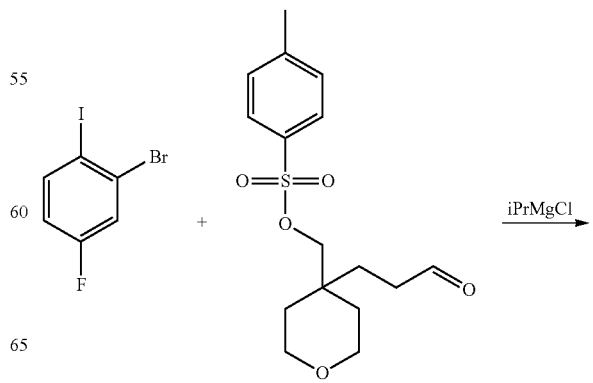

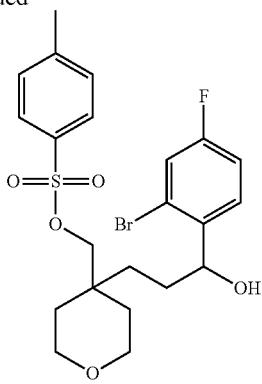

To a solution of 2-bromo-4-fluoroiodobenzene (1.66 mL, 12.8 mmol) in dry toluene (80 mL) at −18° C. under argon atmosphere was added isopropylmagnesium chloride (2M in THF, 6.37 mL, 12.7 mmol). After stirring for 20 minutes, a solution of (4-(3-oxopropyl)tetrahydro-2H-pyran-4-yl) methyl 4-methylbenzenesulfonate (3.2 g, 9.8 mmol) in dry tetrahydrofuran (50 mL) was added. The mixture was allowed to come to room temperature overnight, then quenched by pouring it into saturated aqueous ammonium chloride and extracted with ethyl acetate. The combined organic layers were washed with brine, dried over sodium sulfate and concentrated in vacuo. Purification by column chromatography (silica, 15% to 55% ethyl acetate in heptane) afforded the desired product (4-(3-(2-bromo-4-fluorophenyl)-3-hydroxypropyl)tetrahydro-2H-pyran-4-yl)methyl 4-methylbenzenesulfonate (3.1 g). Yield 63%. $^1$H NMR (400 MHz, Chloroform-d) δ 7.78 (d, J=8.0 Hz, 2H), 7.54-7.46 (m, 1H), 7.34 (d, J=8.0 Hz, 2H), 7.31-7.23 (m, 1H), 7.11-7.01 (m, 1H), 4.98-4.89 (m, 1H), 3.86 (s, 2H), 3.65-3.47 (m, 4H), 2.45 (s, 3H), 2.10 (d, J=4.0 Hz, 1H), 1.80-1.36 (m, 8H).

Step 6: 3-(2-bromo-4-fluorophenyl)-2,9-dioxaspiro[5.5]undecane

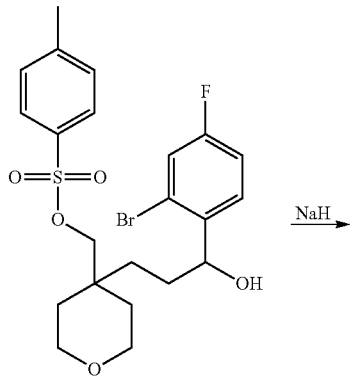

To a solution of (4-(3-(2-bromo-4-fluorophenyl)-3-hydroxypropyl)tetrahydro-2H-pyran-4-yl)methyl 4-methylbenzenesulfonate (3.1 g, 6.2 mmol) in dry tetrahydrofuran (250 mL) under argon atmosphere at room temperature was added sodium hydride (60% dispersion in mineral oil, 0.37 g, 9.3 mmol). The mixture was stirred at room temperature overnight, quenched with saturated aqueous ammonium chloride and extracted three times with ethyl acetate. The combined organic layers were washed with brine, dried over sodium sulfate and concentrated in vacuo. Purification by column chromatography (silica, 2% to 12% ethyl acetate in heptane) afforded the desired product 3-(2-bromo-4-fluorophenyl)-2,9-dioxaspiro[5.5]undecane (844 mg). Yield 42%. $^1$H NMR (400 MHz, Chloroform-d) δ 7.54-7.47 (m, 1H), 7.29-7.22 (m, 1H), 7.09-7.00 (m, 1H), 4.64-4.50 (m, 1H), 4.10-4.02 (m, 1H), 3.80-3.57 (m, 4H), 3.36 (d, J=11.5 Hz, 1H), 2.02-1.83 (m, 3H), 1.77-1.67 (m, 1H), 1.60-1.44 (m, 2H), 1.43-1.31 (m, 2H).

A racemic mixture of 3-(2-bromo-4-fluorophenyl)-2,9-dioxaspiro[5.5]undecane (1.165 gram) was separated by chiral preparative SFC. Apparatus: Waters Prep 100 SFC UV/MS directed system; Waters 2998 Photodiode Array (PDA) Detector; Waters Acquity QDa MS detector; Waters 2767 Sample Manager; Column: Phenomenex Lux Amylose-1 (250×21 mm, 5 μm), column temp: 35° C.; flow: 100 mL/min; ABPR: 120 bar; Eluent A: CO2, Eluent B: 20 mM Ammonia in Isopropanol; Isocratic method: 5% B for 4 min; Loading: 25 mg; Detection: PDA (210-400 nm); fraction collection based on PDA TIC.

The first eluting fraction (stereoisomer A, 0.43 g) was isolated as a white solid, yield 37%. RT: 1.44 min, 100% ee. Apparatus: Waters Acquity UPC$^2$ System; Column: Phenomenex Amylose-1 (100×4.6 mm, 5 μm), column temp: 35° C.; flow: 2.5 mL/min; BPR: 170 bar; Eluent A: CO2, Eluent B: 20 mM Ammonia in Isopropanol; Gradient method: t=0 min 5% B, t=5 min 15% B, t=6 min 15% B. Detection: PDA (210-320 nm). The second eluting fraction (stereoisomer B, 0.43 g) was isolated as a white solid, yield 37%. RT: 1.96 min, 96% ee. Apparatus: Waters Acquity UPC$^2$ System; Column: Phenomenex Amylose-1 (100×4.6 mm, 5 μm), column temp: 35° C.; flow: 2.5 mL/min; BPR: 170 bar; EluentA: CO$_2$, EluentB: 20 mM Ammonia in Isopropanol; Gradient method: t=0 min 5% B, t=5 min 15% B, t=6 min 15% B. Detection: PDA (210-320 nm).

Step 7: (-)-tert-butyl 2-(5-fluoro-2-(2,9-dioxaspiro[5.5]undecan-3-yl)phenyl)acetate steroisomer A

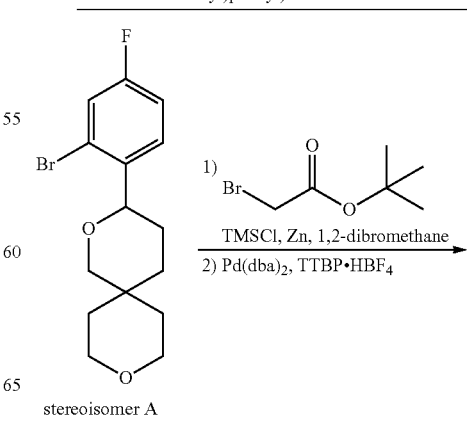

stereoisomer A 3.32 (d, J=11.4 Hz, 1H), 2.04-1.58 (m, 5H), 1.53-1.23 (m, 12H). Specific Optical Rotation: −41.2°, c=0.3, CHCl₃, 20.3° C., 589 nm.

Step 8: tert-butyl 2 bromo-2-(5fluoro-2-((S)-2,9-dioxaspiro[5.5]undecan-3-yl)pheneyl)acetate stereoisomer A

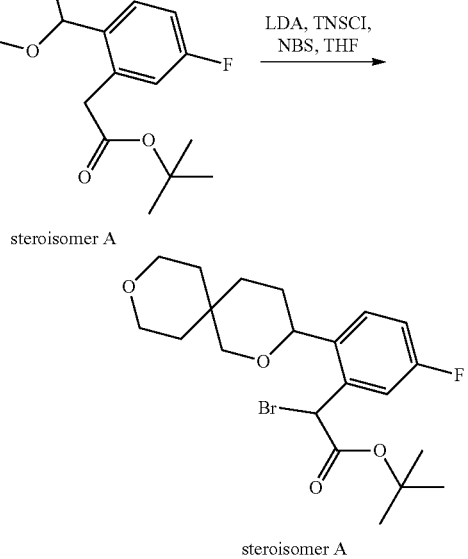

-continued

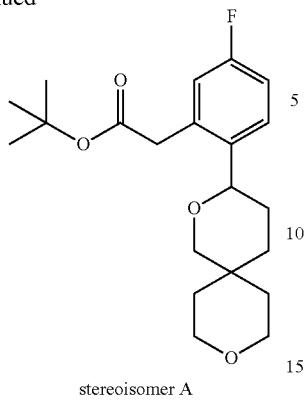

stereoisomer A

An oven dried flask was charged with zinc dust (0.342 g, 5.22 mmol) and heated with a heat gun under an argon flow. After cooling to room temperature, dry tetrahydrofuran (6 mL) was added followed by 1,2-dibromoethane (0.011 mL, 0.13 mmol). The mixture was heated to reflux and cooled to room temperature 3 times. Then, trimethylsilyl chloride (0.017 mL, 0.13 mmol) was added which caused the mixture to reflux spontaneously and the zinc to change morphology. After stirring for 20 minutes, tert-butyl bromoacetate (0.38 mL, 2.61 mmol) was added dropwise, resulting in an exotherm. The mixture was kept at an elevated temperature (45° C.) for 30 minutes and then allowed to cool to room temperature. A separate flask was charged with 3-(2-bromo-4-fluorophenyl)-2,9-dioxaspiro[5.5]undecane stereoisomer A (0.43 g, 1.31 mmol), tri-tert-butylphosphine tetrafluoroborate (0.038 g, 0.13 mmol) and bis-(dibenzylideneacetone) palladium (0.075 g, 0.13 mmol). The reaction vessel was flushed with argon, dry tetrahydrofuran (6 mL) was added and argon was bubbled through for five minutes. The zincate solution was added by syringe, and the reaction mixture was heated to reflux for 2 hours. The mixture was cooled to room temperature overnight, quenched with saturated aqueous ammonium chloride and extracted with ethyl acetate three times. The combined organic layers were dried over sodium sulfate and concentrated in vacuo. Purification by column chromatography (silica, 0% to 15% ethyl acetate in heptane) afforded the desired product (−)-tert-butyl 2-(5-fluoro-2-(2,9-dioxaspiro[5.5]undecan-3-yl)phenyl)acetate stereoisomer A (251 mg). Yield 53%. ¹H NMR (400 MHz, Chloroform-d) δ 7.45-7.38 (m, 1H), 7.01-6.91 (m, 2H), 4.42 (dd, J=11.3, 2.4 Hz, 1H), 4.03 (dd, J=11.4, 2.7 Hz, 1H), 3.78-3.49 (m, 6H), To a solution of tert-butyl 2-(5-fluoro-2-(2,9-dioxaspiro [5.5]undecan-3-yl)phenyl)acetate stereoisomer A (110 mg, 0.32 mmol) in THF (3 mL) at −78° C., was added lithium diisopropylamide solution 2.0 M in THF/hexanes (0.32 mL, 0.64 mmol) dropwise. The reaction was stirred at −78° C. for 30 min, then chlorotrimethylsilane (70 mg, 0.64 mmol) was added and the reaction was stirred at −78° C. for another 30 min. Then a solution of NBS (114 mg, 0.64 mmol) in THE (2 mL) was added and the reaction was stirred at −78° C. for 1 hour. The reaction was quenched with MeOH (2 mL), solvent was removed in vacuo, and the residue was purified by silica gel column (pet ether: EtOAc 10:1) to give the desired product tert-butyl 2-bromo-2-(5-fluoro-2-(2,9-dioxaspiro[5.5]undecan-3-yl)phenyl)acetate stereoisomer A as a yellow oil (120 mg). Yield 85% (ESI 465.0 (M+Na)+).

Step 9: tert-butyl 2-(5-fluoro-2-(2,9-dioxaspiro[5.5]undecan-3-yl)phenyl)-2-((R)-3-(4-5,6,7, 8-tetrahydro-1,8-naphthyridin-2-yl)butoxy)pyrrolidin-1-yl)acetate stereoisomer A

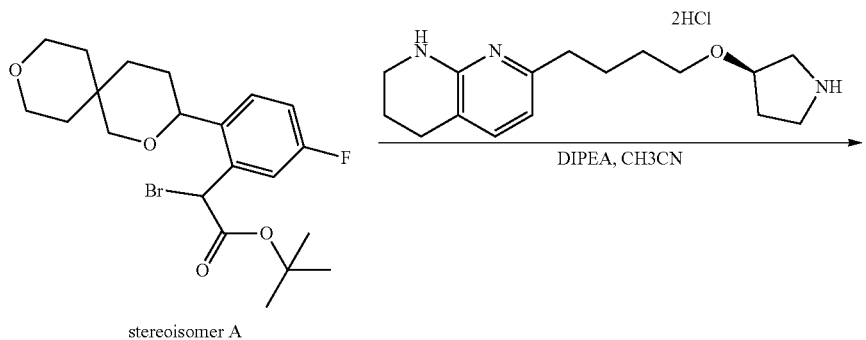

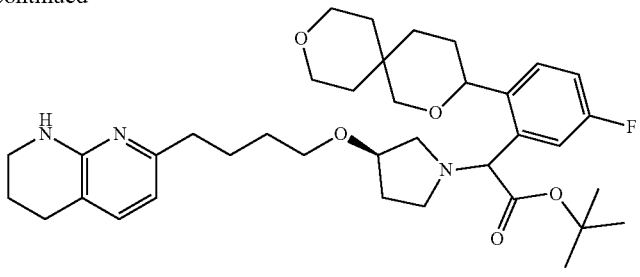

stereoisomer A

A mixture of tert-butyl 2-bromo-2-(5-fluoro-2-(2,9-dioxaspiro[5.5]undecan-3-yl)phenyl)acetate stereoisomer A (120 mg, 0.27 mmol), (R)-7-(4-(pyrrolidin-3-yloxy)butyl)-1,2,3,4-tetrahydro-1,8-naphthyridine (94 mg, 0.27 mmol) and DIPEA (95 mg, 0.74 mmol) in acetonitrile (8 mL) was stirred at rt for 3 hours. Solvent was removed in vacuo, and the residue was purified by silica gel column (DCM: MeOH 10:1) to give the desired product tert-butyl 2-(5-fluoro-2-(2,9-dioxaspiro[5.5]undecan-3-yl)phenyl)-2-((R)-3-(4-(5,6,7,8-tetrahydro-1,8-naphthyridin-2-yl)butoxy)pyrrolidin-1-yl)acetate stereoisomer A as a yellow oil (112 mg). Yield 65% (ESI 638.3 (M+H)+).

Step 10: 2-(5-fluoro-2-(2,9-dioxaspiro[5.5]undecan-3-yl(phenyl)-2-((R)-3-(4-(5,6,7,8-tetrahydro-1,8-naphthyridin-2-yl)butoxy)pyrroldin-1-yl)acetate stereoisomer A (compounds 102-A-e1 and 102-A-E2)

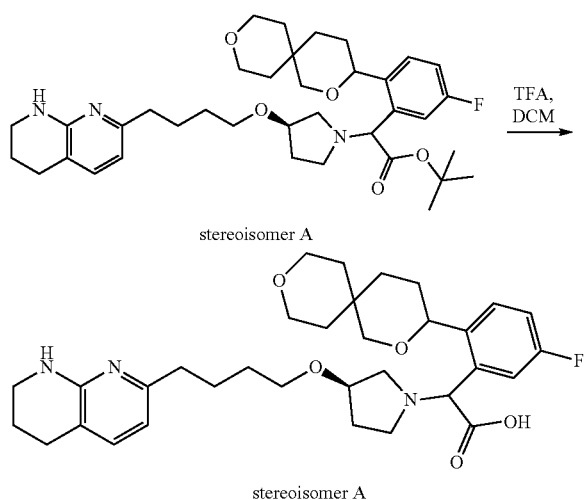

To a solution of 2-(5-fluoro-2-(2,9-dioxaspiro[5.5]undecan-3-yl)phenyl)-2-((R)-3-(4-(5,6,7,8-tetrahydro-1,8-naphthyridin-2-yl)butoxy)pyrrolidin-1-yl)acetate stereoisomer A (112 mg, 0.18 mmol) in DCM (5 mL) was added TFA (0.5 mL), then the mixture was stirred at RT for 18 hours. Solvent was removed in vacuo, and the residue was purified by Prep-HPLC A (30-65% MeCN) to give diastereomeric products 102-A-E1 (20 mg) and 102-A-E2 (11 mg) as white solids.

Compound 102-A-E1 LC/MS ESI 582.3 (M+H)+. 1H NMR (400 MHz, MeOD) δ 7.61 (dd, J=8.8, 5.9 Hz, 1H), 7.46 (dd, J=10.0, 2.7 Hz, 1H), 7.17 (t, J=7.6 Hz, 2H), 6.41 (d, J=7.3 Hz, 1H), 4.93 (s, 1H), 4.75 (d, J=10.7 Hz, 1H), 4.21 (s, 1H), 3.95 (dd, J=11.2, 2.3 Hz, 1H), 3.74-3.37 (m, 11H), 3.27 (s, 1H), 3.05 (s, 1H), 2.72 (t, J=6.2 Hz, 2H), 2.58 (t, J=7.6 Hz, 2H), 2.14-1.87 (m, 7H), 1.83-1.73 (m, 4H), 1.69-1.64 (m, 2H), 1.56-1.50 (m, 1H), 1.33-1.30 (m, 2H).

Compound 102-A-E2 LC/MS ESI 582.3 (M+H)+. 1H NMR (400 MHz, MeOD) δ 7.45 (dd, J=12.3, 6.2 Hz, 2H), 7.22 (d, J=7.0 Hz, 1H), 7.17-7.10 (m, 1H), 6.42 (d, J=7.3 Hz, 1H), 5.14 (s, 1H), 4.73 (d, J=12.9 Hz, 1H), 4.17 (s, 1H), 3.96 (d, J=11.8 Hz, 1H), 3.74-3.37 (m, 11H), 3.09-3.05 (m, 2H), 2.73 (t, J=6.3 Hz, 2H), 2.63-2.59 (m, 2H), 2.17-2.07 (m, 4H), 1.92-1.63 (m, 10H), 1.35-1.31 (m, 2H).

Step 11: 2-(5-fluoro-2-(2,9-dioxaspiro[5.5]undecan-3-yl)phenyl)-2-((R)-3-(4-(5,6,7,8-tetrahydro-1,8-naphthyridin-2-yl)butoxy)pyrrolidin-1-yl)acetic aid stereoisome B (compound 102-B)

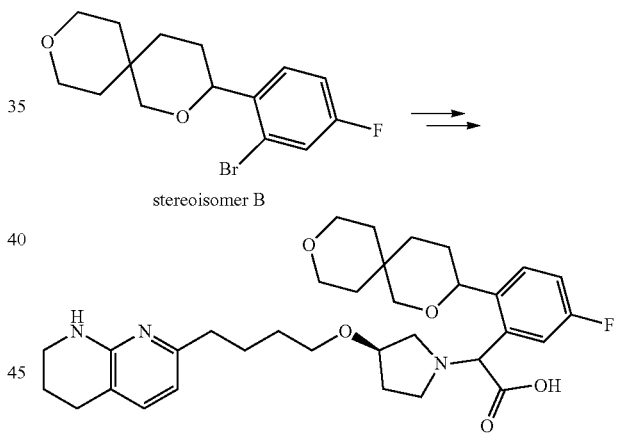

2-(5-fluoro-2-(2,9-dioxaspiro[5.5]undecan-3-yl)phenyl)-2-((R)-3-(4-(5,6,7,8-tetrahydro-1,8-naphthyridin-2-yl)butoxy)pyrrolidin-1-yl)acetic acid stereoisomer B (Compound 102-B) was prepared from 3-(2-bromo-4-fluorophenyl)-2,9-dioxaspiro[5.5]undecane stereoisomer B by the same methods as stereoisomer A.

Compound 102-B LC/MS ESI 582.3 (M+H)+. 1H NMR (400 MHz, MeOD) δ 7.63-7.60 (m, 1H), 7.50-7.47 (m, 1H), 7.25-7.17 (m, 2H), 6.43 (d, J=7.2 Hz, 1H), 4.93 (s, 1H), 4.87-4.77 (m, 1H), 4.19 (s, 1H), 3.96 (d, J=12.0 Hz, 1H), 3.71-3.39 (m, 11H), 3.21-3.18 (m, 2H), 2.73 (t, J=12.0 Hz, 2H), 2.60 (t, J=12 Hz, 2H), 2.18 (s, 2H), 2.06-2.05 (m, 1H), 1.96-1.91 (m, 4H), 1.89-1.52 (m, 7H), 1.35 (t, J=8.0 Hz, 2H).

Example 33: Preparation of 2-((R)-3-(4-(7,7-dimethyl-5,6,7,8-tetrahydro-1,8-naphthyridin-2-yl)butoxy)pyrrolidin-1-yl)-2-(5-fluoro-2-((S)-tetrahydro-2H-pyran-2-yl)phenyl)acetic Acid (Compounds 123-E1 and 123-E2)

Step 1: 4-(2,6-dichloropyridin-3-yl)-2-methylbut-3-yn-2-amine

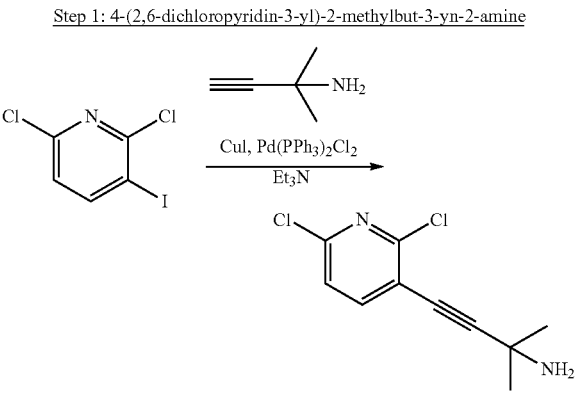

A solution of 2,6-dichloro-3-iodopyridine (4.48 g, 16.4 mmol) in anhydrous acetonitrile (36 mL) and triethylamine (36 mL, 259 mmol) was flushed with argon for 15 minutes. Then, 1,1-dimethyl-prop-2-ynylamine (1.78 mL, 18.0 mmol), copper(I) iodide (94 mg, 0.49 mmol) and bis(triphenylphosphine)palladium(II) dichloride (345 mg, 0.49 mmol) were added. The mixture was placed in a preheated oil bath at 60° C. for 1 hour, then cooled to room temperature, diluted with ethyl acetate, washed twice with water and with saturated aqueous sodium bicarbonate, dried over sodium sulfate and concentrated in vacuo. The residue was purified by column chromatography (silica, gradient 50% to 100% of (3% triethylamine in ethyl acetate) in heptane). to afford the desired 4-(2,6-dichloropyridin-3-yl)-2-methylbut-3-yn-2-amine (2.95 g) as a yellow-orange oil. Yield: 79%. $^1$H NMR (400 MHz, Chloroform-d) δ 7.66 (d, J=8.1 Hz, 1H), 7.22 (d, J=8.0 Hz, 1H), 1.70 (s, 2H), 1.51 (s, 6H).

Step 2: 4-(2,6-dichloropyridin-3-yl)-2-methylbutan-2-amine

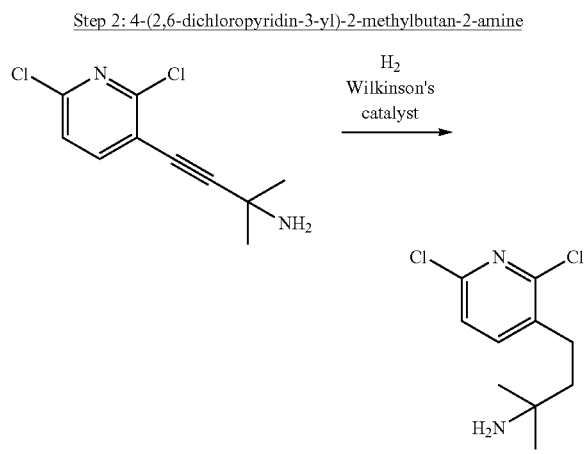

To a solution of 4-(2,6-dichloropyridin-3-yl)-2-methylbut-3-yn-2-amine (2.95 g, 12.9 mmol) in degassed ethanol (90 mL) was added Wilkinson's catalyst (1.19 g, 1.29 mmol). The mixture was flushed with hydrogen and stirred at 35° C. under 5 bar of hydrogen pressure for 3 days. The reaction mixture was concentrated in vacuo, and the residue was purified by column chromatography (silica, 10% to 15% ethyl acetate in heptane) to afford the desired 4-(2,6-dichloropyridin-3-yl)-2-methylbutan-2-amine (1.4 g) as a brown oil. Yield 47%. $^1$H NMR (400 MHz, Chloroform-d) δ 7.52 (d, J=7.9 Hz, 1H), 7.21 (d, J=7.9 Hz, 1H), 2.80-2.71 (m, 2H), 1.67-1.57 (m, 2H), 1.41 (s, 2H), 1.20 (s, 6H).

Step 3: 7-chloro-2,2-dimethyl-1,2,3,4-tetrahydro-1,8-naphthyridine

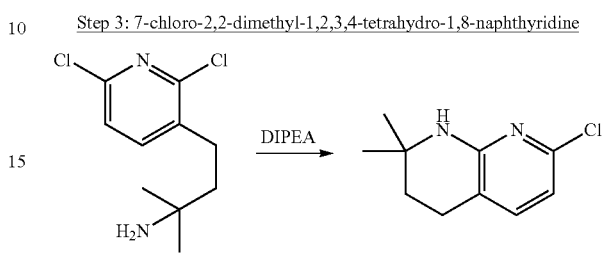

To a solution of 4-(2,6-dichloropyridin-3-yl)-2-methylbutan-2-amine (1.24 g, 4.2 mmol) in dry N,N-dimethylacetamide (40 mL) was added N,N-diisopropylethylamine (8.78 mL, 50.4 mmol). The mixture was heated to 120° C. for 2 days, cooled to room temperature, diluted with water (400 mL) and extracted with a 1:1 mixture of heptane and ethyl acetate three times. The combined organic extracts were washed twice with brine, dried over sodium sulfate and concentrated in vacuo. The residue was purified by column chromatography (silica, 5% to 15% ethyl acetate in heptane) to afford the desired 7-chloro-2,2-dimethyl-1,2,3,4-tetrahydro-1,8-naphthyridine (470 mg) as a light yellow oil which crystallised upon standing. Yield: 57%. $^1$H NMR (400 MHz, Chloroform-d) δ 7.12 (d, J=7.5 Hz, 1H), 6.48 (d, J=7.5 Hz, 1H), 4.78 (s, 1H), 2.70 (t, J=6.6 Hz, 2H), 1.67 (t, J=6.6 Hz, 2H), 1.24 (s, 6H).

Step 4: (R)-tert-butyl 3-(4-(7,7-dimethyl-5,6,7,8-tetrahydro-1,8-naphthyridin-2-yl)butoxy)pyrrolidine-1-carboxylate

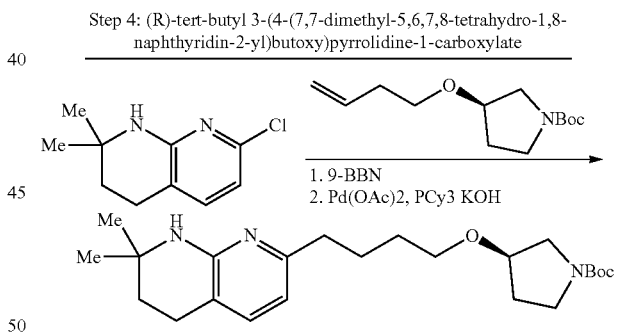

To a solution of (R)-tert-butyl 3-(but-3-enyloxy)pyrrolidine-1-carboxylate (796 mg, 3.3 mmol) in THF (dry, 3 mL) at room temperature under Ar was added 9-BBN solution (0.5M in THF, 13.2 mL, 6.6 mmol). The reaction was stirred at 50° C. for 2 hours, then cooled to room temperature. This solution was added to a mixture of 7-chloro-2,2-dimethyl-1,2,3,4-tetrahydro-1,8-naphthyridine (433 mg, 2.2 mmol), Pd(OAc)2 (25 mg, 0.11 mmol), PCy3 (62 mg, 0.22 mmol) and KOH (148 mg, 2.64 mmol) in THF (5 mL). The reaction mixture was stirred at 70° C. for 3 hours under Ar, then concentrated in vacuo, and the residue was purified by silica gel column (pet ether/EtOAc=30%100%) to give the desired product (R)-tert-butyl 3-(4-(7,7-dimethyl-5,6,7,8-tetrahydro-1,8-naphthyridin-2-yl)butoxy)pyrrolidine-1-carboxylate as a brown oil (764 mg). Yield 86% (ESI 404.2 (M+H)+).

Step 5: (R)-2,2-dimethyl-7-(4-(pyrrolidin-3-yloxy)butyl)-1,2,3,4-tetrahydro-1,8-napthyridine

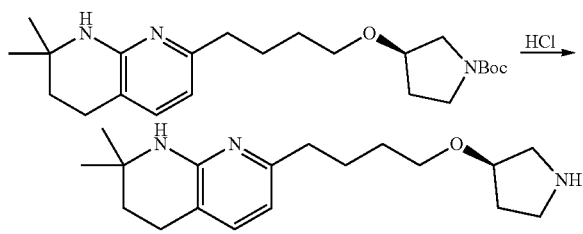

To a solution of (R)-tert-butyl 3-(4-(7,7-dimethyl-5,6,7,8-tetrahydro-1,8-naphthyridin-2-yl)butoxy)pyrrolidine-1-carboxylate (764 mg, 1.89 mmol) in MeOH (5 mL) was added HCl/dioxane (4M, 4.7 mL). The reaction was stirred at room temperature for 2 hours, then quenched with NH3/MeOH (7 N) to pH=7-8. Solvent was removed in vacuo, and the residue was purified by silica gel column (DCM: MeOH=10:1-4:1) to give the desired product (R)-2,2-dimethyl-7-(4-(pyrrolidin-3-yloxy)butyl)-1,2,3,4-tetrahydro-1,8-naphthyridine as an yellow oil (522 mg). Yield 91% (ESI 304.2 (M+H)+).

Step 6: tert-butyl 2-((R)-3-(4-(7,7-dimethyl-5,6,7,8-tetrahydro-1,8-naphthyridin-2-yl)butoxy)pyrrolidin-1-yl)-2-(5-fluoro-2-((S)-tetrahydro-2H-pyran-2-yl)phenyl)acetate

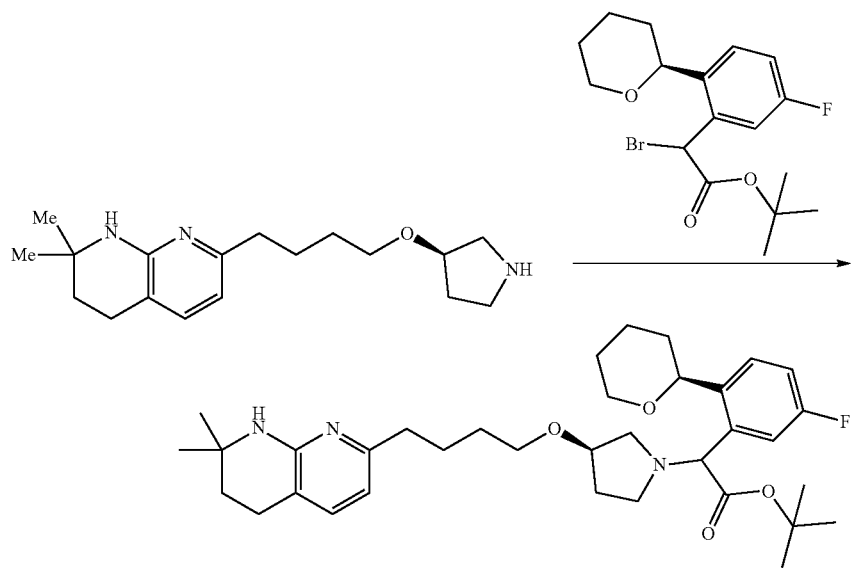

A mixture of (R)-2,2-dimethyl-7-(4-(pyrrolidin-3-yloxy)butyl)-1,2,3,4-tetrahydro-1,8-naphthyridine (405 mg, 1.33 mmol), tert-butyl 2-bromo-2-(5-fluoro-2-((S)-tetrahydro-2H-pyran-2-yl)phenyl)acetate (745 mg, 2.0 mmol) and DIPEA (517 mg, 4.0 mmol) in acetonitrile (12 mL) was stirred at room temperature for 2 hours. Solvent was removed in vacuo, and the residue was purified by silica gel column (DCM:MeOH=100:120:1) to give the desired product tert-butyl 2-((R)-3-(4-(7,7-dimethyl-5,6,7,8-tetrahydro-1,8-naphthyridin-2-yl)butoxy)pyrrolidin-1-yl)-2-(5-fluoro-2-((S)-tetrahydro-2H-pyran-2-yl)phenyl)acetate as a colorless oil (380 mg). Yield 48% (ESI 596.3 (M+H)+).

Step 7: 2-((R)-3-(4-(7,7-dimethyl-5,6,7,8-tetrahydro-1,8-naphthyridin-2-yl)butoxy)pyrrolidin-1-yl)-2-(5-fluoro-2-((S)-tetrahydro-2H-pyran-2-yl)phenyl)acetic acid (compounds 123-E1 and 123-E2)

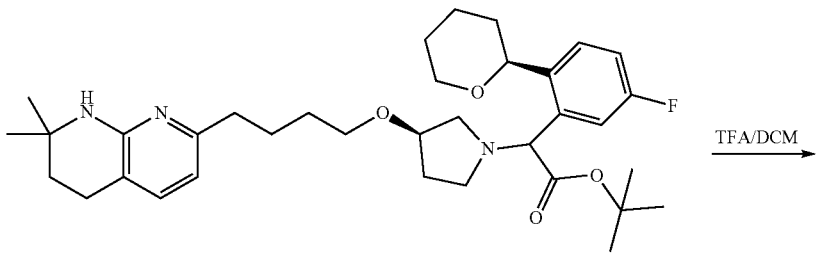

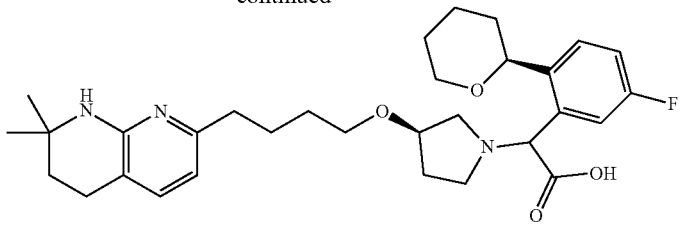

To a solution of tert-butyl 2-((R)-3-(4-(7,7-dimethyl-5,6,7,8-tetrahydro-1,8-naphthyridin-2-yl)butoxy)pyrrolidin-1-yl)-2-(5-fluoro-2-((S)-tetrahydro-2H-pyran-2-yl)phenyl)acetate (380 mg, 0.64 mmol) in DCM (4.0 mL) was added TFA (4.0 mL). The mixture was stirred at room temperature for 18 hours. Solvent was removed in vacuo, and the residue was purified by Prep-HPLC A (30-65% MeCN) to give compound 123-E1 (168 mg) and 123-E2 (25 mg) as white solids.

Compound 123-E1 LC/MS ESI 540.3 (M+H)$^+$. 1H NMR (400 MHz, MeOD) δ 7.60-7.56 (m, 1H), 7.48-7.44 (m, 1H), 7.25 (d, J=7.2 Hz, 1H), 7.18-7.14 (m, 1H), 6.42 (d, J=7.2 Hz, 1H), 4.91 (s, 1H), 4.76-4.75 (m, 1H), 4.19 (s, 1H), 4.04-4.02 (m, 1H), 3.71-3.24 (m, 6H), 3.06-3.03 (m, 1H), 2.74-2.74 (m, 2H), 2.60-2.56 (m, 2H), 2.14-1.98 (m, 4H), 1.79-1.62 (m, 10H), 1.26 (s, 6H).

Compound 123-E2 LC/MS ESI 540.3 (M+H)$^+$. 1H NMR (400 MHz, MeOD) δ 7.46-7.42 (m, 2H), 7.25 (d, J=7.2 Hz, 1H), 7.13-7.10 (m, 1H), 6.42 (d, J=7.2 Hz, 1H), 5.14 (s, 1H), 4.74-4.72 (m, 1H), 4.16-4.08 (m, 2H), 3.69-3.37 (m, 4H), 3.12-3.08 (m, 2H), 2.78-2.74 (m, 2H), 2.61-2.56 (m, 2H), 2.14-2.03 (m, 2H), 1.95-1.82 (m, 3H), 1.75-1.58 (m, 9H), 1.26-1.24 (m, 6H).

Example 34: Preparation of 2-(5-fluoro-2-((S)-tetrahydro-2H-pyran-2-yl)phenyl)-2-((R)-3-(4-(4-methoxy-7-methyl-5,6,7,8-tetrahydro-1,8-naphthyridin-2-yl)butoxy)pyrrolidin-1-yl)acetic Acid Me-Stereoisomer A (Compounds 124-A-E1, 124-A-E2 and 124-B-E1)

Step 1: 2,6-dichloro-4-methoxynicotinaldehyde

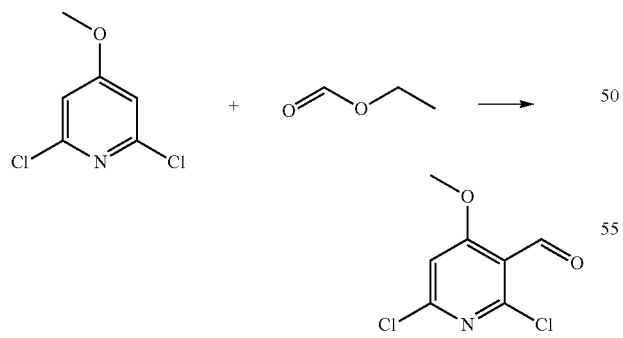

To a solution of 2,6-dichloro-4-methoxypyridine (3.49 g, 19.6 mmol) in dry tetrahydrofuran (100 mL) at −78° C. was added n-butyl lithium (2.5 M solution in hexanes, 8.63 mL, 21.6 mmol). After 30 minutes, ethyl formate (14.2 mL, 177 mmol) was added, and the mixture was stirred at −78° C. for an additional 15 minutes. The reaction was quenched with saturated aqueous ammonium chloride, warmed to room temperature, diluted with water and extracted three times with ethyl acetate. The combined organic layers were washed with brine, dried over sodium sulfate and concentrated in vacuo. Purification by flash column chromatography (silica, 5% to 40% ethyl acetate in heptane) afforded the desired product 2,6-dichloro-4-methoxynicotinaldehyde (1.83 g). Yield 45%. $^1$H NMR (400 MHz, Chloroform-d) δ 10.40 (s, 1H), 6.94 (s, 1H), 4.02 (s, 3H).

Step 2: 4-(2,6-dichloro-4-methoxypyridin-3-yl)but-3-en-2-one

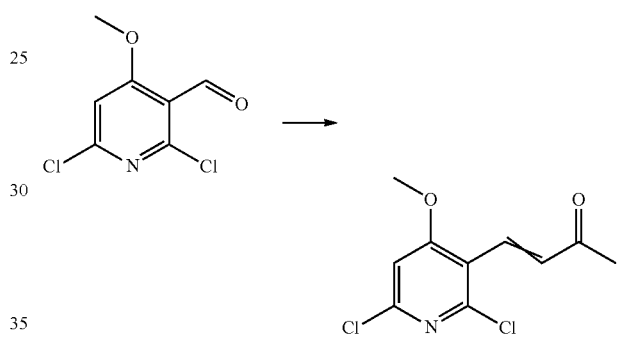

A mixture of 2,6-dichloro-4-methoxynicotinaldehyde (4.43 g, 21.5 mmol), acetonyltriphenylphosphonium chloride (8.01 g, 22.6 mmol), potassium carbonate (5.94 g, 43.0 mmol) and 18-crown-6 (5.68 g, 21.5 mmol) in toluene (150 mL) was heated to 80° C. for 2.5 hours. The mixture was allowed to cool to room temperature, diluted with water and extracted three times with ethyl acetate. The combined organic layers were washed with water and brine, dried over sodium sulfate and concentrated in vacuo. The residue was purified by flash column chromatography (silica, 5% to 40% ethyl acetate in heptane) to afford the desired product 4-(2,6-dichloro-4-methoxypyridin-3-yl)but-3-en-2-one (3.68 g). Yield 69%. $^1$H NMR (400 MHz, Chloroform-d) δ 7.66 (d, J=16.6 Hz, 1H), 7.07 (d, J=16.6 Hz, 1H), 6.88 (s, 1H), 4.00 (s, 3H), 2.40 (s, 3H).

Step 3: 4-(2,6-dichloro-4-methoxypyridin-3-yl)butan-2-one

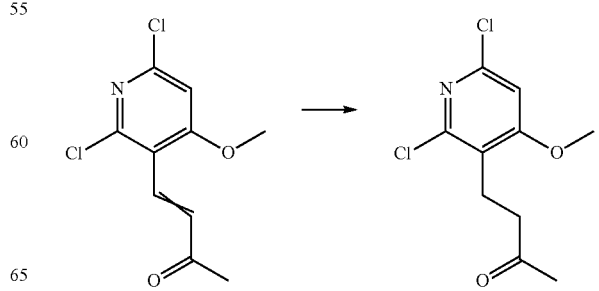

A mixture of 4-(2,6-dichloro-4-methoxypyridin-3-yl)but-3-en-2-one (4.4 g, 17.9 mmol) and Wilkinson's catalyst (716 mg, 1.79 mmol) in ethanol (160 mL) was subjected to 4 Bar hydrogen pressure in an autoclave for 6 hours. The solvent was removed in vacuo, and the residue was purified by flash column chromatography (silica, 5% to 40% ethyl acetate in heptane) to afford the desired product 4-(2,6-dichloro-4-methoxypyridin-3-yl)butan-2-one (3.76 g). Yield 85%. ¹H NMR (400 MHz, Chloroform-d) δ 6.76 (s, 1H), 3.90 (s, 3H), 3.05-2.87 (m, 2H), 2.71-2.53 (m, 2H), 2.19 (s, 3H).

Step 4: tert-butyl (4-(2,6-dichloro-4-methoxypyridin-3-yl)butan-2-yl)carbamate

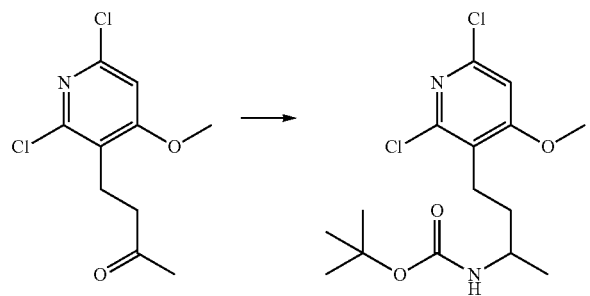

A mixture of 4-(2,6-dichloro-4-methoxypyridin-3-yl)butan-2-one (3.74 g, 15.1 mmol) and ammonium acetate (11.64 g, 151 mmol) in methanol (100 mL) was stirred for 30 minutes. Sodium cyanoborohydride (947 mg, 15.1 mmol) was added. After 2 hours, additional sodium cyanoborohydride (1.89 g, 30.1 mmol) was added, and the mixture was stirred at room temperature for 20 hours. The reaction mixture was quenched with sodium hydroxide (20 mL, 1N solution in water), diluted with water and extracted with ethyl acetate. The aqueous phase was saturated with sodium chloride and extracted three more times with ethyl acetate. The combined organic layers were dried over sodium sulfate and concentrated in vacuo. The residue was diluted with hydrochloric acid (1N solution in water) and washed three times with ethyl acetate. The aqueous layer was concentrated in vacuo, and the residue was dissolved in 1,4-dioxane (27 mL). A solution of sodium hydroxide (1.04 g, 26.1 mmol) in water (27 mL) and di-tertbutyl-dicarbonate (3.03 mL, 13.03 mmol) were added. After 3 hours, the reaction was diluted with water and extracted three times with ethyl acetate. The combined organic layers were dried over sodium sulfate and concentrated in vacuo. The residue was purified by flash column chromatography (silica, 5% to 40% ethyl acetate in heptane) to afford the desired product tert-butyl (4-(2,6-dichloro-4-methoxypyridin-3-yl)butan-2-yl)carbamate (1.48 g). Yield 28%. ¹H NMR (400 MHz, Chloroform-d) δ 6.75 (s, 1H), 4.38 (s, 1H), 3.89 (s, 3H), 3.71 (s, 1H), 2.84-2.61 (m, 2H), 1.71-1.37 (m, 11H), 1.17 (d, J=6.6 Hz, 3H).

Step 5: (4-(2,6-dichloro-4-methoxypyridin-3-yl)butan-2-amine hydrochloride

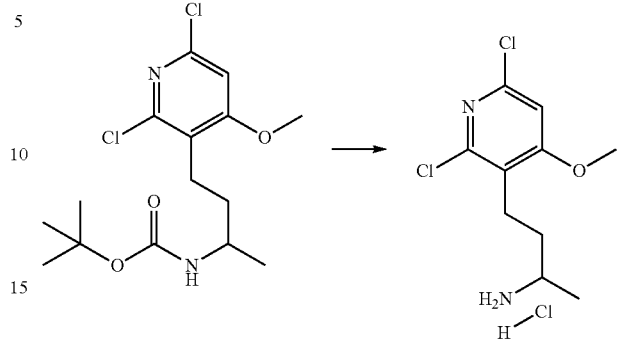

To a solution of tert-butyl (4-(2,6-dichloro-4-methoxypyridin-3-yl)butan-2-yl)carbamate (1.48 g, 4.23 mmol) in methanol (15 mL) was added hydrochloric acid in dioxane (4 M, 30 mL, 120 mmol). After 105 minutes, the mixture was concentrated in vacuo to afford the desired product 4-(2,6-dichloro-4-methoxypyridin-3-yl)butan-2-amine hydrochloride (1.21 g). Yield 100%. ¹H NMR (400 MHz, DMSO-d6) δ 8.07 (s, 3H), 7.28 (s, 1H), 3.95 (s, 3H), 3.22-3.09 (m, 1H), 2.75-2.59 (m, 2H), 1.88-1.72 (m, 1H), 1.65-1.51 (m, 1H), 1.26 (d, J=6.5 Hz, 3H).

Step 6: 7-chloro-5-methoxy-2-methyl-1,2,3,4-tetrahydro-1,8-naphthyridine

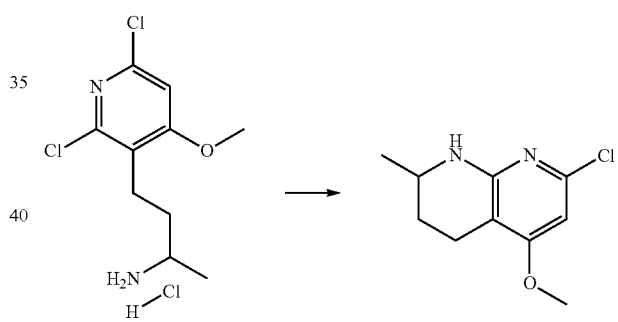

A mixture of 4-(2,6-dichloro-4-methoxypyridin-3-yl)butan-2-amine hydrochloride (1.59 g, 5.57 mmol) and potassium carbonate (2.31 g, 16.7 mmol) in 2-propanol (50 mL) was heated to 120° C. for 68 hours. The mixture was cooled to room temperature, diluted with water and extracted three times with ethyl acetate. The combined organic layers were dried over sodium sulfate and concentrated in vacuo to afford the desired product 7-chloro-5-methoxy-2-methyl-1,2,3,4-tetrahydro-1,8-naphthyridine (1.16 grams). Yield 98%. ¹H NMR (400 MHz, Chloroform-d) δ 6.19 (s, 1H), 4.65 (s, 1H), 3.80 (s, 3H), 3.55-3.38 (m, 1H), 2.77-2.65 (m, 1H), 2.51-2.35 (m, 1H), 1.99-1.86 (m, 1H), 1.55-1.39 (m, 1H), 1.21 (d, J=6.3 Hz, 3H).

A racemic mixture of 7-chloro-5-methoxy-2-methyl-1,2,3,4-tetrahydro-1,8-naphthyridine (1.16 gram) was separated by chiral preparative SFC. Apparatus: Waters Prep 100 SFC UV/MS directed system; Waters 2998 Photodiode Array (PDA) Detector; Waters Acquity QDa MS detector; Waters 2767 Sample Manager; Column: Phenomenex Lux Amylose-1 (250×21 mm, 5 µm); Column temp: 35° C.; Flow: 70 mL/min; ABPR: 120 bar; eluent A: CO2, eluent B: 20 mM ammonia in methanol; Linear gradient: t=0 min 10% B, t=5 min 50% B; t=7.5 min 50% B; Detection: PDA (210-400 nm); Fraction collection based on PDA TIC. The first eluting fraction (stereoisomer A, 425 mg) was isolated as a white solid, yield 36%. $t_R$: 2.078 min, 100% ee. Apparatus: Waters Acquity UPC$^2$: Waters ACQ-ccBSM Binary Pump; Waters ACQ-CCM Convergence Manager; Waters ACQ-SM Sample Manager-Fixed Loop; Waters ACQ-CM Column Manager-30S; Waters ACQ-PDA Photodiode Array Detector; Waters ACQ-ISM Make Up Pump, Waters Acquity QDa MS Detector; Column: Phenomenex Lux Amylose-1 (100× 4.6 mm, 5 μm; Column temp: 35° C.; Flow: 2.5 mL/min; ABPR: 170 bar; EluentA: CO2, Eluent B: 20 mM ammonia in methanol; Linear gradient: t=0 min 5% B, t=5 min 50% B; t=6 min 50% B; Detection: PDA (210-400 nm). Specific Optical Rotation: −59.9°, c=0.5, methanol, 21.4° C., 589 nm.

The second eluting fraction (stereoisomer B, 415 mg) was isolated as a white solid, yield 35%. $t_R$: 3.147 min, 99% ee. Apparatus: Waters Acquity UPC$^2$: Waters ACQ-ccBSM Binary Pump; Waters ACQ-CCM Convergence Manager; Waters ACQ-SM Sample Manager-Fixed Loop; Waters ACQ-CM Column Manager-30S; Waters ACQ-PDA Photodiode Array Detector; Waters ACQ-ISM Make Up Pump, Waters Acquity QDa MS Detector; Column: Phenomenex Lux Amylose-1 (100×4.6 mm, 5 μm; Column temp: 35° C.; Flow: 2.5 mL/min; ABPR: 170 bar; Eluent A: $CO_2$, Eluent B: 20 mM ammonia in methanol; Linear gradient: t=0 min 5% B, t=5 min 50% B; t=6 min 50% B; Detection: PDA (210-400 nm). Specific Optical Rotation: 72.4°, c=0.5, methanol, 21.5° C., 589 nm.

Step 7: tert-butyl 7-chloro-5-methyoxy-2-methyl-3,4-dihydro-1,8-naphthyridine-1(2H)-carboxylate stereoisomer A

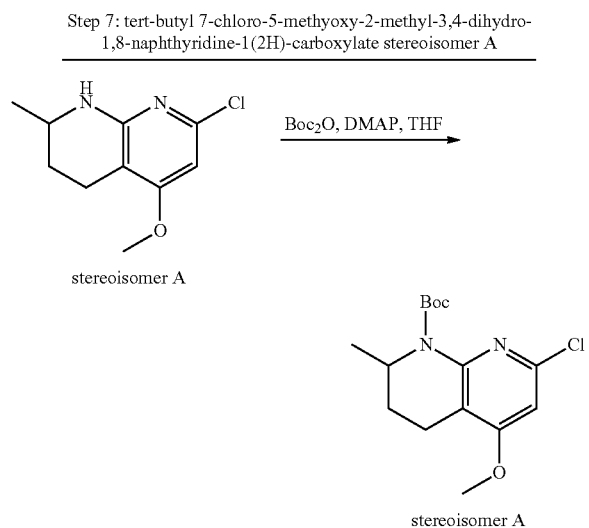

To a mixture of 7-chloro-5-methoxy-2-methyl-1,2,3,4-tetrahydro-1,8-naphthyridine stereoisomer A (190 mg, 0.89 mmol) in THF (8 mL) was added Boc2O (389 mg, 1.78 mmol) and DMAP (218 mg, 1.78 mmol). The reaction mixture was stirred at 60° C. for 16 hours, then quenched with saturated aqueous NH4Cl (20 mL) and extracted with EtOAc (3×20 mL). The combined organic phase was concentrated in vacuo, and the residue was purified by silica gel column (pet ether: EtOAc 10:1) to give the desired product tert-butyl 7-chloro-5-methoxy-2-methyl-3,4-dihydro-1,8-naphthyridine-1(2H)-carboxylate stereoisomer A as a yellow oil (260 mg). Yield 93% (ESI 313.0 (M+H)+).

Step 8: tert-butyl 7-(4-((R)-1-(tert-butoxycarbonyl)pyrrolidin-3-yloxy)butyl)-5-methyoxy-2-methyl-3,4-dihydro-1,8-naphthyridine-1(2H)-carboxylate stereoisomer A

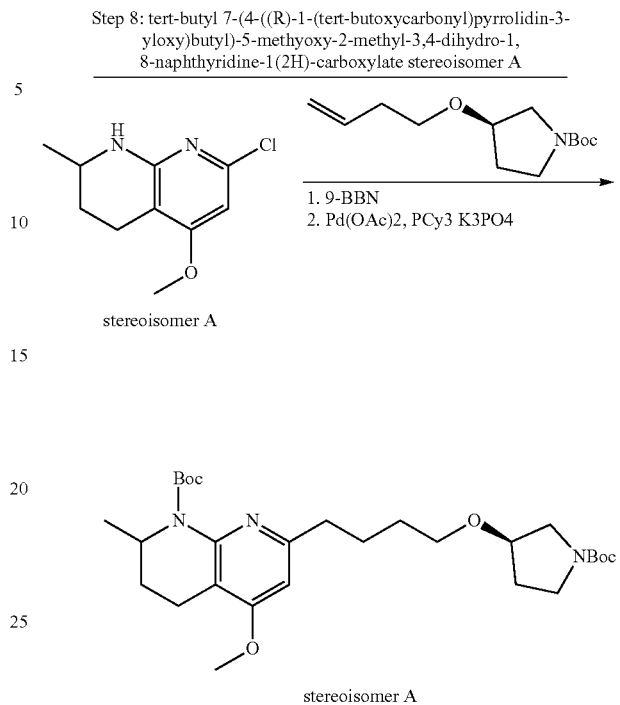

To a solution of (R)-tert-butyl 3-(but-3-enyloxy)pyrrolidine-1-carboxylate (403 mg, 1.67 mmol) in THF (dry, 4 mL) was added 9-BBN solution 0.5M in THF (3.34 mL, 1.67 mmol) at room temperature under Ar. The reaction was stirred at 50° C. for 2 hours, then cooled to room temperature. This solution was added to a mixture of tert-butyl 7-chloro-5-methoxy-2-methyl-3,4-dihydro-1,8-naphthyridine-1(2H)-carboxylate stereoisomer A (260 mg, 0.84 mmol), Pd(OAc)2 (10 mg, 0.042 mmol), PCy3 (23 mg, 0.084 mmol) and K3PO4.H$_2$O (533 mg, 2.51 mmol) in THF (5 mL). The reaction mixture was stirred at 70° C. for 3 hours under Ar. Solvent was removed in vacuo, and the residue was purified by silica gel column (pet ether/ EtOAc=10%50%) to give the desired product tert-butyl 7-(4-((R)-1-(tert-butoxycarbonyl)pyrrolidin-3-yloxy)butyl)-5-methoxy-2-methyl-3,4-dihydro-1,8-naphthyridine-1(2H)-carboxylate stereoisomer A as a yellow oil (350 mg). Yield 80% (ESI 520.0 (M+H)+).

Step 9: 5-methyoxy-2-methyl-7-(4-((R)-pyrrolodin-3-yloxy)butyl)-1,2,3,4-tetrahydro-1,8-naphthyridine stereoisomer A

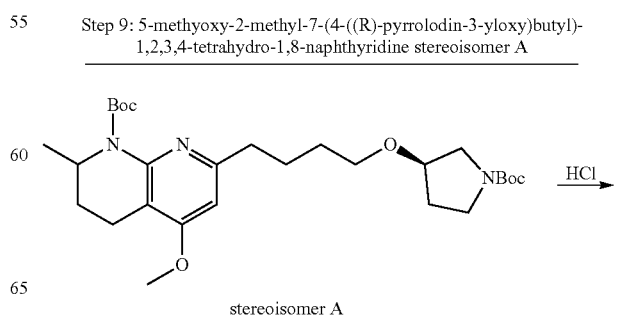

261

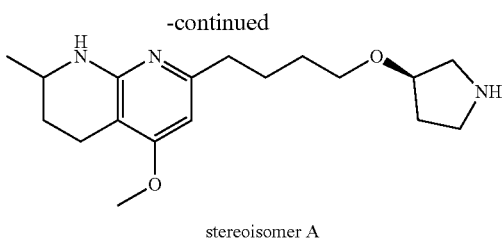

stereoisomer A

To a solution of tert-butyl 7-(4-((R)-1-(tert-butoxycarbonyl)pyrrolidin-3-yloxy)butyl)-5-methoxy-2-methyl-3,4-dihydro-1,8-naphthyridine-1(2H)-carboxylate stereoisomer A (350 mg, 0.67 mmol, 1.0 equiv) in DCM (6 mL) was added HCl solution (4.0 M in 1,4-dioxane, 1.8 mL, 5.36 mmol) dropwise. The reaction was stirred at 25° C. for 16 hours, then concentrated in vacuo to give the desired product 5-methoxy-2-methyl-7-(4-((R)-pyrrolidin-3-yloxy)butyl)-1,2,3,4-tetrahydro-1,8-naphthyridine stereoisomer A as a yellow oil (240 mg). Yield 93% (ESI 320.0 (M+H)+).

262

A mixture of 5-methoxy-2-methyl-7-(4-((R)-pyrrolidin-3-yloxy)butyl)-1,2,3,4-tetrahydro-1,8-naphthyridine stereoisomer A (240 mg, 0.61 mmol), tert-butyl 2-bromo-2-(5-fluoro-2-((S)-tetrahydro-2H-pyran-2-yl)phenyl)acetate (273 mg, 0.73 mmol) and DIPEA (236 mg, 1.83 mmol) in acetonitrile (8 mL) was stirred at 60° C. for 2 hours. Solvent was removed in vacuo, and the residue was purified by silica gel column (DCM: MeOH 10:1) to give the desired product tert-butyl 2-(5-fluoro-2-((S)-tetrahydro-2H-pyran-2-yl)phenyl)-2-((R)-3-(4-(4-methoxy-7-methyl-5,6,7,8-tetrahydro-1,8-naphthyridin-2-yl)butoxy)pyrrolidin-1-yl)acetate Me-stereoisomer A as a yellow oil (160 mg). Yield 42% (ESI 612.0 (M+H)+).

Step 11: 2-(5-fluoro-2-((S)-tetrahydro-2H-pyran-2-yl)phenyl)-2-((R)-3-(4-(4-methoxy-7-methyl-5,6,7,8-tetrahydro-1,8-naphthyridin-2-yl)butoxy)pyrrolidin-1-yl)acetic acid Me-stereoisomer A (compounds 124-A-E1 and 124-A-E2)

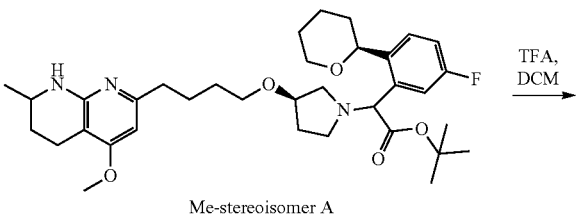

Me-stereoisomer A

Step 10: tert-butyl 2-(5-fluoro-2-((S)-tetrahydro-2H-pyran-2-yl)phenyl)-2-((R)-3-(4-(4-methyoxy-7-methyl-5,6,7,8-tetrahydro-1,8-naphthyridin-2-yl)butoxy)pyrrolidin-1-yl)acetate Me-stereoisomer A

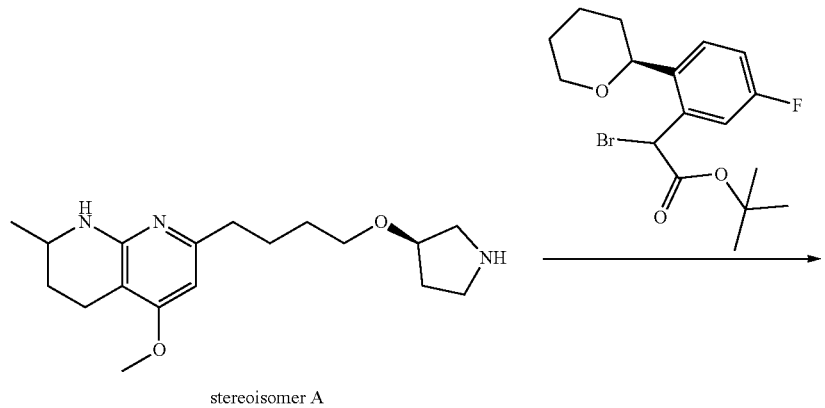

stereoisomer A

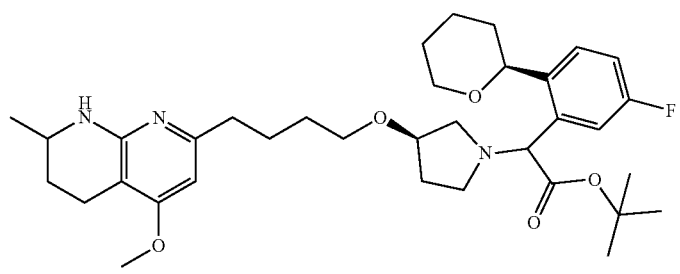

Me-stereoisomer A

-continued

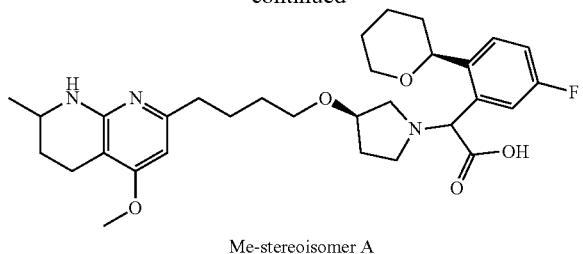

Me-stereoisomer A

To a solution of tert-butyl 2-(5-fluoro-2-((S)-tetrahydro-2H-pyran-2-yl)phenyl)-2-((R)-3-(4-(4-methoxy-7-methyl-5,6,7,8-tetrahydro-1,8-naphthyridin-2-yl)butoxy)pyrrolidin-1-yl)acetate Me-stereoisomer A (160 mg, 0.26 mmol) in DCM (5 mL) was added TFA (1 mL). The reaction was stirred at room temperature for 18 hours. Solvent was removed in vacuo, and the residue was purified by Prep-HPLC A (30-65% MeCN) to give compound 124-A-E1 (22 mg) and compound 124-A-E2 (2 mg) as white solids.

Compound 124-A-E1 LC/MS ESI 556.3 (M+H)+. $^1$H NMR (400 MHz, MeOD) δ 7.59-7.45 (m, 2H), 7.14-7.12 (m, 1H), 6.31 (s, 1H), 4.86 (s, 1H), 4.79 (d, J=9.0 Hz, 1H), 4.18 (s, 1H), 4.03 (d, J=11.4 Hz, 1H), 3.87 (s, 3H), 3.69-3.67 (m, 1H), 3.56-3.40 (m, 3H), 2.99-2.97 (m, 1H), 2.85-2.42 (m, 4H), 2.25-1.89 (m, 6H), 1.88-1.38 (m, 11H), 1.24 (d, J=6.3 Hz, 3H).

Compound 124-A-E2 LC/MS ESI 556.3 (M+H)+. $^1$H NMR (400 MHz, MeOD) δ 7.52-7.44 (m, 2H), 7.12-7.10 (m, 1H), 6.40 (s, 1H), 4.86-4.75 (m, 2H), 4.17-4.08 (m, 2H), 3.92 (s, 3H), 3.69-3.45 (m, 4H), 3.02-2.99 (m, 1H), 2.85-2.42 (m, 4H), 2.25-1.89 (m, 6H), 1.88-1.38 (m, 11H), 1.24 (d, J=6.3 Hz, 3H).

Step 12: Preparation of 2-(5-fluoro-2-((S)-tetrahydro-2H-pyran-2-yl)phenyl)-2-((R)-3-(4-(4-methoxy-7-methyl-5,6,7,8-tetrahydro-1,8-naphthyridin-2-yl)butoxy)pyrrolidin-1-yl)acetic acid Me-stereoisomer B (compound 124-B-E1)

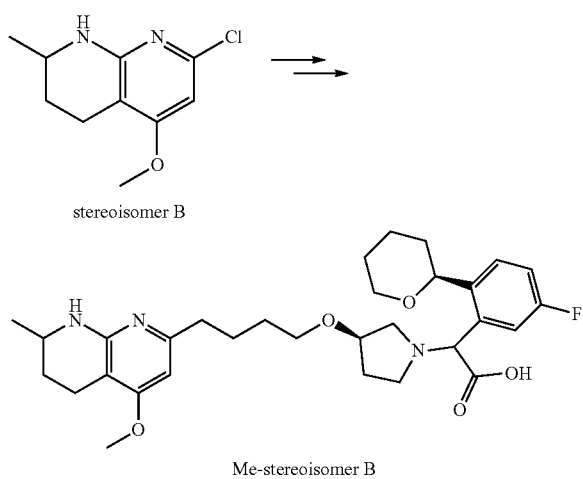

Me-stereoisomer B 2-(5-fluoro-2-((S)-tetrahydro-2H-pyran-2-yl)phenyl)-2-((R)-3-(4-(4-methoxy-7-methyl-5,6,7,8-tetrahydro-1,8-naphthyridin-2-yl)butoxy)pyrrolidin-1-yl)acetic acid Me-stereoisomer B (compound 124-B-E1) was synthesized from 7-chloro-5-methoxy-2-methyl-1,2,3,4-tetrahydro-1,8-naphthyridine stereoisomer B by the same procedures as for stereoisomer A.

Compound 124-B-E1 LC/MS ESI 556.3 (M+H)+. $^1$H NMR (400 MHz, MeOD) δ 7.57-7.54 (m, 1H), 7.49-7.46 (m, 1H), 7.11-7.10 (m, 1H), 6.30 (s, 1H), 4.81 (d, J=8.0 Hz, 1H), 4.73 (s, 1H), 4.15 (s, 1H), 4.05-4.02 (d, J=12.0 Hz, 1H), 3.87 (s, 3H), 3.73-3.68 (m, 1H), 3.51-3.45 (m, 3H), 3.39-3.36 (m, 1H), 3.30-3.22 (m, 1H), 3.12-3.10 (d, J=8.0 Hz, 1H), 2.91-2.86 (m, 1H), 2.76-2.71 (m, 1H), 2.62-2.59 (t, J=12.0 Hz, 2H), 2.52-2.45 (m, 1H), 2.09-1.93 (m, 5H), 1.82-1.60 (m, 8H), 1.51-1.43 (m, 1H), 1.25-1.23 (d, J=8.0 Hz, 3H).

Additional Examples

Compounds 22-91, 103-122, and 125-129 were prepared using general procedures based on the method used to prepare compounds 1-21, 92-102, and 123-124.

2-(2-(cyclopropylmethoxy)phenyl)-2-((R)-3-(4-(5,6,7,8-tetrahydro-1,8-naphthyridin-2-yl)butoxy)pyrrolidin-1-yl)acetic Acid (Diastereomeric Compounds 22-E1 and 22-E2)

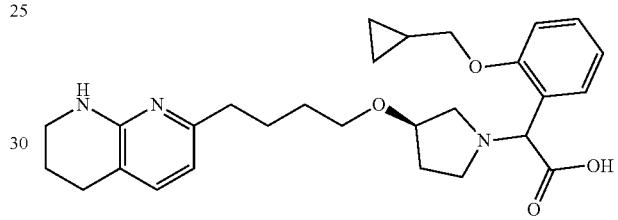

22-E1 LC/MS ESI 480.2 (M+H). $^1$H NMR (400 MHz, MeOD) δ 7.44 (d, J=7.2 Hz, 1H), 7.22 (t, J=8.0 Hz, 1H), 7.01 (d, J=7.2 Hz, 1H), 6.92-6.83 (m, 2H), 6.25 (d, J=7.2 Hz, 1H), 4.89 (s, 1H), 4.04 (s, 1H), 3.82-3.77 (m, 2H), 3.50-3.35 (m, 6H), 2.98-2.80 (m, 2H), 2.59 (t, J=6.4 Hz, 2H), 2.41 (t, J=7.2 Hz, 2H), 1.94-1.17 (m, 9H), 0.49-0.27 (m, 4H). Chiral SFC A (45% MeOH): ee 100%, Rt=2.06 min.

22-E2 LC/MS ESI 480.2 (M+H)+. $^1$H NMR (400 MHz, MeOD) δ 7.44 (d, J=6.4 Hz, 1H), 7.23 (t, J=8.0 Hz, 1H), 7.01 (d, J=7.6 Hz, 1H), 6.92-6.83 (m, 2H), 6.24 (d, J=7.6 Hz, 1H), 4.89 (s, 1H), 4.04 (s, 1H), 3.82-3.77 (m, 2H), 3.45-3.35 (m, 6H), 2.98-2.90 (m, 2H), 2.59 (t, J=6.4 Hz, 2H), 2.41 (t, J=7.2 Hz, 2H), 1.94-1.17 (m, 9H), 0.49-0.27 (m, 4H). Chiral SFC A (45% MeOH): ee 100%, Rt=4.49 min.

2-(2-cyclopropyl-4-fluorophenyl)-2-((R)-3-(4-(5,6,7,8-tetrahydro-1,8-naphthyridin-2-yl)butoxy)pyrrolidin-1-yl)acetic Acid (Diastereomeric Compounds 23-E1 and 23-E2)

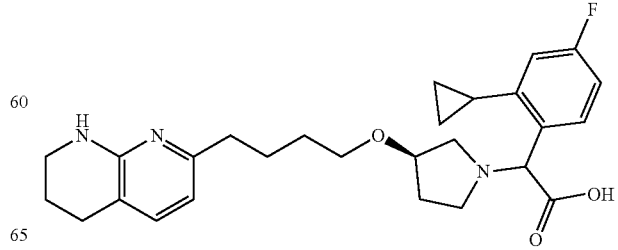

Compound 23-E1 LC/MS ESI 468.6 (M+H)+. ¹H NMR (400 MHz, MeOD) δ 7.54 (d, J=8.5 Hz, 1H), 7.06 (d, J=7.3 Hz, 1H), 6.93-6.69 (m, 2H), 6.27 (d, J=7.3 Hz, 1H), 5.05 (s, 1H), 4.07 (s, 1H), 3.47-3.25 (m, 5H), 3.21-3.13 (m, 2H), 2.60 (t, J=6.2 Hz, 2H), 2.44 (t, J=7.5 Hz, 2H), 2.23-2.01 (m, 3H), 1.85-1.71 (m, 2H), 1.66-1.44 (m, 4H), 1.02-0.78 (m, 3H), 0.54-0.52 (m, 1H). Chiral SFC A (45% MeOH): ee 100%, Rt=3.11 min.

Compound 23-E2 LC/MS ESI 468.6 (M+H)+. ¹H NMR (400 MHz, MeOD) δ 7.53 (d, J=8.4, 1H), 7.03 (d, J=7.3 Hz, 1H), 6.88-6.64 (m, 2H), 6.27 (d, J=7.3 Hz, 1H), 4.95 (s, 1H), 4.06 (s, 1H), 3.50-3.22 (m, 5H), 3.06-2.71 (m, 3H), 2.60 (t, J=6.2 Hz, 2H), 2.42 (t, J=7.5 Hz, 2H), 2.22-2.04 (m, 1H), 2.05-1.95 (m, 2H), 1.85-1.69 (m, 2H), 1.68-1.39 (m, 4H), 0.96-0.72 (m, 3H), 0.46-0.42 (m, 1H). Chiral SFC A (45% MeOH): ee 100%, Rt=2.31 min.

2-(2-cyclopropylphenyl)-2-((R)-3-(5-(5,6,7,8-tetrahydro-1,8-naphthyridin-2-yl)pentyl)pyrrolidin-1-yl)acetic Acid(Diastereomeric Compounds 24-E1 and 24-E2)

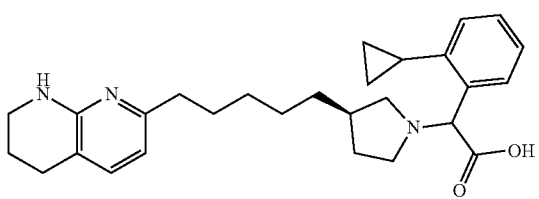 [SMILES: O=C(O)C(c1ccccc1C1CC1)N1CC[C@@H](CCCCCc2ccc3c(n2)NCCC3)C1]

Compound 24-E1 LC/MS ESI 447 (M+H)+ ¹H NMR (400 MHz, MeOD) δ 7.61 (d, J=8.0 Hz, 1H), 7.32-7.25 (m, 2H), 7.16-7.10 (m, 2H), 6.33 (d, J=7.2 Hz, 1H), 5.25 (s, 1H), 3.75-3.36 (m, 3H), 3.33-3.31 (m, 2H), 2.71-2.68 (m, 3H), 2.51-2.18 (m, 5H), 1.90-1.84 (m, 2H), 1.68-1.58 (m, 3H), 1.46-1.33 (m, 6H), 1.09-1.07 (m, 3H), 0.59-0.55-(m, 1H).

Compound 24-E2 LC/MS ESI 447 (M+H)+ ¹H NMR (400 MHz, MeOD) δ 7.61 (d, J=8.0 Hz 1H), 7.33-7.24 (m, 2H), 7.16-7.10 (m, 2H), 6.34 (d, J=7.2 Hz, 1H), 5.24 (s, 1H), 3.85-3.36 (m, 3H), 3.33-3.11 (m, 2H), 2.81-2.68 (m, 3H), 2.52-2.17 (m, 5H), 1.91-1.85 (m, 2H), 1.72-1.3 (m, 9H), 1.11-1.00 (m, 3H), 0.58-0.54 (m, 1H).

2-(2-isopropoxyphenyl)-2-((R)-3-(4-(5,6,7,8-tetrahydro-1,8-naphthyridin-2-yl)butoxy) pyrrolidin-1-yl)acetic Acid (Compound 25)

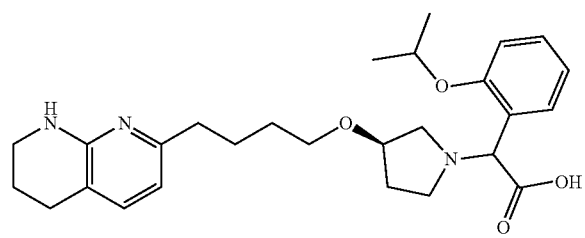 [SMILES: CC(C)Oc1ccccc1C(C(=O)O)N1CC[C@@H](OCCCCc2ccc3c(n2)NCCC3)C1]

Compound 25 LC/MS ESI 468.2 (M+H)+. ¹H NMR (400 MHz, MeOD) δ 7.53-7.35 (m, 2H), 7.14 (d, J=7.2 Hz, 1H), 7.08 (d, J=8.4 Hz, 1H), 6.97 (t, J=7.6 Hz, 1H), 6.39-6.36 (m, 1H), 5.10-4.90 (m, 1H), 4.74-4.72 (m, 1H), 4.25 (s, 1H), 3.55-3.35 (m, 6H), 3.28-3.02 (m, 2H), 2.71 (t, J=6.0 Hz, 2H), 2.20-1.51 (m, 8H), 1.40-1.35 (m, 6H).

2-(4-cyclopropylpyridin-3-yl)-2-((R)-3-(5-(5,6,7,8-tetrahydro-1,8-naphthyridin-2-yl)pentyl)pyrrolidin-1-yl)acetic Acid (Compound 26)

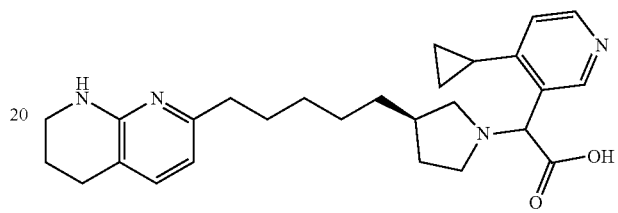

Compound 26 LC/MS ESI 449.4 (M+H)+. ¹H NMR (400 MHz, MeOD) δ 8.73 (d, J=4.4 Hz, 1H), 8.36 (t, J=5.6 Hz, 1H), 7.13-7.10 (m, 1H), 7.01 (d, J=5.2 Hz, 1H), 6.37-6.33 (m, 1H), 5.02-4.95 (m, 1H), 3.65-3.35 (m, 3H), 3.25-2.95 (m, 2H), 2.75-2.65 (m, 3H), 2.55-2.10 (m, 5H), 1.91-1.85 (m, 2H), 1.70-1.60 (m, 3H), 1.50-1.18 (m, 8H), 1.06-1.03 (m, 1H), 0.78-0.74 (m, 1H).

2-(2-cyclopropylphenyl)-2-((S)-3-(4-(5,6,7,8-tetrahydro-1,8-naphthyridin-2-yl)butoxy)pyrrolidin-1-yl)acetic Acid (Diastereomeric Compounds 27-E1 and 27-E2)

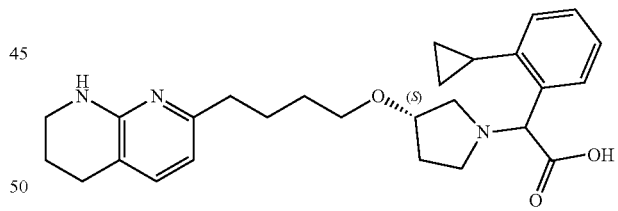

Compound 27-E1 LC/MS ESI 450.2 (M+H). ¹H NMR (400 MHz, MeOD) δ 7.61 (d, J=7.6 Hz, 1H), 7.31-7.14 (m, 4H), 6.37 (d, J=7.2 Hz, 1H), 5.26 (s, 1H), 4.17 (s, 1H), 3.60-3.25 (m, 8H), 2.71 (t, J=6.4 Hz, 2H), 2.54 (t, J=7.2 Hz, 2H), 2.20-1.55 (m, 9H), 1.00-0.90 (m, 3H), 0.58-0.55 (m, 1H). Chiral SFC A (35% MeOH): ee 100%, Rt=3.45 min.

Compound 27-E2 LC/MS ESI 450.2 (M+H)+. ¹H NMR (400 MHz, MeOD) δ 7.60 (d, J=7.6 Hz, 1H), 7.33-7.13 (m, 4H), 6.37 (d, J=7.2 Hz, 1H), 5.31 (s, 1H), 4.22 (s, 1H), 3.60-3.05 (m, 8H), 2.71 (t, J=6.4 Hz, 2H), 2.54 (t, J=7.2 Hz, 2H), 2.20-1.55 (m, 9H), 1.00-0.92 (m, 3H), 0.58-0.55 (m, 1H). Chiral SFC A (35% MeOH): ee 100%, Rt=4.18 min.

2-((R)-3-(4-(5,6,7,8-tetrahydro-1,8-naphthyridin-2-yl)butoxy)pyrrolidin-1-yl)-2-(2-(2,2,2-trifluoroethoxy)phenyl)acetic Acid (Compound 28)

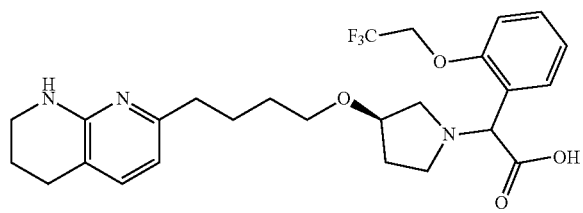 [SMILES: O=C(O)C(c1ccccc1OCC(F)(F)F)N1CC[C@@H](OCCCCc2ccc3c(n2)NCCC3)C1]

Compound 28 LC/MS ESI 508.4 (M+H). $^1$H NMR (400 MHz, MeOD) δ 7.64-7.60 (m, 1H), 7.45-7.43 (m, 1H), 7.18-7.12 (m, 3H), 6.38-6.35 (m, 1H), 5.10-4.95 (m, 1H), 4.72-4.60 (m, 2H), 4.17 (s, 1H), 3.60-3.35 (m, 6H), 3.20-3.00 (m, 2H), 2.75-2.68 (m, 2H), 2.56-2.50 (m, 2H), 2.43-1.85 (m, 4H), 1.75-1.50 (m, 4H).

2-(2-isobutoxyphenyl)-2-((R)-3-(4-(5,6,7,8-tetrahydro-1,8-naphthyridin-2-yl)butoxy) pyrrolidin-1-yl)acetic Acid (Diastereomeric Compounds 29-E1 and 29-E2)

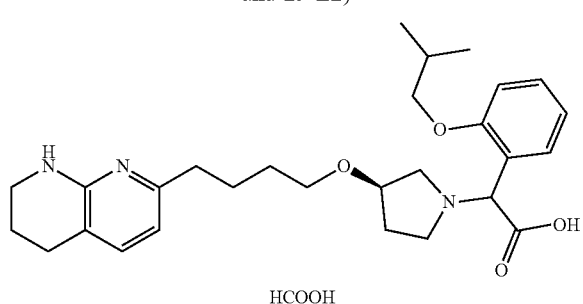

HCOOH

Compound 29-E1 LC/MS ESI 482.4 (M+H)+. $^1$H NMR (400 MHz, MeOD) δ 8.54 (s, 1H), 7.54 (d, J=7.6 Hz, 1H), 7.46-7.38 (m, 2H), 7.12-7.02 (m, 2H), 6.51 (d, J=7.6 Hz, 1H), 5.25 (s, 1H), 4.18 (s, 1H), 3.87-3.80 (m, 2H), 3.64-3.32 (m, 7H), 3.12-3.06 (m, 1H), 2.82-2.57 (m, 4H), 2.18-1.57 (m, 9H), 1.10-1.02 (m, 6H).

Compound 29-E2 LC/MS ESI 482.4 (M+H)+. $^1$H NMR (400 MHz, MeOD) δ 8.54 (s, 1H), 7.53 (d, J=7.6 Hz, 1H), 7.46-7.38 (m, 2H), 7.10-7.01 (m, 2H), 6.49 (d, J=7.6 Hz, 1H), 5.05 (s, 1H), 4.21 (s, 1H), 3.87-3.85 (m, 2H), 3.60-3.22 (m, 8H), 2.82-2.57 (m, 4H), 2.22-1.57 (m, 9H), 1.10-1.02 (m, 6H).

2-(2-isopropoxypyridin-3-yl)-2-((R)-3-(5-(5,6,7,8-tetrahydro-1,8-naphthyridin-2-yl)pentyl)pyrrolidin-1-yl)acetic Acid (Diastereomeric Compounds 30-E1 and 30-E2)

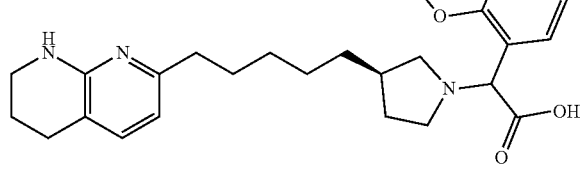

Compound 30-E1 LC/MS ESI 467.2 (M+H)+. $^1$H NMR (400 MHz, MeOD) δ 8.21-8.19 (m, 1H), 7.91-7.88 (m, 1H), 7.12 (d, J=7.6 Hz, 1H), 7.02-6.98 (m, 1H), 6.34 (d, J=7.2 Hz, 1H), 5.45-5.41 (m, 1H), 3.55-3.36 (m, 3H), 3.25-2.95 (m, 3H), 2.70 (t, J=6.4 Hz, 2H), 2.49 (t, J=7.6 Hz, 2H), 2.45-2.15 (m, 2H), 1.91-1.85 (m, 2H), 1.69-1.59 (m, 3H), 1.42-1.33 (m, 13H).

Compound 30-E2 LC/MS ESI 467.2 (M+H)+. $^1$H NMR (400 MHz, MeOD) δ 8.21-8.19 (m, 1H), 7.92-7.89 (m, 1H), 7.12 (d, J=7.6 Hz, 1H), 7.02-6.98 (m, 1H), 6.35 (d, J=7.2 Hz, 1H), 5.45-5.39 (m, 1H), 3.60-3.36 (m, 3H), 3.18-3.13 (m, 1H), 2.85-2.65 (m, 3H), 2.53-2.35 (m, 3H), 2.21-2.17 (m, 1H), 1.91-1.85 (m, 2H), 1.71-1.58 (m, 3H), 1.48-1.32 (m, 13H).

2-(2-cyclopropylphenyl)-2-((S)-3-(5-(5,6,7,8-tetrahydro-1,8-naphthyridin-2-yl)pentyloxy)pyrrolidin-1-yl)acetic Acid (Diastereomeric Compounds 31-E1 and 31-E2)

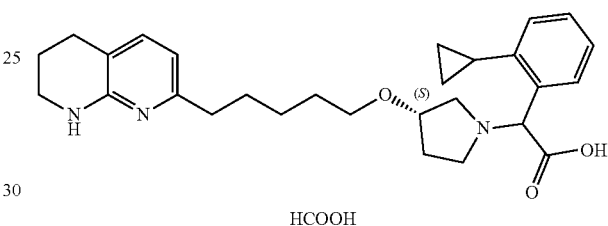

HCOOH

Compound 31-E1 LC/MS ESI 464.3 (M+H)+. $^1$H NMR (400 MHz, MeOD) δ 8.48 (s, 1H), 7.71-7.29 (m, 4H), 7.20 (d, J=7.6 Hz, 1H), 6.53 (d, J=7.2 Hz, 1H), 5.62 (s, 1H), 4.22 (s, 1H), 3.60-3.05 (m, 8H), 2.83-2.65 (m, 4H), 2.38-2.05 (m, 3H), 1.96-1.48 (m, 8H), 1.15-0.90 (m, 3H), 0.58-0.55 (m, 1H).

Compound 31-E2 LC/MS ESI 464.3 (M+H)+. $^1$H NMR (400 MHz, MeOD) δ 8.48 (s, 1H), 7.68 (d, J=6.8 Hz, 1H), 7.45 (d, J=7.6 Hz, 1H), 7.39-7.19 (m, 3H), 6.52 (d, J=7.2 Hz, 1H), 5.33 (s, 1H), 4.22 (s, 1H), 3.58-3.05 (m, 8H), 2.81-2.62 (m, 4H), 2.45-1.78 (m, 8H), 1.56-1.42 (m, 3H), 1.15-0.90 (m, 3H), 0.58-0.55 (m, 1H).

2-(4-isopropylpyrimidin-5-yl)-2-((R)-3-(5-(5,6,7,8-tetrahydro-1,8-naphthyridin-2-yl)pentyl)pyrrolidin-1-yl)acetic Acid (Compound 32)

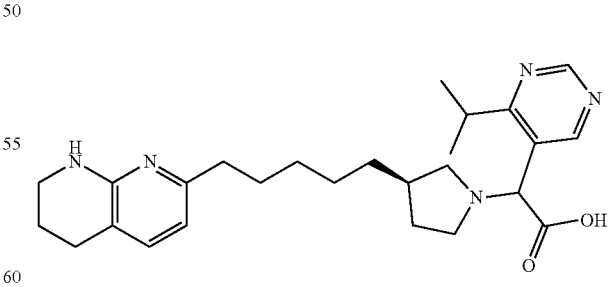

Compound 32 LC/MS ESI 452.6 (M+H)+. $^1$H NMR (400 MHz, MeOD) δ 8.99-8.94 (m, 2H), 7.26 (d, J=6.8 Hz, 1H), 6.41 (d, J=7.2 Hz, 1H), 4.67-4.62 (m, 1H), 3.71-3.69 (m, 1H), 3.47-3.32 (m, 4H), 3.16-2.85 (m, 2H), 2.73-2.63 (m, 5H), 2.41-2.03 (m, 2H), 1.96-1.80 (m, 2H), 1.73-1.52 (m, 3H), 1.52-1.24 (m, 12H).

2-(2-cyclobutoxyphenyl)-2-((R)-3-(4-(5,6,7,8-tetrahydro-1,8-naphthyridin-2-yl)butoxy)pyrrolidin-1-yl) acetic Acid (Diastereomeric Compounds 33-E1 and 33-E2)

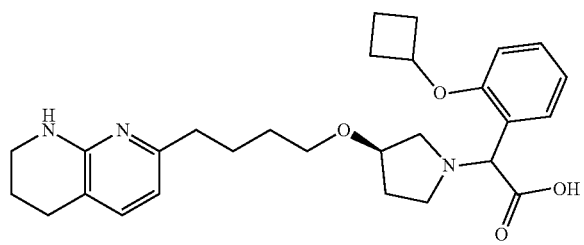 [SMILES: O=C(O)C(c1ccccc1OC1CCC1)N1CC[C@@H](OCCCCc2ccc3c(n2)NCCC3)C1]

Compound 33-E1 LC/MS ESI 480.4 (M+H)+. ¹H NMR (400 MHz, MeOD) δ 7.50 (d, J=6.8 Hz, 1H), 7.38-7.33 (m, 1H), 7.13 (d, J=7.2 Hz, 1H), 7.00-6.90 (m, 2H), 6.37 (d, J=7.2 Hz, 1H), 5.08 (s, 1H), 4.82-4.76 (m, 1H), 4.19 (s, 1H), 3.62-3.05 (m, 8H), 2.78-2.40 (m, 6H), 2.25-1.55 (m, 12H). Chiral SFC A (45% MeOH): ee 99%, Rt=1.82 min.

Compound 33-E2 LC/MS ESI 480.4 (M+H)+. ¹H NMR (400 MHz, MeOD) δ 7.42 (d, J=7.2 Hz, 1H), 7.28-7.22 (m, 1H), 7.03 (d, J=7.6 Hz, 1H), 7.90-6.79 (m, 2H), 6.26 (d, J=7.6 Hz, 1H), 4.95 (s, 1H), 4.75-4.66 (m, 1H), 4.06 (s, 1H), 3.52-3.05 (m, 8H), 2.60 (t, J=6.0 Hz, 2H), 2.44-2.30 (m, 4H), 2.20-1.98 (m, 4H), 1.80-1.45 (m, 8H). Chiral SFC A (45% MeOH): ee 94%, Rt=2.77 min.

2-(2-(pyrrolidin-1-yl)phenyl)-2-((R)-3-(4-(5,6,7,8-tetrahydro-1,8-naphthyridin-2-yl)butoxy)pyrroidin-1-yl)acetic Acid (Diastereomeric Compounds 34-E1 and 34-E2)

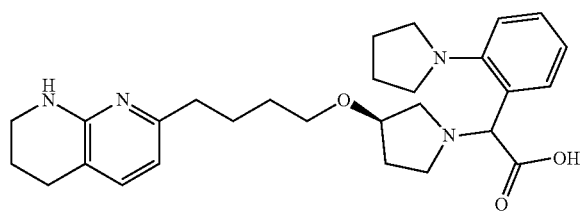 [SMILES: O=C(O)C(c1ccccc1N1CCCC1)N1CC[C@@H](OCCCCc2ccc3c(n2)NCCC3)C1]

Compound 34-E1 LC/MS ESI 479.4 (M+H)+. ¹H NMR (400 MHz, CDCL3) δ 7.50 (d, J=6.8 Hz, 1H), 7.28-7.02 (m, 4H), 6.27 (d, J=7.2 Hz, 1H), 4.68 (s, 1H), 3.94-3.91 (m, 1H), 3.49-3.17 (m, 10H), 2.72-2.49 (m, 6H), 2.06-1.55 (m, 12H).

Compound 34-E2 LC/MS ESI 479.4 (M+H)+. ¹H NMR (400 MHz, CDCL3) δ 7.55 (s, 1H), 7.28-7.02 (m, 4H), 6.27 (d, J=7.2 Hz, 1H), 4.55 (s, 1H), 3.98-3.95 (m, 1H), 3.50-3.07 (m, 10H), 2.85-2.49 (m, 6H), 2.06-1.55 (m, 12H).

2-(2-cyclopropylphenyl)-2-((R)-3-(3-((5,6,7,8-tetrahydro-1,8-naphthyridin-2-yl)methoxy)propyl)pyrrolidin-1-yl)acetic Acid (Compound 35)

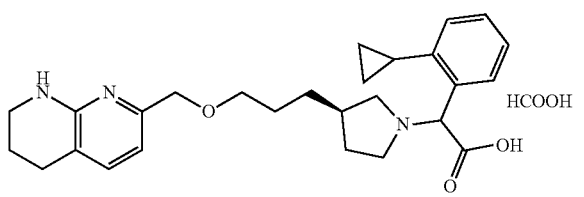 [SMILES: O=C(O)C(c1ccccc1C1CC1)N1CC[C@@H](CCCOCc2ccc3c(n2)NCCC3)C1 ; "HCOOH"]

Compound 35 LC/MS ESI 450 (M+H)⁺ ¹H NMR (400 MHz, MeOD) δ 8.50 (brs, 1H), 7.62-7.60 (m, 1H), 7.41-7.21 (m, 4H), 6.60-6.58 (m, 1H), 5.30-5.28 (m, 1H), 4.37-4.35 (m, 2H), 3.36-3.31 (m, 5H), 3.30-3.11 (m, 2H), 2.85-2.75 (m, 3H), 2.50-1.50 (m, 10H), 1.10-0.50 (m, 4H).

2-(2-cyclopropylphenyl)-2-(cis-3-fluoro-4-(4-(5,6,7,8-tetrahydro-1,8-naphthyridin-2-yl)butoxy)pyrrolidin-1-yl)acetic Acid (Diastereomeric Compounds 36-E1 and 36-E2)

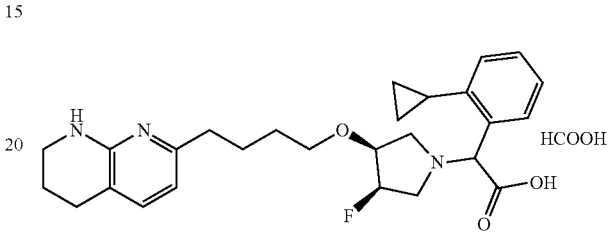

Compound 36-E1 LC/MS ESI 468.3 (M+H)+. ¹H NMR (400 MHz, MeOD) δ 8.53 (s, 1H), 7.70-7.07 (m, 5H), 6.49 (d, J=8.3 Hz, 1H), 5.32-5.19 (m, 2H), 4.30-4.04 (m, 1H), 3.84-3.36 (m, 6H), 3.33-3.24 (m, 1H), 3.00 (t, J=9.7 Hz, 1H), 2.77-2.64 (m, 4H), 2.36-2.18 (m, 1H), 1.98-1.83 (m, 2H), 1.80-1.52 (m, 4H), 1.16-0.87 (m, 3H), 0.58-0.54 (m, 1H).

Compound 36-E2 LC/MS ESI 468.3 (M+H)+. ¹H NMR (400 MHz, MeOD) δ 8.50 (s, 1H), 7.68-7.06 (m, 5H), 6.52 (d, J=7.2 Hz, 1H), 5.42-5.08 (m, 2H), 4.44-4.01 (m, 1H), 3.81-3.33 (m, 6H), 3.33-3.24 (m, 2H), 2.77-2.64 (m, 4H), 2.36-2.18 (m, 1H), 1.98-1.83 (m, 2H), 1.84-1.53 (m, 4H), 1.24-0.85 (m, 3H), 0.58-0.54 (m, 1H).

2-(2-cyclopropyl-5-fluorophenyl)-2-((R)-3-(4-(5,6,7,8-tetrahydro-1,8-naphthyridin-2-yl)butoxy)pyrrolidin-1-yl)acetic Acid (Compound 37)

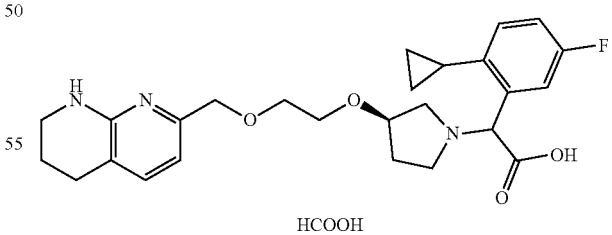

Compound 37 LC/MS ESI 468.3 (M+H)+1H NMR (400 MHz, MeOD) δ 8.52 (s, 1H), 7.48-7.01 (m, 4H), 6.49-6.46 (m, 1H), 5.41-5.28 (m, 1H), 4.24-4.20 (m, 1H), 3.55-3.10 (m, 8H), 2.77-2.61 (m, 4H), 2.29-2.05 (m, 3H), 1.92-1.55 (m, 6H), 1.05-0.80 (m, 3H), 0.55-0.50 (m, 1H).

2-(2-cyclopropyl-6-fluorophenyl)-2-((R)-3-(4-(5,6,7,8-tetrahydro-1,8-naphthyridin-2-yl)butoxy)pyrrolidin-1-yl)acetic Acid (Compound 38)

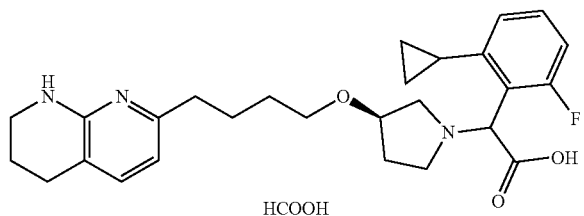 [SMILES: O=C(O)C(c1c(F)cccc1C1CC1)N1CC[C@@H](OCCCCc2ccc3c(n2)NCCC3)C1 ; "HCOOH"]

Compound 38 LC/MS ESI 468.4 (M+H)+1H NMR (400 MHz, MeOD) δ 8.49 (s, 1H), 7.45-7.37 (m, 2H), 7.09-7.03 (m, 2H), 6.54-6.50 (m, 1H), 5.60-5.52 (m, 1H), 4.24-4.20 (m, 1H), 3.59-3.15 (m, 8H), 2.80-2.63 (m, 4H), 2.23-2.13 (m, 3H), 1.92-1.55 (m, 6H), 1.08-0.65 (m, 4H).

2-(2-(methoxymethyl)phenyl)-2-((R)-3-(4-(5,6,7,8-tetrahydro-1,8-naphthyridin-2-yl)butoxy)pyrrolidin-1-yl)acetic Acid (Diastereomeric Compounds 39-E1 and 39-E2)

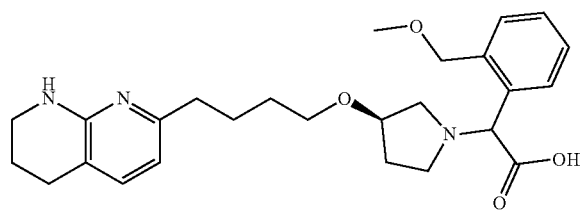 [SMILES: COCc1ccccc1C(C(=O)O)N1CC[C@@H](OCCCCc2ccc3c(n2)NCCC3)C1]

Compound 39-E1 LC/MS ESI 454.2 (M+H)+1H NMR (400 MHz, MeOD) δ 7.66-7.64 (m, 1H), 7.43-7.39 (m, 3H), 7.13 (d, J=7.2 Hz, 1H), 6.36 (d, J=7.2 Hz, 1H), 4.89 (s, 1H), 4.44 (d, J=8.0 Hz, 1H), 4.17 (s, 1H), 3.49-3.36 (m, 8H), 3.14-3.13 (m, 2H), 2.70 (t, J=6.4 Hz, 2H), 2.55 (t, J=7.6 Hz, 2H), 2.14-2.13 (m, 2H), 1.96-1.84 (m, 2H), 1.74-1.59 (m, 5H). Chiral SFC A (40% MeOH): ee 100%, Rt=2.64 min.

Compound 39-E2 LC/MS ESI 454.2 (M+H)+1H NMR (400 MHz, MeOD) δ 7.67-7.65 (m, 1H), 7.42-7.38 (m, 3H), 7.13 (d, J=7.6 Hz, 1H), 6.36 (d, J=7.2 Hz, 1H), 4.81 (s, 1H), 4.45 (s, 1H), 4.17 (s, 1H), 3.36-3.27 (m, 8H), 3.19-3.13 (m, 2H), 2.70 (t, J=6.4 Hz, 2H), 2.55 (t, J=7.6 Hz, 2H), 2.18-2.14 (m, 2H), 1.90-1.84 (m, 2H), 1.73-1.58 (m, 5H). Chiral SFC A (40% MeOH): ee 100%, Rt=4.68 min.

2-(2-(cyclopropylmethyl)phenyl)-2-((R)-3-(4-(5,6,7,8-tetrahydro-1,8-naphthyridin-2-yl)butoxy)pyrrolidin-1-yl)acetic Acid (Diastereomeric Compounds 40-E1 and 40-E2)

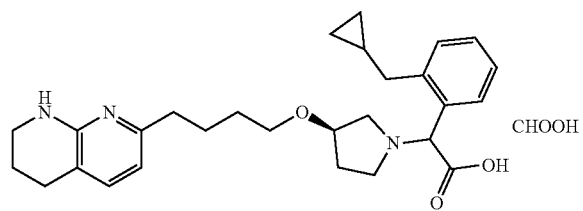

Compound 40-E1 LC/MS ESI 464.4 (M+H)+. 1H NMR (400 MHz, MeOD) δ 8.45 (s, 1H), 7.66-7.30 (m, 5H), 6.54 (d, J=7.2 Hz, 1H), 5.18-4.93 (m, 1H), 4.21 (m, 1H), 3.61-3.41 (m, 6H), 3.28-3.24 (m, 2H), 2.94-2.64 (m, 6H), 2.22-2.18 (m, 2H), 1.94-1.65 (m, 6H), 1.17-1.11 (m, 1H), 0.58-0.52 (m, 2H), 0.27-0.24 (m, 2H).

Compound 40-E2 LC/MS ESI 464.4 (M+H)+. 1H NMR (400 MHz, MeOD) δ 8.46 (s, 1H), 7.63-7.31 (m, 5H), 6.57 (d, J=7.6 Hz, 1H), 5.13 (s, 1H), 4.24 (m, 1H), 3.59-3.42 (m, 6H), 3.18-3.11 (m, 2H), 2.86-2.61 (m, 6H), 2.16-2.13 (m, 2H), 1.93-1.68 (m, 6H), 1.17-1.11 (m, 1H), 0.56-0.51 (m, 2H), 0.27-0.23 (m, 2H).

2-(2-isopropylphenyl)-2-((R)-3-(4-(5,6,7,8-tetrahydro-1,8-naphthyridin-2-yl)butoxy)pyrrolidin-1-yl)acetic Acid (Diastereomeric Compounds 41-E1 and 41-E2)

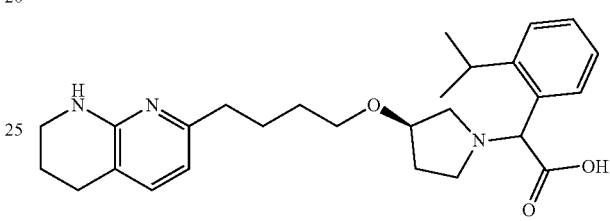

Compound 41-E1 LC/MS ESI 452.2 (M+H)1H NMR (400 MHz, MeOD) δ 7.61 (d, J=7.2 Hz, 1H), 7.41 (d, J=6.4 Hz, 1H), 7.38 (t, J=7.2 Hz, 1H), 7.22 (t, J=7.0 Hz, 1H), 7.14 (d, J=7.2 Hz, 1H), 6.37 (d, J=7.2 Hz, 1H), 4.92 (s, 1H), 4.18 (s, 1H), 3.49-3.36 (m, 6H), 3.32-3.03 (m, 3H), 2.70 (t, J=6.4 Hz, 2H), 2.55 (t, J=7.6 Hz, 2H), 2.21-2.02 (m, 2H), 1.89-1.84 (m, 2H), 1.71-1.69 (m, 2H), 1.62-1.58 (m, 2H), 1.30-1.27 (m, 6H). Chiral SFC F (45% MeOH): ee 100%, Rt=3.67 min.

Compound 41-E2 LC/MS ESI 452.2 (M+H)+1H NMR (400 MHz, MeOD) δ 7.60 (d, J=7.0 Hz, 1H), 7.41 (d, J=6.0 Hz, 1H), 7.38 (t, J=7.2 Hz, 1H), 7.23 (t, J=8.0 Hz, 1H), 7.17 (d, J=7.2 Hz, 1H), 6.40 (d, J=7.6 Hz, 1H), 5.03 (s, 1H), 4.20 (s, 1H), 3.56-3.54 (m, 3H), 3.39-3.36 (m, 3H), 3.08-3.01 (m, 3H), 2.72 (t, J=6.4 Hz, 2H), 2.58 (t, J=7.6 Hz, 2H), 2.19-2.02 (m, 2H), 1.91-1.88 (m, 2H), 1.77-1.62 (m, 2H), 1.61-1.58 (m, 2H), 1.31-1.27 (m, 6H). Chiral SFC F (45% MeOH): ee 96.7%, Rt=8.03 min.

2-(2-cyclopropyl-6-(cyclopropylmethyl)pyridin-3-yl)-2-((R)-3-(3-(5,6,7,8-tetrahydro-1,8-naphthyridin-2-yl)propoxy)pyrrolidin-1-yl)acetic Acid (Compound 42)

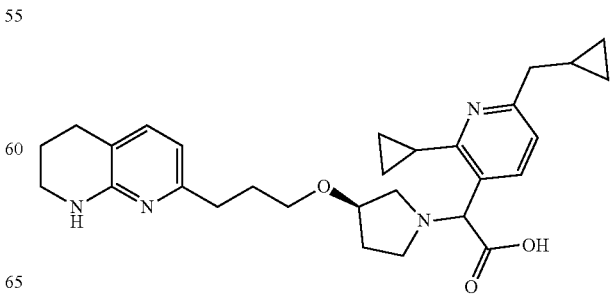

Compound 42 LC/MS ESI 491.6 (M+H)+. ¹H NMR (400 MHz, MeOD) δ 7.67 (d, J=8.1 Hz, 1H), 6.92 (d, J=7.5 Hz, 2H), 6.16 (d, J=7.3 Hz, 1H), 4.78-4.72 (m, 1H), 4.11-3.81 (m, 1H), 3.39-3.13 (m, 5H), 2.97-2.72 (m, 3H), 2.55-2.47 (m, 2H), 2.43-2.19 (m, 5H), 2.05-1.78 (m, 2H), 1.78-1.58 (m, 4H), 1.14-0.98 (m, 1H), 0.94-0.63 (m, 4H), 0.31-0.27 (m, 2H), 0.22-0.18 (m, 2H).

2-(2-cyclopropoxyphenyl)-2-((3R,4S)-3-fluoro-4-(4-(5,6,7,8-tetrahydro-1,8-naphthyridin-2-yl)butoxy)pyrrolidin-1-yl)acetic Acid (Diastereomeric Compounds 43-E1 and 43-E2)

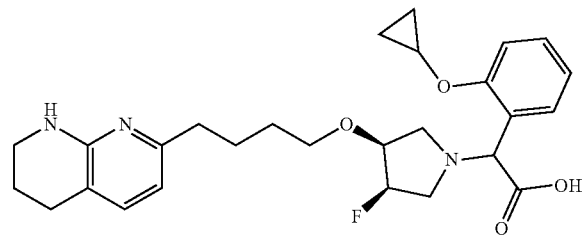 [SMILES: O=C(O)C(c1ccccc1OC1CC1)N1C[C@@H](F)[C@@H](OCCCCc2ccc3c(n2)NCCC3)C1]

Compound 43-E1 LC/MS ESI 484.4 (M+H). ¹H NMR (400 MHz, MeOD) δ 7.49 (d, J=7.5 Hz, 1H), 7.40-7.39 (m, 2H), 7.20-7.18 (m, 1H), 7.06-6.96 (m, 1H), 6.39 (d, J=7.3 Hz, 1H), 5.20 (d, J=54.2 Hz, 1H), 4.89 (s, 1H), 4.10-4.02 (m, 1H), 3.90 (s, 1H), 3.80-3.33 (m, 6H), 3.20-3.03 (m, 2H), 2.71 (t, J=6.2 Hz, 2H), 2.56 (t, J=7.6 Hz, 2H), 1.90-1.82 (m, 2H), 1.75-1.55 (m, 4H), 0.96-0.63 (m, 4H).

Compound 43-E2 LC/MS ESI 484.4 (M+H)⁺. ¹H NMR (400 MHz, MeOD) δ 7.51 (d, J=7.5 Hz, 1H), 7.39-7.37 (m, 2H), 7.20-7.18 (m, 1H), 7.06-6.96 (m, 1H), 6.41 (d, J=7.3 Hz, 1H), 5.12 (d, J=54.2 Hz, 1H), 4.84 (s, 1H), 4.10-4.02 (m, 1H), 3.87 (s, 1H), 3.65-3.33 (m, 6H), 3.20-3.01 (m, 2H), 2.72 (t, J=6.2 Hz, 2H), 2.59 (t, J=7.6 Hz, 2H), 1.90-1.82 (m, 2H), 1.75-1.55 (m, 4H), 0.96-0.63 (m, 4H).

2-(5-fluoro-2-(isopropoxymethyl)phenyl)-2-((R)-3-(4-(5,6,7,8-tetrahydro-1,8-naphthyridin-2-yl)butoxy)pyrrolidin-1-yl)acetic Acid (Diastereomeric Compounds 44-E1 and 44-E2)

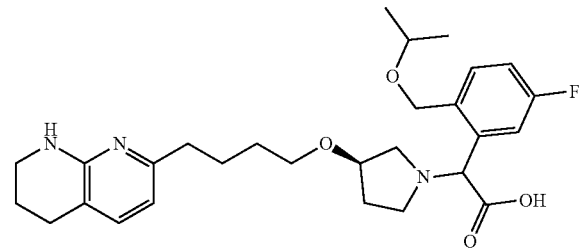 [SMILES: CC(C)OCc1ccc(F)cc1C(C(=O)O)N1CC[C@@H](OCCCCc2ccc3c(n2)NCCC3)C1]

Compound 44-E1 LC/MS ESI 500.3 (M+H)+1H NMR (400 MHz, MeOD) δ 7.55-7.41 (m, 3H), 7.25-7.19 (m, 1H), 6.61 (d, J=7.2 Hz, 1H), 5.29 (s, 1H), 4.83-4.79 (m, 1H), 4.51-4.47 (m, 1H), 4.26 (s, 1H), 3.83-3.23 (m, 9H), 2.84-2.71 (m, 4H), 2.29-1.55 (m, 8H), 1.35-1.20 (m, 6H). Compound 44-E2 LC/MS ESI 500.3 (M+H)+1H NMR (400 MHz, MeOD) δ 7.59-7.41 (m, 3H), 7.25-7.19 (m, 1H), 6.60 (d, J=7.2 Hz, 1H), 5.19 (s, 1H), 4.83-4.79 (m, 1H), 4.51-4.47 (m, 1H), 4.28 (s, 1H), 3.83-3.23 (m, 9H), 2.84-2.71 (m, 4H), 2.29-1.55 (m, 8H), 1.35-1.20 (m, 6H).

2-(2,4-dicyclopropylpyrimidin-5-yl)-2-((R)-3-(4-(5,6,7,8-tetrahydro-1,8-naphthyridin-2-yl)butoxy)pyrrolidin-1-yl)acetic Acid (Compound 45)

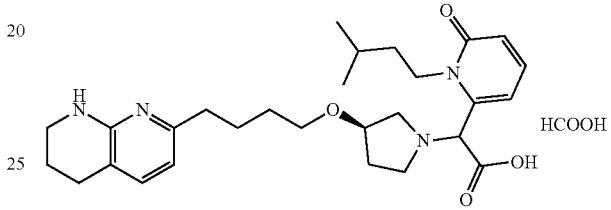

Compound 45 LC/MS ESI 492 (M+H)⁺ ¹H NMR (400 MHz, MeOD) δ 8.60-8.57 (m, 1H), 8.46 (bs, 1H), 7.52 (d, J=7.2 Hz, 1H), 6.59 (d, J=7.6 Hz, 1H), 5.21-5.10 (m, 1H), 4.23-4.21 (m, 1H), 3.70-2.50 (m, 12H), 2.50-1.55 (m, 10H), 1.50-1.00 (m, 8H).

2-(2-(cyclobutoxymethyl)phenyl)-2-((R)-3-(4-(5,6,7,8-tetrahydro-1,8-naphthyridin-2-yl)butoxy)pyrrolidin-1-yl)acetic Acid (Diastereomeric Compounds 46-E1 and 46-E2)

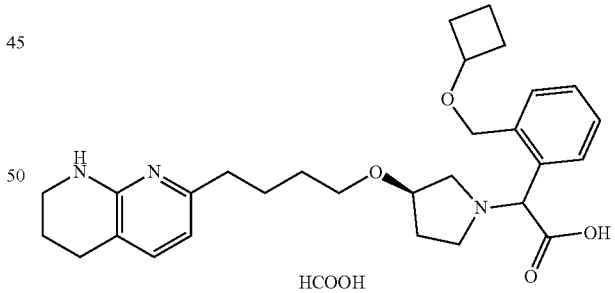

Compound 46-E1 LC/MS ESI 494.3 (M+H)+1H NMR (400 MHz, MeOD) δ 8.51 (s, 1H), 7.68-7.66 (m, 1H), 7.45-7.41 (m, 4H), 6.53 (d, J=7.2 Hz, 1H), 5.06 (s, 1H), 4.82-4.79 (m, 1H), 4.40-4.36 (m, 1H), 4.21-4.09 (m, 2H), 3.63-3.33 (m, 7H), 3.18-3.14 (m, 1H), 2.79-2.68 (m, 4H), 2.24-1.50 (m, 14H).

Compound 46-E2 LC/MS ESI 494.3 (M+H)+1H NMR (400 MHz, MeOD) δ 8.49 (s, 1H), 7.66 (s, 1H), 7.48-7.42 (m, 4H), 6.54 (d, J=7.2 Hz, 1H), 4.94 (s, 1H), 4.80-4.45 (m, 2H), 4.24-4.10 (m, 2H), 3.58-3.15 (m, 8H), 2.80-2.62 (m, 4H), 2.24-1.50 (m, 14H).

2-(2-(3-fluoro-3-methylbutyl)pyridin-3-yl)-2-((R)-3-(4-(5,6,7,8-tetrahydro-1,8-naphthyridin-2-yl)butoxy)pyrrolidin-1-yl)acetic Acid (Compound 47)

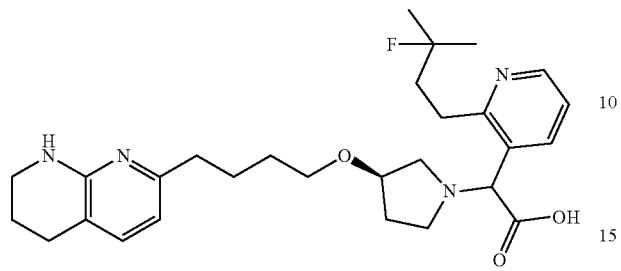

Compound 47 LC/MS ESI 498.9 (M+H)+1H NMR (400 MHz, MeOD) δ 8.43-8.42 (m, 1H), 8.31-8.08 (m, 1H), 7.32-7.23 (m, 2H), 6.44-6.41 (m, 1H), 4.69-4.57 (m, 1H), 4.13-4.12 (m, 1H), 3.49-3.32 (m, 4H), 3.24-2.90 (m, 6H), 2.75-2.56 (m, 4H), 2.25-1.52 (m, 10H), 1.48-1.35 (m, 6H).

2-(3-cyano-2-cyclopropylphenyl)-2-((R)-3-(4-(5,6,7,8-tetrahydro-1,8-naphthyridin-2-yl)butoxy)pyrrolidin-1-yl)acetic Acid (Compound 48)

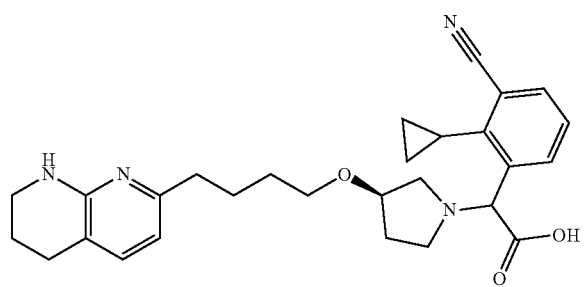 [SMILES: N#Cc1cccc(C(C(=O)O)N2CC[C@@H](OCCCCc3ccc4c(n3)NCCC4)C2)c1C1CC1]

Compound 48 LC/MS ESI 475.3 (M+H)+1H NMR (400 MHz, MeOD) δ 7.85-7.81 (m, 2H), 7.60-7.55 (m, 2H), 6.01 (d, J=7.2 Hz, 1H), 5.90-5.78 (m, 1H), 4.28-4.26 (m, 1H), 3.62-3.46 (m, 7H), 3.28-3.20 (m, 1H), 2.84-2.72 (m, 4H), 2.27-1.67 (m, 9H), 1.26-0.88 (m, 4H).

2-(1-isopentyl-6-oxo-1,6-dihydropyridin-2-yl)-2-((R)-3-(4-(5,6,7,8-tetrahydro-1,8-naphthyridin-2-yl)butoxy)pyrrolidin-1-yl)acetic Acid (Compound 49)

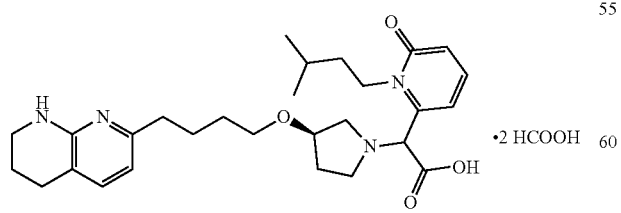

Compound 49 LC/MS ESI 497 (M+H)+ $^1$H NMR (400 MHz, MeOD) δ 8.41 (s, 2H), 7.71 (t, J=7.6 Hz, 1H), 7.52 (d, J=7.6 Hz, 1H), 7.14 (d, J=6.8 Hz, 1H), 6.78 (d, J=8.4 Hz, 1H), 6.55 (d, J=7.6 Hz, 1H), 4.85 (d, J=9.6 Hz, 1H), 4.40-4.21 (m, 3H), 3.70-2.50 (m, 12H), 2.50-1.55 (m, 11H), 0.96-0.94 (m, 6H).

2-(6-cyclopropyl-4-(isopropoxymethyl)pyridin-3-yl)-2-((R)-3-(4-(5,6,7,8-tetrahydro-1,8-naphthyridin-2-yl)butoxy)pyrrolidin-1-yl)acetic Acid (Diastereomeric Compounds 50-E1 and 50-E2)

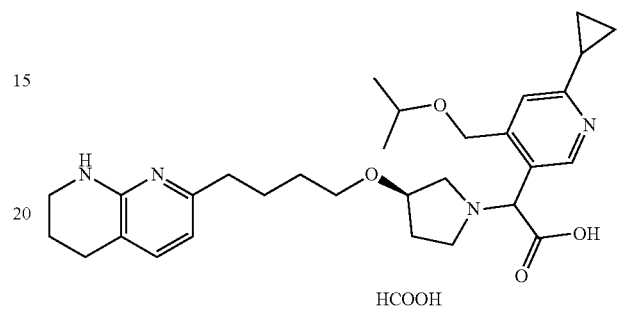

Compound 50-E1 LC/MS ESI 523.3 (M+H)+. $^1$H NMR (400 MHz, MeOD) δ 8.58 (s, 1H), 8.50 (s, 1H), 7.41 (d, J=7.3 Hz, 1H), 7.32 (s, 1H), 6.51 (d, J=7.3 Hz, 1H), 4.78-4.75 (m, 1H), 4.62-4.59 (m, 1H), 4.20 (s, 1H), 3.84-3.76 (m, 1H), 3.69-3.32 (m, 8H), 3.24-3.07 (m, 1H), 2.83-2.39 (m, 4H), 2.12-2.02 (m, 3H), 1.97-1.87 (m, 2H), 1.84-1.61 (m, 4H), 1.27-1.25 (m, 6H), 1.21-0.83 (m, 4H).

Compound 50-E2 LC/MS ESI 523.3 (M+H)+. $^1$H NMR (400 MHz, MeOD) δ 8.57-8.49 (m, 2H), 7.40 (d, J=7.3 Hz, 1H), 7.32 (s, 1H), 6.51 (d, J=7.3 Hz, 1H), 4.89-4.69 (m, 2H), 4.23 (s, 1H), 3.81-3.76 (m, 1H), 3.60-3.32 (m, 7H), 3.24-3.10 (m, 2H), 2.78-2.66 (m, 4H), 2.12-2.02 (m, 3H), 1.97-1.87 (m, 2H), 1.74-1.51 (m, 4H), 1.27-1.25 (m, 6H), 1.21-0.83 (m, 4H).

2-(3-fluoro-2-(isopropoxymethyl)phenyl)-2-((R)-3-(4-(5,6,7,8-tetrahydro-1,8-naphthyridin-2-yl)butoxy)pyrrolidin-1-yl)acetic Acid (Compound 51)

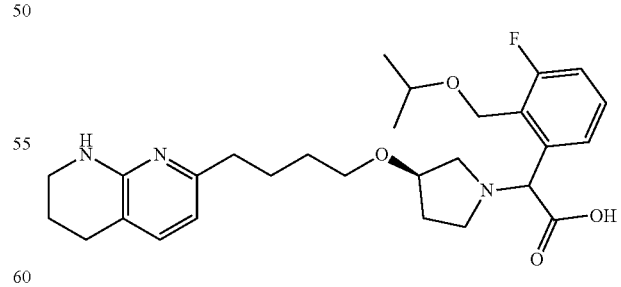

Compound 51 LC/MS ESI 500 (M+H)+. 1H NMR (500 MHz, MeOD) δ 7.52 (d, J=8.0 Hz, 1H), 7.45-7.41 (m, 1H), 7.20-7.15 (m, 1H), 6.39-6.37 (m, 1H), 4.84-4.76 (m, 1H), 4.18 (s, 1H), 3.85-3.81 (m, 1H), 3.49-3.40 (m, 6H), 3.33-3.12 (m, 2H), 2.73-2.70 (m, 2H), 2.56-2.53 (m, 2H), 2.12-2.06 (m, 2H), 1.90-1.58 (m, 6H), 1.26-1.21 (m, 6H).

2-(2,4-dicyclopropylpyrimidin-5-yl)-2-((R)-3-(5-(5,6,7,8-tetrahydro-1,8-naphthyridin-2-yl)pentyl)pyrrolidin-1-yl)acetic Acid (Compound 52)

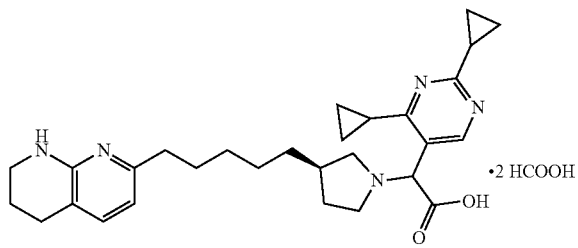 [SMILES: O=C(O)C(c1cnc(C2CC2)nc1C1CC1)N1CC[C@@H](CCCCCc2ccc3c(n2)NCCC3)C1]

Compound 52 LC/MS ESI 490 (M+H)+ ¹H NMR (400 MHz, MeOD) δ 8.61-8.59 (m, 1H), 8.36 (bs, 2H), 7.51 (d, J=7.2 Hz, 1H), 6.55 (d, J=7.2 Hz, 1H), 5.11-5.10 (m, 1H), 3.50-2.50 (m, 8H), 2.50-1.55 (m, 9H), 1.50-1.00 (m, 15H).

2-(2-((cyclopropylmethoxy)methyl)-5-fluorophenyl)-2-((R)-3-(4-(5,6,7,8-tetrahydro-1,8-naphthyridin-2-yl)butoxy)pyrrolidin-1-yl)acetic Acid (Diastereomeric Compounds 53-E1 and 53-E2)

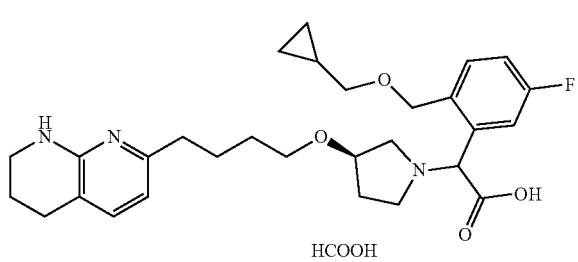 [SMILES: O=C(O)C(c1cc(F)ccc1COCC1CC1)N1CC[C@@H](OCCCCc2ccc3c(n2)NCCC3)C1 ; "HCOOH"]

Compound 53-E1 LC/MS ESI 512.3 (M+H)+ ¹H NMR (400 MHz, MeOD) δ 8.51 (s, 1H), 7.49-7.41 (m, 3H), 7.20-7.15 (m, 1H), 6.52 (d, J=7.2 Hz, 1H), 5.07 (s, 1H), 4.86-4.84 (m, 1H), 4.48-4.45 (m, 1H), 4.22 (s, 1H), 3.62-3.12 (m, 10H), 2.79-2.65 (m, 4H), 2.24-1.55 (m, 8H), 1.08-1.01 (m, 1H), 0.54-0.49 (m, 2H), 0.27-0.24 (m, 2H).

Compound 53-E2 LC/MS ESI 512.3 (M+H)+1H NMR (400 MHz, MeOD) δ 8.51 (s, 1H), 7.49-7.46 (m, 3H), 7.20-7.16 (m, 1H), 6.54 (d, J=7.2 Hz, 1H), 4.98 (s, 1H), 4.85-4.52 (m, 2H), 4.24 (s, 1H), 3.60-3.12 (m, 10H), 2.81-2.65 (m, 4H), 2.29-1.55 (m, 8H), 1.16-1.13 (m, 1H), 0.54-0.49 (m, 2H), 0.27-0.24 (m, 2H).

2-(5-fluoro-2-((1-methylcyclopropoxy)methyl)phenyl)-2-((R)-3-(4-(5,6,7,8-tetrahydro-1,8-naphthyridin-2-yl)butoxy)pyrrolidin-1-yl)acetic Acid (Diastereomeric Compounds 54-E1 and 54-E2)

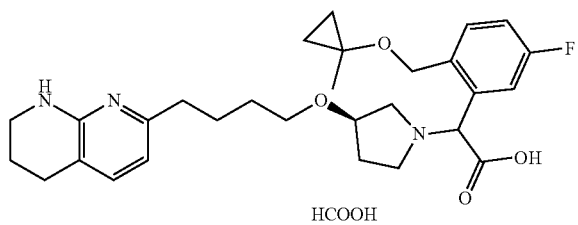 [SMILES: CC1(OCc2ccc(F)cc2C(C(=O)O)N2CC[C@@H](OCCCCc3ccc4c(n3)NCCC4)C2)CC1 ; "HCOOH"]

Compound 54-E1 LC/MS ESI 512.3 (M+H)+ ¹H NMR (400 MHz, MeOD) δ 8.51 (s, 1H), 7.49-7.38 (m, 3H), 7.17-7.11 (m, 1H), 6.50 (d, J=7.6 Hz, 1H), 4.93-4.90 (m, 2H), 4.53-4.50 (m, 1H), 4.21 (s, 1H), 3.66-3.09 (m, 8H), 2.78-2.65 (m, 4H), 2.18-1.62 (m, 8H), 1.50 (s, 3H), 0.87-0.84 (m, 2H), 0.49-0.45 (m, 2H).

Compound 54-E2 LC/MS ESI 512.3 (M+H)+¹H NMR (400 MHz, MeOD) δ 8.51 (s, 1H), 7.47-7.36 (m, 3H), 7.15-7.11 (m, 1H), 6.48 (d, J=7.2 Hz, 1H), 4.85-4.80 (m, 2H), 4.60-4.57 (m, 1H), 4.20 (s, 1H), 3.62-3.09 (m, 8H), 2.77-2.64 (m, 4H), 2.20-1.64 (m, 8H), 1.50 (s, 3H), 0.91-0.88 (m, 2H), 0.49-0.47 (m, 2H).

2-(5-fluoro-2-(isopropoxymethyl)phenyl)-2-((3R)-3-(4-(7-methyl-5,6,7,8-tetrahydro-1,8-naphthyridin-2-yl)butoxy)pyrrolidin-1-yl)acetic Acid (Diastereomeric Compounds 55-E1 and 55-E2)

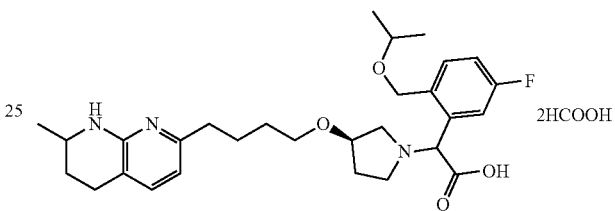

Compound 55-E1 (mixture of 2 stereoisomers) LC/MS ESI 514 (M+H)+ ¹H NMR (400 MHz, MeOD) δ 8.35 (s, 2H), 7.54-7.47 (m, 3H), 7.19-7.15 (m, 1H), 6.57 (d, J=7.2 Hz, 1H), 5.07-5.05 (m, 1H), 4.85 (d, J=7.6 Hz, 1H), 4.50-3.31 (m, 9H), 3.30-2.00 (m, 8H), 1.96-1.20 (m, 14H).

Compound 55-E2 (mixture of 2 stereoisomers) LC/MS ESI 514 (M+H)+ ¹H NMR (400 MHz, MeOD) δ 8.31 (s, 2H), 7.54-7.47 (m, 3H), 7.19-7.15 (m, 1H), 6.58 (d, J=8.8 Hz, 1H), 5.07-5.05 (m, 1H), 4.87-4.35 (m, 3H), 3.80-3.31 (m, 5H), 3.30-2.25 (m, 8H), 2.15-1.20 (m, 16H).

2-(2-((S)-1-isopropoxyethyl)phenyl)-2-((R)-3-(4-(5,6,7,8-tetrahydro-1,8-naphthyridin-2-yl)butoxy)pyrrolidin-1-yl)acetic Acid (Diastereomeric Compounds 56-E1 and 56-E2)

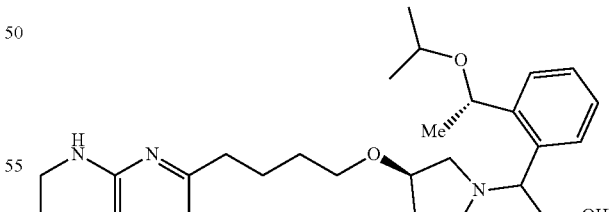

Compound 56-E1 LC/MS ESI 496.3 (M+H)+ ¹H NMR (400 MHz, MeOD) δ 8.56 (s, 1H), 7.71 (d, J=7.2 Hz, 1H), 7.47 (d, J=7.2 Hz, 1H), 7.24-7.19 (m, 1H), 7.11 (d, J=7.6 Hz, 1H), 6.34 (d, J=7.6 Hz, 1H), 5.44-5.42 (m, 1H), 4.19 (s, 1H), 4.02 (s, 1H), 3.56-3.31 (m, 4H), 2.95-2.48 (m, 8H), 2.14-1.81 (m, 4H), 1.68-1.52 (m, 4H), 1.41-1.02 (m, 9H). Chiral SFC F (45% MeOH): ee 100%, Rt=3.77 min.

Compound 56-E2 LC/MS ESI 496.3 (M+H)+ ¹H NMR (400 MHz, MeOD) δ 7.65-7.61 (m, 2H), 7.42-7.31 (m, 2H), 7.17 (d, J=7.6 Hz, 1H), 6.40 (d, J=7.2 Hz, 1H), 5.06-5.04 (m, 1H), 4.20 (s, 1H), 3.53-3.31 (m, 7H), 3.08-2.98 (m, 2H), 2.72 (t, J=6.4 Hz, 2H), 2.57 (t, J=7.2 Hz, 2H), 2.18-1.82 (m, 4H), 1.78-1.50 (m, 4H), 1.45-1.42 (m, 3H), 1.20-1.08 (m, 6H). Chiral SFC F (45% MeOH): ee 100%, Rt=5.60 min.

2-(2-((R)-1-isopropoxyethyl)phenyl)-2-((R)-3-(4-(5,6,7,8-tetrahydro-1,8-naphthyridin-2-yl)butoxy)pyrrolidin-1-yl)acetic Acid (Diastereomeric Compounds 57-E1 and 57-E2)

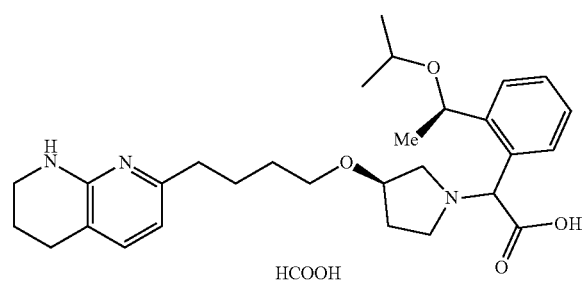 [SMILES: CC(C)O[C@H](C)c1ccccc1C(C(=O)O)N1CC[C@@H](OCCCCc2ccc3c(n2)NCCC3)C1 ; "HCOOH"]

Compound 57-E1 LC/MS ESI 496.4 (M+H)+1H NMR (400 MHz, MeOD) δ 8.47 (s, 1H), 7.70 (d, J=7.6 Hz, 1H), 7.65 (d, J=8.0 Hz, 1H), 7.45-7.34 (m, 3H), 6.53 (d, J=7.2 Hz, 1H), 5.11-5.09 (m, 1H), 4.94 (s, 1H), 4.23 (s, 1H), 3.59-3.28 (m, 9H), 2.78 (t, J=6.4 Hz, 2H), 2.69 (t, J=7.6 Hz, 2H), 2.27-2.14 (m, 2H), 1.93-1.65 (m, 6H), 1.49 (d, J=6.4 Hz, 3H), 1.21-1.12 (m, 6H). Compound 57-E2 LC/MS ESI 496.4 (M+H)+1H NMR (400 MHz, MeOD) δ 8.46 (s, 1H), 7.62 (d, J=8.0 Hz, 1H), 7.53 (d, J=7.2 Hz, 1H), 7.46-7.34 (m, 3H), 6.53 (d, J=7.2 Hz, 1H), 5.23 (s, 1H), 5.10-5.05 (m, 1H), 4.25 (s, 1H), 3.66-3.20 (m, 9H), 2.80-2.67 (m, 4H), 2.17-2.10 (m, 2H), 1.93-1.65 (m, 6H), 1.50-1.47 (m, 3H), 1.21-1.02 (m, 6H).

2-(5-fluoro-2-(isopropoxymethyl)phenyl)-2-((R)-3-(4-(4-fluoro-5,6,7,8-tetrahydro-1,8-naphthyridin-2-yl)butoxy)pyrrolidin-1-yl)acetic Acid (Compound 58)

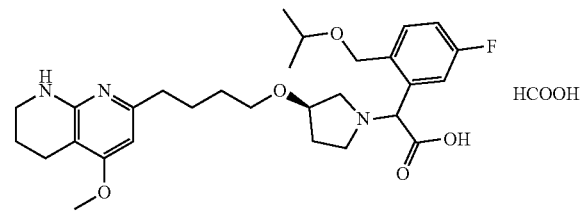 [SMILES: COc1cc(CCCCO[C@@H]2CCN(C(C(=O)O)c3cc(F)ccc3COC(C)C)C2)nc2c1CCCN2 ; "HCOOH"]

Compound 58 LC/MS ESI 518 (M+H)¹H NMR (400 MHz, MeOD) δ 8.50 (bs, 1H), 7.45-7.43 (m, 2H), 7.18-7.14 (m, 1H), 6.25 (d, J=7.6 Hz, 1H), 4.90-4.80 (m, 2H), 4.52-4.48 (m, 1H), 4.22 (s, 1H), 3.80-3.05 (m, 9H), 2.70-2.55 (m, 4H), 2.22-1.54 (m, 8H), 1.25-1.18 (m, 6H).

2-(5-fluoro-2-(isopropoxymethyl)phenyl)-2-((R)-3-(4-(4-methoxy-5,6,7,8-tetrahydro-1,8-naphthyridin-2-yl)butoxy)pyrrolidin-1-yl)acetic Acid(Compound 59)

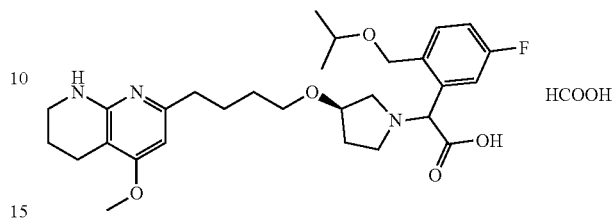

Compound 59 LC/MS ESI 530 (M+H)+ ¹H NMR (400 MHz, MeOD) δ 8.54 (bs, 1H), 7.48-7.45 (m, 2H), 7.13-7.12 (m, 1H), 6.40 (d, J=8.8 Hz, 1H), 4.90-4.83 (m, 2H), 4.52-4.48 (m, 1H), 4.19 (s, 1H), 3.81-3.75 (m, 4H), 3.55-3.02 (m, 8H), 2.68-2.52 (m, 4H), 2.20-1.54 (m, 8H), 1.28-1.20 (m, 6H).

2-(5-fluoro-2-((3-methyloxetan-3-yloxy)methyl)phenyl)-2-((R)-3-(4-(5,6,7,8-tetrahydro-1,8-naphthyridin-2-yl)butoxy)pyrrolidin-1-yl)acetic Acid (Compound 60)

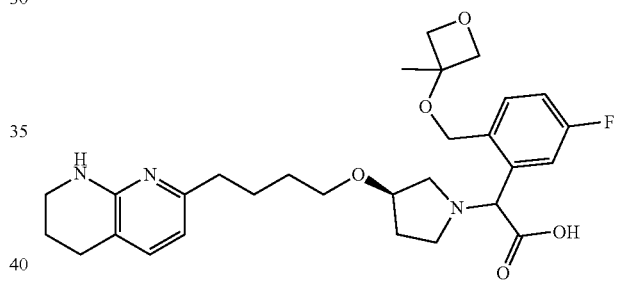

Compound 60 LC/MS ESI 528.3 (M+H)+1H NMR (400 MHz, MeOD) δ 7.52-7.46 (m, 2H), 7.19-7.11 (m, 2H), 6.39 (d, J=7.2 Hz, 1H), 4.88-4.72 (m, 4H), 4.54-4.42 (m, 3H), 4.17 (s, 1H), 3.48-3.31 (m, 6H), 3.18-3.03 (m, 2H), 2.73-2.55 (m, 4H), 2.20-1.84 (m, 4H), 1.78-1.55 (m, 8H).

2-(3-fluoro-2-(((R)-tetrahydrofuran-3-yloxy)methyl)phenyl)-2-((R)-3-(4-(5,6,7,8-tetrahydro-1,8-naphthyridin-2-yl)butoxy)pyrrolidin-1-yl)acetic Acid (Compound 61)

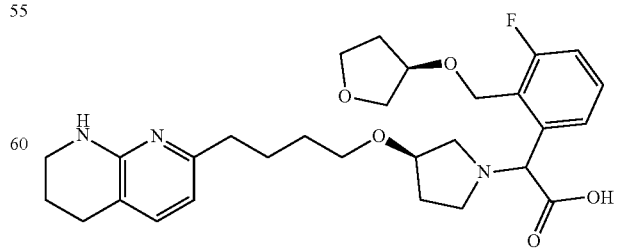

Compound 61 LC/MS ESI 528.3 (M+H)+ ¹H NMR (400 MHz, MeOD) δ 7.56-7.46 (m, 1H), 7.43-7.38 (m, 1H), 7.21-7.18 (m, 2H), 6.41-6.38 (m, 1H), 4.86 (m, 1H), 4.81-4.68 (m, 2H), 4.39-4.35 (m, 1H), 4.30-4.14 (m, 1H), 3.98-3.65 (m, 4H), 3.50-3.39 (m, 5H), 3.18-3.00 (m, 2H), 2.75-2.71 (m, 2H), 2.58-2.55 (m, 2H), 2.21-2.02 (m, 4H), 1.92-1.80 (m, 2H), 1.76-1.65 (m, 2H), 1.62-1.58 (m, 3H).

2-(3-fluoro-2-(((R)-tetrahydrofuran-3-yloxy)methyl)phenyl)-2-((3R)-3-(1-hydroxy-5-(5,6,7,8-tetrahydro-1,8-naphthyridin-2-yl)pentyl)pyrrolidin-1-yl)acetic Acid (Compound 62)

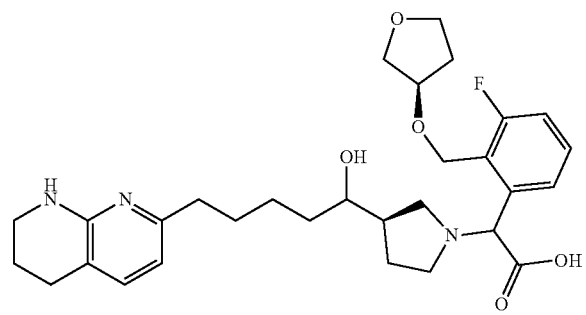 [SMILES: O=C(O)C(c1cccc(F)c1CO[C@@H]1CCOC1)N1CC[C@@H](C(O)CCCCc2ccc3c(n2)NCCC3)C1]

Compound 62 LC/MS ESI 542.4 (M+H)+1H NMR (500 MHz, MeOD) δ 7.42-7.34 (m, 2H), 7.19-7.08 (m, 2H), 6.36-6.33 (m, 1H), 4.68-4.60 (m, 1H), 4.28-4.23 (m, 1H), 3.98-3.50 (m, 5H), 3.44-3.31 (m, 6H), 3.15-2.84 (m, 2H), 2.64-2.45 (m, 4H), 2.20-1.75 (m, 5H), 1.60-1.22 (m, 8H).

2-(3-fluoro-2-((3-methyloxetan-3-yloxy)methyl)phenyl)-2-((R)-3-(4-(5,6,7,8-tetrahydro-1,8-naphthyridin-2-yl)butoxy)pyrrolidin-1-yl)acetic Acid (Compound 63)

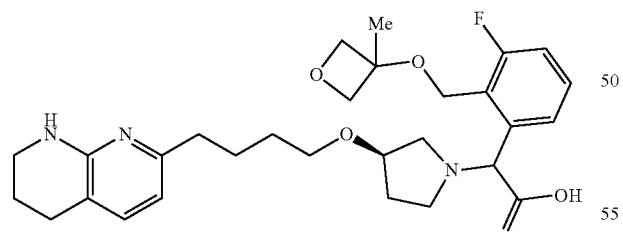

Compound 63 LC/MS ESI 528.3 (M+H)+ 1H NMR (400 MHz, MeOD) δ 7.57-7.45 (m, 2H), 7.24-7.16 (m, 2H), 6.41-6.37 (m, 1H), 4.94-4.71 (m, 4H), 4.47-4.41 (m, 2H), 4.20-4.18 (m, 1H), 3.74-3.02 (m, 8H), 2.72 (t, J=6.4 Hz, 2H), 2.56 (t, J=7.2 Hz, 2H), 2.20-1.84 (m, 4H), 1.78-1.51 (m, 7H).

2-(5-fluoro-2-(((R)-tetrahydrofuran-3-yloxy)methyl)phenyl)-2-((R)-3-(4-(5,6,7,8-tetrahydro-1,8-naphthyridin-2-yl)butoxy)pyrrolidin-1-yl)acetic Acid (Compound 64)

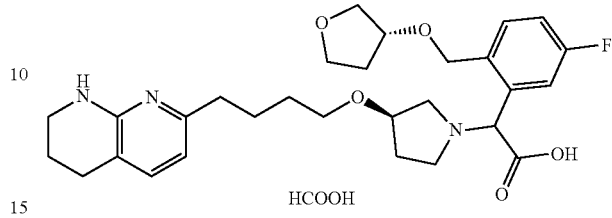

Compound 64 LC/MS ESI 528.4 (M+H)+ 1H NMR (500 MHz, MeOD) δ 8.43 (s, 1H), 7.52-7.49 (m, 3H), 7.19-7.17 (m, 1H), 6.57 (d, J=7.0 Hz, 1H), 5.03-4.83 (m, 2H), 4.57-4.49 (m, 1H), 4.38-4.28 (m, 2H), 3.98-3.22 (m, 12H), 2.82-2.72 (m, 4H), 2.30-2.04 (m, 4H), 1.98-1.58 (m, 6H).

2-(2-cyclobutylphenyl)-2-((R)-3-(4-(5,6,7,8-tetrahydro-1,8-naphthyridin-2-yl)butoxy)pyrrolidin-1-yl)acetic Acid (Compound 65)

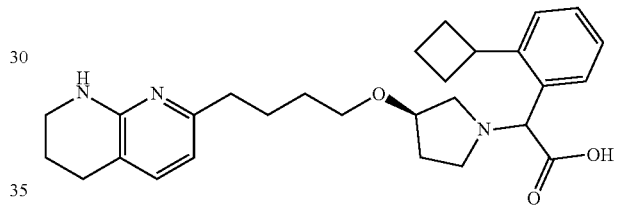

Compound 65 LC/MS ESI 528.4 (M+H)+ 1H NMR (500 MHz, MeOD) δ 7.62-7.59 (m, 1H), 7.51-7.27 (m, 4H), 6.59-6.55 (m, 1H), 5.05-4.91 (m, 1H), 4.30-4.28 (m, 1H), 4.02-3.90 (m, 1H), 3.68-3.05 (m, 8H), 2.81-2.70 (m, 4H), 2.44-1.58 (m, 14H).

2-(2-cyclopropyl-3-methoxyphenyl)-2-[(3R)-3-[4-(5,6,7,8-tetrahydro-1,8-naphthyridin-2-yl)butoxy]pyrrolidin-1-yl]acetic acid (diastereomeric compounds 66-E1 and 66-E2)

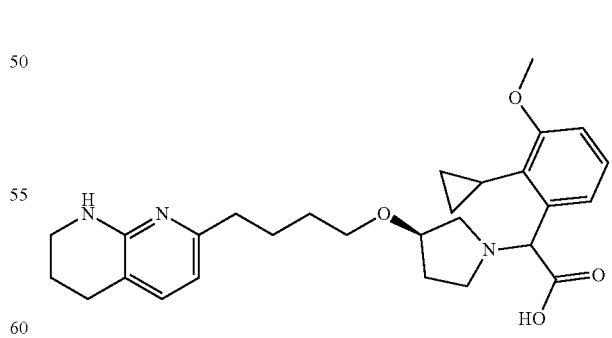

Compound 66-E1 LC/MS ESI 480 (M+H)+ 1H NMR (400 MHz, MeOD) δ 7.46 (d, J=7.2 Hz, 1H), 7.32-7.28 (m, 1H), 7.19 (d, J=7.6 Hz, 1H), 6.99 (d, J=8.4 Hz, 1H), 6.53 (d, J=8.4 Hz, 1H), 5.58 (s, 1H), 4.21-4.18 (m, 1H), 3.86 (s, 3H), 3.61-3.24 (m, 8H), 2.81-2.66 (m, 4H), 2.18-1.61 (m, 9H), 1.11-0.67 (m, 4H).

Compound 66-E2 LC/MS ESI 480 (M+H)+ ¹H NMR (400 MHz, MeOD) δ 7.47 (d, J=7.2 Hz, 1H), 7.34-7.17 (m, 2H), 7.02 (d, J=8.4 Hz, 1H), 6.55 (d, J=7.2 Hz, 1H), 5.76 (s, 1H), 4.21-4.18 (m, 1H), 3.86 (s, 3H), 3.65-3.24 (m, 8H), 2.78-2.54 (m, 4H), 2.22-1.51 (m, 9H), 1.15-0.60 (m, 4H).

2-(2-(cis-2-methoxycyclopropyl)phenyl)-2-((R)-3-(4-(5,6,7,8-tetrahydro-1,8-naphthyridin-2-yl)butoxy)pyrrolidin-1-yl)acetic Acid (Diastereomeric Compounds 67-E1 and 67-E2)

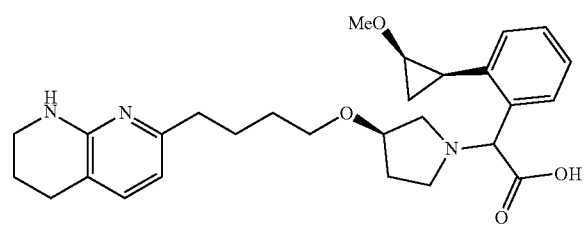 [SMILES: CO[C@@H]1C[C@@H]1c1ccccc1C(C(=O)O)N1CC[C@@H](OCCCCc2ccc3c(n2)NCCC3)C1]

Compound 67-E1 LC/MS ESI 480.3 (M+H)+. ¹H NMR (400 MHz, MeOD) δ 7.69-7.58 (m, 1H), 7.29-7.23 (m, 2H), 7.15-7.09 (m, 2H), 6.37 (d, J=7.3 Hz, 1H), 5.19 (d, J=7.8 Hz, 1H), 4.18-4.17 (m, 1H), 3.70-3.34 (m, 9H), 3.27-3.24 (m, 3H), 2.70 (t, J=6.2 Hz, 2H), 2.61-2.37 (m, 3H), 2.25-2.05 (m, 2H), 1.96-1.79 (m, 2H), 1.79-1.47 (m, 4H), 1.42-0.84 (m, 2H). Chiral K: (45% MeOH): ee 98.4%, Rt=2.78 min.

Compound 67-E2 LC/MS ESI 480.3 (M+H)+. ¹H NMR (400 MHz, MeOD) δ 7.68-7.56 (m, 1H), 7.49-7.26 (m, 4H), 6.51-6.49 (m, 1H), 5.31-5.26 (m, 1H), 4.18-4.17 (m, 1H), 3.72-3.34 (m, 12H), 2.75-2.55 (m, 4H), 2.50-2.42 (m, 1H), 2.25-2.05 (m, 2H), 1.96-1.52 (m, 6H), 1.12-1.04 (m, 2H). Chiral K: (45% MeOH): ee 38%, Rt=5.26 min.

2-(2-(trans-2-methoxycyclopropyl)phenyl)-2-((R)-3-(4-(5,6,7,8-tetrahydro-1,8-naphthyridin-2-yl)butoxy)pyrrolidin-1-yl)acetic Acid (Diastereomeric Compounds 68-E1 and 68-E2)

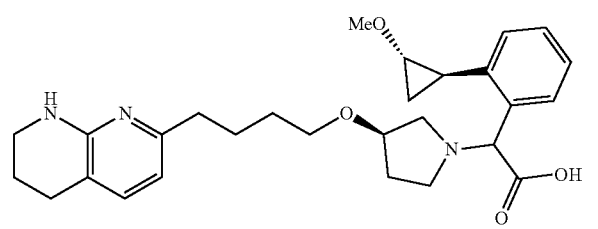 [SMILES: CO[C@H]1C[C@@H]1c1ccccc1C(C(=O)O)N1CC[C@@H](OCCCCc2ccc3c(n2)NCCC3)C1]

Compound 68-E1 LC/MS ESI 480.3 (M+H)+. ¹H NMR (400 MHz, MeOD) δ 7.69-7.58 (m, 1H), 7.29-7.23 (m, 2H), 7.15-7.09 (m, 2H), 6.37 (d, J=7.3 Hz, 1H), 5.24 (d, J=7.8 Hz, 1H), 4.18-4.17 (m, 1H), 3.70-3.34 (m, 9H), 3.27-3.24 (m, 3H), 2.70 (t, J=6.2 Hz, 2H), 2.61-2.37 (m, 3H), 2.25-2.05 (m, 2H), 1.96-1.79 (m, 2H), 1.79-1.47 (m, 4H), 1.42-0.84 (m, 2H). Chiral K: (45% MeOH): ee 98.4%, Rt=2.72 min.

Compound 68-E1 LC/MS ESI 480.3 (M+H)+. ¹H NMR (400 MHz, MeOD) δ 7.62-7.59 (m, 1H), 7.33-7.24 (m, 2H), 7.16-7.07 (m, 2H), 6.37 (d, J=7.3 Hz, 1H), 5.30-5.23 (m, 1H), 4.21 (s, 1H), 3.65-3.02 (m, 12H), 2.70 (t, J=6.2 Hz, 2H), 2.56-2.30 (m, 3H), 2.16-1.98 (m, 2H), 1.96-1.80 (m, 2H), 1.79-1.49 (m, 4H), 1.38-1.05 (m, 2H). Chiral K: (45% MeOH): ee 38%, Rt=5.22 min.

2-(3-fluoro-2-((3-methyloxetan-3-yloxy)methyl)phenyl)-2-((R)-3-(4-(4-methoxy-5,6,7,8-tetrahydro-1,8-naphthyridin-2-yl)butoxy)pyrrolidin-1-yl)acetic Acid (Compound 69)

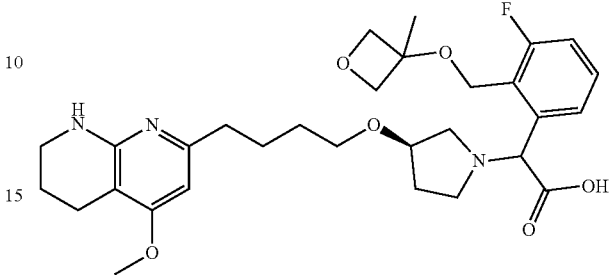

Compound 69 LC/MS ESI 558(M+H)¹H NMR (400 MHz, MeOD) δ 7.62-7.60 (m, 1H), 7.43-7.41 (m, 1H), 7.19-7.14 (m, 1H), 6.28 (s, 1H), 4.90-4.71 (m, 7H), 4.46-4.41 (m, 2H), 4.17-4.12 (m, 1H), 3.87 (s, 3H), 3.55-3.30 (m, 4H), 3.22-2.95 (m, 2H), 2.64-2.52 (m, 4H), 2.20-1.55 (m, 11H).

2-(4-((3-methyloxetan-3-yl)methoxy)pyrimidin-5-yl)-2-((R)-3-(5-(5,6,7,8-tetrahydro-1,8-naphthyridin-2-yl)pentyl)pyrrolidin-1-yl)acetic Acid (Compound 70)

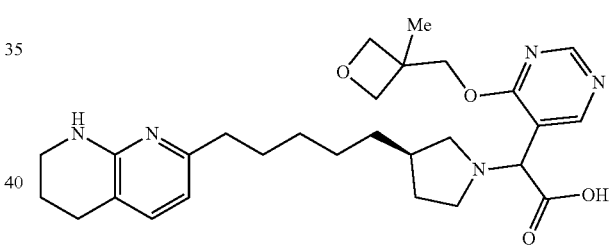

Compound 70 LC/MS ESI 510.3 (M+H)¹H NMR (400 MHz, MeOD) δ 8.74-8.69 (m, 2H), 7.13-7.11 (m, 1H), 6.36-6.33 (m, 1H), 4.80-4.72 (m, 1H), 4.70-4.50 (m, 6H), 3.50-3.30 (m, 3H), 3.22-3.00 (m, 2H), 2.80-2.60 (m, 3H), 2.50-2.40 (m, 2H), 2.35-2.00 (m, 2H), 1.92-1.82 (m, 2H), 1.62-1.48 (m, 3H), 1.42-1.22 (m, 9H).

2-(4-cyclopropoxypyrimidin-5-yl)-2-((R)-3-(5-(5,6,7,8-tetrahydro-1,8-naphthyridin-2-yl)pentyl)pyrrolidin-1-yl)acetic Acid (Compound 71)

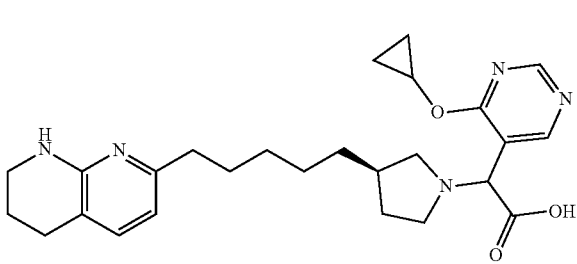 [SMILES: O=C(O)C(c1cncnc1OC1CC1)N1CC[C@@H](CCCCCc2ccc3c(n2)NCCC3)C1]

Compound 71 LC/MS ESI 466.3 (M+H)⁺ ¹H NMR (400 MHz, MeOD) δ 8.75 (d, J=8.4 Hz, 1H), 8.69 (d, J=8.4 Hz, 1H), 7.13-7.11 (m, 1H), 6.36-6.33 (m, 1H), 4.54-4.49 (m, 2H), 3.39-3.37 (m, 3H), 3.18-2.90 (m, 2H), 2.71-2.68 (m, 2H), 2.51-2.47 (m, 2H), 2.30-2.20 (m, 1H), 2.19-2.04 (m, 1H), 1.92-1.82 (m, 2H), 1.62-1.24 (m, 10H), 0.94-0.80 (m, 4H).

2-(2-(cyclopropoxyphenyl)-2-((R)-3-(4-(4-methoxy-5,6,7,8-tetrahydro-1,8-naphthyridin-2-yl)butoxy) pyrrolidin-1-yl)acetic Acid (Diastereomeric Compounds 72-E1 and 72-E2)

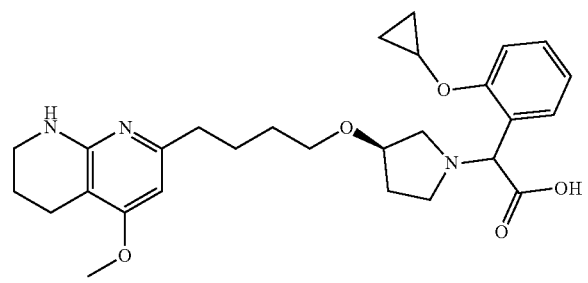 [SMILES: COc1cc(CCCCO[C@@H]2CCN(C(C(=O)O)c3ccccc3OC3CC3)C2)nc2c1CCCN2]

Compound 72-E1 LC/MS ESI 496.3 (M+H)+. ¹H NMR (500 MHz, MeOD) δ 7.42-7.40 (m, 1H), 7.36-7.30 (m, 2H), 6.97-6.95 (m, 1H), 6.20 (s, 1H), 4.91-4.85 (m, 1H), 4.10 (s, 1H), 3.78-3.71 (m, 4H), 3.43-3.38 (m, 4H), 3.22-2.94 (m, 3H), 2.51-2.48 (m, 4H), 2.03-1.57 (m, 8H), 0.73-0.62 (m, 3H).

Compound 72-E2 LC/MS ESI 496.3 (M+H)+. ¹H NMR (500 MHz, MeOD) δ 7.44-7.42 (m, 1H), 7.35-7.33 (m, 2H), 6.96-6.94 (m, 1H), 6.17 (s, 1H), 4.85-4.82 (m, 1H), 4.09 (s, 1H), 3.86-3.77 (m, 4H), 3.40-3.37 (m, 3H), 3.25-3.13 (m, 5H), 2.52-2.48 (m, 4H), 2.12-1.51 (m, 8H), 0.81-0.64 (m, 4H).

2-(5-fluoro-2-((3-methyloxetan-3-yloxy)methyl) phenyl)-2-((R)-3-(4-(4-methoxy-5,6,7,8-tetrahydro-1,8-naphthyridin-2-yl)butoxy)pyrrolidin-1-yl)acetic Acid (Diastereomeric Compounds 73-E1 and 73-E2)

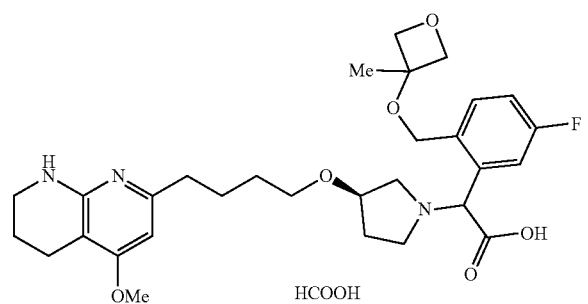 [SMILES: COc1cc(CCCCO[C@@H]2CCN(C(C(=O)O)c3cc(F)ccc3COC3(C)COC3)C2)nc2c1CCCN2 ; "HCOOH"]

Compound 73-E1 LC/MS ESI 558.2 (M+H)⁺ ¹H NMR (400 MHz, MeOD) δ 8.50 (br, 1H), 7.54-7.48 (m, 2H), 7.19-7.15 (m, 1H), 6.52 (s, 1H), 5.00 (s, 1H), 4.87 (d, J=10.8 Hz, 1H), 4.76-4.70 (m, 2H), 4.49-4.40 (m, 3H), 4.22 (s, 1H), 3.97 (s, 3H), 3.66-3.60 (m, 1H), 3.58-3.42 (m, 3H), 3.40-3.37 (m, 3H), 3.13-3.10 (m, 1H), 2.74-2.59 (m, 4H), 2.21-2.15 (m, 2H), 1.92-1.62 (m, 9H).

Compound 73-E2 LC/MS ESI 558.2 (M+H)⁺ ¹H NMR (400 MHz, MeOD) δ 8.50 (br, 1H), 7.54-7.48 (m, 2H), 7.20-7.16 (m, 1H), 6.55 (s, 1H), 5.02-5.00 (s, 1H), 4.93-4.76 (m, 3H), 4.57-4.48 (m, 1H), 4.46-4.40 (m, 2H), 4.23 (s, 1H), 3.98 (s, 3H), 3.80-3.19 (m, 6H), 3.15-3.08 (m, 2H), 2.76-2.60 (m, 4H), 2.27-2.05 (m, 2H), 1.89-1.62 (m, 9H).

2-((R)-3-(4-(5,6,7,8-tetrahydro-1,8-naphthyridin-2-yl)butoxy)pyrrolidin-1-yl)-2-(2-(tetrahydrofuran-3-yl)phenyl)acetic Acid (Compound 74)

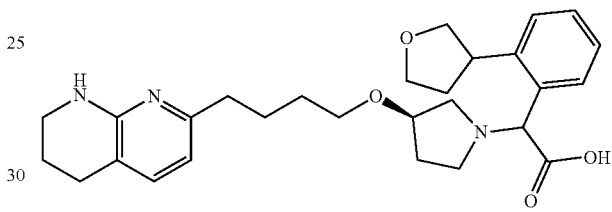

Compound 74: LC/MS ESI 480.2 (M+H)⁺, ¹H NMR (500 MHz, MeOD) δ 7.63 (dd, J=13.4, 7.8 Hz, 1H), 7.47 (d, J=7.2 Hz, 1H), 7.39 (t, J=7.6 Hz, 1H), 7.28 (t, J=7.6 Hz, 1H), 7.17 (d, J=7.3 Hz, 1H), 6.40 (dd, J=7.3, 5.4 Hz, 1H), 4.99 (s, 1H), 4.23-4.14 (m, 2H), 4.13-4.06 (m, 1H), 4.06-3.96 (m, 1H), 3.95-3.80 (m, 2H), 3.75 (m, 1H), 3.52 (m, 2H), 3.40 (m, 3H), 3.30-2.99 (m, 3H), 2.72 (t, J=6.2 Hz, 2H), 2.57 (m, 2H), 2.38 (m, 1H), 2.06 (m, 3H), 1.89 (m, 2H), 1.79-1.68 (m, 2H), 1.67-1.57 (m, 2H).

2-((R)-3-(4-(5,6,7,8-tetrahydro-1,8-naphthyridin-2-yl)butoxy)pyrrolidin-1-yl)-2-(2-(tetrahydro-2H-pyran-3-yl)phenyl)acetic Acid (Compound 75)

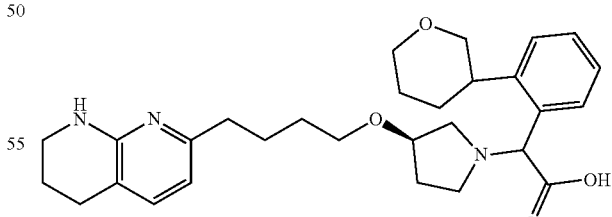

Compound 75: LC/MS ESI 494.2 (M+H)⁺, ¹H NMR (500 MHz, MeOD) δ 7.67 (t, J=7.9 Hz, 1H), 7.41 (d, J=7.9 Hz, 1H), 7.35 (t, J=7.5 Hz, 1H), 7.27 (t, J=7.5 Hz, 1H), 7.16 (d, J=7.3 Hz, 1H), 6.44-6.35 (m, 1H), 4.84 (s, 1H), 4.17 (d, J=23.7 Hz, 1H), 3.94 (m, 2H), 3.66-3.35 (m, 8H), 3.10 (m, 3H), 2.74-2.67 (m, 2H), 2.61-2.52 (m, 2H), 2.21-2.01 (m, 3H), 1.88 (m, 2H), 1.84-1.59 (m, 7H).

2-(2-(3,3-difluorocyclobutyl)pyridin-2-yl)-2-((R)-3-(4-(5,6,7,8-tetrahydro-1,8-naphthyridin-2-yl)butoxy)pyrrolidin-1-yl)acetic Acid (Compound 76)

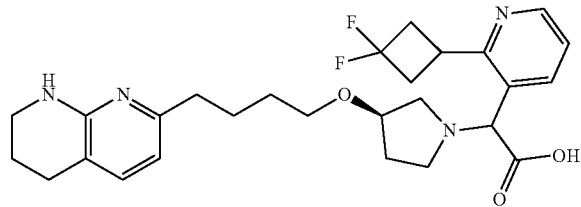 [SMILES: O=C(O)C(c1cccnc1C1CC(F)(F)C1)N1CC[C@@H](OCCCCc2ccc3c(n2)NCCC3)C1]

Compound 76 LC/MS ESI 501.2 (M+H)+. $^1$H NMR (500 MHz, MeOD) δ 8.62-8.58 (m, 1H), 8.04-7.99 (m, 1H), 7.34-7.29 (m, 2H), 6.48 (d, J=7.3 Hz, 1H), 4.84-4.70 (m, 1H), 4.17 (s, 1H), 4.12-3.95 (m, 1H), 3.45-3.32 (m, 4H), 3.28-2.61 (m, 12H), 2.17-1.62 (m, 8H).

2-(2-(trans-3-methoxycyclobutyl)pyridin-3-yl)-2-((R)-3-(4-(5,6,7,8-tetrahydro-1,8-naphthyridin-2-yl)butoxy)pyrrolidin-1-yl)acetic Acid (Compound 77)

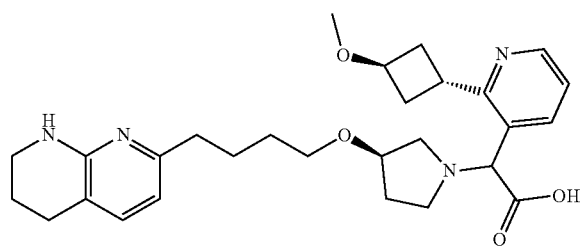 [SMILES: CO[C@H]1C[C@H](c2ncccc2C(C(=O)O)N2CC[C@@H](OCCCCc3ccc4c(n3)NCCC4)C2)C1]

Compound 77 LC/MS ESI 495.3 (M+H)+. $^1$H NMR (500 MHz, MeOD) δ 8.59-8.57 (m, 1H), 8.03-7.98 (m, 1H), 7.32-7.28 (m, 2H), 6.48 (t, J=7.3 Hz, 1H), 4.84-4.71 (m, 1H), 4.26-4.15 (m, 3H), 3.54-3.40 (m, 5H), 3.28 (s, 3H), 3.13-3.10 (m, 2H), 2.78-2.60 (m, 6H), 2.48-2.36 (m, 2H), 2.17-1.64 (m, 8H).

2-(2-(cis-3-methoxycyclobutyl)pyridin-3-yl)-2-((R)-3-(4-(5,6,7,8-tetrahydro-1,8-naphthyridin-2-yl)butoxy)pyrrolidin-1-yl)acetic Acid (Compound 78)

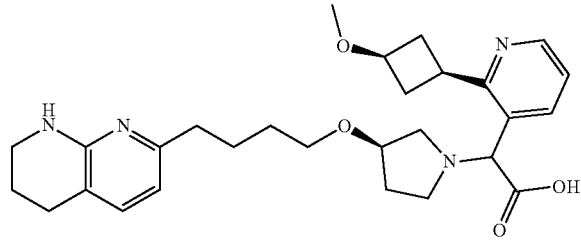 [SMILES: CO[C@H]1C[C@@H](c2ncccc2C(C(=O)O)N2CC[C@@H](OCCCCc3ccc4c(n3)NCCC4)C2)C1]

Compound 78 LC/MS ESI 495.3 (M+H)+. $^1$H NMR (500 MHz, MeOD) δ 8.58-8.56 (m, 1H), 8.00 (dd, J=17.8, 7.9 Hz, 1H), 7.31-7.29 (m, 2H), 6.49-6.46 (m, 1H), 4.91-4.79 (m, 1H), 4.21-4.18 (m, 1H), 3.90-3.87 (m, 1H), 3.71-3.40 (m, 6H), 3.30-3.00 (m, 6H), 2.78-2.59 (m, 6H), 2.51-1.60 (m, 10H).

2-(2-(tert-butoxymethyl)phenyl)-2-((R)-3-(4-(4-methoxy-5,6,7,8-tetrahydro-1,8-naphthyridin-2-yl)butoxy)pyrrolidin-1-yl)acetic Acid (Diastereomeric Compounds 79-E1 and 79-E2)

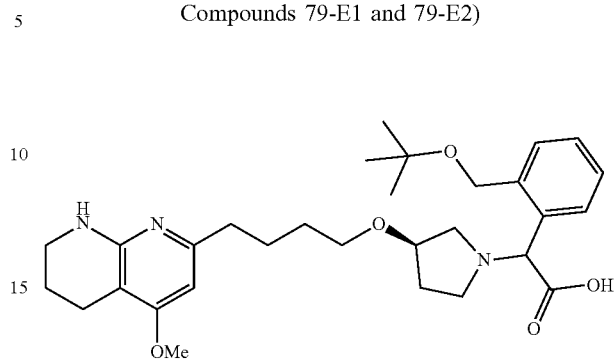

Compound 79-E1 LC/MS ESI 526.2 (M+H)$^+$ $^1$H NMR (400 MHz, MeOD) δ 7.67-7.65 (m, 1H), 7.44-7.38 (m, 3H), 6.36 (s, 1H), 4.96 (s, 1H), 4.83 (d, J=10.4 Hz, 1H), 4.47 (d, J=10.4 Hz, 1H), 4.20 (s, 1H), 3.91 (s, 3H), 3.79-3.42 (m, 4H), 3.39-3.36 (m, 2H), 3.35-3.31 (m, 1H), 3.09-3.07 (m, 1H), 2.64-2.58 (m, 4H), 2.20-2.12 (m, 2H), 1.86-1.62 (m, 6H), 1.29 (s, 9H).

Compound 79-E2 LC/MS ESI 526.2 (M+H)$^+$ $^1$H NMR (400 MHz, MeOD) δ 7.62 (s, 1H), 7.42 (s, 3H), 6.49 (s, 1H), 4.96 (s, 1H), 4.76-4.75 (m, 1H), 4.61-4.55 (m, 1H), 4.24 (s, 1H), 3.96 (s, 3H), 3.64-3.42 (m, 3H), 3.40-3.30 (m, 3H), 3.25-3.15 (m, 2H), 2.79-2.58 (m, 4H), 2.29-2.21 (m, 1H), 2.13-2.02 (m, 1H), 1.96-1.62 (m, 6H), 1.33 (s, 9H).

2-(5-fluoro-2-((1-methylcyclopropyl)methoxy)phenyl)-2-((R)-3-(4-(4-methoxy-5,6,7,8-tetrahydro-1,8-naphthyridin-2-yl)butoxy)pyrrolidin-1-yl)acetic Acid (Diastereomeric Compounds 80-E1 and 80-E2)

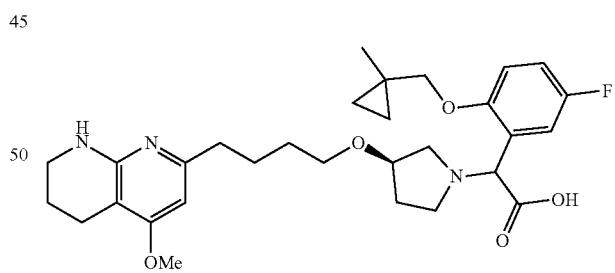

Compound 80-E1 LC/MS ESI 542.2 (M+H)+. $^1$H NMR (400 MHz, MeOD) δ 7.37-7.34 (m, 1H), 7.15-6.93 (m, 2H), 6.31-6.21 (m, 1H), 5.04 (s, 1H), 4.24-3.96 (m, 1H), 3.93-3.74 (m, 5H), 3.56-3.36 (m, 3H), 3.35-3.17 (m, 4H), 3.08-2.88 (m, 1H), 2.59-2.55 (m, 4H), 2.16-1.96 (m, 2H), 1.93-1.48 (m, 6H), 1.24 (s, 3H), 0.79-0.32 (m, 4H).

Compound 80-E2 LC/MS ESI 542.2 (M+H)+. $^1$H NMR (400 MHz, MeOD) δ 7.35-7.33 (m, 2H), 7.18-7.03 (m, 2H), 6.55 (s, 1H), 5.05 (s, 1H), 4.31 (s, 1H), 3.98-3.81 (m, 5H), 3.58-3.31 (m, 8H), 2.82-2.55 (m, 4H), 2.40-2.06 (m, 2H), 1.98-1.52 (m, 6H), 1.24 (s, 3H), 0.55-0.38 (m, 4H).

2-(2-cyclopropoxy-5-fluorophenyl)-2-((R)-3-(4-(4-methoxy-5,6,7,8-tetrahydro-1,8-naphthyridin-2-yl)butoxy)pyrrolidin-1-yl)acetic Acid (Compound 81)

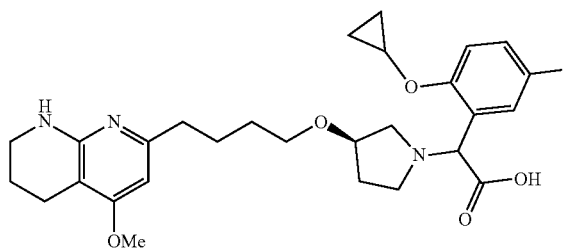

Compound 81 LC/MS ESI 514 (M+H)+. $^1$H NMR (500 MHz, MeOD) δ 7.41-7.39 (m, 1H), 7.35-7.32 (m, 1H), 7.17-7.13 (m, 1H), 6.28 (s, 1H), 4.81 (s, 1H), 4.16 (s, 3H), 3.91-3.90 (m, 1H), 3.87 (s, 3H), 3.50-3.36 (m, 3H), 3.22-3.30 (m, 3H), 3.18-3.14 (m, 2H), 2.62-2.58 (m, 4H), 2.17-2.10 (m, 2H), 1.78-1.72 (m, 2H), 1.66-1.62 (m, 2H), 0.86-0.77 (m, 4H).

2-(2-(2,2-dimethyltetrahydro-2H-pyran-4-yl)pyridin-3-yl)-2-((R)-3-(4-(5,6,7,8-tetrahydro-1,8-naphthyridin-2-yl)butoxy)pyrrolidin-1-yl)acetic Acid (Diastereomeric Compounds 82-E1 and 82-E2)

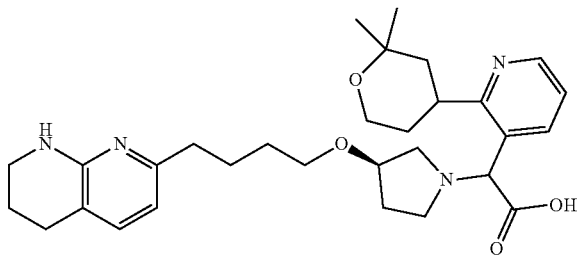 [SMILES: CC1(C)CC(c2ncccc2C(C(=O)O)N2CC[C@@H](OCCCCc3ccc4c(n3)NCCC4)C2)CCO1]

Compound 82-E1 LC/MS ESI 523.3 (M+H)+. $^1$H NMR (500 MHz, MeOD) δ 8.52-8.47 (m, 1H), 8.03-8.01 (m, 1H), 7.31-7.24 (m, 2H), 6.46 (t, J=6.8 Hz, 1H), 4.81-4.76 (m, 1H), 4.16 (s, 1H), 3.88-3.72 (m, 3H), 3.56-3.38 (m, 4H), 3.31-2.99 (m, 4H), 2.78-2.60 (m, 4H), 2.11-1.62 (m, 12H), 1.40-1.38 (m, 3H), 1.26 (s, 3H).

Compound 82-E2 LC/MS ESI 523.3 (M+H)+. $^1$H NMR (500 MHz, MeOD) δ 8.52-8.46 (m, 1H), 8.08-8.02 (m, 1H), 7.30-7.24 (m, 2H), 6.46-6.44 (m, 1H), 4.76-4.66 (m, 1H), 4.14 (s, 1H), 3.81-3.64 (m, 3H), 3.54-3.37 (m, 4H), 3.15-2.95 (m, 4H), 2.78-2.59 (m, 4H), 2.06-1.59 (m, 12H), 1.39-1.36 (m, 3H), 1.27-1.26 (m, 3H).

2-(5-fluoro-2-((oxetan-3-yloxy)methyl)phenyl)-2-((R)-3-((S)-1-fluoro-5-(5,6,7,8-tetrahydro-1,8-naphthyridin-2-yl)pentyl)pyrrolidin-1-yl)acetic Acid (Compound 83)

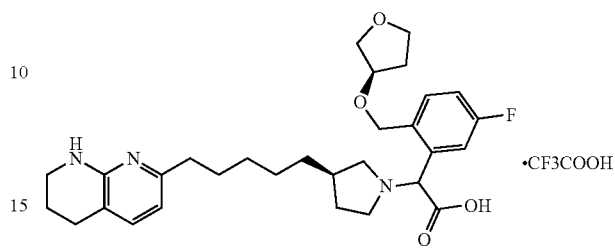

Compound 83 LC/MS ESI 526(M+H)+ $^1$H NMR (400 MHz, MeOD) δ 7.49-7.44 (m, 2H), 7.15-7.11 (m, 2H), 6.36-6.33 (m, 1H), 4.85-4.82 (m, 1H), 4.50-4.35 (m, 2H), 4.10-3.39 (m, 8H), 3.22-2.98 (m, 2H), 2.71-2.68 (m, 2H), 2.52-2.02 (m, 6H), 1.90-1.86 (m, 2H), 1.71-1.24 (m, 10H).

2-(2-cyclopropylphenyl)-2-((R)-3-(5-(5,6,7,8-tetrahydro-1,8-naphthyridin-2-yl)pentyloxy) pyrrolidin-1-yl)acetic Acid (Compound 84)

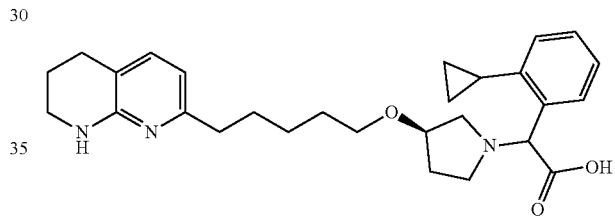

Compound 84 LC/MS ESI 464.2 (M+H)+ $^1$H NMR (500 MHz, MeOD) δ 7.70-7.57 (m, 2H), 7.35-7.24 (m, 4H), 7.21-7.10 (m, 4H), 6.38 (dd, J=7.3, 5.5 Hz, 2H), 5.35 (s, 1H), 5.21 (s, 1H), 4.20 (d, J=23.0 Hz, 2H), 3.66-3.35 (m, 10H), 3.28-3.01 (m, 6H), 2.75-2.63 (m, 4H), 2.60-2.46 (m, 4H), 2.30-2.01 (m, 6H), 1.93-1.83 (m, 4H), 1.74-1.53 (m, 8H), 1.53-1.36 (m, 4H), 1.08-0.92 (m, 6H), 0.65-0.54 (m, 2H).

2-(4-cyclopropylpyridin-3-yl)-2-((R)-3-(5-(5,6,7,8-tetrahydro-1,8-naphthyridin-2-yl)pentyloxy)pyrrolidin-1-yl)acetic Acid (Compound 85)

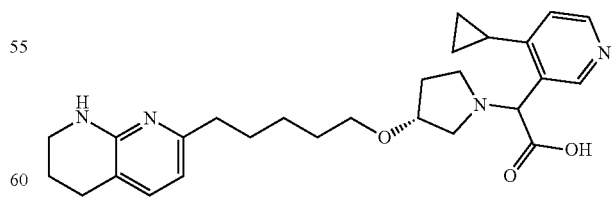

Compound 85 LC/MS ESI 464.9 (M+H)+. $^1$H NMR (500 MHz, MeOD) δ 8.74 (d, J=22.7 Hz, 1H), 8.24 (d, J=5.3 Hz, 1H), 7.14 (m, 1H), 6.92 (d, J=4.6 Hz, 1H), 6.35 (m, 1H), 4.55 (d, J=47.6 Hz, 1H), 4.05 (d, J=18.7 Hz, 1H), 3.38 (m, 4H), 2.84-2.37 (m, 8H), 2.15-1.99 (m, 1H), 1.84 (s, 3H), 1.72-1.42 (m, 5H), 1.37 (d, J=6.0 Hz, 2H), 1.18-1.04 (m, 2H), 1.01-0.89 (m, 1H), 0.69-0.57 (m, 1H).

2-(2-(1,1-difluoroethyl)phenyl)-2-((R)-3-((5-(5,6,7,8-tetrahydro-1,8-naphthyridin-2-yl)pentyl)oxy)pyrrolidin-1-yl)acetic Acid (Diastereomeric Compounds 86-E1 and 86-E2)

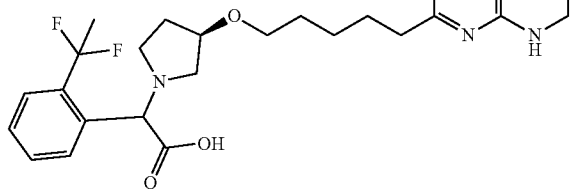

Compound 86-E1 LC/MS ESI 488.2 (M+H)+ ¹H NMR (500 MHz, MeOD) δ 7.87 (d, J=7.7 Hz, 1H), 7.67 (d, J=7.8 Hz, 1H), 7.55 (m, 2H), 7.16 (d, J=7.3 Hz, 1H), 6.39 (d, J=7.3 Hz, 1H), 5.09 (s, 1H), 4.20 (s, 1H), 3.62 (s, 1H), 3.50-3.42 (m, 2H), 3.38 (m, 2H), 3.21 (m, 2H), 3.03 (s, 1H), 2.71 (m, 2H), 2.61-2.50 (m, 2H), 2.19 (m, 4H), 2.04 (s, 1H), 1.94-1.80 (m, 2H), 1.76-1.53 (m, 4H), 1.44 (m, 2H).

Compound 86-E2 LC/MS ESI 488.2 (M+H)+ ¹H NMR (500 MHz, MeOD) δ 7.95 (d, J=7.6 Hz, 1H), 7.66 (d, J=7.7 Hz, 1H), 7.53 (m, 2H), 7.24 (d, J=7.2 Hz, 1H), 6.42 (d, J=7.3 Hz, 1H), 4.17 (s, 1H), 3.59 (s, 1H), 3.49-3.42 (m, 2H), 3.41-3.36 (m, 2H), 3.09 (d, J=12.7 Hz, 3H), 2.73 (t, J=6.2 Hz, 2H), 2.58 (m, 2H), 2.20 (m, 4H), 2.06 (s, 1H), 1.94-1.84 (m, 2H), 1.80-1.63 (m, 2H), 1.58 (s, 3H), 1.50-1.36 (m, 2H).

2-(2-cyclopropyl-5-methylpyridin-3-yl)-2-((R)-3-(4-(5,6,7,8-tetrahydro-1,8-naphthyridin-2-yl)butoxy)pyrrolidin-1-yl)acetic Acid (Compound 87)

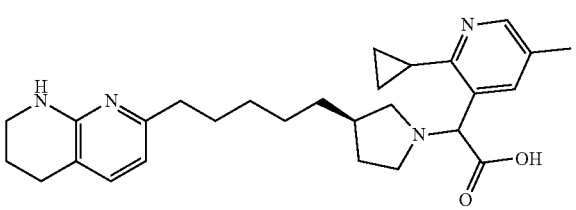 [SMILES: Cc1cnc(C2CC2)c(C(C(=O)O)N2CC[C@@H](CCCCCc3ccc4c(n3)NCCC4)C2)c1]

Compound 87: LC/MS ESI 465.2 (M+H)+, ¹H NMR (500 MHz, MeOD) δ 8.21 (dd, J=5.4, 1.7 Hz, 1H), 7.86 (dd, J=15.8, 1.6 Hz, 1H), 7.26-7.16 (m, 1H), 6.40 (d, J=7.3 Hz, 1H), 5.00 (s, 1H), 4.93 (s, 1H), 4.20-4.11 (m, 1H), 3.47 (m, 2H), 3.38 (m, 2H), 3.33 (m, 1H), 3.19-2.88 (m, 3H), 2.72 (t, J=6.1 Hz, 2H), 2.58 (m, 2H), 2.54-2.40 (m, 1H), 2.28 (d, J=5.5 Hz, 3H), 2.20-2.01 (m, 2H), 1.92-1.84 (m, 2H), 1.75-1.66 (m, 2H), 1.59 (m, 2H), 1.20 (m, 1H), 1.04-0.92 (m, 2H), 0.91-0.82 (m, 1H).

2-(5-fluoro-2-(2-methoxyethoxy)phenyl)-2-((R)-3-(5-(5,6,7,8-tetrahydro-1,8-naphthyridin-2-yl)pentyl)pyrrolidin-1-yl)acetic Acid (Compound 88)

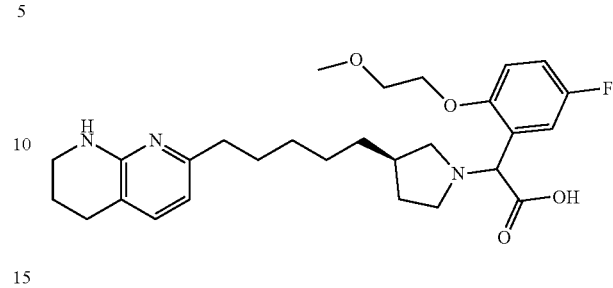

Compound 88 LC/MS A: 95% purity, UV=214 nm, Rt=1.406 min, ESI 500.7 (M+H)+. ¹H NMR (500 MHz, MeOD) δ 7.32 (td, J=9.0, 3.0 Hz, 1H), 7.21-7.03 (m, 3H), 6.36 (dd, J=7.3, 4.1 Hz, 1H), 4.98 (s, 1H), 4.29-4.16 (m, 2H), 3.81 (t, J=4.3 Hz, 2H), 3.46 (d, J=2.2 Hz, 3H), 3.41-3.37 (m, 2H), 3.32 (s, 2H), 3.16 (d, J=31.1 Hz, 2H), 2.71 (t, J=6.2 Hz, 2H), 2.51 (td, J=7.6, 4.4 Hz, 2H), 2.45-2.16 (m, 2H), 1.98-1.84 (m, 2H), 1.64 (m, 3H), 1.40 (m, 6H).

2-(2-(2-methoxyethoxy)phenyl)-2-((R)-3-(5-(5,6,7,8-tetrahydro-1,8-naphthyridin-2-yl)pentyl)pyrrolidin-1-yl)acetic Acid (Compound 89)

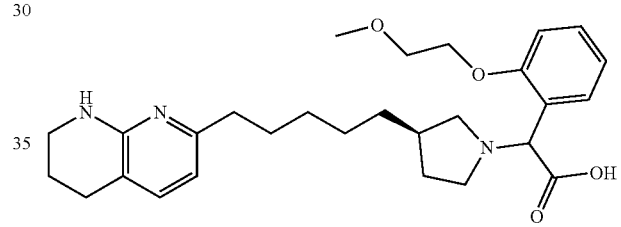

Compound 89: LC/MS ESI 482.2 (M+H)+, ¹H NMR (500 MHz, MeOD) δ 7.56 (s, 1H), 7.51 (d, J=7.5 Hz, 1H), 7.48-7.42 (m, 1H), 7.18 (dd, J=8.2, 4.6 Hz, 1H), 7.12 (t, J=7.5 Hz, 1H), 6.59 (s, 1H), 5.43 (s, 1H), 4.31-4.25 (m, 2H), 4.19-3.96 (m, 1H), 3.82-3.77 (m, 2H), 3.48 (m, 6H), 3.35-3.30 (m, 1H), 3.23-2.92 (m, 2H), 2.81 (d, J=5.3 Hz, 2H), 2.74-2.62 (m, 2H), 2.25 (m, 2H), 1.99-1.90 (m, 2H), 1.80-1.63 (m, 3H), 1.57-1.29 (m, 6H).

2-(5-fluoro-2-(tetrahydrofuran-2-yl)phenyl)-2-((R)-3-(4-(5,6,7,8-tetrahydro-1,8-naphthyridin-2-yl)butoxy)pyrrolidin-1-yl)acetic Acid (Diastereomeric Compounds 90-E1 and 90-E2)

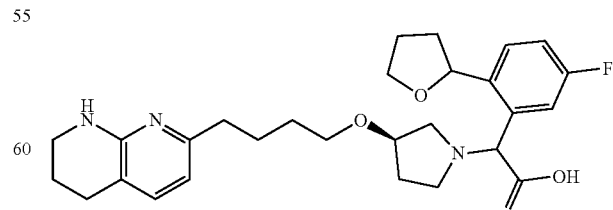

Compound 90-E1 (mixture of 2 isomers) LC/MS ESI 498.1 (M+H)+. ¹H NMR (500 MHz, MeOD) ¹H NMR (500 MHz, MeOD) δ 7.46 (dd, J=8.8, 5.9 Hz, 1H), 7.38-7.26 (m, 1H), 7.12-6.97 (m, 2H), 6.30 (d, J=7.3 Hz, 1H), 5.13 (m, 1H), 4.90 (s, 1H), 4.07 (d, J=15.0 Hz, 1H), 3.95 (m, 1H), 3.83-3.70 (m, 1H), 3.46-3.31 (m, 3H), 3.27 (m, 2H), 3.14-2.88 (m, 2H), 2.61 (t, J=6.2 Hz, 2H), 2.47 (m, 2H), 2.33 (m, 1H), 2.08-1.83 (m, 5H), 1.77 (m, 2H), 1.63 (m, 2H), 1.55-1.45 (m, 2H).

Compound 90-E2 (mixture of 2 isomers) LC/MS ESI 498.1 (M+H)+. ¹H NMR (500 MHz, MeOD¹H NMR (500 MHz, MeOD) δ 7.46-7.31 (m, 2H), 7.00 (dd, J=30.9, 7.6 Hz, 1H), 6.87 (d, J=7.7 Hz, 1H), 6.27 (d, J=7.3 Hz, 1H), 5.22 (m, 1H), 4.53 (m, 1H), 4.29 (m, 1H), 4.05-3.92 (m, 1H), 3.77 (d, J=6.5 Hz, 1H), 3.71-3.55 (m, 2H), 3.32 (m, 5H), 3.06 (t, J=9.7 Hz, 1H), 2.63 (m, 5H), 2.48-2.26 (m, 3H), 1.93 (m, 2H), 1.85-1.73 (m, 4H), 1.52-1.48 (m, 2H).

2-(5-fluoro-2-(tetrahydro-2H-pyran-2-yl)phenyl)-2-((R)-3-(4-(4-methoxy-5,6,7,8-tetrahydro-1,8-naphthyridin-2-yl)butoxy)pyrrolidin-1-yl)acetic Acid (Diastereomeric Compounds 91-A-E1, 91-A-E2, 91-B-E1 and 91-B-E2)

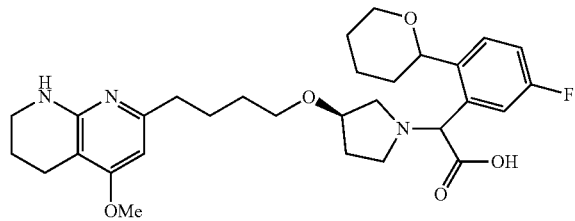 [SMILES: COc1cc(CCCCO[C@@H]2CCN(C(C(=O)O)c3cc(F)ccc3C3CCCCO3)C2)nc2c1CCCN2]

Compound 91-A-E1 LC/MS A: 99% purity, UV=214 nm, Rt=1.64 min, ESI 542.7 (M+H)+. H NMR (500 MHz, MeOD) δ 7.53 (m, 2H), 7.09 (d, J=2.6 Hz, 1H), 6.30 (s, 1H), 4.87 (s, 1H), 4.60 (s, 1H), 4.12 (s, 1H), 4.03 (s, 1H), 3.87 (s, 3H), 3.72 (d, J=2.5 Hz, 1H), 3.55-3.40 (m, 2H), 3.30 (m, 4H), 3.07-2.95 (m, 2H), 2.74-2.53 (m, 4H), 2.18-2.09 (m, 1H), 2.08-1.93 (m, 3H), 1.74 (m, 10H).

Compound 91-B-E1 LC/MS A: 100% purity, UV=214 nm, Rt=1.62 min, ESI 542.7 (M+H)+. ¹H NMR (500 MHz, MeOD) δ 7.52 (m, 2H), 7.11 (d, J=2.7 Hz, 1H), 6.30 (s, 1H), 4.89-4.72 (m, 3H), 4.16 (d, J=2.7 Hz, 1H), 4.02 (s, 1H), 3.87 (s, 3H), 3.70 (d, J=2.2 Hz, 1H), 3.48 (m, 3H), 3.25 (m, 1H), 3.13 (d, J=12.2 Hz, 1H), 2.99-2.85 (m, 2H), 2.60 (m, 4H), 2.08-1.96 (m, 4H), 1.88-1.60 (m, 11H).

Compound 91-B-E2 LC/MS A: 95% purity, UV=214 nm, Rt=1.66 min, ESI 542.7 (M+H)+. ¹H NMR (500 MHz, MeOD) δ 7.47-7.41 (m, 2H), 7.06 (m, 1H), 6.33 (s, 1H), 4.86 (dd, J=13.9, 10.6 Hz, 3H), 4.15-4.06 (m, 2H), 3.73-3.64 (m, 1H), 3.55-3.39 (m, 3H), 3.29 (m, 2H), 3.09-2.92 (m, 3H), 2.71-2.56 (m, 4H), 2.19-1.56 (m, 16H).

2-(2-(6,6-dimethyltetrahydro-2H-pyran-2-yl)phenyl)-2-((R)-3-(4-(5,6,7,8-tetrahydro-1,8-naphthyridin-2-yl)butoxy)pyrrolidin-1-yl)acetic Acid (Diastereomeric Compounds 103-E1 and 103-E2)

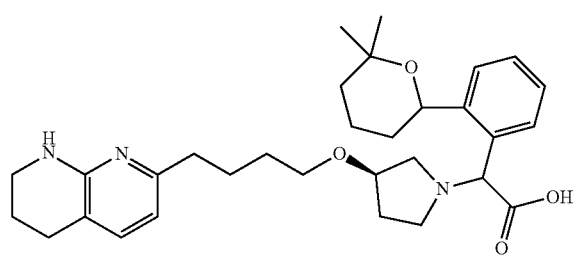 [SMILES: CC1(C)CCCC(c2ccccc2C(C(=O)O)N2CC[C@@H](OCCCCc3ccc4c(n3)NCCC4)C2)O1]

Compound 103-E1 (mixture of 2 stereoisomers) LC/MS ESI 522 (M+H)+. 1H NMR (500 MHz, MeOD) δ 7.72-7.70 (m, 1H), 7.62-7.59 (m, 1H), 7.45-7.35 (m, 2H), 7.21-7.19 (m, 1H), 6.38-6.35 (m, 1H), 5.21-5.19 (m, 1H), 4.92-4.90 (m, 1H), 4.23-4.21 (m, 1H), 3.81-3.61 (m, 1H), 3.51-2.91 (m, 7H), 2.62-2.59 (m, 2H), 2.51-2.49 (m, 2H), 2.18-1.48 (m, 14H), 1.31-1.29 (m, 3H), 1.23-1.21 (m, 3H).

Compound 103-E2 (mixture of 2 stereoisomers) LC/MS ESI 522 (M+H)+. 1H NMR (500 MHz, MeOD) δ 7.70-7.65 (m, 1H), 7.35-7.32 (m, 3H), 7.14 (d, J=7.2 Hz, 1H), 6.37-6.35 (m, 1H), 5.51-5.49 (m, 1H), 4.98-4.92 (m, 1H), 4.18-4.16 (m, 1H), 3.51-3.31 (m, 4H), 3.29-2.81 (m, 4H), 2.72-2.68 (m, 2H), 2.54-2.51 (m, 2H), 2.18-1.48 (m, 14H), 1.34-1.31 (m, 6H).

2-(2-(4,4-dimethyltetrahydrofuran-2-yl)-5-fluorophenyl)-2-((R)-3-(4-(5,6,7,8-tetrahydro-1,8-naphthyridin-2-yl)butoxy)pyrrolidin-1-yl)acetic Acid (Diastereomeric Compounds 104-E1 and 104-E2)

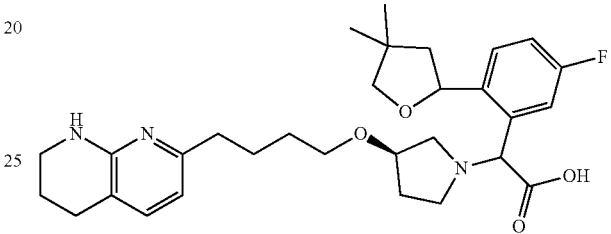

Compound 104-E1 (mixture of 2 stereoisomers) LC/MS ESI 526 (M+H)+. ¹H NMR (400 MHz, MeOD) δ 7.63-7.59 (m, 1H), 7.48-7.45 (dd, J=2.8 Hz, J=10.4 Hz 1H), 7.18-7.14 (m, 2H), 6.38 (d, J=7.1 Hz, J1H), 5.46-5.42 (m, 1H), 4.82 (m, 1H), 4.15-4.14 (m, 1H), 3.75-3.73 (m, 1H), 3.63-3.61 (m, 1H), 3.49-3.32 (m, 5H), 3.23-3.12 (m, 2H), 2.75-2.71 (m, 2H), 2.57-2.54 (m, 2H), 2.37-2.33 (m, 1H), 2.14 (m, 2H), 1.89-1.85 (m, 2H), 1.79-1.60 (m, 6H), 1.21 (s, 3H), 1.16 (s, 3H). Chiral SFC E (45% MeOH): ee 100%, Rt=3.86 min.

Compound 104-E2 (mixture of 2 stereoisomers) LC/MS ESI 526 (M+H)+. ¹H NMR (400 MHz, MeOD) δ 7.61-7.58 (m, 1H), 7.47-7.44 (dd, J=2.8 Hz, J=10.4 Hz 1H), 7.16-7.11 (m, 2H), 6.38 (d, J=7.1 Hz, J1H), 5.46-5.42 (m, 1H), 4.81 (m, 1H), 4.16-4.15 (m, 1H), 3.75-3.73 (m, 1H), 3.63-3.61 (m, 1H), 3.47-3.31 (m, 5H), 3.22-3.11 (m, 2H), 2.94 (m, 1H), 2.72-2.69 (m, 1H), 2.56-2.53 (m, 2H), 2.35-2.31 (m, 1H), 2.09-2.07 (m, 2H), 1.91-1.77 (m, 2H), 1.75-1.69 (m, 3H), 1.65-1.60 (m, 2H), 1.20 (s, 3H), 1.16 (s, 3H). Chiral SFC E (45% MeOH): ee 98%, Rt=4.89 min.

2-(4-fluoro-2-((S)-tetrahydro-2H-pyran-2-yl)phenyl)-2-((R)-3-(4-(5,6,7,8-tetrahydro-1,8-naphthyridin-2-yl)butoxy)pyrrolidin-1-yl)acetic Acid (Diastereomeric Compounds 105-E1 and 105-E2)

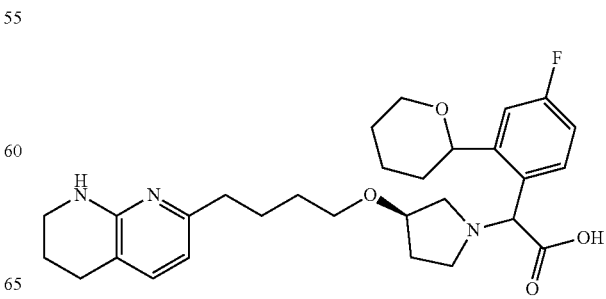

Compound 105-E1 (mixture of 2 stereoisomers) LC/MS ESI 512.3 (M+H)+. ¹H NMR (400 MHz, MeOD) δ 7.80-7.70 (m, 1H), 7.27-7.24 (m, 1H), 7.13 (d, J=8.0 Hz, 1H), 7.10-7.05 (m, 1H), 6.38-6.36 (m, 1H), 4.87-4.65 (m, 2H), 4.16-4.03 (m, 2H), 3.70-3.67 (m, 1H), 3.49-3.36 (m, 5H), 3.25-3.15 (m, 1H), 3.10-2.85 (m, 2H), 2.70 (t, J=6.4 Hz, 2H), 2.54 (t, J=8.0 Hz, 2H), 2.20-1.80 (m, 6H), 1.78-1.55 (m, 8H).

Compound 105-E2 (mixture of 2 stereoisomers) LC/MS ESI 512.3 (M+H)+. ¹H NMR (400 MHz, MeOD) δ 7.75-7.60 (m, 1H), 7.22-7.18 (m, 2H), 7.17-7.00 (m, 1H), 6.39-6.36 (m, 1H), 5.25-4.94 (m, 1H), 4.81-4.58 (m, 1H), 4.20-4.05 (m, 2H), 3.80-3.36 (m, 7H), 3.25-2.95 (m, 2H), 2.71 (t, J=6.4 Hz, 2H), 2.56 (t, J=3.6 Hz, 2H), 2.20-2.00 (m, 2H), 1.99-1.80 (m, 5H), 1.98-1.54 (m, 7H).

2-(2-fluoro-6-(tetrahydro-2H-pyran-2-yl)phenyl)-2-((R)-3-(4-(5,6,7,8-tetrahydro-1,8-naphthyridin-2-yl)butoxy)pyrrolidin-1-yl)acetic Acid (Diastereomeric Compounds 106-E1 and 106-E2)

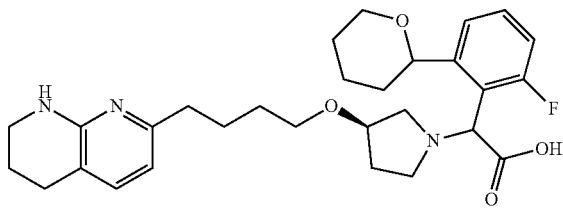 [SMILES: O=C(O)C(c1c(F)cccc1C1CCCCO1)N1CC[C@@H](OCCCCc2ccc3c(n2)NCCC3)C1]

Compound 106-E1 (mixture of 2 stereoisomers) LC/MS ESI 512.3 (M+H)+. ¹H NMR (400 MHz, MeOD) δ 7.35-7.29 (m, 2H), 7.13-7.05 (m, 2H), 6.35 (d, J=8.0 Hz, 1H), 5.18-5.12 (m, 1H), 4.74 (s, 1H), 4.70 (s, 1H), 4.01 (d, J=12.0 Hz, 1H), 3.78-3.61 (m, 1H), 3.54-3.36 (m, 4H), 3.24-2.82 (m, 3H), 2.71-2.68 (m, 2H), 2.53-2.48 (m, 2H), 2.19-2.17 (m, 2H), 2.03-2.00 (m, 1H), 1.94-1.84 (m, 4H), 1.72-1.52 (m, 8H).

Compound 106-E2 (mixture of 2 stereoisomers) LC/MS ESI 512.3 (M+H)+. ¹H NMR (400 MHz, MeOD) δ 7.35-7.29 (m, 2H), 7.13-7.05 (m, 2H), 6.35 (d, J=8.0 Hz, 1H), 5.18-5.12 (m, 1H), 4.72 (s, 1H), 4.05-3.99 (m, 2H), 3.78-3.61 (m, 1H), 3.44-3.36 (m, 4H), 3.24-2.82 (m, 2H), 2.71-2.68 (m, 3H), 2.53-2.48 (m, 2H), 2.19-2.18 (m, 2H), 2.03-2.00 (m, 1H), 1.90-1.86 (m, 4H), 1.69-1.54 (m, 8H).

2-(5-fluoro-2-(5-oxaspiro[2.4]heptan-6-yl)phenyl)-2-((R)-3-(4-(5,6,7,8-tetrahydro-1,8-naphthyridin-2-yl)butoxy)pyrrolidin-1-yl)acetic Acid (Diastereomeric Compounds 107-E1 and 107-E2)

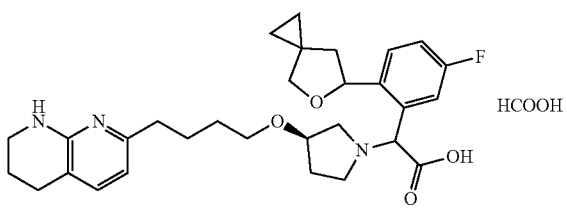 [SMILES: O=C(O)C(c1cc(F)ccc1C1CC2(CC2)CO1)N1CC[C@@H](OCCCCc2ccc3c(n2)NCCC3)C1 ; "HCOOH"]

Compound 107-E1 (mixture of 2 stereoisomers) LC/MS ESI 524(M+H)+. ¹H NMR (500 MHz, MeOD) δ 8.30 (bs, 1H), 7.58-7.54 (m, 1H), 7.40-7.35 (m, 2H), 7.11-7.06 (m, 1H), 6.46 (d, J=7.2 Hz, 1H), 5.43-5.40 (m, 1H), 4.95 (s, 1H), 4.13-4.11 (m, 1H), 3.86-3.84 (m, 1H), 3.66-3.64 (m, 1H), 3.50-3.31 (m, 6H), 3.31-3.20 (m, 2H), 2.72-2.51 (m, 4H), 2.18-2.03 (m, 4H), 1.81-1.59 (m, 6H), 0.60-0.48 (m, 4H). Chiral SFC E (45% MeOH): ee 100%, Rt=4.74 min.

Compound 107-E2 (mixture of 2 stereoisomers) LC/MS ESI 524 (M+H)+. ¹H NMR (500 MHz, MeOD) δ 8.53 (bs, 1H), 7.70-7.67 (m, 1H), 7.52-7.46 (m, 2H), 7.24-7.20 (m, 1H), 6.58 (d, J=7.2 Hz, 1H), 5.49-5.45 (m, 1H), 5.20 (s, 1H), 4.23-4.21 (m, 1H), 3.96-3.91 (m, 1H), 3.75-3.71 (m, 1H), 3.71-3.31 (m, 7H), 3.31-3.20 (m, 1H), 2.82-2.61 (m, 4H), 2.18-2.03 (m, 4H), 1.81-1.59 (m, 6H), 0.70-0.58 (m, 4H). Chiral SFC E (45% MeOH): ee 100%, Rt=6.51 min.

2-(5-fluoro-2-(6-oxaspiro[2.5]octan-5-yl)phenyl)-2-((R)-3-(4-(5,6,7,8-tetrahydro-1,8-naphthyridin-2-yl)butoxy)pyrrolidin-1-yl)acetic Acid (Diastereomeric Compounds 108-E1 and 108-E2)

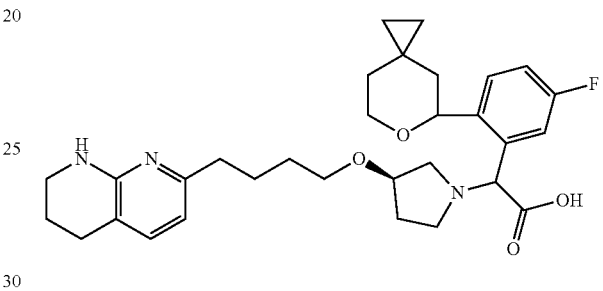

Compound 108-E1 (mixture of 2 stereoisomers) LC/MS ESI 538.2 (M+H)+, ¹H NMR (400 MHz, MeOD) δ 7.55-7.40 (m, 1H), 7.39-7.31 (m, 1H), 7.15-7.01 (m, 2H), 6.28 (d, J=7.2 Hz, 1H), 4.84 (s, 1H), 4.18-4.14 (m, 1H), 4.00-3.85 (m, 1H), 3.80-3.60 (m, 1H), 3.58-3.43 (m, 1H), 3.42-3.35 (m, 2H), 3.33-3.23 (m, 3H), 3.20-3.11 (m, 1H), 2.95-2.90 (m, 1H), 2.60 (t, J=6.4 Hz, 2H), 2.45 (t, J=7.6 Hz, 2H), 2.20-1.85 (m, 4H), 1.83-1.73 (m, 2H), 1.70-1.40 (m, 4H), 1.25-1.15 (m, 2H), 0.80-0.60 (m, 1H), 0.50-0.40 (m, 1H), 0.39-0.20 (m, 3H). Chiral SFC H (40% EtOH): ee 100%, Rt=2.10 min.

Compound 108-E2 (mixture of 2 stereoisomers) LC/MS ESI 538.2 (M+H)+, ¹H NMR (400 MHz, MeOD) δ 7.55-7.43 (m, 1H), 7.41-7.30 (m, 1H), 7.20-6.90 (m, 2H), 6.40-6.20 (m, 1H), 4.70 (s, 1H), 4.20-4.05 (m, 1H), 4.00-3.85 (m, 1H), 3.80-3.60 (m, 1H), 3.58-3.22 (m, 6H), 3.20-2.90 (m, 2H), 2.70-2.55 (m, 2H), 2.50-2.38 (m, 2H), 2.20-1.90 (m, 4H), 1.83-1.73 (m, 2H), 1.70-1.40 (m, 4H), 1.25-1.15 (m, 2H), 0.80-0.60 (m, 1H), 0.50-0.40 (m, 1H), 0.39-0.20 (m, 3H). Chiral SFC H (40% EtOH): ee 100%, Rt=2.51 min.

2-(2-(1,4-dioxan-2-yl)-5-fluorophenyl)-2-((R)-3-(4-(5,6,7,8-tetrahydro-1,8-naphthyridin-2-yl)butoxy)pyrrolidin-1-yl)acetic Acid (Diastereomeric Compounds 109-E1 and 109-E2)

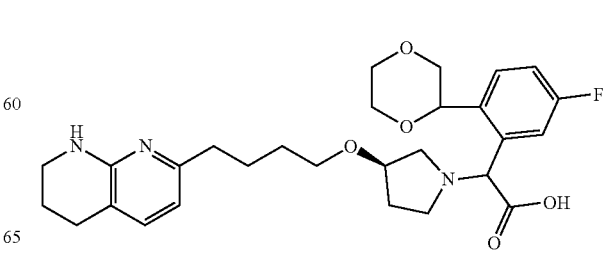

Compound 109-E1 (mixture of 2 stereoisomers) LC/MS ESI 514(M+H)+. $^1$H NMR (400 MHz, MeOD) δ 7.61-7.59 (m, 1H), 7.52-7.48 (m, 1H), 7.22-7.20 (m, 1H), 7.16-7.14 (m, 1H), 6.42-6.40 (m, 1H), 5.21-5.02 (m, 1H), 4.78-4.75 (m, 1H), 4.30-4.26 (m, 1H), 4.20-4.17 (m, 1H), 3.81-3.75 (m, 2H), 3.73-3.68 (m, 2H), 3.50-3.31 (m, 6H), 3.20-2.98 (m, 3H), 2.72-2.68 (m, 2H), 2.54-2.51 (m, 2H), 2.18-2.03 (m, 2H), 1.81-1.59 (m, 6H).

Compound 109-E2 (mixture of 2 stereoisomers) LC/MS ESI 514 (M+H)+. $^1$H NMR (400 MHz, MeOD) δ 7.51-7.49 (m, 2H), 7.32-7.29 (m, 1H), 7.22-7.18 (m, 1H), 6.42-6.39 (m, 1H), 5.30-4.96 (m, 2H), 4.20-4.17 (m, 1H), 3.91-3.70 (m, 6H), 3.52-3.31 (m, 6H), 3.20-2.98 (m, 3H), 2.72-2.68 (m, 2H), 2.54-2.51 (m, 2H), 2.18-2.03 (m, 2H), 1.81-1.56 (m, 6H).

2-(2-(4,4-difluorotetrahydrofuran-2-yl)-5-fluorophenyl)-2-((R)-3-(4-(5,6,7,8-tetrahydro-1,8-naphthyridin-2-yl)butoxy)pyrrolidin-1-yl)acetic Acid (Diastereomeric Compounds 110-E1 and 110-E2)

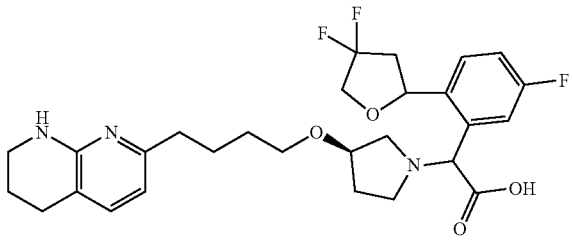 [SMILES: O=C(O)C(c1cc(F)ccc1C1CC(F)(F)CO1)N1CC[C@@H](OCCCCc2ccc3c(n2)NCCC3)C1]

Compound 110-E1 (mixture of 2 stereoisomers) LC/MS ESI 534.2 (M+H)+, $^1$H NMR (400 MHz, MeOD) δ 7.80-7.60 (m, 1H), 7.55-7.45 (m, 1H), 7.35-7.15 (m, 2H), 6.43 (d, J=7.2 Hz, 1H), 5.75-5.60 (m, 1H), 4.77 (s, 1H), 4.30-4.05 (m, 2H), 4.04-3.90 (m, 1H), 3.60-3.50 (m, 1H), 3.45-3.30 (m, 4H), 3.25-2.95 (m, 4H), 2.80-2.70 (m, 2H), 2.65-2.30 (m, 3H), 2.25-2.05 (m, 2H), 1.95-1.85 (m, 2H), 1.80-1.55 (m, 4H). Chiral SFC F (30% MeOH): ee 100%, Rt=4.16 min.

Compound 110-E2 (mixture of 2 stereoisomers) LC/MS ESI 534.2 (M+H)+, $^1$H NMR (400 MHz, MeOD) δ 7.75-7.68 (m, 1H), 7.65-7.40 (m, 1H), 7.35-7.15 (m, 2H), 6.50-6.40 (m, 1H), 5.70-5.40 (m, 1H), 4.78 (s, 1H), 4.40-4.10 (m, 2H), 4.05-3.80 (m, 1H), 3.60-3.45 (m, 2H), 3.42-3.38 (m, 3H), 3.30-2.80 (m, 4H), 2.78-2.70 (m, 2H), 2.65-2.40 (m, 3H), 2.20-2.00 (m, 2H), 1.95-1.85 (m, 2H), 1.80-1.55 (m, 4H). Chiral SFC F (30% MeOH): ee 100%, Rt=5.04 min.

2-(5-fluoro-2-((S)-tetrahydro-2H-pyran-2-yl)phenyl)-2-((S)-3-(4-(5,6,7,8-tetrahydro-1,8-naphthyridin-2-yl)butoxy)pyrrolidin-1-yl)acetic Acid (Diastereomeric Compounds 111-E1 and 111-E2)

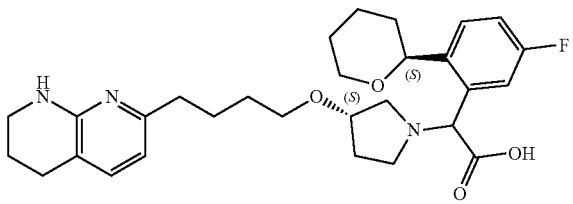

Compound 111-E1 LC/MS ESI 512.3 (M+H)+, $^1$H NMR (500 MHz, MeOD) δ 7.62-7.58 (m, 1H), 7.48-7.46 (m, 1H), 7.22-7.15 (m, 2H), 6.41 (d, J=7.0 Hz, 1H), 4.85-4.79 (m, 2H), 4.18 (s, 1H), 4.05-4.02 (m, 1H), 3.75-3.71 (m, 1H), 3.56-3.31 (m, 6H), 3.21-3.16 (m, 2H), 2.74-2.57 (m, 4H), 2.18-1.62 (m, 14H).

Compound 111-E2 LC/MS ESI 512.3 (M+H)+, $^1$H NMR (500 MHz, MeOD) δ 7.62-7.58 (m, 1H), 7.48-7.46 (m, 1H), 7.22-7.15 (m, 2H), 6.62-6.60 (m, 1H), 6.00 (br, 1H), 4.65-4.61 (m, 1H), 4.25-4.12 (m, 2H), 3.55-3.31 (m, 8H), 2.84-2.65 (m, 5H), 2.18-1.62 (m, 14H).

2-(5-fluoro-2-(tetrahydrofuran-2-yl)phenyl)-2-((R)-3-(4-(4-methoxy-5,6,7,8-tetrahydro-1,8-naphthyridin-2-yl)butoxy)pyrrolidin-1-yl)acetic Acid (THF Stereoisomer A, Diastereomeric Compounds 112-A-E1 and 112-A-E2)

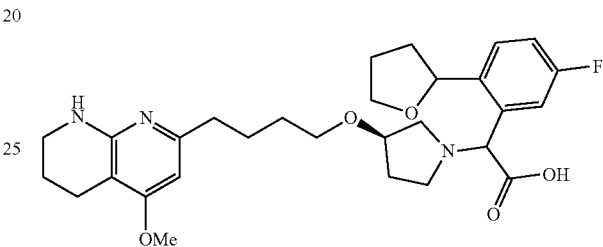

Compound 112-A-E1 LC/MS ESI 528.2 (M+H)+, $^1$H NMR (400 MHz, MeOD) δ 8.53 (s, 1H), 7.60-7.58 (m, 1H), 7.47-7.45 (m, 1H), 7.19-7.15 (m, 1H), 6.49 (s, 1H), 5.20-5.09 (m, 2H), 4.20 (s, 1H), 4.10-4.05 (m, 1H), 3.96 (s, 3H), 3.90-3.81 (m, 1H), 3.56-3.31 (m, 6H), 3.16-3.10 (m, 1H), 2.74-2.69 (m, 4H), 2.40 (s, 1H), 2.08-1.62 (m, 12H).

Compound 112-A-E2 LC/MS ESI 528.2 (M+H)+, $^1$H NMR (400 MHz, MeOD) δ 8.59 (s, 4H), 7.50-7.40 (m, 2H), 7.19-7.15 (m, 1H), 6.49 (s, 1H), 5.16-5.12 (m, 1H), 4.20-4.10 (m, 2H), 3.96 (s, 3H), 3.90-3.81 (m, 1H), 3.56-3.31 (m, 4H), 3.19-3.01 (m, 4H), 2.75-2.69 (m, 4H), 2.40 (s, 1H), 2.20 (s, 1H), 2.09-1.98 (m, 4H), 1.92-1.62 (m, 7H).

2-(5-fluoro-2-((R)-tetrahydro-2H-pyran-2-yl)phenyl)-2-((S)-3-(4-(5,6,7,8-tetrahydro-1,8-naphthyridin-2-yl)butoxy)pyrrolidin-1-yl)acetic Acid (Diastereomeric Compounds 113-E1 and 113-E2)

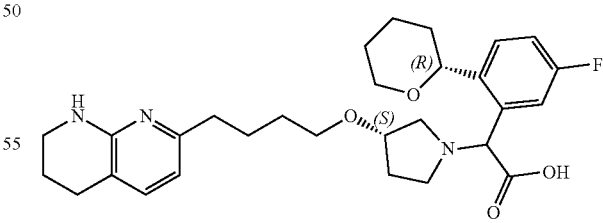

Compound 113-E1 LC/MS ESI 512.3 (M+H)+. $^1$H NMR (400 MHz, MeOD) δ 8.45 (s, 1H), 7.63-7.59 (m, 1H), 7.46 (d, J=8.0 Hz, 2H), 7.21-7.19 (m, 1H), 6.55 (d, J=8.0 Hz, 1H), 5.11 (s, 1H), 4.74 (d, J=8.0 Hz, 1H), 4.34 (s, 1H), 4.06 (d, J=8.0 Hz, 1H), 3.72-3.71 (m, 1H), 3.58-3.33 (m, 6H), 3.15 (s, 1H), 2.81-2.67 (m, 4H), 2.18 (s, 2H), 2.03-1.58 (m, 13H).

Compound 113-E2 LC/MS ESI 512.3 (M+H)+. 1H NMR (400 MHz, MeOD) δ 8.45 (s, 1H), 7.47-7.45 (m, 2H), 7.21-7.19 (m, 1H), 7.16-7.11 (m, 1H), 6.43 (d, J=8.0 Hz, 1H), 5.25 (s, 1H), 4.89 (d, J=8.0 Hz, 1H), 4.19 (s, 1H), 4.10 (d, J=8.0 Hz, 1H), 3.58-3.33 (m, 6H), 3.15-3.12 (m, 2H), 2.75-2.72 (m, 2H), 2.63-2.59 (m, 2H), 2.18-2.16 (m, 2H), 2.03-1.58 (m, 13H).

2-(5-fluoro-2-(tetrahydrofuran-2-yl)phenyl)-2-((R)-3-(4-(7-methyl-5,6,7,8-tetrahydro-1,8-naphthyridin-2-yl)butoxy)pyrrolidin-1-yl)acetic Acid (THF Stereoisomer A, Me Stereoisomers A and B, Diastereomeric Compounds 114-A-E1, 114-A-E2, 114-B-E1 and 114-B-E2)

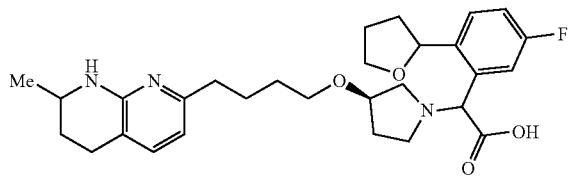 [SMILES: CC1CCc2ccc(CCCCO[C@@H]3CCN(C(C(=O)O)c4cc(F)ccc4C4CCCO4)C3)nc2N1]

Compound 114-A-E1 LC/MS ESI 512.3 (M+H)+. $^1$H NMR (400 MHz, MeOD) δ 7.56-7.49 (m, 2H), 7.18 (d, J=8.0 Hz, 1H) 7.08-7.06 (m, 1H), 6.41 (d, J=8.0 Hz, 1H), 5.33-5.30 (m, 1H), 4.95 (s, 2H), 4.59 (s, 1H), 4.16-4.05 (m, 2H), 3.92-3.85 (m, 1H), 3.59-3.40 (m, 3H), 3.03-2.82 (m, 2H), 2.75-2.72 (m, 3H), 2.57-2.42 (m, 3H), 2.07-2.01 (m, 3H), 2.00-1.82 (m, 3H), 1.75-1.65 (m, 2H), 1.62-1.59 (m, 2H), 1.57-1.55 (m, 1H), 1.22 (d, J=10.8 Hz, 3H). Compound 114-A-E2 LC/MS ESI 512.3 (M+H)+. $^1$H NMR (400 MHz, MeOD) δ 7.51-7.41 (m, 2H), 7.22 (d, J=8.0 Hz, 1H) 7.11-7.08 (m, 1H), 6.42 (d, J=8.0 Hz, 1H), 5.23-5.21 (m, 1H), 4.95 (s, 1H), 4.79 (s, 1H), 4.16-4.05 (m, 2H), 3.92-3.85 (m, 1H), 3.59-3.40 (m, 3H), 3.13-3.03 (m, 3H), 2.75-2.72 (m, 2H), 2.64-2.58 (m, 2H), 2.47-2.42 (m, 1H), 2.07-1.82 (m, 6H), 1.75-1.65 (m, 2H), 1.62-1.59 (m, 2H), 1.57-1.55 (m, 1H), 1.22 (d, J=10.8 Hz, 3H).

Compound 114-B-E1 LC/MS ESI 512.3 (M+H)+. 1H NMR (400 MHz, MeOD) δ 7.56-7.49 (m, 2H), 7.18 (d, J=8.0 Hz, 1H) 7.08-7.06 (m, 1H), 6.41 (d, J=8.0 Hz, 1H), 5.33-5.30 (m, 1H), 4.95 (s, 2H), 4.59 (s, 1H), 4.16-4.05 (m, 2H), 3.92-3.85 (m, 1H), 3.59-3.40 (m, 3H), 3.03-2.82 (m, 2H), 2.75-2.72 (m, 3H), 2.57-2.42 (m, 3H), 2.07-2.01 (m, 3H), 2.00-1.82 (m, 3H), 1.75-1.65 (m, 2H), 1.62-1.59 (m, 2H), 1.57-1.55 (m, 1H), 1.22 (d, J=10.8 Hz, 3H). Compound 114-B-E2 LC/MS ESI 512.3 (M+H)+. $^1$H NMR (400 MHz, MeOD) δ 7.51-7.41 (m, 2H), 7.22 (d, J=8.0 Hz, 1H) 7.11-7.08 (m, 1H), 6.42 (d, J=8.0 Hz, 1H), 5.23-5.21 (m, 1H), 4.95 (s, 1H), 4.79 (s, 1H), 4.16-4.05 (m, 2H), 3.92-3.85 (m, 1H), 3.59-3.40 (m, 3H), 3.13-3.03 (m, 3H), 2.75-2.72 (m, 2H), 2.64-2.58 (m, 2H), 2.47-2.42 (m, 1H), 2.07-1.82 (m, 6H), 1.75-1.65 (m, 2H), 1.62-1.59 (m, 2H), 1.57-1.55 (m, 1H), 1.22 (d, J=10.8 Hz, 3H).

2-(2-(2,2-difluoro-6-oxaspiro[3.5]nonan-7-yl)-5-fluorophenyl)-2-((R)-3-(4-(5,6,7,8-tetrahydro-1,8-naphthyridin-2-yl)butoxy)pyrrolidin-1-yl)acetic Acid (Diastereomeric Compounds 115-A-E1, 115-A-E2, 115-B-E1 and 115-B-E2)

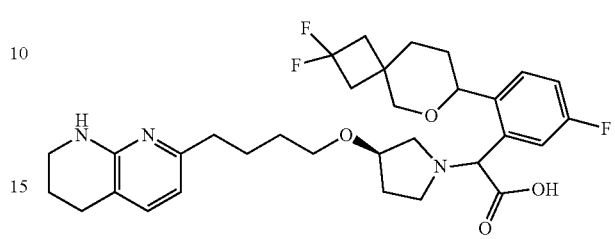

Compound 115-A-E1 LC/MS ESI 588.3 (M+H)+, 1H NMR (400 MHz, MeOD) δ 7.60-7.55 (m, 1H), 7.50-7.20 (m, 1H), 7.20-7.05 (m, 2H), 6.39 (d, J=7.2 Hz, 1H), 4.88-4.80 (m, 1H), 4.75 (s, 1H), 4.25-4.15 (m, 1H), 3.90-3.75 (m, 1H), 3.70-3.60 (m, 1H), 3.58-3.45 (m, 3H), 3.42-3.38 (m, 2H), 3.35-3.18 (m, 1H), 3.17-3.05 (m, 1H), 3.00-2.85 (m, 1H), 2.80-2.70 (m, 2H), 2.65-2.50 (m, 3H), 2.45-2.38 (m, 1H), 2.35-2.15 (m, 2H), 2.10-1.85 (m, 7H), 1.83-1.55 (m, 5H).

Compound 115-A-E2 LC/MS ESI 588.3 (M+H)+, 1H NMR (400 MHz, MeOD) δ 7.60-7.40 (m, 2H), 7.30-7.20 (m, 1H), 7.18-7.05 (m, 1H), 6.42 (d, J=7.2 Hz, 1H), 5.04 (s, 1H), 4.75 (d, J=10.4 Hz, 1H), 4.20-4.10 (m, 1H), 3.95-3.85 (m, 1H), 3.75-3.60 (m, 1H), 3.59-3.50 (m, 2H), 3.48-3.38 (m, 3H), 3.20-3.18 (m, 2H), 2.80-2.70 (m, 2H), 2.68-2.40 (m, 4H), 2.38-2.20 (m, 2H), 2.18-2.00 (m, 3H), 1.98-1.58 (m, 10H).

Compound 115-B-E1 LC/MS ESI 588(M+H)+. 1H NMR (400 MHz, MeOD) δ 7.58-7.48 (m, 2H), 7.19-7.14 (m, 2H), 6.40 (d, J=7.2 Hz, 1H), 4.91-4.77 (m, 2H), 4.16-4.15 (m, 1H), 3.82-3.80 (m, 1H), 3.72-3.70 (m, 1H), 3.50-3.31 (m, 6H), 3.31-3.20 (m, 2H), 2.72-2.41 (m, 6H), 2.31-2.25 (m, 2H), 2.20-1.60 (m, 12H).

Compound 115-B-E2 LC/MS ESI 588 (M+H)+. 1H NMR (400 MHz, MeOD) δ 7.46-7.43 (m, 2H), 7.19-7.14 (m, 2H), 6.39 (d, J=7.2 Hz, 1H), 5.21-5.19 (m, 1H), 4.71-4.69 (m, 1H), 4.19-4.17 (m, 1H), 3.87-3.84 (m, 1H), 3.66-3.64 (m, 1H), 3.40-3.31 (m, 4H), 3.31-2.98 (m, 2H), 2.76-2.50 (m, 6H), 2.28-2.25 (m, 2H), 2.20-1.60 (m, 14H).

2-(2-(5,5-difluorotetrahydro-2H-pyran-2-yl)phenyl)-2-((R)-3-(4-(5,6,7,8-tetrahydro-1,8-naphthyridin-2-yl)butoxy)pyrrolidin-1-yl)acetic Acid (Diastereomeric Compounds 116-E1 and 116-E2)

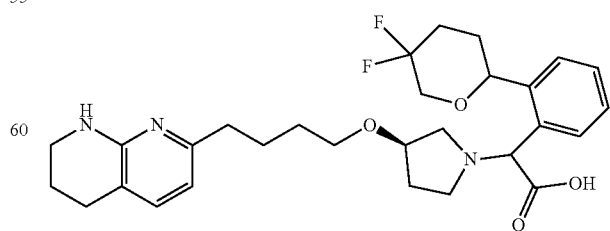

Compound 116-E1 (mixture of 2 stereoisomers) LC/MS ESI 530.2 (M+H)+, 1H NMR (400 MHz, MeOD) δ 7.70-

7.55 (m, 1H), 7.50-7.40 (m, 1H), 7.38-7.20 (m, 2H), 7.10-7.00 (m, 1H), 6.26 (d, J=7.6 Hz, 1H), 4.90 (d, J=10.8 Hz, 1H), 4.72 (s, 1H), 4.10-4.00 (m, 1H), 3.98-3.85 (m, 1H), 3.80-3.65 (m, 1H), 3.60-3.25 (m, 5H), 3.18-3.05 (m, 2H), 2.65-2.55 (m, 2H), 2.50-2.38 (m, 2H), 2.35-1.40 (m, 13H). Chiral SFC F (45% EtOH): ee 100%, Rt=1.89 min. Compound 116-E2 (mixture of 2 stereoisomers) LC/MS ESI 530.2 (M+H)+, 1H NMR (400 MHz, MeOD) δ 7.70-7.55 (m, 1H), 7.50-7.40 (m, 1H), 7.38-7.20 (m, 2H), 7.10-7.00 (m, 1H), 6.26 (d, J=7.2 Hz, 1H), 5.05-4.82 (m, 2H), 4.10-4.00 (m, 1H), 3.98-3.85 (m, 1H), 3.80-3.65 (m, 1H), 3.60-3.43 (m, 1H), 3.42-3.35 (m, 2H), 3.30-3.25 (m, 2H), 3.18-3.08 (m, 1H), 3.05-2.85 (m, 1H), 2.59 (t, J=6.0 Hz, 2H), 2.44 (t, J=7.6 Hz, 2H), 2.35-1.40 (m, 13H). Chiral SFC F (45% EtOH): ee 100%, Rt=4.45 min.

2-(5-fluoro-2-(tetrahydro-2H-pyran-4-yl)phenyl)-2-((R)-3-(4-(5,6,7,8-tetrahydro-1,8-naphthyridin-2-yl)butoxy)pyrrolidin-1-yl)acetic Acid (Diastereomeric Compounds 117-E1 and 117-E2)

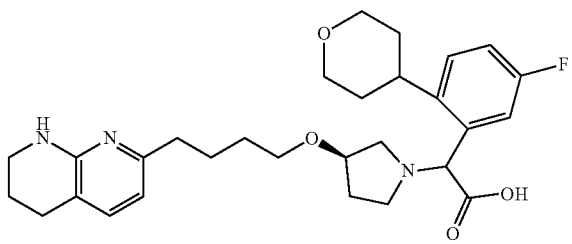 [SMILES: O=C(O)C(c1cc(F)ccc1C1CCOCC1)N1CC[C@@H](OCCCCc2ccc3c(n2)NCCC3)C1]

Compound 117-E1: (ESI 512.63 (M+H)+), 1H NMR (500 MHz, MeOD) δ 7.39-7.26 (m, 2H), 7.10 (d, J=7.3 Hz, 1H), 7.01 (m, 1H), 6.31 (d, J=7.3 Hz, 1H), 4.80 (s, 1H), 4.09 (s, 1H), 3.95-3.85 (m, 2H), 3.49-3.33 (m, 5H), 3.31-3.26 (m, 2H), 3.20-3.13 (m, 2H), 2.97-2.86 (m, 2H), 2.62 (t, J=6.2 Hz, 2H), 2.49 (m, 2H), 2.03-1.93 (m, 2H), 1.87-1.74 (m, 4H), 1.59 (m, 6H).

Compound 117-E2: (ESI 512.63 (M+H)+), 1H NMR (500 MHz, MeOD) δ 7.49-7.39 (m, 2H), 7.22 (d, J=7.3 Hz, 1H), 7.12 (m, 1H), 6.42 (d, J=7.3 Hz, 1H), 4.84 (s, 1H), 4.17 (d, J=3.3 Hz, 1H), 4.05-3.96 (m, 2H), 3.66-3.49 (m, 3H), 3.46-3.34 (m, 5H), 3.26-3.12 (m, 3H), 2.73 (t, J=6.2 Hz, 2H), 2.61 (m, 2H), 2.21-2.10 (m, 2H), 1.96-1.85 (m, 4H), 1.78-1.59 (m, 6H).

2-(5-fluoro-2-((R)-tetrahydro-2H-pyran-2-yl)phenyl)-2-((R)-3-(5-(5,6,7,8-tetrahydro-1,8-naphthyridin-2-yl)pentyloxy)pyrrolidin-1-yl)acetic Acid (Diastereomeric Compounds 118-E1 and 118-E2)

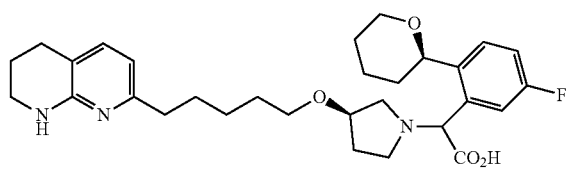 [SMILES: O=C(O)C(c1cc(F)ccc1[C@H]1CCCCO1)N1CC[C@@H](OCCCCCc2ccc3c(n2)NCCC3)C1]

Compound 118-E1: (ESI 526.65 (M+H)+), 1H NMR (500 MHz, MeOD) δ 7.57 (m, 1H), 7.51 (m, 1H), 7.19 (d, J=7.3 Hz, 1H), 7.13 (m, 1H), 6.39 (d, J=7.3 Hz, 1H), 4.87-4.78 (m, 2H), 4.17 (d, J=2.7 Hz, 1H), 4.07 (m, 1H), 3.74 (m, 1H), 3.55 (m, 1H), 3.45 (m, 2H), 3.40-3.35 (m, 2H), 3.24 (m, 1H), 3.13 (d, J=12.5 Hz, 1H), 3.01-2.93 (m, 1H), 2.69 (t, J=6.2 Hz, 2H), 2.56 (t, J=7.6 Hz, 2H), 2.10-1.99 (m, 4H), 1.92-1.83 (m, 2H), 1.74 (m, 2H), 1.64 (m, 6H), 1.43 (m, 2H).

Compound 118-E2: (ESI 526.65 (M+H)+), 1H NMR (500 MHz, MeOD) δ 7.51-7.41 (m, 2H), 7.23 (d, J=7.3 Hz, 1H), 7.08 (m, 1H), 6.40 (d, J=7.3 Hz, 1H), 4.89 (s, 2H), 4.12 (m, 2H), 3.70 (t, J=10.6 Hz, 1H), 3.54-3.45 (m, 2H), 3.44-3.36 (m, 3H), 3.09 (s, 1H), 3.00-2.88 (m, 2H), 2.72 (t, J=6.2 Hz, 2H), 2.66-2.51 (m, 2H), 2.17 (m, 1H), 2.03-1.93 (m, 2H), 1.88 (m, 4H), 1.74 (t, J=10.4 Hz, 3H), 1.69-1.50 (m, 5H), 1.48-1.35 (m, 1H).

2-(5-fluoro-2-(tetrahydrofuran-2-yl)phenyl)-2-((R)-3-(5-(5,6,7,8-tetrahydro-1,8-naphthyridin-2-yl)pentyloxy)pyrrolidin-1-yl)acetic Acid (Diastereomeric Compounds 119-A-E1, 119-A-E2, 119-B-E1 and 119-B-E2)

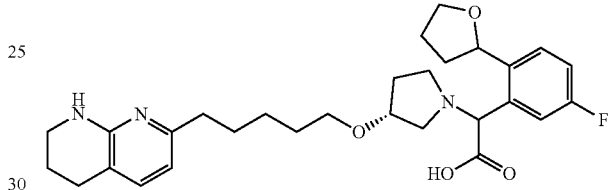

Compound 119-A-E1: (ESI 512.63 (M+H)+), 1H NMR (500 MHz, MeOD) δ 7.55-7.41 (m, 2H), 7.18 (d, J=7.3 Hz, 1H), 7.10 (m, 1H), 6.39 (d, J=7.3 Hz, 1H), 5.22-5.16 (m, 1H), 4.88 (s, 1H), 4.15 (m, 2H), 3.91 (m, 1H), 3.53-3.42 (m, 3H), 3.41-3.37 (m, 2H), 3.25 (d, J=8.8 Hz, 1H), 3.06 (d, J=12.2 Hz, 1H), 3.00-2.94 (m, 1H), 2.71 (t, J=6.2 Hz, 2H), 2.56 (t, J=7.6 Hz, 2H), 2.42 (m, 1H), 2.16-1.98 (m, 5H), 1.91-1.85 (m, 2H), 1.70-1.59 (m, 4H), 1.44 (m, 2H).

Compound 119-A-E2: (ESI 512.63 (M+H)+), 1H NMR (500 MHz, MeOD) δ 7.55 (m, 2H), 7.23 (d, J=7.3 Hz, 1H), 7.12 (m, 1H), 6.41 (d, J=7.3 Hz, 1H), 5.37 (t, J=7.0 Hz, 1H), 4.68 (s, 1H), 4.12 (m, 2H), 3.94 (m, 1H), 3.51-3.36 (m, 5H), 3.17 (s, 1H), 3.06-2.94 (m, 2H), 2.73 (t, J=6.2 Hz, 2H), 2.57 (m, 3H), 2.18 (m, 1H), 2.12-2.01 (m, 3H), 1.97-1.86 (m, 3H), 1.78-1.55 (m, 5H), 1.48-1.40 (m, 1H).

Compound 119-B-E1: (ESI 512.63 (M+H)+), 1H NMR (500 MHz, MeOD) δ 7.58 (m, 1H), 7.47 (m, 1H), 7.22-7.09 (m, 2H), 6.39 (d, J=7.3 Hz, 1H), 5.25 (t, J=7.2 Hz, 1H), 4.93 (s, 1H), 4.18 (d, J=3.4 Hz, 1H), 4.11 (m, 1H), 3.94 (m, 1H), 3.56-3.42 (m, 3H), 3.41-3.36 (m, 2H), 3.27-3.11 (m, 2H), 3.07-2.97 (m, 1H), 2.71 (t, J=6.2 Hz, 2H), 2.56 (t, J=7.6 Hz, 2H), 2.49 (m, 1H), 2.14-2.02 (m, 4H), 2.02-1.92 (m, 1H), 1.91-1.83 (m, 2H), 1.71-1.57 (m, 4H), 1.49-1.38 (m, 2H).

Compound 119-B-E2: (ESI 512.63 (M+H)+), 1H NMR (500 MHz, MeOD) δ 7.51 (m, 2H), 7.25 (d, J=7.3 Hz, 1H), 7.07 (m, 1H), 6.41 (d, J=7.3 Hz, 1H), 5.34 (t, J=7.5 Hz, 1H), 4.58 (s, 1H), 4.15 (m, 2H), 3.92 (m, 1H), 3.49 (m, 1H), 3.45-3.35 (m, 4H), 2.96 (d, J=7.2 Hz, 1H), 2.89 (m, 1H), 2.73 (t, J=6.2 Hz, 2H), 2.66-2.52 (m, 2H), 2.46 (m, 1H), 2.10 (m, 3H), 1.97 (m, 1H), 1.90 (m, 3H), 1.78-1.64 (m, 2H), 1.63-1.51 (m, 3H), 1.44 (m, 1H).

2-(5-fluoro-2-(tetrahydro-2H-pyran-4-yl)phenyl)-2-((R)-3-(5-(5,6,7,8-tetrahydro-1,8-naphthyridin-2-yl)pentyloxy)pyrrolidin-1-yl)acetic Acid (Diastereomeric Compounds 120-E1 and 120-E2)

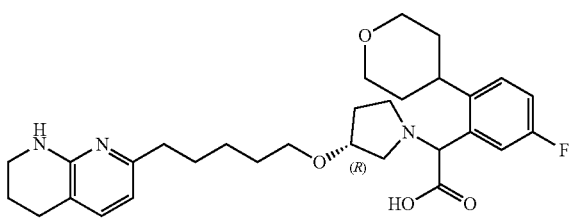

Compound 120-E1: (ESI 526.65 (M+H)+), ¹H NMR (500 MHz, MeOD) δ 7.44 (m, 2H), 7.18 (d, J=7.3 Hz, 1H), 7.10 (m, 1H), 6.40 (d, J=7.3 Hz, 1H), 4.81 (s, 1H), 4.18 (s, 1H), 4.09-4.00 (m, 2H), 3.62 (m, 2H), 3.47 (t, J=6.4 Hz, 2H), 3.44-3.35 (m, 4H), 3.11 (d, J=12.0 Hz, 1H), 2.94 (t, J=7.8 Hz, 2H), 2.71 (t, J=6.2 Hz, 2H), 2.56 (t, J=7.6 Hz, 2H), 2.12-2.00 (m, 2H), 1.96-1.86 (m, 4H), 1.80-1.60 (m, 6H), 1.44 (m, 2H).

Compound 120-E2: (ESI 526.65 (M+H)+), ¹H NMR (500 MHz, MeOD) δ 7.51 (d, J=10.3 Hz, 1H), 7.41 (m, 1H), 7.26 (d, J=7.3 Hz, 1H), 7.09 (m, 1H), 6.42 (d, J=7.3 Hz, 1H), 4.61 (s, 1H), 4.14 (s, 1H), 4.04 (d, J=7.5 Hz, 2H), 3.65 (m, 2H), 3.52 (m, 2H), 3.45-3.37 (m, 4H), 3.19 (s, 1H), 3.02 (s, 1H), 2.92 (s, 1H), 2.73 (t, J=6.2 Hz, 2H), 2.69-2.52 (m, 2H), 2.16 (m, 1H), 2.05 (s, 1H), 1.94-1.86 (m, 4H), 1.81-1.66 (m, 4H), 1.57 (d, J=18.6 Hz, 3H), 1.44 (m, 1H).

(2S)-2-(4-cyano-2-(tetrahydro-2H-pyran-2-yl)phenyl)-2-((R)-3-(4-(5,6,7,8-tetrahydro-1,8-naphthyridin-2-yl)butoxy)pyrrolidin-1-yl)acetic Acid (Diastereomeric Compounds 121-E1 and 121-E2)

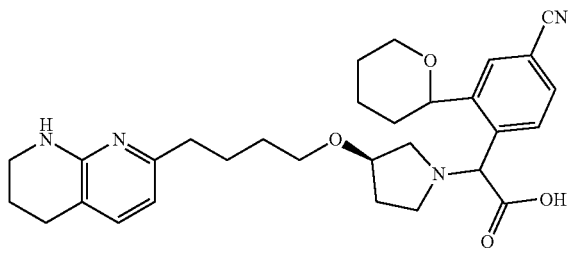 [SMILES: N#Cc1ccc(C(C(=O)O)N2CC[C@@H](OCCCCc3ccc4c(n3)NCCC4)C2)c(C2CCCCO2)c1]

Compound 121-E1 (mixture of 2 stereoisomers) (ESI 519.2 (M+H)+), ¹H NMR (500 MHz, MeOD) δ 7.89 (dd, J=12.0, 8.2 Hz, 2H), 7.76-7.58 (m, 1H), 7.24 (m, 1H), 6.43 (d, J=7.3 Hz, 1H), 4.81 (m, 2H), 4.16 (m, 1H), 4.09 (m, 1H), 3.77-3.67 (m, 1H), 3.52-3.37 (m, 5H), 3.30-2.88 (m, 3H), 2.73 (m, 2H), 2.68-2.53 (m, 2H), 2.21-1.54 (m, 15H).

Compound 121-E2 (mixture of 2 stereoisomers) (ESI 519.2 (M+H)+), ¹H NMR (500 MHz, MeOD) δ 7.84 (dd, J=8.1, 2.7 Hz, 1H), 7.81 (t, J=1.9 Hz, 1H), 7.64 (m, 1H), 7.27 (m, 1H), 6.43 (t, J=6.8 Hz, 1H), 5.02 (d, J=58.4 Hz, 1H), 4.86 (m, 1H), 4.21-4.05 (m, 2H), 3.67 (m, 1H), 3.57-3.34 (m, 5H), 3.30-2.84 (m, 3H), 2.74 (m, 2H), 2.62 (m, 2H), 2.21-1.51 (m, 15H).

(S)-2-(3-fluoro-2-((S)-tetrahydro-2H-pyran-2-yl)phenyl)-2-((R)-3-(4-(5,6,7,8-tetrahydro-1,8-naphthyridin-2-yl)butoxy)pyrrolidin-1-yl)acetic Acid (122-E1)

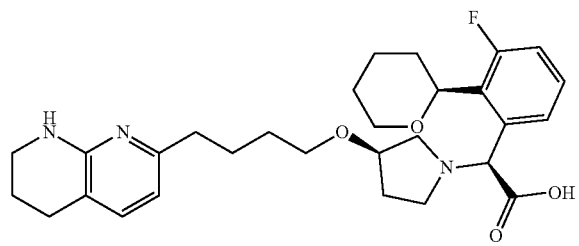 [SMILES: O=C(O)[C@H](c1cccc(F)c1[C@@H]1CCCCO1)N1CC[C@@H](OCCCCc2ccc3c(n2)NCCC3)C1]

Compound 122-E1 LC/MS ESI 512.2 (M+H)+. ¹H NMR (400 MHz, DMSO) δ 8.18 (s, 1H), 67.26-7.33 (m, 2H), 67.03-7.10 (m, 2H), 66.58 (s, 1H), 66.25 (d, J=6 Hz, 1H), 64.96 (d, J=14 Hz, 1H), 64.53 (s, 1H), 63.95-3.99 (m, 1H), 63.91 (d, J=10.8 Hz, 1H), 63.44 (t, J=11.2 Hz, 1H), 63.30 (t, J=6.4 Hz, 2H), 63.22 (t, J=6 Hz, 2H), 62.95 (dd, J=6, 12 Hz, 1H), 62.69-2.80 (m, 2H), 62.60 (t, J=6 Hz, 2H), 62.53-2.55 (m, 1H), 62.43 (t, J=5.6, 2H), 61.90-1.98 (m, 2H), δ1.47-1.82 (m, 12H).

2-(5-fluoro-2-(5-oxaspiro[2.5]octan-6-yl)phenyl)-2-((R)-3-(4-(4-methoxy-5,6,7,8-tetrahydro-1,8-naphthyridin-2-yl)butoxy)pyrrolidin-1-yl)acetic Acid (Diastereomeric Compounds 129-E1 and 129-E2)

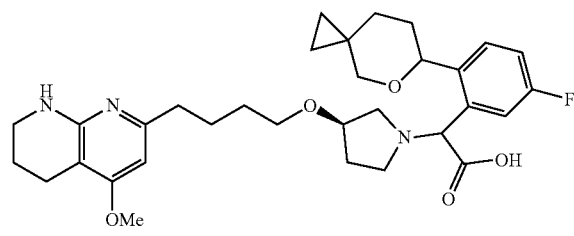 [SMILES: COc1cc(CCCCO[C@@H]2CCN(C(C(=O)O)c3cc(F)ccc3C3CCC4(CC4)CO3)C2)nc2c1CCCN2]

Compound 129-E1: LC/MS ESI 568 (M+H)+. ¹H NMR (400 MHz, MeOD) δ 7.63-7.48 (m, 2H), 7.18-7.15 (m, 1H), 6.30 (s, 1H), 4.92-4.85 (m, 3H), 4.77 (s, 1H), 4.20-4.14 (m, 2H), 3.87 (s, 3H), 3.50-3.32 (m, 3H), 3.30-2.85 (m, 4H), 2.62-2.55 (m, 4H), 2.21-1.60 (m, 12H), 0.60-0.30 (m, 4H). Chiral SFC C (20% EtOH): ee 100%, Rt=1.35 min.

Compound 129-E2: LC/MS ESI 568 (M+H)+. ¹H NMR (400 MHz, MeOD) δ 7.46-7.40 (m, 2H), 6.95-6.92 (m, 1H), 6.14 (s, 1H), 4.85-4.80 (m, 3H), 4.37 (s, 1H), 4.02-3.96 (m, 2H), 3.74 (s, 3H), 3.40-3.22 (m, 2H), 2.98-2.65 (m, 5H), 2.52-2.41 (m, 4H), 2.20-1.40 (m, 12H), 0.44-0.20 (m, 4H). Chiral SFC C (20% EtOH): ee 100%, Rt=2.02 min.

2-(2-(5,5-dimethyl-1,4-dioxan-2-yl)-5-fluorophenyl)-2-((R)-3-(4-(5,6,7,8-tetrahydro-1,8-naphthyridin-2-yl)butoxy)pyrrolidin-1-yl)acetic Acid (Compound 125)

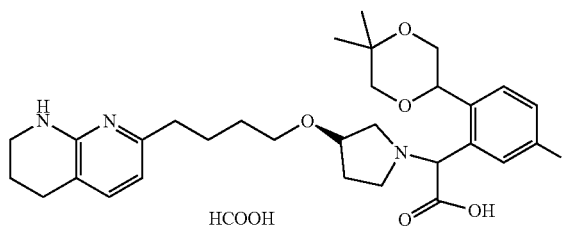

Compound 125 (mixture of 4 stereoisomers) LC/MS ESI 542 (M+H)+. 1H NMR (400 MHz, MeOD) δ 8.42 (s, 1H), 7.76-7.69 (m, 1H), 7.60-7.45 (m, 2H), 7.29-7.19 (m, 1H), 6.62-6.57 (m, 1H), 5.18 (s, 1H), 4.90-4.81 (m, 1H), 4.28-4.24 (m, 1H), 4.18-3.98 (m, 1H), 3.81-3.38 (m, 10H), 3.32-3.16 (m, 1H), 2.82-2.61 (m, 4H), 2.31-2.20 (m, 2H), 1.98-1.55 (m, 6H), 1.49-1.35 (m, 3H)), 1.20-1.08 (m, 3H).

2-(2-(5,5-difluorotetrahydro-2H-pyran-2-yl)-5-fluorophenyl)-2-((R)-3-(4-(4-methoxy-5,6,7,8-tetrahydro-1,8-naphthyridin-2-yl)butoxy)pyrrolidin-1-yl)acetic Acid (Diastereomeric Compounds 126-E1 and 126-E2)

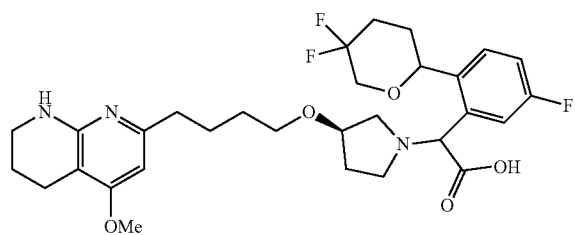 [SMILES: COc1cc(CCCCO[C@@H]2CCN(C(C(=O)O)c3cc(F)ccc3C3CCC(F)(F)CO3)C2)nc2c1CCCN2]

Compound 126-E1 (mixture of 2 stereoisomers) LC/MS ESI 578 (M+H)+, 1H NMR (400 MHz, MeOD) δ 7.60-7.49 (m, 2H), 7.10 (t, J=8.0 Hz, 1H), 6.32 (s, 1H), 5.04 (d, J=10.8 Hz, 1H), 4.59 (s, 1H), 4.12 (s, 1H), 4.02-3.79 (m, 5H), 3.52-3.35 (m, 4H), 3.30-2.75 (m, 6H), 2.68-2.52 (m, 4H), 2.35-1.55 (m, 12H). Chiral SFC A (35% IPA): ee 100%, Rt=4.39 min.

Compound 126-E2 (mixture of 2 stereoisomers) LC/MS ESI 578 (M+H)+, 1H NMR (400 MHz, MeOD) δ 7.62-7.49 (m, 2H), 7.12-7.06 (m, 1H), 6.36 (s, 1H), 5.12-5.04 (m, 1H), 4.50 (s, 1H), 4.13 (s, 1H), 4.02-3.78 (m, 5H), 3.57-3.35 (m, 4H), 3.27-2.83 (m, 6H), 2.79-2.52 (m, 4H), 2.38-1.52 (m, 12H). Chiral SFC A (35% IPA): ee 100%, Rt=5.12 min.

2-(2-(5,5-dimethyltetrahydro-2H-pyran-2-yl)-5-fluorophenyl)-2-((R)-3-(4-(5,6,7,8-tetrahydro-1,8-naphthyridin-2-yl)butoxy)pyrrolidin-1-yl)acetic Acid (Diastereomeric Compounds 127-E1, 127-E2 and 127-E3)

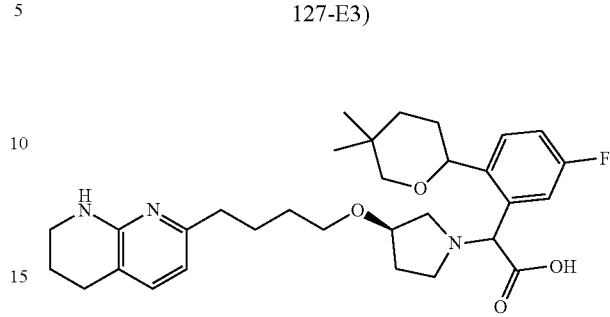

Compound 127-E1 LC/MS ESI 540 (M+H)+. 1H NMR (400 MHz, MeOD) δ 7.64-7.61 (m, 1H), 7.49-7.47 (m, 1H), 7.19-7.15 (m, 2H), 6.41-6.39 (m, 1H), 4.92-4.90 (m, 1H), 4.72-4.70 (m, 1H), 4.19-4.17 (m, 1H), 3.52-3.32 (m, 8H), 3.16-3.14 (m, 1H), 3.02-3.01 (m, 1H), 2.73-2.70 (m, 2H), 2.59-2.56 (m, 2H), 2.11-1.50 (m, 12H), 1.20 (s, 3H), 0.90 (s, 3H). Chiral SFC H (45% IPA): ee 100%, Rt=2.35 min.

Compound 127-E2 LC/MS ESI 540 (M+H)+. 1H NMR (400 MHz, MeOD) δ 7.65-7.63 (m, 1H), 7.52-7.49 (m, 1H), 7.21-7.16 (m, 2H), 6.41-6.39 (m, 1H), 4.82-4.70 (m, 2H), 4.17-4.16 (m, 1H), 3.52-3.32 (m, 8H), 3.20-3.16 (m, 2H), 2.73-2.70 (m, 2H), 2.59-2.56 (m, 2H), 2.24-2.08 (m, 2H), 2.01-1.55 (m, 10H), 1.20 (s, 3H), 0.90 (s, 3H). Chiral SFC H (45% IPA): ee 100%, Rt=3.66 min.

Compound 127-E3 (mixture of 2 stereoisomers) LC/MS ESI 540 (M+H)+. 1H NMR (400 MHz, MeOD) δ 7.66-7.62 (m, 1H), 7.51-7.49 (m, 1H), 7.41-7.17 (m, 2H), 6.48-6.46 (m, 1H), 4.92-4.90 (m, 1H), 4.72-4.70 (m, 1H), 4.19-4.17 (m, 1H), 3.52-3.32 (m, 8H), 3.16-3.10 (m, 2H), 2.73-2.70 (m, 2H), 2.59-2.56 (m, 2H), 2.11-1.50 (m, 12H), 1.20-1.18 (m, 3H), 0.90-0.84 (m, 3H).

2-(2-(5,5-dimethyltetrahydro-2H-pyran-2-yl)-5-fluorophenyl)-2-((R)-3-(4-(4-methoxy-5,6,7,8-tetrahydro-1,8-naphthyridin-2-yl)butoxy)pyrrolidin-1-yl)acetic Acid (Diastereomeric Compounds 128-E1, 128-E2 and 128-E3)

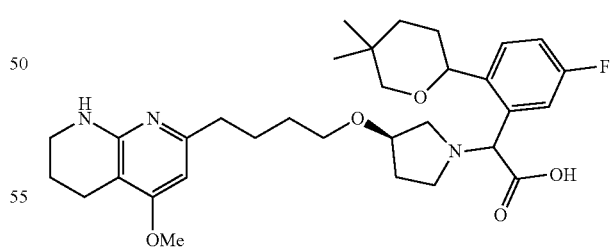

Compound 128-E1 (mixture of 2 stereoisomers) LC/MS ESI 570 (M+H)+, 1H NMR (400 MHz, MeOD) δ 7.65-7.58 (m, 1H), 7.53-7.46 (m, 1H), 7.15-7.11 (m, 1H), 6.32-6.30 (m, 1H), 4.83-4.64 (m, 2H), 4.20-4.12 (m, 1H), 3.88-3.85 (m, 3H), 3.58-3.35 (m, 6H), 3.32-2.91 (m, 4H), 2.75-2.54 (m, 4H), 2.20-1.55 (m, 12H), 1.12 (s, 3H), 0.87 (d, J=4.8 Hz, 3H).

Compound 128-E2 LC/MS ESI 570 (M+H)+, 1H NMR (400 MHz, MeOD) δ 7.47-7.44 (m, 2H), 7.12-7.08 (m, 1H), 6.30 (s, 1H), 5.18 (s, 1H), 4.65 (d, J=8.0 Hz, 1H), 4.13 (s, 1H), 3.87 (s, 3H), 3.61-3.36 (m, 7H), 3.28-2.94 (m, 3H), 2.69-2.56 (m, 4H), 2.19-1.53 (m, 12H), 1.16 (s, 3H), 0.87 (s, 3H).

Compound 128-E3 LC/MS ESI 570 (M+H)+, 1H NMR (400 MHz, MeOD) δ 7.51-7.40 (m, 2H), 7.09-7.05 (m, 1H), 6.35 (s, 1H), 4.79 (d, J=8.0 Hz, 1H), 4.13 (s, 1H), 3.90 (s, 3H), 3.62-3.38 (m, 5H), 3.31-3.20 (m, 2H), 3.02-2.52 (m, 8H), 2.21-1.52 (m, 12H), 1.15 (s, 3H), 0.87 (s, 3H).

Example 35: Fluorescence Polarization Assays of Compounds for αvβ6 Binding

Fluorescence Polarization (FP) assays were used to measure compound activity through binding competition with the fluorescein-labeled peptide GRGDLGRL. In the assay, 10 nM of integrin αvβ6 was incubated with the test compound in 2 mM manganese chloride, 0.1 mM calcium chloride, 20 mM HEPES buffer at pH 7.3, 150 mM sodium chloride, 0.01% Triton X-100, 2% DMSO, and 3 nM of the fluorescein-labeled peptide. The assays were run in 384-well plates. For both assay versions, the integrin protein was pre-incubated with the test compounds for 15 minutes at 22° C. before the fluorescein-labeled peptide was added. After the fluorescein-labeled peptide was added, the assay was incubated at 22° C. for 1 hour and fluorescence polarization was measured. $IC_{50}$ values were determined by nonlinear regression, 4-parameter curve fitting (FIGS. 1 and 2).

Example 36: MDCK Permeability Assays

Compounds were tested for permeability in an MDCK permeability assay. This assay measures the ability of compounds to cross a layer of Madin-Darby Canine Kidney (MDCK) cells from the apical to basolateral side (A→B). This measurement is predictive of the ability of compounds to be absorbed in the gut following oral dosing, an essential characteristic of an orally administered small molecule integrin inhibitor drug.

The assay is run in two formats. One uses wild type MDCK cells with no inhibitor. This method works well in determining the passive permeability of compounds with low efflux by P-glyocprotein (Pgp), and was used to assess permeability of a Reference Compound having the chemical formula shown below. The MDCK value of less than 1 (i.e., less than about 0.23) was obtained for the Reference Compound using this method; an IC50 value of about 96.5 nM was obtained for the Reference Compound using the fluorescence polarization assay of Example 35.

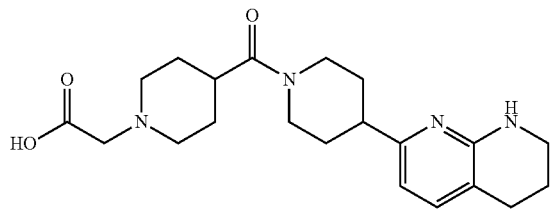 [SMILES: O=C(O)CN1CCC(C(=O)N2CCC(c3ccc4c(n3)NCCC4)CC2)CC1]

| Reference Compound | |
|---|---|
| avb6. (IC50) [nM] | MDCK (A -> B) |
| 96.5 | <0.23 |

However, for compounds with Pgp efflux, it is necessary to include a Pgp inhibitor order to determine passive permeability for A→B transmission. In this case, a MDCK-MDR1 cell line overexpressing Pgp is used, and PGP inhibitor GF120918 is included at sufficient concentration (10 μM) to block activity of Pgp. This procedure (MDCK-MDR1 with PGP inh (A→B) [10⁻6 cm/s]) was used to obtain the data presented in Tables shown in FIGS. 3 and 4. MDCK permeability values of less than 5 10^6 cm/s predict low absorption in the gut, while permeability values greater than 5 10^6 cm/s predict sufficient absorption in the gut for oral dosing of a small molecule drug.

The detailed experimental procedure is as follows:

| EQUIPMENT | REAGENTS |
|---|---|
| 24-well Cell Culture Plate (PET membrane): Millipore #PSHT 010 R5 | GF120918 (Pgp inhibitor) Lucifer Yellow Reference compounds: Quinidine, Metoprolol, Atenolol |
| 24-well feeder tray: Millipore #PSMW 010 R5 | Cell line: MDCK (ATCC) or MDCK MDR1 (NKI) |
| Millicell ERS System - Millipore # MERS 000 01 | Cell culture growth medium (MEM + 10% FBS + 1% NEAA): |
| 96-well U-shape plates (BH Bio# BH-04ML-96U) | Trypsin-EDTA (Invitrogen, Cat# 25200-072) |
| 96-well microplates (Greiner#655209) | Assay and dosing solution buffer: Hanks Balanced Salt Solution |
| 37☐ $CO_2$ Incubator Infinite F2000pro (TECAN) | (HBSS, Invitrogen, Cat# 14025-092) with 25 mM HEPES, pH 7.4 |
| | Test article and reference compound stock solutions were prepared in DMSO, Lucifer Yellow (LY) stock solution was prepared in the assay buffer. |

Cell Culture and Maintenance:
  Cell stock cultures (MDCK or MDCK MDR1) are maintained in MEM+1000 FBS+11% NEAA, grown in 75 cm² tissue culture treated flasks and split (passed) 2 times weekly to maintain desired confluence.
  For maintenance passage: trypsinized cells are routinely distributed into new flasks at a standard passage ratio of 1:20.
Seeding assay plates: MDCK assay plates are seeded with MDCK or MDCK MCR1 cells 3-4 days prior to running the assay. 24-well plates are seeded at a cell density of 0.88× 10⁵/well in a 400 μL apical chamber volume (2.2×10⁵/mL) with a 25 mL volume of growth medium to the 24-well basal chamber. Assay plates are generally provided with a growth medium change 24 hours prior to the assay.
Preparation of the assay plates and Trans-epithelial Electrical Resistance (TEER) measurement: MDCK assay plates are rinsed with HBSS+ prior to running the assay. After rinsing, fresh HBSS+ is added to the assay plate in a 400 μL apical chamber volume and a 0.8 mL HBSS+ basal chamber volume. Measure the electrical resistance across the monolayer using the Millicell ERS system ohm meter. (The cells will be used if TEER is higher than 100 ohm*cm²).
Preparation of dosing solution. Donor solutions are prepared in HBSS+ with 0.4% DMSO and 5 μM test compound. The donor solution contains 5 μM lucifer yellow for apical dosing, but no lucifer yellow for basolateral dosing. The donor solution may also contain 10 μM GF120918 for Pgp inhibition. Receiver solutions are prepared with HBSS+ with 0.4% DMSO. Donor and receiver solutions were centrifuged at 4000 rpm, 5 min, and supernatants were used for compound dosing.

Preparation of the Cell Plates:
  Remove the buffer from the apical side and basolateral side. Add 600 µL of donor solution (for A-to-B) or 500 µL of receiver solution (for B-to-A) to the apical wells based on plate map.
  A fresh basolateral plate is prepared by adding 800 µL of receiver solution (for A-to-B) or 900 µL of donor solution (B-to-A) to the well of a new 24-well plate.
  Put the apical plate and basolateral plate into a 37° C. $CO_2$ incubator.

Preparation of Analytical Plate:
  After 5 min, transfer 100 µL of samples from all donors (for both A-to-B and B-to-A) into appropriate wells of a sample plate for D0. And transfer 100 µL of samples from all apical chambers (the donor of A-to-B and receiver of B-to-A) into appropriate wells of a microplate for Lucifer Yellow D0 (D0 LY)
  Lay the apical plate to the basolateral plate to start transport process.
  At 90 min, separate the apical and basolateral plates and transfer 100 µL of samples from all donors (for both A-to-B and B-to-A) into appropriate wells of a new sample plate for D90, and transfer 200 µL of samples from all receivers into appropriate wells of a sample plate for R90. Transfer 100 µL of samples from all basolateral chambers (receiver of A-to-B and donor of B-to-A) into appropriate wells of a new microplate for Lucifer Yellow R90 (R90 LY).
  Determine LY permeability by reading D0 LY and R90 LY at an excitation wavelength of 485 nm and an emission wavelength of 535 nm using a fluorescent plate reader.

LC/MS/MS Sample preparation:
  For receiver solution: 60 µL of sample+60 µL ACN with IS (200 ng/mL Osalmid)
  For donor solution: 6 µL of sample+54 µL 0.4% DMSO/HBSS+60 µL ACN with IS (200 ng/mL Osalmid)
  The compound standard curve 20× solutions (0.1-60 µM range) are prepared in MeOH:$H_2O$ (1:1). 1× concentrated solutions (0.005-3 M range) are prepared by mixing 3 µL of 20× solution with 57 µL 0.4% DMSO HBSS and 60 µL ACN with IS (200 ng/mL Osalmid).

Calculations

Transepithelial electrical resistance(TEER)=(Resistance sample−Resistance blank)×Effective Membrane Area Lucifer Yellow permeability:

$P_{app}=(V_A/(\text{Area}\times\text{time}))\times([RFU]_{accepter}-[RFU]_{blank})/(([RFU]_{initial,donor}-[RFU]_{blank})\times\text{Dilution Factor})\times100$ Plate drug transport assays using the following equation:

Transepithelial electrical resistance(TEER)=(Resistance sample−Resistance blank)×Effective Membrane Area Drug permeability:

$P_{app}=(V_R/(\text{Area}\times\text{time}))\times([\text{drug}]_{receiver}/(([\text{drug}]_{initial,donor})\times\text{Dilution Factor})$ Where $V_R$ is the volume in the receiver well (0.8 mL for A-to-B and 0.4 mL for B-to-A), area is the surface area of the membrane (0.7 $cm^2$ for Millipore-24 Cell Culture Plates), and time is the total transport time in seconds.

Percentage Recovery=100×(Total compound in donor at 90 min×Dilution Factor+Total compound in receiver at 90 min)/(Total compound in donor at 0 min×Dilution Factor)

INCORPORATION BY REFERENCE

All of the U.S. patents and U.S. patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are encompassed by the following claims.

We claim:
1. A compound having the formula:

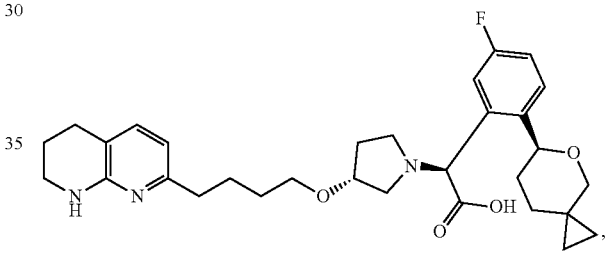

or a pharmaceutically acceptable salt thereof.

2. A compound having the formula:

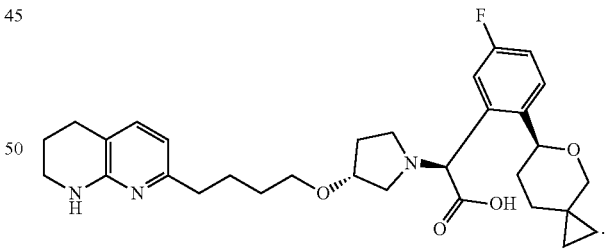

* * * * *